(12) United States Patent
Christiano et al.

(10) Patent No.: US 9,198,911 B2
(45) Date of Patent: Dec. 1, 2015

(54) METHODS FOR TREATING HAIR LOSS DISORDERS

(71) Applicant: The Trustees of Columbia University in the City of New York, New York, NY (US)

(72) Inventors: Angela M. Christiano, Mahwah, NJ (US); Raphael Clynes, West Nyack, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/886,252

(22) Filed: May 2, 2013

(65) Prior Publication Data

US 2014/0065153 A1    Mar. 6, 2014

Related U.S. Application Data

(63) Continuation-in-part of application No. PCT/US2011/059029, filed on Nov. 2, 2011, and a continuation-in-part of application No. PCT/US2013/034688, filed on Mar. 29, 2013.

(60) Provisional application No. 61/409,509, filed on Nov. 2, 2010, provisional application No. 61/617,225, filed on Mar. 29, 2012, provisional application No. 61/645,499, filed on May 10, 2012.

(51) Int. Cl.
| | |
|---|---|
| *A61K 31/52* | (2006.01) |
| *A61K 31/407* | (2006.01) |
| *A61K 31/506* | (2006.01) |
| *A61K 31/713* | (2006.01) |
| *A61K 31/519* | (2006.01) |
| *A61K 31/63* | (2006.01) |
| *A61K 31/7052* | (2006.01) |

(52) U.S. Cl.
CPC .............. *A61K 31/52* (2013.01); *A61K 31/407* (2013.01); *A61K 31/506* (2013.01); *A61K 31/519* (2013.01); *A61K 31/63* (2013.01); *A61K 31/7052* (2013.01); *A61K 31/713* (2013.01)

(58) Field of Classification Search
None
See application file for complete search history.

(56) References Cited

U.S. PATENT DOCUMENTS

| | | | |
|---|---|---|---|
| 5,712,171 A | 1/1998 | Zambias et al. | |
| 5,916,792 A | 6/1999 | Civin et al. | |
| 6,887,471 B1 | 5/2005 | Linsley et al. | |
| 7,015,218 B1 | 3/2006 | Ushio et al. | |
| 7,101,962 B2 | 9/2006 | Burke et al. | |
| 7,112,594 B2 | 9/2006 | Ushio et al. | |
| 7,294,504 B1 | 11/2007 | Wang | |
| 7,422,896 B1 | 9/2008 | Wang | |
| 7,491,732 B2 | 2/2009 | Li et al. | |
| 7,666,417 B2 | 2/2010 | Spies et al. | |
| 7,879,844 B2 | 2/2011 | Inoue et al. | |
| 7,915,273 B2 | 3/2011 | Argade et al. | |
| 8,163,767 B2 | 4/2012 | Inoue et al. | |
| 8,470,880 B2 * | 6/2013 | Hu et al. | 514/557 |
| 2002/0173478 A1 | 11/2002 | Gewirtz | |
| 2003/0044803 A1 | 3/2003 | Pedersen et al. | |
| 2003/0144178 A1 * | 7/2003 | Uckun | 514/2 |
| 2004/0018176 A1 | 1/2004 | Tolentino et al. | |
| 2004/0057937 A1 | 3/2004 | Jahoda et al. | |
| 2004/0198750 A1 * | 10/2004 | Green et al. | 514/260.1 |
| 2005/0009163 A1 | 1/2005 | Tong et al. | |
| 2005/0272150 A1 | 12/2005 | Teumer et al. | |
| 2007/0072204 A1 | 3/2007 | Hannon et al. | |
| 2008/0069791 A1 | 3/2008 | Beissert | |
| 2010/0221364 A1 | 9/2010 | Bruning et al. | |
| 2011/0071149 A1 | 3/2011 | Ma et al. | |
| 2011/0092490 A1 * | 4/2011 | Wang et al. | 514/218 |
| 2011/0117159 A1 | 5/2011 | Zisman | |

FOREIGN PATENT DOCUMENTS

| | | |
|---|---|---|
| WO | WO 91/05058 | 4/1991 |
| WO | WO 95/18972 | 7/1995 |
| WO | WO 96/22529 | 7/1996 |
| WO | WO 98/22103 | 5/1998 |
| WO | WO 99/07409 | 2/1999 |
| WO | WO 99/32619 | 7/1999 |
| WO | WO 00/01846 | 1/2000 |
| WO | WO 00/44895 | 8/2000 |
| WO | WO 00/44914 | 8/2000 |
| WO | WO 01/29058 | 5/2001 |
| WO | WO 01/32840 | 5/2001 |
| WO | WO 01/36646 | 5/2001 |
| WO | WO 2004/044188 | 5/2004 |
| WO | WO 2007/100870 | 9/2007 |
| WO | WO 2009/077483 | 6/2009 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Aagaard et al (Advanced Drug Delivery Reviews 59 (2007) 75-86).*
Warzocha et al (Leukemia and Lymphoma, Val. 24. pp. 267-281).*
Guido et al (Curr Med Chem. 2008;15(1):37-46).*
Clark et al (J. Med. Chem., 2014, 57 (12), pp. 5023-5038).*
Carroll, et al., "Gene array profiling and immunomodulation studies define a cell-mediated immune response underlying the pathogenesis of alopecia areata in a mouse model and humans", *Alopecia Areata Gene Expression*, 119(2):392-402 (2002).
Chang, et al., "JAK3 Inhibition significantly attenuates psoriasiform skin inflammation in Cd18 mutant PL/J mice", *The Journal of Immunology*, 183(3):2183-2192 (2009).
Changelian, et al., "The specificity of JAK3 kinase inhibitors", *Blood*, 111(4):2155-2157 (2008).
Haan, et al., "Jak1 has a dominant role over Jak3 in signal transduction through γc-containing cytokine receptors", *Chemistry & Biology*, 18:314-323 (2011).

(Continued)

*Primary Examiner* — Brian J Gangle
*Assistant Examiner* — Andrea McCollum
(74) *Attorney, Agent, or Firm* — Baker Botts L.L.P.

(57) ABSTRACT

The invention provides for methods for treating a hair loss disorder in a subject by administering a Janus Kinase/Signal Transducers and Activators of Transcription inhibitor.

10 Claims, 106 Drawing Sheets

(56) References Cited

OTHER PUBLICATIONS

Kim, et al., NSC114792, a novel small molecule identified through structure-based computational database screening, selectively inhibits JAK3, *Molecular Cancer*, 9:36 (2010).

Paladini, et al., "Modulation of hair growth with small molecule agonists of the hedgehog signaling pathway", *The Journal of Investigative Dermatology*, 125:638-646 (2005).

Petukhova, et al., "Genome-wide association study in alopecia areata implicates both innate and adaptive immunity", *Nature*, 466(7302):113-117 (2010).

Wong, et al., "Targeting Syk as a treatment for allergic and autoimmune disorders", *Expert Opin. Investig. Drugs*, 13(7):743-762 (2004).

Summary of the 2010 Alopecia Areata Clinical/Translational Research Summit (Oct. 22, 2010) [Retrieved from the internet by WIPO on Feb. 16, 2012: http://www.naaf.org/site/PageServer?pagename=2010_summit_research_highlights [Retrieved from internet on Oct. 23, 2013].

International Search Report and Written Opinion for PCT/US2013/034688, dated Aug. 6, 2013.

\* cited by examiner

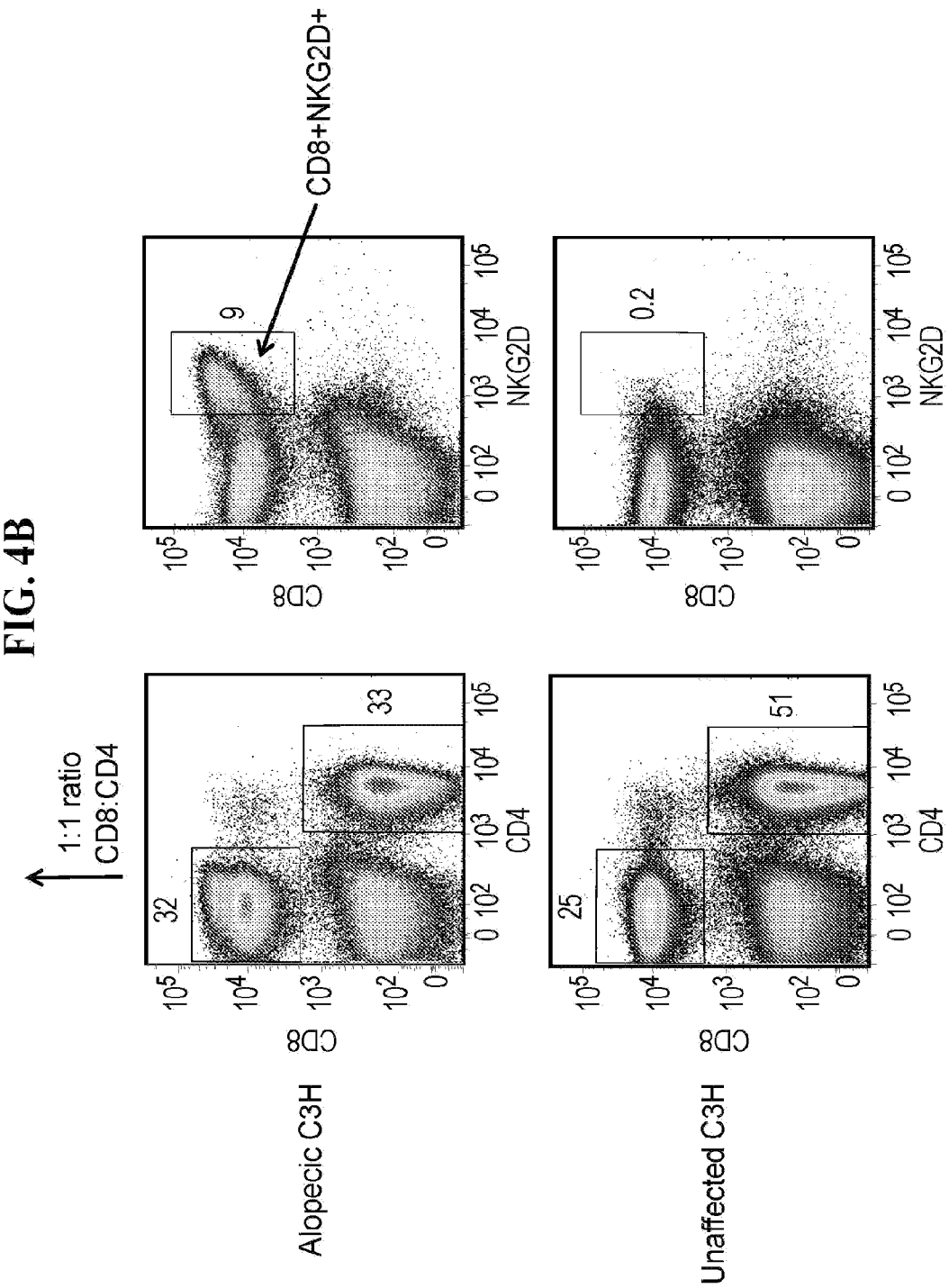

AA
"Pre-2010"
Swarm of Bees
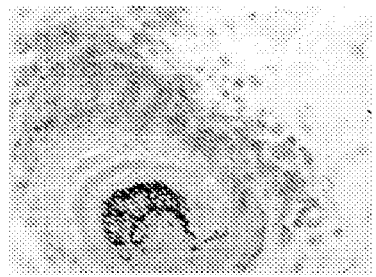
FIG. 11A
AA
"2010": Bees are identified
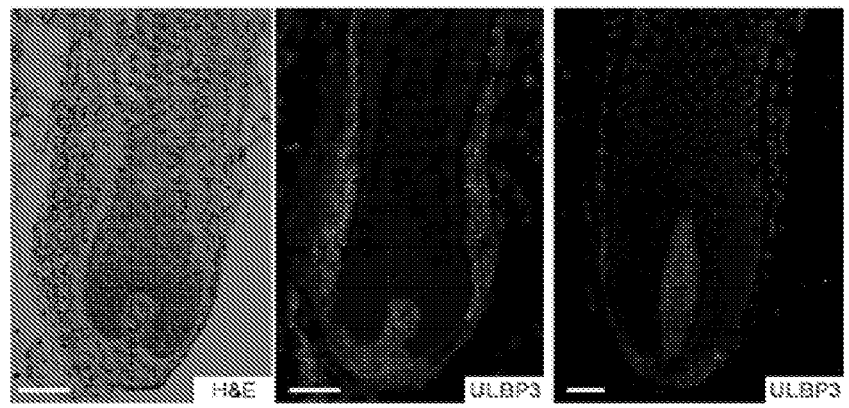
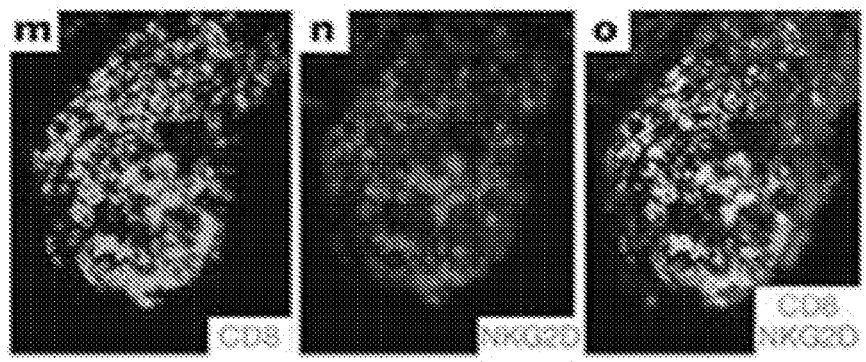
FIG. 11B

All dose groups were statistically significant vs. vehicle at Day 84

A-Spectratyping of cultured
T cells from an AA patient

NKG2D expression
on skin T cells

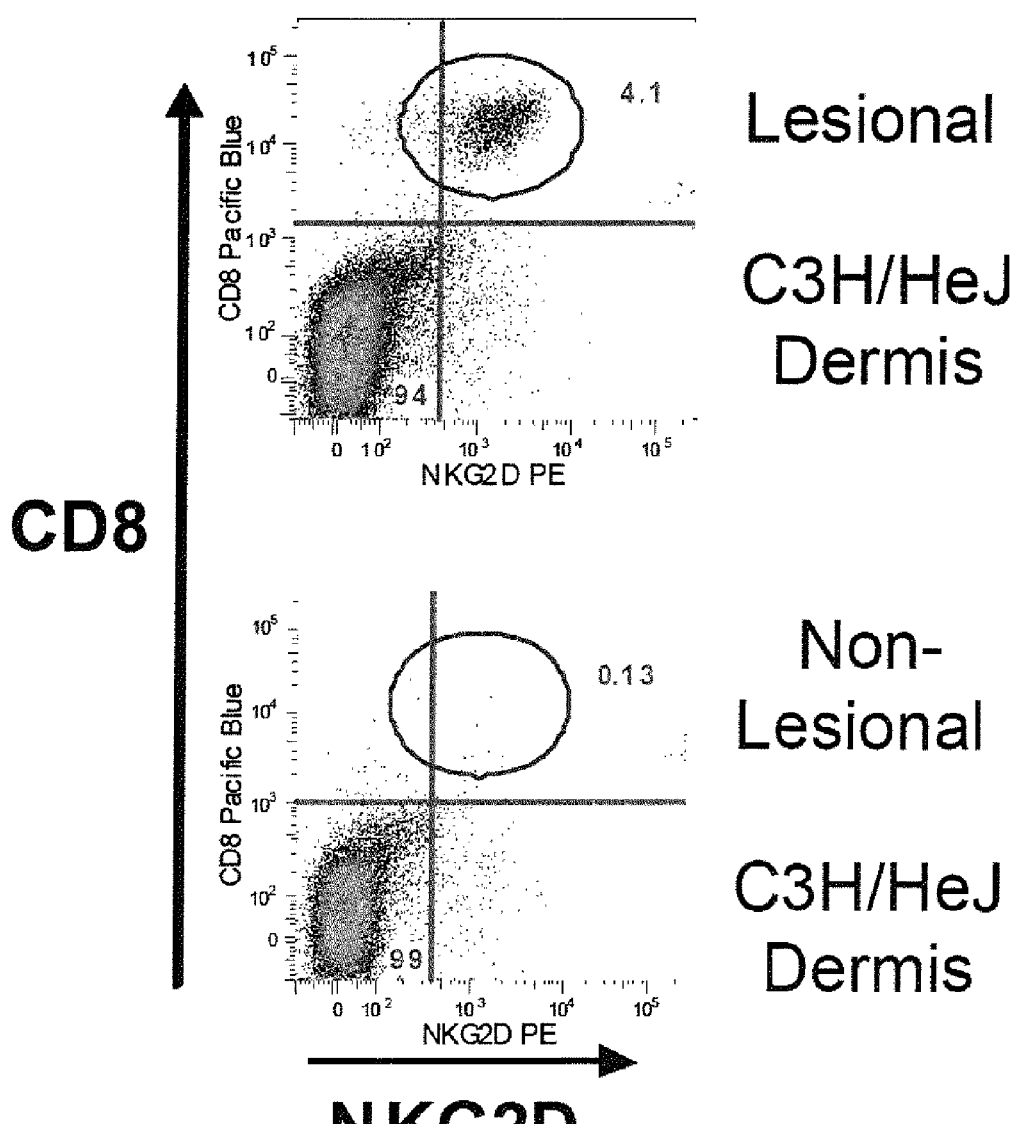
FIG. 43 – CONT.

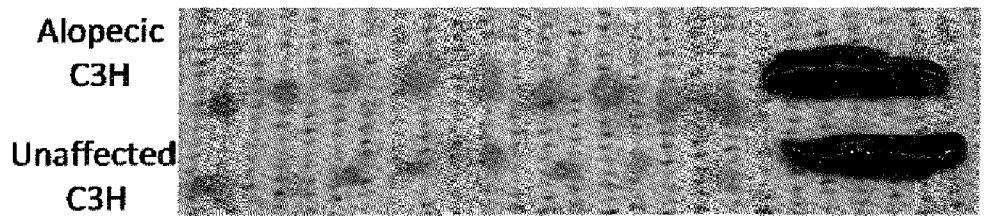
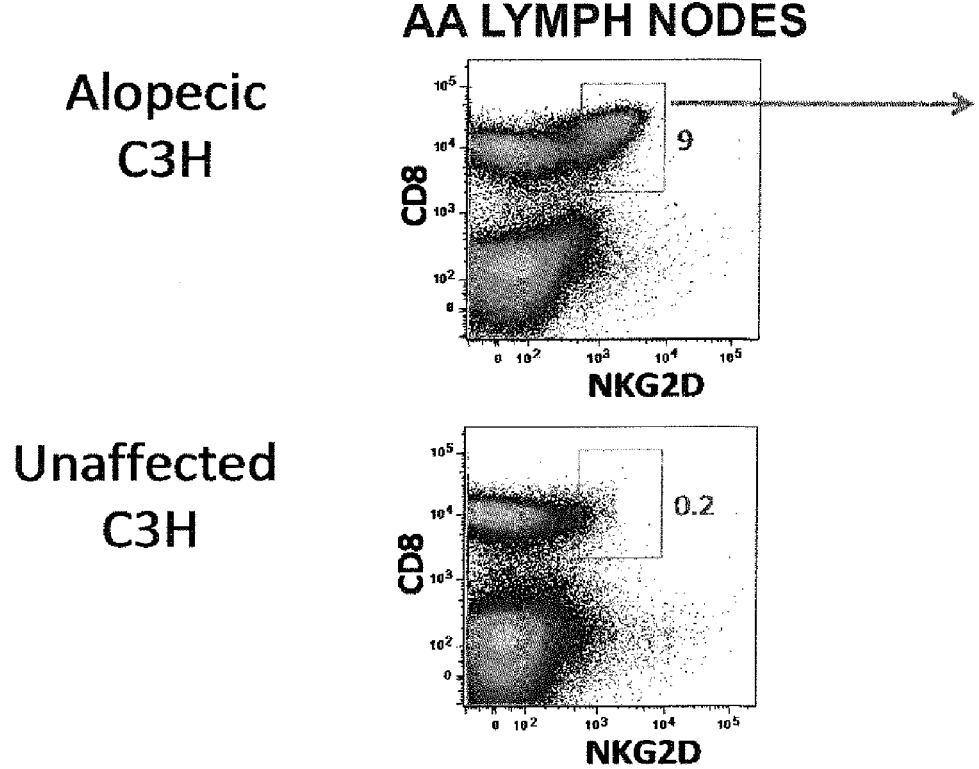
FIG. 45

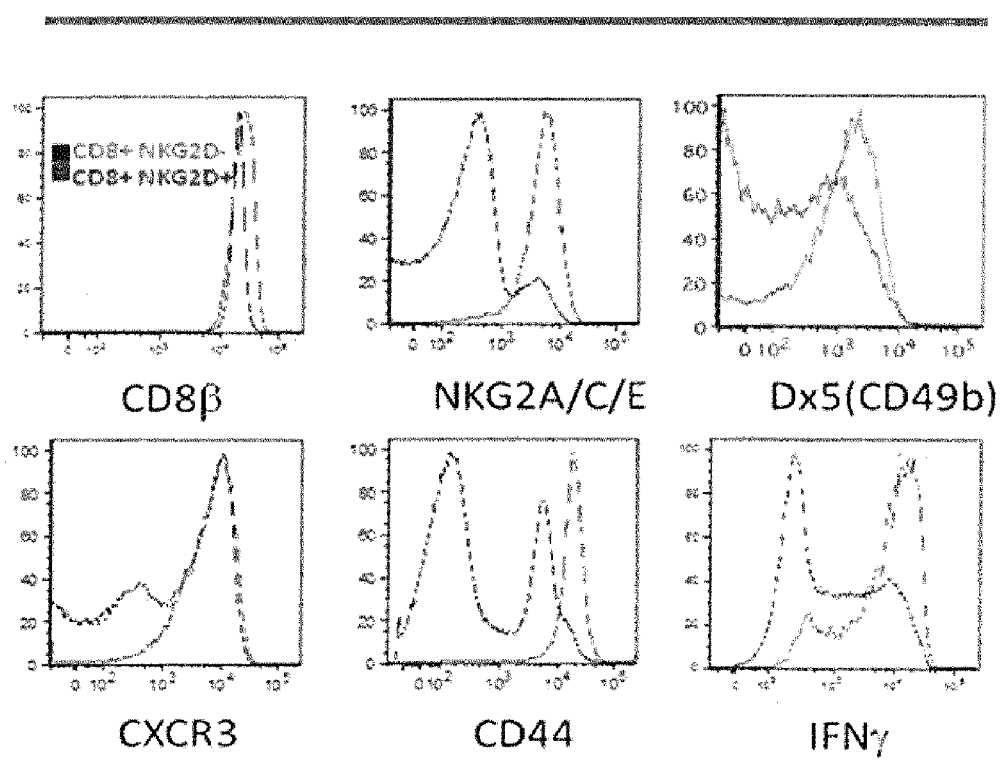
FIG. 45 – CONT.

| JAK 1 and JAK 3 Inhibitors in Clinical Development | | |
|---|---|---|
| DRUG | TARGET | STATUS |
| Tofacitinib | JAK 1,2,3 | RA Phase III |
| | | Psoriasis Phase II |
| | | IBD Phase II |
| VX-509 | JAK3 | RA Phase II |
| R348 | JAK3 | RA Phase I |
| Ruxolitinib | JAK1,2 | FDA approved MF, PV |
| INCB28050 | JAK1,2 | RA Phase II |
| GLPG0634 | JAK1 | RA Phase II |

|  | Prevention Model | Treatment Model | |
|---|---|---|---|
|  | 0 weeks (treatment started at time of graft) | 3-6 weeks (early-onset disease) | 2-3 Months (long-standing disease) |
| Anti-IL15RB Systemic | 100% Positive Response (n=12) | 88% Positive Response (n=8) | n.d. |
| JAK1/2 Inhibitor Systemic | 70 % Positive Response (n=7) | 75% Positive Response (n=8) | n.d. |
| JAK3 Inhibitor Systemic | 100% Positive Response (n=5) | 100% Positive Response (n=7) | n.d. |
| JAK1/2 Inhibitor Topical | n.d. | n.d. | 100% Positive Response (n=6) |
| JAK3 Inhibitor Topical | n.d. | n.d. | 100% Positive Response (n=6) |

Generalized treatment response (whole body) — Anti-IL15RB, JAK1/2 Systemic, JAK3 Systemic Localized treatment response (site of application) — JAK1/2 Topical, JAK3 Topical n.d. – not done
JAK1/2 Inhibitor – ruxolitinib
JAK3 Inhibitor - tofacitinib

FIG. 51

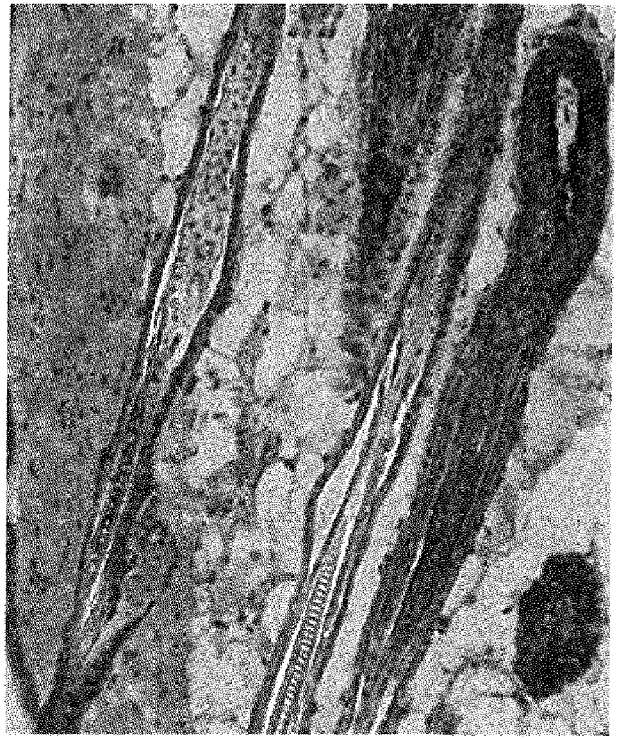
FIG. 53

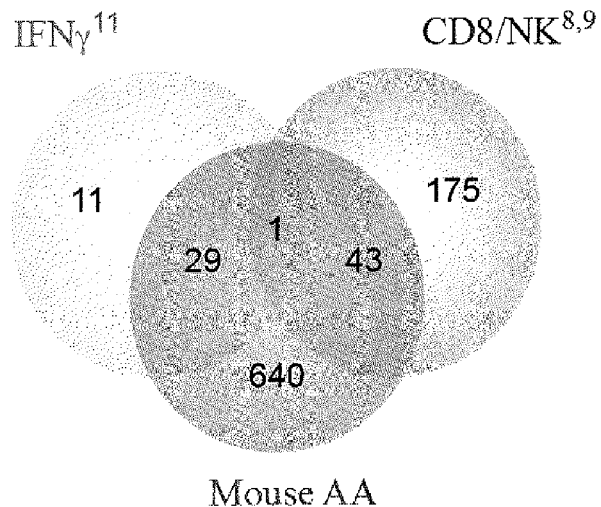

| Signature | Human | Mouse |
|---|---|---|
| CTL | GZMA(3.65x), CD8A(3.04x), GZMB(2.75x), GZMK(2.68x), PRF1(2.30x), LCP2(2.29x), CD2(2.22x), IL7(2.20x), THEMIS(2.14x) | Gzma(56.37x), Cd8a(9.05x), Gzmb(21.74x), Gzmk(2.61x), Prf1(1.62x), Lcp2(2.32x), Cd2(3.32x), Il7(1.99x), Themis(1.84x) |
| IFN | CXCL10(12.37x), CXCL9(9.53x), MMP12(4.04x), IFI44(3.03x), SPP1(2.69x), IRF8(2.64x), PTPRC(2.63x), CCL2(2.54x), RSAD2(2.49x), CCL5(2.36x), IFIT2(2.28x), C1S(2.28x), TLR3(2.25x), IFIT3(2.19x), OAS2(2.12x), GBP1(2.11x), XCL1(2.05x), CCR2(2.04x), CXCL11(1.86x), IFNG(1.57x), STAT1(1.53x), JAK1(0.85x) | Cxcl10(37.58x), Cxcl9(42.30x), Mmp12(10.18x), Ifi44(20.58x), Spp1(10.61x), Irf8(4.44x), Ptprc(2.11x), Ccl2(6.12x), Rsad2(3.20x), Ccl5(27.95x), Ifit2(2.39x), C1s(2.49x), Tlr3(2.34x), Ifit3(4.75x), Oas2(3.97x), Gbp1(17.81x), Xcl1(2.88x), Ccr2(4.66x), Cxcl11(53.33x), Ifng(4.71x), Stat1(14.48x), Jak1(1.40x) |
| IL15 | IL15(2.42x), JAK3(2.10x), IL2RG(2.08x), IL2RB(1.98x), IL15RA(1.60x) | Il15(0.80x), Jak3(1.39x), Il2rg(2.76x), Il2rb(0.92x), Il15ra(1.38x) |
| Other | ST8SIA4(2.94x), GPR65(2.60x), GLIPR1(2.29x), IKZF1(2.29x), CD274(2.17x), SAMD9L(2.16x), LCP1(2.15x), SASH3(2.09x), ATP8B4(2.07x) | St8sia4(1.86x), Gpr65(3.25x), Glipr1(2.33x), Ikzf1(2.34x), Cd274(8.41x), Samd9l(4.37x), Lcp1(2.25x), Sash3(2.76x), Atp8b4(3.44x) |

*FIG. 55A*

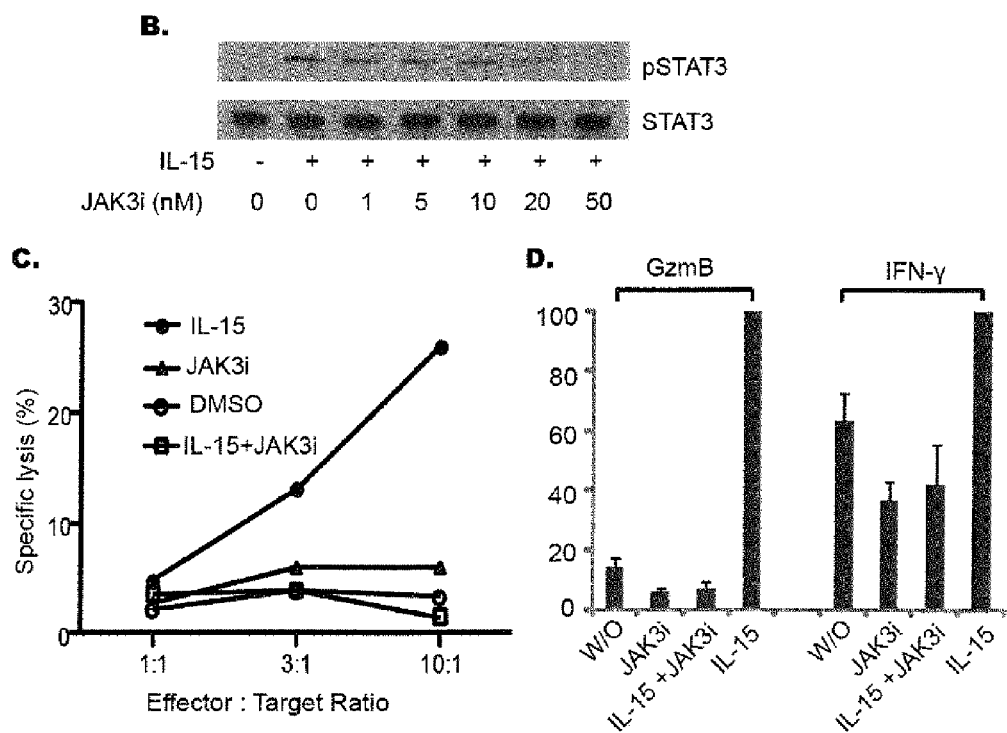
FIGS. 55B-D

Genes overexpressed in D17 compared to D33

| Gene Symbol | Fold Regulation |
|---|---|
| CEBPD | 2.3038 |
| CRP | 12.1061 |
| IL2RA | 3.2916 |
| IL4 | 2.1979 |
| IL6ST | 2.5135 |
| INSR | 2.2396 |
| JAK3 | 2.9987 |
| NR3C1 | 2.4187 |
| OSM | 2.8119 |
| PTPN11 | 3.0958 |
| SOCS3 | 2.7538 |
| STAT5A | 2.0369 |
| STAT5B | 2.0401 |

Genes overexpressed in D23 compared to D33

| Gene Symbol | Fold Regulation |
|---|---|
| CRP | 12.3534 |
| CSF1R | 2.3818 |
| FCER2 | 4.0489 |
| IFNGR1 | 2.6582 |
| IL20 | 4.1697 |
| IL2RA | 2.9377 |
| IL6ST | 2.203 |
| JAK3 | 2.8122 |
| NR3C1 | 2.3099 |
| OAS1 | 3.7125 |
| OSM | 3.0281 |
| PTPN11 | 3.3462 |
| PTPRC | 2.5194 |
| SOCS3 | 2.427 |
| STAT5A | 2.1204 |

Genes overexpressed in D33 compared to D17

| | |
|---|---|
| CCND1 | −3.5852 |
| F2 | −3.0735 |
| LRG1 | −2.139 |
| PRLR | −2.2535 |

Genes overexpressed in D33 compared to D23

| | |
|---|---|
| CCND1 | −2.7924 |
| F2 | −4.5515 |
| JUNB | −3.1623 |
| MPL | −2.5135 |
| PRLR | −2.1067 |

Control Group: D17
Group 1: D23
Group 2: D29
Group 3: D33

FIG. 66-1

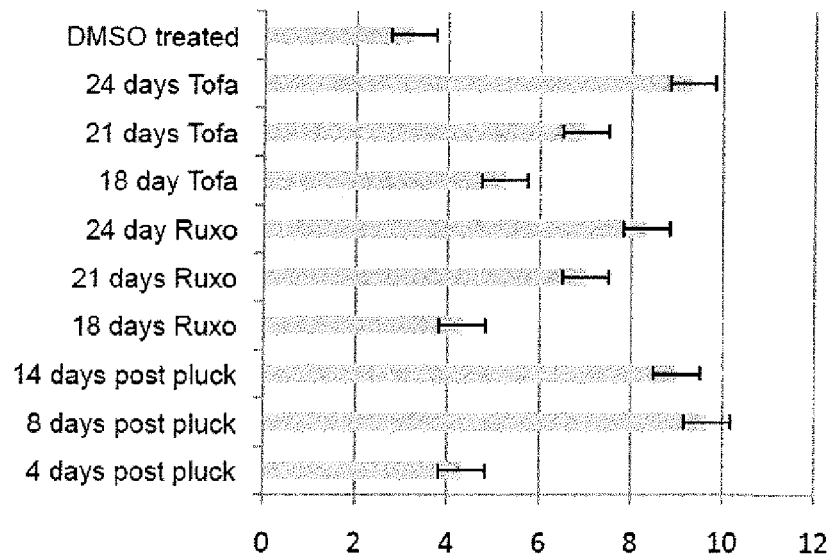
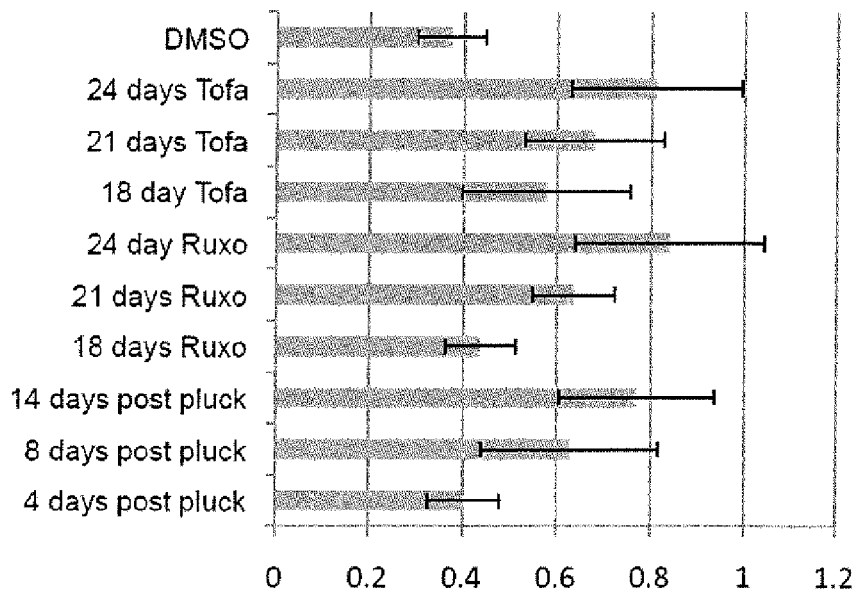
FIG. 71

SEQUENCE LISTING

```
<160> NUMBER OF SEQ ID NOS: 119

<210> SEQ ID NO 1
<211> LENGTH: 1154
<212> TYPE: PRT
<213> ORGANISM: Homo sapiens

<400> SEQUENCE: 1

Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
        35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
        115                 120                 125

His Ser Pro Lys Lys Gln Lys Asn Gly Tyr Glu Lys Lys Lys Ile Pro
    130                 135                 140

Asp Ala Thr Pro Leu Leu Asp Ala Ser Ser Leu Glu Tyr Leu Phe Ala
```

```
145                 150                 155                 160
Gln Gly Gln Tyr Asp Leu Val Lys Cys Leu Ala Pro Ile Arg Asp Pro
                165                 170                 175

Lys Thr Glu Gln Asp Gly His Asp Ile Glu Asn Glu Cys Leu Gly Met
            180                 185                 190

Ala Val Leu Ala Ile Ser His Tyr Ala Met Met Lys Lys Met Gln Leu
        195                 200                 205

Pro Glu Leu Pro Lys Asp Ile Ser Tyr Lys Arg Tyr Ile Pro Glu Thr
    210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

Thr Leu Glu Thr Leu Thr Lys His Tyr Gly Ala Glu Ile Phe Glu Thr
        275                 280                 285

Ser Met Leu Leu Ile Ser Ser Glu Asn Glu Met Asn Trp Phe His Ser
    290                 295                 300

Asn Asp Gly Gly Asn Val Leu Tyr Tyr Glu Val Met Val Thr Gly Asn
305                 310                 315                 320

Leu Gly Ile Gln Trp Arg His Lys Pro Asn Val Val Ser Val Glu Lys
                325                 330                 335

Glu Lys Asn Lys Leu Lys Arg Lys Lys Leu Glu Asn Lys His Lys Lys
            340                 345                 350

Asp Glu Glu Lys Asn Lys Ile Arg Glu Glu Trp Asn Asn Phe Ser Tyr
        355                 360                 365

Phe Pro Glu Ile Thr His Ile Val Ile Lys Glu Ser Val Val Ser Ile
    370                 375                 380

Asn Lys Gln Asp Asn Lys Lys Met Glu Leu Lys Leu Ser Ser His Glu
385                 390                 395                 400

Glu Ala Leu Ser Phe Val Ser Leu Val Asp Gly Tyr Phe Arg Leu Thr
                405                 410                 415

Ala Asp Ala His His Tyr Leu Cys Thr Asp Val Ala Pro Pro Leu Ile
            420                 425                 430

Val His Asn Ile Gln Asn Gly Cys His Gly Pro Ile Cys Thr Glu Tyr
        435                 440                 445

Ala Ile Asn Lys Leu Arg Gln Glu Gly Ser Glu Glu Gly Met Tyr Val
    450                 455                 460

Leu Arg Trp Ser Cys Thr Asp Phe Asp Asn Ile Leu Met Thr Val Thr
465                 470                 475                 480

Cys Phe Glu Lys Ser Glu Gln Val Gln Gly Ala Gln Lys Gln Phe Lys
                485                 490                 495

Asn Phe Gln Ile Glu Val Gln Lys Gly Arg Tyr Ser Leu His Gly Ser
            500                 505                 510

Asp Arg Ser Phe Pro Ser Leu Gly Asp Leu Met Ser His Leu Lys Lys
        515                 520                 525

Gln Ile Leu Arg Thr Asp Asn Ile Ser Phe Met Leu Lys Arg Cys Cys
    530                 535                 540

Gln Pro Lys Pro Arg Glu Ile Ser Asn Leu Leu Val Ala Thr Lys Lys
545                 550                 555                 560

Ala Gln Glu Trp Gln Pro Val Tyr Pro Met Ser Gln Leu Ser Phe Asp
                565                 570                 575
```

```
Arg Ile Leu Lys Lys Asp Leu Val Gln Gly Glu His Leu Gly Arg Gly
            580                 585                 590

Thr Arg Thr His Ile Tyr Ser Gly Thr Leu Met Asp Tyr Lys Asp Asp
        595                 600                 605

Glu Gly Thr Ser Glu Glu Lys Lys Ile Lys Val Ile Leu Lys Val Leu
    610                 615                 620

Asp Pro Ser His Arg Asp Ile Ser Leu Ala Phe Phe Glu Ala Ala Ser
625                 630                 635                 640

Met Met Arg Gln Val Ser His Lys His Ile Val Tyr Leu Tyr Gly Val
                645                 650                 655

Cys Val Arg Asp Val Glu Asn Ile Met Val Glu Glu Phe Val Glu Gly
            660                 665                 670

Gly Pro Leu Asp Leu Phe Met His Arg Lys Ser Asp Val Leu Thr Thr
        675                 680                 685

Pro Trp Lys Phe Lys Val Ala Lys Gln Leu Ala Ser Ala Leu Ser Tyr
    690                 695                 700

Leu Glu Asp Lys Asp Leu Val His Gly Asn Val Cys Thr Lys Asn Leu
705                 710                 715                 720

Leu Leu Ala Arg Glu Gly Ile Asp Ser Glu Cys Gly Pro Phe Ile Lys
                725                 730                 735

Leu Ser Asp Pro Gly Ile Pro Ile Thr Val Leu Ser Arg Gln Glu Cys
            740                 745                 750

Ile Glu Arg Ile Pro Trp Ile Ala Pro Glu Cys Val Glu Asp Ser Lys
        755                 760                 765

Asn Leu Ser Val Ala Ala Asp Lys Trp Ser Phe Gly Thr Thr Leu Trp
    770                 775                 780

Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
            820                 825                 830

Asn Gln Arg Pro Phe Phe Arg Ala Ile Met Arg Asp Ile Asn Lys Leu
        835                 840                 845

Glu Glu Gln Asn Pro Asp Ile Val Ser Glu Lys Lys Pro Ala Thr Glu
    850                 855                 860

Val Asp Pro Thr His Phe Glu Lys Arg Phe Leu Lys Arg Ile Arg Asp
865                 870                 875                 880

Leu Gly Glu Gly His Phe Gly Lys Val Glu Leu Cys Arg Tyr Asp Pro
                885                 890                 895

Glu Gly Asp Asn Thr Gly Glu Gln Val Ala Val Lys Ser Leu Lys Pro
            900                 905                 910

Glu Ser Gly Gly Asn His Ile Ala Asp Leu Lys Lys Glu Ile Glu Ile
        915                 920                 925

Leu Arg Asn Leu Tyr His Glu Asn Ile Val Lys Tyr Lys Gly Ile Cys
    930                 935                 940

Thr Glu Asp Gly Gly Asn Gly Ile Lys Leu Ile Met Glu Phe Leu Pro
945                 950                 955                 960

Ser Gly Ser Leu Lys Glu Tyr Leu Pro Lys Asn Lys Asn Lys Ile Asn
                965                 970                 975

Leu Lys Gln Gln Leu Lys Tyr Ala Val Gln Ile Cys Lys Gly Met Asp
            980                 985                 990
```

| | | | | | | | | | | | | |
|---|---|---|---|---|---|---|---|---|---|---|---|---|
|Tyr|Leu|Gly|Ser|Arg|Gln|Tyr|Val|His|Arg|Asp|Leu|Ala|Ala|Arg|Asn|
| | |995| | | |1000| | | |1005| | | | | |

Val Leu Val Glu Ser Glu His Gln Val Lys Ile Gly Asp Phe Gly
    1010                              1015                          1020

Leu Thr Lys Ala Ile Glu Thr Asp Lys Glu Tyr Tyr Thr Val Lys
    1025                              1030                          1035

Asp Asp Arg Asp Ser Pro Val Phe Trp Tyr Ala Pro Glu Cys Leu
    1040                              1045                          1050

Met Gln Ser Lys Phe Tyr Ile Ala Ser Asp Val Trp Ser Phe Gly
    1055                              1060                          1065

Val Thr Leu His Glu Leu Leu Thr Tyr Cys Asp Ser Asp Ser Ser
    1070                              1075                          1080

Pro Met Ala Leu Phe Leu Lys Met Ile Gly Pro Thr His Gly Gln
    1085                              1090                          1095

Met Thr Val Thr Arg Leu Val Asn Thr Leu Lys Glu Gly Lys Arg
    1100                              1105                          1110

Leu Pro Cys Pro Pro Asn Cys Pro Asp Glu Val Tyr Gln Leu Met
    1115                              1120                          1125

Arg Lys Cys Trp Glu Phe Gln Pro Ser Asn Arg Thr Ser Phe Gln
    1130                              1135                          1140

Asn Leu Ile Glu Gly Phe Glu Ala Leu Leu Lys
    1145                              1150

<210> SEQ ID NO 2
<211> LENGTH: 5053
<212> TYPE: DNA
<213> ORGANISM: Homo sapiens

<400> SEQUENCE: 2

```
tgcagacagt gcgggcctgc gcccagtccc ggctgtcctc gccgcgaccc ctcctcagcc      60
ctgggcgcgc gcacgctggg gccccgcggg gctggccgcc tagcgagcct gccggtcgac     120
cccagccagc gcagcgacgg ggcgctgcct ggcccaggcg cacacggaag tgcgcttctc     180
tgaagtagct ttggaaagta gagaagaaaa tccagtttgc ttcttggaga cactggaca      240 gctgaataaa tgcagtatct aaatataaaa gaggactgca atgccatggc tttctgtgct     300
aaaatgagga gctccaagaa gactgaggtg aacctggagg ccctgagcc aggggtggaa      360 gtgatcttct atctgtcgga cagggagccc tccggctgg gcagtggaga gtacacagca      420
gaggaactgt gcatcagggc tgcacaggca tgccgtatct ctcctctttg tcacaacctc     480
tttgccctgt atgacgagaa caccaagctc tggtatgctc caaatcgcac catcaccgtt     540
gatgacaaga tgtccctccg gctccactac cggatgaggt tctatttcac caattggcat     600
ggaaccaacg acaatgagca gtcagtgtgg cgtcattctc caagaagca gaaaaatggc      660 tacgagaaaa aaaagattcc agatgcaacc cctctccttg atgccagctc actggagtat     720
ctgtttgctc agggacagta tgatttggtg aaatgcctgg ctcctattcg agaccccaag     780
accgagcagg atggacatga tattgagaac gagtgtctag ggatggctgt cctggccatc     840
tcacactatg ccatgataaa gaagatgcag ttgccagaac tgcccaagga catcagctac     900
aagcgatata ttccagaaac attgaataag tccatcagac agaggaacct tctcaccagg     960
atgcggataa ataatgtttt caaggatttc ctaaaggaat taacaacaa gaccatttgt    1020 gacagcagcg tgtccacgca tgacctgaag gtgaaatact ggctaccctt ggaaactttg    1080
acaaaacatt acggtgctga aatatttgag acttccatgt tactgatttc atcagaaaat    1140
```

-continued

```
gagatgaatt ggtttcattc gaatgacggt ggaaacgttc tctactacga agtgatggtg    1200
actgggaatc ttggaatcca gtggaggcat aaaccaaatg ttgtttctgt tgaaaaggaa    1260
aaaaataaac tgaagcggaa aaaactggaa aataaacaca agaaggatga ggagaaaaac    1320
aagatccggg aagagtggaa caattttttct tacttccctg aaatcactca cattgtaata   1380
aaggagtctg tggtcagcat taacaagcag gacaacaaga aaatggaact gaagctctct   1440
tcccacgagg aggccttgtc ctttgtgtcc ctggtagatg ctacttccg gctcacagca    1500 gatgcccatc attacctctg caccgacgtg gcccccccgt tgatcgtcca caacatacag   1560
aatggctgtc atggtccaat ctgtacagaa tacgccatca ataaattgcg gcaagaagga   1620
agcgaggagg ggatgtacgt gctgaggtgg agctgcaccg actttgacaa catcctcatg   1680
accgtcacct gctttgagaa gtctgagcag gtgcagggtg cccagaagca gttcaagaac   1740
tttcagatcg aggtgcagaa gggccgctac agtctgcacg gttcggaccg cagcttcccc   1800
agcttgggag acctcatgag ccacctcaag aagcagatcc tgcgcacgga taacatcagc   1860
ttcatgctaa aacgctgctg ccagcccaag ccccgagaaa tctccaacct gctggtggct   1920
actaagaaag cccaggagtg gcagcccgtc tacccccatga gccagctgag tttcgatcgg   1980
atcctcaaga aggatctggt gcagggcgag caccttggga gaggcacgag aacacacatc   2040
tattctggga ccctgatgga ttacaaggat gacgaaggaa cttctgaaga agaagata   2100 aaagtgatcc tcaaagtctt agaccccagc cacaggata tttcccctggc cttcttcgag   2160 gcagccagca tgatgagaca ggtctcccac aaacacatcg tgtacctcta tggcgtctgt   2220
gtccgcgacg tggagaatat catggtggaa gagtttgtgg aagggggtcc tctggatctc   2280
ttcatgcacc ggaaaagcga tgtccttacc acaccatgga aattcaaagt tgccaaacag   2340
ctggccagtg ccctgagcta cttggaggat aaagacctgg tccatggaaa tgtgtgtact   2400
aaaaacctcc tcctggcccg tgagggcatc gacagtgagt gtggcccatt catcaagctc   2460
agtgaccccg gcatccccat tacgggtgctg tctaggcaag aatgcattga acgaatccca   2520
tggattgctc ctgagtgtgt tgaggactcc aagaacctga gtgtggctgc tgacaagtgg   2580
agctttggaa ccacgctctg ggaaatctgc tacaatggcg agatccccctt gaaagacaag   2640 acgctgattg agaaagagag attctatgaa agccggtgca ggccagtgac accatcatgt   2700
aaggagctgg ctgacctcat gacccgctgc atgaactatg accccaatca gaggcctttc   2760
ttccgagcca tcatgagaga cattaataag cttgaagagc agaatccaga tattgtttca   2820
gaaaaaaaac cagcaactga agtggacccc acacattttg aaaagcgctt cctaaagagg   2880
atccgtgact tgggagaggg ccactttggg aaggttgagc tctgcaggta tgaccccgaa   2940
ggggacaata caggggagca ggtggctgtt aaatctctga gcctgagag tggaggtaac   3000 cacatagctg atctgaaaaa ggaaatcgag atcttaagga acctctatca tgagaacatt   3060
gtgaagtaca aaggaatctg cacagaagac ggaggaaatg gtattaagct catcatggaa   3120
tttctgcctt cgggaagcct taaggaatat cttccaaaga ataagaacaa aataaacctc   3180
aaacagcagc taaatatgc cgttcagatt tgtaagggga tggactattt gggttctcgg   3240
caatacgttc accgggactt ggcagcaaga atgtccttg ttgagagtga acaccaagtg   3300
aaaattggag acttcggttt aaccaaagca attgaaaccg ataaggagta ttacaccgtc   3360
aaggatgacc gggacagccc tgtgttttgg tatgctccag aatgtttaat gcaatctaaa   3420
ttttatattg cctctgacgt ctggtctttt ggagtcactc tgcatgagct gctgacttac   3480
tgtgattcag attctagtcc catggctttg ttcctgaaaa tgataggccc aacccatggc   3540
```

-continued

```
cagatgacag tcacaagact tgtgaatacg ttaaaagaag gaaaacgcct gccgtgccca    3600
cctaactgtc cagatgaggt ttatcaactt atgaggaaat gctgggaatt ccaaccatcc    3660
aatcggacaa gctttcagaa cccttattgaa ggatttgaag cacttttaaa ataagaagca    3720
tgaataacat ttaaattcca cagattatca agtccttctc ctgcaacaaa tgcccaagtc    3780 atttttaaa aatttctaat gaaagaagtt tgtgttctgt ccaaaaagtc actgaactca     3840
tacttcagta catatacatg tataaggcac actgtagtgc ttaatatgtg taaggacttc    3900
ctctttaaat ttggtaccag taacttagtg acacataatg acaaccaaaa tatttgaaag    3960
cacttaagca ctcctccttg tggaaagaat ataccaccat ttcatctggc tagttcacca    4020
tcacaactgc attaccaaaa ggggattttt gaaaacgagg agttgaccaa ataatatct     4080 gaagatgatt gcttttccct gctgccagct gatctgaaat gttttgctgg cacattaatc    4140
atagataaag aaagattgat ggacttagcc ctcaaatttc agtatctata cagtactaga    4200
ccatgcattc ttaaaatatt agataccagg tagtatatat tgtttctgta caaaaatgac    4260
tgtattctct caccagtagg acttaaactt tgtttctcca gtggcttagc tcctgttcct    4320
ttgggtgatc actagcaccc attttttgaga aagctggttc tacatggggg gatagctgtg    4380
gaatagataa tttgctgcat gttaattctc aagaactaag cctgtgccag tgctttccta    4440
agcagtatac cttaatcag aactcattcc cagaacctgg atgctattac acatgctttt    4500
aagaaacgtc aatgtatatc ctttataac tctaccactt tggggcaagc tattccagca    4560
ctggttttga atgctgtatg caaccagtct gaataccaca tacgctgcac tgttcttaga    4620
gggtttccat acttaccacc gatctacaag ggttgatccc tgttttacc atcaatcatc    4680 accctgtggt gcaacacttg aaagacccgg ctagaggcac tatggacttc aggatccact    4740
agacagtttt cagtttgctt ggaggtagct gggtaatcaa aaatgtttag tcattgattc    4800
aatgtgaacg attacggtct ttatgaccaa gagtctgaaa atcttttgt tatgctgttt     4860 agtattcgtt tgatattgtt acttttcacc tgttgagccc aaattcagga ttggttcagt    4920
ggcagcaatg aagttgccat ttaaatttgt tcatagccta catcaccaag gtctctgtgt    4980
caaacctgtg gccactctat atgcactttg tttactcttt atacaaataa atatactaaa    5040
gactttacat gca                                                      5053
```

<210> SEQ ID NO 3
<211> LENGTH: 1132
<212> TYPE: PRT
<213> ORGANISM: Homo sapiens

<400> SEQUENCE: 3

```
Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95
```

-continued

```
Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
            115                 120                 125

Asn Arg Ala Tyr Arg His Gly Ile Ser Arg Gly Ala Glu Ala Pro Leu
        130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
210                 215                 220

Thr Arg Lys Arg Ile Arg Tyr Arg Phe Arg Phe Ile Gln Gln Phe
225                 230                 235                 240

Ser Gln Cys Lys Ala Thr Ala Arg Asn Leu Lys Leu Lys Tyr Leu Ile
            245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
        290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

Ile Asp Gly Tyr Tyr Arg Leu Thr Ala Asp Ala His His Tyr Leu Cys
370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
        435                 440                 445

Tyr Lys His Cys Leu Ile Thr Lys Asn Glu Asn Glu Tyr Asn Leu
450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
```

```
                515                 520                 525
Pro Thr His Met Asn Gln Met Val Phe His Lys Ile Arg Asn Glu Asp
    530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
            580                 585                 590

Ser Phe Phe Glu Ala Ala Ser Met Met Ser Lys Leu Ser His Lys His
        595                 600                 605

Leu Val Leu Asn Tyr Gly Val Cys Val Cys Gly Asp Glu Asn Ile Leu
    610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
            660                 665                 670

Asn Val Cys Ala Lys Asn Ile Leu Leu Ile Arg Glu Glu Asp Arg Lys
        675                 680                 685

Thr Gly Asn Pro Pro Phe Ile Lys Leu Ser Asp Pro Gly Ile Ser Ile
    690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Tyr Leu Pro Tyr Gly Ser Leu Arg Asp Tyr Leu Gln Lys His
    930                 935                 940
```

```
Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro
    1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
    1040                1045                1050

Ser Lys Ser Pro Pro Ala Glu Phe Met Arg Met Ile Gly Asn Asp
    1055                1060                1065

Lys Gln Gly Gln Met Ile Val Phe His Leu Ile Glu Leu Leu Lys
    1070                1075                1080

Asn Asn Gly Arg Leu Pro Arg Pro Asp Gly Cys Pro Asp Glu Ile
    1085                1090                1095

Tyr Met Ile Met Thr Glu Cys Trp Asn Asn Val Asn Gln Arg
    1100                1105                1110

Pro Ser Phe Arg Asp Leu Ala Leu Arg Val Asp Gln Ile Arg Asp
    1115                1120                1125

Asn Met Ala Gly
    1130

<210> SEQ ID NO 4
<211> LENGTH: 5285
<212> TYPE: DNA
<213> ORGANISM: Homo sapiens

<400> SEQUENCE: 4
ctgcaggaag gagagaggaa gaggagcaga aggggggcagc agcggacgcc gctaacggcc      60
tccctcggcg ctgacaggct gggccggcgc ccggctcgct tgggtgttcg cgtcgccact     120
tcggcttctc ggccggtcgg gcccctcggc ccgggcttgc ggcgcgcgtc ggggctgagg     180
gctgctgcgg cgcagggaga ggcctggtcc tcgctgccga gggatgtgag tgggagctga     240
gcccacactg gagggcccccc gagggcccag cctggaggtc gttcagagcc gtgcccgtcc     300
cggggcttcg cagaccttga cccgccgggt aggagccgcc cctgcgggct cgagggcgcg     360
ctctggtcgc ccgatctgtg tagccggttt cagaagcagg caacaggaac aagatgtgaa     420
ctgtttctct tctgcagaaa aagaggctct tcctcctcct cccgcgacgg caaatgttct     480
gaaaaagact ctgcatggga atggcctgcc ttacgatgac agaaatggag ggaacatcca     540
cctcttctat atatcagaat ggtgatattt ctggaaatgc caattctatg aagcaaatag     600
atccagttct tcaggtgtat ctttaccatt cccttgggaa atctgaggca gattatctga     660
cctttccatc tggggagtat gttgcagaag aaatctgtat tgctgcttct aaagcttgtg     720
gtatcacacc tgtgtatcat aatatgtttg ctttaatgag tgaaacagaa aggatctggt     780
atccacccaa ccatgtcttc catatagatg agtcaaccag gcataatgta ctctacagaa     840
taagatttta ctttcctcgt tggtattgca gtggcagcaa cagagcctat cggcatggaa     900
tatctcgagg tgctgaagct cctcttcttg atgactttgt catgtcttac ctctttgctc     960
```

```
agtggcggca tgattttgtg cacggatgga taaaagtacc tgtgactcat gaaacacagg    1020
aagaatgtct tgggatggca gtgttagata tgatgagaat agccaaagaa aacgatcaaa    1080
ccccactggc catctataac tctatcagct acaagacatt cttaccaaaa tgtattcgag    1140
caaagatcca agactatcat attttgacaa ggaagcgaat aaggtacaga tttcgcagat    1200
ttattcagca attcagccaa tgcaaagcca ctgccagaaa cttgaaactt aagtatctta    1260
taaatctgga aactctgcag tctgccttct acacagagaa atttgaagta aaagaacctg    1320
gaagtggtcc ttcaggtgag agattttttg caaccattat aataactgga aacggtggaa    1380
ttcagtggtc aagagggaaa cataaagaaa gtgagacact gacagaacag gatttacagt    1440
tatattgcga ttttcctaat attattgatg tcagtattaa gcaagcaaac caagagggtt    1500
caaatgaaag ccgagttgta actatccata agcaagatgg taaaaatctg gaaattgaac    1560
ttagctcatt aagggaagct ttgtctttcg tgtcattaat tgatggatat tatagattaa    1620
ctgcagatgc acatcattac ctctgtaaag aagtagcacc tccagccgtg cttgaaaata    1680
tacaaagcaa ctgtcatggc ccaattcga tggattttgc cattagtaaa ctgaagaaag    1740
caggtaatca gactggactg tatgtacttc gatgcagtcc taaggacttt aataaatatt    1800
ttttgacttt tgctgtcgag cgagaaaatg tcattgaata taaacactgt ttgattacaa    1860
aaaatgagaa tgaagagtac aacctcagtg ggacaaagaa gaacttcagc agtcttaaag    1920
atcttttgaa ttgttaccag atggaaactg ttcgctcaga caatataatt ttccagttta    1980
ctaaatgctg tcccccaaag ccaaaagata aatcaaaccct tctagtcttc agaacgaatg    2040
gtgtttctga tgtaccaacc tcaccaacat tacagaggcc tactcatatg aaccaaatgg    2100
tgtttcacaa aatcagaaat gaagatttga tatttaatga aagccttggc caaggcactt    2160
ttacaaagat ttttaaaggc gtacgaagag aagtaggaga ctacggtcaa ctgcatgaaa    2220
cagaagttct tttaaaagtt ctggataaag cacacagaaa ctattcagag tctttctttg    2280
aagcagcaag tatgatgagc aagctttctc acaagcattt ggttttaaat tatggagtat    2340
gtgtctgtgg agacgagaat attctggttc aggagtttgt aaaatttgga tcactagata    2400
catatctgaa aaagaataaa aattgtataa atatattatg gaaacttgaa gttgctaaac    2460
agttggcatg ggccatgcat tttctagaag aaaacaccct tattcatggg aatgtatgtg    2520
ccaaaaatat tctgcttatc agagaagaag acaggaagac aggaaatcct cctttcatca    2580
aacttagtga tcctggcatt agtattacag ttttgccaaa ggacattctt caggagagaa    2640
taccatgggt accacctgaa tgcattgaaa atcctaaaaa tttaaatttg gcaacagaca    2700
aatggagttt tggtaccact ttgtgggaaa tctgcagtgg aggagataaa cctctaagtg    2760
ctctggattc tcaaagaaag ctacaatttt atgaagatag gcatcagctt cctgcaccaa    2820
agtgggcaga attagcaaac cttataaata attgtatgga ttatgaacca gatttcaggc    2880
cttctttcag agccatcata cgagatctta acagtttgtt tactccagat tatgaactat    2940
taacagaaaa tgacatgtta ccaaatatga ggataggtgc cctgggttt tctggtgcct    3000 ttgaagaccg ggatcctaca cagtttgaag agagacattt gaaatttcta cagcaacttg    3060
gcaagggtaa ttttgggagt gtggagatgt gccggtatga ccctctacag gacaacactg    3120
gggaggtggt cgctgtaaaa aagcttcagc atagtactga agagcaccta agagactttg    3180
aaagggaaat tgaaatcctg aaatccctac agcatgacaa cattgtaaag tacaagggag    3240
tgtgctacag tgctggtcgg cgtaatctaa aattaattat ggaatattta ccatatggaa    3300
```

```
gtttacgaga ctatcttcaa aaacataaag aacggataga tcacataaaa cttctgcagt    3360
acacatctca gatatgcaag ggtatggagt atcttggtac aaaaaggtat atccacaggg    3420
atctggcaac gagaaatata ttggtggaga acgagaacag agttaaaatt ggagattttg    3480
ggttaaccaa agtcttgcca caagacaaag aatactataa agtaaaagaa cctggtgaaa    3540
gtcccatatt ctggtatgct ccagaatcac tgacagagag caagttttct gtggcctcag    3600
atgtttggag ctttggagtg gttctgtatg aacttttcac atacattgag aagagtaaaa    3660
gtccaccagc ggaatttatg cgtatgattg gcaatgacaa acaaggacag atgatcgtgt    3720
tccatttgat agaactttg aagaataatg gaagattacc aagaccagat ggatgcccag    3780
atgagatcta tatgatcatg acagaatgct ggaacaataa tgtaaatcaa cgcccctcct    3840
ttagggatct agctcttcga gtggatcaaa taagggataa catggctgga tgaaagaaat    3900
gaccttcatt ctgagaccaa agtagattta cagaacaaag ttttatattt cacattgctg    3960
tggactatta ttcatatat cattattata taaatcatga tgctagccag caaagatgtg    4020
aaaatatctg ctcaaaactt tcaaagttta gtaagttttt cttcatgagg ccaccagtaa    4080
aagacattaa tgagaattcc ttagcaagga ttttgtaaga agtttcttaa acattgtcag    4140
ttaacatcac tcttgtctgg caaaagaaaa aaaatagact ttttcaactc agcttttga    4200
gacctgaaaa aattattatg taaattttgc aatgttaaag atgcacagaa tatgtatgta    4260
tagttttac cacagtggat gtataatacc ttggcatctt gtgtgatgtt ttacacacat    4320
gagggctggt gttcattaat actgttttct aattttccca tagttaatct ataattaatt    4380
acttcactat acaaacaaat taagatgttc agataattga ataagtacct ttgtgtcctt    4440
gttcatttat atcgctggcc agcattataa gcaggtgtat acttttagct tgtagttcca    4500
tgtactgtaa atattttca cataaaggga acaaatgtct agttttattt gtataggaaa    4560
tttccctgac cctaaataat acattttgaa atgaaacaag cttacaaaga tataatctat    4620
tttattatgg tttcccttgt atctatttgt ggtgaatgtg ttttttaaat ggaactatct    4680
ccaaattttt ctaagactac tatgaacagt tttctttaa aattttgaga ttaagaatgc    4740
caggaatatt gtcatccttt gagctgctga ctgccaataa cattcttcga tctctgggat    4800
ttatgctcat gaactaaatt taagcttaag ccataaaata gattagattg ttttttaaaa    4860
atggatagct cattaagaag tgcagcaggt taagaatttt ttcctaaaga ctgtatattt    4920
gaggggtttc agaattttgc attgcagtca tagaagagat ttatttcctt tttagagggg    4980
aaatgaggta ataagtaaa aaagtatgct tgttaatttt attcaagaat gccagtagaa    5040
aattcataac gtgtatcttt aagaaaaatg agcatacatc ttaaatctttt tcaattaagt    5100
ataagggggtt gttcgttgtt gtcatttgtt atagtgctac tccactttag acaccatagc    5160
taaaataaaa tatggtgggt tttgtgtgtg tgtgtgtgtg tgtgtgtgtg tgtgtgtgtg    5220
tgttatttat acaaaactta aaatacttgc tgttttgatt aaaaagaaaa tagtttctta    5280
cttta                                                                5285
```

<210> SEQ ID NO 5
<211> LENGTH: 750
<212> TYPE: PRT
<213> ORGANISM: Homo sapiens

<400> SEQUENCE: 5

Met Ser Gln Trp Tyr Glu Leu Gln Gln Leu Asp Ser Lys Phe Leu Glu
1               5                   10                  15

-continued

```
Gln Val His Gln Leu Tyr Asp Asp Ser Phe Pro Met Glu Ile Arg Gln
             20                  25                  30

Tyr Leu Ala Gln Trp Leu Glu Lys Gln Asp Trp Glu His Thr Ala Asn
         35                  40                  45

Asp Val Ser Phe Ala Thr Ile Arg Phe His Asp Leu Leu Ser Gln Leu
 50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
             100                 105                 110

Arg Lys Ile Leu Glu Asn Ala Gln Arg Phe Asn Gln Ala Gln Ser Gly
         115                 120                 125

Asn Ile Gln Ser Thr Val Met Leu Asp Lys Gln Lys Glu Leu Asp Ser
 130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
            180                 185                 190

Lys Gln Glu Gln Leu Leu Leu Lys Met Tyr Leu Met Leu Asp Asn
        195                 200                 205

Lys Arg Lys Glu Val Val His Lys Ile Ile Glu Leu Leu Asn Val Thr
210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
            260                 265                 270

Val Arg Gln Gln Leu Lys Lys Leu Glu Glu Leu Glu Gln Lys Tyr Thr
        275                 280                 285

Tyr Glu His Asp Pro Ile Thr Lys Asn Lys Gln Val Leu Trp Asp Arg
290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
        355                 360                 365

Asn Glu Arg Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu
```

```
                     435                 440                 445
Glu Thr Thr Ser Leu Pro Val Val Ile Ser Asn Val Ser Gln Leu
450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Cys Ala Arg Trp Ala
                485                 490                 495

Gln Leu Ser Glu Val Leu Ser Trp Gln Phe Ser Ser Val Thr Lys Arg
                500                 505                 510

Gly Leu Asn Val Asp Gln Leu Asn Met Leu Gly Glu Lys Leu Leu Gly
                515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
                595                 600                 605

Glu Gly Ala Ile Thr Phe Thr Trp Val Glu Arg Ser Gln Asn Gly Gly
610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
                675                 680                 685

Glu Pro Met Glu Leu Asp Gly Pro Lys Gly Thr Gly Tyr Ile Lys Thr
690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
                740                 745                 750

<210> SEQ ID NO 6
<211> LENGTH: 2353
<212> TYPE: DNA
<213> ORGANISM: Homo sapiens

<400> SEQUENCE: 6
gtgctgtgcg tagctgctcc tttggttgaa tccccaggcc cttgttgggg cacaaggtgg      60
caggatgtct cagtggtacg aacttcagca gcttgactca aaattcctgg agcaggttca     120
ccagctttat gatgacagtt ttcccatgga atcagacag tacctggcac agtggttaga     180
aaagcaagac tgggagcaca ctgccaatga tgtttcattt gccaccatcc gttttcatga     240
cctcctgtca cagctggatg atcaatatag tcgcttttct ttggagaata acttcttgct     300
acagcataac ataaggaaaa gcaagcgtaa tcttcaggat aattttcagg aagacccaat     360
```

```
ccagatgtct atgatcattt acagctgtct gaaggaagaa aggaaaattc tggaaaacgc    420
ccagagattt aatcaggctc agtcggggaa tattcagagc acagtgatgt tagacaaaca    480
gaaagagctt gacagtaaag tcagaaatgt gaaggacaag gttatgtgta tagagcatga    540
aatcaagagc ctggaagatt tacaagatga atatgacttc aaatgcaaaa ccttgcagaa    600
cagagaacac gagaccaatg tgtggcaaaa gagtgatcag aaacaagaac agctgttact    660
caagaagatg tatttaatgc ttgacaataa gagaaaggaa gtagttcaca aaataatgaa    720
gttgctgaat gtcactgaac ttacccagaa tgccctgatt aatgatgaac tagtggagtg    780 gaagcgggaga cagcagagcg cctgtattgg ggggccgccc aatgcttgct tggatcagct    840
gcagaactgg ttcactatag ttgcggagag tctgcagcaa gttcggcagc agcttaaaaa    900
gttggaggaa ttggaacaga aatacaccta cgaacatgac cctatcacaa aaacaaaca    960 agtgttatgg gaccgcacct tcagtctttt ccagcagctc attcagagct cgtttgtggt   1020
ggaaagacag ccctgcatgc caacgcaccc tcagaggccg ctggtcttga agacaggggt   1080
ccagttcact gtgaagttga gactgttggt gaaattgcaa gagctgaatt ataatttgaa   1140
agtcaaagtc ttatttgata agatgtgaaa tgagagaaat acagtaaaag gatttaggaa   1200
gttcaacatt ttgggcacgc acacaaaagt gatgaacatg gaggagtcca ccaatggcag   1260
tctggcggct gaatttcggc acctgcaatt gaaagaacag aaaaatgctg gcaccagaac   1320
gaatgagggt cctctcatcg ttactgaaga gcttcactcc cttagttttg aaacccaatt   1380
gtgccagcct ggtttggtaa ttgacctcga dacgacctct ctgcccgttg tggtgatctc   1440
caacgtcagc cagctcccga gcggttgggc ctccatcctt tggtacaaca tgctggtggc   1500
ggaacccagg aatctgtcct tcttcctgac tccaccatgt gcacgatggg ctcagctttc   1560
agaagtgctg agttggcagt tttcttctgt caccaaaaga ggtctcaatg tggaccagct   1620
gaacatgttg ggagagaagc ttcttggtcc taacgccagc cccgatggtc tcattccgtg   1680
gacgaggttt tgtaaggaaa atataaatga taaaaatttt cccttctggc tttggattga   1740
aagcatccta gaactcatta aaaaacacct gctccctctc tggaatgatg ggtgcatcat   1800
gggcttcatc agcaaggagc gagagcgtgc cctgttgaag gaccagcagc cggggaccct   1860
cctgctgcgg ttcagtgaga gctcccggga agggccatc acattcacat gggtggagcg   1920
gtcccagaac ggaggcgaac ctgacttcca tgcggttgaa ccctacacga agaaagaact   1980
ttctgctgtt actttccctg acatcattcg caattacaaa gtcatggctg ctgagaatat   2040
tcctgagaat ccctgaagt atctgtatcc aaatattgac aaagaccatg cctttggaaa   2100
gtattactcc aggccaaagg aagcaccaga gccaatggaa cttgatggcc taaaggaac    2160 tggatatatc aagactgagt tgatttctgt gtctgaagtt caccttcta gacttcagac    2220 cacagacaac ctgctcccca tgtctcctga ggagtttgac gaggtgtctc ggatagtggg    2280
ctctgtagaa ttcgacagta tgatgaacac agtatagagc atgaattttt ttcatcttct    2340
ctggcgacag ttt                                                       2353
```

<210> SEQ ID NO 7
<211> LENGTH: 851
<212> TYPE: PRT
<213> ORGANISM: Homo sapiens

<400> SEQUENCE: 7

Met Ala Gln Trp Glu Met Leu Gln Asn Leu Asp Ser Pro Phe Gln Asp
1               5                   10                  15

Gln Leu His Gln Leu Tyr Ser His Ser Leu Leu Pro Val Asp Ile Arg
            20                  25                  30
Gln Tyr Leu Ala Val Trp Ile Glu Asp Gln Asn Trp Gln Glu Ala Ala
        35                  40                  45
Leu Gly Ser Asp Asp Ser Lys Ala Thr Met Leu Phe Phe His Phe Leu
    50                  55                  60
Asp Gln Leu Asn Tyr Glu Cys Gly Arg Cys Ser Gln Asp Pro Glu Ser
65                  70                  75                  80
Leu Leu Leu Gln His Asn Leu Arg Lys Phe Cys Arg Asp Ile Gln Pro
                85                  90                  95
Phe Ser Gln Asp Pro Thr Gln Leu Ala Glu Met Ile Phe Asn Leu Leu
            100                 105                 110
Leu Glu Glu Lys Arg Ile Leu Ile Gln Ala Gln Arg Ala Gln Leu Glu
        115                 120                 125
Gln Gly Glu Pro Val Leu Glu Thr Pro Val Glu Ser Gln Gln His Glu
    130                 135                 140
Ile Glu Ser Arg Ile Leu Asp Leu Arg Ala Met Met Glu Lys Leu Val
145                 150                 155                 160
Lys Ser Ile Ser Gln Leu Lys Asp Gln Gln Asp Val Phe Cys Phe Arg
                165                 170                 175
Tyr Lys Ile Gln Ala Lys Gly Lys Thr Pro Ser Leu Asp Pro His Gln
            180                 185                 190
Thr Lys Glu Gln Lys Ile Leu Gln Glu Thr Leu Asn Glu Leu Asp Lys
        195                 200                 205
Arg Arg Lys Glu Val Leu Asp Ala Ser Lys Ala Leu Leu Gly Arg Leu
    210                 215                 220
Thr Thr Leu Ile Glu Leu Leu Pro Lys Leu Glu Glu Trp Lys Ala
225                 230                 235                 240
Gln Gln Gln Lys Ala Cys Ile Arg Ala Pro Ile Asp His Gly Leu Glu
                245                 250                 255
Gln Leu Glu Thr Trp Phe Thr Ala Gly Ala Lys Leu Leu Phe His Leu
            260                 265                 270
Arg Gln Leu Leu Lys Glu Leu Lys Gly Leu Ser Cys Leu Val Ser Tyr
        275                 280                 285
Gln Asp Asp Pro Leu Thr Lys Gly Val Asp Leu Arg Asn Ala Gln Val
    290                 295                 300
Thr Glu Leu Leu Gln Arg Leu Leu His Arg Ala Phe Val Val Glu Thr
305                 310                 315                 320
Gln Pro Cys Met Pro Gln Thr Pro His Arg Pro Leu Ile Leu Lys Thr
                325                 330                 335
Gly Ser Lys Phe Thr Val Arg Thr Arg Leu Leu Val Arg Leu Gln Glu
            340                 345                 350
Gly Asn Glu Ser Leu Thr Val Glu Val Ser Ile Asp Arg Asn Pro Pro
        355                 360                 365
Gln Leu Gln Gly Phe Arg Lys Phe Asn Ile Leu Thr Ser Asn Gln Lys
    370                 375                 380
Thr Leu Thr Pro Glu Lys Gly Gln Ser Gln Gly Leu Ile Trp Asp Phe
385                 390                 395                 400
Gly Tyr Leu Thr Leu Val Glu Gln Arg Ser Gly Ser Gly Lys Gly
                405                 410                 415
Ser Asn Lys Gly Pro Leu Gly Val Thr Glu Glu Leu His Ile Ile Ser
            420                 425                 430
Phe Thr Val Lys Tyr Thr Tyr Gln Gly Leu Lys Gln Glu Leu Lys Thr

-continued

```
            435                 440                 445
Asp Thr Leu Pro Val Ile Ile Ser Asn Met Asn Gln Leu Ser Ile
450                 455                 460
Ala Trp Ala Ser Val Leu Trp Phe Asn Leu Leu Ser Pro Asn Leu Gln
465                 470                 475                 480
Asn Gln Gln Phe Phe Ser Asn Pro Pro Lys Ala Pro Trp Ser Leu Leu
                485                 490                 495
Gly Pro Ala Leu Ser Trp Gln Phe Ser Ser Tyr Val Gly Arg Gly Leu
                500                 505                 510
Asn Ser Asp Gln Leu Ser Met Leu Arg Asn Lys Leu Phe Gly Gln Asn
                515                 520                 525
Cys Arg Thr Glu Asp Pro Leu Leu Ser Trp Ala Asp Phe Thr Lys Arg
530                 535                 540
Glu Ser Pro Pro Gly Lys Leu Pro Phe Trp Thr Trp Leu Asp Lys Ile
545                 550                 555                 560
Leu Glu Leu Val His Asp His Leu Lys Asp Leu Trp Asn Asp Gly Arg
                565                 570                 575
Ile Met Gly Phe Val Ser Arg Ser Gln Glu Arg Leu Leu Lys Lys
                580                 585                 590
Thr Met Ser Gly Thr Phe Leu Leu Arg Phe Ser Glu Ser Ser Glu Gly
                595                 600                 605
Gly Ile Thr Cys Ser Trp Val Glu His Gln Asp Asp Lys Val Leu
610                 615                 620
Ile Tyr Ser Val Gln Pro Tyr Thr Lys Glu Val Leu Gln Ser Leu Pro
625                 630                 635                 640
Leu Thr Glu Ile Ile Arg His Tyr Gln Leu Leu Thr Glu Glu Asn Ile
                645                 650                 655
Pro Glu Asn Pro Leu Arg Phe Leu Tyr Pro Arg Ile Pro Arg Asp Glu
                660                 665                 670
Ala Phe Gly Cys Tyr Tyr Gln Glu Lys Val Asn Leu Gln Glu Arg Arg
                675                 680                 685
Lys Tyr Leu Lys His Arg Leu Ile Val Val Ser Asn Arg Gln Val Asp
690                 695                 700
Glu Leu Gln Gln Pro Leu Glu Leu Lys Pro Glu Pro Glu Leu Glu Ser
705                 710                 715                 720
Leu Glu Leu Glu Leu Gly Leu Val Pro Glu Pro Glu Leu Ser Leu Asp
                725                 730                 735
Leu Glu Pro Leu Leu Lys Ala Gly Leu Asp Leu Gly Pro Glu Leu Glu
                740                 745                 750
Ser Val Leu Glu Ser Thr Leu Glu Pro Val Ile Glu Pro Thr Leu Cys
                755                 760                 765
Met Val Ser Gln Thr Val Pro Glu Pro Asp Gln Gly Pro Val Ser Gln
770                 775                 780
Pro Val Pro Glu Pro Asp Leu Pro Cys Asp Leu Arg His Leu Asn Thr
785                 790                 795                 800
Glu Pro Met Glu Ile Phe Arg Asn Cys Val Lys Ile Glu Glu Ile Met
                805                 810                 815
Pro Asn Gly Asp Pro Leu Leu Ala Gly Gln Asn Thr Val Asp Glu Val
                820                 825                 830
Tyr Val Ser Arg Pro Ser His Phe Tyr Thr Asp Gly Pro Leu Met Pro
                835                 840                 845
Ser Asp Phe
850
```

<210> SEQ ID NO 8
<211> LENGTH: 18648
<212> TYPE: DNA
<213> ORGANISM: Homo sapiens

<400> SEQUENCE: 8

| | | | | | |
|---|---|---|---|---|---|
| tcaagatcag | cctgggcaac | atggcgaaac | cccgtctcta | caataaatac | aaaaaaatta | 60 |
| tcctggcgga | gttatgcacg | ttgtagtccc | aactacctgg | gaggctgagg | cgggagaatc | 120 |
| acctgagcct | gggaggtcga | ggctgcagcg | agccgagatc | ggccgctgca | ttccagcctg | 180 |
| ggtgacagag | cgagaccatg | tctcaaaaaa | taaaaattaa | aaaaaaattg | ttttcattac | 240 |
| ctcagccctc | ctcttcctat | cccaaggcgt | cgaaattccg | gtcccacccc | ttcccatgga | 300 |
| gcccttggcg | tctccaggct | cctcaagcta | gtttcggttc | cgggctcacg | cgcgggttct | 360 |
| cgaaaatcag | ctgtttcagt | cttgggctag | tccactaatt | ggactcctcc | cctcgtagaa | 420 |
| agtgcctact | tgaacttctc | caccaatcgc | tgaagctgca | ggtgtggttt | cggctcagct | 480 |
| tgtcccgccc | tggcggaggg | gcggagttgc | ggcggcgcca | gtgagctcgc | agtctgggaa | 540 |
| gggcttgact | gaatggcagc | cagtgtcggg | gtggcggctg | gaatgggggg | ccgctccgga | 600 |
| cttccgctgc | caactacaag | ggggcgggtc | cgagggggt | tagccgaagt | tgtaggcggg | 660 |
| gcgcgaggtt | ctagtacccg | agctcatact | agggacggga | agtcgcgacc | agagccattg | 720 |
| gagggcgcgg | ggactgcaac | cctaatcagg | tacgggccct | gagagggtgt | gctggggtag | 780 |
| gggtggggt | gagagtgaga | gttcctccga | gggaagggcg | actggcccag | gggttacccc | 840 |
| ctggagaggg | tagcttcctt | ccccagattg | aaataggagc | tgtcgcctgc | tcggtcctcg | 900 |
| atcttcttct | gtccagccta | tctccctaac | cctaatgccc | ctctcccaaa | actgccctgc | 960 |
| agcttccgag | accggaatc | tggcattgtt | atgttggttc | ggtatctgac | gttttttccct | 1020 |
| ctgctctgca | ttattttta | tcttcaccaa | aaaacgatgt | tcaaagatag | ataaatctaa | 1080 |
| aaacaaagat | agataaatct | attacccttg | tttcgtaaaa | agtataagct | actgaaagat | 1140 |
| gaaacgattg | cctaaggtca | cacacaaaat | tcagttcatt | tcagaaaagc | ttcttgagtg | 1200 |
| caaaatatgt | gcctaagaat | gagagataat | gagaaaaaat | tgtttcagcc | ccttaacctc | 1260 |
| agtgtttgca | atccatttgg | ggagaccagg | ttttttgttt | ttgttttcat | atttgaatct | 1320 |
| ttgctgactt | gctcctttaa | tatcagacac | ttaaatcctc | agatgggact | catcatattt | 1380 |
| tttttgagat | ggaatcttca | ctatgttgct | caagcttggt | ctgcaactcc | tggctcaagc | 1440 |
| catcctctcg | tcttgttggg | cctctcgtct | tgtgggcctg | cacaaagtgc | tgggattaca | 1500 |
| ggcatgagcc | attcatgccc | tgggcgcacc | ttggattgcg | atgtgtgtgt | gttgtgaagc | 1560 |
| tttttttttt | ggtatcataa | aagcaataca | gatacatagt | tttaaaaatc | aagcagctac | 1620 |
| taaaagagtt | aaaatgaaaa | tagcccctcc | caatccctcc | cttgttcctg | ctggaggtag | 1680 |
| aaaggcagct | gatgttattc | atgttagtag | aagactctcc | caccccaagc | atttctcttt | 1740 |
| attttgtaat | aaaatcatgt | gacctttta | gaccacaaat | atgcatgaat | tctgttctgt | 1800 |
| taggctcagg | ctgcaacaag | ataagtttca | gtttcctaaa | tagacaccag | ctggcagtga | 1860 |
| gcagggaaca | gtggggagaa | agatgcatgg | gacagcctgc | ttggtgacag | gcaaaaaccg | 1920 |
| gtttgttgtt | cttttagaga | cagagtcttg | ctttgtcacc | caggctggag | tgtagtgatg | 1980 |
| tgatctctgc | ttactgcaac | cctgcctctg | ggtacaagcc | attctcctgc | ctcagcctct | 2040 |
| tgagtagctg | ggattacagg | caacaatttt | aagtgaagtg | aagtttcagg | atctcgagca | 2100 |

```
aagttgtata acctataatc atattcaaga ttcacaggtc ataaacgtgt catattcttg    2160
ggattgagcg acccattgca cagcatttag atgtgcttct agaatggagc tcctccttcc    2220
tatatggagg gcagtttata tggtgtactt acctgaccac caaaaagatt tggctctaaa    2280
aaagcttcag gtggccgggc atggtggttc acccctgtaa tccagcactt tgggaggcag    2340
gtgggcagat cacctgaggt cagaagttca gacagctgga catatggtga aacctcatct    2400
ctactaaaaa tacaaaaatt agactgggca tggtagtggg cgcctgtaat cccagctagt    2460
cgggaggctg aggcaggaga atcccttcaa ctcggacggc agagtttgca gtgaggccga    2520
gatcgtgtca ctgcagtcca gcctgggtga cagagcaaga ctccatctca aaaaagtaa     2580
aaaaaaaaaa aagaaaaaaa aaagcttcag agccagcagg gatcatgctg taataaatac    2640
ttaacatcaa cactgatctt taaatgcttt agcacaatca aatataaata acaaacacac    2700
acataaatgc aaaataaatg aattagggag atagatgaaa taagattgtg gaaatagtaa    2760
tgtttgttaa agctggatgg tgatccttgt actattcact ctactctagt gtgtatttga    2820
aaattaccat taggctggtt atggtggctc atgcctgtta atcccggcat tttggaaggc    2880
tgaggcaggc ggattacttg agctcaggag tttagagtct gcctgggcaa catggcaaaa    2940
tcccatctct acaaaaaatt agctggcatg atggcacact cctgtagtcc cagctccttg    3000
aggggctgag gcagagaatg gcttgaacct gagaggctaa agctgcagtg agccaagatc    3060
atgccactgc actccagcct gggtgaccaa gtgagaccct gtctcaaaaa aaaaaaaaaa    3120
aaaaagaaaa gaaattccc attaaagcac aaaggcccac ttattgaagc tattaaaata    3180
caggttgggg ccggctgggc atcgcgtcac gcctgtaatc ccagcacttt ggaaggccga    3240
ggtaggcgag tcacgagttc aggagatcga gaccatcctg gctaacacgg tgaaacccca    3300
tctctactaa aaatacaaaa aaaaaaatca gccgggcatg gtggcgggag cctatagtcc    3360
cagctactcg ggaggctgag gcaggagaat ggcatgagcc cgggaggcgg agcttgcagt    3420
gagccaaaat cacaccactg cactccagcc tgggcaacag atcgagactc catctgaaga    3480
aaaaaaaaat acaggttggg accacagtgg ctcatgcctg taatcctagt actttgggag    3540
tccgaagtag gtggatcacc tgaggtcagg actttgagac cagcctggcc aacatggcaa    3600
aaccccatct ctactaaaaa atatacaaaa attagctggg cgtggtggtg ggtgcctgta    3660
atcccagcta ctcaggaggc tgaggcagaa gaatcacaac aaccagggg atggtggttg     3720
caatgagcca agatcatctc cacttcactc cggcccaggc aaaagagtga gagtcatctt    3780
aaaaaaaaaa aaaaaaaaaa aaaaaaaata cagattaggc attcctaatc tgaaaaattt    3840
ggctccaaaa tgctccagtc gagcatttcc tttgagtgtc atgtgggtgc tcaaaaagtt    3900
agatttttgg accatttca gatttcagag ttttggatta gggatgctcg actggtaagt    3960
aatcgagata ttccaaaaat ctggacaaat ctgaaatcca aaatgcttgg aatagcagat    4020
actcaactgg tagcactccc tggaagaata tgcaccaaac tgatagcagt ggttaccttc    4080
tggtgaggag gggaaagaac caagattagc agtaggatca acatatattt taatgttttc    4140
tgtatttta ttacttgtat aatttaaaca ttttaaatta gtaataatga acaatcatga      4200
aactatggat gatttagtcc agcaaaatat ccaattggga accctcatcc ttctgcagag    4260
cccaaatggc gcagtgggaa atgctgcaga atcttgacag ccccttttcag gatcagctgc    4320
accagcttta ctcgcacagc ctcctgcctg tggacattcg acagtacttg gctgtctgga    4380
ttgaagacca gaactggtga ggccttcagg aagttggggg aatgaaaaag gtggccttcc    4440
acttctgggc ccccgggatc ctggaatcat taatggcagg aaggggttgg aaagcctcag    4500
```

```
gactacagta acactgcaga gacactaata cttcttattc ctggtcccag gcaggaagct    4560
gcacttggga gtgatgattc caaggctacc atgctattct tccacttctt ggatcagctg    4620
aactatgagt gtggccgttg cagccaggac ccagagtcct tgttgctgca gcacaatttg    4680
cggaaattct gccgggacat tcaggtactt ggaacggttg ggagtgatgg ggtagcactg    4740
ggagcagagc atagaggagt aaggtttgga gaatagaata gtacctggag gtggcaaggg    4800
agacgggaac aaatgtgggg aaaggaggac agagtctgga cttggggaat cactagcaga    4860
gagaagggtt gcatatacgt gacactgttg ggaggatgct atggtgaaaa gacaaagggc    4920
taagaaccCC gaaggaggag gaaatactgt ggacattggt ggggagggtc tagggcaata    4980
ggtcattgag agtggttgaa ttggatcaat cctttctgtt taccttctg ttagcccttt     5040 tcccaggatc ctacccagtt ggctgagatg atctttaacc tccttctgga agaaaaaga    5100 attttgatcc aggctcagag ggcccaattg gtgaggacaa ttcagtggta atgttggaaa    5160
ctcctgaagt agagaggaac catggaaagg actcagggag ttgtctcaga acaggatccc    5220
cccgacatcc tgtggtataa tttcaggcct gaacttaagg catgaaaggc cagagttaaa    5280
acgtgctcag agcctctttt ttcaggaaca aggagagcca gttctcgaaa cacctgtgga    5340
gagccagcaa catgagattg aatcccggat cctggattta agggctatga tggaggttag    5400
tagatgtggt aggagttagg gttgacagtg ttcagcctaa cacctccctg agaagcagcc    5460
tcatcggggt cctctcccct ctgcagaagc tggtaaaatc catcagccaa ctgaaagacc    5520
agcaggatgt cttctgcttc cgatataaga tccaggccaa aggtaggaag cacattgagg    5580
ggctggagaa agataagtgc ctgctgagaa gccggagctg gaagtgaaca ggagaaagct    5640
ccgatgagca gtagtcactg tcagacacac cccactgact acagtcctgc tgccgtgcaa    5700
agctggaatc gtgctttgtg gaggctgagc tggaggtgac agctgagaga cagtaaattg    5760
ttgaggaaat gcatggaaaa ctaacagtgt tttatttgag ggggtgtctg gtccaagatg    5820
accacttcag aatttgcctg gagggtccca caggtgcctg tgctttgctt ggtttccctt    5880
tcttcctccg ccacaaaatt cctccttcct gactctgact gagacccag tcaggaagga    5940 gaggaaagaa cccctggact gactcctgtt cccaccatcc agggaagaca ccctctctgg    6000
acccccatca gaccaaagag cagaagattc tgcaggaaac tctcaatgaa ctggacaaaa    6060
ggagaaaggt gggaggcagc agaacagaac atgtgggcaa caaggacctg aaaaaatgag    6120
ggatgttggg aaccctggta atctagcgct ggcttctttc tttcttcatc cccagttggg    6180
tggtggaggg tgaaagggag agatgctcaa cactcacatt atctctttcc caggaggtgc    6240
tggatgcctc caaagcactg ctaggccgat taactaccct aatcgagcta ctgctgccaa    6300
agttggagga gtgaaggcc cagcagcaaa aagcctgcat cagagctccc attgaccacg     6360
ggttggaaca gctggagaca tggtgagagg taccacccca accctcgtcc tcgccatgcg    6420
ctgtgatttg taagttgcag tgccctgcat atagcaagag atactgttct ctatttgtct    6480
ctgctcccca gaatagagcc ctgctcctg cctgactgca gctctattct gcctcctcag     6540
cctcaccacg cagggaagcc cagaagtccc agtctccttc agggaaagga atgaattaac    6600
ccacaatctg gttttgcttc ttttttttaa tcacccagaa atatatatat atgtattttt    6660 ttttactgc aacgaataca atgacaagaa aggaagggaa ggaaggaagg aagagaaaat     6720 taccattac ctagcttatt aaacaaaaat ggaatcatat tgtccatact attttgaaat     6780 ccatgggtt tttttaagc ttaacagtat tttatatata tatatatata tatatatata    6840
```

```
tatatatata tatatatata tatattttttt tttttttttt tttttttttt ttttgagacg   6900
gagtctctct ctgttccctg gctggcggag cggagtcggc acgatctcag ctcactgcaa   6960
cttccaactc ccacggttca agccaattct cctgtctcag cctcccgagc ctgggattac   7020
caggcacaca ccagcctggc tagttttttt gattttttag tagagacgat gtttctccat   7080
gttggccagg ctggtctcaa actcctgact tcaggtgatc cacccaactt gggctcccaa   7140
agtgctggga ttacaggcgt gacgaccatg cccggccaac agtatattat atttatccat   7200
gttatttctt atgtccacac aacagtcccc tatatggtgg taacataatt taattaatga   7260
actcctattt tcagctattt aggttatttt caatttcttg ttaccttttg ccaggaaacg   7320
tatattttat ggtaattata ttgtgttgta gaaaaatcac tagtctagtc caacttgctt   7380
gaaaaatagc tacttttaa ctattttctc atttaaaaat ttattataat ttagtctttt   7440
agaaatatac caggccaggc atggcgtctc atgcctgtta tcctagtact ttggaaggct   7500
gaggacggag gatcacttca gtcttggggt tgagaccag cccgggaaac ataacaagac   7560
cccatctcta caaaaaaaaa aaattgtttt taattaggca tgtccgacac agtggctcac   7620
acatgtggcc agcactgtgg gaaggccaag gtgggtggat cacttgaggg tcaggagttc   7680
aagaccagcc tggccaatgt ggtgaaaccc catctctact aaaaatacaa aaatttgcca   7740
ggtgtggtgg cgcatgcctg tattcccagc tactcaggag gctaaggcag gaaatcactt   7800
gaactcggag gcagaggttg cagtgagctg tgacaatgcc actgtactcc agcctgggtg   7860
acagagcgag ctccgtctca aaaaaaaaa aaaagatta ggcatggtgg cacacgcctg   7920
tagccctag ctactcagga ggctgaggtg ggaggattgc ttgagcccag gtgttggagg   7980
ctgcagtgag ccatgattat accactgtag tccagcctgg acaacagaac gagaccctgt   8040
ctctaaaagt atatatgtac acataccata atacccagct actgaggagg ctgaggcaga   8100
aagagtgctt gagtccagga gtttgatgtc agcctgagca atatagcaag accctcacct   8160
cttaaaaaaa tttaaagtag attaaaaaaa taccacaatt gctcaggtag attaaaaaaa   8220
taccacaatt gctcaggtag attattgaaa acaggcata tagtacttat ggtacaggac   8280
cagcatgcat gcatgcatgc attgattgat tgattgattg attgattgag acagggtctc   8340
tctctgtctc ccaggctgga gtgcctggcc ttaagtgatc tgcccacctt tgcttcccaa   8400
agtgctgaga ttacaggtgt gagccaccat gtcagctggc gaggcttttt aaaagatagt   8460
tccaagtgtt acagctcttt taggatttgt ctagcaggct ttcaggtttt tgccagaaac   8520
cacccccacc cccaccaaaa aaaaaaaaa aaaaagata tgtacaagtt cccagatagt   8580
gttcccaact gaatctattt ctcatgtgta gtgtatggtt gttttcctgt caccacattg   8640
ctgattatta ttatttttaa ttatagagac agtaaagtac agtagttaaa aatgtgagtt   8700
ggggctgggt gcagtggctc acacctgtaa tcccagcact ttgggaggcc aaggtgggcg   8760
gatcacctga ggtcaggagt tcaagaccag cttggccaac atggcaaaac cccgtctcga   8820
ctaaaaatat atatataa gttagccggg cgtggtggca acattacctg taatcccagc   8880
tactcgggag gccaacaggc aggagaatct cttgaatcca ggaggtggag gttgcagtga   8940
gccagatcac accattgcac tccagcctgg atgacaagag agtgagactg tctaaaaaaa   9000
aaaaacaaag tgtgagttgt acaatgagac tgcctgggat cacatacaag cttcatccct   9060
tactagttgt attgaccta aagcaagtca ctaaccttc tgtgccctcc agttttatca   9120
tctgtaatgt ggggaaaata atagtacctg cctcagaggg ttgttttgag gattaaatgc   9180
attaatatgt ggaaagggct taatataagt tgtacatagc atatgaaaac tgttatgtta   9240
```

```
aatctattag cagttttata tgtgaaaata gctttgattt tcatttcttg gattatgaat    9300
catgttgaat aatcctttat atgcttcctg gattcttttt ttttcttccc cccagtcagt    9360
ttctgactct tctcatattt atagagagat cttggaacct ggatggggga atccaggaaa    9420
ctcatggatt ccttcttcct gaattttatc acccaggttc acagctggag caaagctgtt    9480
gtttcacctg aggcagctgc tgaaggagct gaagggactg agttgcctgg ttagctatca    9540
ggatgaccct ctgaccaaag gggtggacct acgcaacgcc caggtcacag agttgctaca    9600
gcgtctgctc cacaggtcta gaggccaggc aggaaccctg ggggaaagaa ggaacaaggg    9660
aagccattct tacacatact gagctatata ttctctccac acctctctct cctcgagcct    9720
ttgtggtaga aacccagccc tgcatgcccc aaactcccca tcgacccctc atcctcaaga    9780
ctggcagcaa gttcaccgtc cgaacaaggt tggcattcca gaactcattc ccacttcctt    9840
tttccaaccc tgccactgtg tattttctgg ctttacagct actgcccact cttggctttt    9900
tcagtctttc ctgaatctcc ctacctcgtt gatacccat cgtcctcttt ttcaaacacc     9960
tagcctatac aaaagccgac tccgaccaca tttccctata ccccttgact tccccaggct    10020
gctggtgaga ctccaggaag gcaatgagtc actgactgtg gaagtctcca ttgacaggta    10080
aattggagca ggtgaagggt ggccaggaca cgggctgctg gggtggagga gatactcact    10140
cttcacaaca gggccctagg gctatatcct tcctccttcc aatcctacct cacagaaatt    10200
ataattcatt tcttttgttg aacacttact ttgtgacatg cagcatgtca gctactcatt    10260
taattgtcac accaacccca tgaataaact attaccagtg cactgtacaa acaaagatac    10320
aggcttagag agactgatta catctcttct caaggccaca tagctagtga gctcaagtcg    10380
ggtttgaacc gaggtctgtc tgatcccaaa gacgaaactc ctaacttcca tactcttttg    10440
cccaatgatt ttttttaaat ttatttcttt tcaggaatcc tcctcaatta caagggtagg    10500
tgcttgacaa ggacactgca acatctgta cagtgtatga cctgcagaac cggggggattt     10560 gggaaatgga caagggaga tggcgagatc tgaaatggaa gtggaacttc agttttttt       10620 ttttctgctg agttttaca ataattccat tccttgtctc catgtatctt cctcctggaa      10680
cagcttccgg aagttcaaca ttctgacttc aaaccagaaa actttgaccc ccgagaaggg    10740
gcagagtcag ggtttgattt gggactttgg ttacctggta agaatagttt gtgacctatg    10800
cttttattac tattttttatt ttttcgagac ggagtctcac tctgtccccc aggctggagt    10860
gcagtggtgc catcttggct cacaggaacc tccgccctcc ccggttcaag caattcttct    10920
gtctcagcct cctgagtacg tagagctata ggcagcacac caccatgccc ggctaatttt    10980 tgtatttta gtagagatag ggtttcacca tattggtcgg gctggtctcg aactcctgac      11040
ctcaggtgat ccgacccgcc tcagcctccc aaagtgctgg gatcacaggc atgagccacc    11100
atagctggcc tgcttttagt ccaaaggaac aggggttggg ggaagttccc agggcttgag    11160
aggtcttgaa gccaaacagg ggttccaggg agactaggg cccactctg gcattttctc       11220 tccttccctt caattcacag actctggtgg agcaacgttc aggtggttca ggaaagggca    11280
gcaataaggt gagatctgga cagaggactc gaggcagggg gagcttgcca aagagccttc    11340
tgatgactat gtctttgcct gtcccagagg ggccactagg tgtgacagag gaactgcaca    11400
tcatcagctt cacggtcaaa tatacctacc agggtctgaa gcaggagctg aaagtgagtg    11460
aaaatggagg gcaaggagag agaaagcagc tttggaagaa ggcataagaa ggggataaac    11520
agaagcctct tggggagggt tagcactcct ttcctctaac aaatacctgc agctagaaac    11580
```

```
atcacatccc tctctgtgac tcctgtcttc tccccacaca cggacaccct ccctgtggtg    11640
attatttcca acatgaacca gctctcaatt gcctgggctt cagttctctg gttcaatttg    11700
ctcagcccaa accttcaggt aggggagtgg ggccgacagg tcccggcgcg agagcagggg    11760
tgtggaagct tggtgtgata ggttgcttct gagccagcct acactgctcc cacccctgca    11820
gaaccagcag ttcttctcca accccccaa ggcccctgg agcttgctgg gccctgctct      11880
cagttggcag ttctcctcct atgttggccg aggcctcaac tcagaccagc tgagcatgct    11940
gagaaacaag ctgttcggta cagatttcct tttctctcag cctttcccca gccttagtct    12000
tttctgtccc tctgtcctat ctatcccagg acccctggct tccctcacat atctgtggct    12060
atctgtccca cagggcagaa ctgtaggact gaggatccat tattgtcctg ggctgacttc    12120
actaaggtaa ctccctgaat cctgtgggagc tgctggatct agccccacat tccaaatact   12180
ggccttccca cgtgccctcc ttccctacac cagaggcaac tcctcagctt ttgctacctt    12240
tccattcctc cagcgagaga gccctcctgg caagttacca ttctggacat ggctggacaa    12300
aattctggag ttggtacatg accacctgaa ggatctctgg aatgatgggt aaggccttgg    12360
tcacccttcc ctcatgggct tgtgcttccg ggcttgagag tggagtctct gcaccctcac    12420
gtggcaagca gggagagaga gcaaagcacg gtgcaggcca cgtctcctca catttgttaa    12480
gaataataag gccgggtgtg gtggctcaca cctgtaatcc cagcactttg ggaggccgag    12540
gcgggcggat catgaggtca ggagatcgag accatcctgg ctaacacggt gaaaccccgt    12600
ctctactcta aaaatacaaa aaattagccg ggcgtggagg cagacaccct gtagtcccag    12660
ctactcagga ggctgaggca ggaaaatggc gtgaacctgg gagatggagc ttgcagtgag    12720
ccgagattgc gtcactgccc tccagccttg gggtgacgta gcaagactcc gtctcaaaaa    12780
aaaaaaaaaa aaacaaccaa taatagccat aaacagtgtt tttgtgaagc actcctacat    12840
tccagagctt gatgggtgct cttcattaat tctctcatct catccttaca accatgctga    12900
gtggtgggtt ttgccagctt catttcatgt gaggaaactg agtttcagag aagttaaaga    12960
acttacccaa gggacacagt tgatattcaa atccaggcct atgtgactcc aagcccatgc    13020
tctttccacc acactgccta ccaacttgtg tagcatttgg cttttaaaag tgctattcat    13080
gaccaggcac gatggctcac gccttgtaat cccagcattt gggaggccg aggtgggtgg     13140
atcacctgag gtcaggagtt tgagaccagc ctggccaaca tggcgaaacc ccatctctat    13200
taaaaataca aaaattagcc gggtgtggtg gtgggcgcct gtaatcccag ctactcagga    13260
ggctgaggag gagaatcgct tgaatttagg agagaaggtt acagtgagcc aagatcgtgc    13320
cattgcactc cagcctgggt gacagagcaa gactctgtct caaaacaaaa ccaaaaaaaa    13380
gtgctatttg tggccaggcg tggttgctca tgcctgtaat cctagcattt ttggggaggc    13440
tgaggagtac agatcacttg agcccaggag ttcaaaacta ccctgggcca cgtggtgaaa    13500
ccccaaaccc cgtctctacg aaaaatacaa aagttagcca ggatgggtgg tgtgcacctg    13560
tggtcccagc tactctggag gctgagaggt ggggaagatt gcttgagccc gggaggtcga    13620
ggtggcagtg agctgtgatc atgccactat tctccagcct gggtgacaga atacaccctg    13680
tctccctgtc tcccagaaaa aaaaaaaagt gctgttcatc tgtgtgatct cactgaatct    13740
tcgtacttca aaccctcgga aggtggctat tgtcagcaaa gtgaagtgac ttgtaaaaga    13800
taaaaaaaag ctaagtggca gggcttggtc caaagcctgg attccaaacc tgggctgttt    13860
ctccatacaa ggggagcagg gaggcagggg cctgggggg cagggtgttg gcggtgtca      13920
cacgtgacac actgtgctcc agacgcatca tgggctttgt gagtcggagc caggagcgcc    13980
```

```
ggctgctgaa gaagaccatg tctggcacct ttctactgcg cttcagtgaa tcgtcagaag    14040
ggggcattac ctgctcctgg gtggagcacc aggatgatgg tagctgctct gccctgccat    14100
tcccacagcc tctcctttct gcctggctct cctctggccc ctctgcctgc cttgcttcgc    14160
tggctctgaa ctgaatgctc agtggtttgg gactgggcag ccagagagtc agagagctcc    14220
aaggcccggc ctcttccctc aagcccgcct gttcctgcat tcactctcca gacaaggtgc    14280
tcatctactc tgtgcaaccg tacacgaagg aggtgctgca gtcactcccg ctgactgaaa    14340
tcatccgcca ttaccagttg ctcactgagg agaatatacc tgaaaaccca ctgcgcttcc    14400
tctatccccg aatccccggg atgaagcttt tggggtgcta ctaccaggag aaaggtggga    14460
atcgttgaca tacttcattg ctagattgca gagatctacc agacatccat agatcccact    14520
ccttccttta aagcatggga aaactgatat ctagaggaat aagggattc gtccatggga    14580 tactgctggt tactatgggg atgagactgc caggaccatc tgcactaggg gaaaacctca    14640
ggctatatgt ctggcccact gatcttctct gcttcttgta tatgttcctc acagttaatc    14700
tccaggaacg gaggaaatac ctgaaacaca ggctcattgt ggtctctaat agagtgagat    14760
atgaactgtt cattcatcct ccctaatcct tattggctct gcttcagtga atcgtcaaaa    14820
gggggcatta ccttctcctg ggtggagcac caggatgatg gtcagctgct ctgccctgcc    14880
attcccacag cctctccttt ctgccttctc ctaagctgcc cctattccag tctccccagc    14940
cttccctccc tcctagcccc actctagttt tttctggttc tagtctctcc tatctcatat    15000
ttttctgctg ccatccttag gttgtctcca caggggtttc tggataataa tgatcataat    15060
cactggtgtt aaggggtacc tacttgatgc aagcatggag cttttttttt ttccagacag    15120
ggttttgttc tgtcgcccag gctggagtgc agtggtgtga tcctggctca ctgcagcctc    15180
gacctcctga gctcaagcaa tacaggcatg catcaccaaa ctcagctaat ttttttgta    15240 ttttttgtag agatggggtc ttaccatgtt gacgcatcag gctgttctga actcctggac    15300
tcaagcaatc cacccacctt ggcctcccaa aagtcaggga ttacaggcgt gcgaccacac    15360
cccgcatata tatatttttt ttttttttt tttttgagac agggtctctg    15420
ttatccaggc tggagttgca gtggataata tgactacgag ccttgaccta ggggttgaag    15480
caatgctcct gcctcagcca ccaagtgctg agactacagg cacacgccaa tctacactca    15540
atcacactca gctaattttt taaatttttt gtagggatgg ggtatcactg tgtttgccca    15600
ggctggtctt gaactcctgg cctcaagcag tctcctgcct tggcctccca aattgccggg    15660
attgtaggaa tgagccatgg cacttggctg ggggatagaa ttttttttt tttttttt    15720 tttttttttt ttgagacagt ctcactctca ttgcccgggc tggagtgcag tggtgcaatt    15780
tcagctcact gcaacctctg cctcccaggc tcaagcaatt ctcctgcctc agcctataga    15840
gtagctggga ttacaggcga gcgccaccca tgcctggtta attttgttt tttttttgag    15900 acagagtctc gccctgttgc ccaggctgga gtgcagtggc acgatctcag ctcactgcaa    15960
cctctgcctc ccaggctcaa gcaattctcc tgcctcagcc tcctgagtac tgggactaca    16020
agcgcgcaca accaccacac ctggtaattt ttgtatttt agtagagaca gggttttacc    16080
atattggcca ggctggtctc aaactcctga cctcatgatc cgacccacct tggcctccca    16140
aagtgcaggg attacaggcg tgagcctctg cacccggcct aacttttgta tttttagtag    16200
aaacagggtt tcaccatgtt ggccaggctg gtcatgagct cctggcctca agtgatctgc    16260
ccgcctcagc ctcccaaagt gcttggatta caggtgtgag ccacctggcc tgagagttta    16320
```

-continued

```
ttatgcgcca ggcactaggc aaatggtttg catttatttt ctcattttat tgaatctaca    16380
aaatagtcct gtgaagtaaa cactgttact gttttcagct aaggaactgg atttagagta    16440
gtcaagtttt gtacctaagg tacgtggcta atgatacagg tctgttagat tccgtagccc    16500
tgattttaac caccctactg cctctcaaga attactaggt attgttctca tttatagatg    16560
ataaatctga ggctcagaaa agttaggcca cttgcctaag gtcccccagc caggattcaa    16620
actccaggag gcctgattcc aaacccatgc tctttagccc tccgccctac tgccttctta    16680
gactagcttc tgcttattct accattcctg atttcatttg aaccactgag ccctgcccct    16740
ttgtctgtct ttgggtatcc aggcaggtgg atgaactgca acaaccgctg agcttaagc    16800
cagagccaga gctggagtca ttagagctgg aactagggct ggtgccagag ccagagctca    16860
gcctggactt agagccactg ctgaaggcag ggctggatct ggggccagag ctagagtctg    16920
tgctggagtc cactctggag cctgtgatag agcccacact atgcatggta tcacaaacag    16980
tgccagagcc agaccaagga cctgtatcac agccagtgcc agagccagat ttgccctgtg    17040
atctgagaca tttgaacact gagccaatgg aaagtaagtg atgagatgga gtggcacaca    17100
ttccctttcc tacctcttct ccctctccca ttacagaaaa agctgaactc caagctcctc    17160
attggagaga ggtccatctg tgattccttt ttttaggaat tacacatgcc ttccccacc     17220
tccctgctct ttcatcccac aagttccac tcaggctctt cccaggcctt tcctgccatc     17280
ctccctccct tgggctgctg ggttgggaac tcctaactaa gatcggggcc tcactttct    17340
ctctggatta cctagtcttc agaaactgtg taaagattga agaaatcatg ccgaatggtg    17400
acccactgtt ggctggccag aacaccgtgg atgaggttta cgtctcccgc ccagccact    17460
tctacactga tggacccttg atgccttctg acttctagga accacatttc ctctgttctt    17520
ttcatatctc tttgcccttc ctactcctca tagcatgata ttgttctcca aggatgggaa    17580
tcaggcatgt gtcccttcca agctgtgtta actgttcaaa ctcaggcctg tgtgactcca    17640
ttggggtgag aggtgaaagc ataacatggg tacagagggg acaacaatga atcagaacag    17700
atgctgagcc ataggtctaa ataggatcct ggaggctgcc tgctgtgctg ggaggtatag    17760
gggtcctggg ggcaggccag ggcagttgac aggtacttgg agggctcagg gcagtggctt    17820
cttttccagta tggaaggatt tcaacatttt aatagttggt taggctaaac tggtgcatac    17880
tggcattggc cttggtgggg agcacagaca caggatagga ctccatttct ttcttccatt    17940
ccttcatgtc taggataact tgctttcttc tttccttac tcctggctca agccctgaat     18000
ttcttctttt cctgcagggg ttgagagctt tctgccttag cctaccatgt gaaactctac    18060
cctgaagaaa gggatggata ggaagtagac ctcttttttct taccagtctc ctccctact    18120
ctgcccccta agctggctgt acctgttcct ccccataaa atgatcctgc caatctaatg     18180
tgagtgtgaa gtttgcacac tagtttatgc tacctagtct ccactttctc aatgcttagg    18240
agacagatca ctcctggagg ctggggatgg taggattgct ggggattttt ttttttttaa    18300
agagggtctc actctgttgc ccaggctaga gtgcaatggt gcaatcacag ctcactgcag    18360
cctcaacctc ctgggttcaa gcaatcctcc tacctcagcc tcctgggtag ctagcaccat    18420
ggcatcgcca ccatgcccta ttttttttt ttaaagacag gtcttgcta tattgcccag      18480
gctggtcttg aactgggctc aagtgatcct cacgccttgc ctcccaaagt gctgggatta    18540
taggcatgag ccactgtgct tggccaggat ttttttttt tttttttga gatggagttt     18600
ctctcttgtt gtccaggctg gagtgcaatg gtgtgatccg gggaattc                 18648
```

```
<210> SEQ ID NO 9
<211> LENGTH: 19
<212> TYPE: DNA
<213> ORGANISM: Homo sapiens

<400> SEQUENCE: 9
ccacatagct gatctgaaa                                                  19

<210> SEQ ID NO 10
<211> LENGTH: 19
<212> TYPE: DNA
<213> ORGANISM: Homo sapiens

<400> SEQUENCE: 10
cgggaagcct taaggaata                                                  19

<210> SEQ ID NO 11
<211> LENGTH: 19
<212> TYPE: DNA
<213> ORGANISM: Homo sapiens

<400> SEQUENCE: 11
ctgaagagaa gaagataaa                                                  19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acaagaagga tgaggagaa                                                  19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccaagaagac tgaggtgaa                                                  19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagaatacgc catcaataa                                                  19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```
gcacagaaga cggaggaaa                                              19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcgatatatt ccagaaaca                                              19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgagctactt ggaggataa                                              19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gagtgaacac caagtgaaa                                              19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caagaaggat gaggagaaa                                              19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgggaagagt ggaacaatt                                              19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcattaacaa gcaggacaa                                              19

```
<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tttggaaagt agagaagaa                                              19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggaaagtaga gaagaaaat                                              19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggaaccacgc tctgggaaa                                              19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgattgagaa agagagatt                                              19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acattacggt gctgaaata                                              19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gggaagagtg gaacaattt                                              19
```

```
<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agaatatcat ggtggaaga                                                  19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggaaatgtgt gtactaaaa                                                  19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atgagaacat tgtgaagta                                                  19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cacagaagac ggaggaaat                                                  19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctggtggct actaagaaa                                                  19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tctgaagaga agaagataa                                                  19
```

```
<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcaagaatgc attgaacga                                              19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aagaaagatt gatggactt                                              19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aaaataaact gaagcggaa                                              19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atgaggaaat gctgggaat                                              19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aaagaaagat tgatggact                                              19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggacttagcc ctcaaattt                                              19

<210> SEQ ID NO 40
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acactggaca gctgaataa                                                  19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctgaataaat gcagtatct                                                  19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aagaatgcat tgaacgaat                                                  19

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccagtaactt agtgacaca                                                  19

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ttaacaagca ggacaacaa                                                  19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gggagcaggt ggctgttaa                                                  19

<210> SEQ ID NO 46
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aaatcgagat cttaaggaa                                                     19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaaatggta ttaagctca                                                     19

<210> SEQ ID NO 48
<211> LENGTH: 19
<212> TYPE: DNA
<213> ORGANISM: Homo sapiens

<400> SEQUENCE: 48
ccagaatgtt taatgcaat                                                     19

<210> SEQ ID NO 49
<211> LENGTH: 19
<212> TYPE: DNA
<213> ORGANISM: Homo sapiens

<400> SEQUENCE: 49
ggacaagctt tcagaacct                                                     19

<210> SEQ ID NO 50
<211> LENGTH: 19
<212> TYPE: DNA
<213> ORGANISM: Homo sapiens

<400> SEQUENCE: 50
acacataatg acaaccaaa                                                     19

<210> SEQ ID NO 51
<211> LENGTH: 19
<212> TYPE: DNA
<213> ORGANISM: Homo sapiens

<400> SEQUENCE: 51
gcttggaggt agctgggta                                                     19

<210> SEQ ID NO 52
<211> LENGTH: 19
<212> TYPE: DNA
<213> ORGANISM: Homo sapiens

<400> SEQUENCE: 52
cagcagagga actgtgcat                                                     19

<210> SEQ ID NO 53
<211> LENGTH: 19
<212> TYPE: DNA
<213> ORGANISM: Homo sapiens
```

```
<400> SEQUENCE: 53
ccagaaacat tgataagt                                            19

<210> SEQ ID NO 54
<211> LENGTH: 19
<212> TYPE: DNA
<213> ORGANISM: Homo sapiens

<400> SEQUENCE: 54
ctgaaatatt tgagacttc                                           19

<210> SEQ ID NO 55
<211> LENGTH: 19
<212> TYPE: DNA
<213> ORGANISM: Homo sapiens

<400> SEQUENCE: 55
gtacagaata cgccatcaa                                           19

<210> SEQ ID NO 56
<211> LENGTH: 19
<212> TYPE: DNA
<213> ORGANISM: Homo sapiens

<400> SEQUENCE: 56
gcaccgactt tgacaacat                                           19

<210> SEQ ID NO 57
<211> LENGTH: 19
<212> TYPE: DNA
<213> ORGANISM: Homo sapiens

<400> SEQUENCE: 57
gagaagaaga taaaagtga                                           19

<210> SEQ ID NO 58
<211> LENGTH: 19
<212> TYPE: DNA
<213> ORGANISM: Homo sapiens

<400> SEQUENCE: 58
ggaaattcaa agttgccaa                                           19

<210> SEQ ID NO 59
<211> LENGTH: 19
<212> TYPE: DNA
<213> ORGANISM: Homo sapiens

<400> SEQUENCE: 59
agaaagagct tgacagtaa                                           19

<210> SEQ ID NO 60
<211> LENGTH: 19
<212> TYPE: DNA
<213> ORGANISM: Homo sapiens

<400> SEQUENCE: 60
aggaattgga acagaaata                                           19

<210> SEQ ID NO 61
<211> LENGTH: 19
<212> TYPE: DNA
<213> ORGANISM: Homo sapiens
```

```
<400> SEQUENCE: 61
cagcataaca taaggaaaa                                              19

<210> SEQ ID NO 62
<211> LENGTH: 19
<212> TYPE: DNA
<213> ORGANISM: Homo sapiens

<400> SEQUENCE: 62
tcagaaatgt gaaggacaa                                              19

<210> SEQ ID NO 63
<211> LENGTH: 19
<212> TYPE: DNA
<213> ORGANISM: Homo sapiens

<400> SEQUENCE: 63
ggcaaagagt gatcagaaa                                              19

<210> SEQ ID NO 64
<211> LENGTH: 19
<212> TYPE: DNA
<213> ORGANISM: Homo sapiens

<400> SEQUENCE: 64
gcacagtgat gttagacaa                                              19

<210> SEQ ID NO 65
<211> LENGTH: 19
<212> TYPE: DNA
<213> ORGANISM: Homo sapiens

<400> SEQUENCE: 65
agtcatggct gctgagaat                                              19

<210> SEQ ID NO 66
<211> LENGTH: 19
<212> TYPE: DNA
<213> ORGANISM: Homo sapiens

<400> SEQUENCE: 66
gtatagagca tgaaatcaa                                              19

<210> SEQ ID NO 67
<211> LENGTH: 19
<212> TYPE: DNA
<213> ORGANISM: Homo sapiens

<400> SEQUENCE: 67
ggttatgtgt atagagcat                                              19

<210> SEQ ID NO 68
<211> LENGTH: 19
<212> TYPE: DNA
<213> ORGANISM: Homo sapiens

<400> SEQUENCE: 68
gaaaggaagt agttcacaa                                              19

<210> SEQ ID NO 69
<211> LENGTH: 19
<212> TYPE: DNA
```

```
<213> ORGANISM: Homo sapiens

<400> SEQUENCE: 69
gatgtgaatg agagaaata                                                19

<210> SEQ ID NO 70
<211> LENGTH: 19
<212> TYPE: DNA
<213> ORGANISM: Homo sapiens

<400> SEQUENCE: 70
acagagaaca cgagaccaa                                                19

<210> SEQ ID NO 71
<211> LENGTH: 19
<212> TYPE: DNA
<213> ORGANISM: Homo sapiens

<400> SEQUENCE: 71
aagatgtgaa tgagagaaa                                                19

<210> SEQ ID NO 72
<211> LENGTH: 19
<212> TYPE: DNA
<213> ORGANISM: Homo sapiens

<400> SEQUENCE: 72
aggacaaggt tatgtgtat                                                19

<210> SEQ ID NO 73
<211> LENGTH: 19
<212> TYPE: DNA
<213> ORGANISM: Homo sapiens

<400> SEQUENCE: 73
cctgattaat gatgaacta                                                19

<210> SEQ ID NO 74
<211> LENGTH: 19
<212> TYPE: DNA
<213> ORGANISM: Homo sapiens

<400> SEQUENCE: 74
acacaaaagt gatgaacat                                                19

<210> SEQ ID NO 75
<211> LENGTH: 19
<212> TYPE: DNA
<213> ORGANISM: Homo sapiens

<400> SEQUENCE: 75
gcaattgaaa gaacagaaa                                                19

<210> SEQ ID NO 76
<211> LENGTH: 19
<212> TYPE: DNA
<213> ORGANISM: Homo sapiens

<400> SEQUENCE: 76
cgagagctgt ctaggttaa                                                19

<210> SEQ ID NO 77
<211> LENGTH: 19
```

```
<212> TYPE: DNA
<213> ORGANISM: Homo sapiens

<400> SEQUENCE: 77
gaacatgacc ctatcacaa                                               19

<210> SEQ ID NO 78
<211> LENGTH: 19
<212> TYPE: DNA
<213> ORGANISM: Homo sapiens

<400> SEQUENCE: 78
agacaaacag aaagagctt                                               19

<210> SEQ ID NO 79
<211> LENGTH: 19
<212> TYPE: DNA
<213> ORGANISM: Homo sapiens

<400> SEQUENCE: 79
ggacaaggtt atgtgtata                                               19

<210> SEQ ID NO 80
<211> LENGTH: 19
<212> TYPE: DNA
<213> ORGANISM: Homo sapiens

<400> SEQUENCE: 80
tgacaataag agaaaggaa                                               19

<210> SEQ ID NO 81
<211> LENGTH: 19
<212> TYPE: DNA
<213> ORGANISM: Homo sapiens

<400> SEQUENCE: 81
ggaagtagtt cacaaaata                                               19

<210> SEQ ID NO 82
<211> LENGTH: 19
<212> TYPE: DNA
<213> ORGANISM: Homo sapiens

<400> SEQUENCE: 82
tgaaattgca agagctgaa                                               19

<210> SEQ ID NO 83
<211> LENGTH: 19
<212> TYPE: DNA
<213> ORGANISM: Homo sapiens

<400> SEQUENCE: 83
agaaatacac ctacgaaca                                               19

<210> SEQ ID NO 84
<211> LENGTH: 19
<212> TYPE: DNA
<213> ORGANISM: Homo sapiens

<400> SEQUENCE: 84
ccctaaagga actggatat                                               19

<210> SEQ ID NO 85
```

```
<211> LENGTH: 19
<212> TYPE: DNA
<213> ORGANISM: Homo sapiens

<400> SEQUENCE: 85
ggaggaattg gaacagaaa                                                19

<210> SEQ ID NO 86
<211> LENGTH: 19
<212> TYPE: DNA
<213> ORGANISM: Homo sapiens

<400> SEQUENCE: 86
cctaaaggaa ctggatata                                                19

<210> SEQ ID NO 87
<211> LENGTH: 19
<212> TYPE: DNA
<213> ORGANISM: Homo sapiens

<400> SEQUENCE: 87
agcgtaatct tcaggataa                                                19

<210> SEQ ID NO 88
<211> LENGTH: 19
<212> TYPE: DNA
<213> ORGANISM: Homo sapiens

<400> SEQUENCE: 88
tctgaaggaa gaaaggaaa                                                19

<210> SEQ ID NO 89
<211> LENGTH: 19
<212> TYPE: DNA
<213> ORGANISM: Homo sapiens

<400> SEQUENCE: 89
ggaagattta caagatgaa                                                19

<210> SEQ ID NO 90
<211> LENGTH: 19
<212> TYPE: DNA
<213> ORGANISM: Homo sapiens

<400> SEQUENCE: 90
tggcaaagag tgatcagaa                                                19

<210> SEQ ID NO 91
<211> LENGTH: 19
<212> TYPE: DNA
<213> ORGANISM: Homo sapiens

<400> SEQUENCE: 91
agagaaagga agtagttca                                                19

<210> SEQ ID NO 92
<211> LENGTH: 19
<212> TYPE: DNA
<213> ORGANISM: Homo sapiens

<400> SEQUENCE: 92
taatagagtt gctgaatgt                                                19
```

```
<210> SEQ ID NO 93
<211> LENGTH: 19
<212> TYPE: DNA
<213> ORGANISM: Homo sapiens

<400> SEQUENCE: 93
tggaggaatt ggaacagaa                                                  19

<210> SEQ ID NO 94
<211> LENGTH: 19
<212> TYPE: DNA
<213> ORGANISM: Homo sapiens

<400> SEQUENCE: 94
agttgagact gttggtgaa                                                  19

<210> SEQ ID NO 95
<211> LENGTH: 19
<212> TYPE: DNA
<213> ORGANISM: Homo sapiens

<400> SEQUENCE: 95
gataaagatg tgaatgaga                                                  19

<210> SEQ ID NO 96
<211> LENGTH: 19
<212> TYPE: DNA
<213> ORGANISM: Homo sapiens

<400> SEQUENCE: 96
catcgttact gaagagctt                                                  19

<210> SEQ ID NO 97
<211> LENGTH: 19
<212> TYPE: DNA
<213> ORGANISM: Homo sapiens

<400> SEQUENCE: 97
tgaagtatct gtatccaaa                                                  19

<210> SEQ ID NO 98
<211> LENGTH: 19
<212> TYPE: DNA
<213> ORGANISM: Homo sapiens

<400> SEQUENCE: 98
gcacaaggtg gcaggatgt                                                  19

<210> SEQ ID NO 99
<211> LENGTH: 19
<212> TYPE: DNA
<213> ORGANISM: Homo sapiens

<400> SEQUENCE: 99
tgtcacagct ggatgatca                                                  19

<210> SEQ ID NO 100
<211> LENGTH: 19
<212> TYPE: DNA
<213> ORGANISM: Homo sapiens

<400> SEQUENCE: 100
gaaagagctt gacagtaaa                                                  19
```

<210> SEQ ID NO 101
<211> LENGTH: 19
<212> TYPE: DNA
<213> ORGANISM: Homo sapiens

<400> SEQUENCE: 101
tcaagagcct ggaagattt                                                19

<210> SEQ ID NO 102
<211> LENGTH: 19
<212> TYPE: DNA
<213> ORGANISM: Homo sapiens

<400> SEQUENCE: 102
tggaagattt acaagatga                                                19

<210> SEQ ID NO 103
<211> LENGTH: 19
<212> TYPE: DNA
<213> ORGANISM: Homo sapiens

<400> SEQUENCE: 103
atgaactagt ggagtggaa                                                19

<210> SEQ ID NO 104
<211> LENGTH: 19
<212> TYPE: DNA
<213> ORGANISM: Homo sapiens

<400> SEQUENCE: 104
tgagactgtt ggtgaaatt                                                19

<210> SEQ ID NO 105
<211> LENGTH: 19
<212> TYPE: DNA
<213> ORGANISM: Homo sapiens

<400> SEQUENCE: 105
ttgcaagagc tgaattata                                                19

<210> SEQ ID NO 106
<211> LENGTH: 19
<212> TYPE: DNA
<213> ORGANISM: Homo sapiens

<400> SEQUENCE: 106
ggatttagga agttcaaca                                                19

<210> SEQ ID NO 107
<211> LENGTH: 19
<212> TYPE: DNA
<213> ORGANISM: Homo sapiens

<400> SEQUENCE: 107
ggaacttgat ggccctaaa                                                19

<210> SEQ ID NO 108
<211> LENGTH: 19
<212> TYPE: DNA
<213> ORGANISM: Homo sapiens

<400> SEQUENCE: 108
ggaactggat atatcaaga                                                19

<210> SEQ ID NO 109
<211> LENGTH: 1124
<212> TYPE: PRT
<213> ORGANISM: Homo sapiens

<400> SEQUENCE: 109

```
Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Arg Ile Arg Arg Thr Val Arg Arg Ala Leu Arg Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
        275                 280                 285

Leu Gln Pro Phe Cys Asp Phe Pro Glu Ile Val Asp Ile Ser Ile Lys
    290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
            340                 345                 350

Thr Asp Ser Gln His Phe Phe Cys Lys Glu Val Ala Pro Pro Arg Leu
        355                 360                 365

Leu Glu Glu Val Ala Glu Gln Cys His Gly Pro Ile Thr Leu Asp Phe
```

```
                370               375               380
Ala Ile Asn Lys Leu Lys Thr Gly Gly Ser Arg Pro Gly Ser Tyr Val
385               390               395               400

Leu Arg Arg Ser Pro Gln Asp Phe Asp Ser Phe Leu Leu Thr Val Cys
              405               410               415

Val Gln Asn Pro Leu Gly Pro Asp Tyr Lys Gly Cys Leu Ile Arg Arg
              420               425               430

Ser Pro Thr Gly Thr Phe Leu Leu Val Gly Leu Ser Arg Pro His Ser
              435               440               445

Ser Leu Arg Glu Leu Leu Ala Thr Cys Trp Asp Gly Leu His Val
              450               455               460

Asp Gly Val Ala Val Thr Leu Thr Ser Cys Cys Ile Pro Arg Pro Lys
465               470               475               480

Glu Lys Ser Asn Leu Ile Val Val Gln Arg Gly His Ser Pro Pro Thr
              485               490               495

Ser Ser Leu Val Gln Pro Gln Ser Gln Tyr Gln Leu Ser Gln Met Thr
              500               505               510

Phe His Lys Ile Pro Ala Asp Ser Leu Glu Trp His Glu Asn Leu Gly
              515               520               525

His Gly Ser Phe Thr Lys Ile Tyr Arg Gly Cys Arg His Glu Val Val
              530               535               540

Asp Gly Glu Ala Arg Lys Thr Glu Val Leu Leu Lys Val Met Asp Ala
545               550               555               560

Lys His Lys Asn Cys Met Glu Ser Phe Leu Glu Ala Ala Ser Leu Met
              565               570               575

Ser Gln Val Ser Tyr Arg His Leu Val Leu Leu His Gly Val Cys Met
              580               585               590

Ala Gly Asp Ser Thr Met Val Gln Glu Phe Val His Leu Gly Ala Ile
              595               600               605

Asp Met Tyr Leu Arg Lys Arg Gly His Leu Val Pro Ala Ser Trp Lys
              610               615               620

Leu Gln Val Val Lys Gln Leu Ala Tyr Ala Leu Asn Tyr Leu Glu Asp
625               630               635               640

Lys Gly Leu Pro His Gly Asn Val Ser Ala Arg Lys Val Leu Leu Ala
              645               650               655

Arg Glu Gly Ala Asp Gly Ser Pro Pro Phe Ile Lys Leu Ser Asp Pro
              660               665               670

Gly Val Ser Pro Ala Val Leu Ser Leu Glu Met Leu Thr Asp Arg Ile
              675               680               685

Pro Trp Val Ala Pro Glu Cys Leu Arg Glu Ala Gln Thr Leu Ser Leu
              690               695               700

Glu Ala Asp Lys Trp Gly Phe Gly Ala Thr Val Trp Glu Val Phe Ser
705               710               715               720

Gly Val Thr Met Pro Ile Ser Ala Leu Asp Pro Ala Lys Lys Leu Gln
              725               730               735

Phe Tyr Glu Asp Arg Gln Gln Leu Pro Ala Pro Lys Trp Thr Glu Leu
              740               745               750

Ala Leu Leu Ile Gln Gln Cys Met Ala Tyr Glu Pro Val Gln Arg Pro
              755               760               765

Ser Phe Arg Ala Val Ile Arg Asp Leu Asn Ser Leu Ile Ser Ser Asp
              770               775               780

Tyr Glu Leu Leu Ser Asp Pro Thr Pro Gly Ala Leu Ala Pro Arg Asp
785               790               795               800
```

```
Gly Leu Trp Asn Gly Ala Gln Leu Tyr Ala Cys Gln Asp Pro Thr Ile
            805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Gly Asp Asn Thr
            835                 840                 845

Gly Ala Leu Val Ala Val Lys Gln Leu Gln His Ser Gly Pro Asp Gln
            850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
            885                 890                 895

Ser Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
            915                 920                 925

Tyr Ser Ser Gln Ile Cys Lys Gly Met Glu Tyr Leu Gly Ser Arg Arg
            930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
            965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
            995                 1000                1005

Asp Val Trp Ser Phe Gly Val Val Leu Tyr Glu Leu Phe Thr Tyr
            1010                1015                1020

Cys Asp Lys Ser Cys Ser Pro Ser Ala Glu Phe Leu Arg Met Met
            1025                1030                1035

Gly Cys Glu Arg Asp Val Pro Ala Leu Cys Arg Leu Leu Glu Leu
            1040                1045                1050

Leu Glu Glu Gly Gln Arg Leu Pro Ala Pro Pro Ala Cys Pro Ala
            1055                1060                1065

Glu Val His Glu Leu Met Lys Leu Cys Trp Ala Pro Ser Pro Gln
            1070                1075                1080

Asp Arg Pro Ser Phe Ser Ala Leu Gly Pro Gln Leu Asp Met Leu
            1085                1090                1095

Trp Ser Gly Ser Arg Gly Cys Glu Thr His Ala Phe Thr Ala His
            1100                1105                1110

Pro Glu Gly Lys His His Ser Leu Ser Phe Ser
            1115                1120

<210> SEQ ID NO 110
<211> LENGTH: 5449
<212> TYPE: DNA
<213> ORGANISM: Homo sapiens

<400> SEQUENCE: 110
cacacaggaa ggagccgagt gggactttcc tctcgctgcc tcccggctct gcccgccctt      60
cgaaagtcca gggtccctgc cgctaggca agttgcactc atggcacctc caagtgaaga     120
gacgcccctg atccctcagc gttcatgcag cctcttgtcc acggaggctg gtgccctgca     180
tgtgctgctg cccgctcggg gccccgggcc cccccagcgc ctatctttct cctttgggga    240
```

```
ccacttggct gaggacctgt gcgtgcaggc tgccaaggcc agcggcatcc tgcctgtgta    300
ccactccctc tttgctctgg ccacggagga cctgtcctgc tggttccccc cgagccacat    360
cttctccgtg gaggatgcca gcacccaagt cctgctgtac aggattcgct tttacttccc    420
caattggttt gggctggaga agtgccaccg cttcgggcta cgcaaggatt tggccagtgc    480
tatccttgac ctgccagtcc tggagcacct ctttgcccag caccgcagtg acctggtgag    540
tgggcgcctc cccgtgggcc tcagtctcaa ggagcagggt gagtgtctca gcctggccgt    600
gttggacctg cccggatgg cgcgagagca ggcccagcgg ccgggagagc tgctgaagac    660
tgtcagctac aaggcctgcc tacccccaag cctgcgcgac ctgatccagg gcctgagctt    720
cgtgacgcgg aggcgtattc ggaggacggt gcgcagagcc ctgcgccgcg tggccgcctg    780
ccaggcagac cggcactcgc tcatggccaa gtacatcatg gacctggagc ggctggatcc    840
agccggggcc gccgagacct tccacgtggg cctccctggg gcccttggtg ccacgacgg    900
gctgggctg ctccgcgtgg ctggtgacgg cggcatcgcc tggacccagg agaacagga    960
ggtcctccag cccttctgcg actttccaga aatcgtagac attagcatca agcaggcccc   1020
gcgcgttggc ccggccggag agcaccgcct ggtcactgtt accaggacag acaaccagat   1080
tttagaggcc gagttcccag ggctgcccga ggctctgtcg ttcgtggcgc tcgtggacgg   1140
ctacttccgg ctgaccacgg actcccagca cttcttctgc aaggaggtgg caccgccgag   1200
gctgctggag gaagtggccg agcagtgcca cggccccatc actctggact tgccatcaa   1260
caagctcaag actgggggct cacgtcctgg ctcctatgtt ctccgccgca gcccccagga   1320
cttttgacagc ttcctcctca ctgtctgtgt ccagaacccc cttggtcctg attataaggg   1380
ctgcctcatc cggcgcagcc ccacaggaac cttccttctg gttggcctca gccgacccca   1440
cagcagtctt cgagagctcc tggcaacctg ctgggatggg gggctgcacg tagatggggt   1500
ggcagtgacc ctcacttcct gctgtatccc cagacccaaa gaaaagtcca acctgatcgt   1560
ggtccagaga ggtcacagcc cacccacatc atccttggtt cagcccccaat cccaatacca   1620
gctgagtcag atgacatttc acaagatccc tgctgacagc ctggagtggc atgagaacct   1680
gggccatggg tccttcacca agatttaccg gggctgtcgc catgaggtgg tggatgggga   1740
ggcccgaaag acagaggtgc tgctgaaggt catggatgcc aagcacaaga actgcatgga   1800
gtcattcctg gaagcagcga gcttgatgag ccaagtgtcg taccggcatc tcgtgctgct   1860
ccacggcgtg tgcatggctg agacagcac catggtgcag gaatttgtac acctgggggc   1920
catagacatg tatctgcgaa aacgtggcca cctggtgcca gccagctgga agctgcaggt   1980
ggtcaaacag ctggcctacg ccctcaacta tctggaggac aaaggcctgc cccatggcaa   2040
tgtctctgcc cggaaggtgc tcctggctcg gagggggct gatgggagcc cgcccttcat   2100
caagctgagt gaccctgggg tcagccccgc tgtgttaagc ctggagatgc tcaccgacag   2160
gatcccctgg gtggccccg agtgtctccg ggaggcgcag acacttagct tggaagctga   2220
caagtggggc ttcggcgcca cggtctggga agtgtttagt ggcgtcacca tgcccatcag   2280
tgccctggat cctgctaaga aactccaatt ttatgaggac cggcagcagc tgccggcccc   2340
caagtggaca gagctggccc tgctgattca acagtgcatg gcctatgagc cggtccagag   2400
gccctccttc cgagccgtca ttcgtgacct caatagcctc atctcttcag actatgagct   2460
cctctcagac cccacacctg gtgccctggc acctcgtgat gggctgtgga atggtgccca   2520
gctctatgcc tgccaagacc ccacgatctt cgaggagaga cacctcaagt acatctcaca   2580
```

-continued

```
gctgggcaag ggcaactttg gcagcgtgga gctgtgccgc tatgacccgc taggcgacaa  2640
tacaggtgcc ctggtggccg tgaaacagct gcagcacagc gggccagacc agcagaggga  2700 cttttcagcgg gagattcaga tcctcaaagc actgcacagt gatttcattg tcaagtatcg  2760
tggtgtcagc tatggcccgg gccgccgaga cctgcggctg gtcatggagt acctgcccag  2820
cggctgcttg cgcgacttcc tgcagcggca ccgcgcgcgc ctcgatgcca gccgcctcct  2880
tctctattcc tcgcagatct gcaagggcat ggagtacctg gctcccgcc gctgcgtgca  2940 ccgcgacctg gccgcccgaa acatcctcgt ggagagcgag gcacacgtca agatcgctga  3000
cttcggccta gctaagctgc tgccgcttga caaagactac tacgtggtcc gcgagccagg  3060
ccagagcccc attttctggt atgccccga atccctctcg acaacatct tctctcgcca  3120 gtcagacgtc tggagcttcg gggtcgtcct gtacgagctc ttcacctact gcgacaaaag  3180
ctgcagcccc tcggccgagt tcctgcggat gatgggatgt gagcgggatg tccccgccct  3240
ctgccgcctc ttggaactgc tggaggaggg ccagaggctg ccggcgcctc ctgcctgccc  3300
tgctgaggtt cacgagctca tgaagctgtg ctgggcccct agcccacagg accggccatc  3360
attcagcgcc ctgggccccc agctggacat gctgtggagc ggaagccggg ggtgtgagac  3420
tcatgccttc actgctcacc cagagggcaa acaccactcc ctgtccttt catagctcct  3480 gcccgcagac ctctggatta ggtctctgtt gactggctgt gtgaccttag gcccggagct  3540 gccctctct gggcctcaga ggccttatga gggtcctcta cttcaggaac acccccatga  3600
cattgcattt ggggggctc ccgtggcctg tagaatagcc tgtggccttt gcaatttgtt  3660
aaggttcaag acagatgggc atatgtgtca gtggggctct ctgagtcctg gcccaaagaa  3720
gcaaggaacc aaatttaaga ctctcgcatc ttcccaaccc cttaagccct gcccctga  3780 gtttcctttt ctgtctctct cttttattt tttttatttt tattttattt tttgagacag  3840
agcctcgctc tgttacccag ggtggagtgc agtggtgcga tctcggctca gtgcaacctc  3900
tgcttcccag gttcaagcga ttctcctgcc tcagcctccc gagtagctgg gattacaggt  3960
gtgcaccacc acacccggct aattttttt attttaata gagatgaggt ttcaccatga  4020
tggccaggct gatctcgaac tcctaacctc aagtgatcct cccacctcag cctcccaaag  4080
tgttggaata ataggcatga gccactgcac ccaggctttt tttttttaa atttattatt  4140 attattttta agagacagga tcttgctacg ttgcccaggc tggtcttgaa ctcctgggct  4200
acagtgatcc tcctgcctta tcctcctaaa tagctgggac tacagcacct agttttgagt  4260
ttcctgtctt atttccaatg gggacattca tgtagctttt ttttttttt ttttttgag  4320 acggagtctc gctctgtcgc ccaggctgga gtacagtggc gcaatctagg ctcactgcaa  4380
gctccgcctc ctgggttcac accattctct cgcctcagcc tcccaagtag ctgggactac  4440
aggcgcccgc caccacaccc ggctaatttt ttgtattttt agtagagacg gggtttcacc  4500
ttgttagcca ggatggtttc catctcctga cctcgtgatc tgcccgtctc ggcctcccaa  4560
agtgctggga ttacaggcat gagccactgc gcccggccct catgtagctt taaatgtatg  4620
atctgacttc tgctccccga tctctgtttc tctggaggaa gccaaggaca agagcagttg  4680
ctgtggctgg gactctgcct tttaggggag ccgtgtatc tctttgggat cctgaaaggg  4740
ggcaggaaag gctggggtcc cagtccaccc taatggtatc tgagtgtcct agggcttcag  4800
ttttcccacc tgtccaatgg gacccttct gtcctcaccc tacaagggc acaaagggat  4860 gacaccaaac ctggcaggaa cttttcacgc aatcaaggga aggaaggca ttcctggcag  4920 agggaacagc atgccaagcg tgagaaggct cagagtaagg aggttaagag cccaagtatt  4980
```

```
ggagcctaca gttttgcccc ttccatgcag tgtgacagtg ggcaagttcc tttccctctc    5040
tgggtctcag ttctgtcccc tgcaaaatgg tcagagctta ccccttggct gtgcagggtc    5100
aactttctga ctggtgagag ggattctcat gcaggttaag cttctgctgc tcctcctcac    5160
ctgcaaagct tttctgccac ttttgcctcc ttggaaaact cttatccatc tctcaaaact    5220
ccagctacca catccttgca gccttccctc atataccccc actactactg tagccctgtc    5280
cttccctcca gccccactct ggccctgggg ctggggaagt gtctgtgtcc agctgtctcc    5340
cctgacctca gggttccttg ggggctgggc tgaggcctca gtacagaggg ggctctggaa    5400
atgtttgttg actgaataaa ggaattcagt ggaaaaaaaa aaaaaaaa                 5449
```

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 111

His His His His His His
1               5

<210> SEQ ID NO 112
<211> LENGTH: 19
<212> TYPE: DNA
<213> ORGANISM: Homo sapiens

<400> SEQUENCE: 112
tcaactatct ggaggacaa                                                   19

<210> SEQ ID NO 113
<211> LENGTH: 19
<212> TYPE: DNA
<213> ORGANISM: Homo sapiens

<400> SEQUENCE: 113
agacagaggt gctgctgaa                                                   19

<210> SEQ ID NO 114
<211> LENGTH: 19
<212> TYPE: DNA
<213> ORGANISM: Homo sapiens

<400> SEQUENCE: 114
ggtccttcac caagattta                                                   19

<210> SEQ ID NO 115
<211> LENGTH: 19
<212> TYPE: DNA
<213> ORGANISM: Homo sapiens

<400> SEQUENCE: 115
cctggatcct gctaagaaa                                                   19

<210> SEQ ID NO 116
<211> LENGTH: 19
<212> TYPE: DNA
<213> ORGANISM: Homo sapiens

<400> SEQUENCE: 116

-continued

```
cgatcttcga ggagagaca                                           19

<210> SEQ ID NO 117
<211> LENGTH: 19
<212> TYPE: DNA
<213> ORGANISM: Homo sapiens

<400> SEQUENCE: 117
ggacagacaa ccagatttt                                           19

<210> SEQ ID NO 118
<211> LENGTH: 19
<212> TYPE: DNA
<213> ORGANISM: Homo sapiens

<400> SEQUENCE: 118
ggaagctgca ggtggtcaa                                           19

<210> SEQ ID NO 119
<211> LENGTH: 19
<212> TYPE: DNA
<213> ORGANISM: Homo sapiens

<400> SEQUENCE: 119
cccaatacca gctgagtca                                           19
```

METHODS FOR TREATING HAIR LOSS DISORDERS

This application is a continuation-in-part of PCT Application No. PCT/US2011/59029, filed Nov. 2, 2011, which claims the benefit of and priority to U.S. Provisional Application No. 61/409,509, filed Nov. 2, 2010, and this application is also a continuation-in-part of PCT Application No. PCT/US2013/34688, filed Mar. 29, 2013, which claims the benefit of and priority to U.S. Provisional Patent Application No. 61/617,225, filed on Mar. 29, 2012, and U.S. Provisional Patent Application No. 61/645,499, filed on May 10, 2012, and the contents of each of the above-listed applications are hereby incorporated by reference in their entireties.

All patents, patent applications and publications cited herein are hereby incorporated by reference in their entirety. The disclosures of these publications in their entireties are hereby incorporated by reference into this application.

GOVERNMENT INTERESTS

This invention was made with government support under Grant Nos. RO1AR56016 and R21AR061881 awarded by the National Institutes of Health/National Institute of Arthritis and Musculoskeletal and Skin Diseases. The Government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The specification further incorporates by reference the Sequence Listing submitted herewith via EFS on Oct. 21, 2013. Pursuant to 37 C.F.R. §1.52(e)(5), the Sequence Listing text file, identified as 070050.4899_SL.txt, is 110,620 bytes and was created on Aug. 6, 2013. The Sequence Listing, electronically filed herewith, does not extend beyond the scope of the specification and thus does not contain new matter.

BACKGROUND OF THE INVENTION

Alopecia Areata (AA) is one of the most highly prevalent autoimmune diseases affecting over 5 million individuals in the US, and as many as 140 million worldwide AA leads to hair loss due to the collapse of immune privilege of the hair follicle and subsequent autoimmune destruction. AA is a skin disease which leads to hair loss on the scalp and elsewhere. In some severe cases, it can progress to complete loss of hair on the head or body. Although Alopecia Arcata is believed to be caused by autoimmunity, the gene level diagnosis and rationally targeted therapeutics have not been developed. The genetic basis of AA is largely unknown. Its psychological impact on affected patients is devastating, particularly in children.

SUMMARY OF THE INVENTION

An aspect of the invention encompasses a method of treating a hair-loss disorder in a mammalian subject in need thereof, the method comprising administering to the subject an inhibitor of a protein tyrosine kinase (PTK) involved in cytokine signaling. In one embodiment, the inhibitor is a Jak1, Jak2, and/or a Jak3 inhibitor. In one embodiment, the inhibitor is a Stat1 and/or a Stat2 inhibitor. In a further embodiment, the inhibitor is INCB 018424. In one embodiment, the inhibitor is tofacitinib (CP690550). In another embodiment, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis. In one embodiment, the method further comprises determining whether the inhibitor administered induced hair growth in the subject afflicted with a hair loss disorder as compared to the subject's hair growth prior to treatment with the inhibitor. In one embodiment, the inhibitor is an antisense RNA that specifically inhibits expression of the gene that encodes the Jak1 or Jak2 protein; a siRNA that specifically targets the gene that encodes the Jak1 or Jak2 protein; or a small molecule. In one embodiment, the inhibitor is an antibody that specifically binds to a Jak3 protein or a fragment thereof; an antisense RNA or antisense DNA that decreases expression of the gene that encodes the Jak3 protein; an antisense RNA or antisense DNA that decreases expression of the Jak3 protein; a siRNA that specifically targets the Jak3 gene; a small molecule; or a combination thereof. In one embodiment, the small molecule is Janex 1 (WHI-P131), PF-956980, WHI-P154, tofacitinib (CP690550), VX-509, JAK3 Inhibitor IV, NSC114792, or R348. In some embodiments, the antibody specifically binds to a protein comprising SEQ ID NO: 109. In another embodiment, the siRNA is directed to a human nucleic acid sequence comprising SEQ ID NO: 110. In some embodiments, the siRNA directed to a Jak3 gene is any one of the sequences listed in Table 3. In another embodiment, the inhibitor is an antisense RNA that specifically inhibits expression of the gene that encodes the Stat1 or Stat2 protein; a siRNA that specifically targets the gene that encodes the Stat1 or Stat2 protein; or a small molecule. In one embodiment, the small molecule is AG490, CYT387, SB1518, LY3009104, TG101348, BMS-911543, or CEP-701. In another embodiment, the small molecule is WP-1034 (Faderl et al., Anticancer Res. 2005 May-June; 25(3B):1841-50), fludarabine (Fludara, Berlex, Calif.), epigallocatechin-3-gallate (EGCG), or Hyperforin. In another embodiment, the siRNA is directed to a human nucleic acid sequence comprising SEQ ID NOS: 2, 4, 6 or 8. In some embodiments, the siRNA directed to a Jak1 gene is any one of the sequences listed in Table 1. In other embodiments, the siRNA directed to a Stat1 gene is any one of the sequences listed in Table 2. In a further embodiment, the administering comprises a subcutaneous, intra-muscular, intra-peritoneal, or intravenous injection; an infusion; oral, nasal, or topical delivery; or a combination thereof. In some embodiments, the administering occurs daily, weekly, twice weekly, monthly, twice monthly, or yearly. In some embodiments, the inhibitor, e.g., a Jak1, Jak2, and/or Jak3 inhibitor, is administered 1 time per week, 2 times per week, 3 times per week, 4 times per week, 5 times per week, 6 times per week, 7 times per week, 8 times per week, 9 times per week, 10 times per week, 9 times per week, 10 times per week, 11 times per week, 12 times per week, 13 times per week, or 14 times per week. In other embodiments, the subject is administered the inhibitor for at least 1 week, at least 2 weeks, at least 3 weeks, at least 4 weeks, at least 5 weeks, at least 6 weeks, at least 8 weeks, at least 12 weeks, or at least 16 weeks. In some embodiments, the method comprises administering a Jak1/2 inhibitor and a Jak2 inhibitor to the subject. In further embodiments, administering the Jak1/2 inhibitor is conducted simultaneously with the administering of the Jak3 inhibitor. Yet in other embodiments, administering the Jak1/2 inhibitor is conducted sequentially in any order with the administering of the Jak3 inhibitor. In some embodiments, the Jak1/2 inhibitor is INCB 018424, GLPG0634, AG490, CYT387, SB1518, LY3009104 (Baricitinib; INCB28050), AZD1480, TG101348, BMS-911543, or CEP-701.

An aspect of the invention provides for a method for inducing hair growth in a subject where the method comprises administering to the subject an effective amount of an inhibitor of a protein tyrosine kinase (PTK) involved in cytokine signaling. In one embodiment, the inhibitor is a Jak1, Jak2, Jak3, and/or Stat inhibitor. In other embodiments, the inhibitor is INCB 018424. In one embodiment, the inhibitor is a Jak3 inhibitor. In one embodiment, the inhibitor is tofacitinib (CP690550). In some embodiments, the subject is afflicted with a hair-loss disorder. In other embodiments, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis. In some embodiments, the modulating compound can also inhibit hair growth, thus it can be used for treatment of hair growth disorders, such as hypertrichosis. In one embodiment, the method further comprises the step (b) determining whether the inhibitor administered induced hair growth in the subject afflicted with a hair loss disorder as compared to the subject's hair growth prior to treatment with the inhibitor. In one embodiment, the inhibitor is an antisense RNA that specifically inhibits expression of the gene that encodes the Jak1 or Jak2 protein; a siRNA that specifically targets the gene that encodes the Jak1 or Jak2 protein; or a small molecule. In one embodiment, the inhibitor is an antibody that specifically binds to a Jak3 protein or a fragment thereof; an antisense RNA or antisense DNA that decreases expression of the gene that encodes the Jak3 protein; an antisense RNA or antisense DNA that decreases expression of the Jak3 protein; a siRNA that specifically targets the Jak3 gene; a small molecule; or a combination thereof. In one embodiment, the small molecule is Janex 1 (WHI-P131), PF-956980, WHI-P154, tofacitinib (CP690550), VX-509, JAK3 Inhibitor IV, NSC114792, or R348. In some embodiments, the antibody specifically binds to a protein comprising SEQ ID NO: 109. In another embodiment, the siRNA is directed to a human nucleic acid sequence comprising SEQ ID NO: 110. In some embodiments, the siRNA directed to a Jak3 gene is any one of the sequences listed in Table 3. In another embodiment, the inhibitor is an antisense RNA that specifically inhibits expression of the gene that encodes the Stat1 or Stat2 protein; a siRNA that specifically targets the gene that encodes the Stat1 or Stat2 protein; or a small molecule. In one embodiment, the small molecule is AG490, CYT387, SB1518, LY3009104, TG101348, BMS-911543, or CEP-701. In another embodiment, the small molecule is WP-1034 (Faded et al., Anticancer Res. 2005 May-June; 25(3B):1841-50), fludarabine (Fludara, Berlex, Calif.), epigallocatechin-3-gallate (EGCG), or Hyperforin. In another embodiment, the siRNA is directed to a human nucleic acid sequence comprising SEQ ID NOS: 2, 4, 6 or 8. In some embodiments, the siRNA directed to a Jak1 gene is any one of the sequences listed in Table 1. In other embodiments, the siRNA directed to a Stat1 gene is any one of the sequences listed in Table 2. In a further embodiment, the administering comprises a subcutaneous, intra-muscular, intra-peritoneal, or intravenous injection; an infusion; oral, nasal, or topical delivery; or a combination thereof. In some embodiments, the administering occurs daily, weekly, twice weekly, monthly, twice monthly, or yearly. In some embodiments, the inhibitor, e.g., a Jak1, Jak2, and/or Jak3 inhibitor, is administered 1 time per week, 2 times per week, 3 times per week, 4 times per week, 5 times per week, 6 times per week, 7 times per week, 8 times per week, 9 times per week, 10 times per week, 9 times per week, 10 times per week, 11 times per week, 12 times per week, 13 times per week, or 14 times per week. In other embodiments, the subject is administered the inhibitor for at least 1 week, at least 2 weeks, at least 3 weeks, at least 4 weeks, at least 5 weeks, at least 6 weeks, at least 8 weeks, at least 12 weeks, or at least 16 weeks. In some embodiments, the method comprises administering a Jak1/2 inhibitor and a Jak2 inhibitor to the subject. In further embodiments, administering the Jak1/2 inhibitor is conducted simultaneously with the administering of the Jak3 inhibitor. Yet in other embodiments, administering the Jak1/2 inhibitor is conducted sequentially in any order with the administering of the Jak3 inhibitor. In some embodiments, the Jak1/2 inhibitor is INCB 018424, GLPG0634, AG490, CYT387, SB1518, LY3009104 (Baricitinib; INCB28050), AZD1480, TG101348, BMS-911543, or CEP-701.

BRIEF DESCRIPTION OF THE FIGURES

In FIG. 1B, the patient is in regrowth phase. For patients with alopecia universalis, there is a complete lack of body hair and scalp hair (FIG. 1C), while patients with alopecia totalis only lack scalp hair (FIG. 1D). In FIG. 1D, hair regrowth is observed in the parietal region, while no regrowth in either occipital or temporal regions is evident.

FIG. 4B show the results from FACS analysis that NKG2D bearing CD8 and Th1 cells are expanded in murine AA cutaneous lymph nodes.

FIG. 8A shows linkage analysis in families. FIG. 8B shows association analysis in a population cohort.

FIGS. 11A-B show that AA is caused by a "swarm of bees": Killer CD8 T cells attracted by NKG2DL. FIG. 11A shows "pre-2010" swarm of bees in AA. FIG. 11B shows "2012" identification of bees ((m) staining of CD8; (n) staining of NKG2D; and (o) colocalization of NKG2D and CD8).

FIG. 21A: Human: T cells obtained from T cell crawl-outs from AA skin biopsies are uniformly CD8+NKG2D+ and produce IFN-γ upon PMA/Ionomycin stimulation. FIG. 21B: Mouse: C3H/HeJ stimulated lymph node cells from alopecic mice contain 3 times more IFN-γ producing CD8 and CD4 T cells than unaffected mice.

FIG. 45 shows plots depicting that CD8+NKG2D+ Cytotoxic T Cells are IFN-gamma producing cells bearing NK-type receptors.

FIG. 51 shows a summary of pre-clinical studies in alopecia C3H/HeJ mice.

FIG. 53 shows photomicrographs depicting that treatment with Jak3 inhibitor tofacitinib normalizes inflammatory infiltrate.

FIG. 55A shows transcriptional profiling of human and mouse AA skin that reveals evidence for IFNγ, cytotoxic T cells and the IL15 pathway as central to disease pathogenesis, inviting therapeutic targeting using Jak inhibitors. FIG. 24A is a Venn diagram showing overlap of gene list from whole alopecic C3H/HeJ mouse skin (compared with unaffected C3H/HeJ skin) with IFNγ-induced gene expression[11] and CD8 and NK cell gene signatures from ImmGen consortium publications[8,9] (Top panel). Representative list of differentially expressed genes among human AA and C3H/HeJ AA reveals shared inflammatory pathways, in particular IFNγ pathway genes, genes representative of CD8 effectors, and a striking IL-15 pathway signature (Bottom panel).

FIGS. 55B-D show effect of treatment with a Jak3 inhibitor (JAK3i). FIG. 24B, JAK3i (tofacitinib) inhibits IL-15-induced Stat3 activation in T cells. FIG. 24C, JAK3i inhibits IL-15-induced LAK cell cytotoxic function. FIG. 24D, JAK3i inhibits IL-15-induced LAK cell Granzyme B expression and IFNγ production.

FIG. 71 are plots showing JAK-STAT in hair cycle: a drug treatment in mice. Quantification of number and thickness of hair follicles in skin treated with the Jak3 inhibitor, Tofacitinib, and a Jak1/2 inhibitor Ruxolitinib, as compared to plucked skin and vehicle-treated (DMSO). Both the numbers of follicles as well as the thickness of follicles is greater in drug treated skin than in vehicle treated mice.

DETAILED DESCRIPTION OF THE INVENTION

Figure 1:
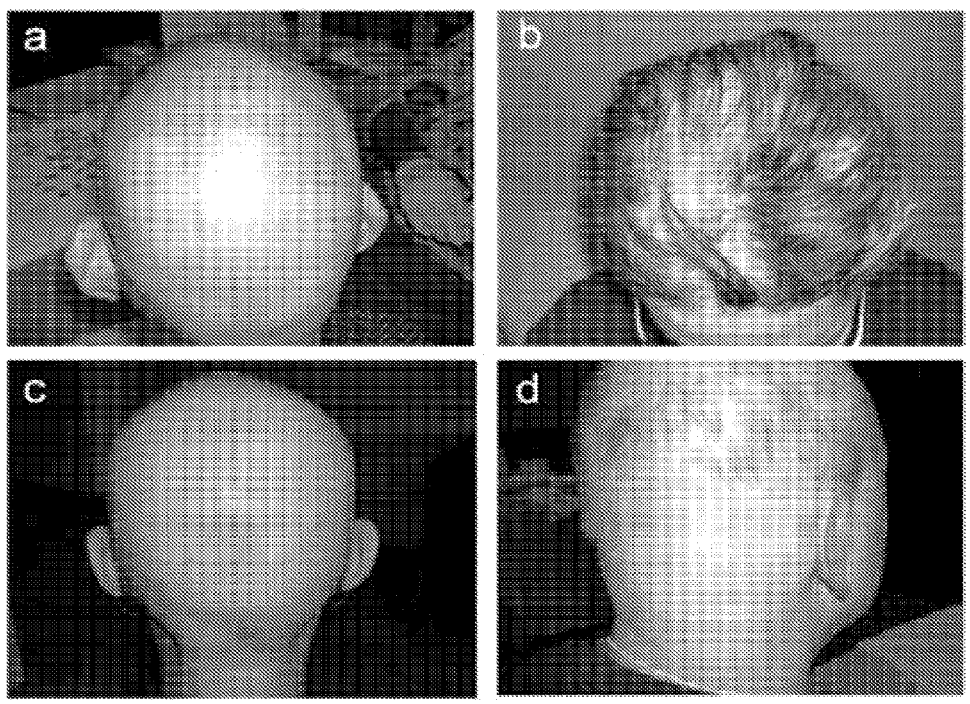
FIG. 1 are photographic images of clinical manifestations of AA. In the upper panels (FIGS. 1A-B), patients with AA multiplex.
Figure 2:
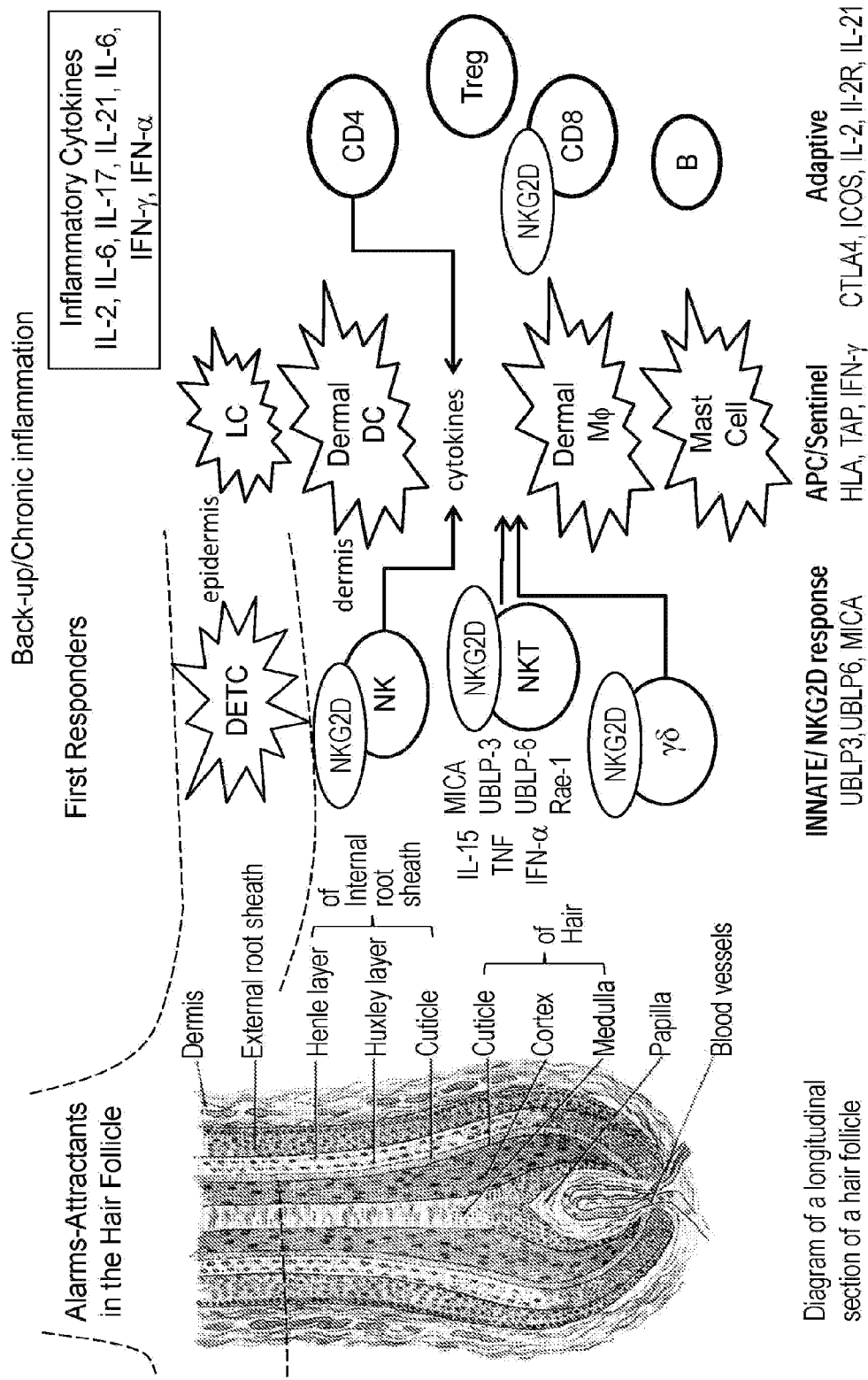
FIG. 2 shows a diagram showing the inflammatory response underlying Alopecia Arcata (AA).
Figure 3:
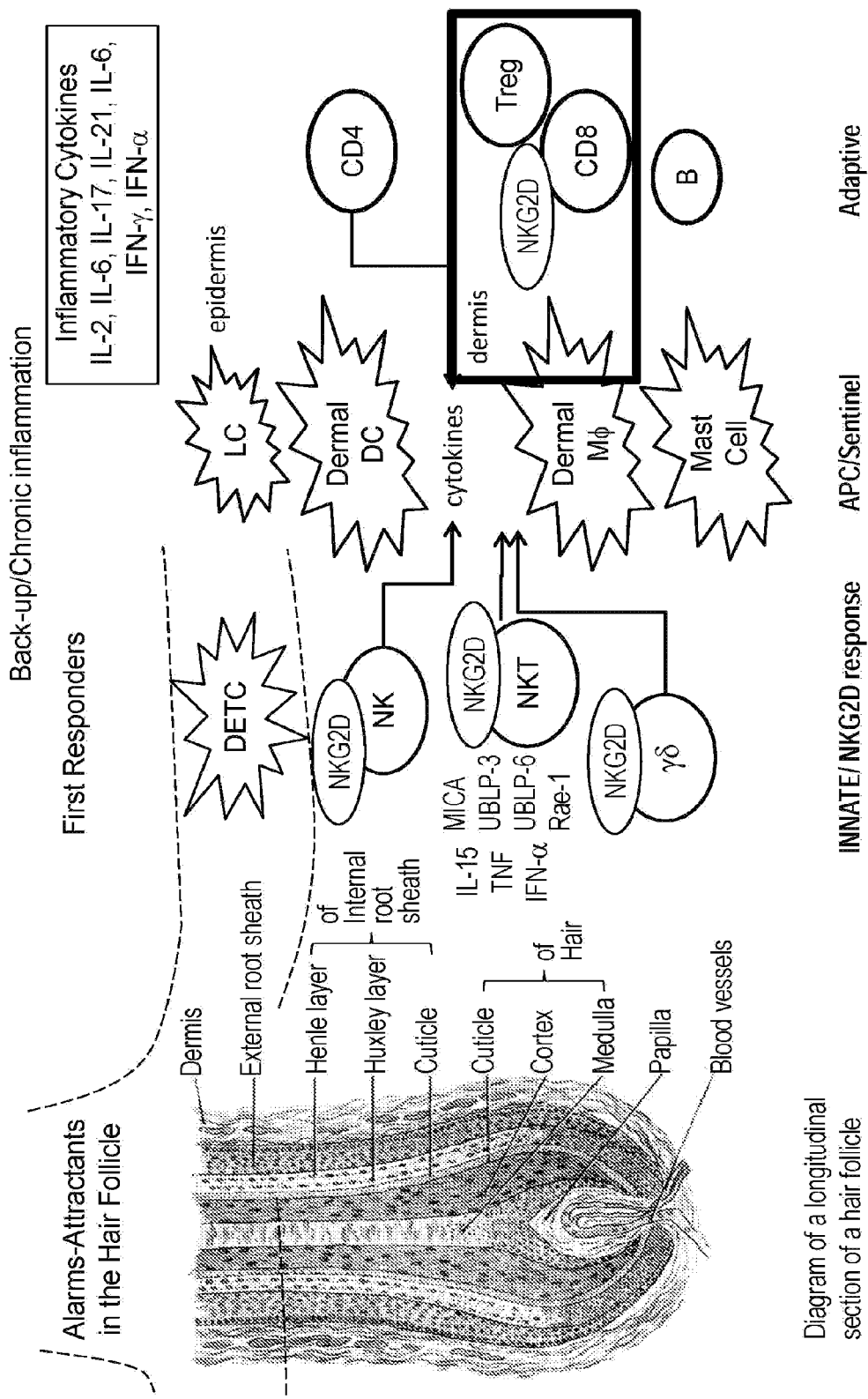
FIG. 3 shows a diagram showing the inflammatory response underlying Alopecia Areata (AA).

The invention provides for methods of treating a hair loss disorder (e.g., Alopecia Areata (AA), a common autoimmune form of hair loss) with an inhibitor of the Jak/Stat pathway, including Jak1, Jak2, Jak3, Stat1, and Stat2. Clinical research in AA has lagged behind its more heavily investigated "sister" autoimmune diseases in which this gene has been implicated (e.g., rheumatoid arthritis (RA), type 1 diabetes mellitus (T1D), multiple sclerosis (MS)). The invention provides for therapeutics previously untested in AA, that can inform one about the clinical relevance of Jak/Stat pathways in AA and related diseases.

Abbreviations and Definitions

The singular forms "a", "an" and "the" include plural reference unless the context clearly dictates otherwise.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Overview of the Integument and Hair Cells

The integument (or skin) is the largest organ of the body and is a highly complex organ covering the external surface of the body. It merges, at various body openings, with the mucous membranes of the alimentary and other canals. The integument performs a number of essential functions such as maintaining a constant internal environment via regulating body temperature and water loss; excretion by the sweat glands; but predominantly acts as a protective barrier against the action of physical, chemical and biologic agents on deeper tissues. Skin is elastic and except for a few areas such as the soles, palms, and ears, it is loosely attached to the underlying tissue. It also varies in thickness from 0.5 mm (0.02 inches) on the eyelids ("thin skin") to 4 mm (0.17 inches) or more on the palms and soles ("thick skin") (Ross M H, *Histology: A text and atlas*, $3^{rd}$ *edition*, Williams and Wilkins, 1995: Chapter 14; Burkitt H G, et al, *Wheater's Functional Histology*, $3^{rd}$ *Edition*, Churchill Livingstone, 1996: Chapter 9).

The skin is composed of two layers: a) the epidermis and b) the dermis. The epidermis is the outer layer, which is comparatively thin (0.1 mm). It is several cells thick and is composed of 5 layers: the stratum germinativum, stratum spinosum, stratum granulosum, stratum lucidum (which is limited to thick skin), and the stratum corneum. The outermost epidermal layer (the stratum corneum) consists of dead cells that are constantly shed from the surface and replaced from below by a single, basal layer of cells, called the stratum germinativum. The epidermis is composed predominantly of keratinocytes, which make up over 95% of the cell population. Keratinocytes of the basal layer (stratum germinativum) are constantly dividing, and daughter cells subsequently move upwards and outwards, where they undergo a period of differentiation, and are eventually sloughed off from the surface. The remaining cell population of the epidermis includes dendritic cells such as Langerhans cells and melanocytes. The epidermis is essentially cellular and non-vascular, containing little extracellular matrix except for the layer of collagen and other proteins beneath the basal layer of keratinocytes (Ross M H, *Histology: A text and atlas*, $3^{rd}$ *edition*, Williams and Wilkins, 1995: Chapter 14; Burkitt H G, et al, *Wheater's Functional Histology*, $3^{rd}$ *Edition*, Churchill Livingstone, 1996: Chapter 9).

The dermis is the inner layer of the skin and is composed of a network of collagenous extracellular material, blood vessels, nerves, and elastic fibers. Within the dermis are hair follicles with their associated sebaceous glands (collectively known as the pilosebaceous unit) and sweat glands. The interface between the epidermis and the dermis is extremely irregular and uneven, except in thin skin. Beneath the basal epidermal cells along the epidermal-dermal interface, the specialized extracellular matrix is organized into a distinct structure called the basement membrane (Ross M H, *Histology: A text and atlas*, $3^{rd}$ *edition*, Williams and Wilkins, 1995: Chapter 14; Burkitt H G, et al, *Wheater's Functional Histology*, $3^{rd}$ *Edition*, Churchill Livingstone, 1996: Chapter 9).

The mammalian hair fiber is composed of keratinized cells and develops from the hair follicle. The hair follicle is a peg of tissue derived from a downgrowth of the epidermis, which lies immediately underneath the skin's surface. The distal part of the hair follicle is in direct continuation with the external, cutaneous epidermis. Although a small structure, the hair follicle comprises a highly organized system of recognizably different layers arranged in concentric series. Active hair follicles extend down through the dermis, the hypodermis (which is a loose layer of connective tissue), and into the fat or adipose layer (Ross M H, *Histology: A text and atlas*, $3^{rd}$ *edition*, Williams and Wilkins, 1995: Chapter 14; Burkitt H G, et al, *Wheater's Functional Histology*, $3^{rd}$ *Edition*, Churchill Livingstone, 1996: Chapter 9).

At the base of an active hair follicle lies the hair bulb. The bulb consists of a body of dermal cells, known as the dermal papilla, contained in an inverted cup of epidermal cells known as the epidermal matrix. Irrespective of follicle type, the germinative epidermal cells at the very base of this epidermal matrix produce the hair fiber, together with several supportive epidermal layers. The lowermost dermal sheath is contiguous with the papilla basal stalk, from where the sheath curves externally around all of the hair matrix epidermal layers as a thin covering of tissue. The lowermost portion of the dermal sheath then continues as a sleeve or tube for the length of the follicle (Ross M H, *Histology: A text and atlas*, $3^{rd}$ *edition*, Williams and Wilkins, 1995: Chapter 14; Burkitt H G, et al, *Wheater's Functional Histology*, $3^{rd}$ *Edition*, Churchill Livingstone, 1996: Chapter 9).

Developing skin appendages, such as hair and feather follicles, rely on the interaction between the epidermis and the dermis, the two layers of the skin. In embryonic development, a sequential exchange of information between these two layers supports a complex series of morphogenetic processes, which results in the formation of adult follicle structures. However, in contrast to general skin dermal and epidermal cells, certain hair follicle cell populations, following maturity, retain their embryonic-type interactive, inductive, and biosynthetic behaviors. These properties can be derived from the very dynamic nature of the cyclical productive follicle, wherein repeated tissue remodeling necessitates a high level of dermal-epidermal interactive communication, which is vital for embryonic development and would be desirable in other forms of tissue reconstruction.

The hair fiber is produced at the base of an active follicle at a very rapid rate. For example, follicles produce hair fibers at a rate 0.4 mm per day in the human scalp and up to 1.5 mm per day in the rat vibrissa or whiskers, which means that cell proliferation in the follicle epidermis ranks amongst the fastest in adult tissues (Malkinson F D and J T Kearn, *Int J Dermatol* 1978, 17:536-551). Hair grows in cycles. The anagen phase is the growth phase, wherein up to 90% of the hair follicles said to be in anagen; catagen is the involuting or regressing phase which accounts for about 1-2% of the hair follicles; and telogen is the resting or quiescent phase of the cycle, which accounts for about 10-14% of the hair follicles. The cycle's length varies on different parts of the body.

Hair follicle formation and cycling is controlled by a balance of inhibitory and stimulatory signals. The signaling cues are potentiated by growth factors that are members of the TGFβ-BMP family. A prominent antagonist of the members of the TGFβ-BMP family is follistatin. Follistatin is a secreted protein that inhibits the action of various BMPs (such as BMP-2, -4, -7, and -11) and activins by binding to said proteins, and purportedly plays a role in the development of the hair follicle (Nakamura M, et al., *FASEB J*, 2003, 17(3):497-9; Patel K *Intl J Biochem Cell Bio*, 1998, 30:1087-93; Ueno N, et al., *PNAS*, 1987, 84:8282-86; Nakamura T, et al., *Nature*, 1990, 247:836-8; Iemura S, et al., *PNAS*, 1998, 77:649-52; Fainsod A, et al., *Mech Dev*, 1997, 63:39-50; Gamer L W, et al., *Dev Biol*, 1999, 208:222-32).

The deeply embedded end bulb, where local dermal-epidermal interactions drive active fiber growth, is the signaling center of the hair follicle comprising a cluster of mesencgymal cells, called the dermal papilla (DP). This same region is also central to the tissue remodeling and developmental changes involved in the hair fiber's or appendage's precise alternation between growth and regression phases. The DP, a key player in these activities, appears to orchestrate the complex program of differentiation that characterizes hair fiber formation from the primitive germinative epidermal cell source (Oliver R F, *J Soc Cosmet Chem,* 1971, 22:741-755; Oliver R F and C A Jahoda, *Biology of Wool and Hair* (eds Roger et al.), 1971, Cambridge University Press: 51-67; Reynolds A J and C A Jahoda, *Development,* 1992, 115:587-593; Reynolds A J, et al., *J Invest Dermatol,* 1993, 101:634-38).

The lowermost dermal sheath (DS) arises below the basal stalk of the papilla, from where it curves outwards and upwards. This dermal sheath then externally encases the layers of the epidermal hair matrix as a thin layer of tissue and continues upward for the length of the follicle. The epidermally-derived outer root sheath (ORS) also continues for the length of the follicle, which lies immediately internal to the dermal sheath in between the two layers, and forms a specialized basement membrane termed the glassy membrane. The outer root sheath constitutes little more than an epidermal monolayer in the lower follicle, but becomes increasingly thickened as it approaches the surface. The inner root sheath (IRS) forms a mold for the developing hair shaft. It comprises three parts: the Henley layer, the Huxley layer, and the cuticle, with the cuticle being the innermost portion that touches the hair shaft. The IRS cuticle layer is a single cell thick and is located adjacent to the hair fiber. It closely interdigitates with the hair fiber cuticle layer. The Huxley layer can comprise up to four cell layers. The IRS Henley layer is the single cell layer that runs adjacent to the ORS layer (Ross M H, *Histology: A text and atlas,* $3^{rd}$ edition, Williams and Wilkins, 1995: Chapter 14; Burkitt H G, et al, *Wheater's Functional Histology,* $3^{rd}$ Edition, Churchill Livingstone, 1996: Chapter 9).

Alopecia Areata

Alopecia areata (AA) is one of the most prevalent autoimmune diseases, affecting approximately 4.6 million people in the US alone, including males and females across all ethnic groups, with a lifetime risk of 1.7% (1) In AA, autoimmunity develops against the hair follicle, resulting in non-scarring hair loss that can begin as patches, which can coalesce and progress to cover the entire scalp (alopecia totalis, AT) or eventually the entire body (alopecia universalis, AU) (FIG. 1). AA was first described by Cornelius Celsus in 30 A.D., using the term "ophiasis", which means "snake", due to the sinuous path of hair loss as it spread slowly across the scalp. Hippocrates first used the Greek word 'alopekia' (fox mange), the modern day term "alopecia areata" was first used by Sauvages in his *Nosologica Medica,* published in 1760 in Lyons, France.

Curiously, AA preferentially affects pigmented hair follicles in the anagen (growth) phase of the hair cycle, and when the hair regrows in patches of AA, it frequently grows back white or colorless. The phenomenon of 'sudden whitening of the hair' is therefore ascribed to AA with an acute onset, and has been documented throughout history as having affected several prominent individuals at times of profound grief, stress or fear (2). Examples include Shahjahan, who upon the death of his wife in 1631 experienced acute whitening of his hair, and in his grief built the Taj Mahal in her honor. Sir Thomas More, author of Utopia, who on the eve of his execution in 1535 was said to have become 'white in both beard and hair'. The sudden whitening of the hair is believed to result from an acute attack upon the pigmented hair follicles, leaving behind the white hairs unscathed.

Several clinical aspects of AA remain unexplained but can hold important clues toward understanding pathogenesis. AA attacks hairs only around the base of the hair follicles, which are surrounded by dense clusters of lymphocytes, resulting in the pathognomic 'swarm of bees' appearance on histology. Based on these observations, it is postulated that a signal(s) in the pigmented, anagen hair follicle is emitted which invokes an acute or chronic immune response against the lower end of the hair follicle, leading to hair cycle perturbation, acute hair shedding, hair shaft anomalies and hair breakage. Despite these dramatic perturbations in the hair follicle, there is no permanent organ destruction and the possibility of hair regrowth remains if immune privilege can be restored.

Throughout history, AA has been considered at times to be a neurological disease brought on by stress or anxiety, or as a result of an infectious agent, or even hormonal dysfunction. The concept of a genetically-determined autoimmune mechanism as the basis for AA emerged during the $20^{th}$ century from multiple lines of evidence. AA hair follicles exhibit an immune infiltrate with activated Th, Tc and NK cells (3, 4) and there is a shift from a suppressive (Th2) to an autoimmune (Th1) cytokine response. The humanized model of AA, which involves transfer of AA patient scalp onto immune-deficient SCID mice illustrates the autoimmune nature of the disease, since transfer of donor T-cells causes hair loss only when co-cultured with hair follicle or human melanoma homogenate (5, 6). Regulatory T cells which serve to maintain immune tolerance are observed in lower numbers in AA tissue (7), and transfer of these cells to C3H/HeJ mice leads to resistance to AA (8). Although AA has long been considered exclusively as a T-cell mediated disease, in recent years, an additional mechanism of disease has been postulated. The hair follicle is defined as one of a select few immune privileged sites in the body, characterized by the presence of extracellular matrix barriers to impede immune cell trafficking, lack of antigen presenting cells, and inhibition of NK cell activity via the local production of immunosuppressive factors and reduced levels of MHC class I expression (9). Thus, the notion of a 'collapse of immune privilege' has also been invoked as part of the mechanism by which AA can arise. Support for a genetic basis for AA comes from multiple lines of evidence, including the observed heritability in first degree relatives (10, 11), twin studies (12), and most recently, from the results of our family-based linkage studies (13).

Treatment of Hair Loss Disorders

This invention provides for the discovery that a known therapeutic, for example an inhibitor of a protein tyrosine kinase (PTK) involved in cytokine signaling, such as JAK/STAT proteins Jak 1, Jak2, Jak3 Stat 1 or Stat 2 (e.g., INCB 018424, tofacitinib (CP690550), Janex 1 (WHI-P131), PF-956980, WHI-P154, VX-509, JAK3 Inhibitor IV, NSC114792, or R348), can be used for the treatment of hair loss disorders. Non-limiting examples of hair loss disorders include: androgenetic alopecia, Alopecia areata, telogen effluvium, alopecia areata, alopecia totalis, and alopecia universalis.

An aspect of the invention encompasses a method of treating a hair-loss disorder in a mammalian subject in need thereof, the method comprising administering to the subject an inhibitor of a protein tyrosine kinase (PTK) involved in cytokine signaling. In one embodiment, the inhibitor is a Jak/Stat inhibitor. In a further embodiment, the inhibitor is INCB 018424. In some embodiments, the Jak3 inhibitor is an antibody that specifically binds to a Jak3 protein or a fragment thereof; an antisense RNA or antisense DNA that decreases expression of the gene that encodes the Jak3 protein; an antisense RNA or antisense DNA that decreases expression of the Jak3 protein; a siRNA that specifically targets the Jak3 gene; a small molecule; or a combination thereof. In one embodiment, the inhibitor is a Jak3 inhibitor. In a further embodiment, the inhibitor is tofacitinib (CP690550). In a further embodiment, the small molecule is Janex 1 (WHI-P131), PF-956980, WHI-P154, VX-509, JAK3 Inhibitor IV, NSC114792, or R348. In another embodiment, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis An aspect of the invention provides for a method for inducing hair growth in a subject where the method comprises administering to the subject an effective amount of an inhibitor of a protein tyrosine kinase (PTK) involved in cytokine signaling. In one embodiment, the inhibitor is a Jak/Stat inhibitor. In other embodiments, the inhibitor is INCB 018424. In some embodiments, the Jak3 inhibitor is an antibody that specifically binds to a Jak3 protein or a fragment thereof; an antisense RNA or antisense DNA that decreases expression of the gene that encodes the Jak3 protein; an antisense RNA or antisense DNA that decreases expression of the Jak3 protein; a siRNA that specifically targets the Jak3 gene; a small molecule; or a combination thereof. In one embodiment, the inhibitor is a Jak3 inhibitor. In a further embodiment, the inhibitor is tofacitinib (CP690550). In a further embodiment, the small molecule is Janex 1 (WHI-P131), PF-956980, WHI-P154, VX-509, JAK3 Inhibitor IV, NSC114792, or R348. In some embodiments, the subject is afflicted with a hair-loss disorder. In other embodiments, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis. In some embodiments, the modulating compound can also inhibit hair growth, thus it can be used for treatment of hair growth disorders, such as hypertrichosis.

An aspect of the invention encompasses a method of treating a hair-loss disorder in a mammalian subject in need thereof, the method comprising administering to the subject a Jak1 or Jak3 inhibitor. In one embodiment, the inhibitor is an antibody or antibody fragment that is directed to SEQ ID NO: 1 (Jak1), SEQ ID NO: 3 (Jak2), or SEQ ID NO: 109 (Jak3). In another embodiment, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis.

An aspect of the invention provides for a method for inducing hair growth in a subject where the method comprises administering to the subject an effective amount of a Jak1, Jak2, or Jak3 inhibitor, thereby controlling hair growth in the subject. In one embodiment, the inhibitor comprises an antibody that specifically binds to a protein comprising SEQ ID NO: 1 (Jak1), SEQ ID NO: 3 (Jak2), or SEQ ID NO: 109 (Jak3). In some embodiments, the subject is afflicted with a hair-loss disorder. In other embodiments, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis. In some embodiments, the modulating compound can also inhibit hair growth, thus it can be used for treatment of hair growth disorders, such as hypertrichosis.

An aspect of the invention encompasses a method of treating a hair-loss disorder in a mammalian subject in need thereof, the method comprising administering to the subject a Stat 1 inhibitor. In one embodiment, the inhibitor is an antibody or antibody fragment that is directed to SEQ ID NO: 5. In another embodiment, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis An aspect of the invention provides for a method for inducing hair growth in a subject where the method comprises administering to the subject an effective amount of a Stat 1 inhibitor, thereby controlling hair growth in the subject. In one embodiment, the inhibitor comprises an antibody that specifically binds to a protein comprising SEQ ID NO: 5. In some embodiments, the subject is afflicted with a hair-loss disorder. In other embodiments, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis. In some embodiments, the modulating compound can also inhibit hair growth, thus it can be used for treatment of hair growth disorders, such as hypertrichosis.

An aspect of the invention encompasses a method of treating a hair-loss disorder in a mammalian subject in need thereof, the method comprising administering to the subject a Stat 2 inhibitor. In one embodiment, the inhibitor is an antibody or antibody fragment that is directed to SEQ ID NO: 7. In another embodiment, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis An aspect of the invention provides for a method for inducing hair growth in a subject where the method comprises administering to the subject an effective amount of a Stat 2 inhibitor, thereby controlling hair growth in the subject. In one embodiment, the inhibitor comprises an antibody that specifically binds to a protein comprising SEQ ID NO: 7. In some embodiments, the subject is afflicted with a hair-loss disorder. In other embodiments, the hair-loss disorder comprises androgenetic alopecia, telogen effluvium, alopecia areata, telogen effluvium, tinea capitis, alopecia totalis, hypotrichosis, hereditary hypotrichosis simplex, or alopecia universalis. In some embodiments, the modulating compound can also inhibit hair growth, thus it can be used for treatment of hair growth disorders, such as hypertrichosis.

This invention provides for the discovery that a number human genes have been identified as a cohort of genes involved in telogen-to-anagen transition of the hair cycle (e.g., Telogen-to-Anagen Hair Cycle (TAHC) gene). These genes were identified as being upregulated in the telogen phase of the hair cycle, and can be correlated with the presence of a hair loss disorder in a subject. These genes, now that they have been identified, can be used for a variety of useful methods; for example, they can be used to determine whether a subject has susceptibility to a hair-loss disorder, such as Alopecia Areata (AA). The genes identified as part of this telogen-to-anagen transition hair cycle cohort or group (i.e., "TAHC genes") include CSF1R (Gene ID Accession No. 1436), FCER2 (Gene ID Accession No. 2208), IFNGR1 (Gene ID Accession No. 3459), IL20 (Gene ID Accession No. 50604), OAS1 (Gene ID Accession No. 4938), PTPRC (Gene ID Accession No. 5788), CEBPD (Gene ID Accession No. 1052), CRP (Gene ID Accession No. 1401), IL2RA (Gene ID Accession No. 3559), IL4 (Gene ID Accession No. 3565), IL6ST (Gene ID Accession No. 3572), INSR (Gene ID Accession No. 3643), JAK3 (Gene ID Accession No. 3718), NR3C1 (Gene ID Accession No. 2908), OSM (Gene ID Accession No. 5008), PTPN11 (Gene ID Accession No. 5781), SOCS3 (Gene ID Accession No. 9021), STAT5A (Gene ID Accession No. 6776), STAT5B (Gene ID Accession No. 6777), CCND1 (Gene ID Accession No. 595), F2 (Gene ID Accession No. 2147), LRG1 (Gene ID Accession No. 116844), PRLR (Gene ID Accession No. 5618), MPL (Gene ID Accession No. 4352), and JUNB (Gene ID Accession No. 3726).

In one embodiment, the invention encompasses a method for detecting the presence of or a predisposition to a hair-loss disorder in a human subject where the method comprises obtaining a biological sample from a human subject; and detecting whether or not there is an alteration in the level of expression of an mRNA or a protein encoded by a TAHC gene in the subject as compared to the level of expression in a subject not afflicted with a hair-loss disorder. In on embodiment, the detecting comprises determining whether mRNA expression or protein expression of the TAHC gene is increased or decreased as compared to expression in a normal sample. In another embodiment, the detecting comprises determining in the sample whether expression of at least 2 TAHC proteins, at least 3 TAHC proteins, at least 4 TAHC proteins, at least 5 TAHC proteins, at least 6 TAHC proteins, at least 6 TAHC proteins, at least 7 TAHC proteins, or at least 8 TAHC proteins is increased or decreased as compared to expression in a normal sample. In some embodiments, the detecting comprises determining in the sample whether expression of at least 2 TAHC mRNAs, at least 3 TAHC mRNAs, at least 4 TAHC mRNAs, at least 5 TAHC mRNAs, at least 6 TAHC mRNAs, at least 6 TAHC mRNAs, at least 7 TAHC mRNAs, or at least 8 TAHC mRNAs is increased or decreased as compared to expression in a normal sample. In one embodiment, an increase in the expression of at least 2 TAHC genes, at least 3 TAHC genes, at least 4 TAHC genes, at least 5 TAHC genes, at least 6 TAHC genes, at least 7 TAHC genes, or at least 8 TAHC genes indicates a predisposition to or presence of a hair-loss disorder in the subject. In another embodiment, a decrease in the expression of at least 2 TAHC genes, at least 3 TAHC genes, at least 4 TAHC genes, at least 5 TAHC genes, at least 6 TAHC genes, at least 7 TAHC genes, or at least 8 TAHC genes indicates a predisposition to or presence of a hair-loss disorder in the subject. In one embodiment, the mRNA expression or protein expression level in the subject is about 5-fold increased, about 10-fold increased, about 15-fold increased, about 20-fold increased, about 25-fold increased, about 30-fold increased, about 35-fold increased, about 40-fold increased, about 45-fold increased, about 50-fold increased, about 55-fold increased, about 60-fold increased, about 65-fold increased, about 70-fold increased, about 75-fold increased, about 80-fold increased, about 85-fold increased, about 90-fold increased, about 95-fold increased, or is 100-fold increased, as compared to that in the normal sample. In some embodiments, the mRNA expression or protein expression level in the subject is at least about 100-fold increased, at least about 200-fold increased, at least about 300-fold increased, at least about 400-fold increased, or is at least about 500-fold increased, as compared to that in the normal sample. In further embodiments, the mRNA expression or protein expression level of the TAHC gene in the subject is about 5-fold to about 70-fold increased, as compared to that in the withal sample. In other embodiments, the mRNA or protein expression level of the TAHC gene in the subject is about 5-fold to about 90-fold increased, as compared to that in the normal sample. In one embodiment, the mRNA expression or protein expression level in the subject is about 5-fold decreased, about 10-fold decreased, about 15-fold decreased, about 20-fold decreased, about 25-fold decreased, about 30-fold decreased, about 35-fold decreased, about 40-fold decreased, about 45-fold decreased, about 50-fold decreased, about 55-fold decreased, about 60-fold decreased, about 65-fold decreased, about 70-fold decreased, about 75-fold decreased, about 80-fold decreased, about 85-fold decreased, about 90-fold decreased, about 95-fold decreased, or is 100-fold decreased, as compared to that in the normal sample. In some embodiments, the mRNA expression or protein expression level in the subject is at least about 100-fold decreased, as compared to that in the normal sample. In some embodiments, the mRNA or protein expression level of the TAHC gene in the subject is about 5-fold to about 70-fold decreased, as compared to that in the normal sample.

In yet other embodiments, the mRNA or protein expression level of the TAHC gene in the subject is about 5-fold to about 90-fold decreased, as compared to that in the normal sample. In further embodiments, the detecting comprises gene sequencing, selective hybridization, selective amplification, gene expression analysis, or a combination thereof. In another embodiment, the hair-loss disorder comprises androgenetic alopecia, alopecia areata, telogen effluvium, alopecia totalis, hypotrichosis, hereditary hypotrichosis simplex, or alopecia universalis. In one embodiment, the TAHC gene is CSF1R, FCER2, IFNGR1, IL20, OAS1, PTPRC, CEBPD, CRP, IL2RA, IL4, IL6ST, INSR, JAK3, NR3C1, OSM, PTPN11, SOCS3, STAT5A, STAT5B, CCND1, F2, LRG1, PRLR, MPL, or JUNB. In another embodiment, the TAHC gene is CRP.

Diagnosis

The invention provides methods to diagnose whether or not a subject is susceptible to or has a hair loss disorder. The diagnostic methods, in one embodiment, are based on monitoring the expression of TAHC genes, such as CSF1R, FCER2, IFNGR1, IL20, OAS1, PTPRC, CEBPD, CRP, IL2RA, IL4, IL6ST, INSR, JAK3, NR3C1, OSM, PTPN11, SOCS3, STAT5A, STAT5B, CCND1, F2, LRG1, PRLR, MPL, or JUNB, in a subject, for example whether they are increased or decreased as compared to a normal sample. As used herein, the term "diagnosis" includes the detection, typing, monitoring, dosing, comparison, at various stages, including early, pre-symptomatic stages, and late stages, in adults and children. Diagnosis can include the assessment of a predisposition or risk of development, the prognosis, or the characterization of a subject to define most appropriate treatment (pharmacogenetics).

The invention provides diagnostic methods to determine whether an individual is at risk of developing a hair-loss disorder, or suffers from a hair-loss disorder, wherein the disease results from an alteration in the expression of TAHC genes. In one embodiment, a method of detecting the presence of or a predisposition to a hair-loss disorder in a subject is provided. The subject can be a human or a child thereof. The method can comprise detecting in a sample from the subject whether or not there is an alteration in the level of expression of a protein encoded by a TAHC gene in the subject as compared to the level of expression in a subject not afflicted with a hair-loss disorder. In one embodiment, the detecting can comprise determining whether mRNA expression of the TAHC is increased or decreased. For example, in a microarray assay, one can look for differential expression of a TAHC gene. Any expression of a TAHC gene that is either 2× higher or 2× lower than TAHC expression observed for a subject not afflicted with a hair-loss disorder (as indicated by a fluorescent read-out) is deemed not normal, and worthy of further investigation. The detecting can also comprise determining in the sample whether expression of at least 2 TAHC proteins, at least 3 TAHC proteins, at least 4 TAHC proteins, at least 5 TAHC proteins, at least 6 TAHC proteins, at least 6 TAHC proteins, at least 7 TAHC proteins, or at least 8 TAHC proteins is increased or decreased. The presence of such an alteration is indicative of the presence or predisposition to a hair-loss disorder.

The presence of an alteration in a TAHC gene in the sample is detected through the genotyping of a sample, for example via gene sequencing, selective hybridization, amplification, gene expression analysis, or a combination thereof. In one embodiment, the sample can comprise blood, serum, sputum, lacrimal secretions, semen, vaginal secretions, fetal tissue, skin tissue, epithelial tissue, muscle tissue, amniotic fluid, or a combination thereof.

The invention provides for a diagnostic kit used to determine whether a sample from a subject exhibits increased expression of at least 2 or more TAHC genes. In one embodiment, the kit comprising a nucleic acid primer that specifically hybridizes to one or more TAHC genes. The invention also provides for a diagnostic kit used to determine whether a sample from a subject exhibits a predisposition to a hair-loss disorder in a human subject. In further embodiments, the TAHC gene is CSF1R, FCER2, IFNGR1, IL20, OAS1, PTPRC, CEBPD, CRP, IL2RA, IL4, IL6ST, INSR, JAK3, NR3C1, OSM, PTPN11, SOCS3, STAT5A, STAT5B, CCND1, F2, LRG1, PRLR, MPL, or JUNB. In another embodiment, the hair-loss disorder comprises androgenetic alopecia, alopecia areata, telogen effluvium, alopecia totalis, hypotrichosis, hereditary hypotrichosis simplex, or alopecia universalis.

DNA and AminoAcid Manipulation Methods and Purification Thereof

The present invention utilizes conventional molecular biology, microbiology, and recombinant DNA techniques available to one of ordinary skill in the art. Such techniques are well known to the skilled worker and are explained fully in the literature. See, e.g., Maniatis, Fritsch & Sambrook, "*Molecular Cloning: A Laboratory Manual*" (1982): "*DNA Cloning: A Practical Approach*," Volumes I and II (D. N. Glover, ed., 1985); "Oligonucleotide Synthesis" (M. J. Gait, ed., 1984); "*Nucleic Acid Hybridization*" (B. D. Hames & S. J. Higgins, eds., 1985); "*Transcription and Translation*" (B. D. Hames & S. J. Higgins, eds., 1984); "*Animal Cell Culture*" (R. I. Freshney, ed., 1986); "*Immobilized Cells and Enzymes*" (IRL Press, 1986): B. Perbal, "*A Practical Guide to Molecular Cloning*" (1984), and Sambrook, et al., "*Molecular Cloning: a Laboratory Manual*" (1989).

One skilled in the art can obtain a protein in several ways, which include, but are not limited to, isolating the protein via biochemical means or expressing a nucleotide sequence encoding the protein of interest by genetic engineering methods.

A protein is encoded by a nucleic acid (including, for example, genomic DNA, complementary DNA (cDNA), synthetic DNA, as well as any form of corresponding RNA). For example, it can be encoded by a recombinant nucleic acid of a gene. The proteins of the invention can be obtained from various sources and can be produced according to various techniques known in the art. For example, a nucleic acid that encodes a protein can be obtained by screening DNA libraries, or by amplification from a natural source. A protein can be a fragment or portion thereof. The nucleic acids encoding aprotein can be produced via recombinant DNA technology and such recombinant nucleic acids can be prepared by conventional techniques, including chemical synthesis, genetic engineering, enzymatic techniques, or a combination thereof. For example, a Jak 1 protein is the polypeptide encoded by the nucleic acid having the nucleotide sequence shown in SEQ ID NO: 2. An example of a Jak 1 polypeptide has the amino acid sequence shown in SEQ ID NO: 1. A Jak 2 protein is the polypeptide encoded by the nucleic acid having the nucleotide sequence shown in SEQ ID NO: 4. An example of a Jak 2 polypeptide has the amino acid sequence shown in SEQ ID NO: 3. A Jak 3 protein is the polypeptide encoded by the nucleic acid having the nucleotide sequence shown in SEQ ID NO: 110. An example of a Jak 3 polypeptide has the amino acid sequence shown in SEQ ID NO: 109. For example, a Stat 1 protein is the polypeptide encoded by the nucleic acid having the nucleotide sequence shown in SEQ ID NO: 6. An example of a Stat 1 polypeptide has the amino acid sequence shown in SEQ ID NO: 5. A Stat 2 protein is the polypeptide encoded by the nucleic acid having the nucleotide sequence shown in SEQ ID NO: 8. An example of a Stat 2 polypeptide has the amino acid sequence shown in SEQ ID NO: 7.

The polypeptide sequence of human Jak 1 is depicted in SEQ ID NO: 1. The nucleotide sequence of human Jak 1 is shown in SEQ ID NO: 2. Sequence information related to Jak 1 is accessible in public databases by GenBank Accession numbers NP_002218 (for protein) and NM_002227.2 (for nucleic acid).

SEQ ID NO: 1 is the human wild type amino acid sequence corresponding to Jak1 (residues 1-1154):

```
  1 MQYLNIKEDC NAMAFCAKMR SSKKTEVNLE APEPGVEVIF YLSDREPLRL GSGEYTAEEL

61 CIRAAQACRI SPLCHNLFAL YDENTKLWYA PNRTITVDDK MSLRLHYRMR FYFTNWHGTN

121 DNEQSVWRHS PKKQKNGYEK KKIPDATPLL DASSLEYLFA QGQYDLVKCL APIRDPKTEQ

181 DGHDIENECL GMAVLAISHY AMMKKMQLPE LPKDISYKRY IPETLNKSIR QRNLLTRMRI

241 NNVFKDFLKE FNNKTICDSS VSTHDLKVKY LATLETLTKH YGAEIFETSM LLISSENEMN

301 WFHSNDGGNV LYYEVMVTGN LGIQWRHKPN VVSVEKEKNK LKRKKLENKH KKDEEKNKIR

361 EEWNNFSYFP EITHIVIKES VVSINKQDNK KMELKLSSHE EALSFVSLVD GYFRLTADAH

421 HYLCTDVAPP LIVHNIQNGC HGPICTEYAI NKLRQEGSEG GMYVLRWSCT DFDNILMTVT

481 CFEKSEQVQG AQKQFKNFQI EVQKGRYSLH GSDRSFPSLG DLMSHLKKQI LRTDNISFML

541 KRCCQPKPRE ISNLLVATKK AQEWQPVYPM SQLSFDRILK KDLVQGEHLG RGTRTHIYSG

601 TLMDYKDDEG TSEEKKIKVI LKVLDPSHRD ISLAFFEAAS MMRQVSHKHI VYLYGVCVRD

661 VENIMVEEFV EGGPLDLFMH RKSDVLTTPW KFKVAKQLAS ALSYLEDKDL VHGNVCTKNL

721 LLAREGIDSE CGPFIKLSDP GIPITVLSRQ ECIERIPWIA PECVEDSKNL SVAADKWSFG

781 TTLWEICYNG EIPLKDKTLI EKERFYESRC RPVTPSCKEL ADLMTRCMNY DPNQRPFFRA

841 IMRDINKLEE QMPDIVSEKK PATEVDPTHF EKRFLKRIRD LGEGHFGKVE LCRYDPEGDN
```

```
 901 TGEQVAVKSL KPESGGNHIA DLKKEIEILR NLYHENIVKY KGICTEDGGN GIKLIMEFLP

9611 SGSLKEYLPK NKNKINLKQQ LKYAVQICKG MDYLGSRQYV HRDLAARNVL VESEHQVKIG

1021 DFGLTKAIET DKEYYTVKDD RDSPVFWYAP ECLMQSKFYI ASDVWSFGVT LHELLTYCDS

1081 DSSPMALFLK MIGPTHGQMT VTRLVNTLKE GKRLPCPPNC PDEVYQLMRK CWEFQPSNRT

1141 SFQNLIEGFE ALLK
```

SEQ ID NO: 2 is the human wild type nucleotide sequence corresponding to Jak1 (nucleotides 1-5053), wherein the underscored bolded "ATG" denotes the beginning of the open reading frame:

```
   1 tgcagacagt gcgggcctgc gcccagtccc ggctgtcctc gccgcgaccc ctcctcagcc 61 ctgggcgcgc gcacgctggg gccccgcggg gctggccgcc tagcgagcct gccggtcgac 121 cccagccagc gcagcgacgg ggcgctgcct ggcccaggcg cacacggaag tgcgcttctc 181 tgaagtagct ttggaaagta gagaagaaaa tccagtttgc ttcttggaga cactggaca 241 gctgaataaa tgcagtatct aaatataaaa gaggactgca atgccatggc tttctgtgct 301 aaaatgagga gctccaagaa gactgaggtg aacctggagg ccctgagcc aggggtggaa 361 gtgatcttct atctgtcgga cagggagccc tccggctgg gcagtggaga gtacacagca 421 gaggaactgt gcatcagggc tgcacaggca tgccgtatct ctcctctttg tcacaacctc 481 tttgccctgt atgacgagaa caccaagctc tggtatgctc caaatcgcac catcaccgtt 541 gatgacaaga tgtccctccg gctccactac cggatgaggt tctatttcac caattggcat 601 ggaaccaacg acaatgagca gtcagtgtgg cgtcattctc caagaagca gaaaaatggc 661 tacgagaaaa aaaagattcc agatgcaacc cctctccttg atgccagctc actggagtat 721 ctgtttgctc agggacagta tgatttggtg aaatgcctgg ctcctattcg agaccccaag 781 accgagcagg atggacatga tattgagaac gagtgtctag ggatggctgt cctggccatc 841 tcacactatg ccatgatgaa gaagatgcag ttgccagaac tgcccaagga catcagctac 901 aagcgatata ttccagaaac attgaataag tccatcagac agaggaacct tctcaccagg 961 atgcggataa ataatgtttt caaggatttc ctaaaggaat ttaacaacaa gaccatttgt 1021 gacagcagcg tgtccacgca tgacctgaag gtgaaatact tggctacctt ggaaactttg 1081 acaaaacatt acggtgctga aatatttgag acttccatgt tactgatttc atcagaaaat 1141 gagatgaatt ggtttcattc gaatgacggt ggaaacgttc tctactacga agtgatggtg 1201 actgggaatc ttggaatcca gtggaggcat aaaccaaatg ttgtttctgt tgaaaaggaa 1261 aaaaataaac tgaagcggaa aaaactggaa aataaacaca agaaggatga ggagaaaaac 1321 aagatccggg aagagtggaa caatttttct tacttccctg aaatcactca cattgtaata 1381 aaggagtctg tggtcagcat taacaagcag acaacaagaa aaatggaact gaagctctct 1441 tcccacgagg aggccttgtc ctttgtgtcc ctggtagatg ctacttccg gctcacagca 1501 gatgccatc attacctctg caccgacgtg gccccccgt tgatcgtcca caacatacag 1561 aatggctgtc atggtccaat ctgtacagaa tacgccatca ataaattgcg gcaagaagga 1621 agcgaggagg ggatgtacgt gctgaggtgg agctgcaccg actttgacaa catcctcatg 1681 accgtcacct gctttgagaa gtctgagcag gtgcagggtg cccagaagca gttcaagaac 1741 tttcagatcg aggtgcagaa gggccgctac agtctgcacg ttcggaccg cagcttcccc 1801 agcttgggag acctcatgag ccacctcaag aagcagatcc tgcgcacgga taacatcagc
```

-continued

```
1861 ttcatgctaa aacgctgctg ccagcccaag ccccgagaaa tctccaacct gctggtggct
1921 actaagaaag cccaggagtg gcagcccgtc tacccatga gccagctgag tttcgatcgg
1981 atcctcaaga aggatctggt gcagggcgag caccttggga gaggcacgag aacacacatc
2041 tattctggga ccctgatgga ttacaaggat gacgaaggaa cttctgaaga agaagaata
2101 aaagtgatcc tcaaagtctt agaccccagc cacagggata tttccctggc cttcttcgag
2161 gcagccagca tgatgagaca ggtctcccac aaacacatcg tgtacctcta tggcgtctgt
2221 gtccgcgacg tggagaatat catggtggaa gagtttgtgg aaggggtcc tctggatctc
2281 ttcatgcacc ggaaaagcga tgtccttacc acaccatgga aattcaaagt tgccaaacag
2341 ctggccagtg ccctgagcta cttggaggat aaagacccgg tccatggaaa tgtgtgtact
2401 aaaaacctcc tcctggcccg tgagggcatc gacagtgagt gtggcccatt catcaagctc
2461 agtgaccccg gcatccccat tacggtgctg tctaggcaag aatgcattga acgaatccca
2521 tggattgctc ctgagtgtgt tgaggactcc aagaacctga gtgtggctgc tgacaagtgg
2581 agctttggaa ccacgctctg ggaaatctgc tacaatggcg agatccccct gaaagacaag
2641 acgctgattg agaaagagag attctatgaa agccggtgca ggccagtgac accatcatgt
2701 aaggagctgg ctgacctcat gacccgctgc atgaactatg accccaatca gaggcctttc
2761 ttccgagcca tcatgagaga cattaataag cttgaagagc agaatccaga tattgtttca
2821 gaaaaaaaac cagcaactga agtggacccc acacataatg aaaagcgctt cctaaagagg
2881 atccgtgact tgggagaggg ccactttggg aaggttgagc tctgcaggta tgaccccgaa
2941 ggggacaata caggggagca ggtggctgtt aaatctctga gcctgagag tggaggtaac
3001 cacatagctg atctgaaaaa ggaaatcgag atcttaagga acctctatca tgagaacatt
3061 gtgaagtaca aaggaatctg cacagaagac ggaggaaatg gtattaagct catcatggaa
3121 tttctgcctt cgggaagcct taaggaatat cttccaaaga ataagaacaa aataaacctc
3181 aaacagcagc taaatatgc cgttcagatt tgtaagggga tggactattt gggttctcgg
3241 caatacgttc accgggactt ggcagcaaga aatgtccttg ttgagagtga acaccaagtg
3301 aaaattggag acttcggttt aaccaaagca attgaaaccg ataaggagta ttacaccgtc
3361 aaggatgacc gggacagccc tgtgttttgg tatgctccag aatttctaat gcaatctaaa
3421 ttttatattg cctctgacgt ctggtctttt ggagtcactc tgcatgagct gctgacttac
3481 tgtgattcag attctagtcc catggctttg ttcctgaaaa tgataggccc aacccatggc
3541 cagatgacga tcacaagact tgtgaatacg ttaaaagaag gaaaacgcct gccgtgccca
3601 cctaactgtc cagatgaggt ttatcaactt atgaggaaat gctgggaatt ccaaccatcc
3661 aatcggacaa gctttcagaa ccttattgaa ggatttgaag cacttttaaa ataagaagca
3721 tgaataacat ttaaattcca cagattatca agtccttctc ctgcaacaaa tgcccaagtc
3781 atttttttaaa aatttctaat gaaagaagtt tgtgttctgt ccaaaaagtc actgaactca
3841 tacttcagta catatacatg tataaggcac actgtagtgc ttaatatgtg tatggacttc
3901 ctctttaaat ttggtaccag taacttagtg acacataatg acaaccaaaa tatttgaaag
3961 cacttaagca ctcctccttg tggaaagaat ataccaccat ttcatctggc tagttcacca
4021 tcacaactgc attaccaaaa ggggattttt gaaaacgagg agttgaccaa aataatatct
4081 gaagatgatt gcttttccct gctgccagct gatctgaaat gttttgctgg cacattaatc
4141 atagataaag aaagattgat ggacttagcc ctcaaatttc agtatctata cagtactaga
4201 ccatgcattt taaaatatt agataccagg tagtatatat tgtttctgta caaaaatgac
4261 tgtattctct caccagtagg acttaaactt tgtttctcca gtggcttagc tcctgttcct
```

```
4321 ttgggtgatc actagcaccc attttgaga aagctggttc tacatgggg gatagctgtg 4381 gaatagataa tttgctgcat gttaattctc aagaactaag cctgtgccag tgctttccta 4441 agcagtatac ctttaatcag aactcattcc cagaacctgg atgctattac acatgctttt 4501 aagaaacgtc aatgtatatc cttttataac tctaccactt tggggcaagc tattccagca 4561 ctggttttga atgctgtatg caaccagtct gaataccaca tacgctgcac tgttcttaga 4621 gggtttccat acttaccacc gatctacaag ggttgatccc tgtttttacc atcaatcatc 4681 accctgtggt gcaacacttg aaagacccgg ctagaggcac tatggacttc aggatccact 4741 agacagtttt cagtttgctt ggaggtagct gggtaatcaa aaatgtttag tcattgattc 4801 aatgtgaacg attacggtct ttatgaccaa gagtctgaaa atcttttgt tatgctgttt 4861 agtattcgtt tgatattgtt acttttcacc tgttgagccc aaattcagga ttggttcagt 4921 ggcagcaatg aagttgccat ttaaatttgt tcatagccta catcaccaag gtctctgtgt 4981 caaacctgtg gccactctat atgcactttg tttactcttt atacaaataa atatactaaa 5041 gactttacat gca
```

The polypeptide sequence of human Jak 2 is depicted in SEQ ID NO: 3. The nucleotide sequence of human Jak 2 is shown in SEQ ID NO: 4. Sequence information related to Jak 2 is accessible in public databases by GenBank Accession numbers NP_04963 (for protein) and NM_004972.3 (for nucleic acid).

SEQ ID NO: 3 is the human wild type amino acid sequence corresponding to Jak2 (residues 1-1132):

```
   1 MGMACLTMTE MEGTSTSSIY QNGDISGNAN SMKQIDPVLQ VYLYHSLGKS EADYLTFPSG

61 EYVAEEICIA ASKACGITPV YHNMFALMSE TERIWYPPNH VFHIDESTRH NVLYRIRFYF

121 PRWYCSGSNR AYREGISRGA EAPLLDDFVM SYLFAQWRHD FVHGWIKVPV THETQEECLG

181 MAVLDMMRIA KENDQTPLAI YNSISYKTFL PKCIRAKIQD YHILTRKRIR YRFRRFIQQF

241 SQCKATARNL KLKYLINLET LQSAFYTEKF EVKEPGSGPS GEEIFATIII TGNGGIQWSR

301 GKHKESETLT EQDLQLYCDF PNIIDVSIKQ ANQEGSNESR VVTIHKQDGK NLEIELSSLR

361 EALSFVSLID GYYRLTADAH HYLCKEVAPP AVLENIQSNC HGPISMDFAI SKLKKAGNQT

421 GLYVLRCSPK DFNKYFLTFA VERENVIEYK HCLITKNENE EYNLSGTKKN FSSLKDLLNC

481 YQMETVRSDN IIFQFTKCCP PKPKDKSNLL VFRTNGVSDV PTSPTLQRPT HMNQMVFHKI

541 RNEDLIFNES LGQGTFTKIF KGVRREVGDY GQLHETEVLL KVLDKAHRNY SESFFEAASM

601 MSKLSHKHLV LNYGVCVCGD ENILVQEFVK FGSLDTYLKK NKNCINILWK LEVAKQLAWA

661 MHFLEENTLI HGNVCAKNIL LIREEDRKTG NPPFIKLSDP GISITVLPKD ILQERIPWVP

721 PECIENPKNL NLATDKWSFG TTLWEICSGG DKPLSALDSQ RKLQFYEDRH QLPAPKWAEL

781 ANLINNCMDY EPDFRPSFRA IIRDLNSLFT PDYELLTEND MLPNMRIGAL GFSGAFEDRD

841 PTQFEERHLK FLQQLGKGNF GSVEMCRYDP LQDNTGEVVA VKKLQHSTEE HLRDFEREIE

901 ILKSLQHDNI VKYKGVCYSA GRRNLKLIME YLPYGSLRDY LQKHKERIDH IKLLQYTSQI

961 CKGMEYLGTK RYIHRDLATR NILVENENRV KIGDFGLTKV LPQDKEYYKV KEPGESPIFW

1021 YAPESLTESK FSVASDVWSF GVVLYELFTY IEKSKSPPAE FMRMIGNDKQ GQMIVFHLIE

1081 LLKNNGRLPR PDGCPDEIYM IMTECWNNNV NQRPSFRDLA LRVDQIRDNM AG
```

SEQ ID NO: 4 is the human wild type nucleotide sequence corresponding to Jak2 (nucleotides 1-5285), wherein the underscored bolded "ATG" denotes the beginning of the open reading frame:

```
   1 ctgcaggaag gagagaggaa gaggagcaga aggggggcagc agcggacgcc gctaacggcc
  61 tccctcggcg ctgacaggct gggccggcgc ccggctcgct tgggtgttcg cgtcgccact
 121 tcggcttctc ggccggtcgg gcccctcggc ccgggcttgc ggcgcgcgtc ggggctgagg
 181 gctgctgcgg cgcagggaga ggcctggtcc tcgctgccga gggatgtgag tgggagctga
 241 gcccacactg gagggccccc gagggcccag cctggaggtc gttcagagcc gtgcccgtcc
 301 cggggcttcg cagaccttga cccgccgggt aggagccgcc cctgcgggct cgagggcgcg
 361 ctctggtcgc ccgatctgtg tagccggttt cagaagcagg caacaggaac aagatgtgaa
 421 ctgtttctct tctgcagaaa aagaggctct tcctcctcct cccgcgacgg caaatgttct
 481 gaaaaagact ctgcatggga atggcctgcc ttacgatgac agaaatggag ggaacatcca
 541 cctcttctat atatcagaat ggtgatattt ctggaaatgc caattctatg aagcaaatag
 601 atccagttct tcaggtgtat ctttaccatt cccttgggaa atctgaggca gattatctga
 661 cctttccatc tggggagtat gttgcagaag aaatctgtat tgctgcttct aaagcttgtg
 721 gtatcacacc tgtgtatcat aatatgtttg ctttaatgag tgaaacagaa aggatctggt
 781 atccacccaa ccatgtcttc catatagatg agtcaaccag gcataatgta ctctacagaa
 841 taagatttta ctttcctcgt tggtattgca gtggcagcaa cagagcctat cggcatggaa
 901 tatctcgagg tgctgaagct cctcttcttg atgactttgt catgtcttac ctctttgctc
 961 agtggcggca tgattttgtg cacggatgga taaaagtacc tgtgactcat gaaacacagg
1021 aagaatgtct tgggatggca gtgttagata tgatgagaat agccaaagaa aacgatcaaa
1081 ccccactggc catctataac tctatcagct acaagacatt cttaccaaaa tgtattcgag
1141 caaagatcca agactatcat attttgacaa ggaagcgaat aaggtacaga tttcgcagat
1201 ttattcagca attcagccaa tgcaaagcca ctgccagaaa cttgaaactt aagtatctta
1261 taaatctgga aactctgcag tctgccttct acacagagaa atttgaagta aaagaacctg
1321 gaagtggtcc ttcaggtgag gagatttttg caaccattat aataactgga aacggtggaa
1381 ttcagtggtc aagagggaaa cataaagaaa gtgagacact gacagaacag gatttacagt
1441 tatattgcga tttttcctaat attattgatg tcagtattaa gcaagcaaac caagagggtt
1501 caaatgaaag ccgagttgta actatccata gcaagatgg taaaaatctg gaaattgaac
1561 ttagctcatt aagggaagct ttgtctttcg tgtcattaat tgatggatat tatagattaa
1621 ctgcagatgc acatcattac ctctgtaaag aagtagcacc tccagccgtg cttgaaaata
1681 tacaaagcaa ctgtcatggc ccaatttcga tggattttgc cattagtaaa ctgaagaaag
1741 caggtaatca gactggactg tatgtacttc gatgcagtcc taaggacttt aataaatatt
1801 ttttgacttt tgctgtcgag cgagaaaatg tcattgaata taaacactgt tgattacaa
1861 aaaatgagaa tgaagagtac aacctcagtg ggacaaagaa gaacttcagc agtcttaaag
1921 atcttttgaa ttgttaccag atggaaactg ttcgctcaga caatataatt ttccagttta
1981 ctaaatgctg tccccaaag ccaaaagata aatcaaacct tctagtcttc agaacgaatg
2041 gtgtttctga tgtaccaacc tcaccaacat tacagaggcc tactcatatg aaccaaatgg
2101 tgtttcacaa aatcagaaat gaagatttga tatttaatga agccttggc caaggcactt
2161 ttacaaagat ttttaaaggc gtacgaagag aagtaggaga ctacggtcaa ctgcatgaaa
2221 cagaagttct tttaaaagtt ctggataaag cacacagaaa ctattcagag tctttctttg
```

-continued

```
2281  aagcagcaag tatgatgagc aagctttctc acaagcattt ggttttaaat tatggagtat
2341  gtgtctgtgg agacgagaat attctggttc aggagtttgt aaaatttgga tcactagata
2401  catatctgaa aaagaataaa aattgtataa atatattatg gaaacttgaa gttgctaaac
2461  agttggcatg ggccatgcat tttctagaag aaaacaccct tattcatggg aatgtatgtg
2521  ccaaaaatat tctgcttatc agagaagaag acaggaagac aggaaatcct cctttcatca
2581  aacttagtga tcctggcatt agtattacag ttttgccaaa ggacattctt caggagagaa
2641  taccatgggt accacctgaa tgcattgaaa atcctaaaaa tttaaatttg caacagaca
2701  aatggagttt tggtaccact ttgtgggaaa tctgcagtgg aggagataaa cctctaagtg
2761  ctctggattc tcaaagaaag ctacaatttt atgaagatag gcatcagctt cctgcaccaa
2821  agtgggcaga attagcaaac cttataaata attgtatgga ttatgaacca gatttcaggc
2881  cttctttcag agccatcata cgagatctta acagtttgtt tactccagat tatgaactat
2941  taacagaaaa tgacatgtta ccaaatatga ggataggtgc cctgggggttt tctggtgcct
3001  ttgaagaccg ggatcctaca cagtttgaag agagacattt gaaatttcta cagcaacttg
3061  gcaagggtaa ttttgggagt gtggagatgt gccggtatga ccctctacag gacaacactg
3121  gggaggtggt cgctgtaaaa aagcttcagc atagtactga agagcaccta agagactttg
3181  aaagggaaat tgaaatcctg aaatccctac agcatgacaa cattgtaaag tacaagggag
3241  tgtgctacag tgctggtcgg cgtaatctaa aattaattat ggaatattta ccatatggaa
3301  gtttacgaga ctatcttcaa aaacataaag aacggataga tcacataaaa cttctgcagt
3361  acacatctca gatatgcaag ggtatggagt atcttggtac aaaaaggtat atccacaggg
3421  atctggcaac gagaaatata ttggtggaga acgagaacag agttaaaatt ggagattttg
3481  ggttaaccaa agtcttgcca caagacaaag aatactaaa agtaaaagaa cctggtgaaa
3541  gtcccatatt ctggtatgct ccagaatcac tgacagagag caagttttct gtggcctcag
3601  atgtttggag ctttggagtg ttctgtatg aacttttcac atacattgag aagagtaaaa
3661  gtccaccagc ggaatttatg cgtatgattg gcaatgacaa acaaggacag atgatcgtgt
3721  tccatttgat agaacttttg aagaataatg gaagattacc aagaccagat ggatgcccag
3781  atgagatcta tatgatcatg acagaatgct ggaacaataa tgtaaatcaa cgcccctcct
3841  ttagggatct agctcttcga gtggatcaaa taagggataa catggctgga tgaaagaaat
3901  gaccttcatt ctgagaccaa agtagattta cagaacaaag ttttatattt cacattgctg
3961  tggactatta ttacacacat cattattata taaatcatga tgctagccag caaagatgtg
4021  aaaatatctg ctcaaaactt tcaaagttta gtaagttttt cttcatgagg ccaccagtaa
4081  aagacattaa tgagaattcc ttagcaagga tttttttaaaa agtttcttaa acattgtcag
4141  ttaacatcac tcttgtctgg caaaagaaaa aaaatagact ttttcaactc agcttttttga
4201  gacctgaaaa aattattatg taaattttgc aatgttaaag atgcacagaa tatgtatgta
4261  tagtttttac cacagtggat gtataatacc ttggcatctt gtgtgatgtt ttacacacat
4321  gagggctggt gttcattaat actgtttttct aattttttcca tagttaatct ataattaatt
4381  acttcactat acaaacaaat taagatgttc agataattga ataagtacct ttgtgtcctt
4441  gttcatttat atcgctggcc agcattataa gcaggtgtat acttttagct tgtagttcca
4501  tgtactgtaa atatttttca cataaaggga acaaatgtct agttttattt gtataggaaa
4561  tttccctgac cctaaataat acattttgaa atgaaacaag cttacaaaga tataatctat
4621  tttattatgg tttcccttgt atctatttgt ggtgaatgtg ttttttaaat ggaactatct
```

```
4681 ccaaattttt ctaagactac tatgaacagt tttcttttaa aattttgaga ttaagaatgc 4741 caggaatatt gtcatccttt gagctgctga ctgccaataa cattcttcga tctctgggat 4801 ttatgctcat gaactaaatt taagcttaag ccataaaata gattagattg ttttttaaaa 4861 atggatagct cattaagaag tgcagcaggt taagaattTt ttcctaaaga ctgtatattt 4921 gaggggtttc agaattttgc attgcagtca tagaagagat ttatttcctt tttagagggg 4981 aaatgaggta aataagtaaa aaagtatgct tgttaatttt attcaagaat gccagtagaa 5041 aattcataac gtgtatcttt aagaaaaatg agcatacatc ttaaatcttt tcaattaagt 5101 ataaggggtt gttcgttgtt gtcatttgtt atagtgctac tccactttag acaccatagc 5161 taaaataaaa tatggtgggt tttgtgtgtg tgtgtgtgtg tgtgtgtgtg tgtgtgtgtg 5221 tgttatttat acaaaactta aaatacttgc tgttttgatt aaaaagaaaa tagtttctta 5281 cttta
```

The polypeptide sequence of human Jak 3 is depicted in SEQ ID NO: 109. The nucleotide sequence of human Jak 3 is shown in SEQ ID NO: 110. Sequence information related to Jak 3 is accessible in public databases by GenBank Accession numbers NP_000206 (for protein) and NM_000215 (for nucleic acid). JAM is a downstream signaling partner of the IL-2 receptor common gamma chain, which is shared with the IL-2, -4, -7, -9, -15, and -21 receptors.

SEQ ID NO: 109 is the human wild type amino acid sequence corresponding to Jak3 (residues 1-1124):

```
   1 MAPPSEETPL IPQRSCSLLS TEAGALHVLL PARGPGPPQR LSFSFGDHLA EDLCVQAAKA

61 SGILPVYHSL FALATEDLSC WFPPSHIFSV EDASTQVLLY RIRFYFPNWF GLEKCHRFGL

121 RKDLASAILD LPVLEHLFAQ HRSDLVSGRL PVGLSLKEQG ECLSLAVLDL ARMAREQAQR

181 PGELLKTVSY KACLPPSLRD LIQGLSFVTR RRIRRTVRRA LRRVAACQAD RHSLMAKYIM

241 DLERLDPAGA AETFHVGLPG ALGGHDGLGL LRVAGDGGIA WTQGEQEVLQ PFCDFPEIVD

301 ISIKQAPRVG PAGEHRLVTV TRTDNQILEA EFPGLPEALS FVALVDGYFR LTTDSQHFFC

361 KEVAPPRLLE EVAEQCHGPI TLDFAINKLK TGGSRPGSYV LRRSPQDFDS FLLTVCVQNP

421 LGPDYKGCLI RRSPTGTFLL VGLSRPHSSL RELLATCWDG GLHVDGVAVT LTSCCIPRPK

481 EKSNLIVVQR GHSPPTSSLV QPQSQYQLSQ MTFHKIPADS LEWHENLGHG SFTKIYRGCR

541 HEVVDGEARK TEVLLKVMDA KHKNCMESFL EAASLMSQVS YRHLVLLHGV CMAGDSTMVQ

601 EFVHLGAIDM YLRKRGHLVP ASWKLQVVKQ LAYALNYLED KGLPHGNVSA RKVLLAREGA

661 DGSPPFIKLS DPGVSPAVLS LEMLTDRIPW VAPECLREAQ TLSLEADKWG FGATVWEVFS

721 GVTMPISALD PAKKLQFYED RQQLPAPKWT ELALLIQQCM AYEPVQRPSF RAVIRDLNSL

781 ISSDYELLSD PTPGALAPRD GLWNGAQLYA CQDPTIFEER HLKYISQLGK GNFGSVELCR

841 YDPLGDNTGA LVAVKQLQHS GPDQQRDFQR EIQILKALHS DFIVKYRGVS YGPGRQSLRL

901 VMEYLPSGCL RDFLQRHRAR LDASRLLLYS SQICKGMEYL GSRRCVHRDL AARNILVESE

961 AHVKIADFGL AKLLPLDKDY YVVREPGQSP IFWYAPESLS DNIFSRQSDV WSFGVVLYEL

1021 PTYCDKSCSP SAEFLRMMGC ERDVPALCRL LELLEEGQRL PAPPACPAEV HELMKLCWAP

1081 SPQDRPSFSA LGPQLDMLWS GSRGCETHAF TAHPEGKHHS LSFS
```

SEQ ID NO: 110 is the human wild type nucleotide sequence corresponding to Jak3 (nucleotides 1-5449), wherein the underscored bolded "ATG" denotes the beginning of the open reading frame:

```
   1 cacacaggaa ggagccgagt gggactttcc tctcgctgcc tcccggctct gcccgccctt
  61 cgaaagtcca gggtccctgc ccgctaggca agttgcactc atggcacctc caagtgaaga
 121 gacgcccctg atccctcagc gttcatgcag cctcttgtcc acggaggctg gtgccctgca
 181 tgtgctgctg cccgctcggg gccccgggcc ccccagcgc ctatctttct cctttgggga
 241 ccacttggct gaggacctgt gcgtgcaggc tgccaaggca agcggcatcc tgcctgtgta
 301 ccactccctc tttgctctgg ccacggagga cctgtcctgc tggttccccc cgagccacat
 361 cttctccgtg gaggatgcca gcacccaagt cctgctgtac aggattcgct tttacttccc
 421 caattggttt gggctggaga agtgccaccg cttcgggcta cgcaaggatt tggccagtgc
 481 tatccttgac ctgccagtcc tggagcacct ctttgcccag caccgcagtg acctggtgag
 541 tgggcgcctc cccgtgggcc tcagtctcaa ggagcagggt gagtgtctca gcctggccgt
 601 gttggacctg gccggatgg cgcgagagca ggcccagcgg ccgggagagc tgctgaagac
 661 tgtcagctac aaggcctgcc tacccccaag cctgcgcgac ctgatccagg gcctgagctt
 721 cgtgacgcgc aggcgtattc ggaggacggt gcgcagagcc ctgcgccgcg tggccgcctg
 781 ccaggcagac cggcactcgc tcatggccaa gtacatcatg gacctggagc ggctggatcc
 841 agccgggggcc gccgagacct tccacgtggg cctccctggg gcccttggtg gccacgacgg
 901 gctggggctg ctccgcgtgg ctggtgacgg cggcatcgcc tggacccagg gagaacagga
 961 ggtcctccag cccttctgcg actttccaga aatcgtagac attagcatca agcaggcccc
1021 gcgcgttggc ccggccggag agcaccgcct ggtcactgtt accaggacag acaaccagat
1081 tttagaggcc gagttcccag ggctgcccga ggctctgtcg ttcgtggcgc tcgtggacgg
1141 ctacttccgg ctgaccacgg actcccagca cttcttctgc aaggaggtgg caccgccgag
1201 gctgctggag gaagtggccg agcagtgcca cggcccccatc actctggact ttgccatcaa
1261 caagctcaag actgggggct cacgtcctgg ctcctatgtt ctccgccgca gccoccagga
1321 ctttgacagc ttcctcctca ctgtctgtgt ccagaacccc cttggtcctg attataaggg
1381 ctgcctcatc cggcgcagcc ccacaggaac cttccttctg gttggcctca gccgaccca
1441 cagcagtctt cgagagctcc tggcaacctg ctgggatggg gggctgcacg tagatggggt
1501 ggcagtgacc ctcacttcct gctgtatccc cagacccaaa gaaaagtcca acctgatcgt
1561 ggtccagaga ggtcacagcc cacccacatc atccttggtt cagccccaat cccaatacca
1621 gctgagtcag atgacatttc acaagatccc tgctgacagc ctggagtggc atgagaacct
1681 gggccatggg tccttcacca agatttaccg gggctgtcgc catgaggtgg tggatgggga
1741 ggcccgaaag acagaggtgc tgctgaaggt catggatgcc aagcacaaga actgcatgga
1801 gtcattcctg gaagcagcga gcttgatgag ccaagtgtcg taccggcatc tcgtgctgct
1861 ccacggcgtg tgcatggctg gagacagcac catggtgcag gaatttgtac acctgggggc
1921 catagacatg tatctgcgaa aacgtggcca cctggtgcca gccagctgga gctgcaggt
1981 ggtcaaacag ctggcctacg ccctcaacta tctggaggac aaaggcctgc ccatggcaa
2041 tgtctctgcc cggaaggtgc tcctggctcg ggagggggct gatgggagcc cgcccttcat
2101 caagctgagt gaccctgggg tcagcccgc tgtgttaagc ctggagatgc tcaccgacag
2161 gatccctgg gtggccccg agtgtctccg ggaggcgcag acacttagct tggaagctga
2221 caagtgggc ttcggcgcca cggtctggga agtgtttagt ggcgtcacca tgcccatcag
2281 tgccctggat cctgctaaga aactccaatt ttatgaggac cggcagcagc tgccggcccc
```

-continued

```
2341 caagtggaca gagctggccc tgctgattca acagtgcatg gcctatgagc cggtccagag 2401 gccctccttc cgagccgtca ttcgtgacct caatagcctc atctcttcag actatgagct 2461 cctctcagac cccacacctg gtgccctggc acctcgtgat gggctgtgga atggtgccca 2521 gctctatgcc tgccaagacc ccacgatctt cgaggagaga cacctcaagt acatctcaca 2581 gctgggcaag ggcaactttg gcagcgtgga gctgtgccgc tatgacccgc taggcgacaa 2641 tacaggtgcc ctggtggccg tgaaacagct gcagcacagc gggccagacc agcagaggga 2701 ctttcagcgg gagattcaga tcctcaaagc actgcacagt gatttcattg tcaagtatcg 2761 tggtgtcagc tatggcccgg gccgccagag cctgcggctg gtcatggagt acctgcccag 2821 cggctgcttg cgcgacttcc tgcagcggca ccgcgcgcgc ctcgatgcca gccgcctcct 2881 tctctattcc tcgcagatct gcaagggcat ggagtacctg gctcccgcc gctgcgtgca 2941 ccgcgacctg gccgcccgaa acatcctcgt ggagagcgag gcacacgtca agatcgctga 3001 cttcggccta gctaagctgc tgccgcttga caaagactac tacgtggtcc gcgagccagg 3061 ccagagcccc atttttctggt atgcccccga atccctctcg acaacatct tctctcgcca 3121 gtcagacgtc tggagcttcg ggtcgtcct gtacgagctc ttcacctact gcgacaaaag 3181 ctgcagcccc tcggccgagt tcctgcggat gatgggatgt gagcgggatg tccccgccct 3241 ctgccgcctc ttggaactgc tggaggaggg ccagaggctg ccggcgcctc ctgcctgccc 3301 tgctgaggtt cacgagctca tgaagctgtg ctgggcccct agcccacagg accggccatc 3361 attcagcgcc ctgggccccc agctggacat gctgtggagc ggaagccggg ggtgtgagac 3421 tcatgccttc actgctcacc cagagggcaa acaccactcc ctgtccttt catagctcct 3481 gcccgcagac ctctggatta ggtctctgtt gactggctgt gtgaccttag gcccggagct 3541 gcccctctct gggcctcaga ggccttatga gggtcctcta cttcaggaac accccatga 3601 cattgcattt gggggggctc ccgtggcctg tagaatagcc tgtggccttt gcaatttgtt 3661 aaggttcaag acagatgggc atatgtgtca gtggggctct ctgagtcctg gcccaaagaa 3721 gcaaggaacc aaatttaaga ctctcgcatc ttcccaaccc cttaagccct ggcccctga 3781 gtttccttt ctgtctctct cttttatt tttttatttt tatttttatt tttgagacag 3841 agcctcgctc tgttacccag ggtggagtgc agtggtgcga tctcggctca gtgcaacctc 3901 tgcttcccag gttcaagcga ttctcctgcc tcagcctccc gagtagctgg gattacaggt 3961 gtgcaccacc acacccggct aattttttt atttttaata gagatgaggt ttcaccatga 4021 tggccaggct gatctcgaac tcctaacctc aagtgatcct cccacctcag cctcccaaag 4081 tgttggaata ataggcatga gccactgcac ccaggctttt ttttttttaa atttattatt 4141 attatttta agagacagga tcttgctacg ttgcccaggc tggtcttgaa ctcctgggct 4201 acagtgatcc tcctgcctta tcctcctaaa tagctgggac tacagcacct agttttgagt 4261 ttcctgtctt atttccaatg gggacattca tgtagctttt ttttttttt ttttttgag 4321 acggagtctc gctctgtcgc ccaggctgga gtacagtggg gcaatctagg ctcactgcaa 4381 gctccgcctc ctgggttcac accattctct cgcctcagcc tcccaagtag ctgggactac 4441 aggcgcccgc caccacaccc ggctaatttt ttgtatttt agtagagacg gggtttcacc 4501 ttgttagcca ggatggtttc catctcctga cctcgtgatc tgcccgtctc ggcctcccaa 4561 agtgctggga ttacaggcat gagccactgc gccggccct catgtagctt taaatgtatg 4621 atctgacttc tgctccccga tctctgtttc tctggaggaa gccaaggaca agagcagttg 4681 ctgtggctgg gactctgcct tttaggggag cccgtgtatc tctttgggat cctgaaaggg 4741 ggcaggaaag gctggggtcc cagtccaccc taatggtatc tgagtgtcct agggcttcag
```

```
4801 ttttcccacc tgtccaatgg gacccttct gtcctcaccc tacaaggggc acaaagggat
4861 gacaccaaac ctggcaggaa cttttcacgc aatcaaggga aggaaaggca ttcctggcag
4921 agggaacagc atgccaagcg tgagaaggct cagagtaagg aggttaagag cccaagtatt
4981 ggagcctaca gttttgcccc ttccatgcag tgtgacagtg ggcaagttcc tttccctctc
5041 tgggtctcag ttctgtcccc tgcaaaatgg tcagagctta ccccttggct gtgcagggtc
5101 aactttctga ctggtgagag ggattctcat gcaggttaag cttctgctgc tcctcctcac
5161 ctgcaaagct tttctgccac ttttgcctcc ttggaaaact cttatccatc tctcaaaact
5221 ccagctacca catccttgca gccttccctc atatacccc actactactg tagccctgtc
5281 cttccctcca gcccctctct ggccctgggg ctggggaagt gtctgtgtcc agctgtctcc
5341 cctgacctca gggttccttg ggggctgggc tgaggcctca gtacagaggg ggctctggaa
5401 atgtttgttg actgaataaa ggaattcagt ggaaaaaaaa aaaaaaaaa
```

The polypeptide sequence of human Stat 1 is depicted in SEQ ID NO: 5. The nucleotide sequence of human Stat 1 is shown in SEQ ID NO: 6. Sequence information related to Stat 1 is accessible in public databases by GenBank Accession numbers ADA59516 (for protein) and GU211347.1 (for nucleic acid).

SEQ ID NO: 5 is the human wild type amino acid sequence corresponding to Stat1 (residues 1-750):

```
  1 MSQWYELQQL DSKFLEQVHQ LYDDSFPMEI RQYLAQWLEK QDWEHTANDV SFATIRFHDL

61 LSQLDDQYSR FSLENNFLLQ HNIRKSKRNL QDNFQEDPIQ MSMIIYSCLK EERKILENAQ

121 RFNQAQSGNI QSTVMLDKQK ELDSKVRNVK DKVMCIEHEI KSLEDLQDEY DFKCKTLQNR

181 EHETNGVAKS DQKQEQLLLK KMYLMLDNKR KEVVHKIIEL LNVTELTQNA LINDELVEWK

241 RRQQSACIGG PPNACLDQLQ NWFTIVAESL QQVRQQLKKL EELEQKYTYE HDPITKNKQV

301 LWDRTFSLFQ QLIQSSFVVE RQPCMPTHPQ RPLVLKTGVQ FTVKLRLLVK LQELNYNLKV

361 KVLFDKDVNE RNTVKGFRKF NILGTHTKVM NMEESTNGSL AAEFRHLQLK EQKNAGTRTN

421 EGPLIVTEEL HSLSFETQLC QPGLVIDLET TSLPVVVISN VSQLPSGWAS ILWYNMLVAE

481 PRNLSFFLTP PCARWAQLSE VLSWQFSSVT KRGLNVDQLN MLGEKLLGPN ASPDGLIPWT

541 RFCKENINDK NFPFWLWIES ILELIKKHLL PLWNDGCIMG FISKERERAL LKDQQPGTFL

601 LRFSESSREG AITFTWVERS QNGGEPDFHA VEPYTKKELS AVTFPDIIRN YKVMAAENIP

661 ENPLKYLYPN IDKDHAFGKY YSRPKEAPEP MELDGPKGTG YIKTELISVS EVHPSRLQTT

721 DNLLPMSPEE FDEVSRIVGS VEFDSMMNTV
```

SEQ ID NO: 6 is the human wild type nucleotide sequence corresponding to Stat1 (nucleotides 1-2353), wherein the underscored bolded "ATG" denotes the beginning of the open reading frame:

```
   1 gtgctgtgcg tagctgctcc tttggttgaa tccccaggcc cttgttgggg cacaaggtgg
  61 caggatgtct cagtggtacg aacttcagca gcttgactca aaattcctgg agcaggttca
 121 ccagctttat gatgacagtt ttcccatgga aatcagacag tacctggcac agtggttaga
 181 aaagcaagac tgggagcaca ctgccaatga tgtttcattt gccaccatcc gttttcatga
 241 cctcctgtca cagctggatg atcaatatag tcgcttttct ttggagaata acttcttgct
 301 acagcataac ataaggaaaa gcaagcgtaa tcttcaggat aattttcagg aagacccaat
 361 ccagatgtct atgatcattt acagctgtct gaaggaagaa aggaaaattc tggaaaacgc
 421 ccagagattt aatcaggctc agtcggggaa tattcagagc acagtgatgt tagacaaaca
 481 gaaagagctt gacagtaaag tcagaaatgt gaaggacaag gttatgtgta tagagcatga
 541 aatcaagagc ctggaagatt tacaagatga atatgacttc aaatgcaaaa ccttgcagaa
 601 cagagaacac gagaccaatg gtgtggcaaa gagtgatcag aaacaagaac agctgttact
 661 caagaagatg tatttaatgc tagacaaaca gagaaaggaa gtagttcaca aaataataga
 721 gttgctgaat gtcactgaac ttacccagaa tgccctgatt aatgatgaac tagtggagtg
 781 gaagcggaga cagcagagcg cctgtattgg ggggccgccc aatgcttgct tggatcagct
 841 gcagaactgg ttcactatag ttgcggagag tctgcagcaa gttcggcagc agcttaaaaa
 901 gttggaggaa ttgaacagaa atacaccta cgaacatgac cctatcacaa aaacaaaca
 961 agtgttatgg gaccgcacct tcagtctttt ccagcagctc attcagagct cgtttgtggt
1021 ggaaagacag ccctgcatgc caacgcaccc tcagaggccg ctggtcttga agacaggggt
1081 ccagttcact gtgaagttga ctgttggt gaaattgcaa gagctgaatt ataatttgaa
1141 agtcaaagtc ttatttgata agatgtgaa tgagagaaat acagtaaaag gatttaggaa
1201 gttcaacatt ttgggcacgc acacaaaagt gatgaacatg gaggagtcca ccaatggcag
1261 tctggcggct gaatttcggc acctgcaatt gaaagaacag aaaaatgctg gcaccagaac
1321 gaatgagggt cctctcatcg ttactgaaga gcttcactcc cttagttttg aaacccaatt
1381 gtgccagcct ggtttggtaa ttgacctcga gacgacctct ctgcccgttg tggtgatctc
1441 caacgtcagc cagctcccga gcggttgggc ctccatcctt tggtacaaca tgctggtggc
1501 ggaacccagg aatctgtcct tcttcctgac tccaccatgt gcacgatggg ctcagctttc
1561 agaagtgctg agttggcagt tttcttctgt caccaaaaga ggtctcaatg tggaccagct
1621 gaacatgttg ggagagaagc ttcttggtcc taacgccagc cccgatggtc tcattccgtg
1681 gacgaggttt tgtaaggaaa atataaatga taaaattttt ccccttctggc tttggattga
1741 aagcatccta gaactcatta aaaaacacct gctccctctc tggaatgatg ggtgcatcat
1801 gggcttcatc agcaaggagc gagagcgtgc cctgttgaag gaccagcagc cggggacctt
1861 cctgctgcgg ttcagtgaga gctcccggga aggggccatc acattcacat gggtggagcg
1921 gtcccagaac ggaggcgaac ctgacttcca tgcggttgaa ccctacacga gaaagaact
1981 ttctgctgtt actttccctg acatcattcg caattacaaa gtcatggctg ctgagaatat
2041 tcctgagaat cccctgaagt atctgtatcc aaatattgac aaagaccatg cctttggaaa
2101 gtattactcc aggccaaagg aagcaccaga gccaatggaa cttgatggcc taaaggaac
2161 tggatatatc aagactgagt tgatttctgt gtctgaagtt caccctttcta gacttcagac
2221 cacagacaac ctgctcccca tgtctcctga ggagtttgac gaggtgtctc ggatagtggg
```

```
2281 ctctgtagaa ttcgacagta tgatgaacac agtatagagc atgaattttt ttcatcttct 2341 ctggcgacag ttt
```

The polypeptide sequence of human Stat 2 is depicted in SEQ ID NO: 7. The nucleotide sequence of human Stat 2 is shown in SEQ ID NO: 8. Sequence information related to Stat 2 is accessible in public databases by GenBank Accession numbers AAA98760 (for protein) and U18671.1 (for nucleic acid).

SEQ ID NO: 7 is the human wild type amino acid sequence corresponding to Stat2 (residues 1-851):

```
  1 MAQWEMLQNL DSPFQDQLHQ LYSHSLLPVD IRQYLAVWIE DQNWQEAALG SDDSKATMLF
 61 FHFLDQLNYE CGRCSQDPES LLLQHNLRKF CRDIQPFSQD PTQLAEMIFN LLLEEKRILI
121 QAQRAQLEQG EPVLETPVES QQHEIESRIL DLRAMMEKLV KSISQLKDQQ DVFCFRYKIQ
181 AKGKTPSLDP HQTKEQKILQ ETLNELDKRR KEVLDASKAL LGRLTTLIEL LLPKLEEWKA
241 QQQKACIRAP IDHGLEQLET WFTAGAKLLF HLRQLLKELK GLSCLVSYQD DPLTKGVDLR
301 NAQVTELLQR LLHRAFVVET QPCMPQTPHR PLILKTGSKF TVRTRLLVRL QEGNESLTVE
361 VSIDRNPPQL QGFRKFNILT SNQKTLTPEK GQSQGLIWDF GYLTLVEQRS GGSGKGSNKG
421 PLGVTEELHI ISFTVKYTYQ GLKQELKTDT LPVVIISNMN QLSIAWASVL WENLLSPNLQ
481 NQQFFSNPPK APWSLLGPAL SWQFSSYVGR GLNSDQLSML RNKLFGQNCR TEDPLLSWAD
541 FTKRESPPGK LPFWTWLDKI LELVHDHLKD LWNDGRIMGF VSRSQERRLL KKTMSGTFLL
601 RFSESSEGGI TCSWVEHQDD DKVLIYSVQP YTKEVLQSLP LTEIIRHYQL LTEENIPENP
661 LRFLYPRIPR DEAFGCYYQE KVNLQERRKY LKHRLIVVSN RQVDELQQPL ELKPEPELES
721 LELELGLVPE PELSLDLEPL LKAGLDLGPE LESVLESTLE PVIEPTLCMV SQTVPEPDQG
781 PVSQPVPEPD LPCDLRHLNT EPMEIFRNCV KIEEIMPNGD PLLAGQNTVD EVYVSRPSHF
841 YTDGPLMPSD F
```

SEQ ID NO: 8 is the human wild type nucleotide sequence corresponding to Stat2 (nucleotides 1-18648), wherein the underscored bolded "ATG" denotes the beginning of the open reading frame:

```
  1 tcaagatcag cctgggcaac atggcgaaac cccgtctcta caataaatac aaaaaaatta
 61 tcctggcgga gttatgcacg ttgtagtccc aactacctgg gaggctgagg cgggagaatc
121 acctgagcct gggaggtcga ggctgcagcg agccgagatc ggccgctgca ttccagcctg
181 ggtgacagag cgagaccatg tctcaaaaaa taaaaattaa aaaaaaattg ttttcattac
241 ctcagccctc ctcttcctat cccaaggcgt cgaaattccg gtcccacccc ttcccatgga
301 gcccttggcg tctccaggct cctcaagcta gtttcggttc cgggctcacg cgcgggttct
361 cgaaaatcag ctgtttcagt cttgggctag tccactaatt ggactcctcc cctcgtagaa
421 agtgcctact tgaacttctc caccaatcgc tgaagctgca ggtgtggttt cggctcagct
481 tgtcccgccc tggcggaggg gcggagttgc ggcggcgcca gtgagctcgc agtctgggaa
541 gggcttgact gaatggcagc cagtgtcggg gtggcggctg gaatgggggg ccgctccgga
601 cttccgctgc caactacaag ggggcgggtc cgaggggggt tagccgaagt tgtaggcggg
661 gcgcgaggtt ctagtacccg agctcatact agggacggga agtcgcgacc agagccattg
721 gagggcgcgg ggactgcaac cctaatcagg tacgggccct gagagggtgt gctggggtag
781 gggtgggggt gagagtgaga gttcctccga gggaagggcg actgggccag ggttaccccc
```

-continued

```
 841 ctggagaggg tagcttcctt ccccagattg aaataggagc tgtcgcctgc tcggtcctcg
 901 atcttcttct gtccagccta tctccctaac cctaatgccc ctctcccaaa actgccctgc
 961 agcttccgag acccggaatc tggcattgtt atgttggttc ggtatctgac gttttccct
1021 ctgctctgca ttatttttta tcttcaccaa aaacgatgt tcaaagatag ataaatctaa
1081 aaacaaagat agataaatct attacccttg tttcgtaaaa agtataagct actgaaagat
1141 gaaacgattg cctaaggtca cacacaaaat tcagttcatt tcagaaaagc ttcttgagtg
1201 caaaatatgt gcctaagaat gagagataat gagaaaaaat tgtttcagcc ccttaacctc
1261 agtgtttgca atccatttgg ggagaccagg tttttttttt ttgttttcat atttgaatct
1321 ttgctgactt gctcctttaa tatcagacac ttaaatcctc agatgggact catcatattt
1381 tttttgagat ggaatcttca ctatgttgct caagcttggt ctgcaactcc tggctcaagc
1441 catcctctcg tcttgttggg cctctcgtct tgtgggcctg cacaaagtgc tgggattaca
1501 ggcatgagcc attcatgccc tgggcgcacc ttggattgcg atgtgtgtgt gttgtgaagc
1561 tttttttttt ggtatcataa aagcaataca gatacatagt tttaaaaatc aagcagctac
1621 taaaagagtt aaaatgaaaa tagcccctcc caatccctcc cttgttcctg ctggaggtag
1681 aaaggcagct gatgttattc atgttagtag aagactctcc caccccaagc atttctcttt
1741 attttgtaat aaaatcatgt gaccttttta gaccacaaat atgcatgaat tctgttctgt
1801 taggctcagg ctgcaacaag ataagtttca gtttcctaaa tagacaccag ctggcagtga
1861 gcagggaaca gtggggagaa agatgcatgg gacagcctgc ttggtgacag gcaaaaaccg
1921 gtttgttgtt cttttagaga cagagtcttg ctttgtcacc caggctgag tgtagtgatg
1981 tgatctctgc ttactgcaac cctgcctctg ggtacaagcc attctcctgc ctcagcctct
2041 tgagtagctg ggattacagg caacaatttt aagtgaagtg aagtttcagg atctcgagca
2101 aagttgtata acctataatc atattcaaga ttcacaggtc ataaacgtgt catattcttg
2161 ggattgagcg acccattgca cagcatttag atgtgcttct agaatggagc tcctccttcc
2221 tatatggagg gcagtttata tggtgtactt acctgaccac caaaaagatt tggctctaaa
2281 aaagcttcag gtggccgggc atggtggttc acccctgtaa tccagcactt tgggaggcag
2341 gtgggcagat cacctgaggt cagaagttca gacagctgga catatggtga aacctcatct
2401 ctactaaaaa tacaaaaatt agactgggca tggtagtggg cgcctgtaat cccagctagt
2461 cgggaggctg aggcaggaga atcccttcaa ctcggacggc agagtttgca gtgaggccga
2521 gatcgtgtca ctgcagtcca gcctgggtga cagagcaaga ctccatctca aaaaaagtaa
2581 aaaaaaaaaa aagaaaaaaa aaagcttcag agccagcagg gatcatgctg taataaatac
2641 ttaacatcaa cactgatctt taaatgcttt agcacaatca atataaata acaaacacac
2701 acataaatgc aaaataaatg aattagggag atagatgaaa taagattgtg gaaatagtaa
2761 tgtttgttaa agctggatgg tgatccttgt actattcact ctactctagt gtgtatttga
2821 aaattaccat taggctggtt atggtggctc atgcctgtta atcccggcat tttggaaggc
2881 tgaggcaggc ggattacttg agctcaggag tttagagtct gcctgggcaa catggcaaaa
2941 tcccatctct acaaaaaatt agctggcatg atggcacact cctatagtcc cagagtcttg
3001 aggggctgag gcagagaatg gcttgaacct gagaggctaa agctgcagtg agccaagatc
3061 atgccactgc actccagcct gggtgaccaa gtgagaccct gtctcaaaaa aaaaaaaaa
3121 aaaagaaaa gaaaattccc attaaagcac aaaggcccac ttattgaagc tattaaaata
3181 caggttgggg ccggctgggc atcgcgtcac gcctgtaatc ccagcacttt ggaaggccga
3241 ggtaggcgag tcacgagttc aggagatcga gaccatcctg gctaacacgg tgaaacccca
```

```
3301  tctctactaa aaatacaaaa aaaaaaatca gccgggcatg gtggcgggag cctatagtcc
3361  cagctactcg ggaggctgag gcaggagaat ggcatgagcc cgggaggcgg agcttgcagt
3421  gagccaaaat cacaccactg cactccagcc tgggcaacag atcgagactc catctgaaga
3481  aaaaaaaaat acaggttggg accacagtgg ctcatgcctg taatcctagt actttgggag
3541  tccgaagtag gtggatcacc tgaggtcagg actttgagac cagcctggcc aacatggcaa
3601  aaccctcatct ctactaaaaa atatacaaaa attagctggg cgtggtggtg ggtgcctgta
3661  atcccagcta ctcaggaggc tgaggcagaa gaatcacaac aaccaggggg atggtggttg
3721  caatgagcca agatcatctc cacttcactc cggcccaggc aaaagagtga gagtcatctt
3781  aaaaaaaaaa aaaaaaaaa aaaaaaaata cagattaggc attcctaatc tgaaaaattt
3841  ggctccaaaa tgctccagtc gagcatttcc tttgagtgtc atgtgggtgc tcaaaaagtt
3901  agattttttgg accatttttca gatttcagag ttttaaatta gggatgctcg actggtaagt
3961  aatcgagata ttccaaaaat ctggacaaat ctgaaatcca aaatgcttgg aatagcagat
4021  actcaactgg tagcactccc tggaagaata tgcaccaaac tgatagcagt ggttaccttc
4081  tggtgaggag gggaagaac caagattagc agtaggatca acatatattt taatgttttc
4141  tgtatttta ttacttgtat aatttaaaca ttttaaatta gtaataatga acaatcatga
4201  aactatggat gatttagtcc agcaaaatat ccaattggga accctcatcc ttctgcagag
4261  cccaaatggc gcagtgggaa atgctgcaga atcttgacag ccccttttcag gatcagctgc
4321  accagcttta ctcgcacagc ctcctgcctg tggacattcg acagtacttg gctgtctgga
4381  ttgaagacca gaactggtga ggccttcagg aagttggggg aatgaaaaag gtggccttcc
4441  acttctgggc ccccgggatc ctggaatcat taatggcagg aaggggttgg aaagcctcag
4501  gactacagta acactgcaga gacactaata cttcttattc ctggtcccag gcaggaagct
4561  gcacttggga gtgatgattc caaggctacc atgctattct tccacttctt ggatcagctg
4621  aactatgagt gtggccgttg cagccaggac ccagagtcct tgttgctgca gcacaatttg
4681  cggaaattct gccgggacat tcaggtactt ggaacggttg ggagtgatgg ggtagcactg
4741  ggagcagagc atagaggagt aaggtttgga gaatagaata gtacctggag gtggcaaggg
4801  agacgggaac aaatgtgggg aaaggaggac agagtctgga cttggggaat cactagcaga
4861  gagaagggtt gcatatacgt gacactgttg ggaggatgct atggtgaaaa gacaaaaggc
4921  taagaacccc gaaggaggag gaaatactgt ggacattggt ggggagggtc tagggcaata
4981  ggtcattgag agtggttgaa ttggatcaat cctttctgtt tacctttctg ttagcccttt
5041  tcccaggatc ctacccagtt ggctgagatg atctttaacc tccttctgga aaaaaaaaa
5101  attttgatcc aggctcagag ggcccaattg gtgaggacaa ttcagtggta atgttggaaa
5161  ctcctgaagt agagaggaac catggaaagg actcagggag ttgtctcaga acaggatccc
5221  cccgacatcc tgtggtataa tttcaggcct gaacttaagg catgaaaggc cagagttaaa
5281  acgtgctcag agcctctttt ttcaggaaca aggagagcca gttctcgaaa cacctgtgga
5341  gagccagcaa catgagattg aatcccggat cctggattta agggctatga tggaggttag
5401  tagatgtggt aggagttagg gttgacagtt tcagcctaa cacctccctg agaagcagcc
5461  tcatcggggt cctctcccct ctgcagaagc tggtaaaatc catcagccaa ctgaaagacc
5521  agcaggatgt cttctgcttc cgatataaga tccaggccaa aggtaggaag cacattgagg
5581  ggctggagaa agataagtgc ctgctgagaa gccggagctg gaagtgaaca ggagaaagct
5641  ccgatgagca gtagtcactg tcagacacac cccactgact acagtcctgc tgccgtgcaa
```

-continued

```
5701  agctggaatc gtgctttgtg gaggctgagc tggaggtgac agctgagaga cagtaaattg
5761  ttgaggaaat gcatggaaaa ctaacagtgt tttatttgag ggggtgtctg gtccaagatg
5821  accacttcag aatttgcctg gagggtccca caggtgcctg tgctttgctt ggtttcccct
5881  tcttcctccg ccacaaaatt cctccttcct gactctgact gagacccag tcaggaagga
5941  gaggaaagaa cccctggact gactcctgtt cccaccatcc agggaagaca ccctctctgg
6001  accccccatca gaccaaagag cagaagattc tgcaggaaac tctcaatgaa ctggacaaaa
6061  ggagaaaggt gggaggcagc agaacagaac atgtgggcaa caaggacctg aaaaaatgag
6121  ggatgttggg aaccctggta atctagcgct ggcttctttc tttcttcatc cccagttggg
6181  tggtggaggg tgaaagggag agatgctcaa cactcacatt atctctttcc caggaggtgc
6241  tggatgcctc caaagcactg ctaggccgat taactaccct aatcgagcta ctgctgccaa
6301  agttggagga gtggaaggcc cagcagcaaa aagcctgcat cagagctccc attgaccacg
6361  ggttggaaca gctggagaca tggtgagagg taccacccca accctcgtcc tcgccatgcg
6421  ctgtgatttg taagttgcag tgccctgcat atagcaagag atactgttct ctatttgtct
6481  ctgctcccca gaatagagcc ctgctccctg cctgactgca gctctattct gcctcctcag
6541  cctcaccacg cagggaagcc cagaagtccc agtctccttc agggaaagga atgaattaac
6601  ccacaatctg gttttgcttc tttttttttaa tcacccagaa atatatatat atgtattttt
6661  tttttactgc aacgaataca atgacaagaa aggaagggaa ggaaggaagg aagagaaaat
6721  tacctattac ctagcttatt aaacaaaaat ggaatcatat tgtccatact attttgaaat
6781  ccatggggtt ttttttaagc ttaacagtat tttatatata tatatatata tatatatata
6841  tatatatata tatatatata tatttttttt tttttttttt tttttgagac g
6901  gagtctctct ctgttccctg gctggcggag cggagtcggc acgatctcag ctcactgcaa
6961  cttccaactc ccacggttca agccaattct cctgtctcag cctcccgagc tgggattac
7021  caggcacaca ccagcctggc tagttttttt gatttttag tagagacgat gtttctccat
7081  gttggccagg ctggtctcaa actcctgact tcaggtgatc cacccaactt gggctcccaa
7141  agtgctggga ttacaggcgt gacgaccatg cccggccaac agtatattat atttatccat
7201  gttatttctt atgtccacac aacagtcccc tatatggtgg taacataatt taattaatga
7261  actcctattt tcagctattt aggttatttt caatttcttg ttacctttg ccaggaaacg
7321  tatattttat ggtaattata ttgtgttgta gaaaaatcac tagtctagtc caacttgctt
7381  gaaaaatagc tactttttaa ctatttctc atttaaaaat ttattataat ttagtcttt
7441  agaaatatac caggccaggc atggcgtctc atgcctgtta tcctagtact ttggaaggct
7501  gaggacggag gatcacttca gtcttgggt ttgagaccag cccgggaaac ataacaagac
7561  cccatctcta caaaaaaaaa aaattgtttt taattaggca tgtccgacac agtggctcac
7621  acatgtggcc agcactgtgg gaaggccaag gtgggtggat cacttgaggg tcaggagttc
7681  aagaccagcc tggccaatgt ggtgaaaccc catctctact aaaaatacaa aaatttgcca
7741  ggtgtggtgg cgcatgcctg tattcccagc tactcaggag gctaaggcag gaaatcactt
7801  gaactcggag gcagaggttg cagtgagctg tgacaatgcc actgtactcc agcctgggtg
7861  acagagcgag ctccgtctca aaaaaaaaaa aaaagatta ggcatggtgg cacacgcctg
7921  tagaccctag ctactcagga ggctgaggtg ggaggattgc ttgagcccag gtgttggagg
7981  ctgcagtgag ccatgattat accactgtag tccagcctgg acaacagaac gagaccctgt
8041  ctctaaaagt atatatgtac acataccata atacccagct actgaggagg ctgaggcaga
```

-continued

```
8101  aagagtgctt gagtccagga gtttgatgtc agcctgagca atatagcaag accctcacct
8161  cttaaaaaaa tttaaagtag attaaaaaaa taccacaatt gctcaggtag attaaaaaaa
8221  taccacaatt gctcaggtag attattgaaa acaggcata  tagtacttat ggtacaggac
8281  cagcatgcat gcatgcatgc attgattgat tgattgattg attgattgag acagggtctc
8341  tctctgtctc ccaggctgga gtgcctggcc ttaagtgatc tgcccacctt gcttcccaa
8401  agtgctgaga ttacaggtgt gagccaccat gtcagctggc gaggcttttt aaaagatagt
8461  tccaagtgtt acagctcttt taggatttgt ctagcaggct ttcaggtttt tgccagaaac
8521  caccccccacc cccaccaaaa aaaaaaaaaa aaaaaagata tgtacaagtt cccagatagt
8581  gttcccaact gaatctattt ctcatgtgta gtgtatggtt gttttcctgt caccacattg
8641  ctgattatta ttatttttaa ttatagagac agtaaagtac agtagttaaa aatgtgagtt
8701  ggggctgggt gcagtggctc acacctgtaa tcccagcact ttgggaggcc aaggtgggcg
8761  gatcacctga ggtcaggagt tcaagaccag cttggccaac atggcaaaac cccgtctcga
8821  ctaaaaatat atatatataa gttagccggg cgtggtggca acattacctg taatcccagc
8881  tactcgggag gccaacaggc aggagaatct cttgaatcca ggaggtggag gttgcagtga
8941  gccagatcac accattgcac tccagcctgg atgacaagag agtgagactg tctaaaaaaa
9001  aaaaacaaag tgtgagttgt acaatgagac tgcctgggat cacatacaag cttcatccct
9061  tactagttgt attgaccctaa agcaagtca  ctaacctttc tgtgccctcc agttttatca
9121  tctgtaatgt ggggaaaata atagtacctg cctcagaggg ttgttttgag gattaaatgc
9181  attaatatgt ggaaagggct taatataagt tgtacatagc atatgaaaac tgttatgtta
9241  aatctattag cagttttata tgtgaaaata gctttgattt tcatttcttg gattatgaat
9301  catgttgaat aatcctttat atgcttcctg gattcttttt ttttcttccc cccagtcagt
9361  ttctgactct tctcatattt atagagagat cttggaacct ggatggggga atccaggaaa
9421  ctcatggatt ccttcttcct gaattttatc acccaggttc acagctggag caaagctgtt
9481  gtttcacctg aggcagctgc tgaaggagct gaagggactg agttgcctgg ttagctatca
9541  ggatgaccct ctgaccaaag gggtggacct acgcaacgcc caggtcacag agttgctaca
9601  gcgtctgctc cacaggtcta gaggccaggc aggaaccctg ggggaaagaa ggaacaaggg
9661  aagccattct tacacatact gagctatata ttctctccac acctctctct cctcgagcct
9721  ttgtggtaga aacccagccc tgcatgcccc aaactcccca tcgacccctc atcctcaaga
9781  ctggcagcaa gttcaccgtc cgaacaaggt tggcattcca gaactcattc ccacttcctt
9841  tttccaaccc tgccactgtg tattttctgg ctttacagct actgcccact cttggctttt
9901  tcagtctttc ctgaatctcc ctacctcgtt gatacccccat cgtcctcttt ttcaaacacc
9961  tagcctataca aaagccgact ccgaccaca  tttccctata cccccttgact tccccaggct
10021 gctggtgaga ctccaggaag gcaatgagtc actgactgtg gaagtctcca ttgacaggta
10081 aattggagca ggtgaagggt ggccaggaca cgggctgctg gggtggagga gatactcact
10141 cttcacaaca gggccctagg gctatatcct tcctccttcc aatcctacct cacagaaatt
10201 ataattcatt tcttttgttg aacacttact ttgtgacatg cagcatgtca gctactcatt
10261 taattgtcac accaacccca tgaataaact attaccagtg cactgtacaa acaaagatac
10321 aggcttagag agactgatta catctcttct caaggccaca tagctagtga gctcaagtcg
10381 ggtttgaacc gaggtctgtc tgatcccaaa gacgaaactc taacttccaa tactcttttg
10441 cccaatgatt ttttttaaat ttatttcttt tcaggaatcc tcctcaatta caagggtagg
```

-continued

```
10501  tgcttgacaa ggacactgca aacatctgta cagtgtatga cctgcagaac cggggga ttt
10561  gggaaatgga caaagggaga tggcgagatc tgaaatggaa gtggaacttc agttttttt t
10621  ttttctgctg agtttttaca ataattccat tccttgtctc catgtatctt cctcctgga a
10681  cagcttccgg aagttcaaca ttctgacttc aaaccagaaa actttgaccc ccgagaagg g
10741  gcagagtcag ggtttgattt gggactttgg ttacctggta agaatagttt gtgacctat g
10801  cttttattac tattttatt ttttcgagac ggagtctcac tctgtccccc aggctggag t
10861  gcagtggtgc catcttggct cacaggaacc tccgccctcc ccggttcaag caattcttc t
10921  gtctcagcct cctgagtacg tagagctata gcagcacac caccatgccc ggctaatt tt
10981  tgtatttta gtagagatag ggtttcacca tattggtcgg gctggtctcg aactcctga c
11041  ctcaggtgat ccgacccgcc tcagcctccc aaagtgctgg gatcacaggc atgagccac c
11101  atagctggcc tgcttttagt ccaaaggaac aggggttggg ggaagttccc agggcttga g
11161  aggtcttgaa gccaaacagg ggttccaggg agactagggt gcccactctg gcattttct c
11221  tccttccctt caattcacag actctggtgg agcaacgttc aggtggttca ggaaagggc a
11281  gcaataaggt gagatctgga cagaggactc gaggcagggg gagcttgcca aagagcctt c
11341  tgatgactat gtctttgcct gtcccagagg ggccactagg tgtgacagag gaactgcac a
11401  tcatcagctt cacggtcaaa tatacctacc agggtctgaa gcaggagctg aaagtgagt g
11461  aaaatggagg gcaaggagag agaaagcagc tttggaagaa ggcataagaa ggggataaa c
11521  agaagcctct tggggagggt tagcactcct ttcctctaac aaatacctgc agctagaaa c
11581  atcacatccc tctctgtgac tcctgtcttc tccccacaca cggacaccct ccctgtggt g
11641  attatttcca acatgaacca gctctcaatt gcctgggctt cagttctctg gttcaattt g
11701  ctcagcccaa accttcaggt aggggagtgg ggccgacagg tcccggcgcg agagcaggg g
11761  tgtggaagct tggtgtgata ggttgcttct gagccagcct acactgctcc caccccctgc a
11821  gaaccagcag ttcttctcca acccccccaa ggcccctgg agcttgctgg gccctgctc t
11881  cagttggcag ttctcctcct atgttggccg aggcctcaac tcagaccagc tgagcatgc t
11941  gagaaacaag ctgttcggta cagatttcct tttctctcag cctttcccca gccttagtc t
12001  tttctgtccc tctgtcctat ctatcccagg accctggct tccctcacat atctgtggc t
12061  atctgtccca cagggcagaa ctgtaggact gaggatccat tattgtcctg ggctgactt c
12121  actaaggtaa ctccctgaat cctgtggagc tgctggatct agccccacat tccaaatac t
12181  ggccttccca cgtgccctcc ttccctacac cagaggcaac tcctcagctt ttgctacct t
12241  tccattcctc cagcgagaga gccctcctgg caagttacca ttctggacat ggctggaca a
12301  aattctggag ttggtacatg accacctgaa ggatctctgg aatgatgggt aaggccttg g
12361  tcaccttcc ctcatgggct tgtgcttccg ggcttgagag tggagtctct gcaccctca c
12421  gtggcaagca gggagagaga gcaaagcacg gtgcaggcca cgtctcctca catttgtta a
12481  gaataataag gccgggtgtg gtggctcaca cctgtaatcc cagcactttg ggaggccga g
12541  gcgggcggat catgaggtca ggagatcgag accatcctgg ctaacacggt gaaaccccg t
12601  ctctactcta aaatacaaa aaattagccg ggcgtggagg cggacaccct gtagtccca g
12661  ctactcagga ggctgaggca ggaaaatggc gtgaacctgg gagatggagc ttgcagtga g
12721  ccgagattgc gtcactgccc tccagccttg gggtgacgta gcaagactcc gtctcaaaa a
12781  aaaaaaaaa aaacaaccaa taatagccat aaacagtgtt tttgtgaagc actcctaca t
12841  tccagagctt gatgggtgct cttcattaat tctctcatct catccttaca accatgctg a
```

-continued

```
12901  gtggtgggtt tgccagctt catttcatgt gaggaaactg agtttcagag aagttaaaga
12961  acttacccaa gggacacagt tgatattcaa atccaggcct atgtgactcc aagcccatgc
13021  tctttccacc acactgccta ccaacttgtg tagcatttgg cttttaaaag tgctattcat
13081  gaccaggcac gatggctcac gccttgtaat cctagcattt tgggaggccg aggtgggtgg
13141  atcacctgag gtcaggagtt tgagaccagc ctggccaaca tggcgaaacc ccatctctat
13201  taaaaataca aaaattagcc gggtgtggtg gtgggcgcct gtaatcccag ctactcagga
13261  ggctgaggag gagaatcgct tgaatttagg agagaaggtt acagtgagcc aagatcgtgc
13321  cattgcactc cagcctgggt gacagagcaa gactctgtct caaaacaaaa ccaaaaaaaa
13381  gtgctatttg tggccaggcg tggttgctca tgcctgtaat cctagcattt tggggaggc
13441  tgaggagtac agatcacttg agcccaggag ttcaaaacta ccctgggcca cgtggtgaaa
13501  ccccaaaccc cgtctctacg aaaaatacaa aagttagcca ggatgggtgg tgtgcacctg
13561  tggtcccagc tactctggag gctgagaggt ggggaagatt gcttgagccc gggaggtcga
13621  ggtggcagtg agctgtgatc atgccactat tctccagcct gggtgacaga atacaccctg
13681  tctccctgtc tcccagaaaa aaaaaaagt gctgttcatc tgtgtgatct cactgaatct
13741  tcgtacttca aaccctcgga aggtggctat tgtcagcaaa gtgaagtgac ttgtaaaaga
13801  taaaaaaaag ctaagtggca gggcttggtc caaagcctgg attccaaacc tgggctgttt
13861  ctccatacaa ggggagcagg gaggcagggg cctgggggg cagggtgttg ggcggtgtca
13921  cacgtgacac actgtgctcc agacgcatca tgggctttgt gagtcggagc caggagcgcc
13981  ggctgctgaa gaagaccatg tctggcacct ttctactgcg cttcagtgaa tcgtcagaag
14041  ggggcattac ctgctcctgg gtggagcacc aggatgatgg tagctgctct gccctgccat
14101  tcccacagcc tctcctttct gcctggctct cctctggccc ctctgcctgc cttgcttcgc
14161  tggctctgaa ctgaatgctc agtggtttgg gactgggcag ccagagagtc agagagctcc
14221  aaggcccggc ctcttccctc aagcccgcct gttcctgcat tcactctcca gacaaggtgc
14281  tcatctactc tgtgcaaccg tacacgaagg aggtgctgca gtcactcccg ctgactgaaa
14341  tcatccgcca ttaccagttg ctcactgagg agaatatacc tgaaaaccca ctgcgcttcc
14401  tctatccccg aatccccgg gatgaagctt ttgggtgcta ctaccaggag aaaggtggga
14461  atcgttgaca tacttcattg ctagattgca gagatctacc agacatccat agatcccact
14521  ccttccttta aagcatggga aaactgatat ctagaggaat taagggattc gtccatggga
14581  tactgctggt tactatgggg atgagactgc caggaccatc tgcactaggg aaaacctca
14641  ggctatatgt ctggcccact gatcttctct gcttcttgta tatgttcctc acagttaatc
14701  tccaggaacg gaggaaatac ctgaaacaca ggctcattgt ggtctctaat agagtgagat
14761  atgaactgtt cattcatcct ccctaatcct tattggctct gcttcagtga atcgtcaaaa
14821  gggggcatta ccttctcctg gtggagcac caggatgatg gtcagctgct ctgccctgcc
14881  attcccacag cctctccttt ctgccttctc ctaagctgcc cctattccag tctccccagc
14941  cttccctccc tcctagcccc actctagttt tttctggttc tagtctctcc tatctcatat
15001  ttttctgctg ccatccttag gttgtctcca caggggtttc tggataataa tgatcataat
15061  cactggtgtt aaggggtacc tacttgatgc aagcatggag cttttttttt ttccagacag
15121  ggttttgttc tgtcgcccag gctggagtgc agtggtgtga tcctggctca ctgaatgctc
15181  gacctcctga gctcaagcaa tacaggcatg catcaccaaa ctcagctaat ttttttttgta
15241  tttttagtag agatggggtc ttaccatgtt gacgcatcag gctgttctga actcctggac
```

-continued

```
15301  tcaagcaatc cacccacctt ggcctcccaa aagtcaggga ttacaggcgt gcgaccacac
15361  cccgcatata tatatttttt ttttttttt ttttttttt ttttgagac agggtctctg
15421  ttatccaggc tggagttgca gtggataata tgactacgag ccttgaccta ggggttgaag
15481  caatgctcct gcctcagcca ccaagtgctg agactacagg cacacgccaa tctacactca
15541  atcacactca gctaattttt taaattttt gtagggatgg ggtatcactg tgtttgccca
15601  ggctggtctt gaactcctgg cctcaagcag tctcctgcct tggcctccca aattgccggg
15661  attgtaggaa tgagccatgg cacttggctg ggggatagaa ttttttttt ttttttttt
15721  ttttttttt ttgagacagt ctcactctca ttgcccggggc tggagtgcag tggtgcaatt
15781  tcagctcact gcaacctctg cctcccaggc tcaagcaatt ctcctgcctc agcctataga
15841  gtagctggga ttacaggcga cgccaccca tgcctggtta attttgttt tttttttgag
15901  acagagtctc gccctgttgc ccaggctgga gtgcagtggc acgatctcag ctcactgcaa
15961  cctctgcctc ccaggctcaa gcaattctcc tgcctcagcc tcctgagtac tgggactaca
16021  agcgcgcaca accaccacac ctggtaattt ttttttttt agtagagaca gggttttacc
16081  atattggcca ggctggtctc aaactcctga cctcatgatc cgacccacct tggcctccca
16141  aagtgcaggg attacaggcg tgagcctctg cacccggcct aacttttgta tttttagtag
16201  aaacagggtt tcaccatgtt ggccaggctg gtcatgagct cctggcctca agtgatctgc
16261  ccgcctcagc ctcccaaagt gcttggatta caggtgtgag ccacctggcc tgagagttta
16321  ttatgcgcca ggcactaggc aaatggtttg catttatttt ctcattttat tgaatctaca
16381  aaatagtcct gtgaagtaaa cactgttact gttttcagct aaggaactgg atttagagta
16441  gtcaagtttt gtacctaagg tacgtggcta atgatacagg tctgttagat tccgtagccc
16501  tgattttaac caccctactg cctctcaaga attactaggt attgttctca tttatagatg
16561  ataaatctga ggctcagaaa agttaggcca cttgcctaag gtcccccagc caggattcaa
16621  actccaggag gcctgattcc aaacccatgc tctttagccc tccgccctac tgccttctta
16681  gactagcttc tgcttattct accattcctg atttcatttg aaccactgag ccctgcccct
16741  ttgtctgtct ttgggtatcc aggcaggtgg atgaactgca acaaccgctg gagcttaagc
16801  cagagccaga gctggagtca ttagagctgg aactagggct ggtgccagag ccagagctca
16861  gcctggactt agagccactg ctgaaggcag ggctggatct ggggccagag ctagagtctg
16921  tgctggagtc cactctggag cctgtgatag agcccacact atgcatggta tcacaaacag
16981  tgccagagcc agaccaagga cctgtatcac agccagtgcc agagccagat ttgccctgtg
17041  atctgagaca tttgaacact gagccaatgg aaagtaagtg atgagatgga gtggcacaca
17101  ttcccttccc tacctcttct ccctctccca ttacagaaaa agctgaactc caagctcctc
17161  attggagaga ggtccatctg tgattccttt ttttaggaat tacacatgcc ttcccccacc
17221  tccctgctct ttcatcccac aagttcccac tcaggctctt cccaggcctt cctgccatc
17281  ctccctccct tgggctgctg ggttgggaac tcctaactaa gatcggggcc tcacttttct
17341  ctctggatta cctagtcttc agaaactgtg taaagattga agaaatcatg ccgaatggtg
17401  acccactgtt ggctggccag aacaccgtgg atgaggttta cgtctcccgc cccagccact
17461  tctacactga tggacccttg atgccttctg acttctagga accacatttc ctctgttctt
17521  ttcatatctc tttgcccttc ctactcctca tagcatgata ttgttctcca aggatgggaa
17581  tcaggcatgt gtcccttcca agctgtgtta actgttcaaa ctcaggcctg tgtgactcca
17641  ttggggtgag aggtgaaagc ataacatggg tacagagggg acaacaatga atcagaacag
```

```
17701  atgctgagcc ataggtctaa ataggatcct ggaggctgcc tgctgtgctg ggaggtatag 17761  gggtcctggg ggcaggccag ggcagttgac aggtacttgg agggctcagg gcagtggctt 17821  ctttccagta tggaaggatt tcaacatttt aatagttggt taggctaaac tggtgcatac 17881  tggcattggc cttggtgggg agcacagaca caggatagga ctccatttct ttcttccatt 17941  ccttcatgtc taggataact tgctttcttc tttcctttac tcctggctca agccctgaat 18001  ttcttctttt cctgcagggg ttgagagctt tctgccttag cctaccatgt gaaactctac 18061  cctgaagaaa gggatggata ggaagtagac ctcttttct taccagtctc ctcccctact 18121  ctgcccccta agctggctgt acctgttcct cccccataaa atgatcctgc caatctaatg 18181  tgagtgtgaa gtttgcacac tagtttatgc tacctagtct ccactttctc aatgcttagg 18241  agacagatca ctcctggagg ctggggatgg taggattgct ggggattttt tttttttaa 18301  agagggtctc actctgttgc ccaggctaga gtgcaatggt gcaatcacag ctcactgcag 18361  cctcaacctc ctgggttcaa gcaatcctcc tacctcagcc tcctgggtag ctagcaccat 18421  ggcatcgcca ccatgcccta ttttttttt ttaaagacag ggtcttgcta tattgcccag 18481  gctggtcttg aactgggctc aagtgatcct cacgccttgc ctcccaaagt gctgggatta 18541  taggcatgag ccactgtgct tggccaggat tttttttttt tttttttga gatggagttt 18601  ctctcttgtt gtccaggctg gagtgcaatg gtgtgatccg gggaattc
```

Protein variants can include amino acid sequence modifications. For example, amino acid sequence modifications fall into one or more of three classes: substitutional, insertional or deletional variants. Insertions can include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture.

Nucleic acid sequences comprising a gene, such as a Jak1, Jak2, Jak3, Stat 1, and/or Stat 2 gene, that encodes a polypeptide can be synthesized, in whole or in part, using chemical methods known in the art. Alternatively, a polypeptide, such as a Jak1, Jak2, Jak3, Stat 1, and/or Stat 2, can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of Jak1, Jak2, Jak3, Stat 1, and/or Stat 2 polypeptides can be separately synthesized and combined using chemical methods to produce a full-length molecule.

As used herein, a Jak1, Jak2, Jak3, Stat 1, or Stat 2 "molecule" can be a nucleic acid which encodes a polypeptide that exhibits Jak1, Jak2, Jak3, Stat 1, and/or Stat 2 activity, or a polypeptide or peptidomimetic that exhibits Jak1, Jak2, Jak3, Stat 1, and/or Stat 2 activity. For example, a Jak1, Jak2, Jak3, Stat 1, or Stat 2 molecule can include the human Jak1, Jak2, Jak3, Stat 1, or Stat 2 protein, or a variant thereof, such as a fragment thereof, that exhibits Jak1, Jak2, Jak3, Stat 1, and/or Stat 2 activity. Jak1, Jak2, Jak3, Stat 1, and/or Stat 2 activity can encompass signaling events by way of type I cytokine receptors (e.g., IL-2, IL-4, IL-7, IL-9, IL-15, IL-21) that use the common gamma chain (γc). For example, Jak1, Jak2, Jak3, Stat 1, and/or Stat 2 activity can be a signal transduced in response to its activation via tyrosine phosphorylation by interleukin receptors.

The nucleic acid can be any type of nucleic acid, including genomic DNA, complementary DNA (cDNA), synthetic or semi-synthetic DNA, as well as any form of corresponding RNA. For example, a Jak1, Jak2, Jak3, Stat 1, or Stat 2 molecule can comprise a recombinant nucleic acid encoding human Jak1, Jak2, Jak3, Stat 1, or Stat 2 protein. In one embodiment, a Jak1, Jak2, Jak3, Stat 1, or Stat 2 molecule can comprise a non-naturally occurring nucleic acid created artificially (such as by assembling, cutting, ligating or amplifying sequences). A Jak1, Jak2, Jak3, Stat 1, or Stat 2 molecule can be double-stranded. A Jak1, Jak2, Jak3, Stat 1, or Stat 2 molecule can be single-stranded. The Jak1, Jak2, Jak3, Stat 1, and/or Stat 2 molecules of the invention can be obtained from various sources and can be produced according to various techniques known in the art. For example, a nucleic acid that is a Jak1, Jak2, Jak3, Stat 1, or Stat 2 molecule can be obtained by screening DNA libraries, or by amplification from a natural source. The Jak1, Jak2, Jak3, Stat 1, and/or Stat 2 molecules can be produced via recombinant DNA technology and such recombinant nucleic acids can be prepared by conventional techniques, including chemical synthesis, genetic engineering, enzymatic techniques, or a combination thereof. Non-limiting examples of a Jak1, Jak2, Jak3, Stat 1, or Stat 2 molecule that is a nucleic acid. Another example of a Jak1, Jak2, Jak3, Stat 1, or Stat 2 molecule is a fragment of a nucleic acid, wherein the fragment exhibits Jak1, Jak2, Jak3, Stat 1, and/or Stat 2 activity. A Jak1, Jak2, Jak3, Stat 1, or Stat 2 molecule of this invention also encompasses variants of the human nucleic acid encoding the Jak1, Jak2, Jak3, Stat 1, or Stat 2 protein, or variants of the human Jak1, Jak2, Jak3, Stat 1, or Stat 2 proteins that exhibit Jak1, Jak2, Jak3, Stat 1, and/or Stat 2 activity. A Jak1, Jak2, Jak3, Stat 1, or Stat 2 molecule can also include a fragment of the human Jak1, Jak2, Jak3, Stat 1, or Stat 2 nucleic acid which encodes a polypeptide that exhibits Jak1, Jak2, Jak3, Stat 1, and/or Stat 2 activity. A Jak1, Jak2, Jak3, Stat 1, or Stat 2 molecule can encompass a fragment of the human Jak1, Jak2, Jak3, Stat 1, or Stat 2 protein that exhibits Jak1, Jak2, Jak3, Stat 1, and/or Stat 2 activity.

A Jak1, Jak2, Jak3, Stat 1, or Stat 2 molecule can also encompass Jak1, Jak2, Jak3, Stat 1, or Stat 2 ortholog genes, which are genes conserved among different biological species such as humans, dogs, cats, mice, and rats, that encode proteins (for example, homologs (including splice variants), mutants, and derivatives) having biologically equivalent functions as the human-derived protein (such as a Jak3 protein). Jak1, Jak2, Jak3, Stat 1, or Stat 2 orthologs include any mammalian ortholog of Jak1, Jak2, Jak3, Stat 1, or Stat 2 inclusive of the ortholog in humans and other primates, experimental mammals (such as mice, rats, hamsters and guinea pigs), mammals of commercial significance (such as horses, cows, camels, pigs and sheep), and also companion mammals (such as domestic animals, e.g., rabbits, ferrets, dogs, and cats).

The Jak1, Jak2, Jak3, Stat 1, and Stat 2 variants can comprise, for instance, naturally-occurring variants due to allelic variations between individuals (e.g., polymorphisms), mutated alleles related to alopecia areata, or alternative splicing forms. In one embodiment, a Jak1, Jak2, Jak3, Stat 1, or Stat 2 molecule is a nucleic acid variant of the nucleic acid having the sequence shown in herein, wherein the variant has a nucleotide sequence identity to a corresponding sequence disclosed herein of about 65%, about 75%, about 85%, about 90%, about 91%, about 92%, about 93%, about 94%, about 95%, about 96%, about 97%, about 98%, or about 99%. In one embodiment, a Jak1, Jak2, Jak3, Stat 1, or Stat 2 molecule encompasses any portion of about 8 consecutive nucleotides of a corresponding sequence disclosed herein. In one embodiment, the fragment can comprise about 15 nucleotides, about 20 nucleotides, or about 30 nucleotides of a corresponding sequence disclosed herein. Fragments include all possible nucleotide lengths between about 8 and 100 nucleotides, for example, lengths between about 15 and 100, or between about 20 and 100.

The invention further provides for nucleic acids that are complementary to a nucleic acid encoding a Jak1, Jak2, Jak3, Stat 1, or Stat 2 protein. Such complementary nucleic acids can comprise nucleic acid sequences, which hybridize to a nucleic acid sequence encoding a Jak1, Jak2, Jak3, Stat 1, or Stat 2 protein under stringent hybridization conditions. Non-limiting examples of stringent hybridization conditions include temperatures above 30° C., above 35° C., in excess of 42° C., and/or salinity of less than about 500 mM, or less than 200 mM. Hybridization conditions can be adjusted by the skilled artisan via modifying the temperature, salinity and/or the concentration of other reagents such as SDS or SSC.

In one embodiment, a Jak1, Jak2, Jak3, Stat 1, or Stat 2 molecule comprises a protein or polypeptide encoded by a Jak1, Jak2, Jak3, Stat 1, or Stat 2 nucleic acid sequence, such as the corresponding sequence disclosed herein. In another embodiment, the polypeptide can be modified, such as by glycosylations and/or acetylations and/or chemical reaction or coupling, and can contain one or several non-natural or synthetic amino acids. An example of a Jak1, Jak2, Jak3, Stat 1, or Stat 2 molecule is the polypeptide having the amino acid sequence disclosed herein. In another embodiment, a Jak1, Jak2, Jak3, Stat 1, or Stat 2 molecule can be a fragment of a Jak1, Jak2, Jak3, Stat 1, or Stat 2 protein. For example, the Jak1, Jak2, Jak3, Stat 1, or Stat 2 molecule can encompass any portion of about 8 consecutive amino acids of the corresponding sequence disclosed herein. The fragment can comprise about 10 amino acids, a least about 20 amino acids, about 30 amino acids, about 40 amino acids, a least about 50 amino acids, about 60 amino acids, or about 75 amino acids of the corresponding sequence disclosed herein. Fragments include all possible amino acid lengths between about 8 and 100 about amino acids, for example, lengths between about 10 and 100 amino acids, between about 15 and 100 amino acids, between about 20 and 100 amino acids, between about 35 and 100 amino acids, between about 40 and 100 amino acids, between about 50 and 100 amino acids, between about 70 and 100 amino acids, between about 75 and 100 amino acids, or between about 80 and 100 amino acids.

In certain embodiments, the Jak1, Jak2, Jak3, Stat 1, or Stat 2 molecule includes variants of the human Jak1, Jak2, Jak3, Stat 1, or Stat 2 protein (comprising the corresponding sequence disclosed herein). Such variants can include those having at least from about 46% to about 50% identity to the corresponding sequence disclosed herein, or having at least from about 50.1% to about 55% identity to the corresponding sequence disclosed herein, or having at least from about 55.1% to about 60% identity to SEQ ID NO: 1, or having from about 60.1% to about 65% identity to the corresponding sequence disclosed herein, or having from about 65.1% to about 70% identity to the corresponding sequence disclosed herein, or having at least from about 70.1% to about 75% identity to the corresponding sequence disclosed herein, or having at least from about 75.1% to about 80% identity to the corresponding sequence disclosed herein, or having at least from about 80.1% to about 85% identity to the corresponding sequence disclosed herein, or having at least from about 85.1% to about 90% identity to the corresponding sequence disclosed herein, or having at least from about 90.1% to about 95% identity to the corresponding sequence disclosed herein, or having at least from about 95.1% to about 97% identity to the corresponding sequence disclosed herein, or having at least from about 97.1% to about 99% identity to the corresponding sequence disclosed herein.

Techniques for making substitution mutations at predetermined sites in DNA having a known sequence are well known, for example M13 primer mutagenesis and PCR mutagenesis. Amino acid substitutions can be single residues, but can occur at a number of different locations at once. In one non-limiting embodiment, insertions can be on the order of about from 1 to about 10 amino acid residues, while deletions can range from about 1 to about 30 residues. Deletions or insertions can be made in adjacent pairs (for example, a deletion of about 2 residues or insertion of about 2 residues). Substitutions, deletions, insertions, or any combination thereof can be combined to arrive at a final construct. The mutations cannot place the sequence out of reading frame and should not create complementary regions that can produce secondary mRNA structure. Substitutional variants are those in which at least one residue has been removed and a different residue inserted in its place.

Substantial changes in function or immunological identity are made by selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions that can produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

There can be minor variations in the amino acid sequences of the corresponding sequence disclosed herein for each of Jak1, Jak2, Jak3, Stat 1, and/or Stat 2. The variations in the amino acid sequence can be when the sequence maintains about 30%, about 40%, about 50%, about 60%, about 70%, about 75%, about 80%, about 90%, about 95%, or about 99% identity to the corresponding sequence disclosed herein. For example, conservative amino acid replacements can be utilized. Conservative replacements are those that take place within a family of amino acids that are related in their side chains, wherein the interchangeability of residues have similar side chains.

Genetically encoded amino acids are generally divided into families: (1) acidic amino acids are aspartate, glutamate; (2) basic amino acids are lysine, arginine, histidine; (3) nonpolar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) a group of amino acids having aliphatic-hydroxyl side chains, such as serine and threonine; (ii) a group of amino acids having amide-containing side chains, such as asparagine and glutamine; (iii) a group of amino acids having aliphatic side chains such as glycine, alanine, valine, leucine, and isoleucine; (iv) a group of amino acids having aromatic side chains, such as phenylalanine, tyrosine, and tryptophan; and (v) a group of amino acids having sulfur-containing side chains, such as cysteine and methionine. Useful conservative amino acids substitution groups are: valine-leucine-isoleucine, phenylalanine-tyrosine, lysine-arginine, alanine valine, glutamic-aspartic, and asparagine-glutamine.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

In another embodiment, the Jak1, Jak2, Jak3, Stat 1, or Stat 2 molecule encompasses a peptidomimetic which exhibits Jak1, Jak2, Jak3, Stat 1, or Stat 2 activity. A peptidomimetic is a small protein-like chain designed to mimic a peptide that can arise from modification of an existing peptide in order to protect that molecule from enzyme degradation and increase its stability, and/or alter the molecule's properties (e.g., modifications that change the molecule's stability or biological activity). These modifications involve changes to the peptide that cannot occur naturally (such as altered backbones and the incorporation of non-natural amino acids). Drug-like compounds can be developed from existing peptides. A peptidomimetic can be a peptide, partial peptide, or non-peptide molecule that mimics the tertiary binding structure or activity of a selected native peptide or protein functional domain (e.g., binding motif or active site). These peptide mimetics include recombinantly or chemically modified peptides.

In one embodiment, a Jak1, Jak2, Jak3, Stat 1, or Stat 2 molecule comprising the corresponding sequence disclosed herein, variants of such, or fragments thereof, can be modified to produce peptide mimetics by replacement of one or more naturally occurring side chains of the 20 genetically encoded amino acids (or D amino acids) with other side chains. This can occur, for instance, with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4,5-, 6-, to 7-membered heterocyclics. For example, proline analogs can be made in which the ring size of the proline residue is changed from 5 members to 4, 6, or 7 members. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include the furazanyl, ifuryl, imidazolidinyl imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics can also have amino acid residues that have been chemically modified by phosphorylation, sulfonation, biotinylation, or the addition or removal of other moieties. For example, peptidomimetics can be designed and directed to amino acid sequences encoded by a Jak1, Jak2, Jak3, Stat 1, or Stat 2 molecule comprising the corresponding sequence disclosed herein.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, *Ann. Rep. Med. Chem.* 24, 243-252, 1989). Certain peptidomimetic compounds are based upon the amino acid sequence of the peptides of the invention. Peptidomimetic compounds can be synthetic compounds having a three-dimensional structure (i.e. a peptide motif) based upon the three-dimensional structure of a selected peptide. The peptide motif provides the peptidomimetic compound with the desired biological activity, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life. Peptidomimetic design strategies are readily available in the art (see, e.g., Ripka & Rich (1998) *Curr. Op. Chem. Biol.* 2:441-452; Hruby et al. (1997) *Curr. Op. Chem. Biol.* 1:114-119; Hruby & Balse, (2000) *Curr. Med. Chem.* 9:945-970).

Cell Transfection

A eukaryotic expression vector can be used to transfect cells in order to produce proteins encoded by nucleotide sequences of the vector. Mammalian cells (such as isolated cells from the hair bulb; for example dermal sheath cells and dermal papilla cells) can contain an expression vector (for example, one that contains a gene encoding a Jak 1, Jak 2, Jak3, Stat 1 or Stat 2 protein or polypeptide) via introducing the expression vector into an appropriate host cell via methods known in the art.

A host cell strain can be chosen for its ability to modulate the expression of the inserted sequences or to process the expressed polypeptide encoded by a gene, such as a Jak 1, Jak 2, Jak3, Stat 1 or Stat 2 gene, in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

An exogenous nucleic acid can be introduced into a cell via a variety of techniques known in the art, such as lipofection, microinjection, calcium phosphate or calcium chloride precipitation, DEAE-dextran-mediated transfection, or electroporation. Electroporation is carried out at approximate voltage and capacitance to result in entry of the DNA construct(s) into cells of interest (such as cells of the end bulb of a hair follicle, for example dermal papilla cells or dermal sheath cells). Other transfection methods also include modified calcium phosphate precipitation, polybrene precipitation, liposome fusion, and receptor-mediated gene delivery.

Cells that will be genetically engineered can be primary and secondary cells obtained from various tissues, and include cell types which can be maintained and propagated in culture. Non-limiting examples of primary and secondary cells include epithelial cells (for example, dermal papilla cells, hair follicle cells, inner root sheath cells, outer root sheath cells, sebaceous gland cells, epidermal matrix cells), neural cells, endothelial cells, glial cells, fibroblasts, muscle cells (such as myoblasts) keratinocytes, formed elements of the blood (e.g., lymphocytes, bone marrow cells), and precursors of these somatic cell types.

Vertebrate tissue can be obtained by methods known to one skilled in the art, such a punch biopsy or other surgical methods of obtaining a tissue source of the primary cell type of interest. In one embodiment, a punch biopsy or removal can be used to obtain a source of keratinocytes, fibroblasts, endothelial cells, or mesenchymal cells (for example, hair follicle cells or dermal papilla cells). In another embodiment, removal of a hair follicle can be used to obtain a source of fibroblasts, keratinocytes, endothelial cells, or mesenchymal cells (for example, hair follicle cells or dermal papilla cells). A mixture of primary cells can be obtained from the tissue, using methods readily practiced in the art, such as explanting or enzymatic digestion (for examples using enzymes such as pronase, trypsin, collagenase, elastase dispase, and chymotrypsin). Biopsy methods have also been described in United States Patent Application Publication 2004/0057937 and PCT application publication WO 2001/32840, and are hereby incorporated by reference.

Primary cells can be acquired from the individual to whom the genetically engineered primary or secondary cells are administered. However, primary cells can also be obtained from a donor, other than the recipient, of the same species. The cells can also be obtained from another species (for example, rabbit, cat, mouse, rat, sheep, goat, dog, horse, cow, bird, or pig). Primary cells can also include cells from an isolated vertebrate tissue source grown attached to a tissue culture substrate (for example, flask or dish) or grown in a suspension; cells present in an explant derived from tissue; both of the aforementioned cell types plated for the first time; and cell culture suspensions derived from these plated cells. Secondary cells can be plated primary cells that are removed from the culture substrate and replated, or passaged, in addition to cells from the subsequent passages. Secondary cells can be passaged one or more times. These primary or secondary cells can contain expression vectors having a gene that encodes a protein of interest (for example, a Jak 1, Jak 2, Jak3, Stat 1 or Stat 2 protein or polypeptide).

Cell Culturing

Various culturing parameters can be used with respect to the host cell being cultured. Appropriate culture conditions for mammalian cells are well known in the art (Cleveland W L, et al., *J Immunol Methods*, 1983, 56(2): 221-234) or can be determined by the skilled artisan (see, for example, *Animal Cell Culture: A Practical Approach 2nd Ed.*, Rickwood, D. and Hames, B. D., eds. (Oxford University Press: New York, 1992)). Cell culturing conditions can vary according to the type of host cell selected. Commercially available medium can be utilized. Non-limiting examples of medium include, for example, Minimal Essential Medium (MEM, Sigma, St. Louis, Mo.); Dulbecco's Modified Eagles Medium (DMEM, Sigma); Ham's F10 Medium (Sigma); HyClone cell culture medium (HyClone, Logan, Utah); RPMI-1640 Medium (Sigma); and chemically-defined (CD) media, which are formulated for various cell types, e.g., CD-CHO Medium (Invitrogen, Carlsbad, Calif.).

The cell culture media can be supplemented as necessary with supplementary components or ingredients, including optional components, in appropriate concentrations or amounts, as necessary or desired. Cell culture medium solutions provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that can be required at very low concentrations, usually in the micromolar range.

The medium also can be supplemented electively with one or more components from any of the following categories: (1) salts, for example, magnesium, calcium, and phosphate; (2) hormones and other growth factors such as, serum, insulin, transferrin, and epidermal growth factor; (3) protein and tissue hydrolysates, for example peptone or peptone mixtures which can be obtained from purified gelatin, plant material, or animal byproducts; (4) nucleosides and bases such as, adenosine, thymidine, and hypoxanthine; (5) buffers, such as HEPES; (6) antibiotics, such as gentamycin or ampicillin; (7) cell protective agents, for example pluronic polyol; and (8) galactose. In one embodiment, soluble factors can be added to the culturing medium.

The mammalian cell culture that can be used with the present invention is prepared in a medium suitable for the type of cell being cultured. In one embodiment, the cell culture medium can be any one of those previously discussed (for example, MEM) that is supplemented with serum from a mammalian source (for example, fetal bovine serum (FBS)).

In another embodiment, the medium can be a conditioned medium to sustain the growth of epithelial cells or cells obtained from the hair bulb of a hair follicle (such as dermal papilla cells or dermal sheath cells). For example, epithelial cells can be cultured according to Barnes and Mather in *Animal Cell Culture Methods* (Academic Press, 1998), which is hereby incorporated by reference in its entirety. In a further embodiment, epithelial cells or hair follicle cells can be transfected with DNA vectors containing genes that encode a polypeptide or protein of interest (for example, a Jak 1, Jak 2, Jak3, Stat 1 or Stat 2 protein or polypeptide). In other embodiments of the invention, cells are grown in a suspension culture (for example, a three-dimensional culture such as a hanging drop culture) in the presence of an effective amount of enzyme, wherein the enzyme substrate is an extracellular matrix molecule in the suspension culture. For example, the enzyme can be a hyaluronidase. Epithelial cells or hair follicle cells can be cultivated according to methods practiced in the art, for example, as those described in PCT application publication WO 2004/044188 and in U.S. Patent Application Publication No. 2005/0272150, or as described by Harris in *Handbook in Practical Animal Cell Biology: Epithelial Cell Culture* (Cambridge Univ. Press, Great Britain; 1996; see Chapter 8), which are hereby incorporated by reference.

A suspension culture is a type of culture wherein cells, or aggregates of cells (such as aggregates of DP cells), multiply while suspended in liquid medium. A suspension culture comprising mammalian cells can be used for the maintenance of cell types that do not adhere or to enable cells to manifest specific cellular characteristics that are not seen in the adherent form. Some types of suspension cultures can include three-dimensional cultures or a hanging drop culture. A hanging-drop culture is a culture in which the material to be cultivated is inoculated into a drop of fluid attached to a flat surface (such as a coverglass, glass slide, Petri dish, flask, and the like), and can be inverted over a hollow surface. Cells in a hanging drop can aggregate toward the hanging center of a drop as a result of gravity. However, according to the methods of the invention, cells cultured in the presence of a protein that degrades the extracellular matrix (such as collagenase, chondroitinase, hyaluronidase, and the like) will become more compact and aggregated within the hanging drop culture, for degradation of the ECM will allow cells to become closer in proximity to one another since less of the ECM will be present. See also International PCT Publication No. WO2007/100870, which is incorporated by reference.

Cells obtained from the hair bulb of a hair follicle (such as dermal papilla cells or dermal sheath cells) can be cultured as a single, homogenous population (for example, comprising DP cells) in a hanging drop culture so as to generate an aggregate of DP cells. Cells can also be cultured as a heterogeneous population (for example, comprising DP and DS cells) in a hanging drop culture so as to generate a chimeric aggregate of DP and DS cells. Epithelial cells can be cultured as a monolayer to confluency as practiced in the art. Such culturing methods can be carried out essentially according to methods described in Chapter 8 of the *Handbook in Practical Animal Cell Biology: Epithelial Cell Culture* (Cambridge Univ. Press, Great Britain; 1996); Underhill C B, *J Invest Dermatol*, 1993, 101(6):820-6); in Armstrong and Armstrong, (1990) *J Cell Biol* 110:1439-55; or in *Animal Cell Culture Methods* (Academic Press, 1998), which are all hereby incorporated by reference in their entireties.

Three-dimensional cultures can be formed from agar (such as Gey's Agar), hydrogels (such as matrigel, agarose, and the like; Lee et al., (2004) *Biomaterials* 25: 2461-2466) or polymers that are cross-linked. These polymers can comprise natural polymers and their derivatives, synthetic polymers and their derivatives, or a combination thereof. Natural polymers can be anionic polymers, cationic polymers, amphipathic polymers, or neutral polymers. Non-limiting examples of anionic polymers can include hyaluronic acid, alginic acid (alginate), carageenan, chondroitin sulfate, dextran sulfate, and pectin. Some examples of cationic polymers, include but are not limited to, chitosan or polylysine. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73). Examples of amphipathic polymers can include, but are not limited to collagen, gelatin, fibrin, and carboxymethyl chitin. Non-limiting examples of neutral polymers can include dextran, agarose, or pullulan. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73).

Cells suitable for culturing according to methods of the invention can harbor introduced expression vectors, such as plasmids. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 2001, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

Obtaining and Purifying Polypeptides

A polypeptide molecule encoded by a gene, such as a Jak 1, Jak 2, Jak3, Stat 1, or Stat 2 gene, or a variant thereof, can be obtained by purification from human cells expressing a protein or polypeptide encoded by a Jak 1, Jak 2, Jak3, Stat 1, or Stat 2 gene via in vitro or in vivo expression of a nucleic acid sequence encoding a Jak 1, Jak 2, Jak3, Stat 1, or Stat 2 protein or polypeptide; or by direct chemical synthesis.

Detecting Polypeptide Expression.

Host cells which contain a nucleic acid encoding a Jak 1, Jak 2, Jak3, Stat 1, or Stat 2 protein or polypeptide, and which subsequently express a protein encoded by a Jak 1, Jak 2, Jak3, Stat 1, or Stat 2 gene, can be identified by various procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a nucleic acid encoding a Jak 1, Jak 2, Jak3, Stat 1, or Stat 2 protein or polypeptide can be detected by DNA-DNA or DNA-RNA hybridization or amplification using probes or fragments of nucleic acids encoding a Jak 1, Jak 2, Jak3, Stat 1, or Stat 2 protein or polypeptide. In one embodiment, a fragment of a nucleic acid of a Jak 1, Jak 2, Jak3, Stat 1, or Stat 2 gene can encompass any portion of at least about 8 consecutive nucleotides of the corresponding sequence disclosed herein. In another embodiment, the fragment can comprise at least about 10 consecutive nucleotides, at least about 15 consecutive nucleotides, at least about 20 consecutive nucleotides, or at least about 30 consecutive nucleotides of the corresponding sequence disclosed herein. Fragments can include all possible nucleotide lengths between about 8 and about 100 nucleotides, for example, lengths between about 15 and about 100 nucleotides, or between about 20 and about 100 nucleotides. Nucleic acid amplification-based assays involve the use of oligonucleotides selected from sequences encoding a polypeptide encoded by a Jak 1, Jak 2, Jak3, Stat 1, or Stat 2 gene to detect transformants which contain a nucleic acid encoding a Jak 1, Jak 2, Jak3, Stat 1, or Stat 2 protein or polypeptide.

Protocols for detecting and measuring the expression of a polypeptide encoded by a gene, such as a Jak 1, Jak 2, Jak3, Stat 1 or Stat 2 gene, using either polyclonal or monoclonal antibodies specific for the polypeptide are well established. Non-limiting examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a polypeptide encoded by a gene, such as a Jak 1, Jak 2, Jak3, Stat 1 or Stat 2 gene, can be used, or a competitive binding assay can be employed.

Labeling and conjugation techniques are known by those skilled in the art and can be used in various nucleic acid and amino acid assays. Methods for producing labeled hybridization or PCR probes for detecting sequences related to nucleic acid sequences encoding a protein, such as Jak 1, Jak 2, Jak3, Stat 1 or Stat 2, include, but are not limited to, oligolabeling, nick translation, end-labeling, or PCR amplification using a labeled nucleotide. Alternatively, nucleic acid sequences encoding a polypeptide encoded by a gene, such as a Jak 1, Jak 2, Jak3, Stat 1 or Stat 2 gene, can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, and/or magnetic particles.

Expression and Purification of Polypeptides.

Host cells transformed with a nucleic acid sequence encoding a polypeptide, such as Jak 1, Jak 2, Jak3, Stat 1 or Stat 2, can be cultured under conditions suitable for the expression and recovery of the protein from cell culture. The polypeptide produced by a transformed cell can be secreted or contained intracellularly depending on the sequence and/or the vector used. Expression vectors containing a nucleic acid sequence encoding a polypeptide, such as Jak 1, Jak 2, Jak3, Stat 1 or Stat 2, can be designed to contain signal sequences which direct secretion of soluble polypeptide molecules encoded by a gene, such as a Jak 1, Jak 2, Jak3, Stat 1 or Stat 2 gene, or a variant thereof, through a prokaryotic or eukaryotic cell membrane or which direct the membrane insertion of membrane-bound a polypeptide molecule encoded by a Jak 1, Jak 2, Jak3, Stat 1 or Stat 2 gene or a variant thereof.

Other constructions can also be used to join a gene sequence encoding a Jak 1, Jak 2, Jak3, Stat 1 or Stat 2 polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Including cleavable linker sequences (i.e., those specific for Factor Xa or enterokinase (Invitrogen, San Diego, Calif.)) between the purification domain and a polypeptide encoded by a Jak 1, Jak 2, Jak3, Stat 1 or Stat 2 gene also can be used to facilitate purification. One such expression vector provides for expression of a fusion protein containing a polypeptide encoded by a Jak 1, Jak 2, Jak3, Stat 1 or Stat 2 gene and 6 histidine (SEQ ID NO: 111) residues preceding a thioredoxin or an enterokinase cleavage site. The histidine residues facilitate purification by immobilized metal ion affinity chromatography, while the enterokinase cleavage site provides a means for purifying the polypeptide encoded by a Jak 1, Jak 2, Jak3, Stat 1 or Stat 2 gene.

A Jak 1, Jak 2, Jak3, Stat 1 or Stat 2 polypeptide can be purified from any human or non-human cell which expresses the polypeptide, including those which have been transfected with expression constructs that express a Jak 1, Jak 2, Jak3, Stat 1 or Stat 2 protein. A purified Jak 1, Jak 2, Jak3, Stat 1 or Stat 2 protein can be separated from other compounds which normally associate with a protein encoded by a Jak 1, Jak 2, Jak3, Stat 1 or Stat 2 gene in the cell, such as certain proteins, carbohydrates, or lipids, using methods practiced in the art. Non-limiting methods include size exclusion chromatography, ammonium sulfate fractionation, ion exchange chromatography, affinity chromatography, and preparative gel electrophoresis.

Chemical Synthesis.

Nucleic acid sequences comprising a gene, such as a Jak 1, Jak 2, Jak3, Stat 1 or Stat 2 gene, that encodes a polypeptide can be synthesized, in whole or in part, using chemical methods known in the art. Alternatively, a polypeptide, such as Jak 1, Jak 2, Jak3, Stat 1 or Stat 2, can be produced using chemical methods to synthesize its amino acid sequence, such as by direct peptide synthesis using solid-phase techniques. Protein synthesis can either be performed using manual techniques or by automation. Automated synthesis can be achieved, for example, using Applied Biosystems 431A Peptide Synthesizer (Perkin Elmer). Optionally, fragments of Jak 1, Jak 2, Jak3, Stat 1 or Stat 2 polypeptides can be separately synthesized and combined using chemical methods to produce a full-length molecule. In one embodiment, a fragment of a nucleic acid sequence that comprises a Jak 1, Jak 2, Jak3, Stat 1 or Stat 2 gene can encompass any portion of at least about 8 consecutive nucleotides of the corresponding sequence disclosed herein. In one embodiment, the fragment can comprise at least about 10 nucleotides, at least about 15 nucleotides, at least about 20 nucleotides, or at least about 30 nucleotides of the corresponding sequence disclosed herein. Fragments include all possible nucleotide lengths between about 8 and about 100 nucleotides, for example, lengths between about 15 and about 100 nucleotides, or between about 20 and about 100 nucleotides.

A Jak 1, Jak 2, Jak3, Stat 1 or Stat 2 fragment can be a fragment of a protein, such as Jak 1, Jak 2, Jak3, Stat 1 or Stat 2. For example, the Jak 1, Jak 2, Jak3, Stat 1 or Stat 2 fragment can encompass any portion of at least about 8 consecutive amino acids of the corresponding sequence disclosed herein. The fragment can comprise at least about 10 consecutive amino acids, at least about 20 consecutive amino acids, at least about 30 consecutive amino acids, at least about 40 consecutive amino acids, a least about 50 consecutive amino acids, at least about 60 consecutive amino acids, at least about 70 consecutive amino acids, or at least about 75 consecutive amino acids of the corresponding sequence disclosed herein. Fragments include all possible amino acid lengths between about 8 and 100 about amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids.

A synthetic peptide can be substantially purified via high performance liquid chromatography (HPLC). The composition of a synthetic polypeptide of Jak 1, Jak 2, Jak3, Stat 1 or Stat 2 can be confirmed by amino acid analysis or sequencing. Additionally, any portion of an amino acid sequence comprising a protein encoded by a Jak 1, Jak 2, Jak3, Stat 1 or Stat 2 gene can be altered during direct synthesis and/or combined using chemical methods with sequences from other proteins to produce a variant polypeptide or a fusion protein.

Identifying Jak 1, Jak 2, Jak3, Stat 1 or Stat 2 Modulating Compounds

The invention provides methods for identifying compounds which can be used for controlling and/or regulating hair growth (for example, hair density) or hair pigmentation in a subject. Since the invention has provided the identification of the genes listed herein as genes associated with a hair loss disorder, the invention also provides methods for identifying compounds that modulate the expression or activity of a gene and/or protein of Jak 1, Jak 2, Jak3, Stat 1 or Stat 2. In addition, the invention provides methods for identifying compounds which can be used for the treatment of a hair loss disorder. The invention also provides methods for identifying compounds which can be used for the treatment of hypotrichosis (for example, hereditary hypotrichosis simplex (HHS)). Non-limiting examples of hair loss disorders include: androgenetic alopecia, Alopecia areata, telogen effluvium, alopecia areata, alopecia totalis, and alopecia universalis. The methods can comprise the identification of test compounds or agents (e.g., peptides (such as antibodies or fragments thereof), small molecules, nucleic acids (such as siRNA or antisense RNA), or other agents) that can bind to a polypeptide molecule encoded by a Jak 1, Jak 2, Jak3, Stat 1 or Stat 2 gene and/or have a stimulatory or inhibitory effect on the biological activity of a protein encoded by a Jak 1, Jak 2, Jak3, Stat 1 or Stat 2 gene or its expression, and subsequently determining whether these compounds can regulate hair growth in a subject or can have an effect on symptoms associated with the hair loss disorders in an in vivo assay (i.e., examining an increase or reduction in hair growth).

As used herein, a "Jak 1, Jak 2, Jak3, Stat 1 or Stat 2 modulating compound" refers to a compound that interacts with a Jak 1, Jak 2, Jak3, Stat 1 or Stat 2 gene or a Jak 1, Jak 2, Jak3, Stat 1 or Stat 2 protein or polypeptide and modulates its activity and/or its expression. The compound can either increase the activity or expression of a protein encoded by a Jak 1, Jak 2, Jak3, Stat 1 or Stat 2 gene. Conversely, the compound can decrease the activity or expression of a protein encoded by a Jak 1, Jak 2, Jak3, Stat 1 or Stat 2 gene. The compound can be a Jak 1, Jak 2, Jak3, Stat 1 or Stat 2 agonist or a Jak 1, Jak 2, Jak3, Stat 1 or Stat 2 antagonist (e.g., a Jak1 inhibitor, a Jak2 inhibitor, a Stat1 inhibitor, or a Stat2 inhibitor). Some non-limiting examples of Jak 1, Jak 2, Jak3, Stat 1 or Stat 2 modulating compounds include peptides (such as peptide fragments comprising a polypeptide encoded by a Jak 1, Jak 2, Jak3, Stat 1 or Stat 2 gene, or antibodies or fragments thereof), small molecules, and nucleic acids (such as siRNA or antisense RNA specific for a nucleic acid comprising a Jak 1, Jak 2, Jak3, Stat 1 or Stat 2 gene). Agonists of a Jak 1, Jak 2, Jak3, Stat 1 or Stat 2 protein can be molecules which, when bound to a Jak 1, Jak 2, Jak3, Stat 1 or Stat 2 protein, increase or prolong the activity of the Jak 1, Jak 2, Jak3, Stat 1 or Stat 2 protein. Jak 1, Jak 2, Jak3, Stat 1 or Stat 2 agonists include, but are not limited to, proteins, nucleic acids, small molecules, or any other molecule which activates a Jak 1, Jak 2, Jak3, Stat 1 or Stat 2 protein. Antagonists of a Jak 1, Jak 2, Jak3, Stat 1 or Stat 2 protein can be molecules which, when bound to a Jak 1, Jak 2, Jak3, Stat 1 or Stat 2 protein decrease the amount or the duration of the activity of the Jak 1, Jak 2, Jak3, Stat 1 or Stat 2 protein. Antagonists include proteins, nucleic acids, antibodies, small molecules, or any other molecule which decrease the activity of a Jak 1, Jak 2, Jak3, Stat 1 or Stat 2 protein.

The term "modulate," as it appears herein, refers to a change in the activity or expression of a gene or protein of Jak 1, Jak 2, Jak3, Stat 1 or Stat 2. For example, modulation can cause an increase or a decrease in protein activity, binding characteristics, or any other biological, functional, or immunological properties of a Jak 1, Jak 2, Jak3, Stat 1 or Stat 2 protein.

In one embodiment, a Jak 1, Jak 2, Jak3, Stat 1 or Stat 2 modulating compound can be a peptide fragment of a Jak 1, Jak 2, Jak3, Stat 1 or Stat 2 protein that binds to the protein. For example, the Jak 1, Jak 2, Jak3, Stat 1 or Stat 2 polypeptide can encompass any portion of at least about 8 consecutive amino acids of the corresponding sequence disclosed herein. The fragment can comprise at least about 10 consecutive amino acids, at least about 20 consecutive amino acids, at least about 30 consecutive amino acids, at least about 40 consecutive amino acids, at least about 50 consecutive amino acids, at least about 60 consecutive amino acids, or at least about 75 consecutive amino acids of the corresponding sequence disclosed herein. Fragments include all possible amino acid lengths between and including about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) *Solid Phase Peptide Synthesis: a Practical Approach*. IRL Press, Oxford, England). The Jak 1, Jak 2, Jak3, Stat 1 or Stat 2 peptide fragments can be isolated from a natural source, genetically engineered, or chemically prepared. These methods are well known in the art.

A Jak 1, Jak 2, Jak3, Stat 1 or Stat 2 modulating compound can be a protein, such as an antibody (monoclonal, polyclonal, humanized, chimeric, or fully human), or a binding fragment thereof, directed against a polypeptide encoded by a Jak 1, Jak 2, Jak3, Stat 1 or Stat 2 gene. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab')$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) *Ann. Rev. Biomed. Eng.* 2:339-76; Hudson (1998) *Curr. Opin. Biotechnol.* 9:395-402). Antibodies can be obtained commercially, custom generated, or synthesized against an antigen of interest according to methods established in the art (Janeway et al., (2001) *Immunobiology*, 5th ed., Garland Publishing). In one embodiment, an antibody or binding fragment thereof is directed against SEQ ID NO: 1, 3, 5 or 7. Antibodies can be obtained commercially, custom generated, or synthesized against an antigen of interest according to methods established in the art (Janeway et al., (2001) *Immunobiology*, 5th ed., Garland Publishing). For example, antibodies directed to Jak1, Jak2, Stat1, or Stat2 can be obtained commercially from Abcam, Santa Cruz Biotechnology, Abnova Corp., BD Biosciences, Antigenix America Inc., etc. Human antibodies directed to either Jak1, Jak2, Stat1, or Stat2 (such as monoclonal, humanized, or chimeric antibodies) can be useful antibody therapeutics for use in humans.

Inhibition of RNA encoding a polypeptide encoded by a Jak 1, Jak 2, Jak3, Stat 1 or Stat 2 gene can effectively modulate the expression of a Jak 1, Jak 2, Jak3, Stat 1 or Stat 2 gene from which the RNA is transcribed. Inhibitors are selected from the group comprising: siRNA; interfering RNA or RNAi; dsRNA; RNA Polymerase III transcribed DNAs; ribozymes; and antisense nucleic acids, which can be RNA, DNA, or an artificial nucleic acid.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the DNA sequence encoding a polypeptide encoded by a Jak 1, Jak 2, Jak3, Stat 1 or Stat 2 gene can be synthesized, e.g., by conventional phosphodiester techniques (Dallas et al., (2006) *Med. Sci. Monit.* 12(4):RA67-74; Kalota et al., (2006) *Handb. Exp. Pharmacol.* 173:173-96; Lutzelburger et al., (2006) *Handb. Exp. Pharmacol.* 173:243-59). Antisense nucleotide sequences include, but are not limited to: morpholinos, 2'-O-methyl polynucleotides, DNA, RNA and the like.

siRNA comprises a double stranded structure containing from about 15 to about 50 base pairs, for example from about 21 to about 25 base pairs, and having a nucleotide sequence identical or nearly identical to an expressed target gene or RNA within the cell. The siRNA comprise a sense RNA strand and a complementary antisense RNA strand annealed together by standard Watson-Crick base-pairing interactions. The sense strand comprises a nucleic acid sequence which is substantially identical to a nucleic acid sequence contained within the target miRNA molecule. "Substantially identical" to a target sequence contained within the target mRNA refers to a nucleic acid sequence that differs from the target sequence by about 3% or less. The sense and antisense strands of the siRNA can comprise two complementary, single-stranded RNA molecules, or can comprise a single molecule in which two complementary portions are base-paired and are covalently linked by a single-stranded "hairpin" area. See also, McMnaus and Sharp (2002) *Nat Rev Genetics*, 3:737-47, and Sen and Blau (2006) *FASEB J.*, 20:1293-99, the entire disclosures of which are herein incorporated by reference.

The siRNA can be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides. One or both strands of the siRNA can also comprise a 3' overhang. As used herein, a 3' overhang refers to at least one unpaired nucleotide extending from the 3'-end of a duplexed RNA strand. For example, the siRNA can comprise at least one 3' overhang of from 1 to about 6 nucleotides (which includes ribonucleotides or deoxyribonucleotides) in length, or from 1 to about 5 nucleotides in length, or from 1 to about 4 nucleotides in length, or from about 2 to about 4 nucleotides in length. For example, each strand of the siRNA can comprise 3' overhangs of dithymidylic acid ("TT") or diuridylic acid ("uu").

siRNA can be produced chemically or biologically, or can be expressed from a recombinant plasmid or viral vector (for example, see U.S. Pat. No. 7,294,504 and U.S. Pat. No. 7,422,896, the entire disclosures of which are herein incorporated by reference). Exemplary methods for producing and testing dsRNA or siRNA molecules are described in U.S. Patent Application Publication No. 2002/0173478 to Gewirtz, U.S. Patent Application Publication No. 2007/0072204 to Hannon et al., and in U.S. Patent Application Publication No. 2004/0018176 to Reich et al., the entire disclosures of which are herein incorporated by reference.

In one embodiment, an siRNA directed to a human nucleic acid sequence comprising a Jak 1, Jak 2, Jak3, Stat 1 or Stat 2 gene can be generated against any one of SEQ ID NOS: 2, 4, 6 or 8. In another embodiment, an siRNA directed to a human nucleic acid sequence comprising a Jak1 gene can comprise any one of the sequences listed in Table 1. In another embodiment, an siRNA directed to a human nucleic acid sequence comprising a Stat1 gene can comprise any one of the sequences listed in Table 2. In another embodiment, an siRNA directed to a human nucleic acid sequence comprising a Jak3 gene can comprise any one of the sequences listed in Table 3.

In another embodiment, the siRNA directed to Jak1 is listed in Table 1.

TABLE 1

| siRNA SEQUENCES for Jak1 |
|---|
| (SEQ ID NOS: 9-32, respectively, in order of appearance) |
| CCACATAGCTGATCTGAAA |
| CGGGAAGCCTTAAGGAATA |
| CTGAAGAGAAGAAGATAAA |
| ACAAGAAGGATGAGGAGAA |
| CCAAGAAGACTGAGGTGAA |
| CAGAATACGCCATCAATAA |
| GCACAGAAGACGGAGGAAA |
| GCGATATATTCCAGAAACA |
| TGAGCTACTTGGAGGATAA |
| GAGTGAACACCAAGTGAAA |
| CAAGAAGGATGAGGAGAAA |
| CGGGAAGAGTGGAACAATT |
| GCATTAACAAGCAGGACAA |
| TTTGGAAAGTAGAGAAGAA |
| GGAAAGTAGAGAAGAAAAT |
| GGAACCACGCTCTGGGAAA |
| TGATTGAGAAAGAGAGATT |

TABLE 1-continued siRNA SEQUENCES for Jak1

ACATTACGGTGCTGAAATA

GGGAAGAGTGGAACAATTT

AGAATATCATGGTGGAAGA

GGAAATGTGTGTACTAAAA

ATGAGAACATTGTGAAGTA

CACAGAAGACGGAGGAAAT (SEQ ID NOS: 33-58, respectively,
in order of appearance)

TCTGAAGAGAAGAAGATAA

GCAAGAATGCATTGAACGA

AAGAAAGATTGATGGACTT

AAAATAAACTGAAGCGGAA

ATGAGGAAATGCTGGGAAT

AAAGAAAGATTGATGGACT

GGACTTAGCCCTCAAATTT

ACACTGGACAGCTGAATAA

CTGAATAAATGCAGTATCT

AAGAATGCATTGAACGAAT

CCAGTAACTTAGTGACACA

TTAACAAGCAGGACAACAA

GGGAGCAGGTGGCTGTTAA

AAATCGAGATCTTAAGGAA

GGAAATGGTATTAAGCTCA

CCAGAATGTTTAATGCAAT

GGACAAGCTTTCAGAACCT

AGACATAATGACAACCAAA

GCTTGGAGGTAGCTGGGTA

CAGCAGAGGAACTGTGCAT

CCAGAAACATTGAATAAGT

CTGAAATATTTGAGACTTC

GTACAGAATACGCCATCAA

GCACCGACTTTGACAACAT

GAGAAGAAGATAAAAGTGA

GGAAATTCAAAGTTGCCAA

In another embodiment, the siRNA directed to Stat1 is listed in Table 2.

TABLE 2 siRNA SEQUENCES for Stat1

(SEQ ID NOS: 59-81, respectively,
in order of appearance)

AGAAAGAGCTTGACAGTAA

AGGAATTGGAACAGAAATA

CAGCATAACATAAGGAAAA

TCAGAAATGTGAAGGACAA

GGCAAAGAGTGATCAGAAA

GCACAGTGATGTTAGACAA

AGTCATGGCTGCTGAGAAT

GTATAGAGCATGAAATCAA

GGTTATGTGTATAGAGCAT

GAAAGGAAGTAGTTCACAA

GATGTGAATGAGAGAAATA

ACAGAGAACACGAGACCAA

AAGATGTGAATGAGAGAAA

AGGACAAGGTTATGTGTAT

CCTGATTAATGATGAACTA

ACACAAAAGTGATGAACAT

GCAATTGAAAGAACAGAAA

CGAGAGCTGTCTAGGTTAA

GAACATGACCCTATCACAA

AGACAAACAGAAAGAGCTT

GGACAAGGTTATGTGTATA

TGACAATAAGAGAAAGGAA

GGAAGTAGTTCACAAAATA

TGAAATTGCAAGAGCTGAA

AGAAATACACCTACGAACA

CCCTAAAGGAACTGGATAT

GGAGGAATTGGAACAGAAA (SEQ ID NOS: 82-108, respectively,
in order of appearance)

CCTAAAGGAACTGGATATA

AGCGTAATCTTCAGGATAA

TCTGAAGGAAGAAAGGAAA

GGAAGATTTACAAGATGAA

TGGCAAAGAGTGATCAGAA

AGAGAAAGGAAGTAGTTCA

TABLE 2-continued siRNA SEQUENCES for Stat1

~~TAATAGAGTTGCTGAATGT~~

TGGAGGAATTGGAACAGAA

~~AGTTGAGACTGTTGGTGAA~~

GATAAAGATGTGAATGAGA

~~CATCGTTACTGAAGAGCTT~~

TGAAGTATCTGTATCCAAA

~~GCACAAGGTGGCAGGATGT~~

TGTCACAGCTGGATGATCA

~~GAAAGAGCTTGACAGTAAA~~

TCAAGAGCCTGGAAGATTT

~~TGGAAGATTTACAAGATGA~~

ATGAACTAGTGGAGTGGAA

~~TGAGACTGTTGGTGAAATT~~

TTGCAAGAGCTGAATTATA

~~GGATTTAGGAAGTTCAACA~~

GGAACTTGATGGCCCTAAA

~~GGAACTGGATATATCAAGA~~

In another embodiment, the siRNA directed to Jak3 is listed in Table 3.

TABLE 3 siRNA SEQUENCES for Jak3

| siRNA sequences | |
|---|---|
| TCAACTATCTGGAGGACAA | (SEQ ID NO: 112) |
| AGACAGAGGTGCTGCTGAA | (SEQ ID NO: 113) |
| GGTCCTTCACCAAGATTTA | (SEQ ID NO: 114) |
| CCTGGATCCTGCTAAGAAA | (SEQ ID NO: 115) |
| CGATCTTCGAGGAGAGACA | (SEQ ID NO: 116) |
| GGACAGACAACCAGATTTT | (SEQ ID NO: 117) |
| GGAAGCTGCAGGTGGTCAA | (SEQ ID NO: 118) |
| CCCAATACCAGCTGAGTCA | (SEQ ID NO: 119) |

RNA polymerase III transcribed DNAs contain promoters, such as the U6 promoter. These DNAs can be transcribed to produce small hairpin RNAs in the cell that can function as siRNA or linear RNAs that can function as antisense RNA. The Jak 1, Jak 2, Jak3, Stat 1 or Stat 2 modulating compound can contain ribonucleotides, deoxyribonucleotides, synthetic nucleotides, or any suitable combination such that the target RNA and/or gene is inhibited. In addition, these forms of nucleic acid can be single, double, triple, or quadruple stranded. (see for example Bass (2001) *Nature,* 411, 428 429; Elbashir et al., (2001) *Nature,* 411, 494 498; and PCT Publication Nos. WO 00/44895, WO 01/36646, WO 99/32619, WO 00/01846, WO 01/29058, WO 99/07409, WO 00/44914).

A Jak 1, Jak 2, Jak3, Stat 1 or Stat 2 modulating compound can be a small molecule that binds to a Jak 1, Jak 2, Jak3, Stat 1 or Stat 2 protein and disrupts its function, or conversely, enhances its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules that modulate a Jak 1, Jak 2, Jak3, Stat 1 or Stat 2 protein can be identified via in silica screening or high-through-put (HIP) screening of combinatorial libraries (e.g., see Potyrailo et al., (2011) *ACS Comb Set.* 13(6):579-633; Mensch et al., (2009) *J Pharm Sci.* 98(12):4429-68; Schnur (2008) *Curr Opin Drug Discov Devel.* 11(3):375-80; and Jhoti (2007) *Ernst Schering Found Symp Proc.* (3):169-85, each of which are hereby incorporated by reference in their entireties). Most conventional pharmaceuticals, such as aspirin, penicillin, and many chemotherapeutics, are small molecules, can be obtained commercially, can be chemically synthesized, or can be obtained from random or combinatorial libraries as described below (Werner et al., (2006) *Brief Funct. Genomic Proteomic* 5(1):32-6).

Non-limiting examples of Jak1/Jak2 inhibitors include: AG490 (Caceres-Cortes, Anticancer Agents Med Chem. 2008 October; 8(7):717-22); CYT387 (Pardanani et al., Leukemia. 2009 August; 23(8):1441-5; Monaghan et al., Leukemia. 2011 Jul. 26. doi: 10.1038/leu.2011.175. [Epub ahead of print]); SB1518 (William et al., J Med Chem. 2011 Jul. 14; 54(13):4638-58; Hart et al., Leukemia. 2011 Jun. 21. doi: 10.1038/leu.2011.148. [Epub ahead of print]); LY3009104 (INCB28050) (Incyte and Lilly); TG101348 (Wernig et al., Cancer Cell. 2008 April; 13(4):311-20; Pardanani et al., J Clin Oncol. 2011 Mar. 1; 29(7):789-96); and BMS-911543 (Purandare et al., Leukemia. 2011 Oct. 21. doi: 10.1038/leu.2011.292. [Epub ahead of print]), each of the references of which are incorporated by reference in their entireties.

JAK1/2 inhibitors in clinical development include a) INCB018424, topical and oral; 5 nM activity (Incyte); b) CEP-701 (Cephalon); and c) TG101348.

a)

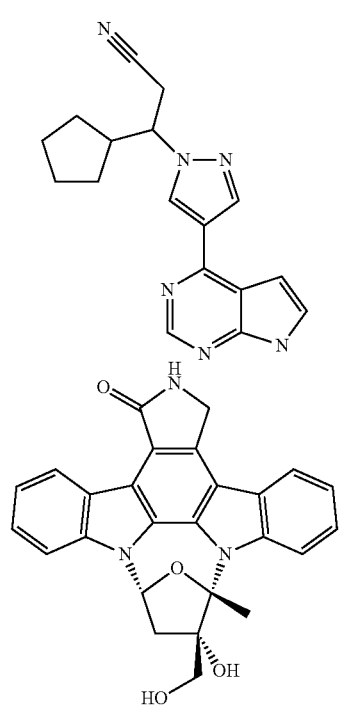

b)

-continued c)
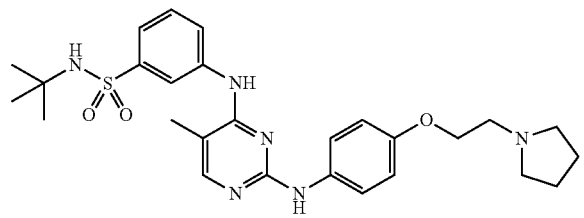

JAK3 inhibitors are currently in clinical trials in humans for the treatment of acute kidney transplant rejection and rheumatoid arthritis. Non-limiting examples of Jak3 inhibitors include: Janex 1 (WHI-P131) (Changelian et al., (2008) *Blood*, 111(4):2155-7); Uckun ey al., (1999) *Clin Cancer Res.* 5(10):2954-62; Uckun et al., (2010) *Arzneimittelforschung.* 60(4):218-25), PF-956980 (Sigma Product # PZ0151 (St. Louis, Mo., sigmaaldrich.com/catalog/product/sigma/pz0151?lang=en&region=US)); Changelian et al., (2008) *Blood*, 111(4):2155-7), WHI-P154 (Calbiochem Product #420104-5MG (San Diego, Calif., emdbiosciences.com)); Changelian et al., (2008) *Blood*, 111(4):2155-7), VX-509 (oral from Vertex Pharmaceuticals, Cambridge Mass.; Fleischmann et al. (2011) *Arthritis Rheum*, 63:LB3; Fleischmann et al., (2012) *Curr Opin Rheumatol.* February 18, PMID: 22357358), JAK3 Inhibitor IV (ZM-39923) Calbiochem Product #420121-10MG (San Diego, Calif., emdbiosciences.com, WO1998022103), NSC114792 (Kim et al., (2010) *Mol Cancer.* 2010, 9:36), tofacitinib (CP690550) (Changelian et al., (2008) *Blood*, 111(4):2155-7; Vijayakrishnan et al. (2011) *Trends Pharmacol Sci.* 32(1):25-34; Fleischmann et al., (2012) *Curr Opin Rheumatol.* February 18, PMID: 22357358), and R348 (topical and oral from Rigel Pharmaceuticals, San Francisco Calif.; Deuse et al., (2008) *Transplantation.* 85(6):885-92; Vijayakrishnan et al. (2011) *Trends Pharmacol Sci.* 32(1):25-34), each of the references of which are incorporated by reference in their entireties.

Structures of JAK3 inhibitors useful for the invention include a) Janex 1, oral and topical; b) PF-956980, i.v. infusion; c) WHI-P154; d) ZM-39923; e) NSC114792; f) tofacitinib (CP690550), oral.

a)
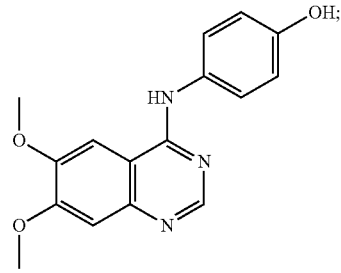

b)
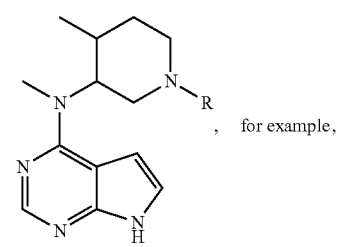
, for example, c)
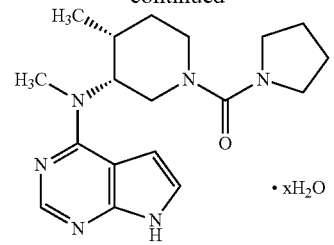
• xH₂O c)
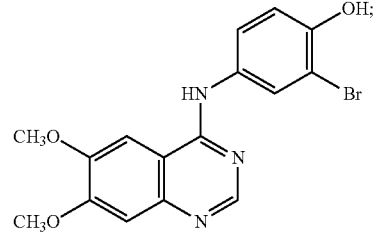

d)
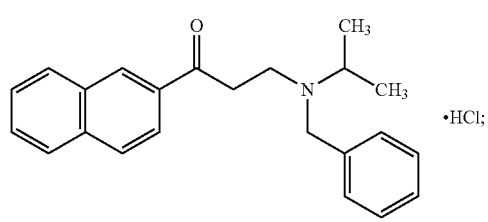
•HCl;

e)
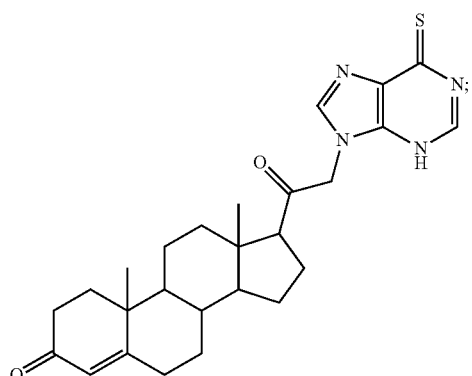

NSC114792
$C_{26}H_{32}N_4O_2S$ f)
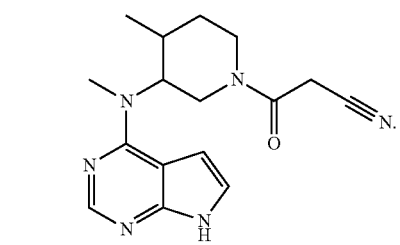

Non-limiting examples of JAK inhibitors (for example, Type I and Type II Jak Inhibitors) are discussed in O'Shea and Plenge (Immunity, 2012 Apr. 20; 36(4):542-50), LaFave and Levine (Trends Pharmacol Sci. 2012 November; 33(11):574-82), Kontzias et al, (Curr Opin Pharmacol. 2012 August; 12(4):464-70), Norman (Expert Opin Ther Pat. 2012 October; 22(10):1233-49), and Wilson (Expert Opin Ther Pat. 2010 May; 20(5):609-23), each of which are hereby incorporated by reference in their entireties.

Non-limiting examples of Stat inhibitors include: WP-1034 (Faderl et al., Anticancer Res. 2005 May-June; 25(3B):1841-50), fludarabine (Fludara, Berlex, Calif.), epigallocatechin-3-gallate (EGCG), and Hyperforin. Other compounds directed to Jak/Stat signaling are described in Ivanenkov et al., Mini Rev Med Chem. 2011 January; 11(1): 55-78, the contents of which are incorporated by reference in its entirety.

Knowledge of the primary sequence of a molecule of interest, such as a polypeptide encoded by a Jak 1, Jak 2, Jak3, Stat 1 or Stat 2 gene, and the similarity of that sequence with proteins of known function, can provide information as to the inhibitors or antagonists of the protein of interest in addition to agonists. Identification and screening of agonists and antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Test compounds, such as Jak 1, Jak 2, Jak3, Stat 1 or Stat 2 modulating compounds, can be screened from large libraries of synthetic or natural compounds (see Wang et al., (2007) *Curr Med Chem,* 14(2):133-55; Mannhold (2006) *Curr Top Med Chem,* 6 (10):1031-47; and Hensen (2006) *Curr Med Chem* 13(4):361-76). Numerous means are currently used for random and directed synthesis of saccharide, peptide, and nucleic acid based compounds. Synthetic compound libraries are commercially available from Maybridge Chemical Co. (Trevillet, Cornwall, UK), AMRI (Albany, N.Y.), ChemBridge (San Diego, Calif.), and MicroSource (Gaylordsville, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) *Tib Tech* 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. For example, libraries can also include, but are not limited to, peptide-on-plasmid libraries, synthetic small molecule libraries, aptamer libraries, in vitro translation-based libraries, polysome libraries, synthetic peptide libraries, neurotransmitter libraries, and chemical libraries.

Examples of chemically synthesized libraries are described in Fodor et al., (1991) *Science* 251:767-773; Houghten et al., (1991) *Nature* 354:84-86; Lam et al., (1991) *Nature* 354:82-84; Medynski, (1994) *BioTechnology* 12:709-710; Gallop et al., (1994) *J. Medicinal Chemistry* 37(9):1233-1251; Ohlmeyer et al., (1993) *Proc. Natl. Acad. Sci. USA* 90:10922-10926; Erb et al., (1994) *Proc. Natl. Acad. Sci. USA* 91:11422-11426; Houghten et al., (1992) *Biotechniques* 13:412; Jayawickreme et al., (1994) *Proc. Natl. Acad. Sci. USA* 91:1614-1618; Salmon et al., (1993) *Proc. Natl. Acad. Sci. USA* 90:11708-11712; PCT Publication No. WO 93/20242, dated Oct. 14, 1993; and Brenner et al., (1992) *Proc. Natl. Acad. Sci. USA* 89:5381-5383.

Examples of phage display libraries are described in Scott et al., (1990) *Science* 249:386-390; Devlin et al., (1990) *Science,* 249:404-406; Christian, et al., (1992) *J. Mol. Biol.* 227:711-718; Lenstra, (1992) *J. Immunol. Meth.* 152:149-157; Kay et al., (1993) *Gene* 128:59-65; and PCT Publication No. WO 94/18318.

In vitro translation-based libraries include but are not limited to those described in PCT Publication No. WO 91/05058; and Mattheakis et al., (1994) *Proc. Natl. Acad. Sci. USA* 91:9022-9026.

As used herein, the term "ligand source" can be any compound library described herein, or tissue extract prepared from various organs in an organism's system, that can be used to screen for compounds that would act as an agonist or antagonist of a Jak 1, Jak 2, Jak3, Stat 1 or Stat 2 protein. Screening compound libraries listed herein [also see U.S. Patent Application Publication No. 2005/0009163, which is hereby incorporated by reference in its entirety], in combination with in vivo animal studies, functional and signaling assays described below can be used to identify Jak 1, Jak 2, Jak3, Stat 1 or Stat 2 modulating compounds that regulate hair growth or treat hair loss disorders.

Screening the libraries can be accomplished by any variety of commonly known methods. See, for example, the following references, which disclose screening of peptide libraries: Parmley and Smith, (1989) *Adv. Exp. Med. Biol.* 251:215-218; Scott and Smith, (1990) *Science* 249:386-390; Fowlkes et al., (1992) *BioTechniques* 13:422-427; Oldenburg et al., (1992) *Proc. Natl. Acad. Sci. USA* 89:5393-5397; Yu et al., (1994) *Cell* 76:933-945; Staudt et al., (1988) *Science* 241: 577-580; Bock et al., (1992) *Nature* 355:564-566; Tuerk et al., (1992) *Proc. Natl. Acad. Sci. USA* 89:6988-6992; Ellington et al., (1992) *Nature* 355:850-852; U.S. Pat. Nos. 5,096, 815; 5,223,409; and 5,198,346, all to Ladner et al.; Rebar et al., (1993) *Science* 263:671-673; and PCT Pub. WO 94/18318.

Small molecule combinatorial libraries can also be generated and screened. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

In one non-limiting example, non-peptide libraries, such as a benzodiazepine library (see e.g., Bunin et al., (1994) *Proc. Natl. Acad. Sci. USA* 91:4708-4712), can be screened. Peptoid libraries, such as that described by Simon et al., (1992) *Proc. Natl. Acad. Sci. USA* 89:9367-9371, can also be used.

Another example of a library that can be used, in which the amide functionalities in peptides have been permethylated to generate a chemically transformed combinatorial library, is described by Ostresh et al. (1994), *Proc. Natl. Acad. Sci. USA* 91:11138-11142.

Computer modeling and searching technologies permit the identification of compounds, or the improvement of already identified compounds, that can modulate the expression or activity of a Jak 1, Jak 2, Jak3, Stat 1 or Stat 2 protein. Having identified such a compound or composition, the active sites or regions of a Jak 1, Jak 2, Jak3, Stat 1 or Stat 2 protein can be subsequently identified via examining the sites to which the compounds bind. These sites can be ligand binding sites and can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

The three dimensional geometric structure of a site, for example that of a polypeptide encoded by a Jak 1, Jak 2, Jak3, Stat 1 or Stat 2 gene, can be determined by known methods in the art, such as X-ray crystallography, which can determine a complete molecular structure. Solid or liquid phase NMR can be used to determine certain intramolecular distances. Any other experimental method of structure determination can be used to obtain partial or complete geometric structures. The geometric structures can be measured with a complexed ligand, natural or artificial, which can increase the accuracy of the active site structure determined.

Other methods for preparing or identifying peptides that bind to a target are known in the art. Molecular imprinting, for instance, can be used for the de novo construction of macromolecular structures such as peptides that bind to a molecule. See, for example, Kenneth J. Shea, *Molecular Imprinting of Synthetic Network Polymers: The De Novo synthesis of Macromolecular Binding and Catalytic Sites*, TRIP Vol. 2, No. 5, May 1994; Mosbach, (1994) *Trends in Biochem. Sci.*, 19(9); and Wulff, G., in *Polymeric Reagents and Catalysts* (Ford, W. T., Ed.) ACS Symposium Series No. 308, pp 186-230, American Chemical Society (1986). One method for preparing mimics of a Jak 1, Jak 2, Jak3, Stat 1 or Stat 2 modulating compound involves the steps of: (i) polymerization of functional monomers around a known substrate (the template) that exhibits a desired activity; (ii) removal of the template molecule; and then (iii) polymerization of a second class of monomers in, the void left by the template, to provide a new molecule which exhibits one or more desired properties which are similar to that of the template. In addition to preparing peptides in this manner other binding molecules such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are prepared by the free radical polymerization of functional monomers, resulting in a compound with a nonbiodegradable backbone. Other methods for designing such molecules include for example drug design based on structure activity relationships, which require the synthesis and evaluation of a number of compounds and molecular modeling.

Screening Assays

Jak 1, Jak 2, Jak3, Stat 1 or Stat 2 Modulating Compounds.

A Jak 1, Jak 2, Jak3, Stat 1 or Stat 2 modulating compound can be a compound that affects the activity and/or expression of a Jak 1, Jak 2, Jak3, Stat 1 or Stat 2 protein in vivo and/or in vitro. Jak 1, Jak 2, Jak3, Stat 1 or Stat 2 modulating compounds can be agonists and antagonists of a Jak 1, Jak 2, Jak3, Stat 1 or Stat 2 protein, and can be compounds that exert their effect on the activity of a Jak 1, Jak 2, Jak3, Stat 1 or Stat 2 protein via the expression, via post-translational modifications, or by other means.

Test compounds or agents which bind to a Jak 1, Jak 2, Jak3, Stat 1 or Stat 2 protein, and/or have a stimulatory or inhibitory effect on the activity or the expression of a Jak 1, Jak 2, Jak3, Stat 1 or Stat 2 protein, can be identified by two types of assays: (a) cell-based assays which utilize cells expressing a Jak 1, Jak 2, Jak3, Stat 1 or Stat 2 protein or a variant thereof on the cell surface; or (b) cell-free assays, which can make use of isolated Jak 1, Jak 2, Jak3, Stat 1 or Stat 2 proteins. These assays can employ a biologically active fragment of a Jak 1, Jak 2, Jak3, Stat 1 or Stat 2 protein, full-length proteins, or a fusion protein which includes all or a portion of a polypeptide encoded by a Jak 1, Jak 2, Jak3, Stat 1 or Stat 2 gene. A Jak 1, Jak 2, Jak3, Stat 1 or Stat 2 protein can be obtained from any suitable mammalian species (e.g., human, rat, chick, xenopus, equine, bovine or murine). The assay can be a binding assay comprising direct or indirect measurement of the binding of a test compound. The assay can also be an activity assay comprising direct or indirect measurement of the activity of a Jak 1, Jak 2, Jak3, Stat 1 or Stat 2 protein. The assay can also be an expression assay comprising direct or indirect measurement of the expression of Jak 1, Jak 2, Jak3, Stat 1 or Stat 2 mRNA nucleic acid sequences or a protein encoded by a Jak 1, Jak 2, Jak3, Stat 1 or Stat 2 gene. The various screening assays can be combined with an in vivo assay comprising measuring the effect of the test compound on the symptoms of a hair loss disorder or disease in a subject (for example, androgenetic alopecia, alopecia areata, alopecia totalis, or alopecia universalis), loss of hair pigmentation in a subject, or even hypotrichosis.

An in vivo assay can also comprise assessing the effect of a test compound on regulating hair growth in known mammalian models that display defective or aberrant hair growth phenotypes or mammals that contain mutations in the open reading frame (ORF) of nucleic acid sequences comprising a Jak 1, Jak 2, Jak3, Stat 1 or Stat 2 gene that affects hair growth regulation or hair density, or hair pigmentation. In one embodiment, controlling hair growth can comprise an induction of hair growth or density in the subject. Here, the compound's effect in regulating hair growth can be observed either visually via examining the organism's physical hair growth or loss, or by assessing protein or mRNA expression using methods known in the art.

Assays for screening test compounds that bind to or modulate the activity of a Jak 1, Jak 2, Jak3, Stat 1 or Stat 2 protein can also be carried out. The test compound can be obtained by any suitable means, such as from conventional compound libraries. Determining the ability of the test compound to bind to a membrane-bound form of the Jak 1, Jak 2, Jak3, Stat 1 or Stat 2 protein can be accomplished via coupling the test compound with a radioisotope or enzymatic label such that binding of the test compound to the cell expressing a Jak 1, Jak 2, Jak3, Stat 1 or Stat 2 protein can be measured by detecting the labeled compound in a complex. For example, the test compound can be labeled with $^{3}H$, $^{14}C$, $^{35}S$, or $^{125}I$, either directly or indirectly, and the radioisotope can be subsequently detected by direct counting of radioemmission or by scintillation counting. Alternatively, the test compound can be enzymatically labeled with, for example, horseradish peroxidase, alkaline phosphatase, or luciferase, and the enzymatic label detected by determination of conversion of an appropriate substrate to product.

Cell-based assays can comprise contacting a cell expressing Jak 1, Jak 2, Jak3, Stat 1 or Stat 2 with a test agent and determining the ability of the test agent to modulate (such as increase or decrease) the activity or the expression of the membrane-bound molecule. Determining the ability of the test agent to modulate the activity of the membrane-bound Jak 1, Jak 2, Jak3, Stat 1 or Stat 2 molecule can be accomplished by any method suitable for measuring the activity of such a molecule, such as monitoring downstream signaling events (e.g., You et al., Ann N Y Acad Sci. 2008 December; 1150:300-10; Posadas et al., Expert Rev Clin Immunol. 2009 January; 5(1):9-17; Korhonen et al., Basic Clin Pharmacol Toxicol. 2009 April; 104(4):276-84; Vital et al., Ther Clin Risk Manag. 2006 December; 2(4):365-75; Malek and Castro, Immunity. 2010 Aug. 27; 33(2):153-65; Cheng et al., Immunol Rev. 2011 May; 241(1):63-76; Lanier, *Nat Immunol.* 2008 May; 9(5):495-502; Lowell, Cold Spring Harb Perspect Biol. 2011 Mar. 1; 3(3). pii: a002352; Mócsai et al., Nat Rev Immunol. 2010 June; 10(6):387-402; Bradshaw, Cell Signal. 2010 August; 22(8):1175-84; Ivanenkov et al., Mini Rev Med Chem. 2011 January; 11(1):55-78; Himpe et al., Biofactors. 2009 January-February; 35(1):76-81, each of which are incorporated by reference in their entireties).

A Jak 1, Jak 2, Jak3, Stat 1 or Stat 2 protein or the target of a Jak 1, Jak 2, Jak3, Stat 1 or Stat 2 protein can be immobilized to facilitate the separation of complexed from uncomplexed forms of one or both of the proteins. Binding of a test compound to a Jak 1, Jak 2, Jak3, Stat 1 or Stat 2 protein or a variant thereof, or interaction of a Jak 1, Jak 2, Jak3, Stat 1 or Stat 2 protein with a target molecule in the presence and absence of a test compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix (for example, glutathione-S-transferase (GST) fusion proteins or glutathione-S-transferase fusion proteins can be adsorbed onto glutathione sepharose beads (Sigma Chemical; St. Louis, Mo.) or glutathione derivatized microliter plates).

A Jak 1, Jak 2, Jak3, Stat 1 or Stat 2 protein, or a variant thereof, can also be immobilized via being bound to a solid support. Non-limiting examples of suitable solid supports include glass or plastic slides, tissue culture plates, microliter wells, tubes, silicon chips, or particles such as beads (including, but not limited to, latex, polystyrene, or glass beads). Any method known in the art can be used to attach a polypeptide (or polynucleotide) corresponding to Jak 1, Jak 2, Jak3, Stat 1 or Stat 2 or a variant thereof, or test compound to a solid support, including use of covalent and non-covalent linkages, or passive absorption.

The expression of a Jak 1, Jak 2, Jak3, Stat 1 or Stat 2 protein can also be monitored. For example, regulators of the expression of a Jak 1, Jak 2, Jak3, Stat 1 or Stat 2 protein can be identified via contacting a cell with a test compound and determining the expression of a protein encoded by a Jak 1, Jak 2, Jak3, Stat 1 or Stat 2 gene or Jak 1, Jak 2, Jak3, Stat 1 or Stat 2 mRNA nucleic acid sequences in the cell. The expression level of a protein encoded by a Jak 1, Jak 2, Jak3, Stat 1 or Stat 2 gene or Jak 1, Jak 2, Jak3, Stat 1 or Stat 2 mRNA nucleic acid sequences in the cell in the presence of the test compound is compared to the protein or mRNA expression level in the absence of the test compound. The test compound can then be identified as a regulator of the expression of a Jak 1, Jak 2, Jak3, Stat 1 or Stat 2 protein based on this comparison. For example, when expression of a protein encoded by a Jak 1, Jak 2, Jak3, Stat 1 or Stat 2 gene or Jak 1, Jak 2, Jak3, Stat 1 or Stat 2 mRNA nucleic acid sequences in the cell is statistically or significantly greater in the presence of the test compound than in its absence, the test compound is identified as a stimulator/enhancer of expression of a protein encoded by a Jak 1, Jak 2, Jak3, Stat 1 or Stat 2 gene or Jak 1, Jak 2, Jak3, Stat 1 or Stat 2 mRNA nucleic acid sequences in the cell. The test compound can be said to be a Jak 1, Jak 2, Jak3, Stat 1 or Stat 2 modulating compound (such as an agonist).

Alternatively, when expression of a protein encoded by a Jak 1, Jak 2, Jak3, Stat 1 or Stat 2 gene or Jak 1, Jak 2, Jak3, Stat 1 or Stat 2 mRNA nucleic acid sequences in the cell is statistically or significantly less in the presence of the test compound than in its absence, the compound is identified as an inhibitor of the expression of a protein encoded by a Jak 1, Jak 2, Jak3, Stat 1 or Stat 2 gene or Jak 1, Jak 2, Jak3, Stat 1 or Stat 2 mRNA nucleic acid sequences in the cell. The test compound can also be said to be a Jak 1, Jak 2, Jak3, Stat 1 or Stat 2 modulating compound (such as an antagonist). The expression level of a protein encoded by a Jak 1, Jak 2, Jak3, Stat 1 or Stat 2 gene or Jak 1, Jak 2, Jak3, Stat 1 or Stat 2 mRNA nucleic acid sequences in the cell in cells can be determined by methods previously described.

For binding assays, the test compound can be a small molecule which binds to and occupies the binding site of a polypeptide encoded by a Jak 1, Jak 2, Jak3, Stat 1 or Stat 2 gene, or a variant thereof. This can make the ligand binding site inaccessible to substrate such that normal biological activity is prevented. Examples of such small molecules include, but are not limited to, small peptides or peptide-like molecules. In binding assays, either the test compound or a polypeptide encoded by a Jak 1, Jak 2, Jak3, Stat 1 or Stat 2 gene can comprise a detectable label, such as a fluorescent, radioisotopic, chemiluminescent, or enzymatic label (for example, alkaline phosphatase, horseradish peroxidase, or luciferase). Detection of a test compound which is bound to a polypeptide encoded by a Jak 1, Jak 2, Jak3, Stat 1 or Stat 2 gene can then be determined via direct counting of radioemmission, by scintillation counting, or by determining conversion of an appropriate substrate to a detectable product.

Determining the ability of a test compound to bind to a Jak 1, Jak 2, Jak3, Stat 1 or Stat 2 protein also can be accomplished using real-time Biamolecular Interaction Analysis (BIA) [McConnell et al., 1992, *Science* 257, 1906-1912; Sjolander, Urbaniczky, 1991, *Anal. Chem* 63, 2338-23459]. BIA is a technology for studying biospecific interactions in real time, without labeling any of the interactants (for example, BIACORE™). Changes in the optical phenomenon surface plasmon resonance (SPR) can be used as an indication of real-time reactions between biological molecules.

To identify other proteins which bind to or interact with a Jak 1, Jak 2, Jak3, Stat 1 or Stat 2 protein and modulate its activity, a polypeptide encoded by a Jak 1, Jak 2, Jak3, Stat 1 or Stat 2 gene can be used as a bait protein in a two-hybrid assay or three-hybrid assay (Szabo et al., 1995, *Curr. Opin. Struct. Biol.* 5, 699-705; U.S. Pat. No. 5,283,317), according to methods practiced in the art. The two-hybrid system is based on the modular nature of most transcription factors, which consist of separable DNA-binding and activation domains.

Functional Assays.

Test compounds can be tested for the ability to increase or decrease the activity of a Jak 1, Jak 2, Jak3, Stat 1 or Stat 2 protein, or a variant thereof. Activity can be measured after contacting a purified Jak 1, Jak 2, Jak3, Stat 1 or Stat 2 protein, a cell membrane preparation, or an intact cell with a test compound. A test compound that decreases the activity of a Jak 1, Jak 2, Jak3, Stat 1 or Stat 2 protein by at least about 10%, at least about 20%, at least about 30%, at least about 40%, at least about 50%, at least about 60%, at least about 70%, at least about 75%, at least about 80%, at least about 90%, at least about 95% or 100% is identified as a potential agent for decreasing the activity of a Jak 1, Jak 2, Jak3, Stat 1 or Stat 2 protein, for example an antagonist. A test compound that increases the activity of a Jak 1, Jak 2, Jak3, Stat 1 or Stat 2 protein by at least about 10%, at least about 20%, at least about 30%, at least about 40%, at least about 50%, at least about 60%, at least about 70%, at least about 75%, at least about 80%, at least about 90%, at least about 95% or 100% is identified as a potential agent for increasing the activity of a Jak 1, Jak 2, Jak3, Stat 1 or Stat 2 protein, for example an agonist.

Treatment and Prevention

The invention also provides a method for treating or preventing a hair-loss disorder in a subject. In one embodiment, the method comprises detecting the presence of an alteration in a Jak 1, Jak 2, Jak3, Stat 1 or Stat 2 gene in a sample from the subject, the presence of the alteration being indicative of a hair-loss disorder, or the predisposition to a hair-loss disorder, and, administering to the subject in need a therapeutic treatment against a hair-loss disorder. The therapeutic treatment can be a drug administration (for example, a pharmaceutical composition comprising a siRNA directed to a Jak 1, Jak 2, Jak3, Stat 1 or Stat 2 nucleic acid). In one embodiment, the therapeutic molecule to be administered comprises a polypeptide encoded by a Jak 1, Jak 2, Jak3, Stat 1 or Stat 2 gene, comprising at least about 75%, at least about 80%, at least about 85%, at least about 90%, at least about 93%, at least about 95%, at least about 97%, at least about 98%, at least about 99%, or 100% of the amino acid sequence of the corresponding sequence disclosed herein, and exhibits the function of decreasing expression of a protein encoded by a Jak 1, Jak 2, Jak3, Stat 1 or Stat 2 gene. This can restore the capacity to initiate hair growth in cells derived from hair follicles or skin. In another embodiment, the therapeutic molecule to be administered comprises a nucleic acid sequence comprising a Jak 1, Jak 2, Jak3, Stat 1 or Stat 2 gene that encodes a polypeptide, comprising at least about 75%, at least about 80%, at least about 85%, at least about 90%, at least about 93%, at least about 95%, at least about 97%, at least about 98%, at least about 99%, or 100% of the nucleic acid sequence of the corresponding sequence disclosed herein, and encodes a polypeptide with the function of decreasing expression of a protein encoded by a Jak 1, Jak 2, Jak3, Stat 1 or Stat 2 gene, thus restoring the capacity to initiate hair growth in cells derived from hair follicle cells or skin.

The alteration can be determined at the level of the DNA, RNA, or polypeptide. Optionally, detection can be determined by performing an oligonucleotide ligation assay, a confirmation based assay, a hybridization assay, a sequencing assay, an allele-specific amplification assay, a microsequencing assay, a melting curve analysis, a denaturing high performance liquid chromatography (DHPLC) assay (for example, see Jones et al, (2000) Hum Genet., 106(6):663-8), or a combination thereof. In another embodiment, the detection is performed by sequencing all or part of a Jak 1, Jak 2, Jak3, Stat 1 or Stat 2 gene or by selective hybridization or amplification of all or part of a Jak 1, Jak 2, Jak3, Stat 1 or Stat 2 gene. A Jak 1, Jak 2, Jak3, Stat 1 or Stat 2 gene specific amplification can be carried out before the alteration identification step.

An alteration in a chromosome region occupied by a Jak 1, Jak 2, Jak3, Stat 1 or Stat 2 gene can be any form of mutation(s), deletion(s), rearrangement(s) and/or insertions in the coding and/or non-coding region of the locus, alone or in various combination(s). Mutations can include point mutations. Insertions can encompass the addition of one or several residues in a coding or non-coding portion of the gene locus. Insertions can comprise an addition of between 1 and 50 base pairs in the gene locus. Deletions can encompass any region of one, two or more residues in a coding or non-coding portion of the gene locus, such as from two residues up to the entire gene or locus. Deletions can affect smaller regions, such as domains (introns) or repeated sequences or fragments of less than about 50 consecutive base pairs, although larger deletions can occur as well. Rearrangement includes inversion of sequences. The alteration in a chromosome region occupied by a Jak 1, Jak 2, Jak3, Stat 1 or Stat 2 gene can result in amino acid substitutions, RNA splicing or processing, product instability, the creation of stop codons, frame-shift mutations, and/or truncated polypeptide production. The alteration can result in the production of a polypeptide encoded by a Jak 1, Jak 2, Jak3, Stat 1 or Stat 2 gene with altered function, stability, targeting or structure. The alteration can also cause a reduction, or even an increase in protein expression. In one embodiment, the alteration in the chromosome region occupied by a Jak 1, Jak 2, Jak3, Stat 1 or Stat 2 gene can comprise a point mutation, a deletion, or an insertion in a Jak 1, Jak 2, Jak3, Stat 1 or Stat 2 gene or corresponding expression product. In another embodiment, the alteration can be a deletion or partial deletion of a Jak 1, Jak 2, Jak3, Stat 1 or Stat 2 gene. The alteration can be determined at the level of the DNA, RNA, or polypeptide.

In another embodiment, the method can comprise detecting the presence of altered RNA expression. Altered RNA expression includes the presence of an altered RNA sequence, the presence of an altered RNA splicing or processing, or the presence of an altered quantity of RNA. These can be detected by various techniques known in the art, including sequencing all or part of the RNA or by selective hybridization or selective amplification of all or part of the RNA. In a further embodiment, the method can comprise detecting the presence of altered expression of a polypeptide encoded by a Jak 1, Jak 2, Jak3, Stat 1 or Stat 2 gene. Altered polypeptide expression includes the presence of an altered polypeptide sequence, the presence of an altered quantity of polypeptide, or the presence of an altered tissue distribution. These can be detected by various techniques known in the art, including by sequencing and/or binding to specific ligands (such as antibodies).

Various techniques known in the art can be used to detect or quantify altered gene or RNA expression or nucleic acid sequences, which include, but are not limited to, hybridization, sequencing, amplification, and/or binding to specific ligands (such as antibodies). Other suitable methods include allele-specific oligonucleotide (ASO), oligonucleotide ligation, allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, denaturing HLPC, melting curve analysis, heteroduplex analysis, RNase protection, chemical or enzymatic mismatch cleavage, ELISA, radio-immunoassays (RIA) and immuno-enzymatic assays (IEMA). Some of these approaches (such as SSCA and CGGE) are based on a change in electrophoretic mobility of the nucleic acids, as a result of the presence of an altered sequence. According to these techniques, the altered sequence is visualized by a shift in mobility on gels. The fragments can then be sequenced to confirm the alteration. Some other approaches are based on specific hybridization between nucleic acids from the subject and a probe specific for wild type or altered gene or RNA. The probe can be in suspension or immobilized on a substrate. The probe can be labeled to facilitate detection of hybrids. Some of these approaches are suited for assessing a polypeptide sequence or expression level, such as Northern blot, ELISA and RIA. These latter require the use of a ligand specific for the polypeptide, for example, the use of a specific antibody.

Sequencing.

Sequencing can be carried out using techniques well known in the art, using automatic sequencers. The sequencing can be performed on the complete Jak 1, Jak 2, Jak3, Stat 1 or Stat 2 gene or on specific domains thereof, such as those known or suspected to carry deleterious mutations or other alterations.

Amplification.

Amplification is based on the formation of specific hybrids between complementary nucleic acid sequences that serve to initiate nucleic acid reproduction. Amplification can be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Useful techniques in the art encompass real-time PCR, allele-specific PCR, or PCR-SSCP. Amplification usually requires the use of specific nucleic acid primers, to initiate the reaction. Nucleic acid primers useful for amplifying sequences from a Jak 1, Jak 2, Jak3, Stat 1 or Stat 2 gene or locus are able to specifically hybridize with a portion of a Jak 1, Jak 2, Jak3, Stat 1 or Stat 2 gene locus that flank a target region of the locus, wherein the target region is altered in certain subjects having a hair-loss disorder. In one embodiment, amplification can comprise using forward and reverse PCR primers comprising nucleotide sequences of the corresponding sequence disclosed herein.

The invention provides for a nucleic acid primer, wherein the primer can be complementary to and hybridize specifically to a portion of a Jak 1, Jak 2, Jak3, Stat 1 or Stat 2 coding sequence (e.g., gene or RNA) altered in certain subjects having a hair-loss disorder. Primers of the invention can be specific for altered sequences in a Jak 1, Jak 2, Jak3, Stat 1 or Stat 2 gene or RNA. By using such primers, the detection of an amplification product indicates the presence of an alteration in a Jak 1, Jak 2, Jak3, Stat 1 or Stat 2 gene or the absence of such gene. Primers can also be used to identify single nucleotide polymorphisms (SNPs) located in or around a Jak 1, Jak 2, Jak3, Stat 1 or Stat 2 gene locus; SNPs can comprise a single nucleotide change, or a cluster of SNPs in and around a Jak 1, Jak 2, Jak3, Stat 1 or Stat 2 gene. Examples of primers of this invention can be single-stranded nucleic acid molecules of about 5 to 60 nucleotides in length, or about 8 to about 25 nucleotides in length. The sequence can be derived directly from the sequence of a Jak 1, Jak 2, Jak3, Stat 1 or Stat 2 gene. Perfect complementarity is useful to ensure high specificity; however, certain mismatch can be tolerated. For example, a nucleic acid primer or a pair of nucleic acid primers as described above can be used in a method for detecting the presence of or a predisposition to a hair-loss disorder in a subject.

Amplification methods include, e.g., polymerase chain reaction, PCR (PCR PROTOCOLS, A GUIDE TO METHODS AND APPLICATIONS, ed. Innis, Academic Press, N.Y., 1990 and PCR STRATEGIES, 1995, ed. Innis, Academic Press, Inc., N.Y., ligase chain reaction (LCR) (see, e.g., Wu, Genomics 4:560, 1989; Landegren, Science 241:1077, 1988; Barringer, Gene 89:117, 1990); transcription amplification (see, e.g., Kwoh, Proc. Natl. Acad. Sci. USA 86:1173, 1989); and, self-sustained sequence replication (see, e.g., Guatelli, Proc. Natl. Acad. Sci. USA 87:1874, 1990); Q Beta replicase amplification (see, e.g., Smith, J. Clin. Microbiol. 35:1477-1491, 1997), automated Q-beta replicase amplification assay (see, e.g., Burg, Mol. Cell. Probes 10:257-271, 1996) and other RNA polymerase mediated techniques (e.g., NASBA, Cangene, Mississauga, Ontario); see also Berger, Methods Enzymol. 152:307-316, 1987; Sambrook; Ausubel; U.S. Pat. Nos. 4,683,195 and 4,683,202; Sooknanan, Biotechnology 13:563-564, 1995. All the references stated above, an throughout the description, are incorporated by reference in their entireties.

Selective Hybridization.

Hybridization detection methods are based on the formation of specific hybrids between complementary nucleic acid sequences that serve to detect nucleic acid sequence alteration(s). A detection technique involves the use of a nucleic acid probe specific for wild type or altered gene or RNA, followed by the detection of the presence of a hybrid. The probe can be in suspension or immobilized on a substrate or support (for example, as in nucleic acid array or chips technologies). The probe can be labeled to facilitate detection of hybrids. For example, a sample from the subject can be contacted with a nucleic acid probe specific for a wild type Jak 1, Jak 2, Jak3, Stat 1 or Stat 2 gene or an altered Jak 1, Jak 2, Jak3, Stat 1 or Stat 2 gene, and the formation of a hybrid can be subsequently assessed. In one embodiment, the method comprises contacting simultaneously the sample with a set of probes that are specific, respectively, for a wild type Jak 1, Jak 2, Jak3, Stat 1 or Stat 2 gene and for various altered forms thereof. Thus, it is possible to detect directly the presence of various forms of alterations in a Jak 1, Jak 2, Jak3, Stat 1 or Stat 2 gene in the sample. Also, various samples from various subjects can be treated in parallel.

According to the invention, a probe can be a polynucleotide sequence which is complementary to and can specifically hybridize with a (target portion of a) Jak 1, Jak 2, Jak3, Stat 1 or Stat 2 gene or RNA, and that is suitable for detecting polynucleotide polymorphisms associated with alleles of a Jak 1, Jak 2, Jak3, Stat 1 or Stat 2 gene (or genes) which predispose to or are associated with a hair-loss disorder. Useful probes are those that are complementary to a Jak 1, Jak 2, Jak3, Stat 1 or Stat 2 gene, RNA, or target portion thereof. Probes can comprise single-stranded nucleic acids of between 8 to 1000 nucleotides in length, for instance between 10 and 800, between 15 and 700, or between 20 and 500. Longer probes can be used as well. A useful probe of the invention is a single stranded nucleic acid molecule of between 8 to 500 nucleotides in length, which can specifically hybridize to a region of a Jak 1, Jak 2, Jak3, Stat 1 or Stat 2 gene or RNA that carries an alteration. For example, the probe can be directed to a chromosome region occupied by a Jak 1, Jak 2, Jak3, Stat 1 or Stat 2 gene.

The sequence of the probes can be derived from the sequences of a Jak 1, Jak 2, Jak3, Stat 1 or Stat 2 gene and RNA as provided herein. Nucleotide substitutions can be performed, as well as chemical modifications of the probe. Such chemical modifications can be accomplished to increase the stability of hybrids (e.g., intercalating groups) or to label the probe. Some examples of labels include, without limitation, radioactivity, fluorescence, luminescence, and enzymatic labeling.

A guide to the hybridization of nucleic acids is found in e.g., Sambrook, ed., *Molecular Cloning: A Laboratory Manual* (3rd Ed.), Vols. 1-3, Cold Spring Harbor Laboratory, 2001; *Current Protocols in Molecular Biology*, Ausubel, ed. John Wiley & Sons, Inc., New York, 1997; *Laboratory Techniques in Biochemistry and Molecular Biology: Hybridization with Nucleic Acid Probes, Part I*. Theory and Nucleic Acid Preparation, Tijssen, ed. Elsevier, N.Y., 1993.

Specific Ligand Binding

As discussed herein, alteration in a chromosome region occupied by a Jak 1, Jak 2, Jak3, Stat 1 or Stat 2 gene or alteration in expression of a Jak 1, Jak 2, Jak3, Stat 1 or Stat 2 gene, can also be detected by screening for alteration(s) in a sequence or expression level of a polypeptide encoded by a Jak 1, Jak 2, Jak3, Stat 1 or Stat 2 gene. Different types of ligands can be used, such as specific antibodies. In one embodiment, the sample is contacted with an antibody specific for a polypeptide encoded by a Jak 1, Jak 2, Jak3, Stat 1 or Stat 2 gene and the formation of an immune complex is subsequently determined. Various methods for detecting an immune complex can be used, such as ELISA, radioimmunoassays (RIA) and immuno-enzymatic assays (IEMA).

For example, an antibody can be a polyclonal antibody, a monoclonal antibody, as well as fragments or derivatives thereof having substantially the same antigen specificity. Fragments include Fab, Fab'2, or CDR regions. Derivatives include single-chain antibodies, humanized antibodies, or poly-functional antibodies. An antibody specific for a polypeptide encoded by a Jak 1, Jak 2, Jak3, Stat 1 or Stat 2 gene can be an antibody that selectively binds such a polypeptide, namely, an antibody raised against a polypeptide encoded by a Jak 1, Jak 2, Jak3, Stat 1 or Stat 2 gene or an epitope-containing fragment thereof. Although non-specific binding towards other antigens can occur, binding to the target polypeptide occurs with a higher affinity and can be reliably discriminated from non-specific binding. In one embodiment, the method can comprise contacting a sample from the subject with an antibody specific for a wild type or an altered form of a polypeptide encoded by a Jak 1, Jak 2, Jak3, Stat 1 or Stat 2 gene, and determining the presence of an immune complex. Optionally, the sample can be contacted to a support coated with antibody specific for the wild type or altered form of a polypeptide encoded by a Jak 1, Jak 2, Jak3, Stat 1 or Stat 2 gene. In one embodiment, the sample can be contacted simultaneously, or in parallel, or sequentially, with various antibodies specific for different forms of a polypeptide encoded by a Jak 1, Jak 2, Jak3, Stat 1 or Stat 2 gene, such as a wild type and various altered forms thereof.

Gene Therapy and Protein Replacement Methods

Delivery of nucleic acids into viable cells can be effected ex vivo, in situ, or in vivo by use of vectors, such as viral vectors (e.g., lentivirus, adenovirus, adeno-associated virus, or a retrovirus), or ex vivo by use of physical DNA transfer methods (e.g., liposomes or chemical treatments). Non-limiting techniques suitable for the transfer of nucleic acid into mammalian cells in vitro include the use of liposomes, electroporation, microinjection, cell fusion, DEAE-dextran, and the calcium phosphate precipitation method (See, for example, Anderson, Nature, supplement to vol. 392, no. 6679, pp. 25-20 (1998)). Introduction of a nucleic acid or a gene encoding a polypeptide of the invention can also be accomplished with extrachromosomal substrates (transient expression) or artificial chromosomes (stable expression). Cells can also be cultured ex vivo in the presence of therapeutic compositions of the present invention in order to proliferate or to produce a desired effect on or activity in such cells. Treated cells can then be introduced in vivo for therapeutic purposes.

Nucleic acids can be inserted into vectors and used as gene therapy vectors. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Biandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Non-limiting examples of in vivo gene transfer techniques include transfection with viral (e.g., retroviral) vectors (see U.S. Pat. No. 5,252,479, which is incorporated by reference in its entirety) and viral coat protein-liposome mediated transfection (Dzau et al., Trends in Biotechnology 11:205-210 (1993), incorporated entirely by reference). For example, naked DNA vaccines are generally known in the art; see Brower, Nature Biotechnology, 16:1304-1305 (1998), which is incorporated by reference in its entirety. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

For reviews of gene therapy protocols and methods see Anderson et al., Science 256:808-813 (1992); U.S. Pat. Nos. 5,252,479, 5,747,469, 6,017,524, 6,143,290, 6,410,010 6,511,847; and U.S. Application Publication Nos. 2002/0077313 and 2002/00069, which are all hereby incorporated by reference in their entireties. For additional reviews of gene therapy technology, see Friedmann, Science, 244:1275-1281 (1989); Verma, Scientific American: 68-84 (1990); Miller, Nature, 357: 455-460 (1992); Kikuchi et al., J Dermatol Sci. 2008 May; 50(2):87-98; Isaka et al., Expert Opin Drug Deliv. 2007 September; 4(5):561-71; Jager et al., Curr Gene Ther. 2007 August; 7(4):272-83; Waehler et al., Nat Rev Genet. 2007 August; 8(8):573-87; Jensen et al., Ann Med. 2007; 39(2):108-15; Herweijer et al., Gene Ther. 2007 January; 14(2):99-107; Eliyahu et al., Molecules, 2005 Jan. 31; 10(0: 34-64; and Altaras et al., Adv Biochem Eng Biotechnol. 2005; 99:193-260, all of which are hereby incorporated by reference in their entireties.

Protein replacement therapy can increase the amount of protein by exogenously introducing wild-type or biologically functional protein by way of infusion. A replacement polypeptide can be synthesized according to known chemical techniques or can be produced and purified via known molecular biological techniques. Protein replacement therapy has been developed for various disorders. For example, a wild-type protein can be purified from a recombinant cellular expression system (e.g., mammalian cells or insect cells—see U.S. Pat. No. 5,580,757 to Desnick et al.;

U.S. Pat. Nos. 6,395,884 and 6,458,574 to Selden et al.; U.S. Pat. No. 6,461,609 to Calhoun et al.; U.S. Pat. No. 6,210,666 to Miyamura et al.; U.S. Pat. No. 6,083,725 to Selden et al.; U.S. Pat. No. 6,451,600 to Rasmussen et al.; U.S. Pat. No. 5,236,838 to Rasmussen et al. and U.S. Pat. No. 5,879,680 to Ginns et al.), human placenta, or animal milk (see U.S. Pat. No. 6,188,045 to Reuser et al.), or other sources known in the art. After the infusion, the exogenous protein can be taken up by tissues through non-specific or receptor-mediated mechanism.

A polypeptide encoded by a Jak 1, Jak 2, Jak3, Stat 1 or Stat 2 gene can also be delivered in a controlled release system. For example, the polypeptide can be administered using intravenous infusion, an implantable osmotic pump, a transdermal patch, liposomes, or other modes of administration. In one embodiment, a pump can be used (see is Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

Pharmaceutical Compositions and Administration for Therapy

Jak 1, Jak 2, Jak3, Stat 1 or Stat 2 proteins and Jak 1, Jak 2, Jak3, Stat 1 or Stat 2 modulating compounds of the invention can be administered to the subject once (e.g., as a single injection or deposition). Alternatively, Jak 1, Jak 2, Jak3, Stat 1 or Stat 2 proteins and Jak 1, Jak 2, Jak3, Stat 1 or Stat 2 modulating compounds can be administered once or twice daily to a subject in need thereof for a period of from about two to about twenty-eight days, or from about seven to about ten days. Jak 1, Jak 2, Jak3, Stat 1 or Stat 2 proteins and Jak 1, Jak 2, Jak3, Stat 1 or Stat 2 modulating compounds can also be administered once or twice daily to a subject for a period of 1, 2, 3, 4, 5, 6, 7, 8, 9, 10, 11, 12 times per year, or a combination thereof. Furthermore, Jak 1, Jak 2, Jak3, Stat 1 or Stat 2 proteins and Jak 1, Jak 2, Jak3, Stat 1 or Stat 2 modulating compounds of the invention can be co-administrated with another therapeutic. Where a dosage regimen comprises multiple administrations, the effective amount of the Jak 1, Jak 2, Jak3, Stat 1 or Stat 2 proteins and Jak 1, Jak 2, Jak3, Stat 1 or Stat 2 modulating compounds administered to the subject can comprise the total amount of gene product administered over the entire dosage regimen.

Jak 1, Jak 2, Jak3, Stat 1 or Stat 2 proteins and Jak 1, Jak 2, Jak3, Stat 1 or Stat 2 modulating compounds can be administered to a subject by any means suitable for delivering the Jak 1, Jak 2, Jak3, Stat 1 or Stat 2 proteins and Jak 1, Jak 2, Jak3, Stat 1 or Stat 2 modulating compounds to cells of the subject, such as the dermis, epidermis, dermal papilla cells, or hair follicle cells. For example, Jak 1, Jak 2, Jak3, Stat 1 or Stat 2 proteins and Jak 1, Jak 2, Jak3, Stat 1 or Stat 2 modulating compounds can be administered by methods suitable to transfect cells. Transfection methods for eukaryotic cells are well known in the art, and include direct injection of the nucleic acid into the nucleus or pronucleus of a cell; electroporation; liposome transfer or transfer mediated by lipophilic materials; receptor mediated nucleic acid delivery, bioballistic or particle acceleration; calcium phosphate precipitation, and transfection mediated by viral vectors.

The compositions of this invention can be formulated and administered to reduce the symptoms associated with a hair-loss disorder by any means that produces contact of the active ingredient with the agent's site of action in the body of a subject, such as a human or animal (e.g., a dog, cat, or horse). They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

A therapeutically effective dose of Jak 1, Jak 2, Jak3, Stat 1 or Stat 2 modulating compounds can depend upon a number of factors known to those or ordinary skill in the art. The dose(s) of the Jak 1, Jak 2, Jak3, Stat 1 or Stat 2 modulating compounds can vary, for example, depending upon the identity, size, and condition of the subject or sample being treated, further depending upon the route by which the composition is to be administered, if applicable, and the effect which the practitioner desires the Jak 1, Jak 2, Jak3, Stat 1 or Stat 2 modulating compounds to have upon the nucleic acid or polypeptide of the invention. These amounts can be readily determined by a skilled artisan. Any of the therapeutic applications described herein can be applied to any subject in need of such therapy, including, for example, a mammal such as a dog, a cat, a cow, a horse, a rabbit, a monkey, a pig, a sheep, a goat, or a human.

Pharmaceutical compositions for use in accordance with the invention can be formulated in conventional manner using one or more physiologically acceptable carriers or excipients. The therapeutic compositions of the invention can be formulated for a variety of routes of administration, including systemic and topical or localized administration. Techniques and formulations generally can be found in *Remmington's Pharmaceutical Sciences*, Meade Publishing Co., Easton, Pa. (20$^{th}$ Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

The invention also provides for a kit that comprises a pharmaceutically acceptable carrier and a Jak 1, Jak 2, Jak3, Stat 1 or Stat 2 modulating compound identified using the screening assays of the invention packaged with instructions for use. For modulators that are antagonists of the activity of a Jak 1, Jak 2, Jak3, Stat 1 or Stat 2 protein, or which reduce the expression of a Jak 1, Jak 2, Jak3, Stat 1 or Stat 2 protein, the instructions would specify use of the pharmaceutical composition for promoting the loss of hair on the body surface of a mammal (for example, arms, legs, bikini area, face).

For Jak 1, Jak 2, Jak3, Stat 1 or Stat 2 modulating compounds that are agonists of the activity of a Jak 1, Jak 2, Jak3, Stat 1 or Stat 2 protein or increase the expression of one or more proteins encoded by Jak 1, Jak 2, Jak3, Stat 1 or Stat 2 genes, the instructions would specify use of the pharmaceutical composition for regulating hair growth. In one embodiment, the instructions would specify use of the pharmaceutical composition for the treatment of hair loss disorders. In a further embodiment, the instructions would specify use of the pharmaceutical composition for restoring hair pigmentation. For example, administering an agonist can reduce hair graying in a subject.

A pharmaceutical composition containing a Jak 1, Jak 2, Jak3, Stat 1 or Stat 2 modulating compound can be administered in conjunction with a pharmaceutically acceptable carrier, for any of the therapeutic effects discussed herein. Such pharmaceutical compositions can comprise, for example antibodies directed to polypeptides encoded by genes comprising a Jak 1, Jak 2, Jak3, Stat 1 or Stat 2 gene, or variants thereof, or agonists and antagonists of a polypeptide encoded by a Jak 1, Jak 2, Jak3, Stat 1 or Stat 2 gene. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

Sterile injectable solutions can be prepared by incorporating the Jak 1, Jak 2, Jak3, Stat 1 or Stat 2 modulating compound (e.g., a polypeptide or antibody) in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

In some embodiments, the Jak 1, Jak 2, Jak3, Stat 1 or Stat 2 modulating compound can be applied via transdermal delivery systems, which slowly releases the active compound for percutaneous absorption. Permeation enhancers can be used to facilitate transdermal penetration of the active factors in the conditioned media. Transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Various routes of administration and various sites of cell implantation can be utilized, such as, subcutaneous or intramuscular, in order to introduce the aggregated population of cells into a site of preference. Once implanted in a subject (such as a mouse, rat, or human), the aggregated cells can then stimulate the formation of a hair follicle and the subsequent growth of a hair structure at the site of introduction. In another embodiment, transfected cells (for example, cells expressing a protein encoded by a Jak 1, Jak 2, Jak3, Stat 1 or Stat 2 gene are implanted in a subject to promote the formation of hair follicles within the subject. In further embodiments, the transfected cells are cells derived from the end bulb of a hair follicle (such as dermal papilla cells or dermal sheath cells). Aggregated cells (for example, cells grown in a hanging drop culture) or transfected cells (for example, cells produced as described herein) maintained for 1 or more passages can be introduced (or implanted) into a subject (such as a rat, mouse, dog, cat, human, and the like).

"Subcutaneous" administration can refer to administration just beneath the skin (i.e., beneath the dermis). Generally, the subcutaneous tissue is a layer of fat and connective tissue that houses larger blood vessels and nerves. The size of this layer varies throughout the body and from person to person. The interface between the subcutaneous and muscle layers can be encompassed by subcutaneous administration.

This mode of administration can be feasible where the subcutaneous layer is sufficiently thin so that the factors present in the compositions can migrate or diffuse from the locus of administration and contact the hair follicle cells responsible for hair formation. Thus, where intradermal administration is utilized, the bolus of composition administered is localized proximate to the subcutaneous layer.

Administration of the cell aggregates (such as DP or DS aggregates) is not restricted to a single route, but can encompass administration by multiple routes. For instance, exemplary administrations by multiple routes include, among others, a combination of intradermal and intramuscular administration, or intradermal and subcutaneous administration. Multiple administrations can be sequential or concurrent. Other modes of application by multiple routes will be apparent to the skilled artisan.

In other embodiments, this implantation method will be a one-time treatment for some subjects. In further embodiments of the invention, multiple cell therapy implantations will be required. In some embodiments, the cells used for implantation will generally be subject-specific genetically engineered cells. In another embodiment, cells obtained from a different species or another individual of the same species can be used. Thus, using such cells can require administering an immunosuppressant to prevent rejection of the implanted cells. Such methods have also been described in United States Patent Application Publication 2004/0057937 and PCT application publication WO 2001/32840, and are hereby incorporated by reference.

Inhibitors

Cytokines are produced to activate neighboring cells to communicate danger signals to one another and spread and amplify the inflammatory response. Over the years, it was learned how to both neutralize these cytokines with blocking antibodies and inhibit their signaling in responding cells by small molecule protein tyrosine kinase inhibitors FDA approved drugs exist for both approaches, e.g., IL-2 and TNF blocking antibodies and the small orally available molecule Gleevec™ that blocks cytokine signaling. Whenever possible, the center will pursue topical small molecule formulations that should improve efficacy while limiting systemic toxicity (improved therapeutic indexes) encouraging clinical evaluation in AA of other small molecule inhibitors in the biopharmaceutical pipeline.

To block signaling of cytokine receptors, topical/oral JAK1/2 inhibitor (Incyte), which has already demonstrated safety and efficacy in patients with psoriaisis and RA, can be used. Similarly, topical and/or oral JAK3 inhibitors as described herein (e.g., tofacitinib (CP690550), R348 and VX-509), which have demonstrated preliminary safety and efficacy in patients with RA, can be used.

The inhibitors can comprise peptides (such as antibodies or fragments thereof), small molecules, nucleic acids (such as siRNA or antisense RNA), or other agents) that can bind to a polypeptide molecule encoded by a gene of interest and/or molecules that have an inhibitory effect on the biological activity of a protein of interest or its expression.

As used herein, a "Jak 1 inhibitor" refers to a compound that interacts with a Jak 1 gene or a Jak 1 protein or polypeptide and inhibits its activity and/or its expression. The compound can decrease the activity or expression of a protein encoded by Jak 1.

In one embodiment, a Jak 1 inhibitor can be a peptide fragment that binds a protein comprising SEQ ID NO: 1. For example, the fragment can encompass any portion of at least about 8 consecutive amino acids of SEQ ID NO: 1. The fragment can comprise at least about 10 consecutive amino acids, at least about 20 consecutive amino acids, at least about 30 consecutive amino acids, at least about 40 consecutive amino acids, at least about 50 consecutive amino acids, at least about 60 consecutive amino acids, or at least about 75 consecutive amino acids of SEQ ID NO: 1. Fragments include all possible amino acid lengths between and including about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) *Solid Phase Peptide Synthesis: a Practical Approach*. IRL Press, Oxford, England).

As used herein, a "Jak 2 inhibitor" refers to a compound that interacts with a Jak 2 gene or a Jak 2 protein or polypeptide and inhibits its activity and/or its expression. The compound can decrease the activity or expression of a protein encoded by Jak 2.

In one embodiment, a Jak 2 inhibitor can be a peptide fragment that binds a protein comprising SEQ ID NO: 3. For example, the fragment can encompass any portion of at least about 8 consecutive amino acids of SEQ ID NO: 3. The fragment can comprise at least about 10 consecutive amino acids, at least about 20 consecutive amino acids, at least about 30 consecutive amino acids, at least about 40 consecutive amino acids, at least about 50 consecutive amino acids, at least about 60 consecutive amino acids, or at least about 75 consecutive amino acids of SEQ ID NO: 3. Fragments include all possible amino acid lengths between and including about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) *Solid Phase Peptide Synthesis: a Practical Approach*. IRL Press, Oxford, England).

As used herein, a "Jak 3 inhibitor" can be a compound that interacts with a Jak 3 gene, or a Jak 3 protein or polypeptide, and inhibits its activity and/or its expression. The compound can decrease the activity or expression of a protein encoded by Jak 3. In one embodiment, a Jak3 inhibitor can be a Jak3 modulating compound.

In one embodiment, a Jak 3 inhibitor can be a peptide fragment that binds a protein comprising SEQ ID NO: 109. For example, the fragment can encompass any portion of about 8 consecutive amino acids of SEQ ID NO: 109. The fragment can comprise about 10 consecutive amino acids, about 20 consecutive amino acids, about 30 consecutive amino acids, about 40 consecutive amino acids, about 50 consecutive amino acids, about 60 consecutive amino acids, or about 75 consecutive amino acids of SEQ ID NO: 109. Fragments include all possible amino acid lengths between and including about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) *Solid Phase Peptide Synthesis: a Practical Approach*. IRL Press, Oxford, England).

An inhibitor of the invention can be a protein, such as an antibody (monoclonal, polyclonal, humanized, chimeric, or fully human), or a binding fragment thereof, directed against a polypeptide encoded by SEQ ID NO: 109. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab')$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) *Ann. Rev. Biomed. Eng.* 2:339-76; Hudson (1998) *Curr. Opin. Biotechnol.* 9:395-402). Antibodies can be obtained commercially, custom generated, or synthesized against an antigen of interest according to methods established in the art (see Roland E. Kontermann and Stefan Dübel (editors), *Antibody Engineering, Vol. I & II*, (2010) 2$^{nd}$ ed., Springer; Antony S. Dimitrov (editor), *Therapeutic Antibodies: Methods and Protocols (Methods in Molecular Biology)*, (2009), Humana Press; Benny Lo (editor) *Antibody Engineering: Methods and Protocols (Methods in Molecular Biology)*, (2004) Humana Press, each of which are hereby incorporated by reference in their entireties).

As used herein, a "Stat 1 inhibitor" refers to a compound that interacts with a Stat 1 gene or a Stat 1 protein or polypeptide and inhibits its activity and/or its expression. The compound can decrease the activity or expression of a protein encoded by Stat 1.

In one embodiment, a Stat 1 inhibitor can be a peptide fragment that binds a protein comprising SEQ ID NO: 5. For example, the fragment can encompass any portion of at least about 8 consecutive amino acids of SEQ ID NO: 5. The fragment can comprise at least about 10 consecutive amino acids, at least about 20 consecutive amino acids, at least about 30 consecutive amino acids, at least about 40 consecutive amino acids, at least about 50 consecutive amino acids, at least about 60 consecutive amino acids, or at least about 75 consecutive amino acids of SEQ ID NO: 5. Fragments include all possible amino acid lengths between and including about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) Solid Phase Peptide Synthesis: a Practical Approach. IRL Press, Oxford, England).

As used herein, a "Stat 2 inhibitor" refers to a compound that interacts with a Stat 2 gene or a Stat 2 protein or polypeptide and inhibits its activity and/or its expression. The compound can decrease the activity or expression of a protein encoded by Stat 2.

In one embodiment, a Stat 2 nhibitor can be a peptide fragment that binds a protein comprising SEQ ID NO: 7. For example, the fragment can encompass any portion of at least about 8 consecutive amino acids of SEQ ID NO: 7. The fragment can comprise at least about 10 consecutive amino acids, at least about 20 consecutive amino acids, at least about 30 consecutive amino acids, at least about 40 consecutive amino acids, at least about 50 consecutive amino acids, at least about 60 consecutive amino acids, or at least about 75 consecutive amino acids of SEQ ID NO: 7. Fragments include all possible amino acid lengths between and including about 8 and about 100 amino acids, for example, lengths between about 10 and about 100 amino acids, between about 15 and about 100 amino acids, between about 20 and about 100 amino acids, between about 35 and about 100 amino acids, between about 40 and about 100 amino acids, between about 50 and about 100 amino acids, between about 70 and about 100 amino acids, between about 75 and about 100 amino acids, or between about 80 and about 100 amino acids. These peptide fragments can be obtained commercially or synthesized via liquid phase or solid phase synthesis methods (Atherton et al., (1989) Solid Phase Peptide Synthesis: a Practical Approach. IRL Press, Oxford, England).

As used herein, a "Jak/Stat inhibitor" refers to a compound that interacts with a Jak1/Jak2/Jak3/Stat1/Stat2 gene or a Jak1/Jak2/Jak3/Stat1/Stat2 protein or polypeptide and inhibits its activity and/or its expression. The compound can decrease the activity or expression of a protein encoded by Jak1/Jak2/Jak3/Stat1/Stat2.

An inhibitor of the invention can be a protein, such as an antibody (monoclonal, polyclonal, humanized, chimeric, or fully human), or a binding fragment thereof, directed against a polypeptide encoded by the corresponding sequence disclosed herein. An antibody fragment can be a form of an antibody other than the full-length form and includes portions or components that exist within full-length antibodies, in addition to antibody fragments that have been engineered, Antibody fragments can include, but are not limited to, single chain Fv (scFv), diabodies, Fv, and (Fab')$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) Ann. Rev. Biomed. Eng. 2:339-76; Hudson (1998) Curr. Opin. Biotechnol. 9:395-402). Antibodies can be obtained commercially, custom generated, or synthesized against an antigen of interest according to methods established in the art (Janeway et al., (2001) Immunobiology, 5th ed., Garland Publishing).

An inhibitor of the invention can also be a small molecule that binds to a protein and disrupts its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules that modulate a protein can be identified via in silico screening or high-through-put (HTP) screening of combinatorial libraries. Most conventional pharmaceuticals, such as aspirin, penicillin, and many chemotherapeutics, are small molecules, can be obtained commercially, can be chemically synthesized, or can be obtained from random or combinatorial libraries (Werner et al., (2006) Brief Funct. Genomic Proteomic 5(1):32-6). In some embodiments, the agent is a small molecule that binds, interacts, or associates with a target protein or RNA. Such a small molecule can be an organic molecule that, when the target is an intracellular target, is capable of penetrating the lipid bilayer of a cell to interact with the target. Small molecules include, but are not limited to, toxins, chelating agents, metals, and metalloid compounds. Small molecules can be attached or conjugated to a targeting agent so as to specifically guide the small molecule to a particular cell.

Pharmaceutical Compositions and Administration for Therapy

An inhibitor or agonist of the invention can be incorporated into pharmaceutical compositions suitable for administration, for example the inhibitor and a pharmaceutically acceptable carrier.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a dog, a cat, a cow, a horse, a rabbit, a monkey, a pig, a sheep, a goat, or a human.

A pharmaceutical composition of the invention can be administered in conjunction with a pharmaceutically acceptable carrier, for any of the therapeutic effects discussed herein. Such pharmaceutical compositions can comprise, for example antibodies directed to polypeptides. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, CREMOPHOR EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the inhibitor (e.g., a polypeptide or antibody or small molecule) or agonist of the invention in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The dosage administered can be a therapeutically effective amount of the composition sufficient to result in amelioration of symptoms of alopecia areata, and can vary depending upon known factors such as the pharmacodynamic characteristics of the active ingredient and its mode and route of administration; age, sex, health and weight of the recipient; nature and extent of symptoms; kind of concurrent treatment, frequency of treatment and the effect desired.

In some embodiments, the effective amount of the administered Jak3 modulating compound (e.g., a compound described herein that is directed to Jak3, such as a small molecule JAK3 inhibitor) is about 0.0001 µg/kg body weight, about 0.00025 µg/kg body weight, about 0.0005 µg/kg body weight, about 0.00075 µg/kg body weight, about 0.001 µg/kg body weight, about 0.0025 µg/kg body weight, about 0.005 µg/kg body weight, about 0.0075 µg/kg body weight, about 0.01 µg/kg body weight, about 0.025 µg/kg body weight, about 0.05 µg/kg body weight, about 0.075 µg/kg body weight, about 0.1 µg/kg body weight, about 0.25 µg/kg body weight, about 0.5 µg/kg body weight, about 0.75 µg/kg body weight, about 1 µg/kg body weight, about 5 µg/kg body weight, about 10 µg/kg body weight, about 25 µg/kg body weight, about 50 µg/kg body weight, about 75 µg/kg body weight, about 100 µg/kg body weight, about 150 µg/kg body weight, about 200 µg/kg body weight, about 250 µg/kg body weight, about 300 µg/kg body weight, about 350 µg/kg body weight, about 400 µg/kg body weight, about 450 µg/kg body weight, about 500 µg/kg body weight, about 550 µg/kg body weight, about 600 µg/kg body weight, about 650 µg/kg body weight, about 700 µg/kg body weight, about 750 µg/kg body weight, about 800 µg/kg body weight, about 850 µg/kg body weight, about 900 µg/kg body weight, about 950 µg/kg body weight, about 1000 µg/kg body weight, about 2000 µg/kg body weight, about 3000 µg/kg body weight, about 4000 µg/kg body weight, about 5000 µg/kg body weight, about 6000 µg/kg body weight, about 7000 µg/kg body weight, about 8000 µg/kg body weight, about 95000 µg/kg body weight, or about 10,000 µg/kg body weight.

In some embodiments, the effective amount of the administered Jak3 modulating compound (e.g., a small molecule JAK3 inhibitor) is about 1 mg/kg body weight, about 1.5 mg/kg body weight, about 2 mg/kg body weight, about 2.5 mg/kg body weight, about 3 mg/kg body weight, about 3.5 mg/kg body weight, about 4 mg/kg body weight, about 4.5 mg/kg body weight, about 5 mg/kg body weight, about 5.5 mg/kg body weight, about 6 mg/kg body weight, about 6.5 mg/kg body weight, about 7 mg/kg body weight, about 7.5 mg/kg body weight, about 8 mg/kg body weight, about 9.5 mg/kg body weight, about 10 mg/kg body weight, about 10.5 mg/kg body weight, about 11.0 mg/kg body weight, about 11.5 mg/kg body weight, about 12 mg/kg body weight, about 12.5 mg/kg body weight, about 13 mg/kg body weight, about 13.5 mg/kg body weight, about 14 mg/kg body weight, about 14.5 mg/kg body weight, about 15 mg/kg body weight, about 15.5 mg/kg body weight, about 16 mg/kg body weight, about 16.5 mg/kg body weight, about 17 mg/kg body weight, about 17.5 mg/kg body weight, about 18 mg/kg body weight, about 19.5 mg/kg body weight, about 20 mg/kg body weight, about 21.5 mg/kg body weight, about 22 mg/kg body weight, about 22.5 mg/kg body weight, about 23 mg/kg body weight, about 23.5 mg/kg body weight, about 24 mg/kg body weight, about 24.5 mg/kg body weight, about 25 mg/kg body weight, about 25.5 mg/kg body weight, about 26 mg/kg body weight, about 26.5 mg/kg body weight, about 27 mg/kg body weight, about 27.5 mg/kg body weight, about 28 mg/kg body weight, about 29.5 mg/kg body weight, or about 30 mg/kg body weight.

In other embodiments, the administered Jak3 modulating compound (e.g., a compound described herein that is directed to Jak3, such as a small molecule JAK3 inhibitor), can be administered as a topical cream. In some embodiments, the effective amount of the administered Jak3 modulating compound (such as a small molecule JAK3 inhibitor) is present at a concentration of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%. In some embodiments, the effective amount of the administered Jak3 modulating compound (such as a small molecule JAK3 inhibitor) is present at a concentration of about 3.5%, about 4%, about 4.5%, about 5%, about 5.5%, about 6%, about 6.5%, about 7%, about 7.5%, about 8%, about 8.5%, about 9%, about 9.5%, or of about 10%.

In some embodiments, the Jak3 modulating compound (e.g., a compound described herein that is directed to Jak3, such as a small molecule JAK3 inhibitor), can be co-administered with a second JAK inhibitor (such as a JAK1/2 inhibitor). In one embodiment, the JAK1/2 inhibitor can be administered as a topical cream. In some embodiments, the effective amount of the administered small molecule JAK1/2 inhibitor is present at a concentration of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0%. In some embodiments, the effective amount of the administered JAK1/2 inhibitor is present at a concentration of about 3.5%, about 4%, about 4.5%, about 5%, about 5.5%, about 6%, about 6.5%, about 7%, about 7.5%, about 8%, about 8.5%, about 9%, about 9.5%, or of about 10%.

Toxicity and therapeutic efficacy of therapeutic compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

Those skilled in the art will recognize, or be able to ascertain, using no more than routine experimentation, numerous equivalents to the specific substances and procedures described herein. Such equivalents are considered to be within the scope of this invention, and are covered by the following claims.

All publications and other references mentioned herein are incorporated by reference in their entirety, as if each individual publication or reference were specifically and individually indicated to be incorporated by reference. Publications and references cited herein are not admitted to be prior art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Interferon γ has been shown to be a target in murine AA (see Nakamura, et al. 2008, Am J Pathol, 172(3): 650-658; see also Freyschmidt-Paul et al., Br J Dermatol., 155(3):515-521; see also Gilhar et al., Journal Invest. Dermatol., 124(1): 288-289). In human AA, AA PBMCs show Th1 skewing, AA skin shows IFN signature and GWAS genes (SOCS/IFN-g/). but also IL-2/6/13/21/26.

Figure 7:
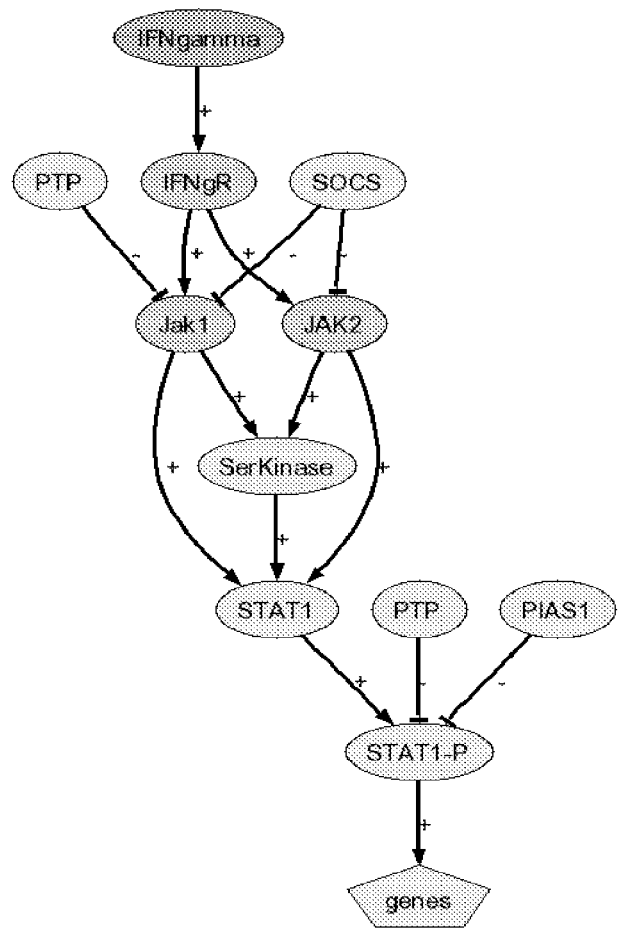
FIG. 7 shows a diagram showing the interferon γ pathway.
Figure 8A:
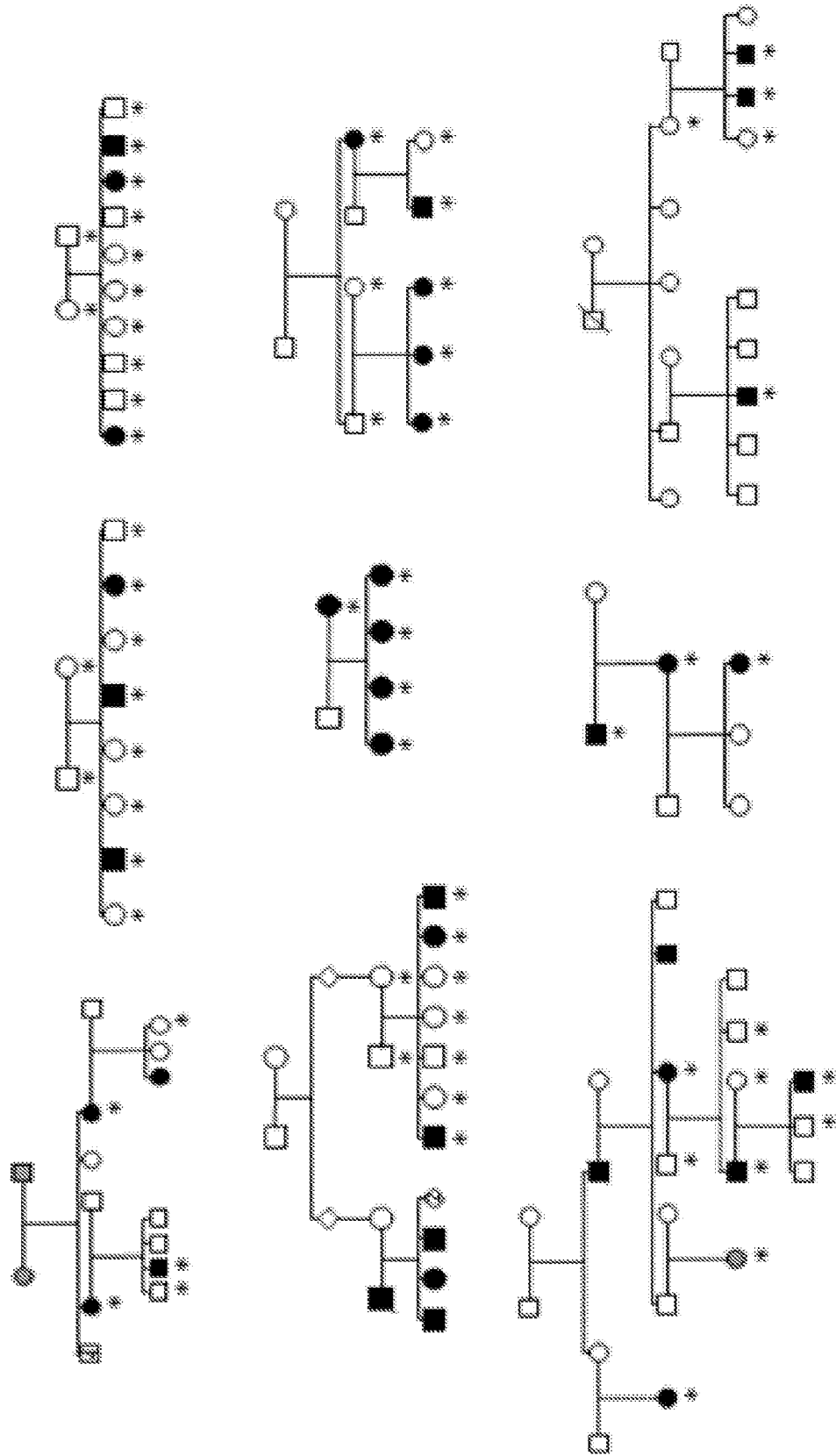
FIGS. 8A-B shows two gene mapping approaches.
Figure 8B:
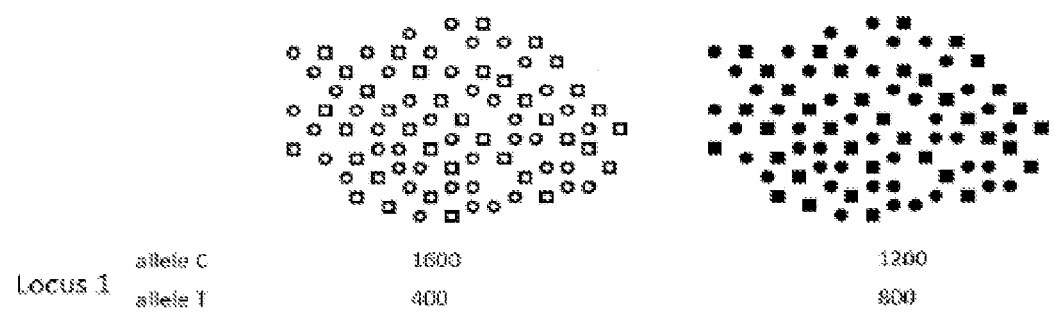

The interferon γ pathway (FIG. 7) induces NKG2DL in target HF cells, enhances antigen presentation by DCs, promotes Th1 cellular autoimmunity and augments NK and CTL mediated-cytolysis.

JAK1/2 inhibitors in clinical development include a) INCB018424, topical and oral; 5 nM activity (Incyte); b) CEP-701 (Cephalon); and c) TG101348.

a)

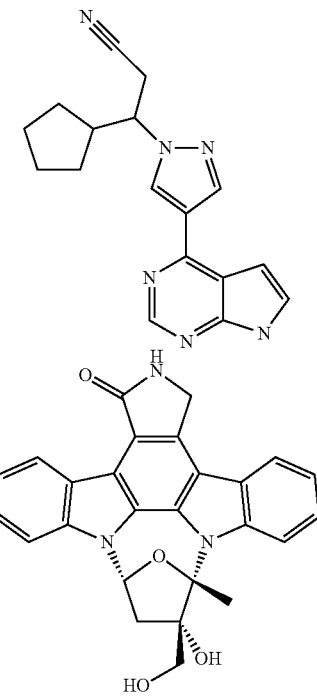

b)

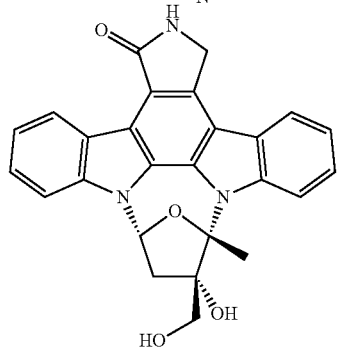

c)

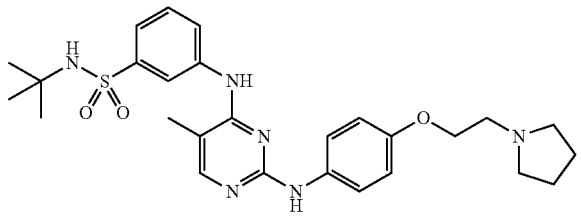

TABLE 4

INCB18424-203: Treatment-Emergent Adverse Events in Descending Order (all casualties) (oral delivery is considered an acceptable profile)

| Medra Preferred Term | Vehicle (n = 50) | Active (n = 149) |
|---|---|---|
| Application site irritation, pruritus | 7 (14.0) | 14 (9.3) |
| Nasopharyngitis | 1 (2.0) | 10 (6.7) |
| Upper respiratory tract infection | 3 (6.0) | 10 (6.7) |
| Sinusitis | 1 (2.0) | 6 (4.0) |
| Back Pain | 0 (0.0) | 5 (3.4) |
| Headache | 0 (0.0) | 4 (2.7) |
| Influenza | 2 (4.0) | 4 (2.7) |
| Abdominal pain | 0 (0.0) | 3 (2.0) |

Six SAEs, none treatment realted: prostate ca, prolonged hospitalization for cholecystitis, cholelithiasis (1.5%); herniated disc repair, coronary occlusion with hx ASHD (0.5%). CVA (vehicle)

Figure 9:
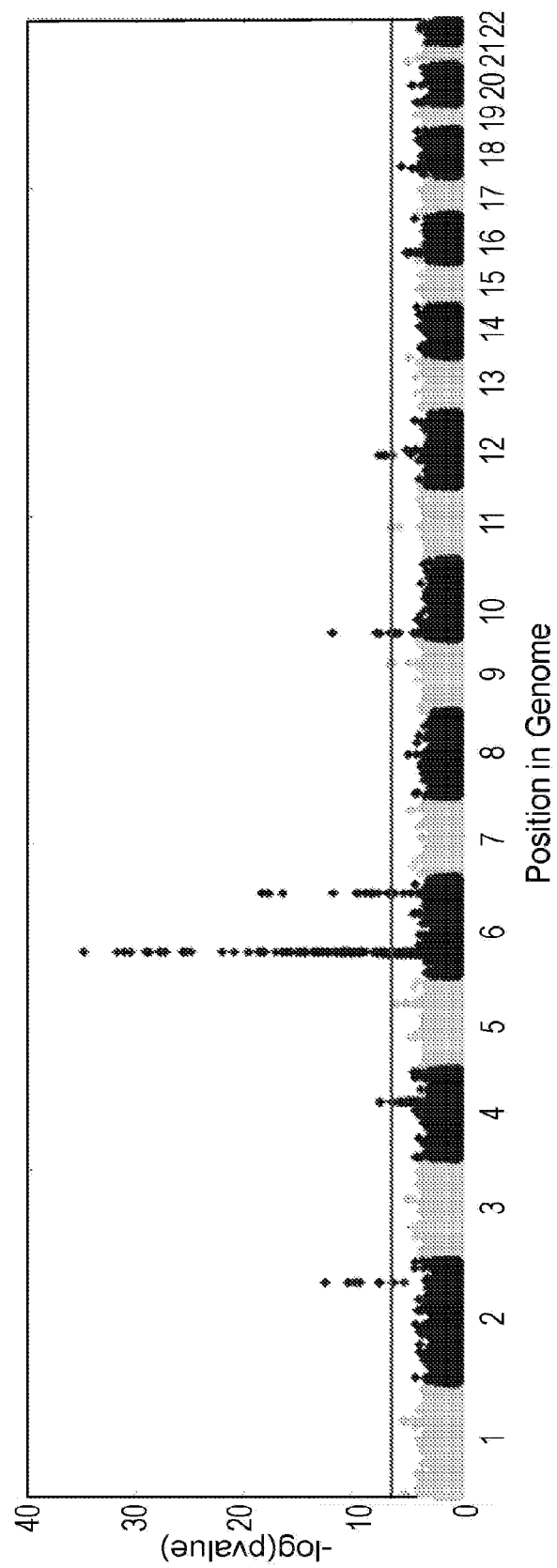
FIG. 9 shows a Genomewide Association Study (GWAS) in AA.
Figure 10A:
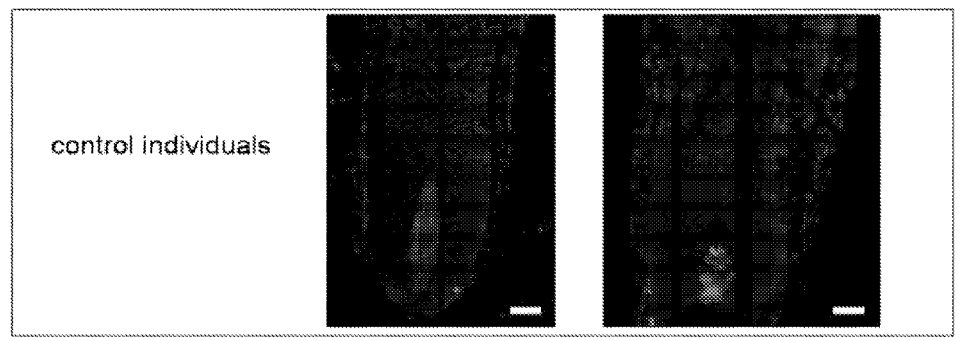
FIGS. 10A-B show danger signals: ULBP3 expression in the hair follicle in both control individuals (FIG. 10A) and AA patients (FIG. 10B).
Figure 10B:
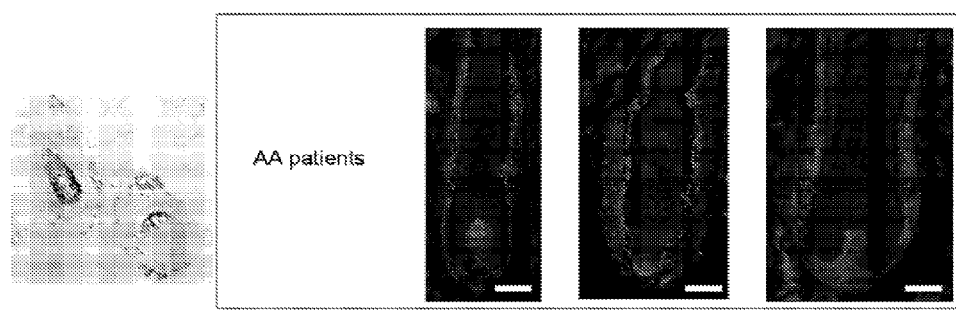
Figure 12:
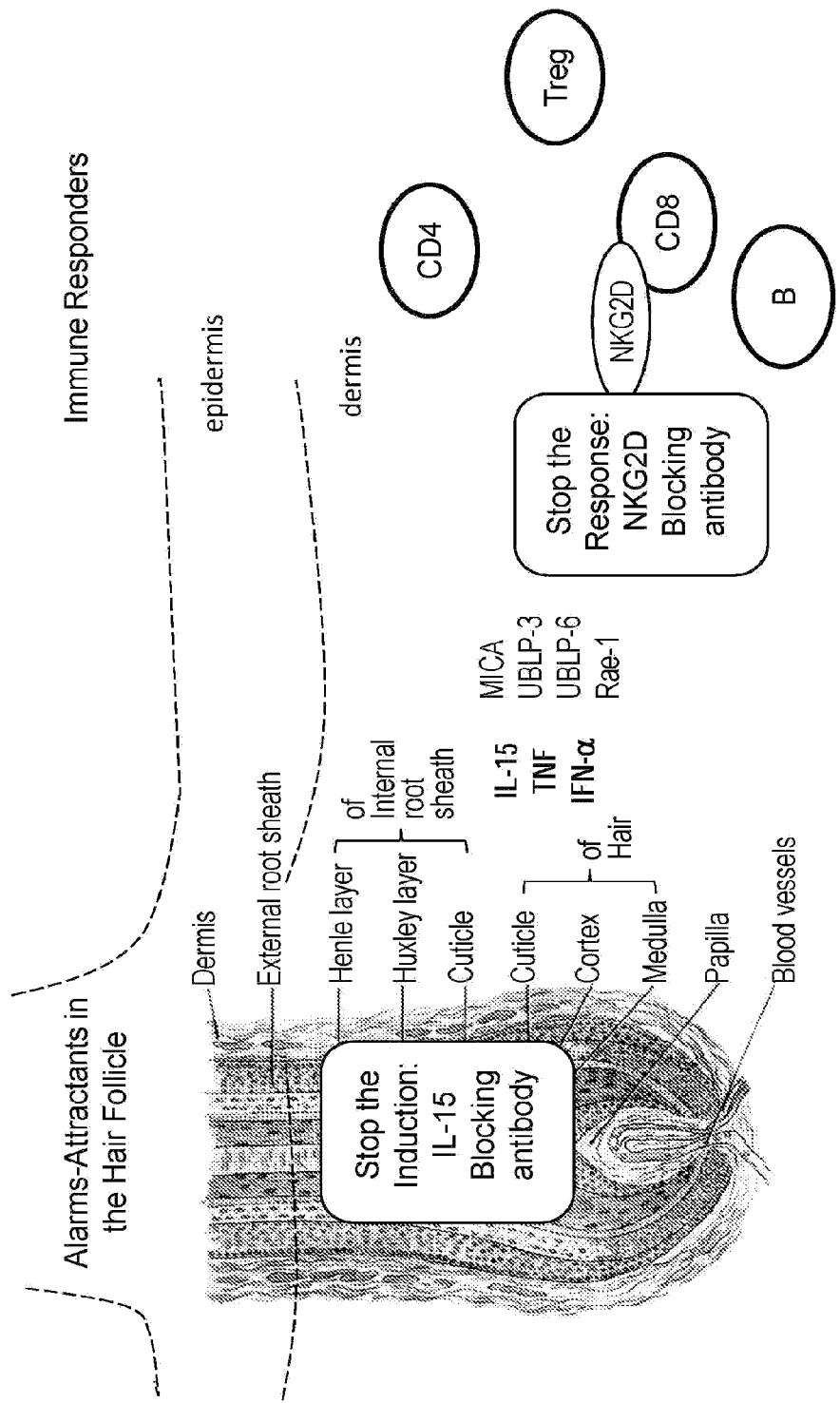
FIG. 12 shows a diagram that shows the inflammatory response underlying AA.
Figure 13:
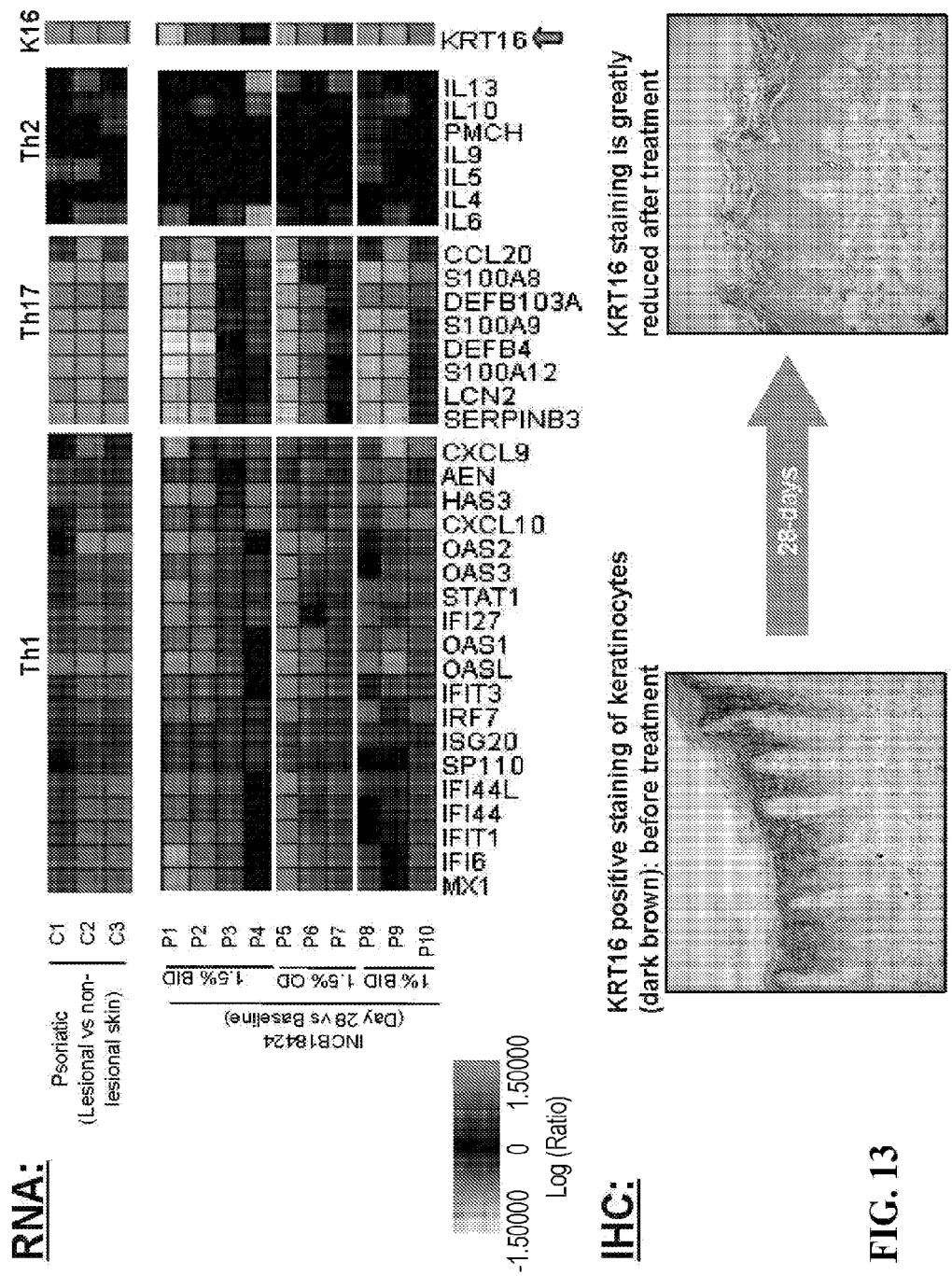
FIG. 13 shows INCB18424-202: Th1 and Th17 transcript markers and keratin 16 are decreased with topical INCB18424, a JAK1 and JAK2 inhibitor, treatment.
Figure 14:
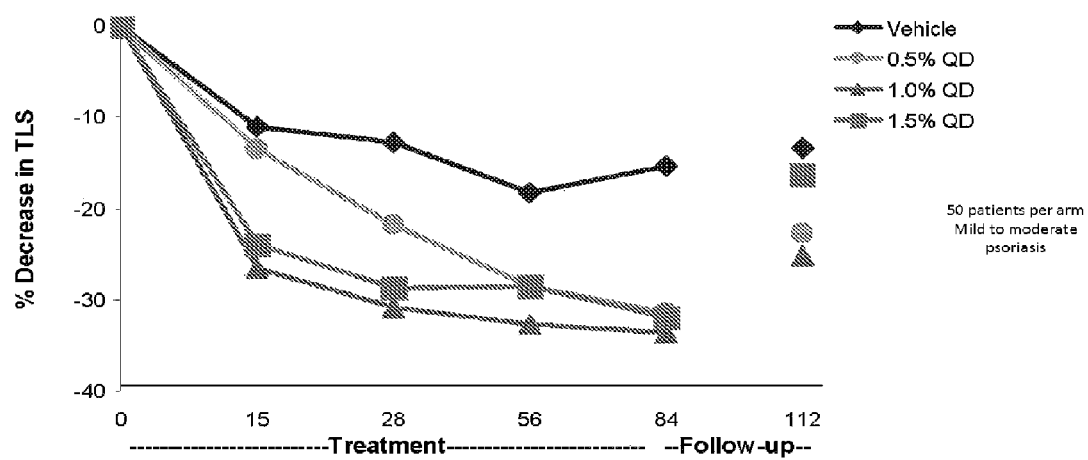
FIG. 14 shows the Key Total Lesion Score results for INCB 18424-203. The results how that Total Lesion Score for all dose groups ≥2× decrease over vehicle, achieving significance after control for multiplicity.
Figure 15A:
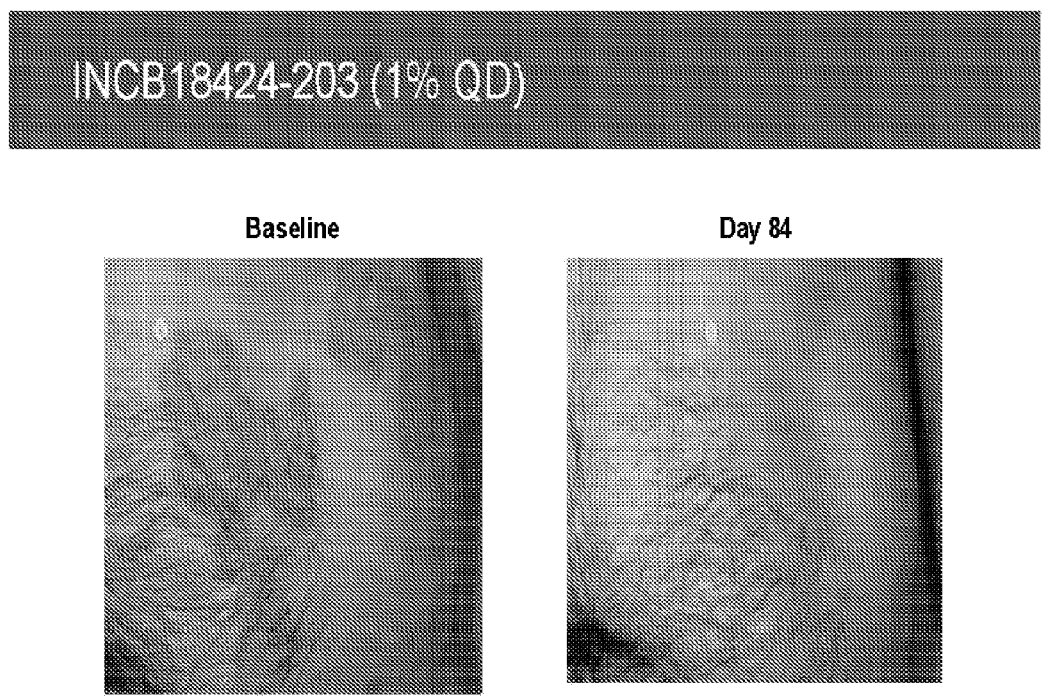
FIGS. 15A-B show that treatment with INCB018424 markedly reduces epidermal thickening and dermal inflammation. No pathological skin thinning is observed.
Figure 15B:
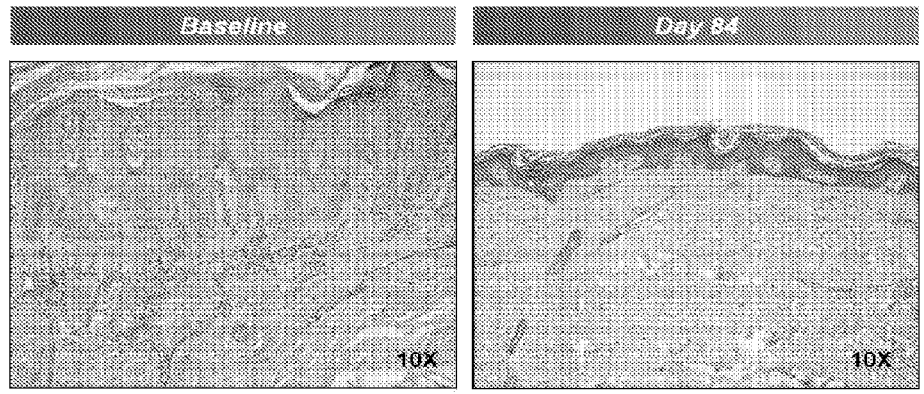
Figure 16:
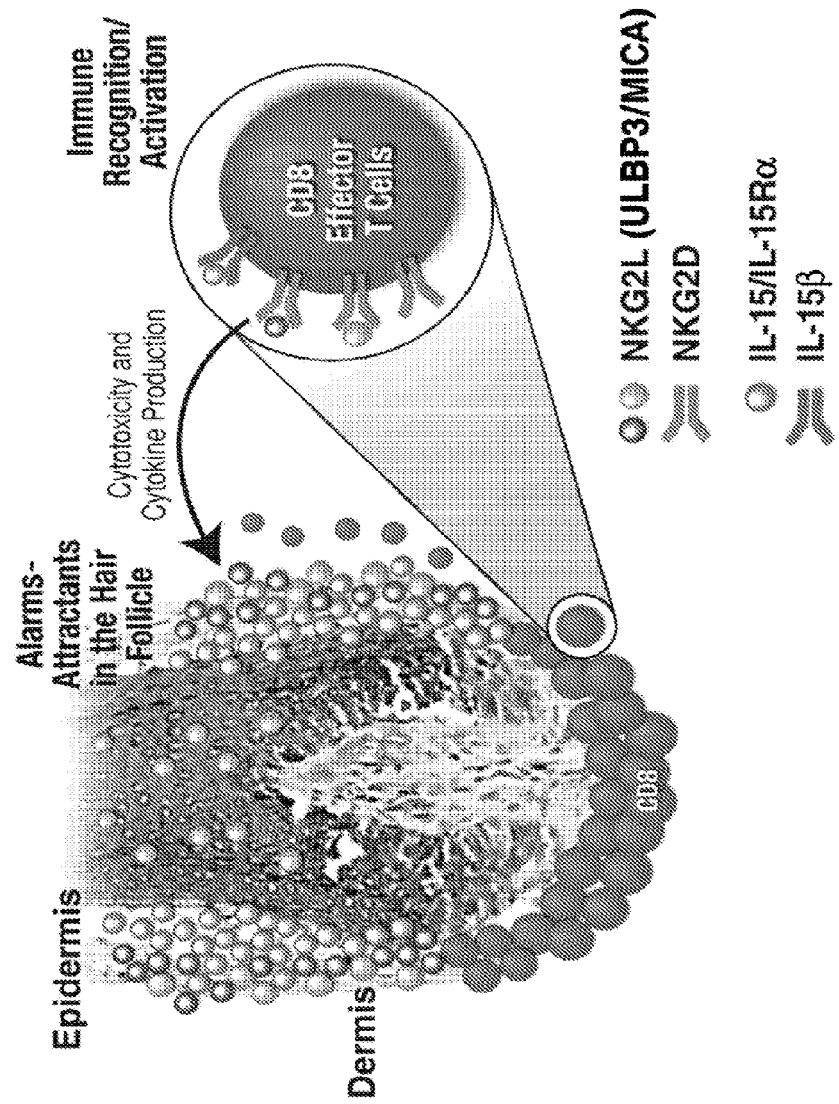
FIG. 16 is a schematic that shows the pre-clinical strategies to interrupt AA pathogenesis are aimed at interruption of the induction and effector function of CD8 T cells and include blocking IFN-γ signals.

Clinical programs in AA include the following:
Mild-Moderate AA: Phase 2/3 Psoriasis and oral Phase 3 Myelofibrosis, using a topical JAK inhibitor A population-based cohort evaluated cases ascertained through National Alopecia Areata Registry vs. controls ascertained through New York City Cancer project. They were matched for Northern European ancestry using AIMS.
Cases: n=1080 (Alopecia Universalis=482; Alopecia Totalis=120; Alopecia Areata Transient=176; Alopecia Areata Patchy=302)
Controls: n=1053
FIG. 9 presents a Genomewide Association Study (GWAS) in alopecia areata.

TABLE 5

List of Genes implicated in AA.

| Region | Gene | Function | Stongest association (pvalue) | Maximum odds ratio |
|---|---|---|---|---|
| 2q33.2 | CTLA4 | T-cell proliferation | $3.55 \times 10^{-13}$ | 1.44 |
|  | ICOS | T-cell proliferation | $4.33 \times 10^{-08}$ | 132 |
| 4q27 | IL21/IL2 | T-, B- and NK-cell proliferation | $4.27 \times 10^{-08}$ | 1.34 |
| 6q25.1 | ULBP6 | NKG2D activating ligand | $4.49 \times 10^{-19}$ | 1.65 |
|  | ULBP3 | NKG2D activating ligand | $4.43 \times 10^{-17}$ | 1.52 |
| 9q31.1 | STX17 | premature hair graying | $3.60 \times 10^{-07}$ | 1.33 |
| 10p15.1 | IL2RA (CD25) | T-cell proliferation | $1.74 \times 10^{-12}$ | 1.41 |
| 11q13 | PRDX5 | antioxidant enzyme | $4.14 \times 10^{-07}$ | 1.33 |
| 12q13 | Eos (IKZF4) | T-cell proliferation | $3.21 \times 10^{-08}$ | 1.34 |
|  | ERBB3 | epidermal growth factor receptor | $1.27 \times 10^{-07}$ | 1.34 |
| 6p21.32 (HLA) | MICA | NKG2D activating ligand | $1.19 \times 10^{-07}$ | 1.44 |
|  | NOTCH4 | T-cell differentiation | $1.03 \times 10^{-08}$ | 1.61 |
|  | BTNL2 | T-cell proliferation | $2.11 \times 10^{-26}$ | 2.70 |
|  | HLA-DRA | Antigen presentation | $2.93 \times 10^{-31}$ | 2.62 |
|  | HLA-DQA1 | Antigen presentation | $3.60 \times 10^{-17}$ | 2.15 |
|  | HLA-DQA2 | Antigen presentation | $1.38 \times 10^{-35}$ | 5.43 |
|  | HLA-DQB2 | Antigen presentation | $1.73 \times 10^{-13}$ | 1.60 |
|  | HLA-DOB | Antigen presentation | $2.07 \times 10^{-08}$ | 1.72 |

TABLE 6

Common Cause Model of Skin Autoimmune Diseases. See also
http://www.genome.gov/gwastudies (for psoriasis) and Jin et al., 2010, *NEJM*, 362: 1686-1697.

| Region | Gene | Stongest association (pvalue) | Maximum odds ratio | | Involved in other autoimmune disease |
|---|---|---|---|---|---|
| 2q33.2 | CTLA4 | $3.55 \times 10^{-13}$ | 1.44 | | T1D, RA, CeD, MS, SLE, GD |
| | ICOS | $4.33 \times 10^{-08}$ | 1.32 | | T1D, RA, CeD, MS, SLE, GD |
| 4q27 | IL21/IL2 | $4.27 \times 10^{-08}$ | 1.34 | ● | T1D, RA, CeD, PS |
| 6q25.1 | ULBP6 | $4.49 \times 10^{-19}$ | 1.65 | | none |
| | ULBP3 | $4.43 \times 10^{-17}$ | 1.52 | | none |
| 9q31.1 | STX17 | $3.60 \times 10^{-07}$ | 1.33 | | none |
| 10p15.1 | IL2RA (CD25) | $1.74 \times 10^{-12}$ | 1.41 | ● | T1D, MS, GD, GV |
| 11q13 | PRDX5 | $4.14 \times 10^{-07}$ | 1.33 | | MS |
| 12q13 | Eos (IKZF4) | $3.21 \times 10^{-08}$ | 1.34 | | T1D, SLE |
| | ERBB3 | $1.27 \times 10^{-07}$ | 1.34 | | T1D, SLE |
| 6p21.32 (HLA) | MICA | $1.19 \times 10^{-07}$ | 1.44 | ● | T1D, RA, CeD, UC, PS, SLE |
| | NOTCH4 | $1.03 \times 10^{-06}$ | 1.61 | | T1D, RA, MS |
| | C6orf10 | $1.45 \times 10^{-16}$ | 2.36 | ●● | T1D, RA, PS, GV |
| | BTNL2 | $2.11 \times 10^{-26}$ | 2.70 | ● | T1D, RA, UC, CD, SLE, MS, GV |
| | HLA-DRA | $2.93 \times 10^{-31}$ | 2.62 | ● | T1D, RA, CeD, MS, GV |
| | HLA-DQA1 | $3.60 \times 10^{-17}$ | 2.15 | ●● | T1D, RA, CeD, MS, SLE, PS, CD, UC, GD, GV |
| | HLA-DQA2 | $1.38 \times 10^{-35}$ | 5.43 | | T1D, RA |
| | HLA-DQB2 | $1.73 \times 10^{-13}$ | 1.60 | | RA |
| | HLA-DOB | $2.07 \times 10^{-08}$ | 1.72 | | |

Type I diabetes (T1D), rheumatoid arthritis (RA), celiac disease (CeD), multiple sclerosis (MS), system lupus erythematosus (SLE), Graves disease (GD), psoriasis (PS), Generalized Vitiligo (GV).

TABLE 7

Common Cause Model of Skin Autoimmune Diseases. See also
http://www.genome.gov/gwastudies (for psoriasis) and Jin el al.,
2010, *NEJM*, 362:1686-1697.

| Region | Gene | Stongest association (pvalue) | Maximum odds ratio | Involved in other autoimmune disease |
|---|---|---|---|---|
| 2q33.2 | CTLA4 | $3.55 \times 10^{-13}$ | 1.44 | T1D, RA, CeD, MS, SLE, GD |
| | ICOS | $4.33 \times 10^{-08}$ | 1.32 | T1D, RA, CeD, MS, SLE, GD |
| 4q27 | IL21/IL2 | $4.27 \times 10^{-08}$ | 1.34 | TIP, RA, CeD, PS |
| 6q25.1 | ULBP6 | $4.49 \times 10^{-19}$ | 1.65 | none |
| | ULBP3 | $4.43 \times 10^{-17}$ | 1.52 | none |
| 9q31.1 | STX17 | $3.60 \times 10^{-07}$ | 1.33 | none |
| 10p15.1 | IL2RA (CD25) | $1.74 \times 10^{-12}$ | 1.41 | T1D, MS, GD, GV |
| 11q13 | PRDX5 | $4.14 \times 10^{-07}$ | 1.33 | MS |
| 12q13 | Eos (IKZF4) | $3.21 \times 10^{-08}$ | 1.34 | T1D, SLE |
| | ERBB3 | $1.27 \times 10^{-07}$ | 1.34 | T1D, SLE |
| 6p21.32 (HLA) | MICA | $1.19 \times 10^{-07}$ | 1.44 | T1D, RA, CeD, UC, PS, SLE |
| | NOTCH4 | $1.03 \times 10^{-08}$ | 1.61 | T1D, RA, MS |
| | C6orf10 | $1.45 \times 10^{-16}$ | 2.36 | T1D, RA, PS, GV |
| | BTNL2 | $2.11 \times 10^{-26}$ | 2.70 | T1D, RA, UC, CD, SLE, MS, GV |
| | HLA-DRA | $2.93 \times 10^{-31}$ | 2.62 | T1D, RA, CeD, MS, GV |
| | HLA-DQA1 | $3.60 \times 10^{-17}$ | 2.15 | T1D, RA, CeD, MS, SLE, PS, CD, UC, GD, GV |
| | HLA-DQA2 | $1.38 \times 10^{-35}$ | 5.43 | T1D, RA |
| | HLA-DQB2 | $1.73 \times 10^{-13}$ | 1.60 | RA |
| | HLA-DOB | $2.07 \times 10^{-08}$ | 1.72 | |

Type I diabetes (T1D), rheumatoid arthritis (RA), celiac disease (CeD), multiple sclerosis (MS), system lupus erythematosus (SLE), Graves disease (GD), psoriasis (PS), Generalized Vitiligo (GV).

TABLE 8

List of Genes implicated in AA. Black circles indicate genes that affect NKG2D;
gray circles indicate genes that affect T-cell regulation; black circles
with star indicate genes that affect end organs

| Region | | Gene | Function | Stongest association (pvalue) | Maximum odds ratio |
|---|---|---|---|---|---|
| 2q33.2 | ● | CTLA4 | T-cell proliferation | $3.55 \times 10^{-13}$ | 1.44 |
| | | ICOS | T-cell proliferation | $4.33 \times 10^{-08}$ | 1.32 |
| 4q27 | ● | IL21/IL2 | T-, B- and NK-cell proliferation | $4.27 \times 10^{-08}$ | 1.34 |
| 6q25.1 | ● | ULBP6 | NKG2D activating ligand | $4.49 \times 10^{-19}$ | 1.65 |
| | ● | ULBP3 | NKG2D activating ligand | $4.43 \times 10^{-17}$ | 1.52 |
| 9q31.1 | ● | STX17 | premature hair graying | $3.60 \times 10^{-07}$ | 1.33 |
| 10p15.1 | ● | IL2RA (CD25) | T-cell proliferation | $1.74 \times 10^{-12}$ | 1.41 |
| 11q13 | ● | PRDX5 | antioxidant enzyme | $4.14 \times 10^{-07}$ | 1.33 |
| 12q13 | ● | Eos (IKZF4) | T-cell proliferation | $3.21 \times 10^{-08}$ | 1.34 |
| | | ERBB3 | epidermal growth factor receptor | $1.27 \times 10^{-07}$ | 1.34 |

TABLE 8-continued

List of Genes implicated in AA. Black circles indicate genes that affect NKG2D; gray circles indicate genes that affect T-cell regulation; black circles with star indicate genes that affect end organs

| Region | Gene | Function | Stongest association (pvalue) | Maximum odds ratio |
|---|---|---|---|---|
| 6p21.32 (HLA) | ● MICA | NKG2D activating ligand | $1.19 \times 10^{-07}$ | 1.44 |
| | NOTCH4 | T-cell differentiation | $1.03 \times 10^{-08}$ | 1.61 |
| | C6orf10 | | $1.45 \times 10^{-16}$ | 2.36 |
| | BTNL2 | T-cell proliferation | $2.11 \times 10^{-26}$ | 2.70 |
| | HLA-DRA | Antigen presentation | $2.93 \times 10^{-31}$ | 2.62 |
| | HLA-DQA1 | Antigen presentation | $3.60 \times 10^{-17}$ | 2.15 |
| | HLA-DQA2 | Antigen presentation | $1.38 \times 10^{-35}$ | 5.43 |
| | HLA-DQB2 | Antigen presentation | $1.73 \times 10^{-13}$ | 1.60 |
| | HLA-DOB | Antigen presentation | $2.07 \times 10^{-08}$ | 1.72 |

Genes which enhance the NK cell cytotoxic response; triggers T cells to produce proinflammatory cytokines; and induces CD4(+) T cells to differentiate into Th17 cells.

Genes which pivotal role in regulating the adaptive immune system by controlling the survival and proliferation of regulatory T (Treg) cells, which are required for the maintenance of immune tolerance.

Activating receptors expressed on natural killer (NK) cells, NK1.1 (+) T cells, and T cells. NKG2D ligands include MHC class I chain-related (MIC)A, MICB.

Candidate compounds for treatment of AA include compounds directed to Jak/Stat signaling are described in Ivanenkov et al., Mini Rev Med Chem. 2011 January; 11(1):55-78. which is hereby incorporated by reference in its entirety.

Example 2

The following genetic studies will be performed:
A replication study with another 1000 AA patients
Deep sequencing of candidate regions
Collection of 10,000 patients
Common Genetic Studies T1D, CeO and AA
An immunology study using NK activating ligands will be performed using ULBP3, ULBP6
inducible transgenics, new mouse models.

TABLE 9

Genes with Nominal Significance on the GWAS studies

| Gene | Mb | Count of SNPs $<1 \times 10^{-4}$ | Min p-value observed | Min p-value imputed | Autoimmune Reports | GO classification |
|---|---|---|---|---|---|---|
| Chromosome 2 | | | | | | |
| HDAC4 | 240.03 | 1 | 8.10E−05 | 5.59E−05 | | inflammatory response |
| Chromosome 3 | | | | | | |
| CACNA2D3 | 55.02 | 1 | 7.28E−05 | 1.47E−05 | CeD | |
| Chromosome 5 | | | | | | |
| IL13 | 132.02 | 2 | 1.87E−06 | | Asthma | immune response |
| Chromosome 6 | | | | | | |
| HLA-G | 29.94 | 1 | 1.07E−04 | 4.54E−06 | RA, MS, SLE, PS, T1D, Asthma, | immune response |
| HLA-A | 30.01 | 1 | 1.00E−04 | 2.72E−05 | MS, T1D, PS, GD, Asthma, Vitilago | immune response |
| MICB | 31.59 | 2 | 1.89E−05 | 1.97E−05 | MS, T1D, UC, RA, CeD, Asthma | immune response |
| TAP2 | 32.91 | 1 | 6.42E−06 | 1.28E−05 | T1D, RA, SLE, PS, GD | immune response |
| Chromosome 7 | | | | | | |
| IL6 | 22.72 | 2 | 7.72E−05 | 4.84E−05 | RA, T1D, CeD | inflammatory response |
| CHCHD3 | 132.44 | 1 | 3.07E−05 | 2.02E−05 | CeD | |
| Chromosome 8 | | | | | | |
| CSMD1 | 3.02 | 1 | 8.65E−05 | 8.38E−05 | CeD, MS, PS | |
| Chromosome 12 | | | | | | |
| IFNG | 66.84 | 1 | 1.55E−05 | 1.29E−05 | CeD, T1D, RA, MS, SLE, PS, GD, Asthma | |
| IL26 | 66.87 | 2 | 7.18E−05 | 6.45E−05 | MS, Asthma | immune response |
| Chromosome 16 | | | | | | |
| KIAA0350 (CLEC16A) | 11.11 | 6 | 1.77E−05 | 1.15E−05 | T1D, MS, Thyroid Disease | |
| SOCS1 | 11.24 | 2 | 1.16E−05 | 8.66E−06 | CeD, T1D, Asthma | |

TABLE 9-continued

Genes with Nominal Significance on the GWAS studies

| Gene | Mb | Count of SNPs <1 × 10⁻⁴ | Min p-value observed | Min p-value imputed | Autoimmune Reports | GO classification |
|---|---|---|---|---|---|---|
| Chromosome 18 | | | | | | |
| ANKRD12 | 9.25 | 2 | 3.59E−05 | 1.55E−05 | | |
| PTPN2 | 12.80 | 1 | 4.09E−06 | 3.38E−07 | CD, T1D | |

TABLE 10

Pathway analysis of nominal genes (see http://david.abcc.ncifcrf.gov/)

| Category | Term | Genes |
|---|---|---|
| hsa05332 | Graft-versus-host disease | IL6, IFNG, HLA-A, HLA-DMA, HLA-G |
| hsa04612 | Antigen processing and presentation | HSPA1L, TAP2, HLA-A, HLA-DMA, HLA-G |
| hsa04630 | Jak-STAT signaling pathway | SPRY2, IL6, SOCS1, IFNG, IL26, IL13 |
| hsa05330 | Allograft rejection | IFNG, HLA-A, HLA-DMA, HLA-G |
| hsa04940 | Type I diabetes mellitus | IFNG, HLA-A, HLA-DMA, HLA-G |
| hsa04650 | Natural killer cell mediated cytotoxicity | MICB, IFNG, HLA-A, HLA-G |
| hsa05320 | Autoimmune thyroid disease | HLA-A, HLA-DMA, HLA-G |
| hsa05416 | Viral myocarditis | HLA-A, HLA-DMA, HLA-G |
| hsa04060 | Cytokine-cytokine receptor interaction | IL6, IFNG, IL26, IL13 |

Example 3

Study Samples, Genotyping, Quality Control and Population Stratification

Alopecia areata (AA) is a major medical problem and is the most prevalent autoimmune disease in the US (Table 11), affecting approximately 4.6 million people, including males and females across all ethnic groups, with a lifetime risk of 1.7% (Kyriakis K P, Paltatzidou K, Kosma E, Sofouri E, Tadros A, Rachioti E. Alopecia areata prevalence by gender and age. *J Eur Acad Dermatol Venereol.* 23:572-3, 2009). Additionally, AA represents the second most common form of human hair loss, second only to androgenetic alopecia, and causes significant disfigurement and psychological distress to affected individuals (FIG. 1). AA affects more individuals than most other autoimmune diseases combined, including lupus erythematosus (LE), type 1 diabetes (T1D), psoriasis, multiple sclerosis (MS) and rheumatoid arthritis (RA) (Table 11).

TABLE 11

Automimmune Disease Prevalence

| Autoimmune Disease | Rate per 100,000 |
|---|---|
| Alopecia Areata | 1700 |
| Psoriasis | 696-1527 |
| Rheumatoid arthritis | 310-800 |
| Type 1 diabetes | 227-355 |
| Multiple sclerosis | 177-358 |
| Systemic lupus erythematosus | 34-150 |

In stark contrast to these other conditions, research into the pathogenesis and the development of innovative therapies in AA has lagged far behind. This can be due in part to the perception that AA is merely a cosmetic disorder. In reality, AA carries one of the highest burdens among any skin diseases, particularly among children and adolescents whose self-image is so closely linked to their appearance (Bickers D R, Lim H W, Margolis D, Weinstock M A, Goodman C, Faulkner E, Gould C, Gemmen E, Dall T; American Academy of Dermatology Association; Society for Investigative Dermatology. The burden of skin diseases: 2004 a joint project of the American Academy of Dermatology Association and the Society for Investigative Dermatology. *J Am Acad Dermatol.* 55:490-5, 2006).

Despite its high prevalence, there are no evidence-based treatments for AA. A comprehensive Cochrane analysis assessment of seventeen randomized clinical trials (RCTs) involving a total of 540 participants found no proven treatment of AA (Delamere F M, Sladden M M, Dobbins H M, Leonardi-Bee J. Interventions for alopecia areata. *Cochrane Database Syst Rev.* 2:CD004413, 2008). Each trial included from 6 to 85 participants and assessed a range of interventions that included topical and oral corticosteroids, topical cyclosporin, photodynamic therapy and topical minoxidil. Overall, none of the interventions showed significant treatment benefit in terms of hair growth when compared with placebo. It was concluded that, few, (if any), treatments for AA are proven to be effective. No RCTs on the use of diphencyprone, dinitrochlorobenzene, intralesional corticosteroids or dithranol were found, although these drugs are commonly used for the treatment of AA. Similarly, although topical corticosteroids and minoxidil are widely prescribed and appear to be safe, there is no convincing evidence that they are beneficial in the long-term. Most trials have been poorly reported and/or are so small that any important clinical benefits are inconclusive. These observations underscore the importance of defining the genetic basis of AA and determining its pathogenesis, so that rational therapeutic approaches can be developed and translational research can begin.

Pre-Clinical Evaluation of Jak/Stat Targeting in Alopecia Areata

The NKG2D receptor (NKG2D), functions to eliminate cells emitting danger signals and dysregulation of this recognition process often leads to development of autoimmunity.

The influences of JAK and NF-kb inhibition will be pursued, where, without being bound by theory, NKG2DL expression will be inhibited at the transcriptional level. INCB18424, a JAK1/JAK2 inhibitor (po/topical), is in Phase II Clinical Trials for Myeloproliferative/Myelofibrosis Disorders and in Psoriasis.

TABLE 12

Small Molecule Inhibitors of Jak1/Jak2
Small molecules

| JAK1/JAK2 Inhibitor (INCB18424) | PTKi: ATP-Binding Cleft Competitive Antagonist | Interferon Signaling | Topical | Phase II/Psoriasis |
|---|---|---|---|---|

GWAS studies revealed a number of risk loci shared by with other forms of autoimmunity, such as rheumatoid arthritis (RA), type I diabetes (TID), celiac disease (CeD), systemic lupus erythematosus (SLE), multiple sclerosis (MS) and psoriasis (PS), in particular, CTLA-4, IL2/IL2RA, IL21 and genes critical to Treg maintenance.

A genetic basis of AA provide avenues of exploration for therapies based on the underlying mechanisms of AA. Such therapies will focus not only on T cell subsets and mechanisms common to other forms of autoimmunity, but also on unique mechanisms that involve signaling pathways of Jak1/Jak2 and downstream effectors.

The origin of autoimmunity in AA can reside in the hair follicle itself. The studies herein are focused on defining putative danger signals in the hair follicle that contribute to the pathogenesis of AA. Pathogenic alleles that reside within the MHC, which can contribute to immune dysregulation driving the pathogenesis of AA, will also be identified. This can be due in part to the importance of antigen-presenting cells (APCs) in the presentation of danger signals as neoantigens to the immune system.

The mechanisms of Jak1/Jak2 signaling will be investigated, and the importance of Jak1/Jak2/Stat1/Stat2 interactions as drivers of disease induction will be evaluated. Pharmacologic approaches interrupting the Jak1/Jak2/Stat1/Stat2 signaling will be pursued.

C3H IFN-γ deficient mice are protected from AA development. It is shown that IFNs are capable of upregulating NKG2DL in cultured human dermal keratinocytes and fibroblasts. Further NKG2D-cross-linking induces IFN-γ production by innate NK, NKT and γδ T cells, thus creating a potential positive feedback loop, driving adaptive autoreactive immunity. Thus adoptive transfer and antibody depletion/blockade experiments will define the NKG2D-bearing cells involved.

Pharmacologic interventions aimed at interruption of the CD8 NKG2D axis will be examined. Interfering with the upregulation of NKG2DL or the activation of NKG2D-bearing cells are both rational approaches that will be pursued. It is shown that the IFN→JAK/STAT pathway can induce NKG2DL expression.

Whether the IFN→JAK/STAT pathway is pivotal to NKG2DL induction in normal and diseased skin will be assessed. The IFN JAK/STAT signaling pathway can be effectively inhibited with topical JAK1/JAK2 inhibitors, including an agent that has had early clinical success in Psoriasis. If the Type I interferon response underlies NKG2D ligand upregulation, JAK1/JAK2 inhibitors can block this induction, as well as block the IFN-gamma dependent components of the adaptive immune response.

References

1. Safavi K H, Muller S A, Suman V J, Moshell A N, Melton L J, 3rd. Incidence of alopecia areata in Olmsted County, Minn., 1975 through 1989. Mayo Clin Proc 1995; 70:628-33.
2. Jelinek J E. Sudden whitening of the hair. Bull N Y Acad Med 1972; 48:1003-13.
3. Ito T, Ito N, Saatoff M, et al. Maintenance of hair follicle immune privilege is linked to prevention of NK cell attack. The Journal of investigative dermatology 2008; 128:1196-206.
4. Todes-Taylor N, Turner R, Wood G S, Stratte P T, Morhenn V B. T cell subpopulations in alopecia areata. J Am Acad Dermatol 1984; 11:216-23.
5. Gilhar A, Landau M, Assy B, et al. Transfer of alopecia areata in the human scalp graft/Prkdc(scid) (SCID) mouse system is characterized by a TH1 response. Clin Immunol 2003; 106:181-7.
6. Gilhar A, Shalaginov R, Assy B, Serafimovich S, Kalish R S. Alopecia areata is a T-lymphocyte mediated autoimmune disease: lesional human T-lymphoeytes transfer alopecia areata to human skin grafts on SCID mice. J Investig Dermatol Symp Proc 1999; 4:207-10.
7. Zoller M, McElwee K J, Engel P, Hoffmann R. Transient CD44 variant isoform expression and reduction in CD4(+)/CD25(+) regulatory T cells in C3H/HeJ mice with alopecia areata. The Journal of investigative dermatology 2002; 118:983-92.
8. McElwee K J, Freyschmidt-Paul P, Hoffmann R, et al. Transfer of CD8(+) cells induces localized hair loss whereas CD4(+)/CD25(-) cells promote systemic alopecia areata and CD4(+)/CD25(+) cells blockade disease onset in the C3H/HeJ mouse model. The Journal of investigative dermatology 2005; 124:947-57.
9. Ito T, Meyer K C, Ito N, Paus R. Immune privilege and the skin. Curr Dir Autoimmun 2008; 10:27-52,
10. McDonagh A J, Tazi-Ahnini R. Epidemiology and genetics of alopecia areata. Clin Exp Dermatol 2002; 27:405-9.
11. van der Steen P, Traupe H, Happle R, Boezeman J, Strater R, Hamm H. The genetic risk for alopecia areata in first degree relatives of severely affected patients. An estimate. Acta Derm Venereol 1992; 72:373-5.
12. Jackow C, Puffer N, Hordinsky M, Nelson J, Tarrand J, Duvic M. Alopecia areata and cytomegalovirus infection in twins: genes versus environment? J Am Acad Dermatol 1998; 38:418-25.
13. Martinez-Mir A, Zlotogorski A, Gordon D, et al. Genomewide scan for linkage reveals evidence of several susceptibility loci for alopecia areata. Am J Hum Genet 2007; 80:316-28.
14. Nakamura et al., 2008, Controlled Delivery of T-box21 Small Interfering RNA Ameliorates Autoimmune Alopecia (Alopecia Areata) in a C3H/HeJ Mouse Model, *Am J Pathol.*, 172(3): 650-658.
15. Freyschmidt-Paul, K. J. McElwee, R. Hoffmannl, J. P. Sundberg, M. Vitacolonna, S. Kissling, M. Zoller, 2006, Interferon-gamma-deficient mice are resistant to the development of alopecia areata, *Br J Dermatol.*, 155(3):515-21.
16. Gilhar A., Kam Y., Assy B. and Kalish R., 2005, Alopecia areata induced in C3H/HeJ mice by interferon-gamma: evidence for loss of immune privilege, *Journal Invest. Dermatol.*, 124(1):288-9.
17. Wong et al., 2005, Inhibitors of the tyrosine kinase signaling cascade for asthma, *Curr. Opin. Pharmacol.*, 5(3): 264-71.

18. Mourich and Iverson, 2009, Splicing in the immune system: Potential targets for therapeutic intervention by antisense-mediated alternative splicing, *Curr. Opinion Mol. Ther.*, 11(2): 124-132.

19. Jin et al., 2010, Variant of TYR and Autoimmunity Susceptibility Loci in Generalized Vitiligo, NEJM, 362:1686-1697.

Example 4

Specific autoimmune mechanisms underlying Alopecia Arcata (AA) have remained obscure and therefore clinical investigation of AA has historically lagged behind other autoimmune diseases. Despite the large number of new biotherapeutics available for clinical evaluation in autoimmunity, intralesional or systemic steroids remain the standard of care and only two small randomized clinical trials have been published in the last decade. The insights provided by the discovery of GWAS genes provide a roadmap for closing this gap, by investigating GWAS-identified immunological pathways both for mechanistic and therapeutic relevance.

Identify Effective, Clinically-Relevant, Therapies in Mouse Models of Alopecia Areata.

In the normal state, hair follicles (HF) represent an immuneprivileged (IP) sanctuary, expressing little or no classical HLA class I molecules. In active AA, the IP status is lost, since HLA class I expression and NKG2D ligand expression are markedly upregulated. Given the strong genetic association of NKG2D ligand loci with human AA, without being bound by theory, aberrant NKG2DL upregulation and persistent NKG2D activation on immune effector cells drives inflammatory AA initiation and progression. Without being bound by theory, in AA, as for Celiac Disease, IL-15 can drive CD8 T cell effector differentiation enabling promiscuous "NK-type" CD8 cytotoxicity. Indeed, the local HF IL-15/NKG2DL inflammatory signals are accompanied by a dense infiltrate of $CD8^+$ T cells expressing NK markers, likely the critical AA immune effectors responsible for IFNγ production and HF cytotoxicity. These collective observations, made in both the human and mouse, invite therapeutic evaluation.

The therapeutic potential of blocking NK-like reprogramming and cytotoxicity by interfering with relevant cytokines (IFN-γ and relevant immunoreceptor signaling pathways (NKG2D). A graft model of alopecia in which all grafted C3H mice develop AA in a timely manner, within 12 weeks, will be used. This greatly accelerates drug screening since evaluation of prevention/reversal of spontaneous disease in C3H/HeJ is otherwise impractical given the late onset (>6 months of age) and low cumulative incidence (15%). Both small molecule approaches, that have the advantage of potential topical delivery, and biotherapeutic proteins (antibodies) that have superior biologic specificity, will be evaluated. The overarching goals are to use biotherapeutics to establish critical immune pathways that might be targeted by more clinically tenable, small molecule topical approaches.

Identify Disease-Associated AA Biomarkers and their Reversal with Effective Therapy in C3H Mice.

Approaches using GWAS and transcriptional profiling, for example, as well as approaches using immunostains and FACs of T cell subsets, for example, have been taken to identify several pathogenic AA biomarkers in the skin and blood of AA mice. These mouse studies will continue to inform developing a translational biomarker platform in human AA. In the skin, the studies in alopecic C3H/Hej mice demonstrated that IFN-induced genes are dramatically upregulated, including the chemokines CXCL9-11, which are likely responsible for recruitment of a dense infiltrate of HF-associated IFN-γ-producing $CXCR3^+$ NKG2D-bearing CD8 T effectors. Spectratype data provide striking evidence that these circulating $NKG2D^+$ CD8 T effectors are bona fide autoantigen-driven effector T cells that increase with disease progression. Temporal assessment of these serologic, cutaneous and cellular biomarkers in mice during treatment will enable one to identify dynamic, mechanistically important, prescient inflammatory biomarkers that predict therapeutic outcome and inform clinical biomarker discovery/utilization.

Preclinical Validation of Targeted Approaches Using AA Human Tissues Ex Vivo.

To expedite clinical development of treatments that demonstrate "proof-of-concept" in the AA mouse model, human AA tissues will be used for target validation and correlative studies. The "crawl-outs" system will provide a convenient ex vivo human bioassay to validate that agents that reverse mouse AA translate to the human, effectively inhibiting human AA T cell survival/expansion/function.

Just as the human DNA from thousands of alopecic subjects provided GWAS genes and unique insight into the human disease, human tissues, blood and skin from AA subjects will be used to continue to interrogate these genetically implicated immune pathways ultimately for therapeutic utility. Conceptually, the mouse model of alopecia areata this human pursuit, providing the pre-clinical testing grounds for therapeutic approaches in alopecia areata.

Autoimmune diseases affect an estimated 23 million individuals in the US (1) and although the prevalence of AA is not established, it is one of the most prevalent autoimmune diseases (2, 3). In 1999-2000, there were an estimated 2.4 million office visits for AA, half of which by patients in their 20 s and 30 s. AA causes significant disfigurement and psychological distress to affected individuals and carries one of the highest burdens among any skin diseases, particularly among children and adolescents whose self-image is so closely linked to their appearance (4). At present, the prognosis of AA is unpredictable and there is no definitive treatment. Current therapies include steroids and topical immune therapy, and induce durable remissions in only one third of patients (5, 6). Despite its high prevalence, a comprehensive Cochrane analysis assessment concluded that there are no evidence-based treatments for AA (7).

In stark contrast to other autoimmune conditions, research into the pathogenesis and the development of innovative therapies in AA has lagged far behind. In the era of targeted immunological therapies, only two clinical studies evaluating protein biotherapeutics in AA have been reported (8, 9) (both targeting T cell trafficking). In part this has been due to the limited understanding of specific AA immune pathways that would prompt evaluation of rational therapeutic approaches. Based on new understanding of the genetic and pathogenic basis of AA pre-clinical proof-of-concept data that will prompt clinical evaluation of rational therapeutic approaches in this disease will be obtained.

The GWAS (10) study revealed a number of risk loci shared by with other forms of autoimmunity, such as RA, T1D, celiac disease (CeD), SLE, MS and PS, in particular, CTLA4, IL2/IL2RA, IL21, NKG2D Ligands and genes critical to Treg function (Eos). The genetic commonality with RA, T1D, and CeD is especially noteworthy in light of the pathogenic significance of the expression of an NK ligand in the end organ (synovium, islet, gut and skin), and the involvement of the NKG2DL/NKG2D pathway in the pathogenesis of each of these three diseases (11, 14). One advantage of immunotherapeutic studies in the skin is the relative ease of access of the target organ. Thus, the studies herein examining the skin can provide important insight into NKG2D and IL-15 triggered CD8 cytotoxicity, IFN-triggered injury, etc., that impact the understanding of these other related human diseases in which the target organ is not accessible. Indeed positive studies in any one of these autoimmune diseases that share a common cause can serve as the basis for common treatments.

Specific autoimmune mechanisms underlying AA have remained obscure beyond the prevailing view that it is the result of T cell mediated attack of the hair follicle. In the normal state, hair follicles represent an immuneprivileged (IP) sanctuary (15-17), expressing little or no classical HLA class I molecules and instead express the inhibitory HLA ligands HLA-E and HLA-G, thus simultaneously avoiding immune recognition by class I restricted CD8 cells while negatively regulating NK cells, that might otherwise react to "missing self" (16, 18-21). In active AA, the IP status of the normal hair follicle is not operative, since HLA class I expression is markedly upregulated. Previous studies have noted both CD4 and CD8 T cell infiltrates surround the hair follicle in alopecic areas of skin in the mouse and human (22, 23). Indeed transfer of total T cells, but not B cells or sera, can transfer disease from an alopecic mouse or human to a normal WT (24) or SCID mouse (25), implicating effector T cells as the pathogenic cells. However molecular mediators of site-specific inflammation have not been previously identified.

Guided by the GWAS findings and previous immunobiological studies, new insight into this common autoimmune disorder is provided, that will lead to the development of innovative, rationally targeted treatments to fill the unmet needs of patients with AA.

AA Immunological Pathways Identified by GWAS Studies

The most highly-significant genetic loci found associated with alopecia areata are shown in Table 13: (the gray area denotes "nominally significant" genes). These seminal studies have been validated in a confirmatory study in a distinct population. Underlined genes are HF expressed genes while bold genes are genes expressed in immune cells. Overall, many susceptible loci are shared by other tissue-specific autoimmune states, with Type I diabetes exhibiting the most striking overlap (right column). The commonality with RA, T1D and CeD is particularly noteworthy, as NKG2D has been shown to have a significant role in the pathogenesis of each of these three diseases (11-14). Thus insight in any one of these disease/model systems is likely to shed light on common pathogenic pathways shared by multiple autoimmune states. The most highly significant alleles identified (other than HLA) were four NKG2D ligands (UBLP-3/UBLP-6/MICA/MICB in Bold italics) and one inhibitory ligand (HLA-G). The NKG2D receptor (NKG2D), functions to eliminate cells emitting danger signals and dysregulation of this recognition process often leads to development of autoimmunity (26). Other HF expressed genes that contribute to risk include HLA, antigen processing genes (TAP) and PRDX/STX17.

TABLE 13

Genetic loci associated with AA.

| | | | | |
|---|---|---|---|---|
| 2q33.2 | CTLA4 | Inhibits costim | $3.6 \times 10^{-13}$ | T1D, RA, CeD, MS, SLE, GD |
| | ICOS | T-cell costim | $4.3 \times 10^{-08}$ | T1D, RA, CeD, MS, SLE |
| 4q27 | IL21 | NK funtion/Th17 | $4.3 \times 10^{-08}$ | T1D, RA, CeD, PS |
| | IL2 | T-cell./Treg prolif. | $3.6 \times 10^{-04}$ | T1D, RA, CD, MS, CD, SLE, PS, GD |
| 6q25.1 | *ULBP6* | NKG2D ligand | $4.5 \times 10^{-19}$ | None |
| | *ULBP3* | NKG2D ligand | $4.4 \times 10^{-17}$ | None |
| 9q31.1 | STX17 | hair graying | $3.6 \times 10^{-07}$ | None |
| 10p15 | IL2RA | T-cell prolif./Treg | $1.7 \times 10^{-12}$ | T1D, MS, GD |
| 11q13 | PRDX5 | antiox enz | $4.1 \times 10^{-07}$ | MS |
| 12q13 | Eos | T-reg programming | $3.2 \times 10^{-08}$ | T1D, SLE |
| 6p21.3 | *MICA* | NKG2D ligand | $1.2 \times 10^{-07}$ | T1D, RA, CeD, UC, PS, SLE |
| (HLA) | NOTCH4 | Hematopoiesis | $1.0 \times 10^{-08}$ | T1D, RA, MS |
| | BTNL2 | T cell costim. | $2.1 \times 10^{-26}$ | T1D, RA, UC, CD, SLE, MS |
| | HLA-DRA | Ag presentation | $2.9 \times 10^{-31}$ | T1D, RA, CeD, MS |
| | HLA-DQA1 | Ag presentation | $3.6 \times 10^{-17}$ | T1D, RA, CeD, MS, SLE, S, CD UC, GD |

TABLE 13-continued

Genetic loci associated with AA.

| | | | | |
|---|---|---|---|---|
| | HLA-DQA2 | Ag presentation | $1.4 \times 10^{-35}$ | T1D, RA |
| | HLA-DQB2 | Ag presentation | $1.7 \times 10^{-13}$ | RA |
| | HLA-DOB | Ag presentation | $2.1 \times 10^{-08}$ | SLE |
| 5 | IL-13 | Th2 polarization | $1.9 \times 10^{-06}$ | Asthma |
| 6 | HLA-G | NKG2A inhibition | $1.0 \times 10^{-04}$ | RA, MS, SLE, PS, T1D, Asthma |
| | HLA-A | Ag presentation | $1.0 \times 10^{-04}$ | MS, T1D, PS, GD, Asthma, Vitiligo |
| | MICB | NKG2D ligand | $1.9 \times 10^{-05}$ | MS, T1D, UC, RA, CeD, Asthma |
| | TAP2 | Ag presentation | $6.4 \times 10^{-06}$ | T1D, RA, SLE, PS, GD |
| 7 | IL-6 | Inflammation | $7.7 \times 10^{-05}$ | RA, T1D, CeD |
| 12 | IFNG | Th1/inflamm. | $1.5 \times 10^{-05}$ | CD, T1D, RA, MS, SLE, PS, GD, Asthm |
| | IL-26 | T polarization | $7.2 \times 10^{-05}$ | MS, Asthma |
| 16 | CLEC16A | C-type lectin receptor | $1.8 \times 10^{-05}$ | T1D, MS, GD |
| | SOCS1 | JAK/STAT inh | $1.2 \times 10^{-05}$ | CeD, T1D, Asthma |
| 18 | PTPN2 | phosphatase | $4.2 \times 10^{-06}$ | CeD, T1D |

IFN-γ production by activated NKG2D-bearing CD8 effectors can reverse immunologic privilege and perpetuate the inflammatory loop.

IFN-γ related pathways can be undermined with existing therapeutics under clinical investigation, expediting the path to translation. Over the last ten years, several small molecule inhibitors of protein tyrosine kinases (PTKi) have been successfully developed clinically both for oral and topical delivery. PTKi approaches will be pursued to blocking CD8 mediated inflammatory responses in AA, namely inhibition of JAK/STAT signaling, responsible for cytokine responsiveness, downstream of the CD8 effector cytokine IFN-γ.

Identify Clinically-Relevant Therapies Targeting Effector T Cell Responses in Alopecic Mice.

Figure 4A:
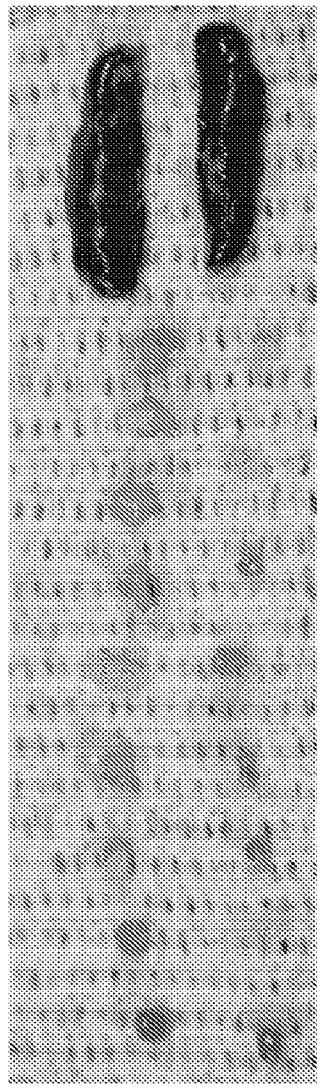
FIG. 4A is a photograph of lymph nodes and spleen isolated from C3H mice afflicted with AA (top) and control mice (bottom).
Figure 4C:
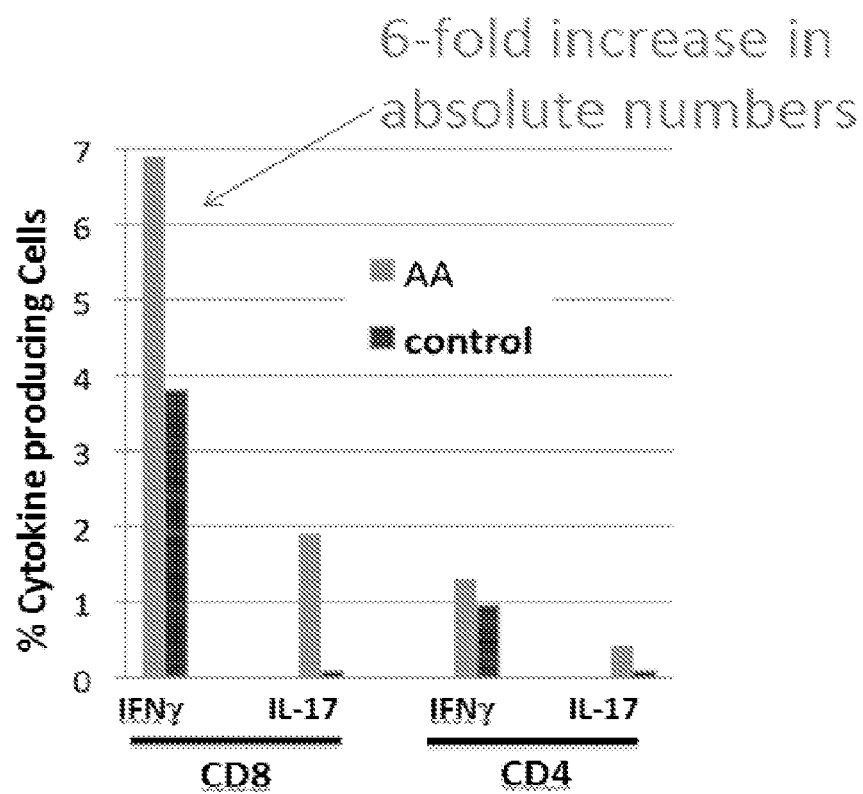
FIG. 4C is a bar graph that shows a 6-fold increase in the number of cytokine producing cells in C3H mice afflicted with AA as compared to control mice.
Figure 5A:
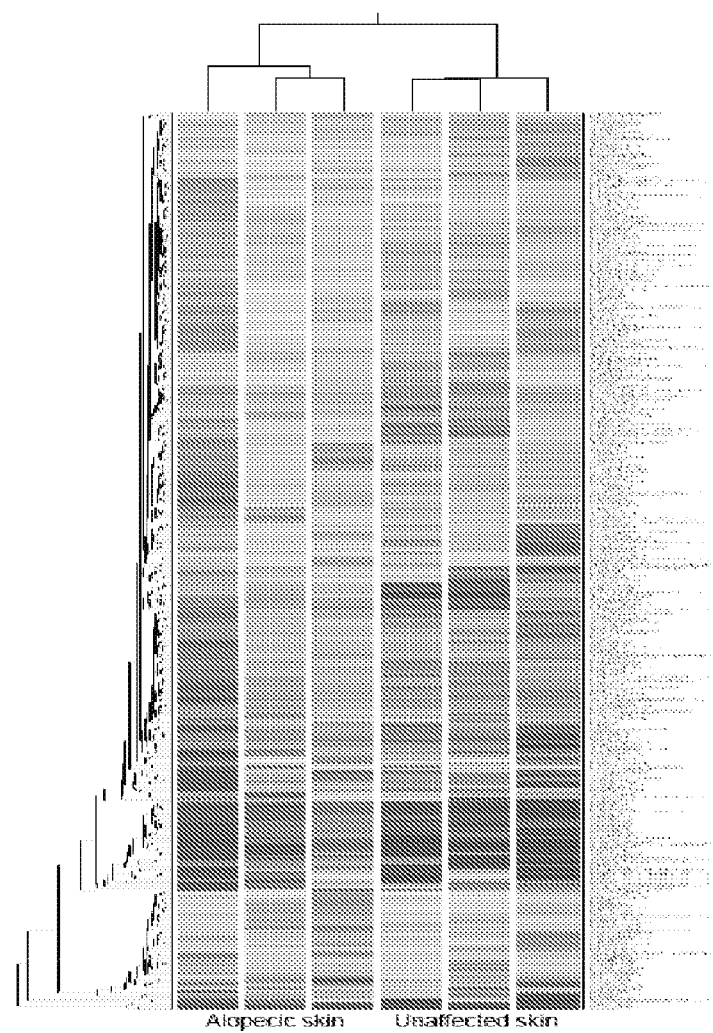
FIG. 5A is a RNA signature of alopecic skin in C3H mice. The heat map shows that 16 of the top 20 unregulated genes are Interferon-Response Genes. 16 of top 20 upregulated genes are Interferon Responsive Genes (IFN-γ but not Type I IFNs are elevevated).
Figure 5B:
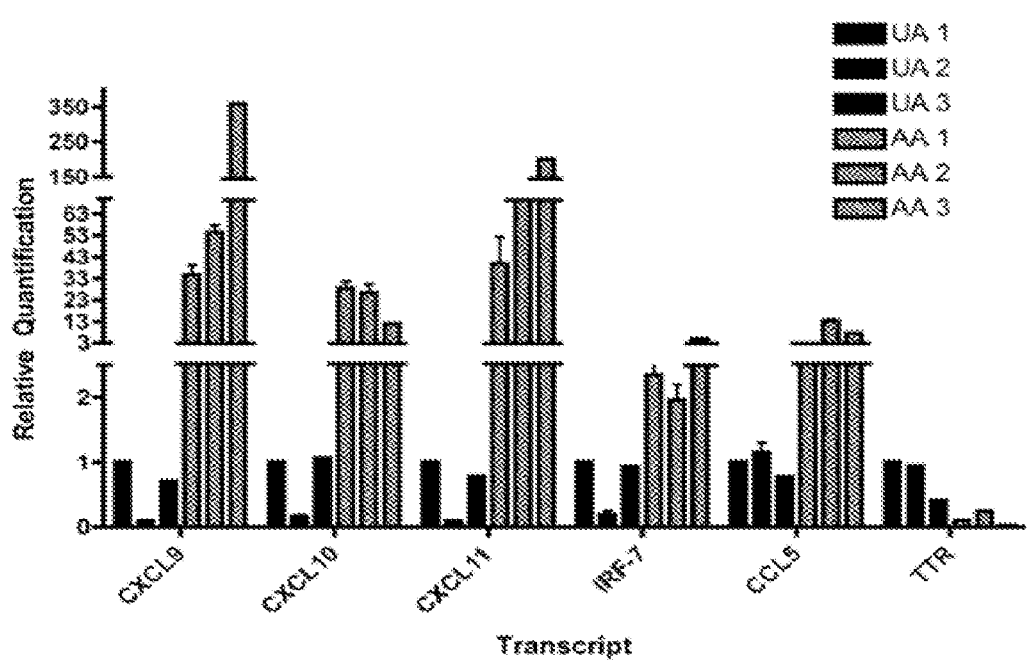
FIG. 5B shows transcriptional profiling of AA skin. qPCR verification of single genes picked from the list generated shows an average fold change over 3 experiments.
Figure 6:
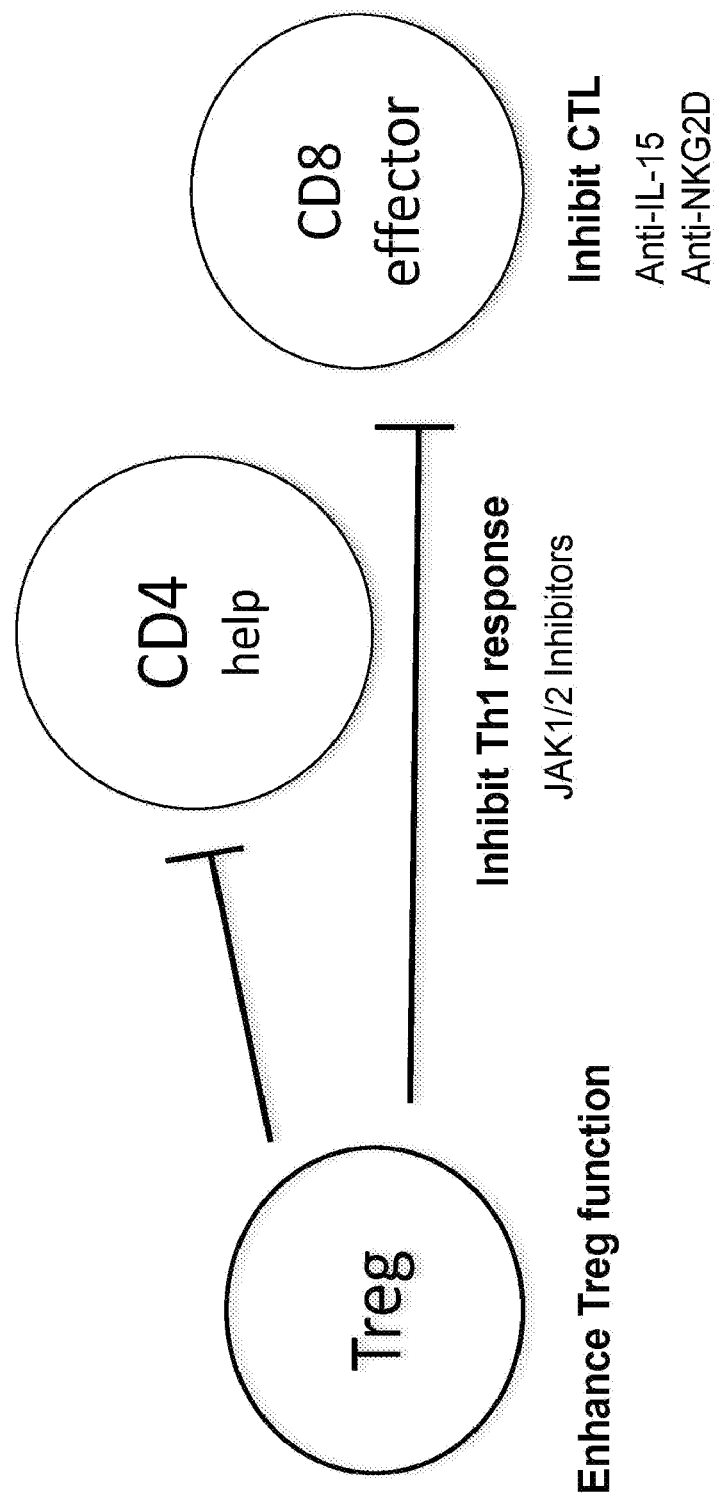
FIG. 6 is a diagram showing the targets in AA.
Figure 17:
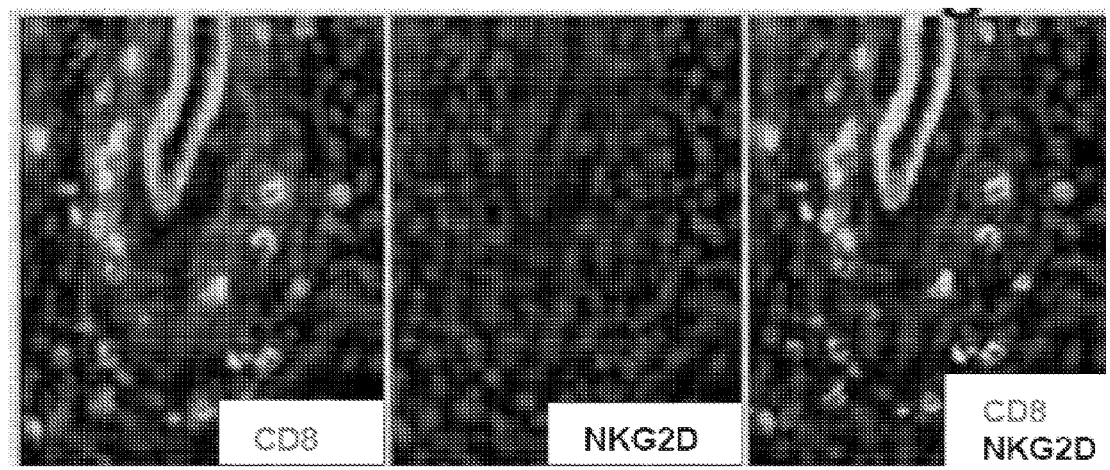
FIG. 17 shows that CD8+ NKG2D+ T cells infiltrate AA hair follicles in both mouse and human. Top panel: Human Alopecia Areata (Pethukova et al., 2010, Nature, 466(7302): 113-7); bottom panel—C3H/HeJ Alopecia Areata.
Figure 18:
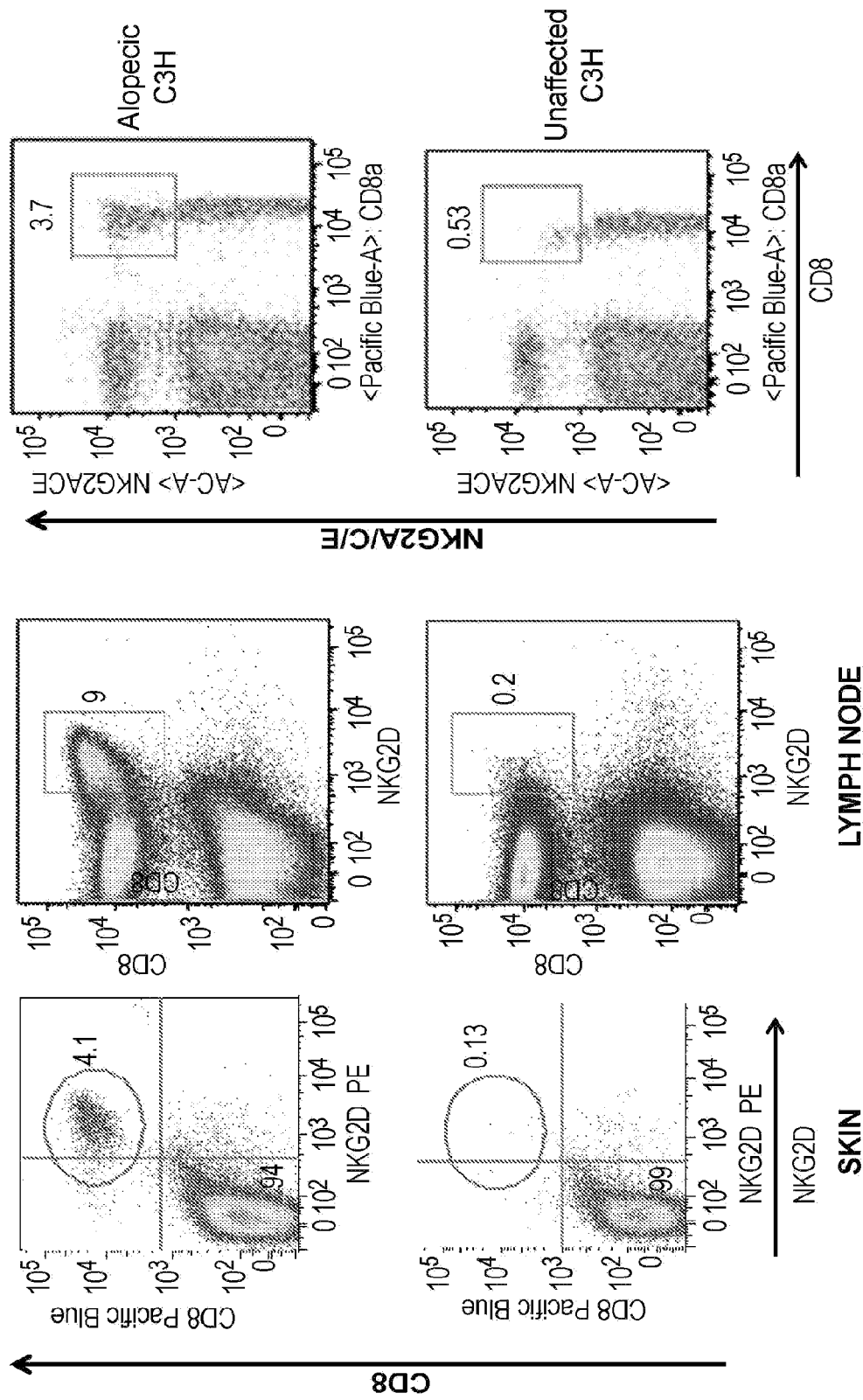
FIG. 18 shows CD8+ NKG2D+ T cells in alopecic C3H mice CD8αβ $^+$NKG2D$^+$ T cells are massively expanded in the skin, lymph node and blood of alopecic C3H mice. (NKG2D$^+$γδ T cells are present in both affected and unaffected skin).
Figure 19:
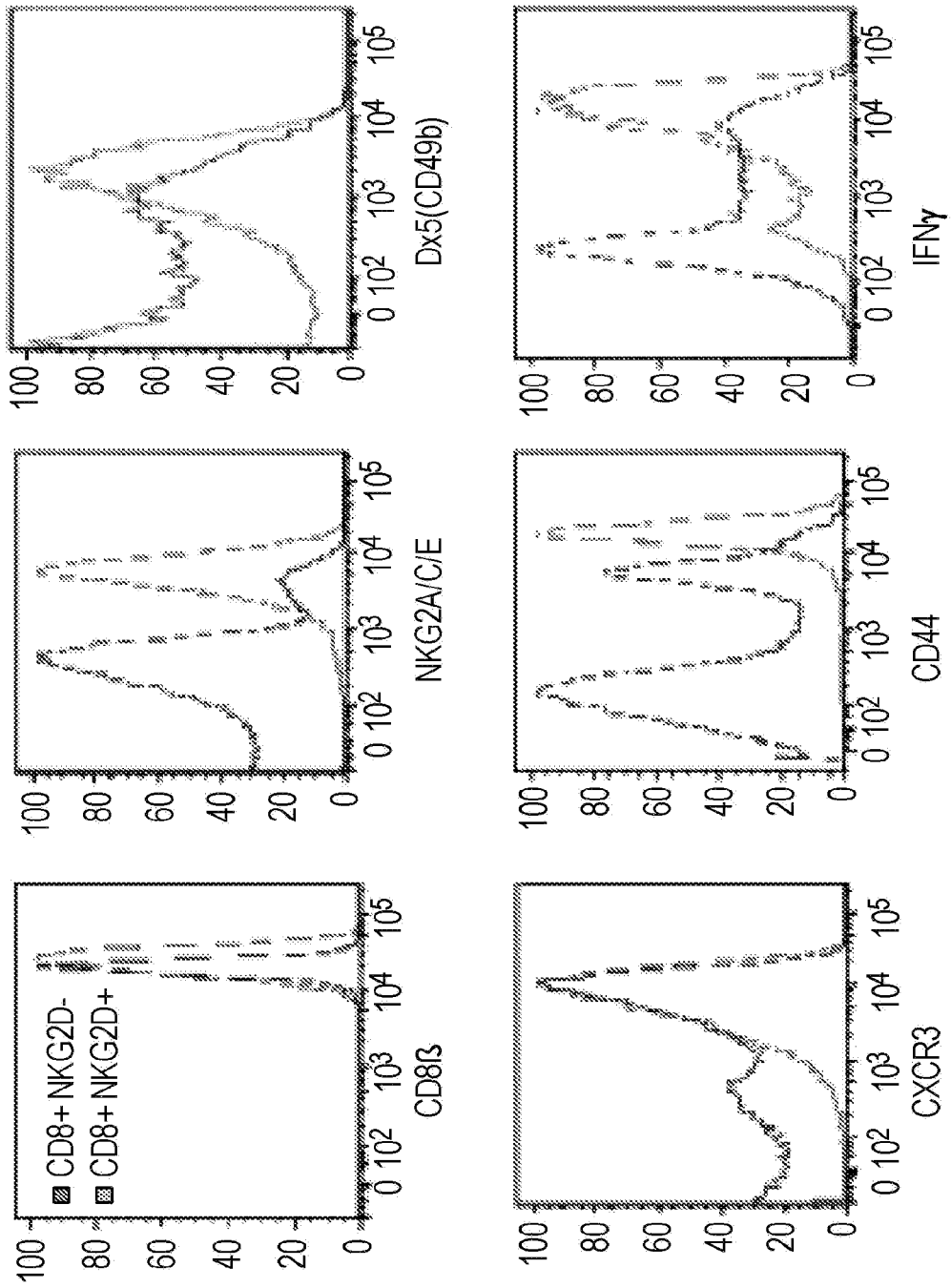
FIG. 19. shows CD8+NKG2D+ T cells in alopecic C3H mice. Immunophenotype of gated LN CD8α$^+$NKG2D$^+$ populations shows that they are uniformly CD8αβ$^+$CD44$^+$ CXCR3$^+$DX5$^+$NKG2A/C/E+IFN-γ producing memory T cells.
Figure 21A:
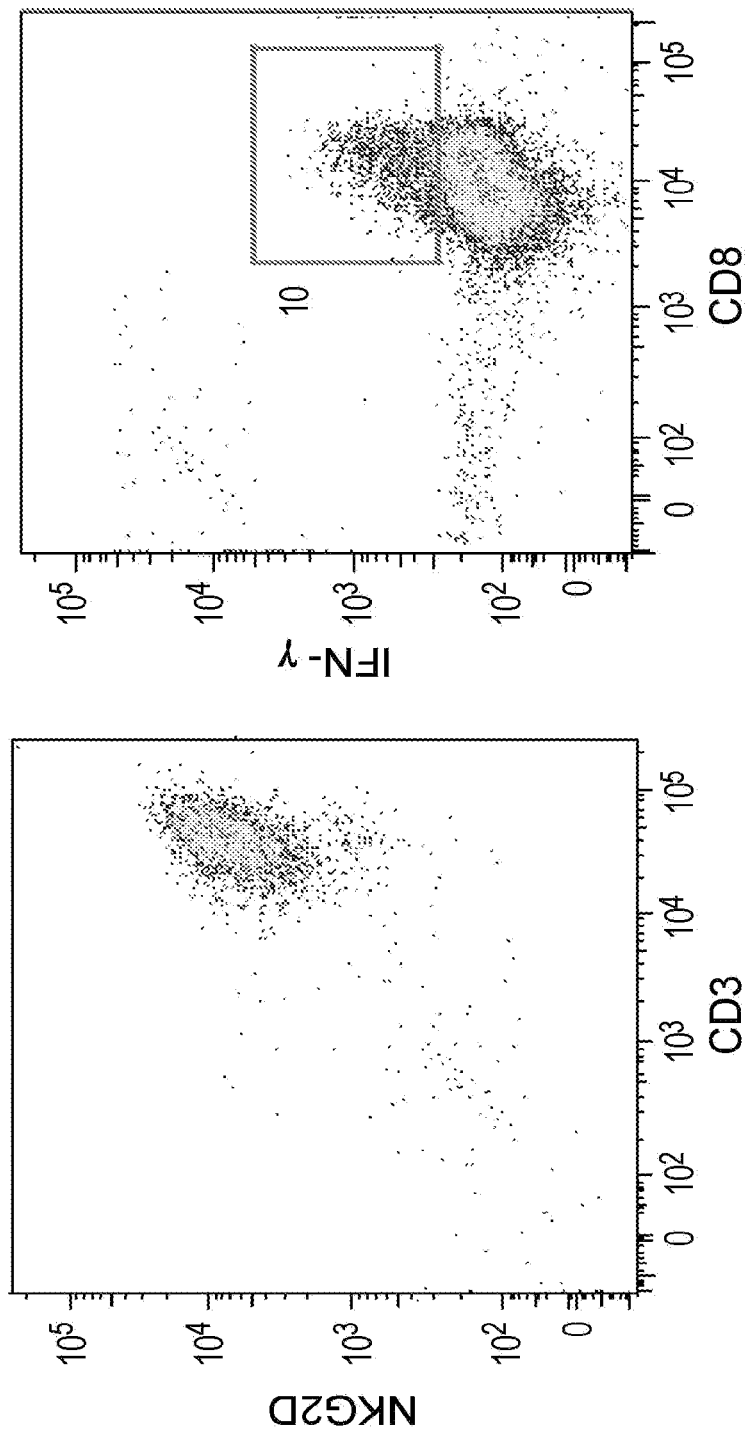
FIGS. 21A-B show that IFN-γ producing CD8 T cells dominate human and mouse AA.
Figure 21B:
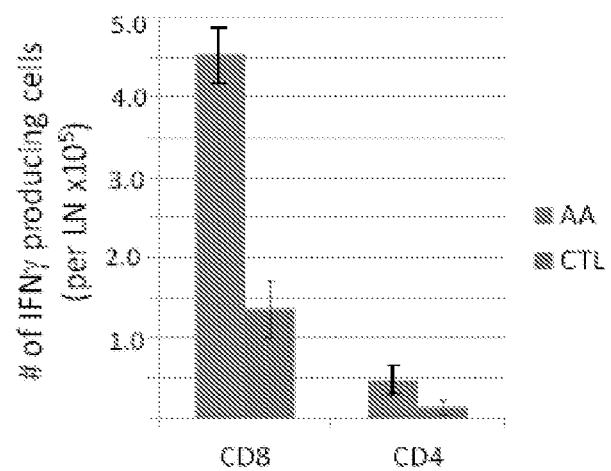

Using immunostaining and flow cytometric analysis of total cellular populations from AA skin, CD8$^+$NKG2D$^+$ T cells were found infiltrating the hair follicle (FIG. 17) and expanded in AA but not normal skin (FIG. 18 and FIG. 4A). Furthermore AA mice exhibit cutaneous lymphadenopathy, at least in part due to dramatic systemic expansion of the CD8$^+$NKG2D$^+$ population, in both the AA cutaneous lymph node and in the blood, representing fully 6+/−1% of total LN cells are 2.4+/−1.3% of total PBMCs, each more than ten-fold higher than that seen in normal C3H mice. These CD8$^+$ NKG2D$^+$ T cells are potently cytotoxic against HF dermal sheath cells (FIG. 21). Further immunophenotypic analysis of CD8$^+$NKG2D$^+$ T cells revealed that this population expressed the T memory marker CD44$^+$ and multiple "NK markers", including DX5, NKG2A/C/E, and NKp46 (FIG. 19).

Figure 20:
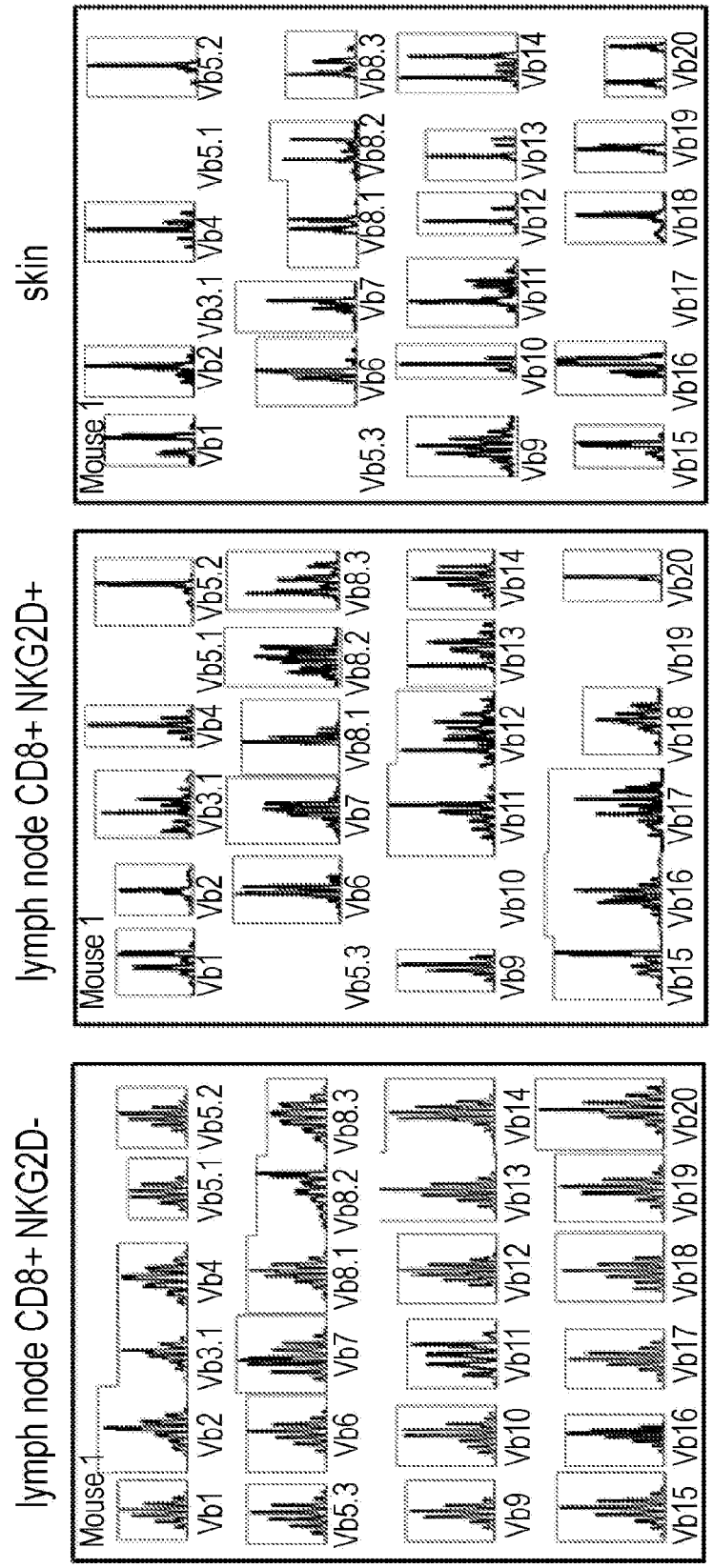
FIG. 20 shows spectratype analysis of C3H T cells in skin and LN: Similar TCR repertoires are shared by total skin and sorted CD8+NKG2D+LN T cells identifying these as the relevant effectors.

To provide proof that the circulating CD8$^+$NKG2D$^+$ population represented the bona fide "AA-specific" effector population, without being bound by theory, the CD8$^+$NKG2D$^+$ T cells found in the lymph node can express a similar TCR repertoire to the total T cells found infiltrating AA skin. FIG. 20 shows that CD8$^+$NKG2D$^-$ lymph node populations exhibit a normal distribution of CDR lengths, a pattern reflective of an unrestricted polyclonal T cell population. In contrast, the TCR repertoire of skin T cells are highly restricted with nearly all Vβ family members dominated by a small number of CDR lengths, indicative of an oligoclonal population of antigen-driven T cells. CD8$^+$NKG2D$^+$ T cells from the cutaneous lymph node cells are also highly restricted and show a strikingly similar pattern with total cutaneous T cells.

These data confirm that CD8$^+$NKG2D$^+$ T cells contain most of the oligoclonal T cell populations found in the skin. Moreover the evidence for the expansion of common oligoclonal T cells in the skin and lymph node argues against the possibility that these LN populations (or even markers) are expanded/activated as a reactive process to inflammatory events. For instance, Treg cells (CD4$^+$CD25$^+$FoxP3$^+$) are also increased in numbers in AA lymph nodes, however, this is likely a reactive process, since their spectratype is diverse and unlike those present in the skin. Note that some TCR/clones are found in skin but not in draining cutaneous lymph nodes, e.g., Vβ10. These likely include CD4$^+$ T cell populations found in AA skin but not present in the sorted CD8+ LN fraction. These data establish that the CD8$^+$NKG2D$^+$ T cells are the pathogenic NKG2D$^+$ effectors in mouse AA, establishing a parallel of the mouse model to human AA.

Pre-Clinical AA Model to Establish Proof of Concept for Therapeutic Approaches In Vivo C3H/HeJ Skin Graft Model:

The C3H/HeJ mouse model for alopecia areata has been studied since it was first reported this model in 1994 (29, 30, 31). While other mouse models for alopecia areata were found (32), this model remains the most studied and used in the field today. Having done a variety of drug trials with this model over the years (33), a variety of protocols have been optimized (34).

Full thickness skin grafting from alopecic C3H/HeJ mice to 2-3 month-old unaffected C3H/HeJ female mice results in patchy alopecia within 10 weeks of grafting in all recipients, progressing to generalized alopecia at 20 weeks. A variety of comprehensive and efficient histological scoring systems are employed building on the traditional training of histopathologists where the adjective used in descriptions (normal, 0; mild, 1; moderate, 2; severe, 3; and extreme, 4) are converted to a numerical value for importation into a relational database (Mouse Disease Information System [or MoDIS]: research.jax.org/faculty/sundberg/registration.php) (35, 36). This database is exportable via Excel for importation into a statistical analysis or other software program. Alopecia areata is graded based on severity, location of inflammatory cells, types and relative numbers of inflammatory cells (granulocytes, mast cells, lymphocytes), follicular dystrophy, etc. Molecular RNA and protein biomarkers will be incorporated in this panel, and generation and analysis of this multiple variable database will be done.

Protocol#1: In the prevention setting, recipient mice will be treated beginning the first week after grafting.

Protocol#2: For treatment, grafted mice with early-established AA will be treated to reverse AA progression.

Agents will first be examined in the prevention model. Agents that successfully prevent AA will then move forward for secondary evaluation in the setting of established disease, while those that fail the first test will be discarded, permitting entry of other innovative approaches. The following are the initial therapeutic approaches, both specific biologics and small molecules, chosen for preclinical evaluation.

Small molecule JAK protein tryosine kinase inhibitors (PTKis) that target activation pathways involved in the T effector response will be tested. These PTKis are already in Phase III clinical trials easing translation and potential clinical development of "NK-type" T cell-targeted topicals.

Therapeutic Interventions with Small Molecule PTKi Interventions

Topical delivery has obvious advantages in limiting systemic exposures and toxicities. Pre-clinical and clinical studies have demonstrated that small molecule PTKi delivery in cream can overcome the skin barrier and achieve effective local concentrations in the dermis with limited systemic exposure (78). Key PTKs pivotal to effector T responses in AA will be targeted, namely the cytokine IFNγ.

Figure 22:
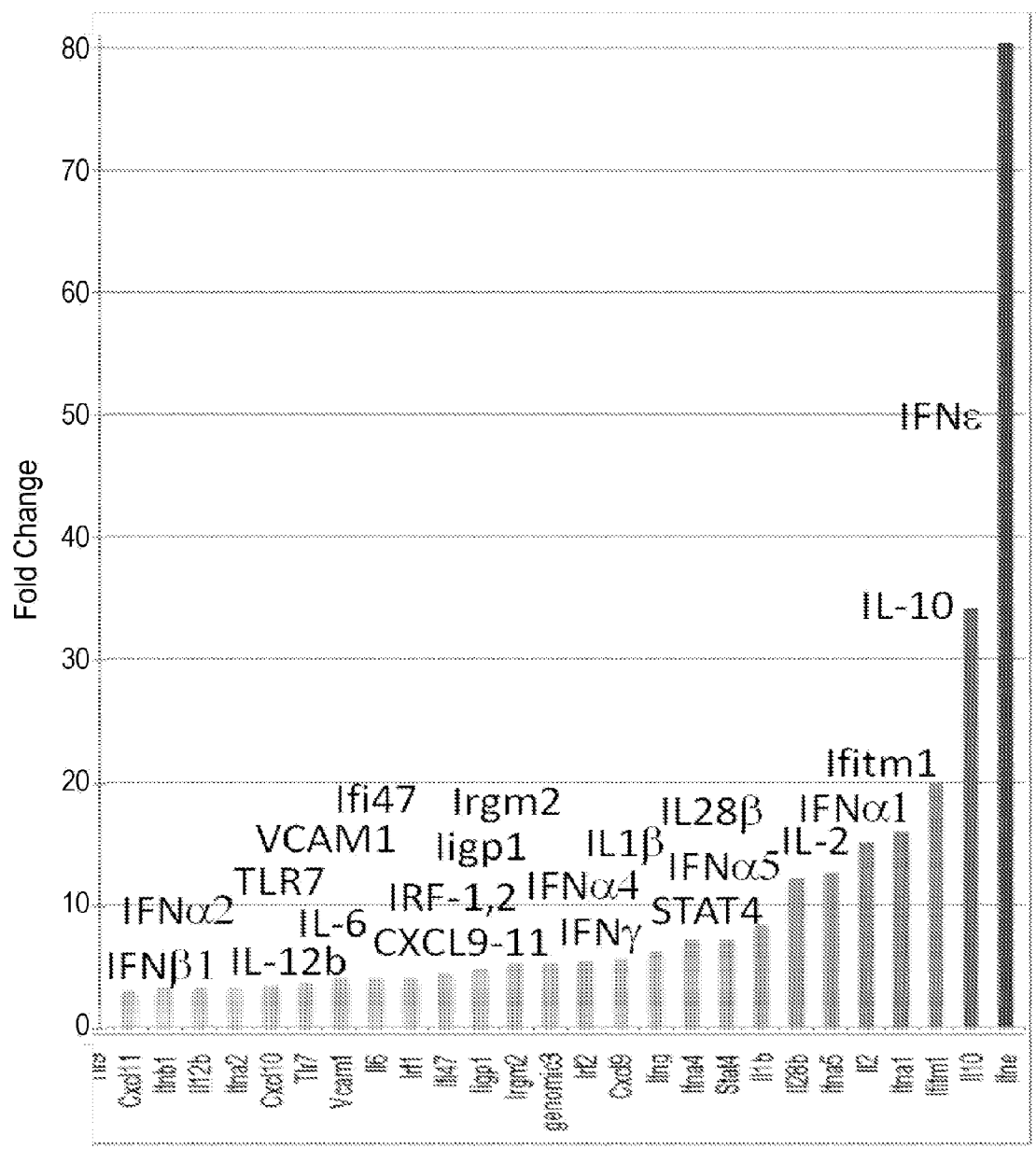
FIG. 22 show that Type I and II IFNs are upregulated in C3H mouse AA skin: fold changes in expression of interferon genes (normalized to 18S) between 3 affected and 3 non affected C3H/HeJ mice, utilizing an interferon signaling and response qPCR array (Stellarray Lonza Cat #00189608).
Figure 23:
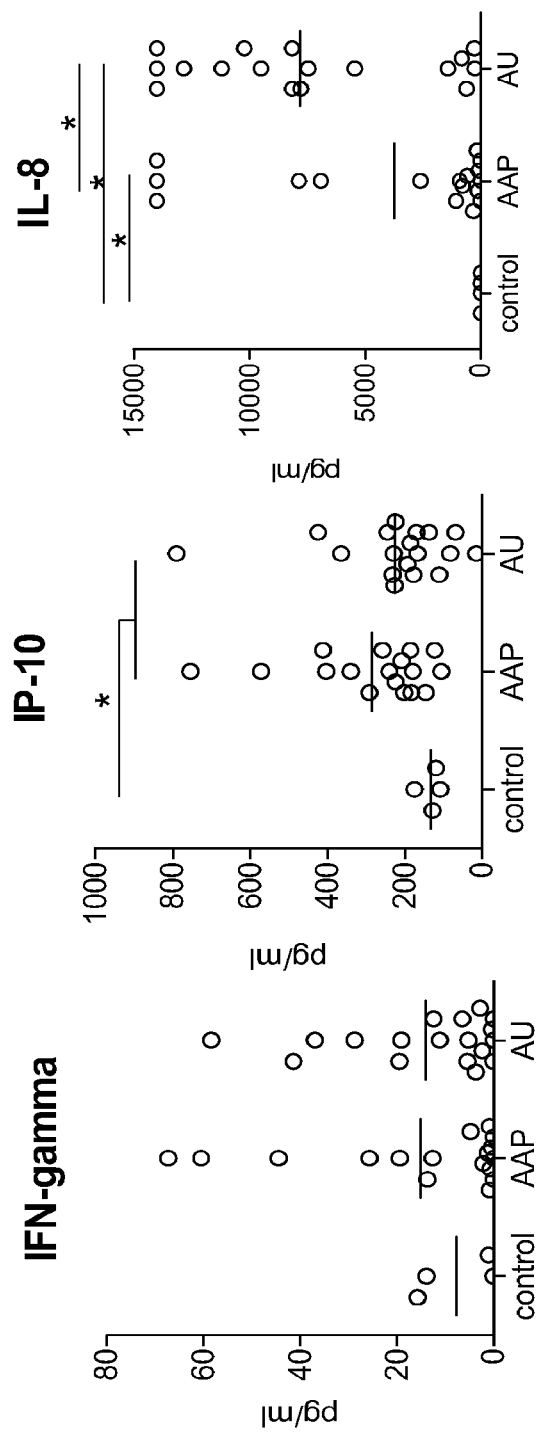
FIG. 23 shows graphs that show elevated serum chemokines and cytokines in Human AA. Interferon-γ and IFN-induced chemokines (e.g., IP-10/CXCL10) are elevated in the serum of human AA, in some cases correlating with disease severity, i.e., patchy disease (AAP) vs. universalis (AU).

Targeting IFNs with Jak1/2 Inhibitors:

Interferons are an attractive therapeutic target in AA since they likely participate at several steps in the inflammatory response; including eliminating HF immunologic privilege and inducing the cellular inflammatory response. Interferons upregulate several relevant pro-inflammatory molecules in the hair follicle end organ, including NKG2DL, adhesion molecules (e.g., ICAM-1), antigenic processing/presentation (TAP1/2, LMP, proteosome, MHCI and II) and moreover drive the immune effector response (increased Th1-type responses, DC activation and IFN-γ-mediated cytotoxicity). In the C3H-HeJ mouse model of AA, IFN-γ is required for pathogenesis (89, 90) and administration of interferon-γ accelerates disease (91). Importantly, administration of IFN-γ neutralizing antibodies reverses AA pathogenesis in the C3H-HeJ mouse (92, 93). Likewise, in the human, alopecia areata has been noted in several series as a side-effect of Type I interferon therapy (94-104) and transcriptional profiles of human AA skin have noted a Type I IFN response in lesional biopsies (105) and Th1 skewing and elevated IFN-response cytokines/chemokines in the peripheral blood (FIGS. 22, 23) (106-110) and reviewed in (111). T cells obtained from AA skin biopsy explants were uniformly CD8$^+$NKG2D+ cells and when stimulated produced IFN-γ (FIG. 21A) but not IL-4 or IL-17. In stark contrast, the majority of T cells obtained from normal skin explants are CD4$^+$ (112, 113). The situation is similar in AA mice, IFN-γ producing CD8 T cells are expanded in the cutaneous lymph node (FIGS. 19, 21). In the skin, our transcriptional profiling studies of total skin isolated from lesional vs. non-lesional C3H skin has identified an interferon response as the dominant signature with 17 of the top 20 upregulated genes being interferon response genes (FIG. 22). Indeed, IFNs upregulate NKG2DL expression on hair follicle targets, closing an IFN-mediated pathogenic circle, in which IFN-γ made by CD8 effectors drive the HF NKG2D ligands that lead to CD8$^+$NKG2D$^+$ activation.

Clinical JAK1/2 Inhibitors:

Both blocking antibodies (114, 115) and small molecule PTKis are under clinical development targeting the IFN response in autoimmunity. IFN induced STAT1/2 activation is mediated by Jak1/Jak2/Tyk kinases and clinical data have emerged using oral Jak1/Jak2 PTKis in several autoimmune conditions, including RA and psoriasis. Topical therapies have the added advantage of an improved therapeutic index limiting the potential for systemic immunosuppression. INCB018424 inhibits Jak1 and Jak2 ($IC_{50}$=1 nM) and is the only topical JAK inhibitor (78) currently in clinical investigation and its safety profile to date has been acceptable. Proof-of-concept with oral delivery has been demonstrated in a Jak-dependent disease (myelofibrosis) (116) and in a dermatological disease driven by local cytokine production (psoriasis models) (78). In psoriasis subjects, topical INCB018424 induced rapid clinical responses and normalization of cutaneous Th1/Th17 cytokine responses (unpublished data from clinicaltrials.gov/ct2/show/NCT00820950). Taken together, topical INCB018424 is a safe intervention predicted to have efficacy in Alopecia Areata, an inflammatory state dominated by an IFN-signature.

Approach: Protocol #1: Systemic Delivery of INCB018424:

Twice daily (90 mg/kg) orogastric gavage provides good systemic exposure given the $t_{1/2}$ half-life of 3-6 hours in the rodent. In this manner we can assess if JAK1/2 inhibition prevents AA progression.

Protocol #2: Topical Delivery of INCB018424 (1.5%):

Reversal of patchy AA by topical JAK1/JAK2 inhibitor. Daily topical treatment (78) will begin to new affected patchy areas in grafted mice that begin to emerge 6-10 weeks after grafting. Topical treatment can be restricted to specific areas of mouse skin by appropriate bandaging to prevent systemic exposures from grooming, licking etc. Importantly, by treating affected areas we can assess the clinically relevant question of whether topical exposure can reverse AA progression.

Identification of Murine Biomarkers of AA Disease Activity that Inform Clinical Investigation The identification of immunological events that accompany treatment outcome in these pre-clinical studies, is important, both to validate the proposed mechanism of action and to provide useful biomarkers that will inform potential clinical evaluation of these same therapies in AA patients. Since in clinical evaluation, biospecimens will be limited to blood and skin samples, the focus will be on mouse biomarkers in the mouse that are easily sampled from these sites. Approaches using GWAS and transcriptional profiling, for example, as well as approaches using immunostains and FACs of T cell subsets, for example, have been taken to identify several pathogenic biomarkers in the skin and blood of AA mice. The studies in alopecic C3H/HeJ mice have already identified several skin biomarkers upregulated in AA, such as IFN-induced genes (FIG. 22). Spectratype data (FIG. 20) has provided striking evidence that these circulating NKG2D$^+$ CD8 T effectors are bona fide autoantigen-driven effector T cells. Temporal assessment of these serologic, cutaneous and cellular biomarkers in mice, with and without treatment, will enable one to identify dynamic, mechanistically important, prescient inflammatory biomarkers that predict therapeutic outcome and inform clinical biomarker discovery/utilization.

Cellular Biomarkers of Circulating Immune Effectors in AA:

"NK-type" CD8 T cells are expanded in the skin, blood and lymph node in AA mice and are a valuable tool to investigate pathogenesis. Moreover, the cellular subset appears directly relevant to the human disease.

Spectratype-Based Immunomonitoring:

NK-type CD8 T cells will be identified in AA mice in the circulation by flow cytometry of 50 μl of whole blood (FIG. 18). The total numbers and spectratype of this CD8$^+$NKG2D$^+$ sorted T cell subset, will be assessed every three weeks after grafting to monitor the evolution of clonal dominance/epitope spreading within a single mouse. Spectratype analysis will be used to confirm that immunophenotypic loss of CD8$^+$ NKG2D$^+$ T cells is due to treatment-related elimination of the circulating alopecic T cell clones. This non-invasive immunomonitoring approach will be used to follow mice on all treatments. For instance, 3 weeks of treatment with the JAK1/2 inhibitor INCB018424 did not. Without being bound by theory, JAK1/2 inhibitors are expected to abrogate the downstream inflammatory consequences of T cell derived effector cytokines (IFN-γ, IL-17) in the target tissue.

Immune "Proteomic" Signatures in Serum:

Cytokines and chemokines in the serum are a reflection of the inflammatory milieu in the target organ. The data in the human demonstrate elevations of several cytokines and chemokine some of which correlate with disease activity (for instance IL-8), extending the observations of prior studies (106, 107, 109). Consistent with our overall findings implicating IL-15 and IFN-γ in AA pathogenesis, it is seen that IFN-γ and the well-known IFN-γ inducible chemokine IP-10 (CXCL10) are upregulated in human AA sera. Functionally relevant inflammatory cytokine/chemokine biomarkers will be identified in the sera from AA mice using a multianalyte approach (LUMINEX™ platform). The advantage of biomarker development in the mouse, besides genetic homogeneity, is the relative ease of longitudinal studies to identify biomarkers that occur early or late in disease progression and conversely with treatment response. At the RNA level, C3H mouse skin IFN microarrays demonstrated that both Type I IFNs (IFNα$_{1-3}$, ε and type II IFN (IFN-γ were upregulated as well several IFN-associated chemokines (CXCL9-11, CCL5). Cytokine/chemokines production will be examined in sera using custom multianalyte LUMINEX™ assay (R&D), comprehensively addressing serum levels of 9 chemokines (CCL2-5, CCL11, CXCL5, CXCL9, CXCL10, CXCL11) and 14 cytokines (IFNα, IFNγ, IL-1, IL-2, IL-4, IL-5, IL-6, IL-10, IL-12, IL-13, IL-15, IL-17, TNF, GM-CSF). We will include antibody pairs to detect serum levels of NKG2DLs (117) and IL-15Rα.

Transcriptional Profiling of Skin:

In human AA, published studies of small series of patients have noted a Type I IFN response in lesional biopsies (105) and Th1 skewing and elevated IFN-response cytokines/chemokines in the peripheral blood (106-110) and reviewed in (111). These data are mirrored in the analysis of the C3H mouse. Transcriptional profiling of RNA isolated from alopecic mouse skin revealed a dominant IFN response. 18 of the top 21 upregulated genes in AA skin were IFN response genes, which was confirmed by real-time PCR (FIG. 22). The upregulation of the IFN-response genes CXCL9-11 are notable since the CD8$^+$NKG2D$^+$ cells also uniformly express their shared chemokine receptor, CXCR3, a receptor upregulated on short-lived immune effectors (118-120). These chemokines are also upregulated in the sera of human AA subjects and thus can be a functionally relevant AA skin biomarker in the skin (mRNA) and in the blood (protein). Work in this area will continue, building a database of skin RNA signatures collected before and during ongoing treatment, that can be used to tailor treatment plans and as early indicators of treatment response. Towards these goals, parallel studies will be performed in the mouse with both intralesional steroids and CTLA4-Ig, as well as with therapeutic interventions, to provide a transcriptional profile database that will be useful in cross-referencing the human treatment studies (comparative genomic analysis between studies and for potential clinical development of more novel approaches).

Human Subjects

Skin biopsies from the scalp will be collected from a minimum of 100 Alopecia Areata patients and approximately 100 controls. The subject population will consist of AA patients and unaffected control subjects receiving hair transplantation. Approval for collection of these samples underwent expedited review/exemption since they are discarded tissue. A protocol for collection of scalp biopsies from AA patients is in preparation. A minimum of 100 AA subjects will be recruited, but collection of greater than 100 will be beneficial and increase the power of this approach.

In order to achieve maximum homogeneity among samples for generating the expression interactome, hair follicles will be collected exclusively from middle aged Caucasian male subjects with AA, since the matching control donors are most commonly from this group. Therefore, despite the fact that AA shows no ethnic or gender predilection, the AA patients will be selected to match in age and gender to the controls for the purpose of this study (middle aged Caucasian males). Patients with active disease (ie: with some remaining hair follicles) will also be selected so that they can be efficiently microdissected.

Vertebrate Animals

Young C3H/HeJ mice (2-3 months) and retired breeders showing visible hair loss will be acquired from Jackson Labs. The animals will be kept under standard conditions in the animal facilities.

The mice will be administered drugs or antibodies by either systemic injections or topically. For topical applications, the mice skin will be shaved on the dorsal surface with electric clippers. One week after shaving, mice will receive topical application of the chemicals dissolved in acetone or 10% v/v in propylene glycol as vehicles. Injections will be given either intraperitonealy or subcutaneously. The dosage as well as frequency of administration will be followed as per established protocols. The mice will be monitored daily for signs of distress throughout the duration of treatment.

References

1. NTH Biennial Report of the Director, National Institutes of Health Fiscal Years 2006 & 2007, Summary of Activities by Disease Category, Autoimmune Diseases. (2007).
2. Tobias, L. A Briefing Report on Autoimmune Diseases and AARDA: Past, Present, and Future, (2010).
3. Safavi, K. H., Muller, S. A., Suman, V. J., Moshell, A. N. & Melton, L. J., 3rd Incidence of alopecia areata in Olmsted County, Minn., 1975 through 1989. *Mayo Clin Proc* 70, 628-633 (1995).
4. Wasserman, D., Guzman-Sanchez, D. A., Scott, K. & McMichael, A. Alopecia areata. *Int Dermatol* 46, 121-131 (2007).
5. Alkhalifah, A., Alsantali, A., Wang, E., McElwee, K. J. & Shapiro, J. Alopecia areata update: part II. Treatment. *J Am Acad Dermatol* 62, 191-202, quiz 203-194.
6. Alkhalifah, A., Alsantali, A., Wang, E., McElwee, K. J. & Shapiro, J. Alopecia areata update: part I. Clinical picture, histopathology, and pathogenesis. *J Am Acad Dermatol* 62, 177-188, quiz 189-190.
7. Delamere, Sladden, M. M., Dobbins, H. M. & Leonardi-Bee, J. Interventions for alopecia areata. *Cochrane Database Syst Rev,* CD004413 (2008).

8. Kaelin, U., Hassan, A. S., Braathen, L. R. & Yawalkar, N. Treatment of alopecia areata partim universalis with efalizumab. *J Am Acad Dermatol* 55, 529-532 (2006).
9. Strober, B. E. et al. Alefacept for severe alopecia areata: a randomized, double-blind, placebo-controlled study. *Arch Dermatol* 145, 1262-1266 (2009).
10. Petukhova, L. et al. Genome-wide association study in alopecia areata implicates both innate and adaptive immunity. *Nature* 466, 113-117 (2010).
11. Abadie, V., Sollid, L. M., Barreiro, L. B. & Jabri, B. Integration of genetic and immunological insights into a model of celiac disease pathogenesis. *Annu Rev Immunol* 29, 493-525 (2011).
12. Champsaur, M. & Lanier, L. L. Effect of NKG2D ligand expression on host immune responses. *Immunol Rev* 235, 267-285 (2010).
13. Van Belle, T. L. & von Herrath, M. G. The role of the activating receptor NKG2D in autoimmunity. *Mol Immunol* 47, 8-11 (2009).
14. Caillat-Zucman, S. How NKG2D ligands trigger autoimmunity? *Hum Immunol* 67, 204-207 (2006).
15. Paus, R., Ito, N., Takigawa, M. & Ito, T. The hair follicle and immune privilege. *J Investig Dermatol Symp Proc* 8, 188-194 (2003).
16. Paus, R., Nickoloff, B. J. & Ito, T. A 'hairy' privilege. *Trends Immunol* 26, 32-40 (2005).
17. Paus, R., Slominski, A. & Czarnetzki, B. M. Is alopecia areata an autoimmune-response against melanogenesis-related proteins, exposed by abnormal MHC class I expression in the anagen hair bulb? *Yale J Biol Med* 66, 541-554 (1993).
18. Gilhar, A., Paus, R. & Kalish, R. S. Lymphocytes, neuropeptides, and genes involved in alopecia areata. *J Clin Invest* 117, 2019-2027 (2007).
19. Ito, T. et al. Collapse and restoration of MHC class-1-dependent immune privilege: exploiting the human hair follicle as a model. *Am J Pathol* 164, 623-634 (2004).
20. Ito, T. et al. Maintenance of hair follicle immune privilege is linked to prevention of NK cell attack. *J Invest Dermatol* 128, 1196-1206 (2008).
21. Ito, T., Meyer, K. C., Ito, N. & Paus, R. Immune privilege and the skin. *Curr Dir Autoimmun* 10, 27-52 (2008).
22. Sundberg, J. P., Boggess, D., Montagutelli, X., Hogan, M. E. & King, L. E., Jr. C3H/HeJ mouse model for alopecia areata. *J Invest Dermatol* 104, 16S-17S (1995).
23. Sundberg, J. P., Oliver, R. F., McElwee, K. J. & King, L. E., Jr. Alopecia areata in humans and other mammalian species. *J Invest Dermatol* 104, 32S-33S (1995).
24. McElwee, K. J. et al. Transfer of CD8(+) cells induces localized hair loss whereas CD4(+)/CD25(−) cells promote systemic alopecia areata and CD4(+)/CD25(+) cells blockade disease onset in the C3H/HeJ mouse model. *J Invest Dermatol* 124, 947-957 (2005).
25. Gilhar, A. et al. Transfer of alopecia areata in the human scalp graft/Prkdc(scid) (SCID) mouse system is characterized by a TH1 response. *Clin Immunol* 106, 181-187 (2003).
26. Van Belle, T. L. & von Herrath, M. G. The role of the activating receptor NKG2D in autoimmunity. *Molecular Immunology* 47, 8-11 (2009).
29. Sun, J., Silva, K. A., McElwee, K. J., King, L. E., Jr. & Sundberg, J. P. The C3H/HeJ mouse and DEBR rat models for alopecia areata: review of preclinical drug screening approaches and results. *Exp Dermatol* 17, 793-805 (2008).
30. Sundberg, J. P., Cordy, W. R. & King, L. E., Jr. Alopecia areata in aging C3H/HeJ mice. *J Invest Dermatol* 102, 847-856 (1994).
31. Sundberg, Cordy, W. R. & King, L. E. Alopecia areata in aging C3H/HeJ mice. *J Invest Dermatol* 102, 847-856 (1994).
32. McElwee, K., Boggess, D., Miller, J., King, L. & Sundberg, J. Spontaneous alopecia areata-like hair loss in one congenic and seven inbred laboratory mouse strains. *J Invest Dermatol Symp Proc* 4, 202-206 (1999).
33. Sun, J., Silva, K. A., McElwee, K. J., King, L. E. & Sundberg, J. P. The C3H/HeJ mouse and DEBR rat models for alopecia areata: preclinical drug screening tools *Exp Dermatol* 17, 793-805 (2008).
34. Sundberg, J. P., Silva, K. A., McPhee, C. & King, L. E. Skin diseases in laboratory mice: approaches to drug target identification and efficacy screening. *Methods Mol Biol* 602, 193-213 (2010).
35. Sundberg, B. A., Schofield, P. N., Gruenberger, M. & Sundberg, J. P. A data capture tool for mouse pathology phenotyping. *Vet Pathol* 46, 1230-1240 (2009).
36. Sundberg, J. P., Sundberg, B. A. & Schofield, P. N. Integrating mouse anatomy and pathology ontologies into a diagnostic/phenotyping database: tools for record keeping and teaching. *Mammalian Genome* 19, 413-419 (2008).
74. Dandekar, A. A., O'Malley, K. & Perlman, S. Important roles for gamma interferon and NKG2D in gammadelta T-cell-induced demyelination in T-cell receptor beta-deficient mice infected with a coronavirus. *J Virol* 79, 9388-9396 (2005).
78. Fridman, J. S. et al. Preclinical evaluation of local JAK1 and JAK2 inhibition in cutaneous inflammation. *J Invest Dermatol* 131, 1838-1844 (2011).
81. Karaman, M. W. et al. A quantitative analysis of kinase inhibitor selectivity. *Nat Biotechnol* 26, 127-132 (2008).
89. Freyschmidt-Paul, P. et al. Interferon-gamma-deficient mice are resistant to the development of alopecia areata. *Br J Dermatol* 155, 515-521 (2006).
90. Hirota, R. et al. Induction of hair regrowth in the alopecia site of IFN-gamma knockout mice by allografting and IFN-gamma injection into the transplantation site. *J Interferon Cytokine Res* 23, 433-439 (2003).
91. Gilhar, A., Kam, Y., Assy, B. & Kalish, R. S. Alopecia areata induced in C3H/HeJ mice by interferon-gamma: evidence for loss of immune privilege. *J Invest Dermatol* 124, 288-289 (2005).
92. Skurkovich, S., Korotky, N. G., Sharova, N. M. & Skurkovich, B. Treatment of alopecia areata with anti-interferon-gamma antibodies. *J Investig Dermatol Symp Proc* 10, 283-284 (2005).
93. Nakamura, M., Jo, J., Tabata, Y. & Ishikawa, O. Controlled delivery of T-box21 small interfering RNA ameliorates autoimmune alopecia (Alopecia Areata) in a C3H/HeJ mouse model. *Am J Pathol* 172, 650-658 (2008).
94. Mistry, N., Shapero, J. & Crawford, R. I. A review of adverse cutaneous drug reactions resulting from the use of interferon and ribavirin. *Can J Gastroenterol* 23, 677-683 (2009).
95. Maticic, M., Poljak, M., Lunder, T., Rener-Sitar, K. & Stojanovic, L. Lichen planus and other cutaneous manifestations in chronic hepatitis C: pre- and post-interferon-based treatment prevalence vary in a cohort of patients from low hepatitis C virus endemic area. *J Eur Acad Dermatol Venereol* 22, 779-788 (2008).
96. Kartal, E D., Alpat, S. N., Ozgunes, I. & Usluer, G. Adverse effects of high-dose interferon-alpha-2a treatment for chronic hepatitis B. *Adv Ther* 24, 963-971 (2007).
97. Kartal, E D., Alpat, S. N., Ozgunes, I. & Usluer, G. Reversible alopecia universalis secondary to PEG-interferon alpha-2b and ribavirin combination therapy in a patient with chronic hepatitis C virus infection. *Eur J Gastroenterol Hepatol* 19, 817-820 (2007).
98. Demirturk, N., Aykin, N., Demirdal, T. & Cevik, F. Alopecia universalis: a rare side effect seen on chronic hepatitis C treatment with peg-IFN and ribavirin. *Eur J Dermatol* 16, 579-580 (2006).
99. Yu, M. L. et al. A randomised study of peginterferon and ribavirin for 16 versus 24 weeks in patients with genotype 2 chronic hepatitis C. *Gut* 56, 553-559 (2007).
100. Taliani, G. et al. Reversible alopecia universalis during treatment with PEG-interferon and ribavirin for chronic hepatitis C. *J Chemother* 17, 212-214 (2005).
101. Radny, P. et al. Alopecia areata induced by adjuvant treatment with alpha-interferon in malignant melanoma? *Dermatology* 209, 249-250 (2004).
102. Agesta, N., Zabala, R. & Diaz-Perez, J. L. Alopecia areata during interferon alpha-2b/ribavirin therapy. *Dermatology* 205, 300-301 (2002).
103. Kernland, K. H. & Hunziker, T. Alopecia areata induced by interferon alpha? *Dermatology* 198, 418-419 (1999).
104. Lang, A. M., Norland, A. M., Schuneman, R. L. & Tope, W. D. Localized interferon alfa-2b-induced alopecia. *Arch Dermatol* 135, 1126-1128 (1999).
105. Ghoreishi, M., Martinka, M. & Dutz, J. P. Type 1 interferon signature in the scalp lesions of alopecia areata. *Br J Dermatol*.
106. Barahmani, N. et al. Serum T helper 1 cytokine levels are greater in patients with alopecia areata regardless of severity or atopy. *Clin Exp Dermatol* (2009).
107. Kuwano, Y. et al. Serum chemokine profiles in patients with alopecia areata. *Br J Dermatol* 157, 466-473 (2007).
108. Arca, E., Musabak, U., Akar, A., Erbil, A. H. & Tastan, H. B. Interferon-gamma in alopecia areata. *Eur J Dermatol* 14, 33-36 (2004).
109. Benoit, S., Toksoy, A., Goebeler, M. & Gillitzer, R. Selective expression of chemokine monokine induced by interferon-gamma in alopecia areata. *J Invest Dermatol* 121, 933-935 (2003).
110. Hoffmann, R. et al. Cytokine mRNA levels in Alopecia areata before and after treatment with the contact allergen diphenylcyclopropenone. *J Invest Dermatol* 103, 530-533 (1994).
111. Gregoriou, S. et al Cytokines and other mediators in alopecia areata. *Mediators Inflamm* 2010, 928030.
112. Clark, R. A. et al. The vast majority of CLA+ T cells are resident in normal skin. *J Immunol* 176, 4431-4439 (2006).
113. Clark, R. A. et al. A novel method for the isolation of skin resident T cells from normal and diseased human skin. *J Invest Dermatol* 126, 1059-1070 (2006).
114. Bissonnette, R. et al. A randomized, double-blind, placebo-controlled, phase I study of MEDI-545, an anti-interferon-alfa monoclonal antibody, in subjects with chronic psoriasis. *J Am Acad Dermatol* 62, 427-436.
115. Hommes, D. W. et al. Fontolizumab, a humanised anti-interferon gamma antibody, demonstrates safety and clinical activity in patients with moderate to severe Crohn's disease. *Gut* 55, 1131-1137 (2006).
116. Verstovsek, S. et al. Safety and efficacy of INCB018424, a JAK1 and JAK2 inhibitor, in myelofibrosis. *N Engl J Med* 363, 1117-1127 (2010).
117. Nuckel, H. et al. The prognostic significance of soluble NKG2D ligands in B-cell chronic lymphocytic leukemia. *Leukemia* 24, 1152-1159 (2010).
118. Hu, J. K., Kagari, T., Clingan, J. M. & Matloubian, M. Expression of chemokine receptor CXCR3 on T cells affects the balance between effector and memory CD8 T-cell generation. *Proc Natl Acad Sci USA* 108, E118-127.
119. Kohlmeier, J. E. et al. Inflammatory chemokine receptors regulate CD8(+) T cell contraction and memory generation following infection. *J Exp Med* 208, 1621-1634.
120. Kurachi, M. et al. Chemokine receptor CXCR3 facilitates CD8(+) T cell differentiation into short-lived effector cells leading to memory degeneration. *J Exp Med* 208, 1605-1620.
125. Ramsborg, C. G. & Papoutsakis, E. T. Global transcriptional analysis delineates the differential inflammatory response interleukin-15 elicits from cultured human T cells. *Exp Hematol* 35, 454-464 (2007).
126. Chiossone, L. et al. Molecular analysis of the methylprednisolone-mediated inhibition of NK-cell function: evidence for different susceptibility of IL-2-versus IL-15-activated NK cells. *Blood* 109, 3767-3775 (2007).
127. Creed, T. J. et al. The effects of cytokines on suppression of lymphocyte proliferation by dexamethasone. *J Immunol* 183, 164-171 (2009).
128. Goleva, E., Kisich, K. O. & Leung, D. Y. A role for STAT5 in the pathogenesis of IL-2-induced glucocorticoid resistance. *J Immunol* 169, 5934-5940 (2002).
129. Rentzos, M. et al. Circulating interleukin-15 and RANTES chemokine in MS patients: effect of treatment with methylprednisolone in patients with relapse. *Neurol Res* 32, 684-689 (2009).
130. Tliba, O. et al. Cytokines induce an early steroid resistance in airway smooth muscle cells: novel role of interferon regulatory factor-1. *Am J Respir Cell Mol Biol* 38, 463-472 (2008).
131. Xu, Q., Goleva, E., Ou, L. S., Li, L. B. & Leung, D. Y. CD56+ cells induce steroid resistance in B cells exposed to IL-15. *J Immunol* 172, 7110-7115 (2004).

Example 5

Alopecic effector T cells were identified in the lymph node and blood of alopecic mice using spectratyping of flow sorted cells. A blood-based assay was developed to monitor these alopecic T cells during treatment. Cytotoxic assays have been developed for evaluating functional components of the hair follicle (HF) interactions with CTLs, in both human and mice.

Using human biospecimens obtained from AA subjects, it was demonstrated that circulating T cells express high levels of NKG2D and primary T cells obtained from the skin are dominated by a CD8$^+$NKG2D$^+$ IFN-γ producing cells establishing parallels between the mouse and human disease.

Immunophenotyping and Skin Immunobiology

To study pathways in biospecimens requires analysis of heterogeneous cell populations in the skin and in the blood. In the clinical investigation of human autoimmunity, alopecia areata provides a unique opportunity because of the accessibility of the end-organ enabling study/isolation of the pathogenic immune effectors in their relevant microenvironment. Analytic tools and personnel required will be provided for optimal study of these precious end-organ skin biospecimens, and their cellular/serological counterparts in the blood obtained from the same individual.

Preparation and Analysis of Biospecimens:

The following will be provided to assist in the analysis of blood:

i) Multianalyte cytokine/chemokine analysis from serum samples.
ii) Flow cytometric immunophenotyping, including cytokine analysis of human PBMCs from AA subjects.
iii) Flow sorting for downstream applications using T cell subsets (RNA profiling, spectratyping).

The following will be provided to assist in the analysis of skin:

i) Preparation/analysis of viable cellular fractions of both primary hair follicle and T cell components for functional (cytotoxicity) and analytic studies (T cell cloning, spectratyping).
ii) Immunostaining and transcriptional profiling of whole skin
iii) Flow cytometric immunophenotyping of dermal lymphocytes from human and mouse AA skin.

Scientific Experiments

Pathogenic HF-specific cellular subsets in the peripheral blood of AA subjects will be identified. To this end, spectratype analysis will be used as a tool to identify circulating human alopecic T cells populations, as was done for the mouse model, by matching the spectratype found in total skin T cells with the spectratypes of specific sorted peripheral blood T cell subsets in the peripheral blood obtained from the same patients.

Th1-predominance in human AA will be established and the rationale and biomarker platform for Th1-targeted therapies will be developed. Therapeutic targeting of disease-specific Th-pathways has succeeded in other human skin inflammatory diseases, most notably in psoriasis a prototypical Th17 disease. There is substantial data in the AA animal model for AA as a predominant Th1 disease. The Th-profile of infiltrating dermal AA T cells and relevant circulating T cell subsets in the blood will be addressed using a multi-prong approach, including multianalyte, RNA profiling, immunstaining and intracellular flow cytometric analysis from the skin and blood.

An integrative approach to translational research begins with basic studies identifying targetable pathways in AA, then testing these pathways therapeutically in preclinical models, longitudinal biomarker assessment in clinical trials and pursuing population-based research based on genetic studies. The pre-clinical therapeutic effects of interventions will be evaluated in the grafted AA mouse models, treatment effects on the inflammatory responses will be assessed in the skin and blood and human biospecimens will be provided for validation of human relevance in ex vivo studies.

Monitoring the pathogenic interactions between immune cells and target cells in the skin in humans requires sophisticated processing and analysis of primary human tissues and blood.

Flow cytometry has become the primary tool for the identification of cell populations according to specific parameters, and is therefore employed by an ever-growing number of biomedical scientists.

The immunobiology of the skin presents specific characteristics and challenges; the special architecture of the tissue including its barrier functions, its associated unique immune cell populations and its close proximity/interactions with microbial flora, and the practical difficulties of isolating infiltrating lymphocytes, are all part of the complexities needed to be understood in the approach to immunological diseases of the skin. Services that provide assistance with tissue processing and staining, as well as cell isolation, and essential to insuring high quality consistent results are available.

Flow cytometry is a tool for clinical investigators and a working knowledge of its use is required for all translational immunologists. Four flow cytometers, including two workhorse instruments (FACs CANTO™] and FACs CALIBER™) a 6-laser LSR II™ and a 4-laser BD INFLUX™ Influx are available. The LSR II™ and BD INFLUX™ have been designed to have comparable lasers/detectors to facilitate transition from analysis to preparative sorting. The LSR II™ is equipped with 6 lasers, capable of detecting in total 19 colors simultaneously providing versatility to detect both fluorescent proteins (mBanana, GFP, BFP, RFP/dsRed, mCherry mRasberry) and fluorescent dyes/chemical fluorochromes. LSR II™ can analyze diverse cell types within heterogeneous cell populations from tissues using a wide array of organic and inorganic fluorochromes. These additional fluorescent parameters allow detection of coordinated functional events in specific cell types in mixed populations (e.g. intracellular IFN-gamma, IL-10 production and phosphoprotein detection in T cell populations from cutaneous tissues and draining lymph nodes). The basic LSR II™ instrument is equipped with three lasers; blue (488 nm), red (633 nm), violet (405 nm). The custom designed LSR II™ contains in addition, three additional lasers permitting up to 20-color detection and a 96-well plate reader. "Leave one out" 10-color panel designs for T cell subsets (for example, Tregs), B cells and monocyte have been designed to take advantage of the 100 W yellow-green 594 laser which has exquisite sensitivity for "red" ALEXA™ 594. Thus, investigators may adopt a "leave-one out" design to sensitively examine expression for a specific marker of interest by staining with ALEXA™ 594 conjugated antibodies.

Quality:

Panel development for immunophenotyping lymphocyte populations in human peripheral blood and other experiments will be conducted. Because of the capacity of the 6 laser system of the LSR II™, a common "easy-to use" set of colors that can be used without the need for compensation was established. The ability to do a 5/6-color experiment without the need for fluorescent compensation gives increased data resolution as the fluorochromes as far apart from each other in the spectrum, and excited independently by each laser line. This allows for the ability of populations to clearly separate, something that is rare when compensation is applied. The current selected fluorochrome combination is DAPI (gated on the DAPI negative cells) Pacific Blue, FITC, PE, ALEXA FLUOR™ 594 and APC, however other combinations of fluors are currently being tested and used. This 5-flourochrome set serves as the base platform for panels, to which additional fluorochromes can be added. In a proof-of-concept experiment, the use of 5 flurochromes was shown simultaneously without the need for compensation. C57BL/6 splenocytes were stained with CD8 Pacific Blue, CD3 FITC, CD45R (B220) PE, CD11b Bio+Streptavidin ALEXA FLUOR™ 594, and CD4 APC.

Maintenance and Quality Control for Skin Immunobiology:

The procedure used for the isolation of lymphocytes from skin biopsies has been adapted from a method developed by Clark and Kupper (2) in which biopsies are culture on 3-dimensional tantalum-coated cellfoam matrices to promote migration of T cells from the biopsies. Of each isolated cell populations a minor fraction will be used for CD45/CD3 staining to assess the number of leucocytes/T lymphocytes by flow cytometry prior to further studies or cryopreservation. For re-use, the matrices will be soaked for 30 min in 10% bleach, then rinsed in water and transferred into a solution of ENZYTE™ enzyme cleaner (Decon Labs). The matrices will be left in this solution on a hot plate with stirrer for 24 hrs, rinsed with distilled water and let dry before autoclaving.

Whole skin analytic techniques (e.g., immunostaining) will be provided. The following will be provided: 1) critical expertise in skin immunobiology for the preparation/analysis of viable cellular fractions of both primary hair follicles and cutaneous T cells; 2) biomarker development capabilities for clinical biospecimens including multianalyte analysis (LU- MINEX™) and transcriptional profiling of precious clinical biospecimens (skin and blood from subjects enrolled in clinical trials). The tools to investigate biological processes and monitor the inflammatory AA mechanisms in pre-clinical and clinical samples from both the blood and the AA target end organ, the skin will be provided.

Capabilities in microarray data analysis and storage, sequence and pathway analysis are available for the studies herein, and extend all the way to the most recent algorithms for regulatory network reverse engineering. A number of widely-used databases are created and maintained. In addition, all important sequence and structure databases are maintained centrally. This allows direct large-scale searches, if need be using custom algorithms and cluster computing. Many of the research methods developed are packaged into software applications and computational services, freely available to the scientific community (c2b2.columbia.edu/page.php?pageid=10).

Figure 24:
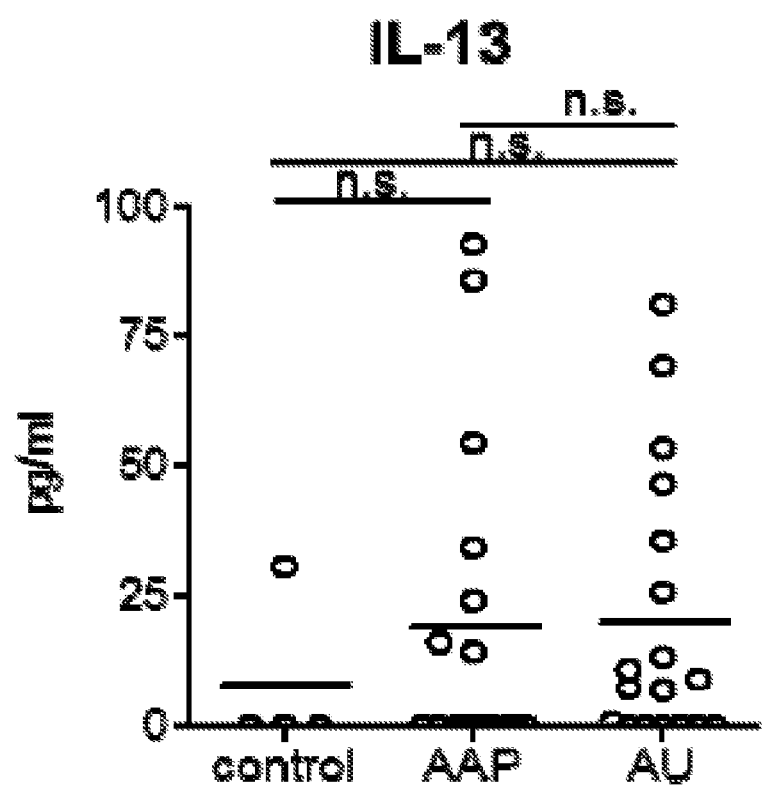
FIG. 24 is a luminex analysis that shows elevated IL-13 in the serum of Human AA subjects, in some cases correlating with disease severity, i.e., patchy disease (AAP) vs. universalis (AU).

The following services are available:
1. Immunomonitoring:
a. Multianalyte Cytokine & Chemokine Analysis from Serum Samples Two approaches are available: a) The multiplex bead based immunoassays systems (e.g. CBA/FLOWCYTOMIX™) provides multiple analytes that allow 10 or more cytokines/chemokines to be assessed on a single read of a small volume (50 µl) sample. The LSR II™ 96 well high throughput capacity provides ease of use combined with efficiency. Software ("snap-to" gating) is available in house for data analysis. A multiplex bead-based assay system will also be developed to quantify soluble human and murine NKG2DL in the sera, for which specific antibody sets are commercially available. b) Multiplex analysis using the LUMINEX™ platform is available in the CTSA for analysis of commercially available mouse and human cytokine and chemokine arrays (FIG. 24). The LUMINEX™ assays are provided on a fee-for-service basis, with reagents purchased by the user. Once an AA serum biomarker platform bulk purchase of selected analytes will enable cost-savings.

Flow Cytometric Immunophenotyping

Figure 25:
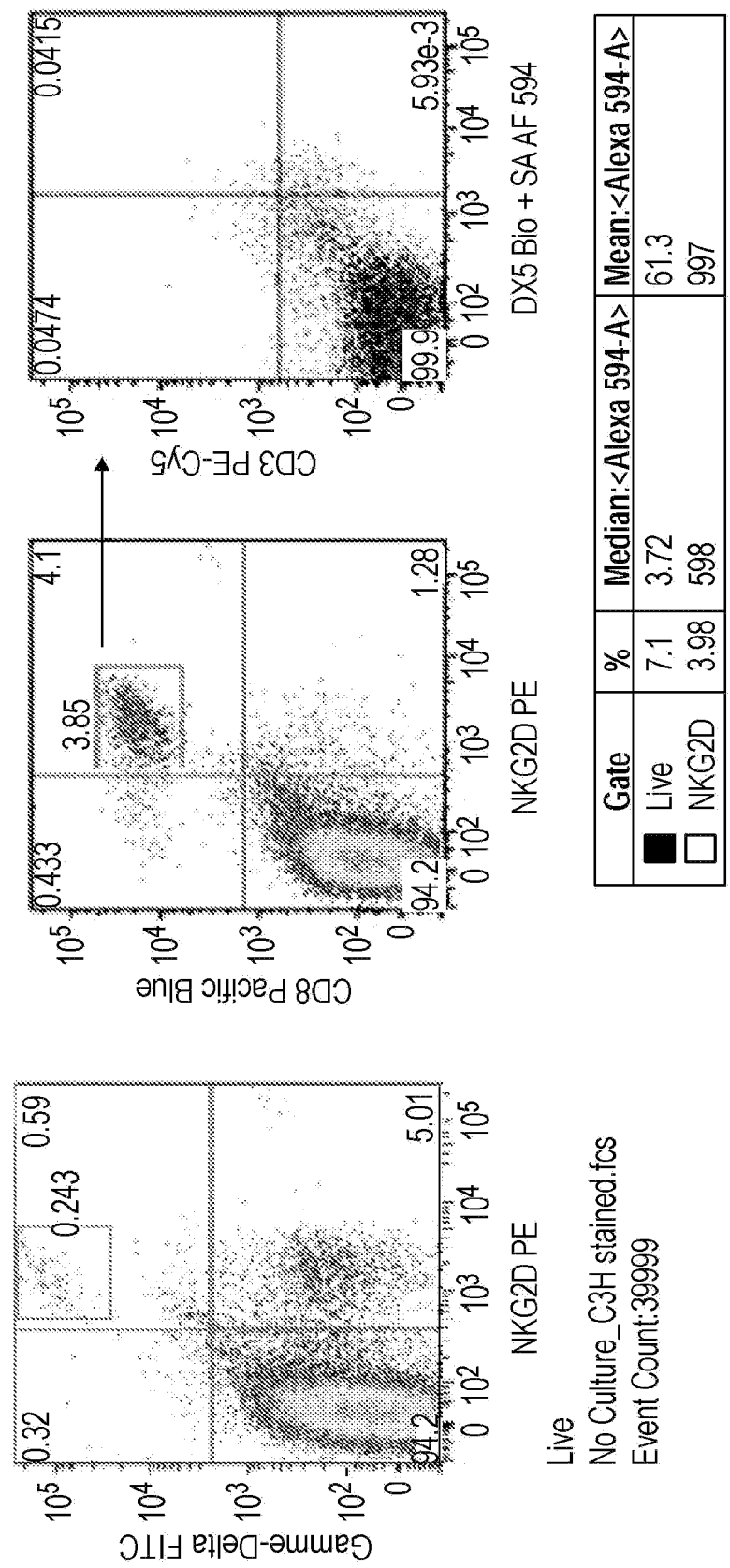
FIG. 25 shows flow cytometry data that were gathered on a LSRII using the following mAbs in one tube to stain the entire population of C3H dermal cells liberated from a 0.5 cm by 2 cm patch of alopecic skin after 30 minutes collagenase digestion: (MHC II, CD11b, CD11c, CD19, 120G8, CD3, CD4, CD8, DX5, NKG2D). γδNKG2D positive cells and CD8+ DX5+NKG2D+ population are identified. These cells were also CD3+, with γδ CD3 expression 100× higher than that seen in CD8+NK+ T cells. >95% of the total CD3 positive cells were accounted.
Figure 26:
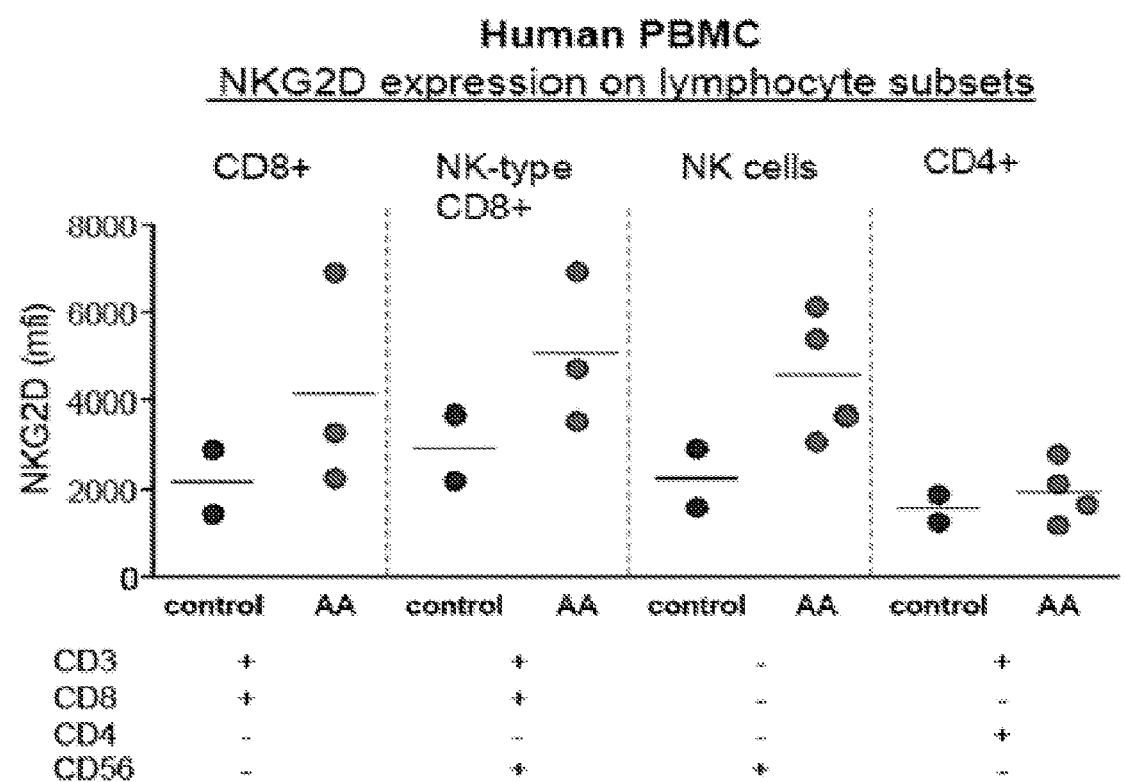
FIG. 26 is a graph that shows the evaluation of PBMCs from four AA subjects. NKG2D expression was increased in subsets of lymphocytes.

It has been established using multiparameter flow that CD8+NKG2D+ cells dominate the dermal leukocyte population harvested from the skin of mice with spontaneous alopecia (FIG. 25). To address the human situation, flow panels have been developed to define quantitative alterations in any of 30 PBMC subsets focusing on NK and CD4 and CD8 T cell populations using 3 FACS tubes (T cell subset tube, NK-marker tube for CD4, CD8 and NK cells and a third non-T cell tube); Lineage Markers: CD3, CD4, CD8α, CD8β, CD14, CD19, CD20, CD56, CD64; T cell subset Markers: CD45Ra, CD45Ro, CD56, CD62L, CCR7, CD127, FoxP3, Helio; Cutaneous Chemokine Receptor Analysis: CCR4, CCR8, CCR10, CLA, E and P-selectin; NK immunoreceptor family members: Inhibitory: KIR/CD158, CD94/NKG2A, LILR/ILT, LAIR1 NKR-P1 Activatory: NKp46, NKp30, NKp44, NKG2C, NKG2D. In the initial evaluation of PBMCs from four AA subjects, increased NKG2D expression was observed on CD56+CD8+ T cells and NK cells, but not on CD4+ T cells (FIG. 26).

Cytokine Analysis:

Activation of freshly isolated buffy coat peripheral T cells with PMA/ionomycin will drive cytokine production by circulating memory T cells. After a 4 hour incubation with brefeldin, cells are cell surface marker stained, fixed and permeabilized prior to intracellular staining for IL-2, IFN-γ, TNF, IL-4, IL-17, and FOXP3/helios. These cytokines/transcription factors together with the surface markers CD3, CD4, CD8, CD25, CD56, CD62L, NKG2D, CD45Ra, CD45Ro, CLA/CCR4 will delineate the fraction of Th1/Th2/Th17/Tregs in the total and cutaneous CD4/CD8 naïve and memory T cell compartment and their expression of NKG2D. Without being bound by theory, using a LSRII, which enables multi-parametric testing from a single tube, 2-4 million PBMCs will be more than sufficient for this analysis. This will leave enough PBMCs (>20 million cells) from a 30 ml blood draw to provide for other goals.

Flow Sorting for Downstream Applications Using T Cell Subsets

The goal is to provide potential alopecic T cells for downstream functional analysis. For example, flow sorted T cell subsets will be provided for RNA profiling, for instance, transcriptional profiling of NK-type T cells. For biomarker studies, honing in on the appropriate cellular subset will improve the resolution of the analysis, which will otherwise be diluted by the presence of RNA from the mixed heterogenous PBMC population.

Studies in the AA mouse indicate that the alopecic T cells (FIG. 24), are recirculating and can be readily found and isolated from the blood and cutaneous lymph nodes. More than 5 million CD8+NKG2D+ T cells can be isolated by flow sorting from the cutaneous lymph nodes of a single mouse. This is an impressive number of fresh primary "pathogenic" T cells for downstream study and is a substantial improvement on the cell yields one can expect to recover from "crawl-outs" from alopecic skin. The identification of pathogenic T cell subsets in the blood of AA subjects human AA subjects is a scientific goal. Flow isolated T cell subsets will be provided for downstream applications including biomarker studies, functional studies and spectratyping to provide evidence for immuopathogenic relevance of specific T cells subsets.

i) Spectratype Analysis of TCR Repertoire

Figure 27:
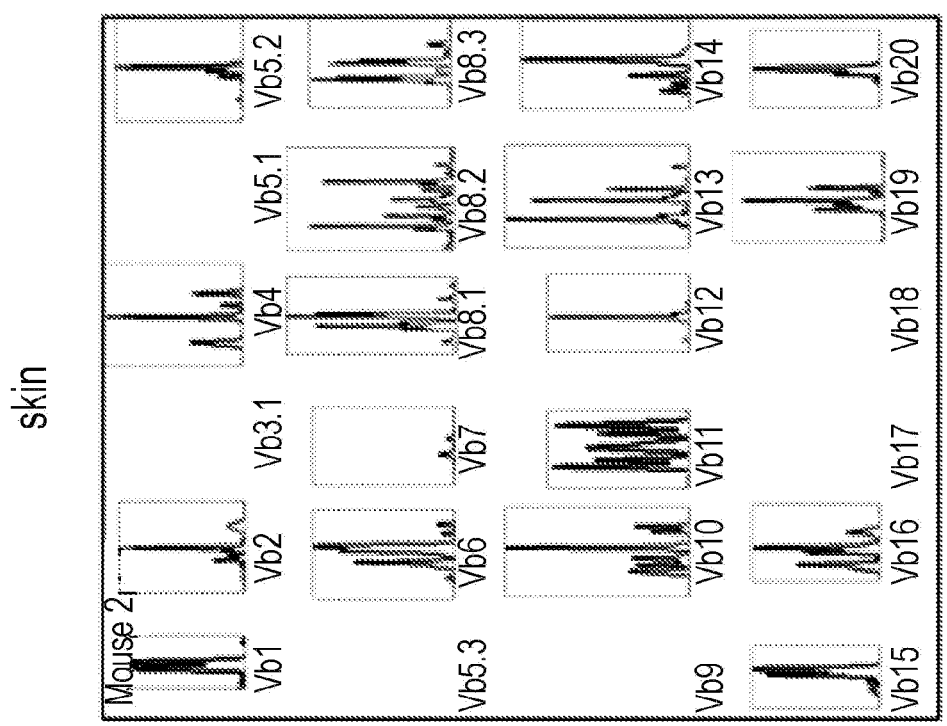
FIG. 27 shows spectratyping in a C3H-HeJ mouse. RNA was Isolated from skin biopsies, and from sorted NKG2D– and NKG2D+CD8+ T cells from cutaneous lymph nodes of C3H-He mice. Spectratyping analysis shows CDR3 length skewing in several Vbeta families. Some of the skewed Vbeta families are shared between skin and NKG2D+ lymph node CD8+ T cell populations (e.g., Vbeta2, Vbeta5.2, Vbeta20) whereas additional Vbeta families are skewed in skin (reflecting the CD4+ T cell population).

Spectratyping or TCR β-chain length distribution analysis of RNA from tissues or phenotypically separated lymphocyte subsets provides a qualitative portrait of the TCR clonotype utilization/repertoire of the infiltrating T cells. In recent years this technique has been used by others (5-7) as a highly sensitive and accurate method to delineate the proportion of clonally expanded T cells in a sample. Oligoclonality, evidence of expansion of subsets of T cells with restricted TCRs is indicative of antigenic drive in inflammatory processes and can be used as a first step to identify pathogenic T cell clones. Since each TCR rearrangement varies in CDR3 length in multiples of three nucleotides, heterogeneity of CDR3 length within a population of T cells can be used as a measure of TCR diversity. The principle of this technique is to PCR amplify the cDNA obtained from a T cell population using an upstream specific Vβ family member primers and a downstream constant region primer that together span the CDR3 region made by combinatorial and junctional VDJ joining. The PCR products are then fluorochrome-labelled in a primer extension ("run-off") reaction using a fluorescently labeled constant region primer. The products are then run on the ABI PRISM 3700 DNA analyzer. With Gene Mapper software the size of the peaks corresponding to discrete CDR3 lengths can be displayed and analyzed (FIGS. 20 and 27). The data are exported and compared to reference polyclonal repertoires, and measures of oligoclonality such as the Hamming distance are calculated. The area of the peaks in each histogram reflects the expression frequency of each CDR3 length within each family. A predominance of clonal expansions in the skin indicates a primary role for dermal antigens in driving disease and will enable focused investigation of pathogenic T cells. In contrast a polyclonal repertoire of unexpanded clones will indicate recruitment by non-clonally specific chemokine receptors. Comparisons of the TCR repertoire in non-lesional skin and blood of the same individuals will indicate whether clonally expanded skin resident T cell populations might also be found in the circulation. Similarly sorted T cell subsets can be used for source RNA material for repertoire analysis. For instance, FIGS. 20 and 27 demonstrates that in C3H mice an oligoclonal population is found in the lesional skin, a repertoire that is also over-represented in NKG2D positive but not negative CD8 lymph node populations. These data confirm that CD8+NKG2D+ T cells contain most (but not all) of the oligoclonal T cell populations found in the skin. Note that some TCR/clones are found in skin but not in draining cutaneous lymph nodes, e.g., Vβ10. These likely include CD4+ T cell populations found in AA skin but not present in the sorted CD8+ LN fraction. This approach provides powerful evidence for "antigen-drive", and combined with flow sorting as shown here, identifies pathogenic T cell subsets amongst populations of cells.

This evidence of clonal sharing or oligoclonality will be investigated and validated in mouse and human samples at the level of clonotype resolution by preparing bacterial libraries of the PCR products using topoisomerase-based cloning, and sequencing the TCR β-chain of resulting clones in a high throughput manner using 96-well based techniques as described (5-7). Usually 48 or 96 clones are selected and sequenced for each PCR product. The sequences are exported and aligned in GENEIDUS™ and the fine structure of VDJ element usage and joining is determined using Vquest. This allows definitive identification of shared clones and lymphocyte trafficking in different regions, as well as precise enumeration of the clonotypic composition of a sample. Furthermore, clonotypic TCRs can be used for gene transduction studies to generate T cells and retrogenic mice expressing alopecic TCRs. This effort can also lead to development of "humanized" transgenic TCR models of alopecia using transgenically expressed human alopecic TCRs in HLA02 transgenic mice.

ii) Transcriptional Biomarkers of Circulating Immune Cells

A transcriptional signature marking aggressive, drug refractory Lupus can be identified within the CD8 T cell compartment, but not when using RNA of total PBMCs (8) Thus combining flow sorting with transcriptional profiling greatly powers the analytic capacity. In alopecia areata the pathogenic cellular subset in the appears to be CD8+ NKG2Dhi T cells that envelop the hair follicle and may be of pathogenic relevance broadly in autoimmunity (9) including both celiac disease (4, 10), Type I diabetes (11) and rheumatoid arthritis (12-14). Transcriptional profiling of these cells in celiac disease (4, 10) previously described an NK-like transcriptional programming of these cells that will be similarly assessed in sort-purified circulating and skin-derived CD8 T cells. It will be important to specifically address the transcriptional profiles of these cellular populations to identify biological pathways central to these cells.

Epigenetically regulated autoimmune genes using ILLUMINA™-based genomic approaches were identified and DNA was obtained from sorted autoimmune human T cells from patients with Type I diabetes, alopecia areata and celiac disease. Hypermethylation of the promoter regions that downregulate the expression of important immunoregulatory genes including CD3, PD-1 and FasL was identified.

iii) Cellular Immunology

Flow cytometryic analysis of activated PBMCs can be used for intracellular cytokine analysis and or signaling activation of phosphorylated proteins. Classic antigen specific, mitogenic or mixed lymphocyte responses can be appreciated with CFSE-stained T cells or with thymidine incorporation. Available equipment includes a cell harvester and Microbeta/Trilux plate reader (for thymidine based proliferation and chromium release cytotoxicity assays), ELISA plate readers/washers, ELISPOT readers.

Skin Immunobiology

Figure 28:
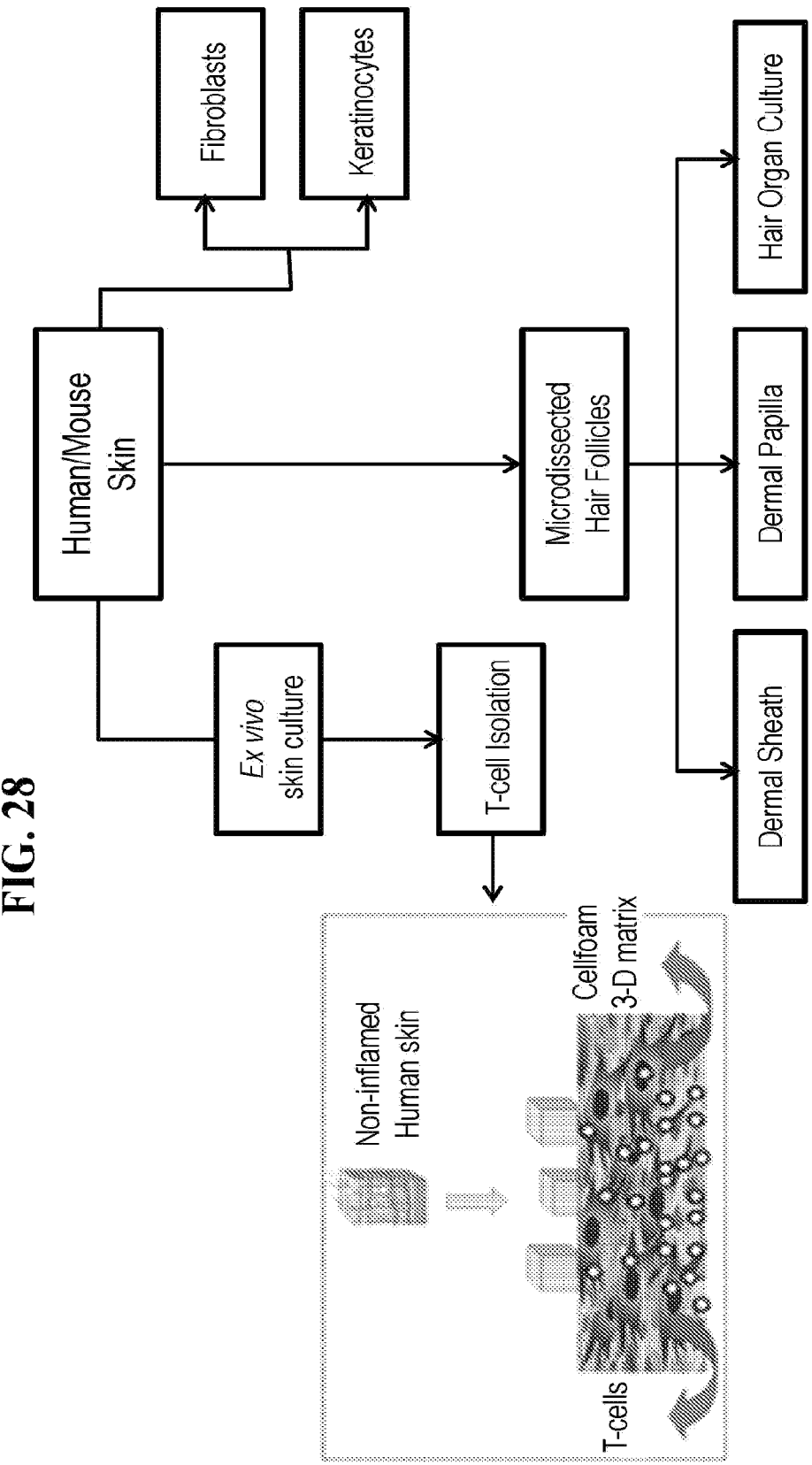
FIG. 28 is a schematic showing that human scalp skin procured from control or AA affected individuals can be used to establish primary cultures of individual cellular populations within the skin and hair follicle.
Figure 29A:
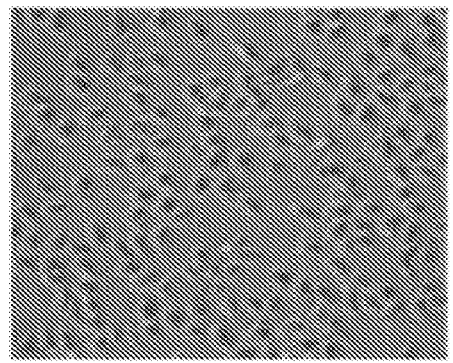
FIG. 29A is a heatmap depicting the significantly and differentially expressed genes between C3H/HeJ affected and unaffected skin.
Figure 29B:
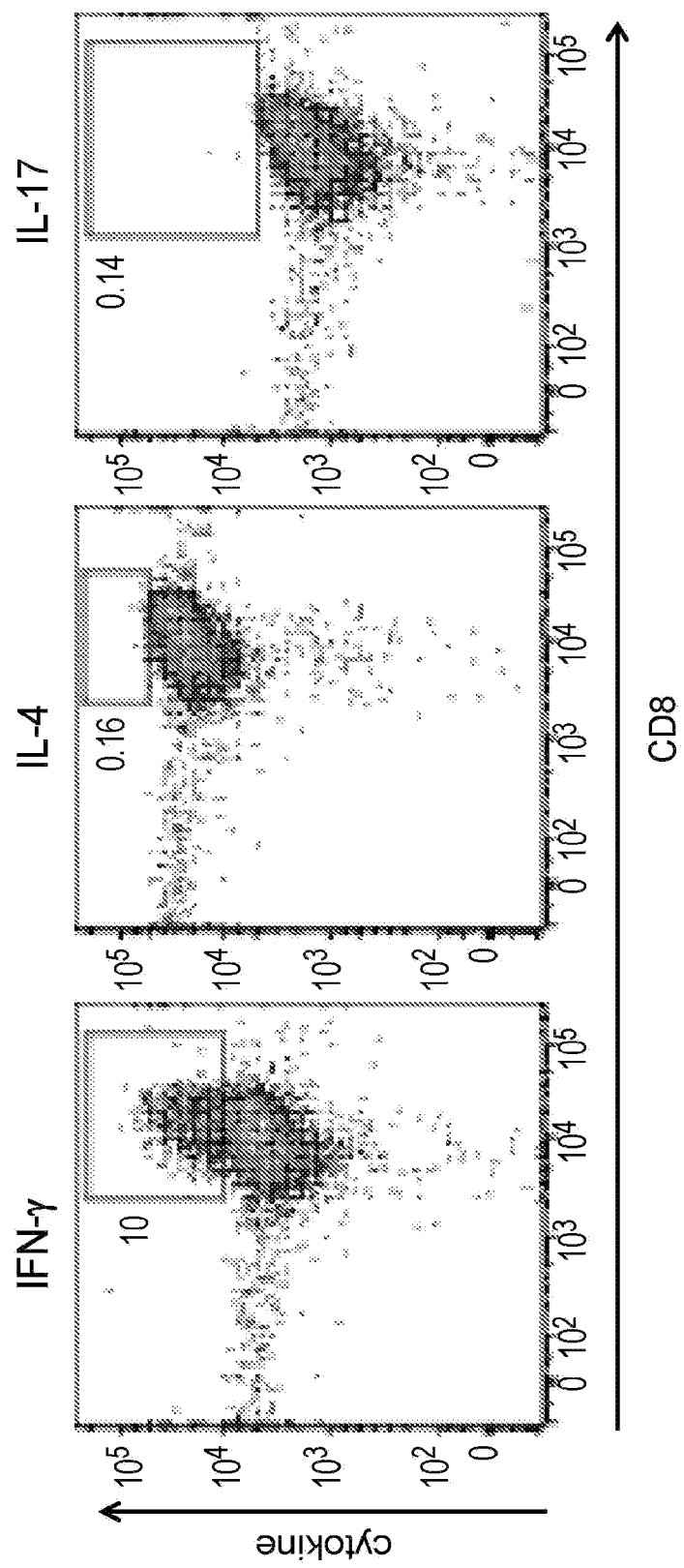
FIG. 29B shows validation by qRT-PCR of several selected immune-related genes from this list whose expression levels are significantly upregulated in AA lesional skin compared to unaffected skin, where each bar represents the average fold change of three independent experiments. UA=unaffected; AA=affected.
Figure 29D:
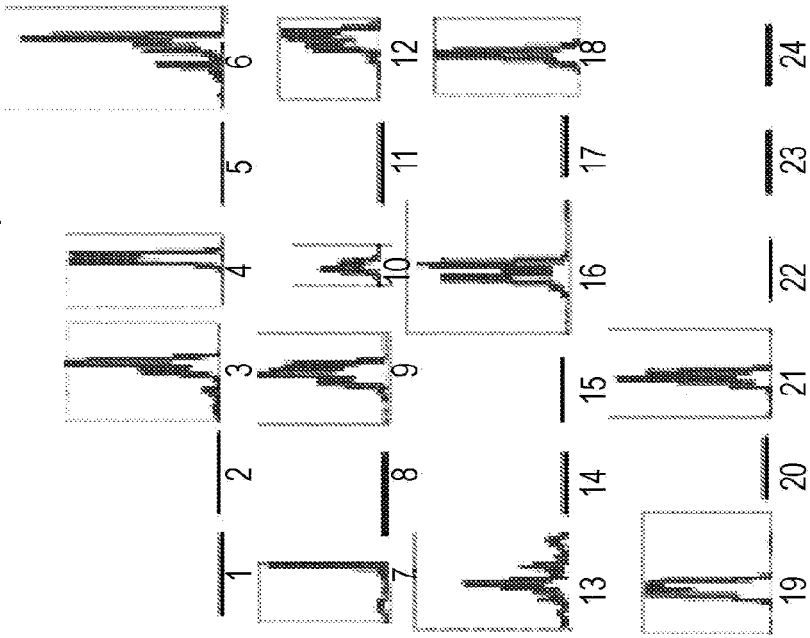
FIG. 29 shows a T cell 'crawl-out' assay, in which cultured human dermis obtained from punch skin biopsies are used as source material for flow cytometric analysis. Trisected skin punch biopsies of a 6 mm skin biopsy is obtained from alopecic lesional and non-lesional areas. After removing the fat, the finely minced skin is gently pressed in a Cellfoam matrix and then transferred, skin side-up, to a well of a 24-well plate containing 2 mls of SkinT medium with IL-2 (6 ng/ml) and IL-15 (10 ng/ml). T cells crawl outs are shown in FIG. 29A after the matrix is removed 3 days later. Flow cytometry (FIGS. 29B-C) and spectratyping (FIG. 29D) of these cells are also shown.
Figure 29C:
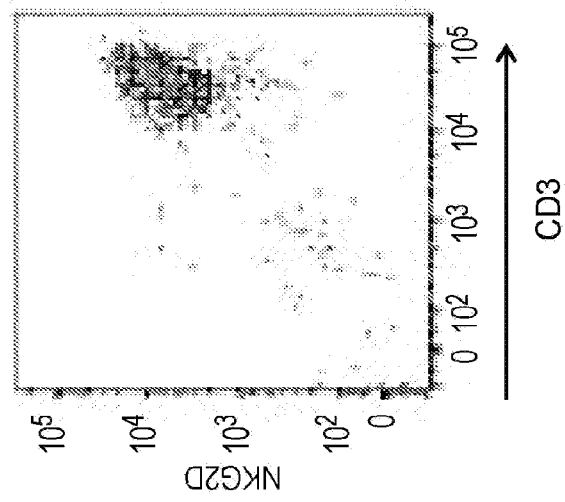
Figure 30:
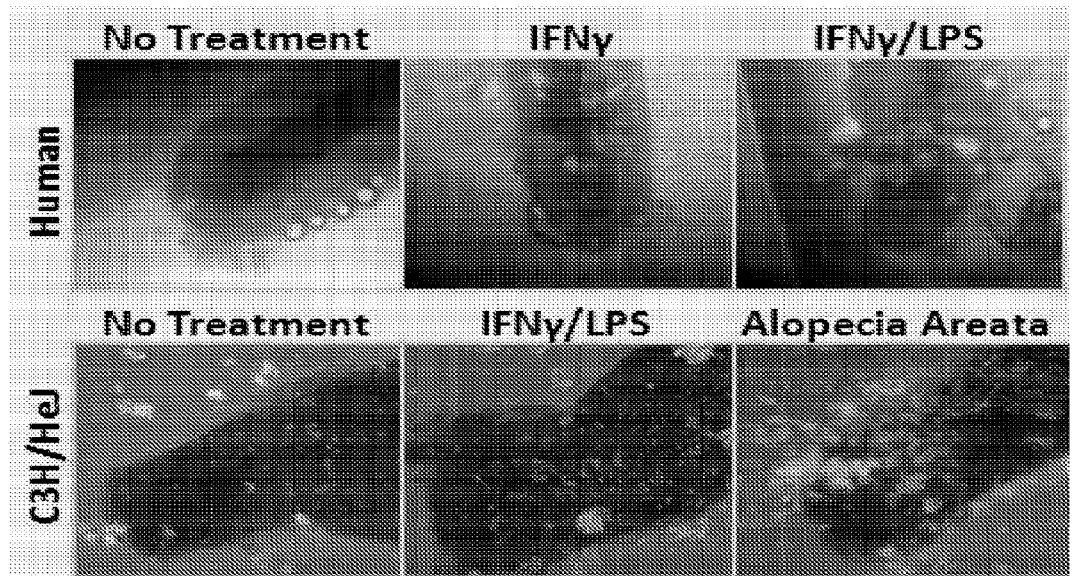
FIG. 30 shows that human peripheral blood mononuclear cells (PBMC), top panels or murine splenocytes were cultured in high dose IL-2 (1000/ml) to generate lymphokine-activated killer (LAK) cells. The CFSE green fluorescence labeled LAK cells were incubated with human hair follicle organ culture (top panels), or mouse hair follicle culture (bottom panels) from non-lesion region (bottom left two) or lesion.

Preparation of primary hair follicle and T cell components for functional (cytotoxicity), preparative (T cell cloning) and analytic studies (spectratyping, RNA profiling). Biopsy specimens from AA patients on study are precious, with immunostaining and transcriptional profiling studies taking the highest priority given the feasibility and informative power of these two approaches. Routinely human scalp skin is procured from control individuals (hair transplant donors) to establish primary cultures of individual cellular populations within the skin and hair follicle.

a) Culture of T Cells and Hair Follicle Components, Hair Follicle Organ Culture and Skin Organ Culture.

i) HF Targets:

Human scalp skin procured from control or AA affected individuals will be used to establish primary cultures of individual cellular populations within the skin and hair follicle (FIG. 28) to study the regulation of NKG2DL in primary HF populations and to evaluate HF populations as targets in CTL assays. Interfollicular skin will be dispase treated to separate the epidermal and dermal components and enzymatically processed to establish primary cultures of keratinocytes and fibroblasts. The hair follicles will be microdissected to separate the mesenchymal components and further used to culture dermal sheath cells (DSC) and dermal papilla cells (DPC). Serum free hair follicle organ culture established in the laboratory modeled after protocols from Kondo and Philpott et al (15) (FIG. 30) will be used to routinely culture individual follicles from control individuals, as well as lesional (when possible) and control skin from AA patients. The follicles are cultured in serum free growth conditions and show normal anagen growth for 7-10 days, followed by catagen entry and disintegration of the matrix (16). For cytotoxicity assays, the follicles will be transferred to media which sustains cytotoxic T-Cells or NK cells (MYELOCULT™, Stemcell Technologies) for 4-8 hrs. The skin explants maintain normal skin architecture, as well as the immune microenvironment, and will be used for functional studies (17).

ii) T Cell Effectors:

Isolation of sufficient numbers of T cells from enzymatically digested/dispersed human skin can be difficult; however cultured T cells weren expanded using the dermal crawl-out approach developed by Clark (2). Skin explants have been used to expand the resident T-cell population of the skin by culturing the explants on cell foam matrices for 3 weeks in IMDM containing 20% FCS, IL-2 and IL-15. This technique yields 0.3-3.0×106 T cells per 4 mm biopsy enabling immunophenotyping, T cell cloning, Th-profiling, and other downstream applications (e.g., transcriptional profiling, cytotoxicity and other functional assays). For AA patients on intervention trials, if sufficient T cells are obtained after three weeks of expansion (>1×10$^6$) they will be divided, with half the population used for RNA isolation/profiling and the other half used for flow immunophenotyping/Th profiling. If the yields are less than 1×106 total cells, studies will be limited to RNA profiling. For AA patients that are not on study, there will be more latitude for using crawl-out T cells and autologous HF targets for alternative functional studies, including for instance cytolyic assays and studies with antibody blockade/small molecules. As an example of the ability to analyse rare clinical populations of T cells, FIG. 29 illustrates a T cell "crawl-out" assay, in which cultured human dermis obtained from punch skin biopsies are used as source material for flow cytometric analysis.

Note that T cells obtained from AA skin biopsies are oligoclonal IFN-γ producing CD8+NKG2D+ T cells in striking contrast to the expected polyclonal CD4 population seen in crawl-outs from normal skin (2, 18).

b.) Interaction of the Skin and the Immune Components in Alopecia Areata Models

Established protocols are available for assessing skin-immune interactions for the studies herein. Primary cultured cells, as well as organ-cultured follicles, can be used as targets using cytotoxic T cells from control or patient peripheral blood lymphocytes, or those derived from the skin (FIG. 29). The immune effector cells can be co-cultured with CFSE-labeled target cells/hair follicles and the cytolysis will be measured colorimetrically by LDH release, or alternatively, the dead cells will be stained with 7-AAD and the cell numbers counted by flow cytometry. These assays can be used to determine molecular requirements for the interaction of immune effectors and HF targets, including cytotoxicity. For instance as shown here, cytotoxicity required NKG2D engagement and prior sensitization of targets with cytokines/TLR ligands known to upregulate NKG2DL transcription and surface expression.

Evaluation of Skin Biomarkers of Pathogenesis: Immunostaining and Transcriptional Profiling AA shows high correlation with several autoimmune disorders, making the hair follicle a highly accessible organ in which to study basic mechanisms of autoimmunity. There has been substantial interest in identifying early surrogate biological markers of pathogenesis. As such, AA represents a model system for biomarker development which may have relevance to a broad range of diseases. The following biomarkers are currently used to monitor AA development and response to treatment both in humans and in mice.

a) Immunohistochemical Staining for Lymphocytic Infiltration.

AA is associated with the presence of intrafollicular, and parafollicular immune infiltrate. For immunohistochemistry, tissue will be either fixed in 10% formalin in PBS for 8 hours at room temperature and stored in 70% ethanol for paraffin sections or embedded directly in CRYOMATRIX™ (Shandon, Waltham, Mass.) on dry ice for frozen sections which are stored at −80° C.

Figure 31:
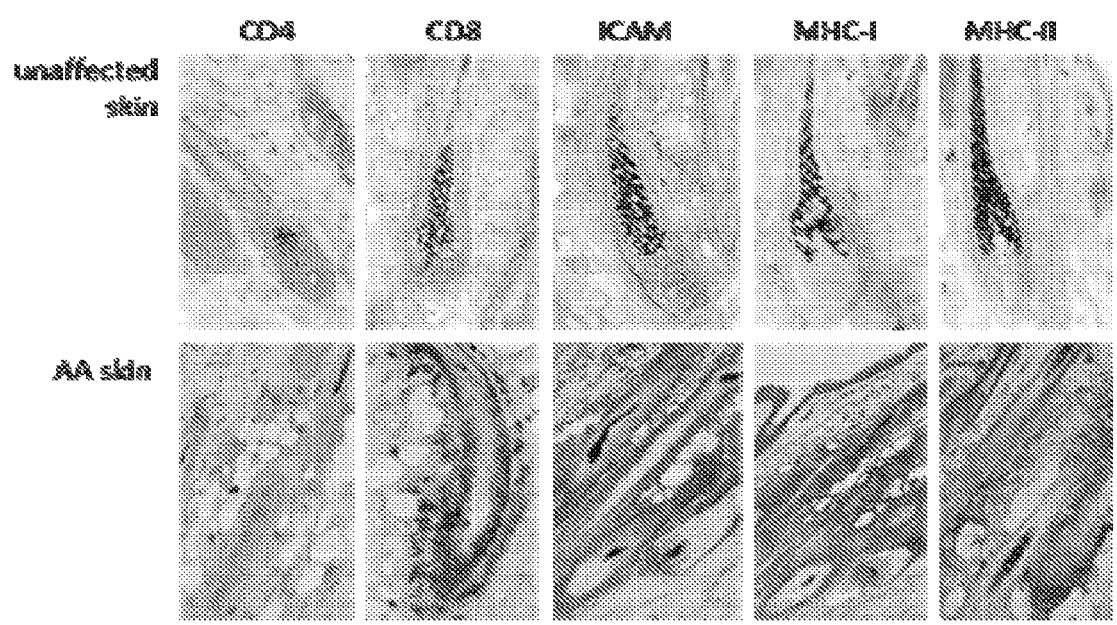
FIG. 31 shows immunohistochemical (IHC) staining of unaffected and affected AA skin in C3H-HeJ mice.

Paraffin-embedded tissue blocks are cut into 8-m sections, and hematoxylin and eosin (H&E) staining is carried out for histological studies. Frozen tissue is also sectioned to a thickness of 8 μm and fixed in 4% paraformaldehyde for immunofluorescence staining. Sections are stained with fluorescence-labeled secondary antibodies and immunofluorescence imaging carried out using Zeiss Axioskop microscope. Basic immunohistological/fluorescent staining will include staining with primary antibodies to CD3, CD4, CD8. As an example of the immunostains, evidence that MHC I and II and ICAM-1 are massively upregulated in alopecic HFs which are associated with a dense CD8 dominated infiltrate is provided (FIG. 31).

b) Isolation of Total Skin RNA and Quantitative PCR for Inflammatory Markers.

The human and mouse skin will be tested for elevation of inflammatory gene transcripts already defined, including IFN-response genes, and gene signatures to be defined, including "NK-type" CD8 T cell transcripts. Total RNA will be extracted from skin using an RNeasy purification kit (Qiagen). DNase-treated total RNA will be reverse-transcribed using SuperScript II reverse transcriptase (Invitrogen, Carlsbad, Calif.).

RT-PCR shall be performed using SYBR™ Green Master Mix and an ABI PRISM 7000™ Sequence Detection System (Applied Biosystems, Foster City. Calif.). GAPDH and -actin will be used as internal normalization control genes.

One of the goals of the studies herein is to establish the phenotype of circulating AA effector populations by matching spectratypes of sorted peripheral blood AA T cell subsets with those found in total skin T cells from the same patient. Flow cytometric sorting techniques will be combined with spectratype analysis to identify pathogenic T cells in the circulation of AA patients. This same approach was used in the mouse model to show that CD8+NKG2D+ lymph node cells contain the majority of the T cell clones found in alopecic skin. In AA subjects, the TCR repertoire will be compared in lesional and non-lesional skin and blood of the same individuals to identify whether clonally expanded skin resident T cell populations are also be found in the circulation. By progressive refinement of the sort criteria to isolate source RNA material from circulating T cell subsets one should be able to (at least partially) match the TCR repertoire found in total skin from the same patient and in this way indentify the immunophenotypic markers of pathogenic CD4 and CD8 T cells. Identification of pathogenic T cell subsets will be enormously valuable for monitoring clinical studies, refining biomarker development and would provide unique cellular materials for bedside-to-bench studies of pathogenesis.

Another goal of the studies herein is to establish the Th profile of AA T cells infiltrating the dermis and circulating in the peripheral blood. Pathogenic AA T cell Effector Differentiation/Cytokine Profile: Therapeutic targeting of specific Th-pathways has succeeded in other human skin inflammatory diseases, most notably in psoriasis a prototypical Th17 disease. There is substantial data in the AA animal model for AA as a predominant Th1 disease (19-23). To establish Th1-predominance in humans and develop the rationale and biomarker platform for Th1-targeted therapies, the Th-profile of infiltrating dermal AA T cells and relevant circulating T cell subsets in the blood will be addressed using a multi-prong approach including multianalyte, RNA profiling, immunostaining and intracellular flow cytometric analysis from the skin and blood. Refining the immunophenotypic markers for AA CD4 and CD8 T cells will of course allow detection of Th-profiles of the potential alopecic-specific T cells amongst the polyclonal circulating population.

Although transcriptional profiling of AA lesions from a small series of subjects are indicative of Th1-type skewing (24), without being bound by theory, AA is not "one disease". The common occurrence in AA subjects of co-morbid immune conditions that reflect both an underlying Th2 or Th1/17 bias that predisposes to diseases with common pathogenic pathways. including hypersensitivity (25) (dermatitis) and other autoimmune conditions (26-33) (see studies described herein) suggests that there may be a Th2-type AA as well as a Th1 or Th17 type of AA. Thus it is important to identify functional T cell responses in PBMCs from the periphery and from AA lesional tissue explants from a large number of patients that might identify subsets of AA with different Th profiles and to correlate these immune function biomarker parameters with the presence or absence of the relevant SNPs.

The T cell immunophenotype of peripheral T cells and lesional T cells will be assessed. 50 AA patients and 50 normal controls will be studied from the GWAS, with attached clinical history. Assessment of Th-profiles of total circulating T cells is straight forward but multi-parametric flow will be applied to T cell subsets for more granular assessment, as aided ultimately by definition of immunophenotypic markers of AA pathogenic populations. Isolation of sufficient numbers of T cells from enzymatically digested/dispersed human skin can be difficult, and maybe altered by culture conditions. Correlation will be performed with transcriptional profiling using whole skin approaches and microdissected skin samples to describe the cytokine profile within the follicular sheath infiltrate as well as from infiltrates in the interfollicular epithelium.

Human Subjects

Skin biopsies from the scalp will be collected from normal subjects consist of AA patients and unaffected control subjects receiving hair transplantation. Additional biopsies will be obtained from subjects on clinical trials.

The sources of research material will be scalp skin biopsies from AA patients and controls. RNA from small tissue samples, including microdissected hair follicle compartments are routinely obtained. Tissue biopsies from AA patients and controls will be provided.

Vertebrate Animals

Young C3H/HeJ mice (2-3 months) and retired breeders showing visible hair loss will be acquired from Jackson Labs. The mice strains established by each participating principle investigator will be housed in their respective animal housing suites. Mice will be given free access to water and pellet diet (5010 rodent diet, LabDiet, PMI Nutrition International).

Primary cell culture for individual skin and follicle components as well as hair/skin organ cultures will be established for wild-type and transgenic or knock-out mice. These studies also involve hair follicle and skin tissue characterization. The mice will be euthanised by $CO_2$ asphyxiation followed by cervical dislocation, a veterinary-approved and widely recommended method. It is the quickest and most humane method that is not associated with any pain or stress for the animals. Mice will be shaved on the dorsal surface with electric clipper and then skin tissue will be dissected out. The isolation scheme of individual cellular components of the skin and hair follicle as well the T-cells isolation from skin explants is described in FIGS. 25, 28 and 29. Skin Samples will also be embedded in OCT and paraffin. In addition to skin, spleen and thymus will also be dissected from the animals and further used for flow cytometry. Serum from the animals will also be collected by tail bleeding and used for cytokine profiling.

References 1. de Jong, A., Pena-Cruz, V., Cheng, T X., Clark, R. A., Van Rhijn, I., and Moody, D. B. 2010. CD1a-autoreactive T cells are a normal component of the human alphabeta T cell repertoire. *Nat Immunol* 11:1102-1109.
2. Clark, R. A., Chong, B. F., Mirchandani, N., Yamanaka, K., Murphy, G. F., Dowgiert, R. K., and Kupper, T. S. 2006. A novel method for the isolation of skin resident T cells from normal and diseased human skin. *J Invest Dermatol* 126:1059-1070.
3. Bhagat, G., Naiyer, A. J., Shah, J. G., Harper, J., Jabri, B., Wang, T. C., Green, P. H., and Manavalan, J. S. 2008. Small intestinal CD8+TCRgammadelta+NKG2A+ intraepithelial lymphocytes have attributes of regulatory cells in patients with celiac disease. *J Clin Invest* 118:281-293.
4. Meresse, B., Chen, Z., Ciszewski, C., Tretiakova, M., Bhagat, G., Krausz, T. N., Raulet, D. H., Lanier, L. L., Groh, V., Spies, T., et al. 2004. Coordinated induction by IL15 of a TCR-independent NKG2D signaling pathway converts CTL into lymphokine-activated killer cells in celiac disease. *Immunity* 21:357-366.
5. Winchester, R., Wiesendanger, M., O'Brien, W., Zhang, H. Z., Maurer, M. S., Gillam, L. D., Schwartz, A., Marboe, C., and Stewart, A. S. 2011. Circulating activated and effector memory T cells are associated with calcification and clonal expansions in bicuspid and tricuspid valves of calcific aortic stenosis. *J Immunol* 187:1006-1014.
6. Wu, H. D., Maurer, M. S., Friedman, R. A., Marboe, C. C., Ruiz-Vazquez, E. M., Ramakrishnan, R., Schwartz, A., Tilson, M. D., Stewart, A. S., and Winchester, R. 2007. The lymphocytic infiltration in calcific aortic stenosis predominantly consists of clonally expanded T cells. *J Immunol* 178:5329-5339.
7. Curran, S. A., FitzGerald, O. M., Costello, P. J., Selby, J. M., Kane, D. J., Bresnihan, B., and Winchester, R. 2004. Nucleotide sequencing of psoriatic arthritis tissue before and during methotrexate administration reveals a complex inflammatory T cell infiltrate with very few clones exhibiting features that suggest they drive the inflammatory process by recognizing autoantigens. *J Immunol* 172:1935-1944.
8. McKinney, E F., Lyons, P. A., Can, E. J., Hollis, J. L., Jayne, D. R., Willcocks, L. C., Koukoulaki, M., Brazma, A., Jovanovic, V., Kemeny, D. M., et al. 2010. A CD8+ T cell transcription signature predicts prognosis in autoimmune disease. *Nat Med* 16:586-591, 581 p following 591.
9. Van Belle, T. L., and von Herrath, M. G. 2009. The role of the activating receptor NKG2D in autoimmunity. *Mol Immunol* 47:8-11.
10. Meresse, B., Curran, S. A., Ciszewski, C., Orbelyan, G., Setty, M., Bhagat, G., Lee, L., Tretiakova, M., Semrad, C., Kistner, R, et al. 2006. Reprogramming of CTLs into natural killer-like cells in celiac disease. *J Exp Med* 203:1343-1355.
11. Ogasawara, K., Hamerman, J. A., Ehrlich, L. R., Bour-Jordan, H., Santamaria, P., Bluestone, J. A., and Lanier, L. L. 2004. NKG2D blockade prevents autoimmune diabetes in NOD mice. *Immunity* 20:757-767.
12. Andersson, A. K., Sumariwalla, P I., McCann, F. E., Amjadi, P., Chang, C., McNamee, K., Tornehave, D., Haase, C., Agerso, H., Stennicke, V. W., et al. 2011. Blockade of NKG2D ameliorates disease in mice with collagen-induced arthritis: A potential pathogenic role in chronic inflammatory arthritis. *Arthritis Rheum* 63:2617-2629.
13. Groh, V., Bruhl, A., El-Gabalawy, H., Nelson, J. L., and Spies, T. 2003. Stimulation of T cell autoreactivity by anomalous expression of NKG2D and its MIC ligands in rheumatoid arthritis. *Proc Natl Acad Sci USA* 100:9452-9457.
14. Killock, D. 2011. Experimental arthritis: NKG2D: a potential therapeutic target in RA? *Nat Rev Rheumatol* 7:438.
15. Philpott, M. P., Sanders, D. A., and Kealey, T. 1996. Whole hair follicle culture. *Dermatol Clin* 14:595-607.
16. Kondo, S., Hozumi, Y., and Aso, K. 1990. Organ culture of human scalp hair follicles: effect of testosterone and oestrogen on hair growth. *Arch Dermatol Res* 282:442-445.
17. Companjen, A. R., van der Wel, L. I., Wei, L., Laman, J. D., and Prens, E. P. 2001. A modified ex vivo skin organ culture system for functional studies. *Arch Dermatol Res* 293:184-190.
18. Clark, R. A., Chong, B., Mirchandani, N., Brinster, N. K., Yamanaka, K., Dowgiert, R. K., and Kupper, T. S. 2006. The vast majority of CLA+ T cells are resident in normal skin. *J Immunol* 176:4431-4439.
19. Freyschmidt-Paul, P., McElwee, K. J., Hoffmann, R., Sundberg, J. P., Vitacolonna, M., Kissling, S., and Zoller, 20. Hirota, R., Tajima, S., Yoneda, Y., Okada, M., Tashiro, J., Ueda, K., Kubota, T., and Yoshida, R. 2003. Induction of hair regrowth in the alopecia site of IFN-gamma knockout mice by allografting and IFN-gamma injection into the transplantation site. *J Interferon Cytokine Res* 23:433-439.
21. Gilhar, A., Kam, Y., Assy, B., and Kalish, R. S. 2005. Alopecia areata induced in C3H/HeJ mice by interferon-gamma: evidence for loss of immune privilege. *J Invest Dermatol* 124:288-289.
22. Skurkovich, S., Korotky, N. G., Sharova, N. M., and Skurkovich, B. 2005. Treatment of alopecia areata with anti-interferon-gamma antibodies. *J Investig Dermatol Symp Proc* 10:283-284.
23. Nakamura, M., Jo, J., Tabata, Y., and Ishikawa, O. 2008. Controlled delivery of T-box21 small interfering RNA ameliorates autoimmune alopecia (Alopecia Areata) in a C3H/HeJ mouse model. *Am J Pathol* 172:650-658.
24. Subramanya, R. D., Coda, A. B., and Sinha, A. A. 2010. Transcriptional profiling in alopecia areata defines immune and cell cycle control related genes within disease-specific signatures. *Genomics* 96:146-153.
25. Barahmani, N., Lopez, A., Babu, D., Hernandez, M., Donely, S. E., and Duvic, M. 2009. Serum T helper 1 cytokine levels are greater in patients with alopecia areata regardless of severity or atopy. *Clin Exp Dermatol*.
26. Chu, S. Y., Chen, Y. J., Tseng, W. C., Lin, M. W., Chen, T J., Hwang, C. Y., Chen, C. C., Lee, D. D., Chang, Y. T., Wang, W. J., et al. 2011. Comorbidity profiles among patients with alopecia areata: The importance of onset age, a nationwide population-based study. *J Am Acad Dermatol*.
27. Du Vivier, A., and Munro, D. D. 1975. Alopecia areata, autoimmunity, and Down's syndrome. *Br Med J* 1:191-192.
28. Goh, C., Finkel, M., Christos, P. J., and Sinha, A. A. 2006. Profile of 513 patients with alopecia areata: associations of disease subtypes with atopy, autoimmune disease and positive family history. *J Eur Acad Dermatol Venereol* 20:1055-1060.
29. Kasumagic-Halilovic, E. 2008. Thyroid autoimmunity in patients with alopecia areata. *Acta Dermatovenerol Croat* 16:123-125.
30. Puavilai, S., Puavilai, G., Charuwichitratana, S., Sakuntabhai, A., and Sriprachya-Anunt, S. 1994. Prevalence of thyroid diseases in patients with alopecia areata. *Int J Dermatol* 33:632-633.
31. Seyrafi, H., Akhiani, M., Abbasi, H., Mirpour, S., and Gholamrezanezhad, A. 2005. Evaluation of the profile of alopecia areata and the prevalence of thyroid function test abnormalities and serum autoantibodies in Iranian patients. *BMC Dermatol* 5:11.
32. Wang, S. J., Shohat, T., Vadheim, C., Shellow, W., Edwards, J., and Rotter, J. I. 1994. Increased risk for type I (insulin-dependent) diabetes in relatives of patients with alopecia areata (AA). *Am J Med Genet.* 51:234-239.
33. Yano, S., Ihn, H., Nakamura, K., Okochi, H., and Tamaki, K. 1999. Antinuclear and antithyroid antibodies in 68 Japanese patients with alopecia areata. *Dermatology* 199:191.

Example 6

In vivo pre-clinical studies of blocking Jak1/Jak2 was performed using the INCB018424 Jak1/Jak2 inhibitor in the grafted animal model of the disease, C3H-HeJ mice. 0/5 mice developed alopecia after treatment with INCB018424, whereas 2/5 placebo treated mice developed AA.

Example 7

Mouse Transplant Model for Alopecia Areata

Alopecia areata (AA) is one of the most prevalent autoimmune diseases and manifests as nonscarring hair loss. The course of the disease is unpredictable, and there are currently no consistently efficacious treatments available. Although research into disease pathogenesis and the development of targeted therapies are lacking, the creation of a mouse transplant model with a high incidence of disease has opened up new avenues of preclinical experimentation.

Several lines of evidence support the potential efficacy of JAK3 inhibitors in the treatment of AA: (1), a recently completed genome-wide association study of AA identified a number of gene-associated loci with immunological relevance, including those for IL-2/IL-2RA and IL-21; (2) initial findings in a preclinical mouse model suggested disruption of IL-15/IL-15R signaling ameliorates the disease; and (3) data indicate that T cells, dependent on IL-7 and IL-15 for survival, mediate the disease in the mouse model and in humans.

We therefore assessed the efficacy of JAK3 inhibition on the development of alopecia in a preclinical mouse model. Alopecic C3H/HeJ skin grafts were transplanted onto unaffected C3H/HeJ mouse recipients and subsequently treated with a JAK3 inhibitor administered by osmotic pump, vehicle administered by osmotic pump, or PBS injections. While 4/4 PBS-treated and 2/2 vehicle-pump treated mice developed alopecia by six weeks following transplantation, 0/5 mice treated with the JAK3 inhibitor developed alopecia. Microarray analysis of skin, immunohistochemical stains of skin for T cell infiltrate, and serum marker assessments demonstrated decreased inflammatory profiles in mice treated with JAK3 inhibitors. In total, our findings suggest JAK3 inhibitors may be an effective treatment in patients with AA.

Example 8

Targeting the Immune Effector Response in AA

Specific autoimmune mechanisms underlying Alopecia Areata (AA) have remained obscure and therefore clinical investigation of AA has historically lagged behind other autoimmune diseases.
Identify Effective, Clinically Relevant, Therapies in Mouse Models of Alopecia Areata.

In both human AA and in the AA mouse model, local hair follicle (HF) IL-15/NKG2DL upregulation was identified as key inflammatory signals that recruit/activate $CD8^+$ T cells, likely the critical AA immune effectors responsible for IFN-gamma (γ) production and hair follicle (HF) cytotoxicity. These observations provided the rationale for the studies to therapeutically target the IL-15/NKG2D.

It has been shown that the IL-15 pathway can be blocked using JAK3 protein tyrosine kinase inhibitors (PTKi).
Small Molecule PTKi Prevents AA.

Figure 32:
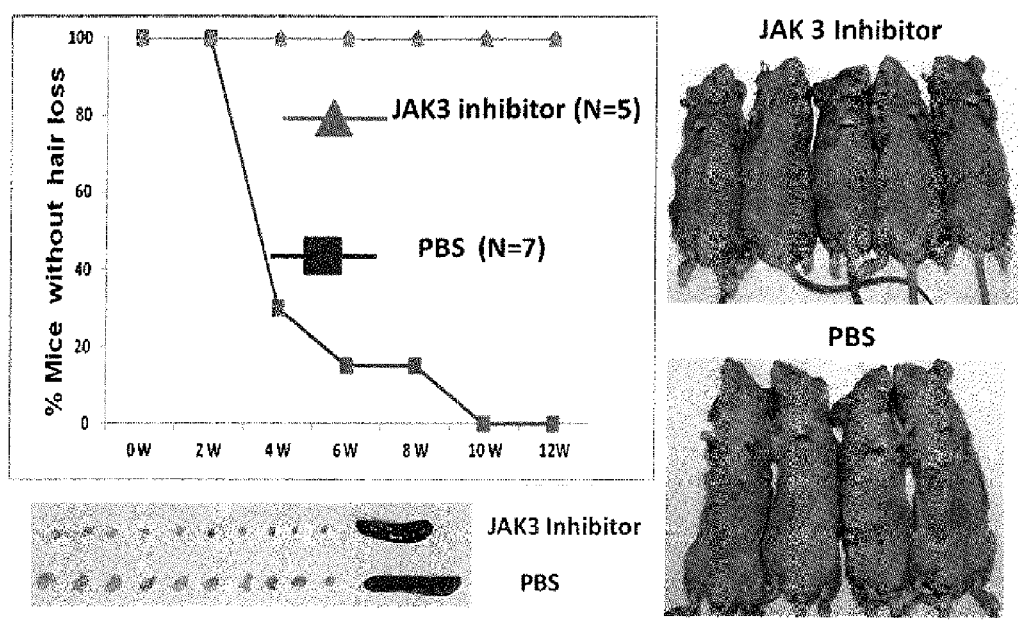
FIG. 32 shows that treatment of mice with the Jak3 inhibitor (tofacitinib; CP-69055) prevents alopecia areata (AA).

5 mice were treated systemically with tofacitinib (CP-69055; 10 mg/kg/day within an Alzet pump). Tofacitinib is a JAK3 inhibitor known to inhibit IL-15 signaling in human whole blood assays. None of the treated mice developed alopecia areata or cutaneous lymphadenopathy, whereas untreated mice manifested both AA and associated cutaneous lymphadenopathy (FIG. 32). Topical delivery approaches will be pursued for AA reversal in the mouse model that has the major benefit of an improved therapeutic index for clinical development.

Identify Disease-Associated AA Biomarkers and their Reversal with Effective Therapy in C3H Mice.

Figure 33A:
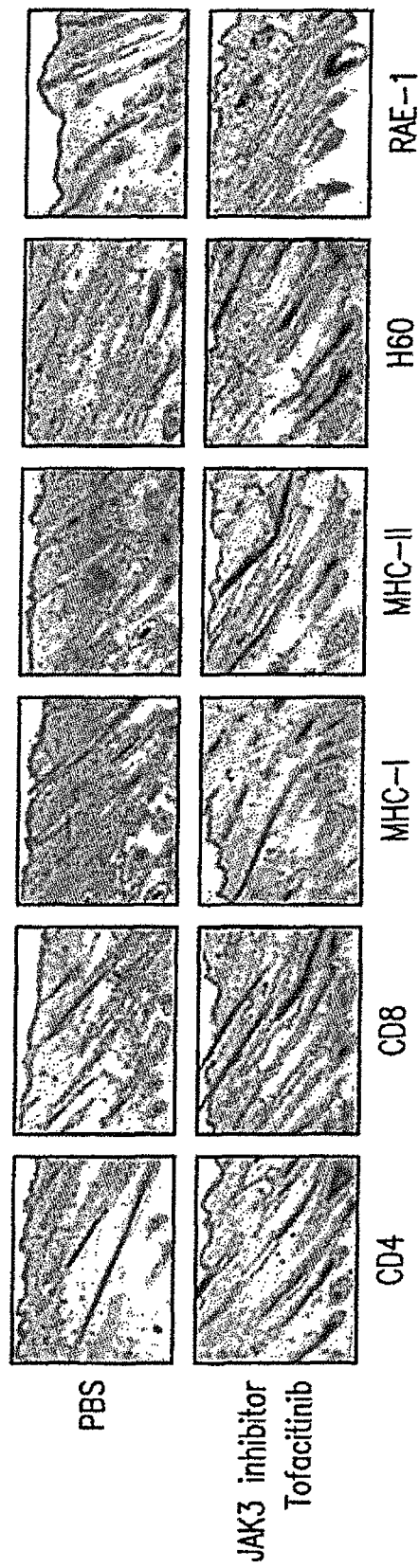
FIG. 33 shows treatment related elimination of dermal T cell infiltrates and inflammatory biomarkers by immunostaining (FIG. 33A) and by flow cytometry (FIG. 33B). CD8+ NKG2D+ T cells, which represent up to 25% of dermal cells in AA skin, are completely eliminated with treatment. The flow cytometry is of single cell suspensions from the skin. The cells in the right upper quadrant are not observed in normal healthy mice and are CD8+NKG2D+ effector T cells. CD8+NKG2D+ effector T cells are found in alopecic mice after skin grafting. Mice treated with the JAK3 inhibitor do not develop alopecia and their skin is devoid of these cells.
Figures 1, 33B:
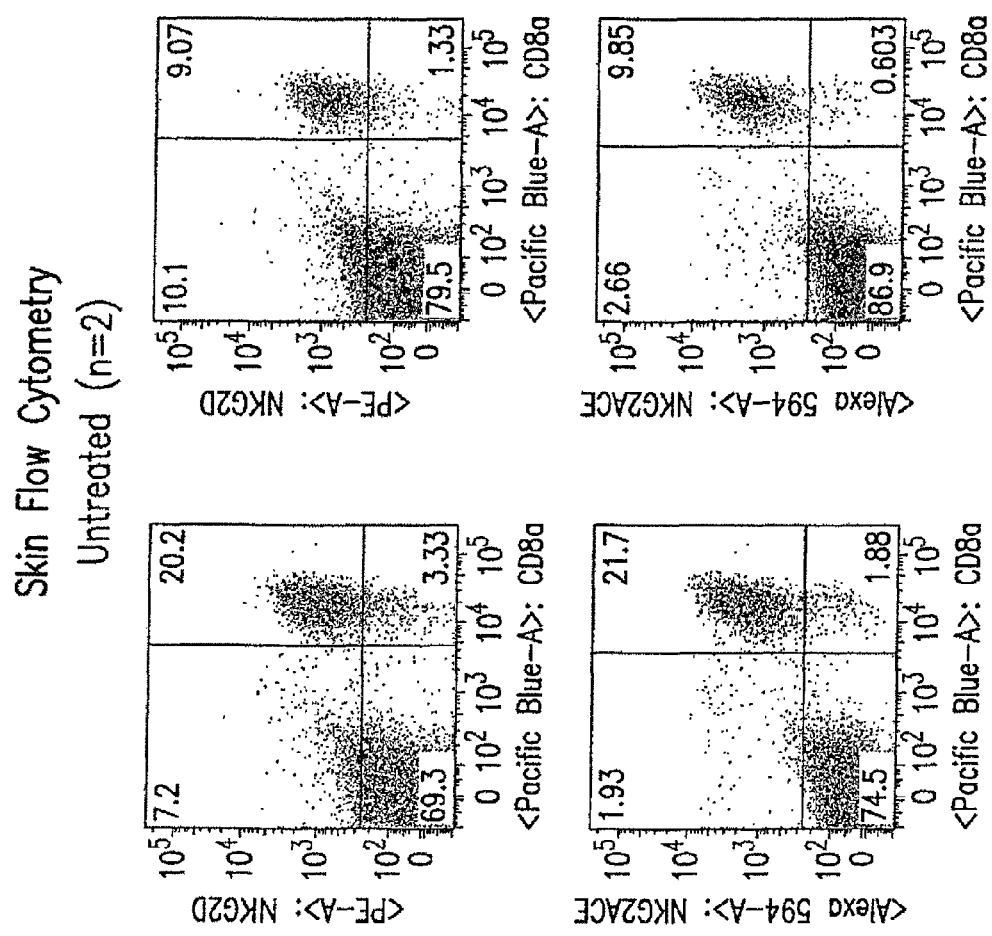
Figures 2, 33B:
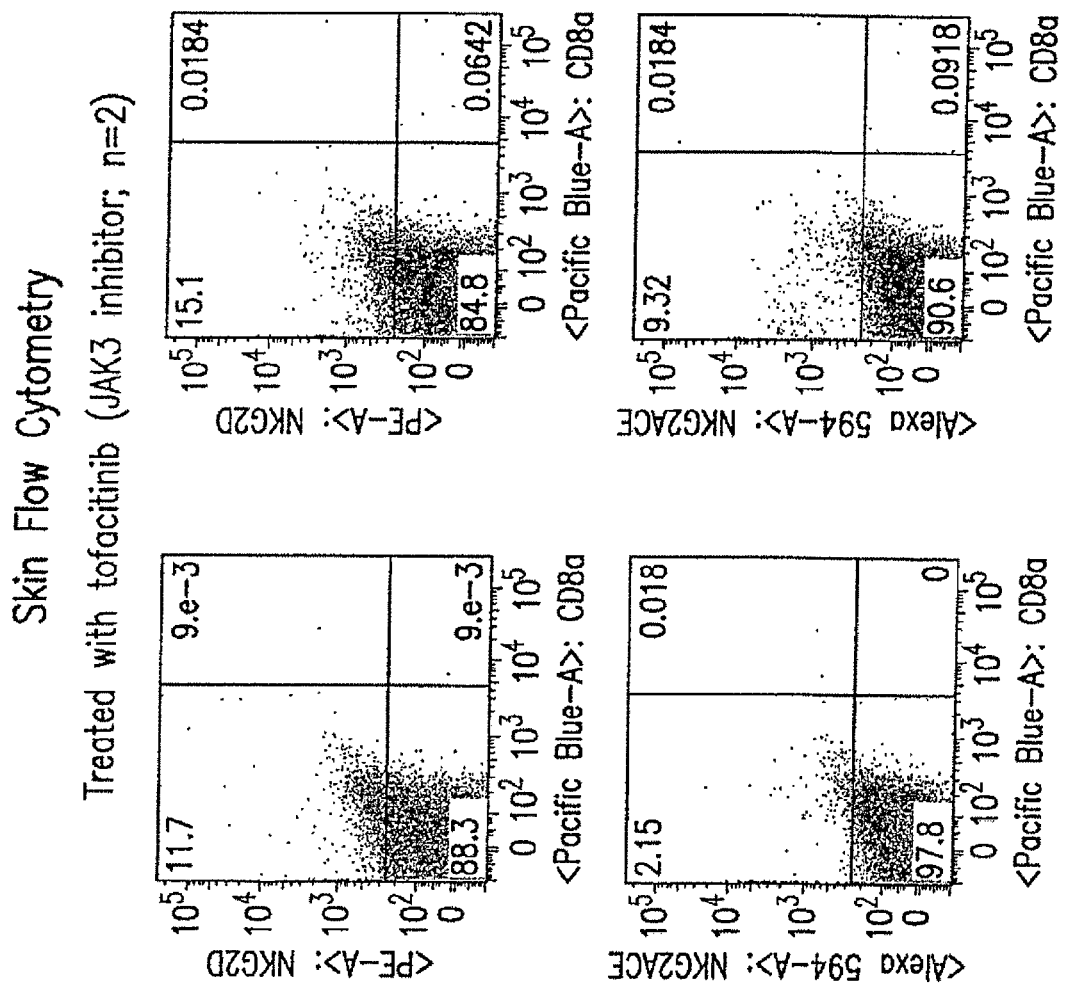
Figure 34:
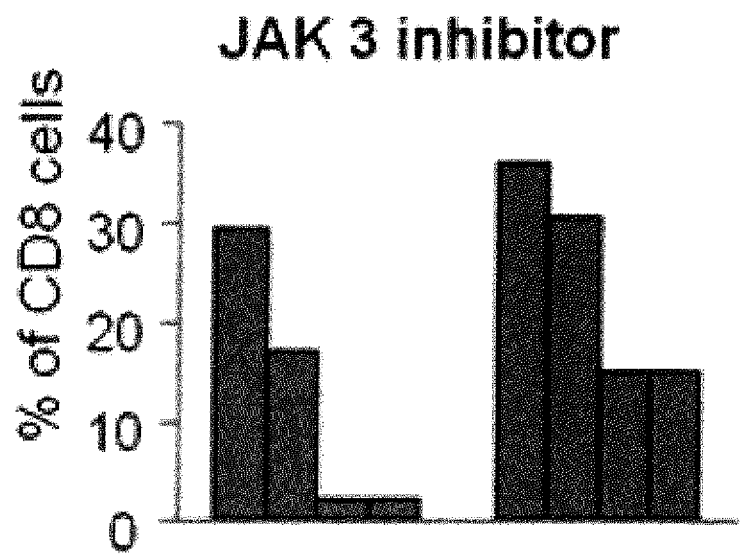
FIG. 34 are graphs that show treatment elimination of IFN-γ producing "NK-type" CD8 T cells in cutaneous LN, and loss of circulating IFN-inducible chemokines. The bar graphs in the left panel show intracellular flow cytometry of PMA/Iono stimulated LN cells from individually treated and untreated mice stained for CD8.NKG2A/C/D/E.IFNγ. Two mice per group are shown.

Cellular, inflammatory, and molecular biomarkers have been assessed in treated mice. Targeted therapy with tofacitinib eliminated the pathogenic CD8$^+$NKG2D$^{hi}$ cells from both the skin and the cutaneous draining lymph nodes and moreover down-regulated inflammatory biomarkers in the skin, including MHC molecules and the AA-associated IFN signature (FIG. 33). HF NKG2DL expression was reduced although not completely eliminated (e.g. H60 expression by immunostain) (FIGS. 33 and 34), indicating H60 upregulation as a proximal event.

Transcriptional profiling analysis of treated vs. untreated skin shows abrogation of the cutaneous IFN-signature with treatment. These murine transcriptional profiles will be integrated computationally with transcriptional profiles obtained from human skin biopsies from untreated alopecic subjects to identify candidate dynamic human biomarkers that are associated with patchy stable disease vs. progressive disease vs. alopecia universals.

Interpretation of PTKi Targeted Approaches.

PTKi's vary greatly in their selectivity of their target kinases. For tofacitinib, JAK sensitivity is greater for JAK3>JAK1>>JAK2 (IC$_{50}$ is 28-50 nM, 140-180 nM, 1000-5000 nM, in whole blood assays, respectively). In the treated mice, tofacitinib serum levels would be 30-40 nM, and potential impacts will be assessed on both JAK1 and 3 activity. For ruxolitinib (a JAK1/2 inhibitor), sensitivity is JAK2>JAK1>>JAK3 (IC$_{50}$ is 3.3 nM, 2.8 nM, and 428 nM for in vitro kinase inhibition, respectively). Pharmacodynamic JAK inhibition in the mouse is likely to be transient since ruxolitinib dosing is once daily and the half-life in rodents is 3-6 hours.

For example, a Jak3 inhibitor can exert selective inhibition activity of its JAK3 target at about 10 nM, about 15 nM, about 20 nM, about 25 nM, about 30 nM, about 35 nM, about 40 nM, about 45 nM, about 50 nM, or at about 55 nM. A Jak3 inhibitor can also exert selective inhibition activity of its JAK3 target at about 60 nM, about 65 nM, about 70 nM, about 75 nM, about 80 nM, about 85 nM, about 90 nM, about 95 nM, about 100 nM, about 105 nM, about 110 nM, about 115 nM, about 120 nM, about 125 nM, about 130 nM, or at about 135 nM.

For example, a Jak3 inhibitor can also exert inhibition activity of its JAK3 target, while also able to promiscuously exert inhibition activity of a JAK1 target, at about 140 nM, about 145 nM, about 150 nM, about 155 nM, about 160 nM, about 165 nM, about 170 nM, about 175 nM, about 180 nM, about 185 nM, about 190 nM, about 195 nM, about 200 nM, about 205 nM, about 210 nM, about 215 nM, about 220 nM, or at about 225 nM.

For example, a Jak3 inhibitor can also exert inhibition activity of its JAK3 target at about 250 nM, about 300 nM, about 350 nM, about 400 nM, about 450 nM, about 500 nM, about 650 nM, about 700 nM, about 750 nM, about 800 nM, about 850 nM, about 900 nM, or at about 950 nM.

For example, a Jak3 inhibitor can also exert inhibition activity of its JAK3 target, while also able to promiscuously exert inhibition activity of a JAK2 target, at about 1000 nM, about 1250 nM, about 1500 nM, about 1750 nM, about 2000 nM, about 2250 nM, about 2500 nM, about 2750 nM, about 3000 nM, about 3250 nM, about 3500 nM, about 3750 nM, about 4000 nM, about 4250 nM, about 4500 nM, about 4750 nM, about 5000 nM, about 5250 nM, about 5500 nM, about 5750 nM, about 6000 nM, about 6250 nM, about 6500 nM, about 6750 nM, about 7000 nM, about 7250 nM, about 7500 nM, about 7750 nM, or at about 8000 nM.

For example, a Jak1/2 inhibitor can exert selective inhibition activity of its JAK1 and/or JAK2 target at about 0.5 nM, about 1.0 nM, about 1.5 nM, about 2.0 nM, about 2.5 nM, about 3.0 nM, about 3.5 nM, about 4.0 nM, about 4.5 nM, about 5.0 nM, about 5.5 nM, 6.0 nM, about 6.5 nM, about 7.0 nM, about 7.5 nM, about 8.0 nM, about 8.5 nM, about 9.0 nM, about 9.5 nM, or about 10.0 nM. For example, a Jak1/2 inhibitor can exert selective inhibition activity of its JAK1 and/or JAK2 target at about 15 nM, about 20 nM, about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM, about 100 nM, about 150 nM, about 200 nM, about 250 nM, about 300 nM, about 350 nM, or at about 400 nM.

For example, a Jak1/2 inhibitor can also exert inhibition activity of its JAK1 and/or JAK2 target, while also able to promiscuously exert inhibition activity of a JAK3 target, at about 425 nM, about 450 nM, about 475 nM, about 500 nM, about 525 nM, about 550 nM, about 575 nM, about 600 nM, about 625 nM, about 650 nM, about 675 nM, about 700 nM, about 725 nM, about 750 nM, about 775 nM, about 800 nM, about 825 nM, about 850 nM, about 875 nM, about 900 nM, about 925 nM, about 950 nM, about 975 nM, or at about 1000 nM.

To activate a Jak protein target in the skin, the skin should be penetrated at about 0.5 mm, about 1 mm, about 1.5 mm, about 2 mm, about 2.5 mm, about 3 mm, about 3.5 mm, or at about 4 mm. Depending on the depth of penetration, the concentration of a JAK inhibitor, such as a JAK1/2 inhibitor or a JAK3 inhibitor, can range from about 25 nM to about 5000 nM. At the higher concentration ranges, one JAK inhibitor can elicit an inhibitory effect not only of its target but also of other JAK proteins.

Integration of Human and Mouse Gene Expression Profiles.

Figure 35:
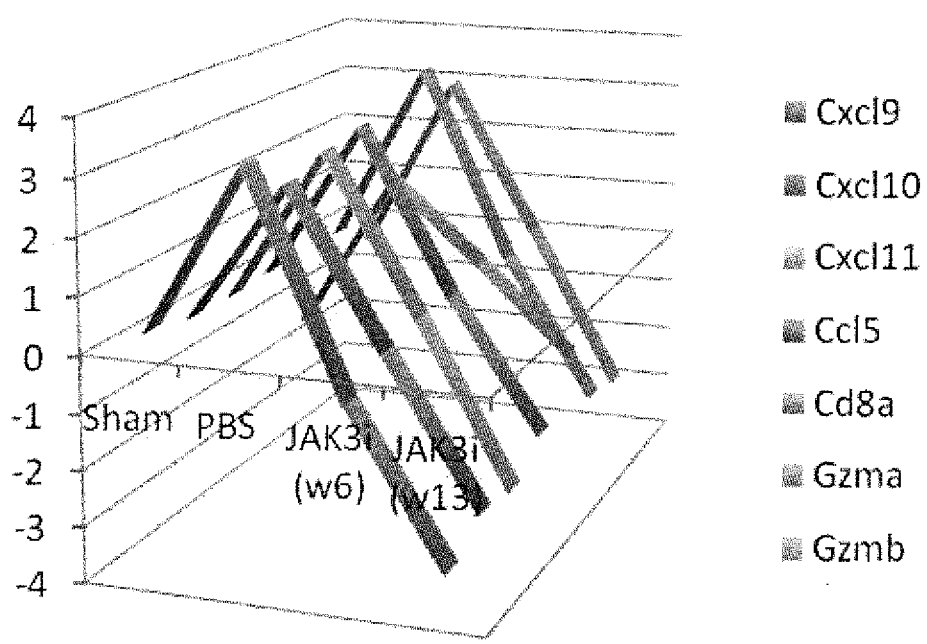
FIG. 35 is a ribbon diagram that shows C3H/HeJ graft recipients were treated with a JAK3 inhibitor (right panel), or PBS. RNA was extracted from skin harvested at weeks 6 (w6) and 13 (w13) following treatment and also from mice that had undergone sham surgery and subsequently interrogated by microarray analysis.
Figure 36:
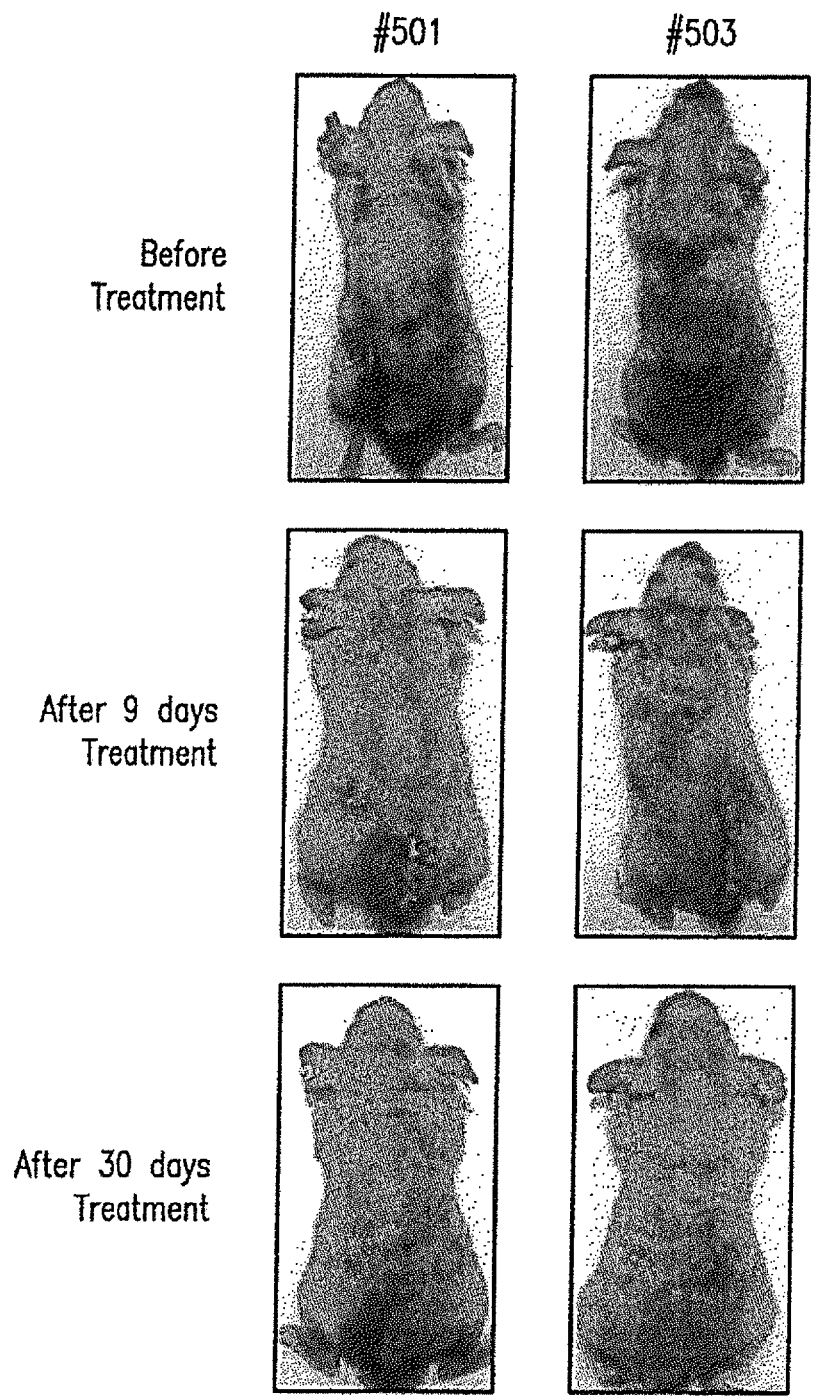
FIG. 36 shows photographs of mice before (top panel) and after topical treatment (9 days (middle panel) and 30 days (bottom panel)) with cream only.
Figure 37:
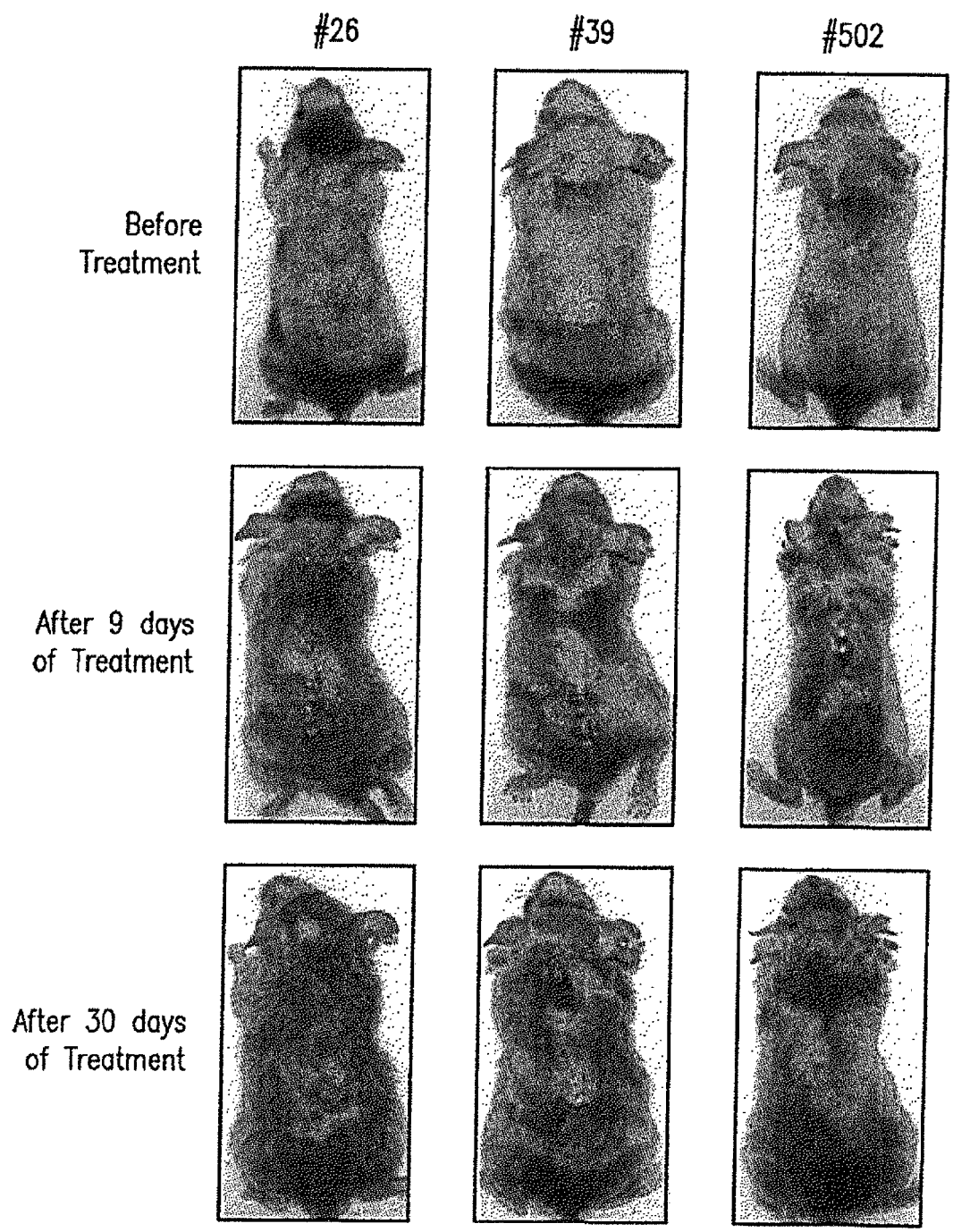
FIG. 37 shows photographs of mice before (top panel) and after topical treatment (9 days (middle panel) and 30 days (bottom panel)) with the Jak3 inhibitor, tofacitinib.
Figure 38:
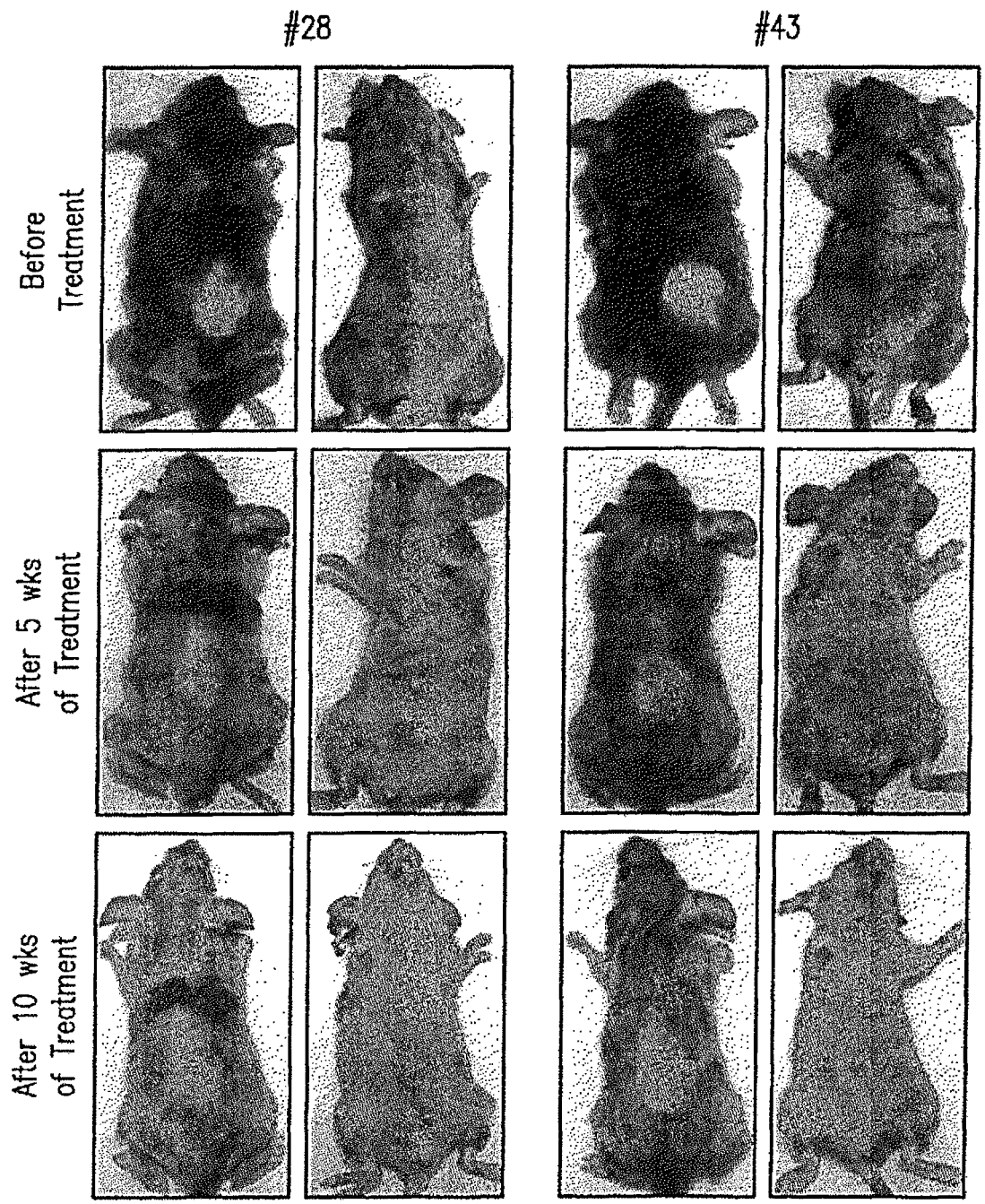
FIG. 38 shows photographs of mice before (top panel) and after a control infusion (5 weeks (middle panel) and 10 weeks (bottom panel)) without the Jak3 inhibitor, tofacitinib.
Figure 39:
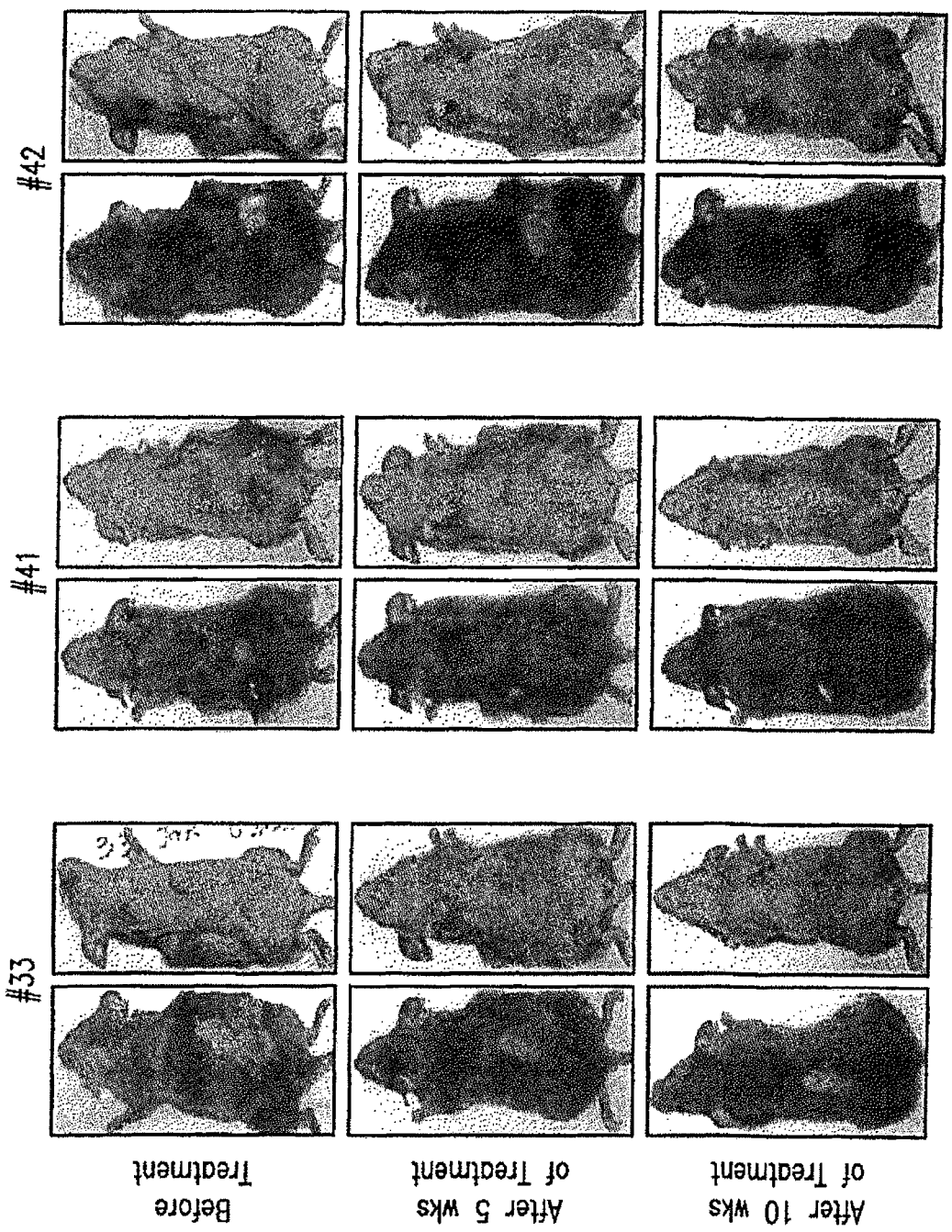
FIG. 39 shows photographs of mice before (top panel) and after a pump infusion (5 weeks (middle panel) and 10 weeks (bottom panel)) with the Jak3 inhibitor, tofacitinib.
Figure 40:
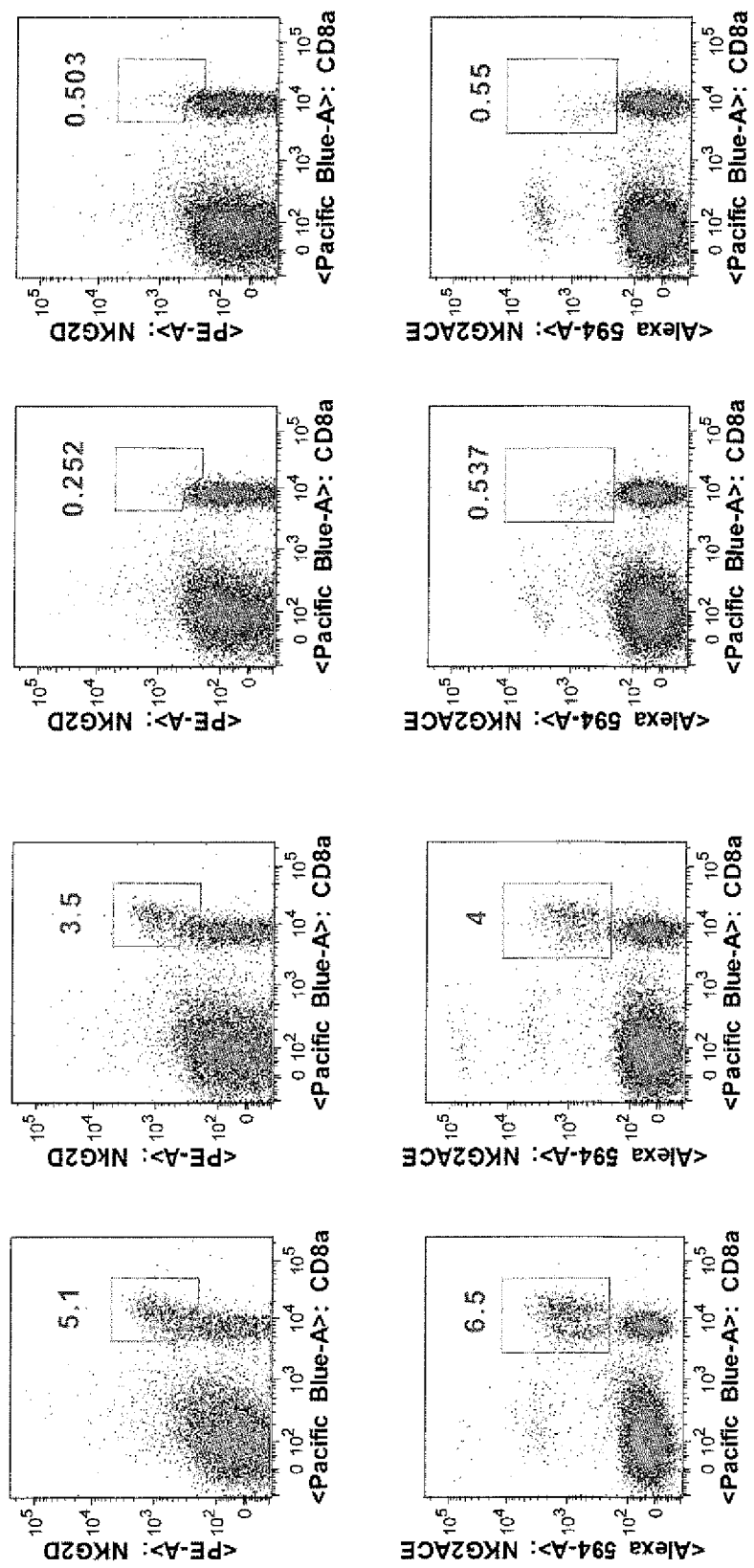
FIG. 40 shows treatment related elimination of dermal T cell infiltrates and inflammatory biomarkers by flow cytometry. The flow cytometry is of lymph node cells. The cells in the right upper quadrant are not observed in normal healthy mice and represent CD8+NKG2D+ effector T cells. CD8+NKG2D+ effector T cells are found in alopecic mice after skin grafting. Alopecic mice treated with the JAK3 inhibitor exhibit hair regrowth and their lymph nodes are devoid of these cells.
Figure 41:
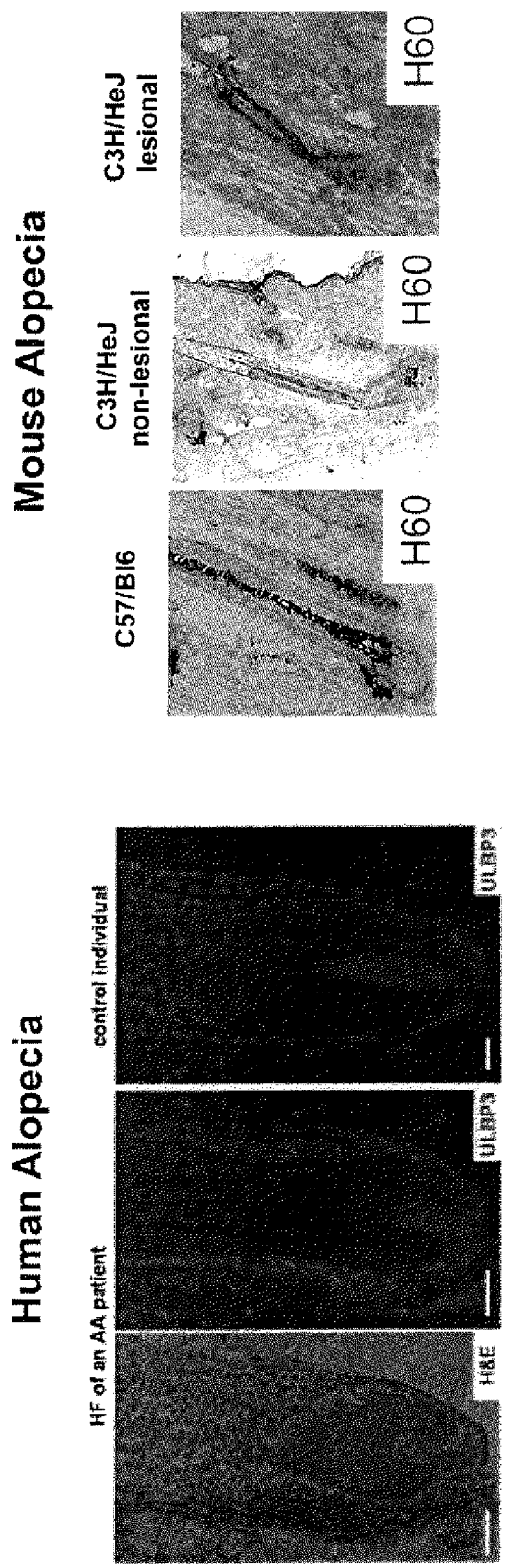
FIG. 41 shows that NKG2D "stress ligands" are upregulated in the hair follicle, and demonstrates the shared pathogenesis in human and mouse.
Figure 42:
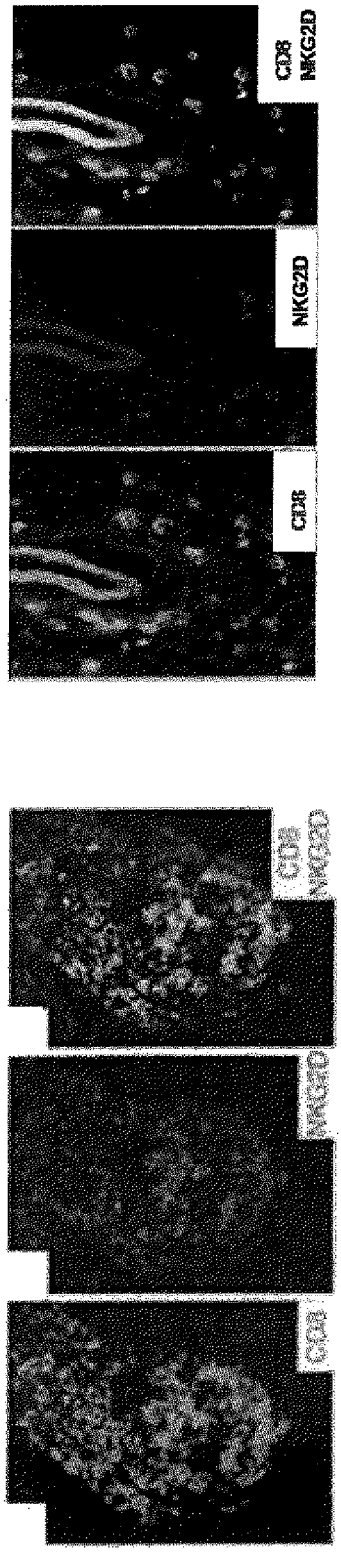
FIG. 42 is a photomicrograph of an immunostain showing that $CD8^+$ $NKG2D^+$ T cells infiltrate the hair follicle, and demonstrates the shared pathogenesis in human and mouse.
Figure 43:
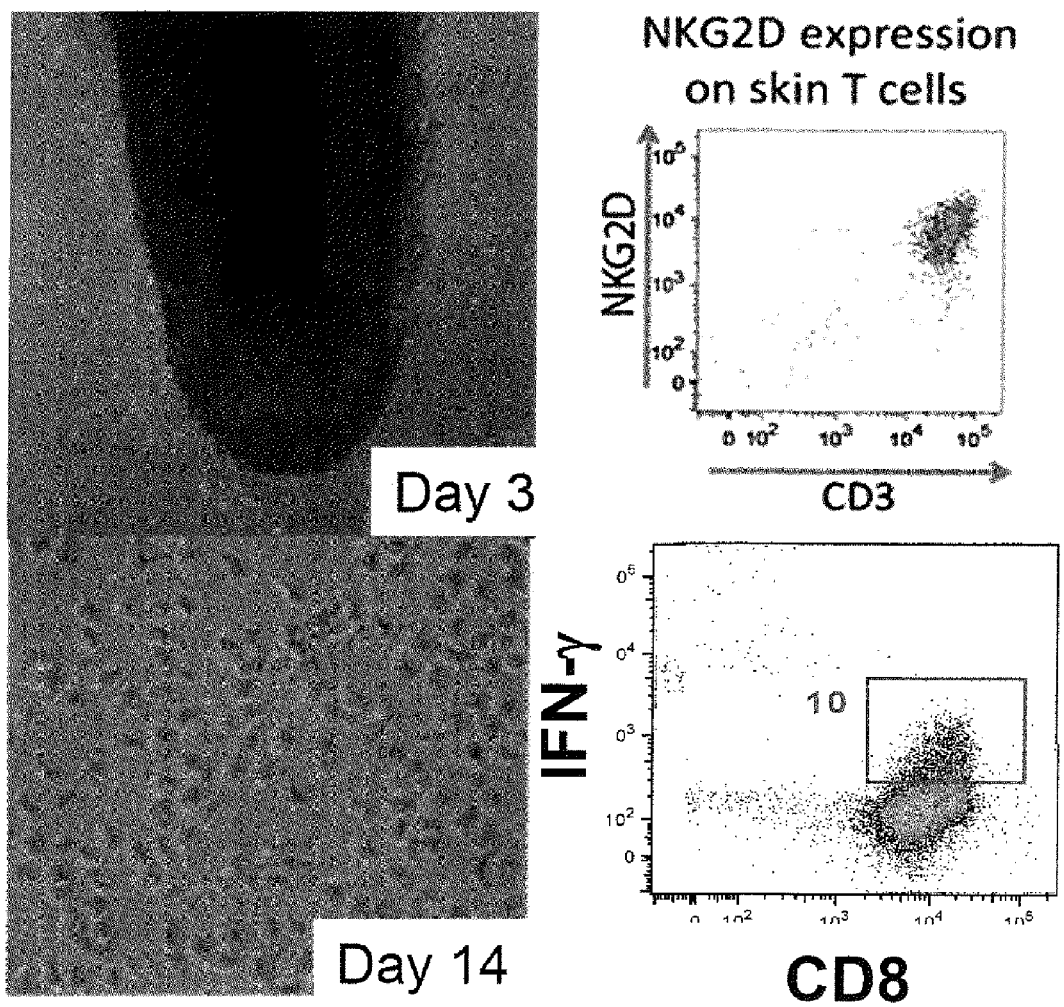
FIG. 43 shows flow cytometric analysis that shows that $NKG2D^+CD8^+$ T cells are the dominant infiltrating cells, and demonstrates the shared pathogenesis in human and mouse. (e.g., see Clark, et al., (2006) *J Invest Dermatol.* 126(5):1059-70, reporting a method for isolating T cell crawlouts from the skin).
Figure 44:
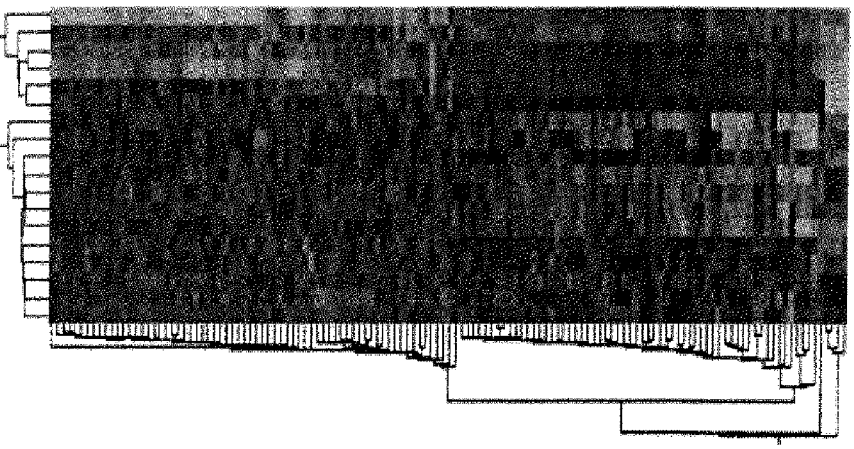
FIG. 44 shows that comparative transcriptomics reveals a shared IFN response signature, and demonstrates shared pathogenesis in human and mouse.
Figure 46:
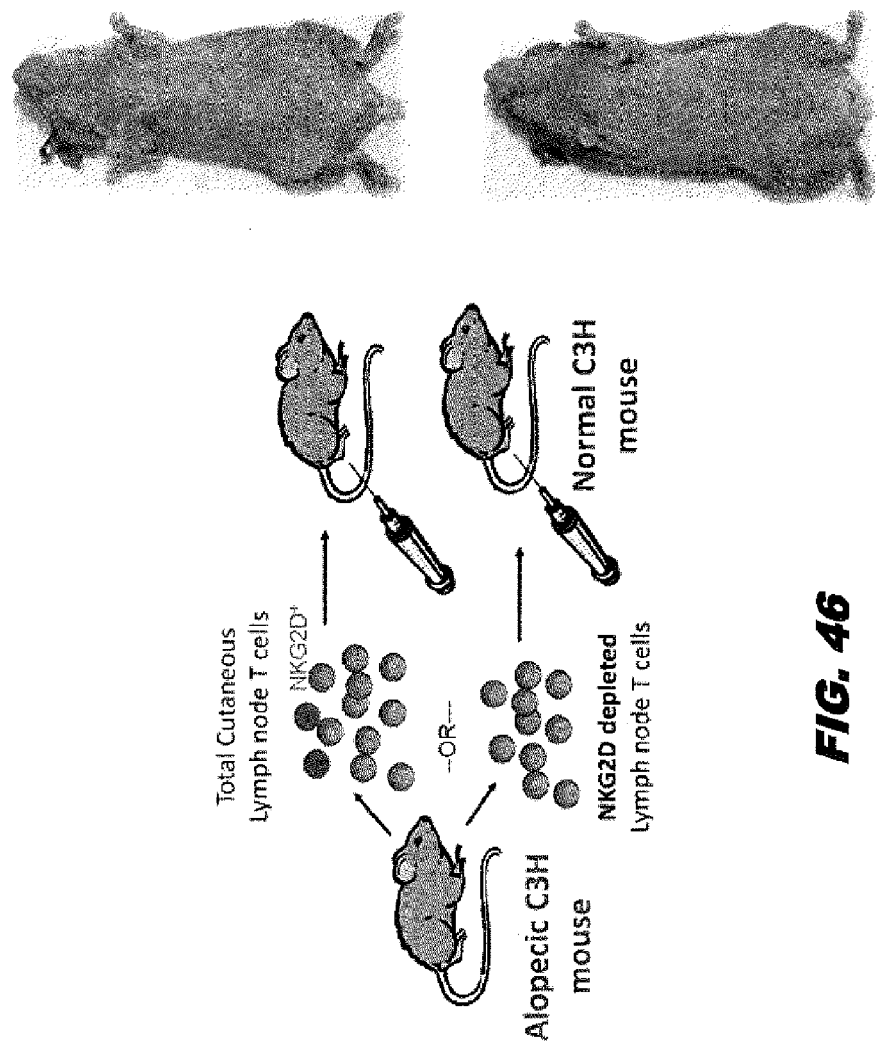
FIG. 46 shows that NK Type CD8 T cells are required for T Cell transfer of Alopecia Areata.
Figure 47:
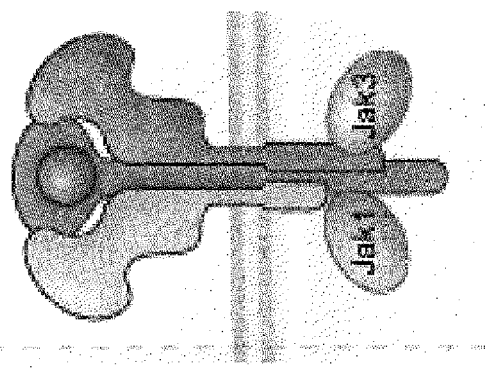
FIG. 47 shows pre-clinical studies using systemic JAK inhibitors in the C3H-HeJ mouse model of alopecia areata (for example, see O'Shea, *Immunity.* 2012 Apr. 20; 36(4): 542-50).
Figure 48:
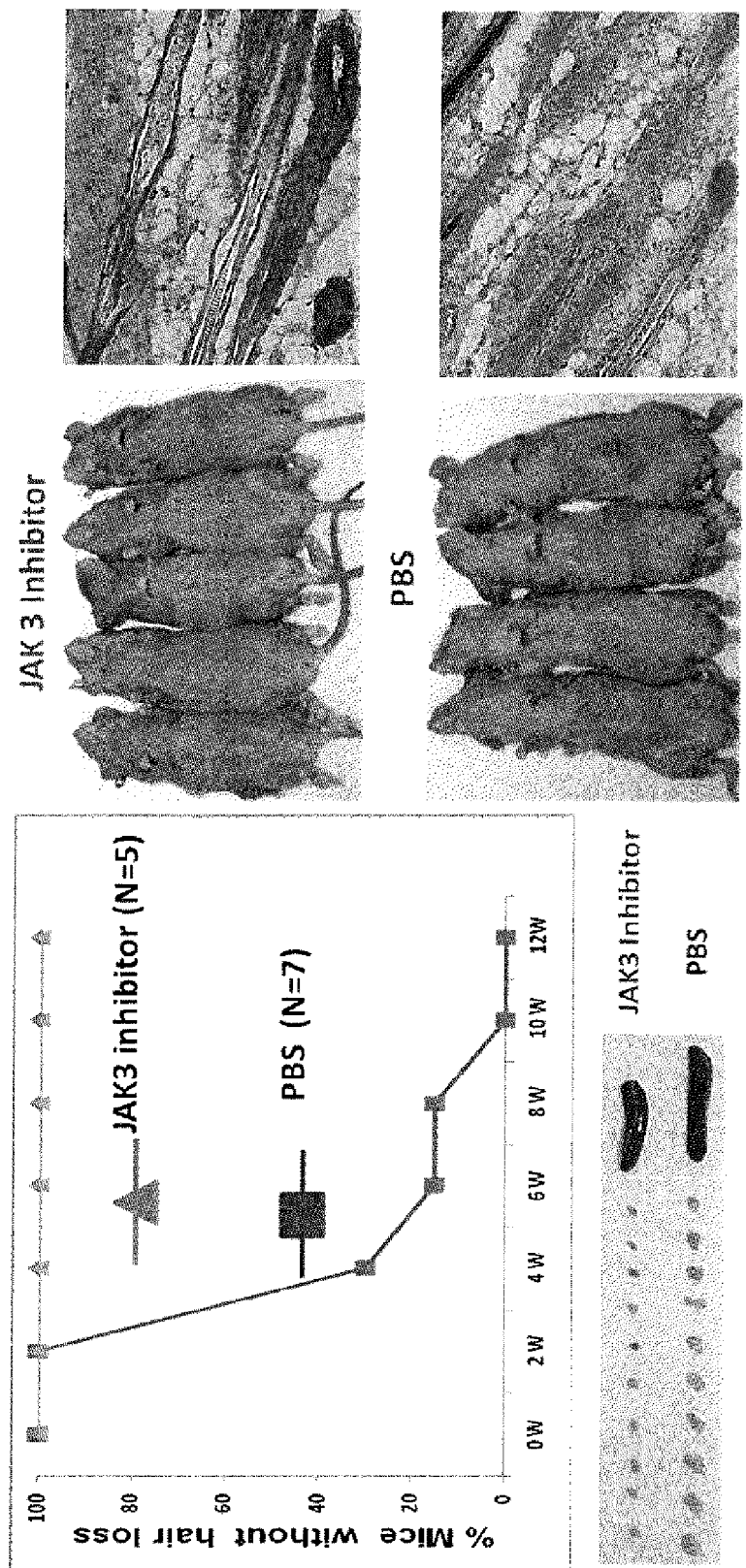
FIG. 48 shows the results of pre-clinical studies with systemic delivery of JAK3 inhibitor (tofacitinib), and tofacitinib treatment prevents Alopecia Areata.
Figure 49:
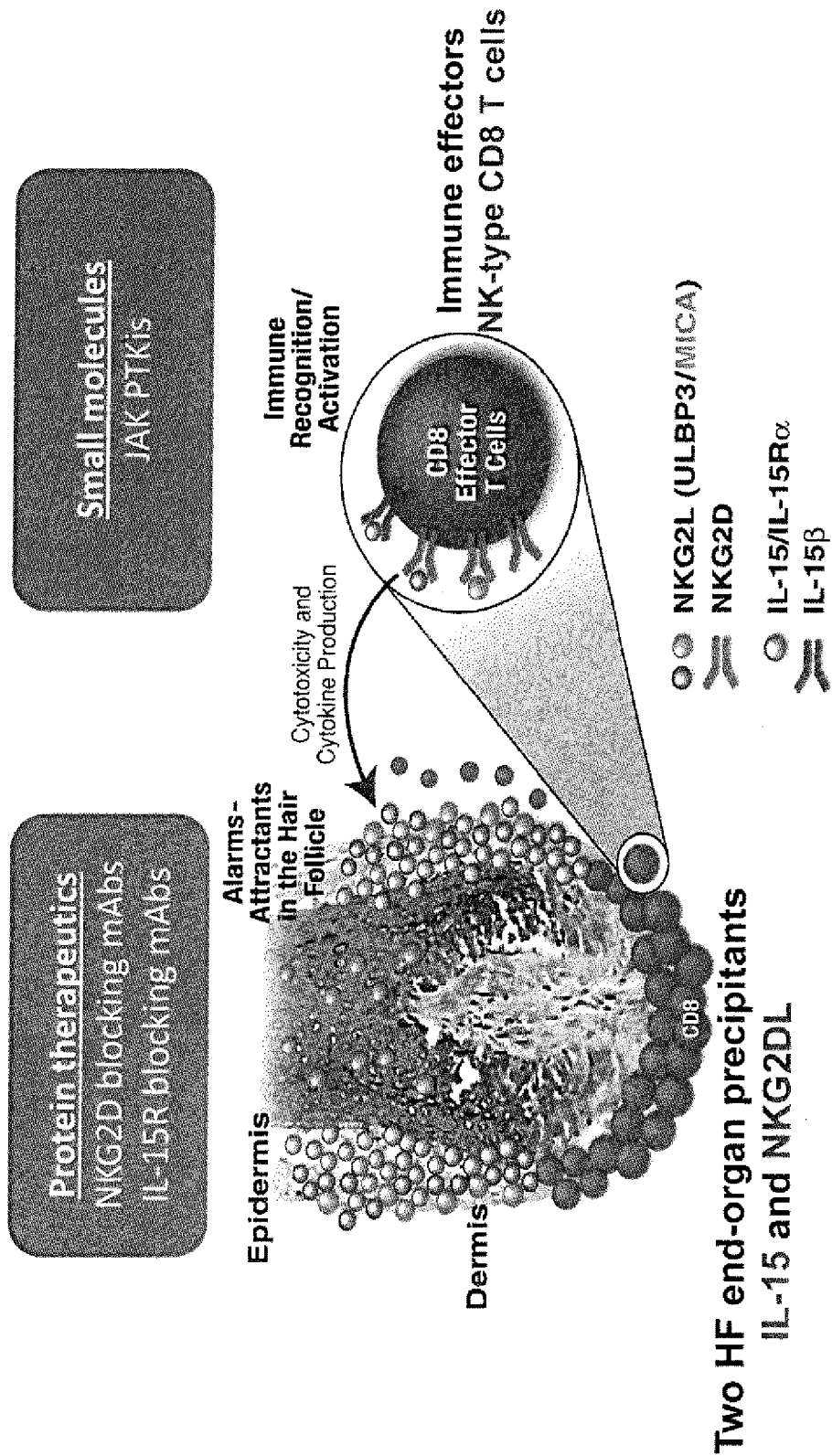
FIG. 49 is a diagram depicting different examples of targeted therapies for alopecia areata. These topical therapies can be used to reverse the established disease.
Figure 50:
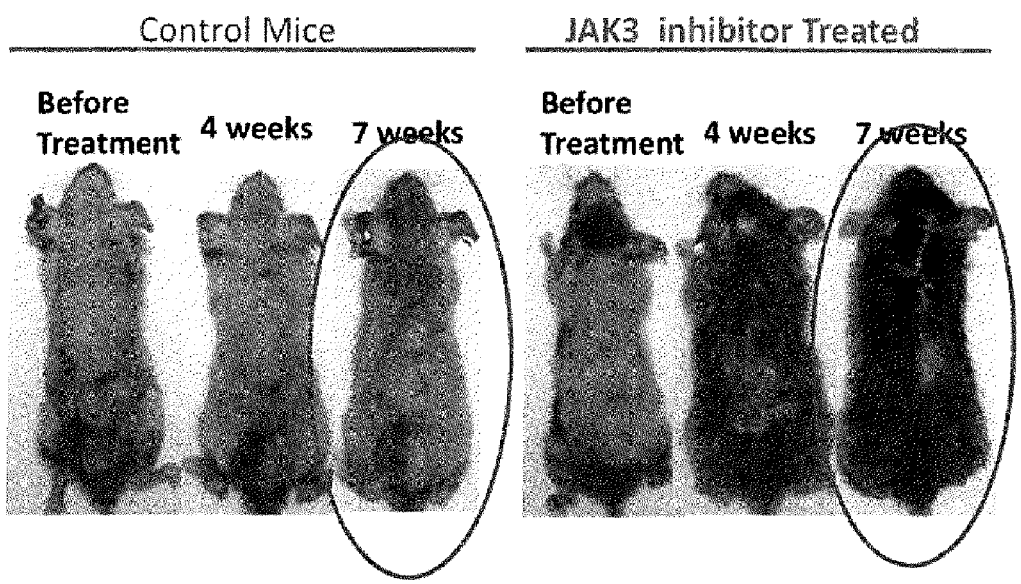
FIG. 50 shows pre-clinical studies with topical delivery of JAK3 inhibitor (tofacitinib). Topical treatment using JAK3 inhibitor results in reversal of long-standing AA (2-3 months duration). Before treatment, all mice had hair loss for 2-3 months. Control mice were applied with cream daily. Mice treated with the JAK3 inhibitor, Tofacitnib, were treated daily with a topical cream containing 0.5% Tofacitnib.
Figure 52:
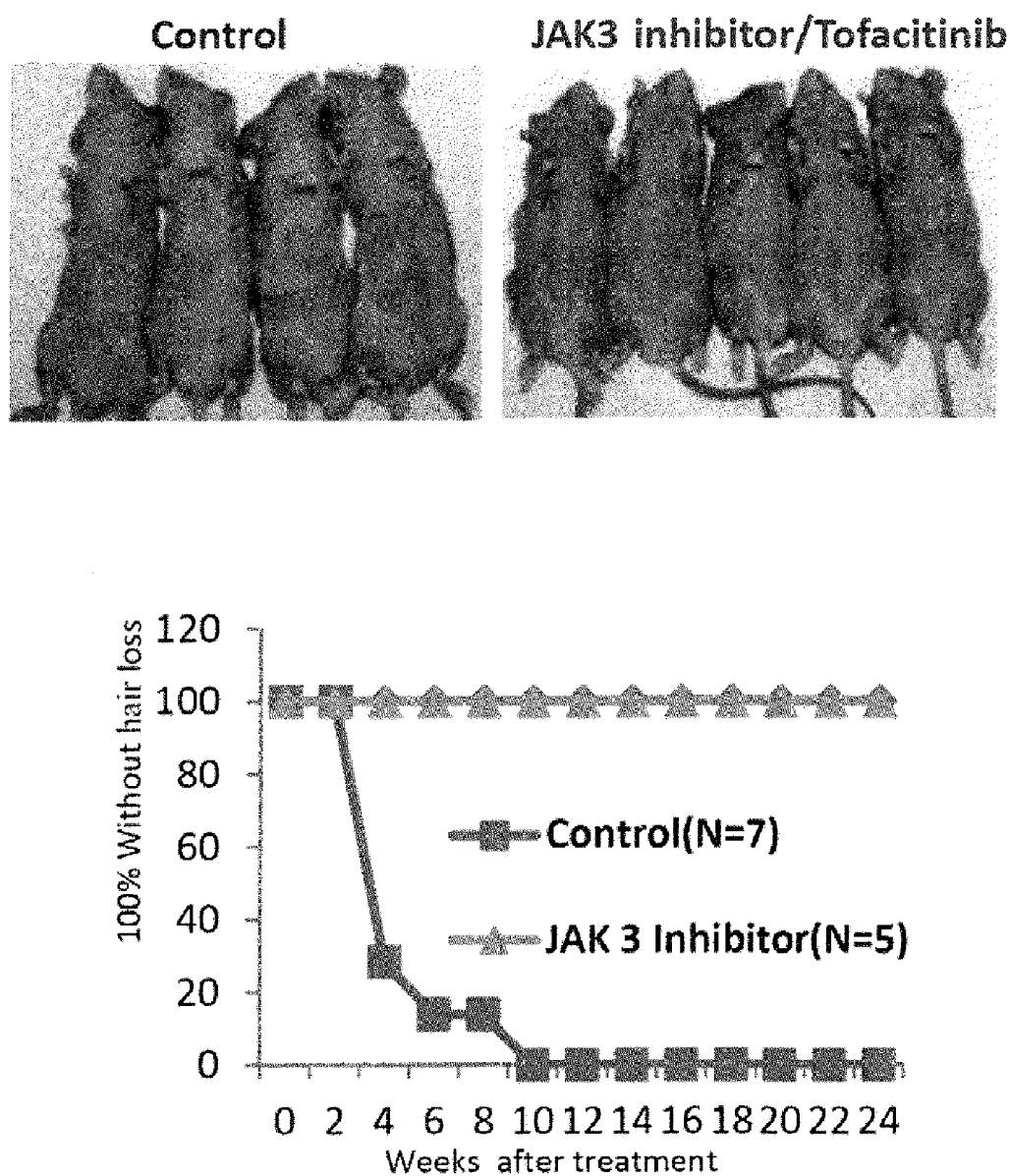
FIG. 52 shows the prevention of AA with systemic treatment with a JAK3 inhibitor given at the time of skin grafting. All reagents are started at time of graft (prevention). JAK3 inhibitor (CP690550) was delivered using Alzet osmotic mini-pumps (28-day pumps, Model 2004) implanted subcutaneously, 10 mg/kg/day or vehicle (PEG300).

The ribbon plots shown in FIG. 35 depict microarray data of normalized skin expression profiles of select genes from mice treated with 13 weeks of the JAK3 inhibitor CP690550 and PBS control. Briefly, after 13 weeks of treatment with the JAK3 inhibitor, skin was harvested and subjected to microarray analysis and compared with that of mice treated with PBS. The data show treatment-related elimination of the IFN-response chemokines and markers of CD8 cytotoxic effectors. Expression arrays from mouse and human will be integrated to compare expression profiles and eventually response to treatment.

Example 9

Systemic Treatment with JAK3i

"NK-type" CD8αβ+ T cells are massively expanded in alopecic skin and draining LNs, and are required for T cell mediated transfer implicating this cytotoxic cell subset as the likely pathogenic effectors.

IL-15 is a key cytokine responsible for inducing CD8 T effectors in vitro. Moreover, IL-15 is produced by intestinal epithelial cells and is a known precipitant of CD8 cytotoxicity in celiac disease.

Alopecia areata is marked by IL-15/IL-15Ra upregulation in the human and murine hair follicle and implicates this cytokine as an end-organ trigger of CD8-mediated autoreactivity in AA.

Systemic IL-15 blockade with a small molecule JAK3 PTKi effectively prevented alopecia areata, eliminating expansion of the pathogenic NK-type CD8 population and ablating the inflammatory signature in the skin. FIG. 53 shows reversal of established disease with topical therapies.

Example 10

Cellular Identity of Cytotoxic T Lymphocytes in Alopecia Areata Defines a Therapeutic Strategy Alopecia areata (AA) is a common autoimmune disease resulting in an immune attack on the hair follicle. Although T cells have been implicated in the disease process, the pathways underlying their activation had not been determined[2]. Prior to the GWAS study, the genetic basis of AA was largely undefined. Unexpectedly, a region of strong association was identified within the ULBP gene cluster on chromosome 6q25.1, encoding activating ligands of the natural killer cell receptor, NKG2D, which had never before been implicated in an autoimmune disease. Guided by the GWAS studies implicating NKG2D ligands (NKG2DL)[3], here 'NK-type' CD8+ T cells were identified as the dominant effectors, which are both necessary and sufficient for disease induction. Global transcriptional profiling of mouse and human AA skin revealed striking signatures indicative of a robust IFNγ response and the presence of a cytotoxic T cell infiltrate.

Using the graft model of C3H/HeJ mouse skin to transfer AA, disease prevention can be recapitulated when treating at the time of grafting, as well as reversal of established disease by allowing grafted mice to first lose their hair. Systemically-administered pharmacological inhibitors of the JAK3 protein tyrosine kinases eliminated the IFN-signature and prevented the development of AA, and topical administration reversed established disease. Notably, these effects were durable up to 3 months after cessation of therapy. These findings illustrate the power of GWAS studies in uncovering new disease mechanisms, which have rapidly translated into new therapeutic opportunities in AA.

AA is a T cell mediated autoimmune disease characterized by hair loss and, histologically, by infiltrating T cells surrounding the hair follicle bulb, the so-called "swarm of bees"[1, 2]. Previous studies have shown that transfer of total T cells (but not B cells or sera), can confer the disease in human xenograft models as well as the C3H/HeJ mouse model[4,5]. However, the identity of the specific pathogenic T cell subsets in either human or mouse AA has not yet been defined.

Guided by a previous GWAS study, which identified ULBP3/6 as the most highly significant non-HLA risk locus in AA (p=2×10$^{-20}$)[3], a focus has been centered on establishing NKG2DLs as potential "danger signals" in the disease process. Upregulation of ULBP3 has previously shown in human AA hair follicles, associated with a dense infiltrate of CD8+NKG2D+ T cells[3]. Here, the role of these cells in AA immunopathogenesis, as well as a target for potential therapeutic intervention, was investigated.

Figure 54A:
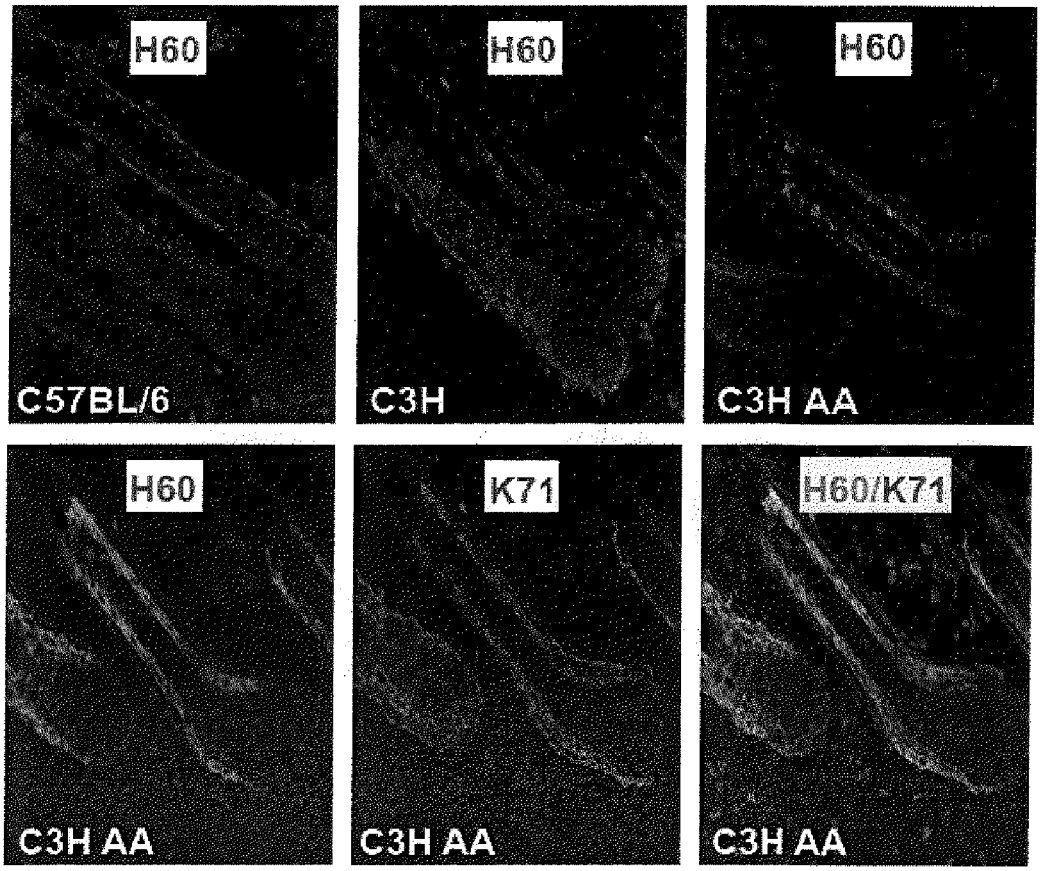
FIG. 54A shows the upregulation of NKG2DL in the hair follicle of C3H/HeJ alopecic mice. Immunofluorescence staining of NKG2D ligands (H60) in the hair follicle inner root sheath (marked by K71).
Figure 54B:
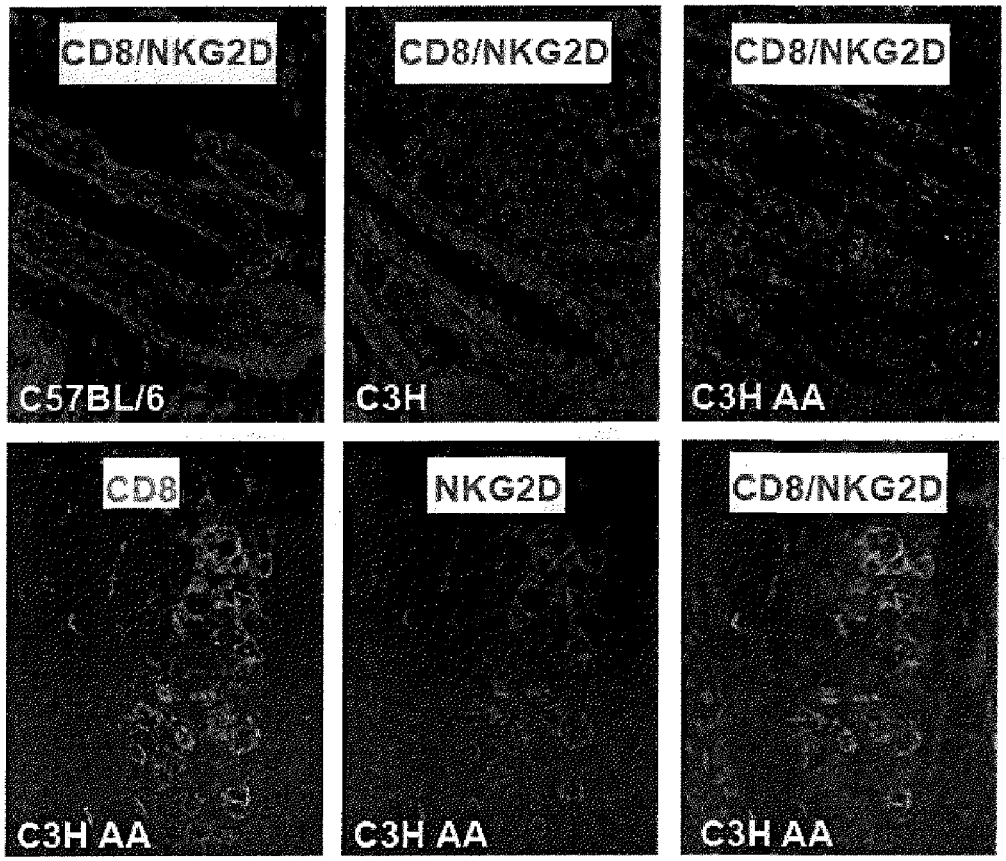
FIG. 54B shows the cellular phenotype and function of $CD8^+NKG2D^+$ cytotoxic T lymphocytes in AA mice. Immunofluorescence staining of $CD8^+NKG2D^+$ cells in hair follicles of C57BL/6, healthy C3H/HeJ and C3H/HeJ AA mice.
Figure 54C:
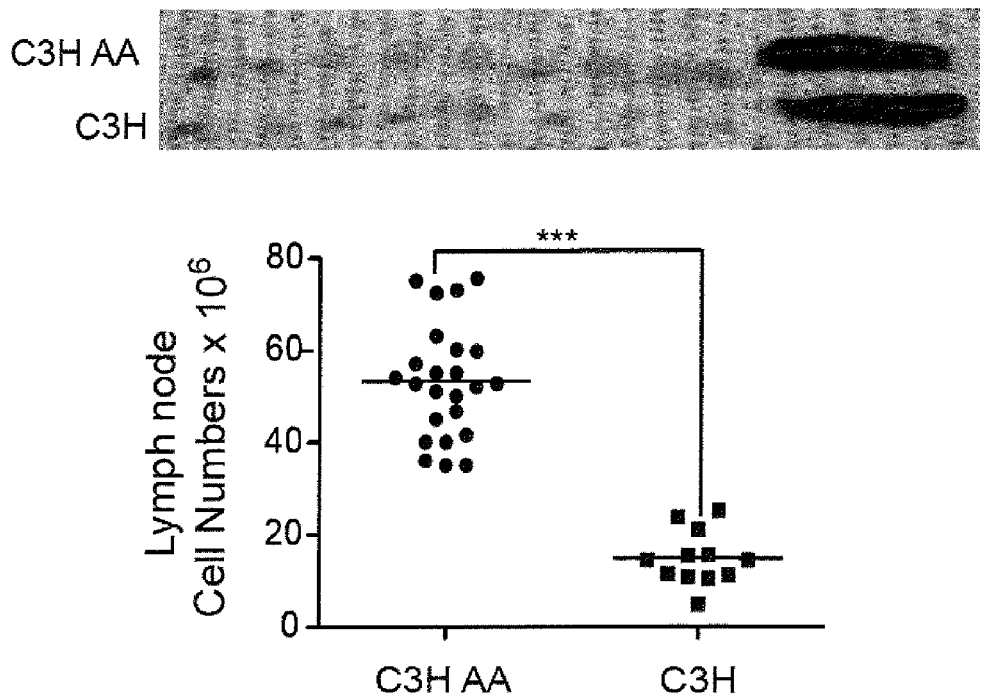
FIG. 54C shows the cellular phenotype and function of $CD8^+NKG2D^+$ cytotoxic T lymphocytes in AA mice. Striking cutaneous lymphadenopathy and cellularity in C3H/HeJ mice that developed AA.
Figure 54D:
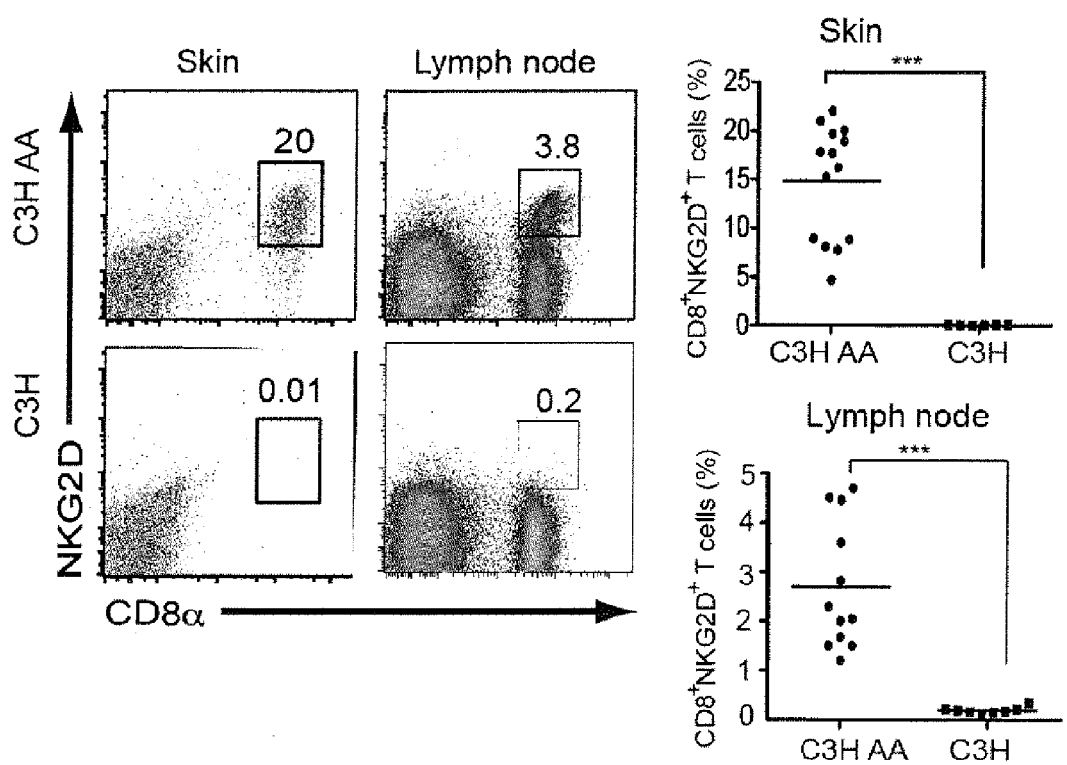
FIG. 54D shows the cellular phenotype and function of $CD8^+NKG2D^+$ cytotoxic T lymphocytes in AA mice. Plots show the frequency of $CD8^+NKG2D^+$ T cells from skin and skin-draining lymph nodes in alopecic mice vs. ungrafted mice.
Figure 58A:
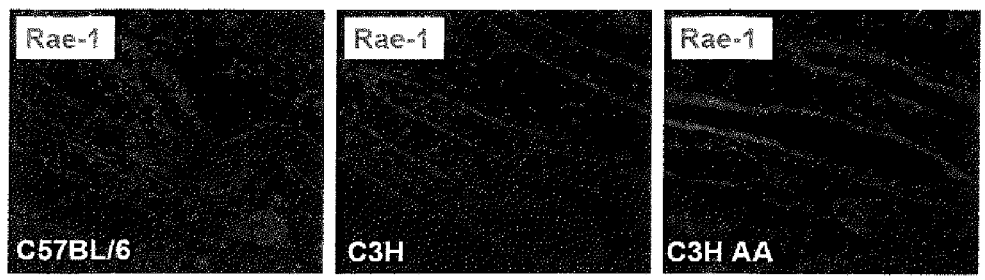
FIG. 58A shows that Rae-1 is upregulated in the AA HF. Immunostaining of lesional using a pan-Rae-1 antibody in C3H/HeJ alopecic mice, unaffected C3H/HeJ mice and C57B1.6 mice.
Figure 58B:
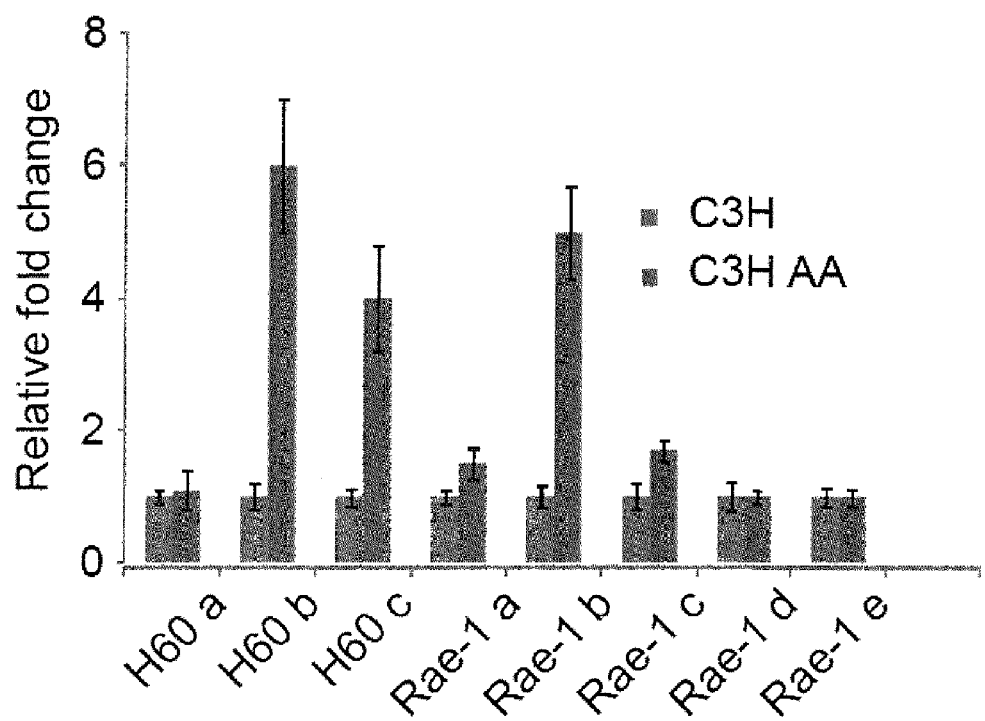
FIG. 58B shows that H60 and Rae-1 are overexpressed in AA. NKG2DL RNA expression in alopecic lesional skin from C3H/HeJ mice compared with non-lesional skin from unaffected C3H/HeJ mice. RT-PCR data from cDNA from 3 mice are shown and represented as relative fold-induction.
Figure 58C:
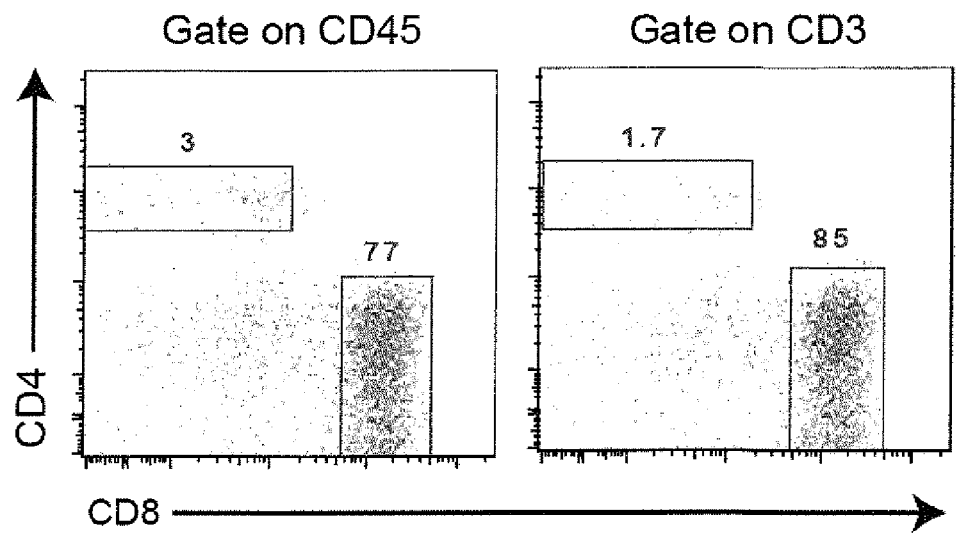
FIG. 58C shows that CD4 T cells are infrequent in AA lesional skin: Flow cytometric evaluation of lesional alopecic skin. Quantitation of CD4 and CD8 T cells as a percentage of total gated CD3+ or CD45+ cells.

To determine the mechanistic importance of these cells in pathogenesis, the C3H/HeJ mouse model of AA was used, in which spontaneous disease develops with ~15% incidence between 6 and 12 months of age[6], and the graft-transfer C3H model was used, in which grafts from affected animals can transfer disease to 100% of C3H/HeJ recipients in 8-12 weeks time[7]. Lesional skin biopsies revealed that CD8+NKG2D+ T cells infiltrate the epithelial layers of the hair follicle that overexpress the NKG2DLs H60 and Rae-1, analogous to the situation in human AA (FIG. 54A-B and FIG. 58A-13). Flow cytometric examination of the CD45+ leukocyte population in the skin identified a striking expansion of CD8+NKG2D+ T cells (FIG. 54D). Other cell types, including CD4+ T cells were present in much smaller numbers (FIG. 58C). C3H/HeJ mice exhibit striking cutaneous lymphadenopathy (FIG. 54C) with increased total cellularity and, as noted in the skin, a dramatic expansion of a CD8+NKG2D+ cell population not present in disease-free C3H/HeJ mice (FIG. 54C-D).

Figure 54E:
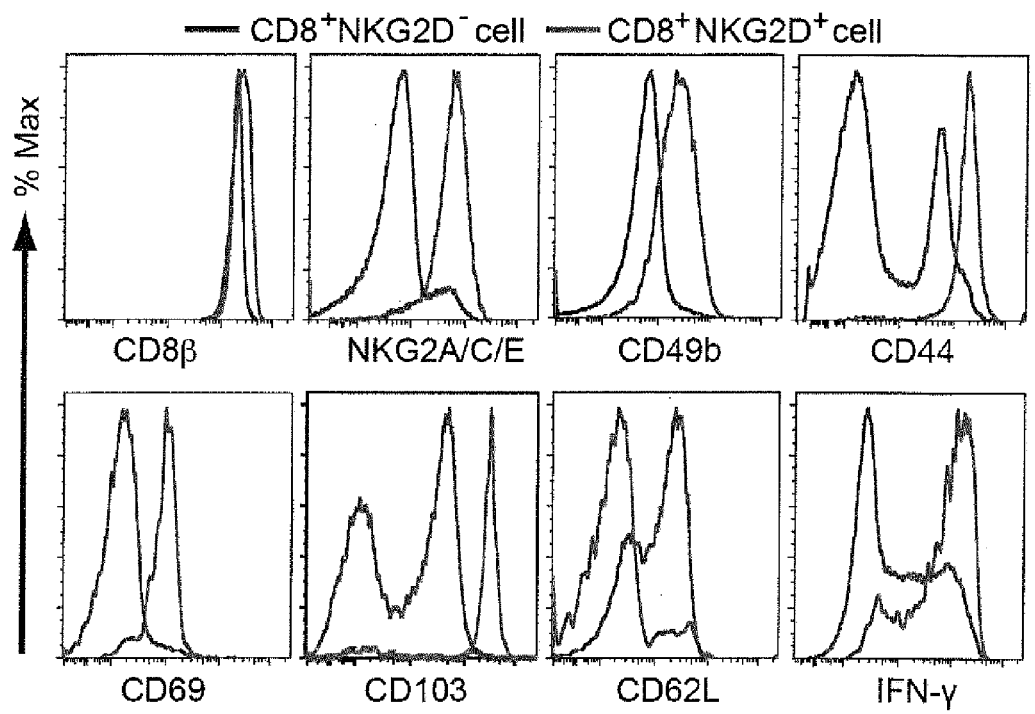
FIG. 54E shows the cellular phenotype and function of $CD8^+NKG2D^+$ cytotoxic T lymphocytes in AA mice. Plots shows the immunophenotype of $CD8^+NKG2D^+$ T cells in cutaneous lymph nodes in C3H/HeJ alopecic mice.
Figure 54F:
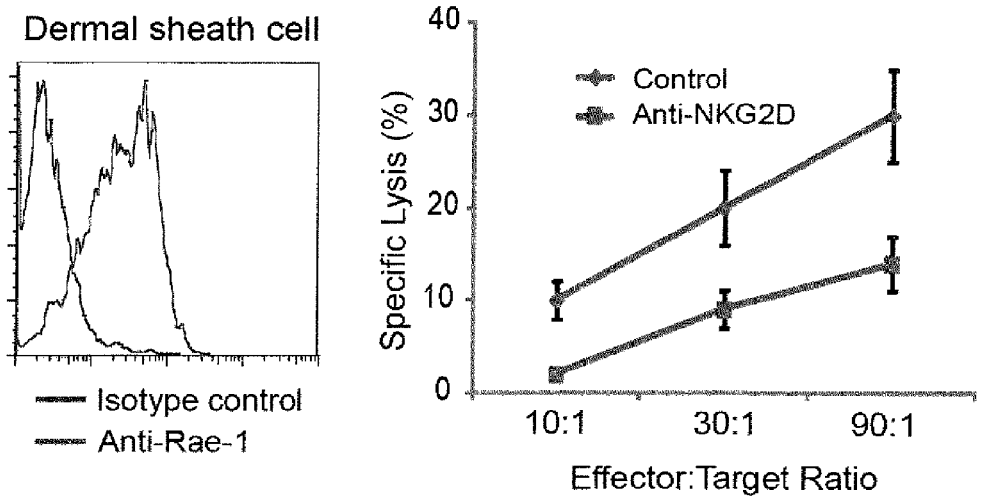
FIG. 54F shows the cellular phenotype and function of $CD8^+NKG2D^+$ cytotoxic T lymphocytes in AA mice. Graphs demonstrate that $CD8^+NKG2D^+$ T cells isolated from AA mice cutaneous LNs kill Rae-1 expressing dermal sheath cells grown from C3H/HeJ hair follicles in an NKG2D-dependent manner.
Figure 54G:
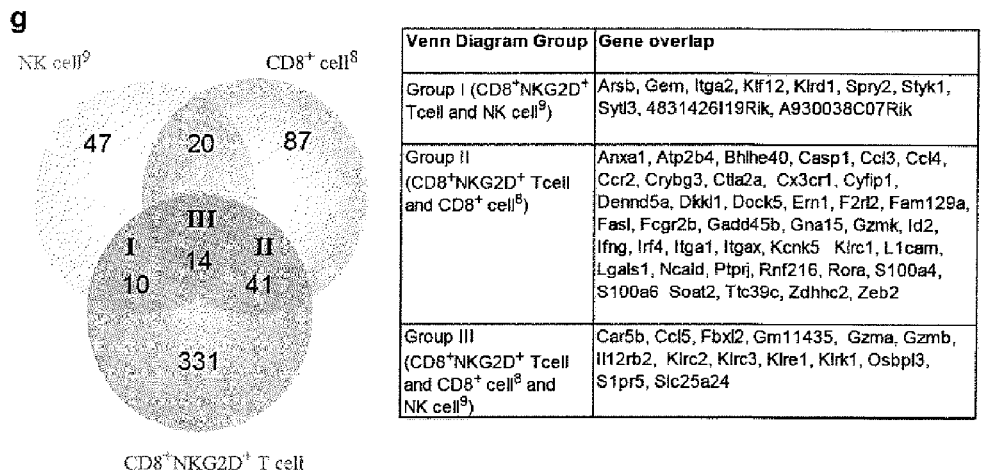
FIG. 54G shows the cellular phenotype and function of $CD8^+NKG2D^+$ cytotoxic T lymphocytes in AA mice. RNAseq was performed on CD8+NKG2D+ and CD8+NKG2D− T cells sort purified from AA cutaneous lymph nodes. Transcripts upregulated in CD8+NKG2D+ T cells were compared with CTL gene expression and NK cell gene expression in the literature[8,9], and overlapping gene signatures are displayed in this Venn Diagram.
Figure 58D:
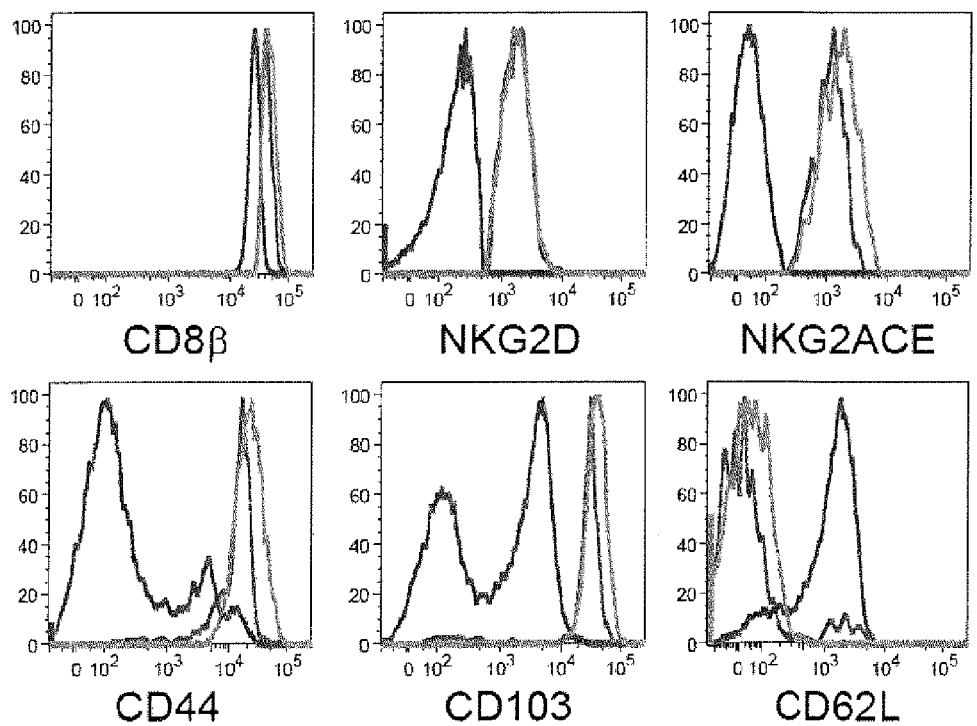
FIG. 58D shows that effector memory immunophenotype of CD8+NKG2D+T cells are similar in lesional skin and in the cutaneous draining lymph node. Gated CD8alpha+NKG2D+ T cells are displayed for CD8beta, NKG2D, NKG2A/C/E, CD44, CD103 and CD62L expression.
Figure 59:
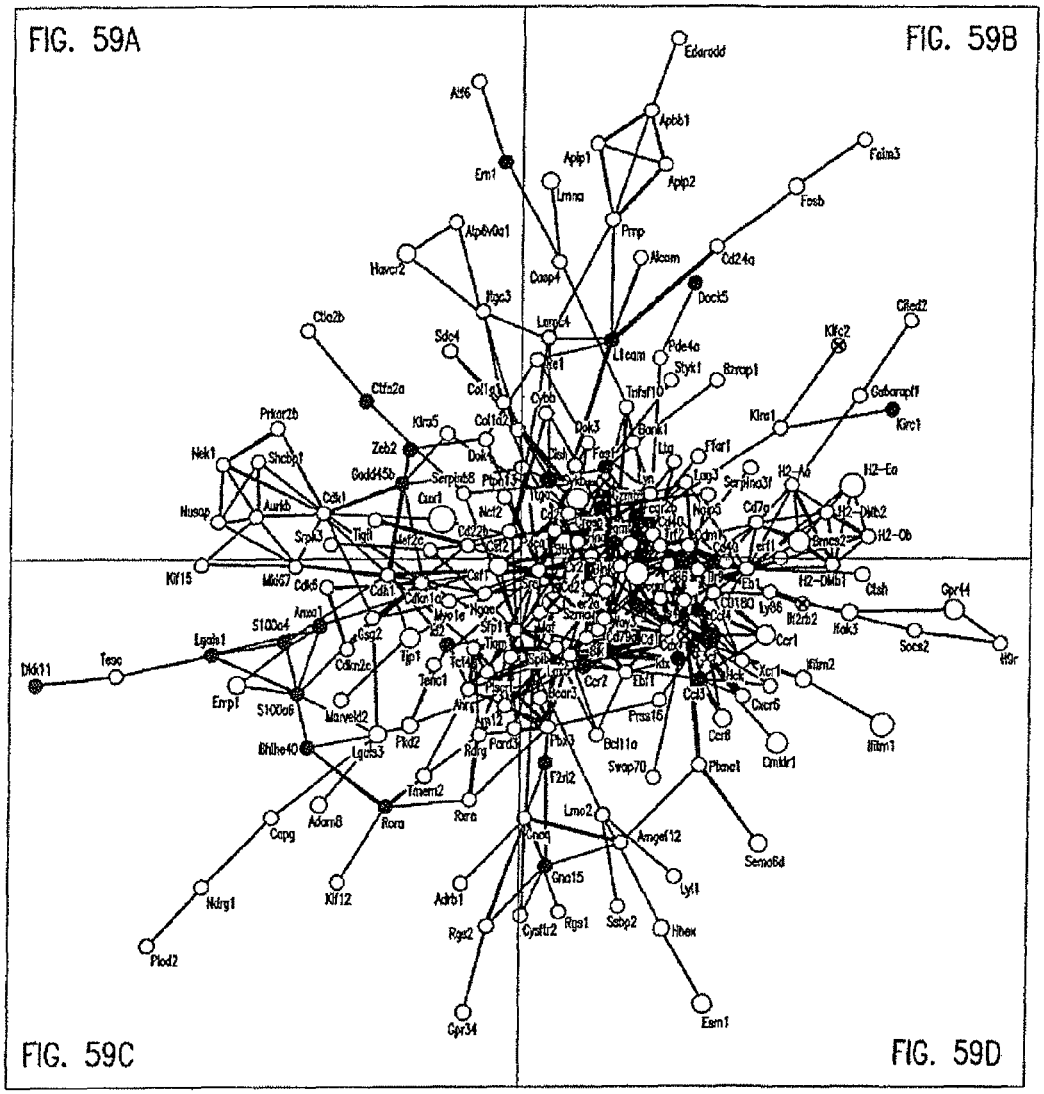
FIG. 59 is a network map of differentially expressed upregulated genes in CD3+ CD8+NKG2D+ LN cells vs. CD8+NKG2D− cells. String.db was used to create a biological interaction score matrix with the differentially expressed genes. The network map was created using cytoscape; only biological interactions >0.75 were used. Nodes represent genes, and edges represent biological interactions as derived from string.db. Node size is proportional to fold change, and edge width is proportional to biological interaction.
Figure 59A:
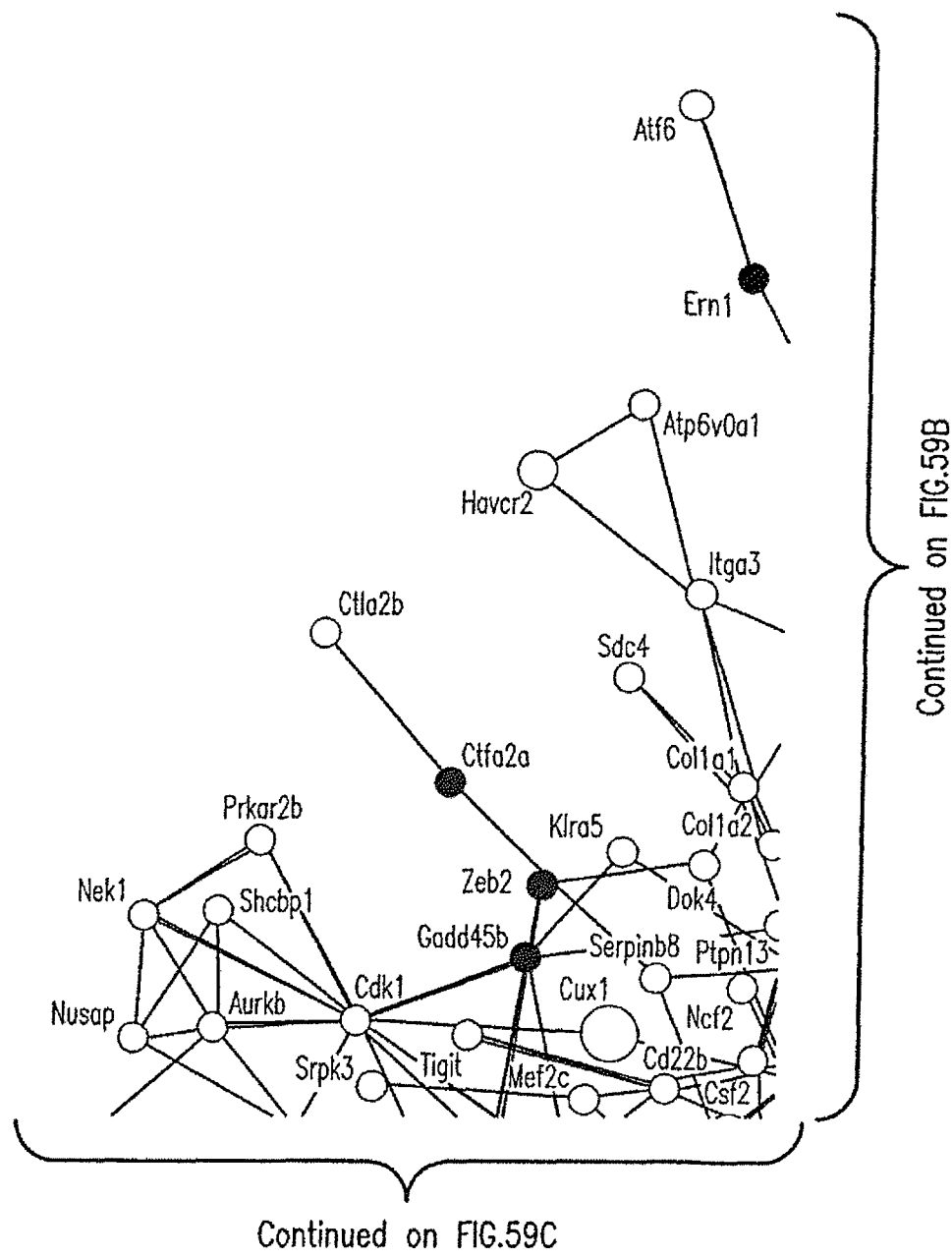
Figure 59B:
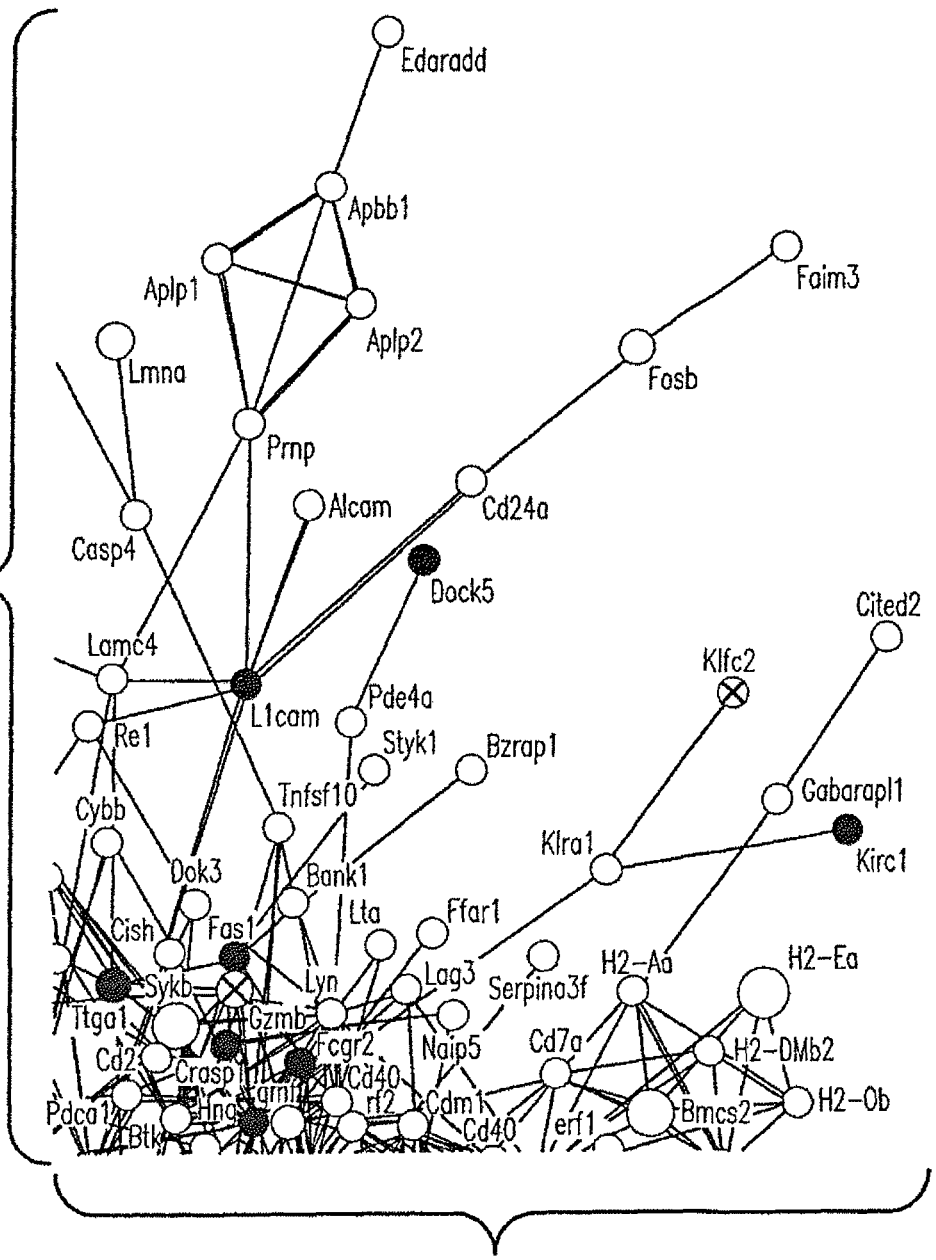
Figure 59C:
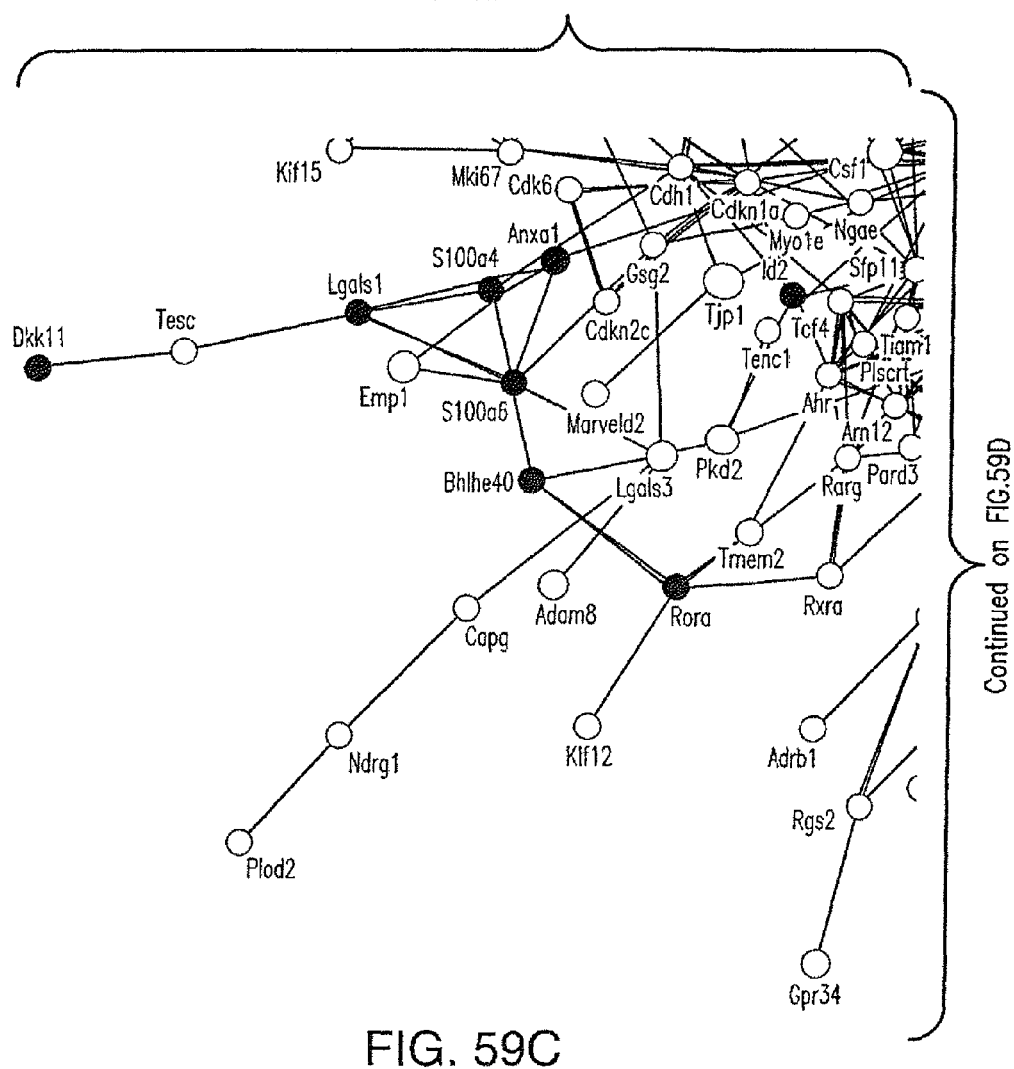
Figure 59D:
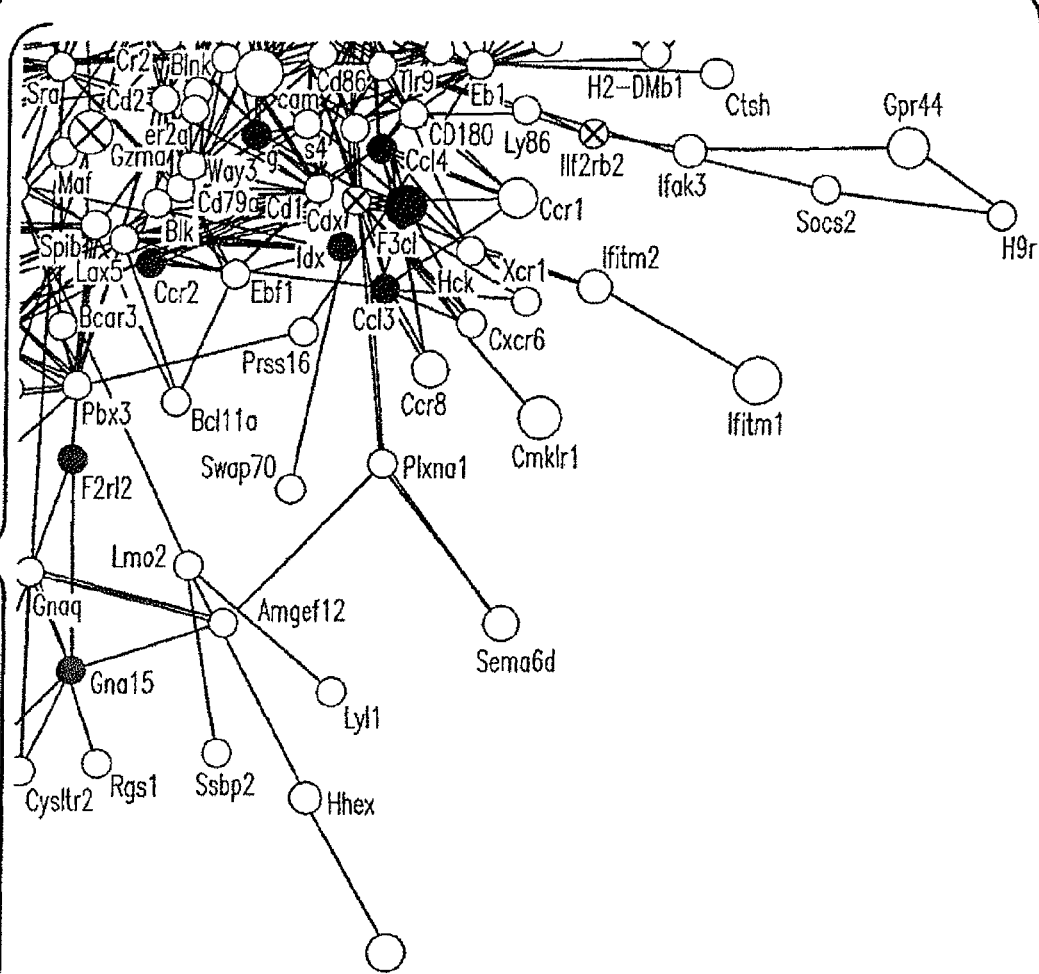
Figures 2, 59:
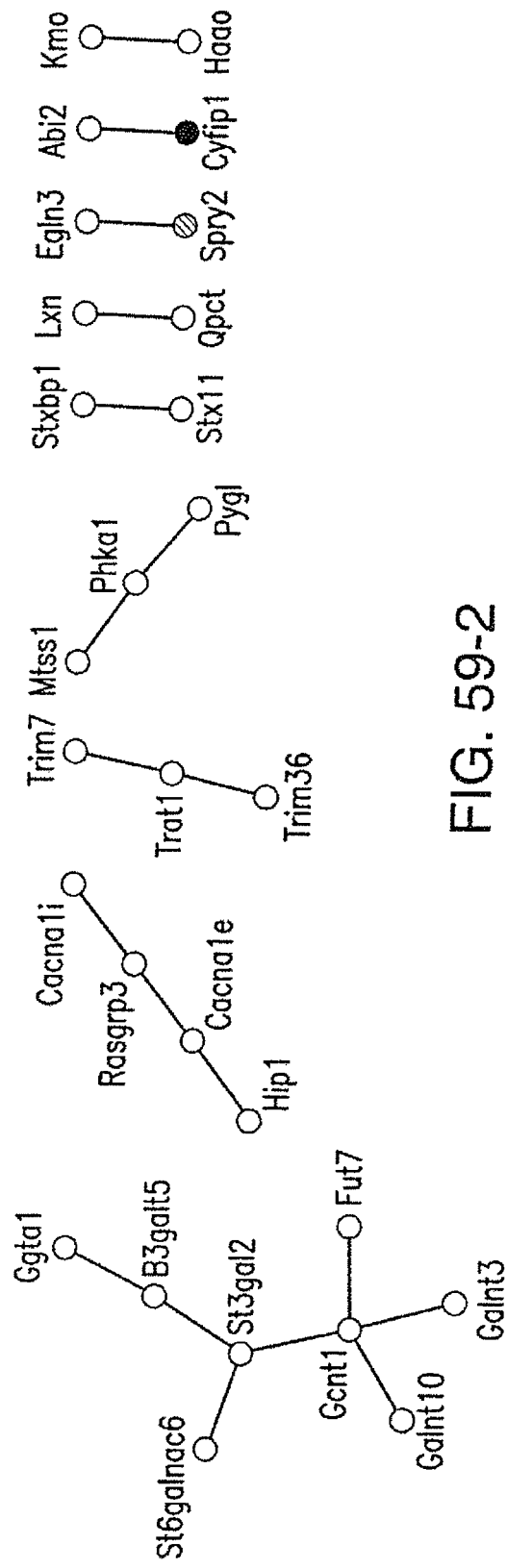

The immunophenotype of the skin-infiltrating CD8+ T cells were similar to the CD8+NKG2D+ population found in the cutaneous lymph nodes: CD8ab+ effector memory T cells (CD8$^{hi}$ CD44$^{hi}$ CD62L$^{low}$ CD103+) bearing several NK immunoreceptors, including CD49b and NKG2A/C/E (FIG. 54E and FIG. 58D). These 'NK-type' CD8+ T cells expressed high levels of IFNg and exhibited NKG2D-dependent cytotoxicity against ex vivo expanded syngeneic dermal sheath target cells (FIG. 54F). Gene expression analysis of the CD8+ NKG2D+ T cells isolated from alopecic C3H/HeJ lymph node cells using RNAseq demonstrated a transcriptional profile characteristic of effector CTLs as defined by the ImmGen Consortium[8-10] and identified several additional "NK-specific" transcripts (FIG. 54G and FIG. 59 and Table 14).

TABLE 14

Differentially expressed genes in CD8+NKG2D+ memory T cells vs. CD8+NKG2D− memory T cells isolated from cutaneous lymph nodes obtained from alopecic mice. RNAseq was performed on cRNA made isolated from flow-sorted cells (BD influx) from total cutaneous lymph nodes from two alopecic mice.

| GeneSymbol | FC |
| --- | --- |
| Gstm5 | 63.99 |
| Gzma | 52.13 |
| Ifitm1 | 44.81 |
| Cx3cr1 | 38.24 |
| Sprn | 35.20 |
| Tjp1 | 34.76 |
| Igsf5 | 32.13 |
| Tmem132e | 31.71 |
| Cmklr1 | 30.91 |
| 5430421N21Rik | 30.69 |
| Csf1 | 29.97 |
| Olfr60 | 28.79 |
| 4933431E20Rik | 27.87 |
| Metrnl | 27.44 |
| Epdr1 | 27.43 |
| Cd244 | 27.22 |
| Gpr141 | 26.45 |
| Ccr1 | 26.17 |
| Ccr8 | 23.75 |
| Pkd2 | 23.23 |
| Lgals3 | 22.66 |
| Esm1 | 21.59 |
| AI661453 | 20.69 |
| Sema6d | 20.58 |
| Tmem171 | 19.13 |
| Havcr2 | 19.01 |
| Rasgrf1 | 18.32 |
| Bean1 | 18.25 |
| Adora3 | 18.13 |
| Itga1 | 17.66 |
| Tpbg | 17.52 |
| Gzmb | 17.43 |
| Gpr44 | 17.11 |
| Stk32c | 16.81 |
| Bear1 | 16.72 |
| Cntn1 | 16.70 |
| Slc38a8 | 16.65 |
| Adam8 | 16.15 |
| Usp44 | 15.85 |
| B4galnt4 | 15.50 |
| Cass4 | 14.94 |
| Galr3 | 14.86 |
| Ifitm2 | 14.77 |
| Rimbp2 | 14.64 |

TABLE 14-continued

Differentially expressed genes in CD8+NKG2D+ memory T cells vs. CD8⁺NKG2D⁻ memory T cells isolated from cutaneous lymph nodes obtained from alopecic mice. RNAseq was performed on cRNA made isolated from flow-sorted cells (BD influx) from total cutaneous lymph nodes from two alopecic mice.

| GeneSymbol | FC |
|---|---|
| Fam171b | 14.02 |
| Srxn1 | 13.78 |
| Ptger3 | 13.70 |
| Lrat | 13.48 |
| Trpm6 | 13.43 |
| Lrrn2 | 13.17 |
| Arnt2 | 13.06 |
| Yap1 | 13.04 |
| Anxa1 | 12.85 |
| Gpr56 | 12.78 |
| Rai14 | 12.59 |
| Lypd3 | 12.52 |
| Gm5127 | 12.23 |
| Pdgfrb | 12.13 |
| Tktl1 | 11.87 |
| Gzmk | 11.63 |
| Olfr525 | 11.61 |
| AF529169 | 11.57 |
| Olfr523 | 11.48 |
| Selm | 11.43 |
| Sema4c | 11.25 |
| Ppp2r2c | 11.12 |
| Fxyd4 | 11.09 |
| Sept5 | 11.07 |
| Styk1 | 11.04 |
| Myadm | 10.84 |
| Wnt10b | 10.65 |
| Fgl2 | 10.61 |
| Gcnt4 | 10.59 |
| Emp1 | 10.44 |
| Cacng8 | 10.38 |
| Car5b | 10.36 |
| Ly6g5b | 10.32 |
| Lmna | 10.16 |
| Vipr2 | 10.08 |
| Ptpn5 | 10.01 |
| Plekhf1 | 9.92 |
| Il13 | 9.87 |
| 9430020K01Rik | 9.87 |
| Klrk1 | 9.80 |
| Itsn1 | 9.65 |
| Ret | 9.62 |
| Itgae | 9.58 |
| Col6a3 | 9.50 |
| Nbea | 9.41 |
| Rab27b | 9.41 |
| Clec12a | 9.36 |
| Mgat3 | 9.35 |
| Zfp57 | 9.30 |
| S100a4 | 9.27 |
| AI414108 | 9.22 |
| Trim58 | 9.19 |
| Irak3 | 9.18 |
| Gpr34 | 9.15 |
| Mt3 | 9.04 |
| AW555464 | 9.02 |
| Perp | 9.00 |
| Ace | 8.94 |
| Tmeff2 | 8.92 |
| Slc35f3 | 8.81 |
| Dyrk3 | 8.81 |
| Nxnl2 | 8.72 |
| Galnt3 | 8.67 |
| Cish | 8.63 |
| Vash1 | 8.58 |
| Klre1 | 8.58 |
| Dmrt2 | 8.56 |
| Wnt9a | 8.48 |
| Dusp14 | 8.43 |
| Dmd | 8.29 |
| St6galnac2 | 8.26 |
| Slc41a2 | 8.26 |
| Cdh1 | 8.22 |
| Tead1 | 8.09 |
| Msc | 8.05 |
| Ttc39c | 8.01 |
| Slc27a6 | 7.94 |
| Hlx | 7.85 |
| Mid2 | 7.73 |
| Plod2 | 7.70 |
| Prkcc | 7.68 |
| Ptgs1 | 7.63 |
| 6430571L13Rik | 7.60 |
| Specc1 | 7.55 |
| Prss16 | 7.53 |
| Fam129b | 7.49 |
| Spns3 | 7.49 |
| Lonrf3 | 7.45 |
| Fat4 | 7.41 |
| Nphs2 | 7.39 |
| Cpd | 7.34 |
| Cdkn2a | 7.26 |
| Il17rd | 7.14 |
| Nebl | 7.12 |
| Src | 7.10 |
| Scn1b | 7.07 |
| Sccpdh | 7.04 |
| Igsf9b | 7.03 |
| Crispld2 | 7.02 |
| Plscr4 | 7.01 |
| Tmigd1 | 6.96 |
| Camk2n1 | 6.95 |
| Trat1 | 6.87 |
| Mtap6 | 6.85 |
| Qpct | 6.85 |
| Thsd7b | 6.82 |
| Tceal3 | 6.76 |
| Nlrp12 | 6.75 |
| 2010002N04Rik | 6.70 |
| Lat2 | 6.68 |
| Susd2 | 6.61 |
| Ptprj | 6.61 |
| P2ry14 | 6.56 |
| Csgalnact1 | 6.55 |
| Klri2 | 6.54 |
| 1700001C19Rik | 6.48 |
| Spp1 | 6.43 |
| Hlf | 6.41 |
| Gpx8 | 6.39 |
| a | 6.37 |
| Rtn4r | 6.31 |
| Lamc1 | 6.25 |
| Kndc1 | 6.23 |
| Slc22a15 | 6.19 |
| Id2 | 6.15 |
| Tnfsf13b | 6.14 |
| Elovl4 | 6.13 |
| 5830411N06Rik | 6.04 |
| Plxnd1 | 6.00 |
| Vstm2a | 5.98 |
| Rora | 5.96 |
| Il2 | 5.93 |
| Klrc1 | 5.92 |
| Tesc | 5.86 |
| Cd40lg | 5.84 |
| Glis2 | 5.84 |
| Mt1 | 5.83 |
| Mdfic | 5.82 |
| P2ry2 | 5.73 |
| Hpse | 5.72 |
| Ttc16 | 5.70 |
| Kitl | 5.66 |
| Arhgef25 | 5.65 |
| Foxf2 | 5.62 |

TABLE 14-continued

Differentially expressed genes in CD8+NKG2D+ memory T cells vs. CD8+NKG2D− memory T cells isolated from cutaneous lymph nodes obtained from alopecic mice. RNAseq was performed on cRNA made isolated from flow-sorted cells (BD influx) from total cutaneous lymph nodes from two alopecic mice.

| GeneSymbol | FC |
| --- | --- |
| Kir3dl2 | 5.56 |
| Unc79 | 5.52 |
| Aim1l | 5.47 |
| Rgag4 | 5.44 |
| Pygl | 5.41 |
| Efcab6 | 5.39 |
| Htra3 | 5.39 |
| Card10 | 5.39 |
| Nek6 | 5.38 |
| 6720401G13Rik | 5.36 |
| Fam131b | 5.36 |
| Grb14 | 5.34 |
| Pde1c | 5.33 |
| Pld1 | 5.31 |
| Gipc2 | 5.30 |
| 8430427H17Rik | 5.30 |
| Gabarapl1 | 5.29 |
| Olfr527 | 5.28 |
| Tenc1 | 5.27 |
| Snx7 | 5.27 |
| Rgs8 | 5.25 |
| Slc16a7 | 5.24 |
| Alcam | 5.23 |
| Tmbim1 | 5.23 |
| Nefl | 5.22 |
| Pdcd1 | 5.21 |
| 2810030E01Rik | 5.21 |
| Abhd3 | 5.19 |
| Clnk | 5.18 |
| Nlrp1b | 5.14 |
| Cav2 | 5.13 |
| Aff2 | 5.12 |
| Kbtbd13 | 5.10 |
| Ppap2a | 5.07 |
| Gm14718 | 5.06 |
| Pde4a | 5.03 |
| Cnga2 | 4.95 |
| Acvrl1 | 4.92 |
| Mapkapk3 | 4.92 |
| Ccr2 | 4.87 |
| Hip1 | 4.84 |
| Pkp2 | 4.83 |
| Nap1l3 | 4.83 |
| Gorasp1 | 4.82 |
| Zfp651 | 4.82 |
| Hmga2-ps1 | 4.81 |
| Tceal1 | 4.81 |
| Atp1a2 | 4.81 |
| 2200002K05Rik | 4.81 |
| Mmp2 | 4.77 |
| Ankrd35 | 4.77 |
| Klrc2 | 4.77 |
| Ptgfrn | 4.74 |
| Ildr1 | 4.66 |
| Ptpn3 | 4.64 |
| 5031425F14Rik | 4.62 |
| 2510009E07Rik | 4.58 |
| Emilin2 | 4.58 |
| 2900026A02Rik | 4.57 |
| Cd101 | 4.54 |
| 9030425E11Rik | 4.52 |
| 1500009L16Rik | 4.50 |
| Cdh17 | 4.48 |
| Clec5a | 4.48 |
| Dnahc9 | 4.47 |
| Gpr25 | 4.45 |
| Ifng | 4.44 |
| Socs2 | 4.42 |
| Pard3 | 4.42 |
| Nhsl2 | 4.41 |
| Layn | 4.40 |
| Csf2 | 4.35 |
| Crybb3 | 4.30 |
| Cxcr6 | 4.30 |
| Zeb2 | 4.27 |
| Prkar2b | 4.27 |
| Fam70a | 4.26 |
| Gdpd5 | 4.23 |
| Gm8773 | 4.22 |
| Fbn1 | 4.20 |
| Itgax | 4.20 |
| Rbpj | 4.17 |
| Cxcl13 | 4.15 |
| Tmem2 | 4.14 |
| Tmem205 | 4.14 |
| Klrc3 | 4.13 |
| Gcnt1 | 4.13 |
| Zc3h12c | 4.12 |
| Mir1199 | 4.09 |
| Ermn | 4.08 |
| Agap1 | 4.07 |
| 1810033B17Rik | 4.07 |
| Klf8 | 4.06 |
| 4831426I19Rik | 4.06 |
| Ninl | 4.06 |
| Fbxo44 | 4.04 |
| Rab39b | 4.03 |
| Tspan2 | 4.02 |
| Adrb1 | 4.00 |
| Spns2 | 3.98 |
| Osbpl3 | 3.97 |
| Rapsn | 3.96 |
| Dhrs9 | 3.94 |
| Mboat2 | 3.90 |
| Pparg | 3.90 |
| Clip4 | 3.89 |
| Apol9a | 3.88 |
| Marveld2 | 3.86 |
| Capn5 | 3.86 |
| Ranbp17 | 3.86 |
| Ncam1 | 3.85 |
| Ctnnd2 | 3.85 |
| Slc25a24 | 3.85 |
| Palm | 3.84 |
| Fcer1g | 3.79 |
| Gzmc | 3.78 |
| Prdm1 | 3.78 |
| Scn8a | 3.75 |
| Fkbp9 | 3.72 |
| Gstt1 | 3.71 |
| Adssl1 | 3.71 |
| Prrg4 | 3.71 |
| Kir3dl1 | 3.70 |
| Ssbp2 | 3.67 |
| Swap70 | 3.67 |
| Trp73 | 3.67 |
| Il12rb2 | 3.66 |
| Phka1 | 3.66 |
| Xcr1 | 3.65 |
| Stau2 | 3.64 |
| 9130019P16Rik | 3.63 |
| Clec7a | 3.63 |
| 6430531B16Rik | 3.63 |
| Marco | 3.62 |
| Sulf2 | 3.61 |
| Reep1 | 3.61 |
| Anxa4 | 3.61 |
| Procr | 3.60 |
| Slc40a1 | 3.60 |
| Tnfrsf8 | 3.59 |
| Matk | 3.56 |
| Cysltr2 | 3.56 |
| Smtn | 3.55 |
| Rasl11b | 3.54 |

TABLE 14-continued

Differentially expressed genes in CD8+NKG2D+ memory T cells vs. CD8⁺NKG2D⁻ memory T cells isolated from cutaneous lymph nodes obtained from alopecic mice. RNAseq was performed on cRNA made isolated from flow-sorted cells (BD influx) from total cutaneous lymph nodes from two alopecic mice.

| GeneSymbol | FC |
| --- | --- |
| Amph | 3.52 |
| Cysltr1 | 3.52 |
| Klri1 | 3.52 |
| B4galt2 | 3.51 |
| Mlf1 | 3.49 |
| B4galt4 | 3.49 |
| Slc4a11 | 3.47 |
| Htra1 | 3.47 |
| Ebf1 | 3.44 |
| Mpp2 | 3.44 |
| Ica1 | 3.44 |
| Tigit | 3.43 |
| Lzts1 | 3.43 |
| Epha3 | 3.43 |
| Mrgpre | 3.43 |
| Vdr | 3.42 |
| Npnt | 3.41 |
| D630039A03Rik | 3.40 |
| Rapgef3 | 3.37 |
| Cnksr1 | 3.37 |
| Napsa | 3.37 |
| E030011O05Rik | 3.37 |
| 1700019E19Rik | 3.37 |
| Ncald | 3.37 |
| Ccl8 | 3.36 |
| Dhrs3 | 3.36 |
| Ppap2b | 3.36 |
| Gas2l1 | 3.36 |
| St3gal2 | 3.35 |
| Phactr2 | 3.34 |
| Rasd1 | 3.34 |
| Mafa | 3.33 |
| Olfr433 | 3.33 |
| L1cam | 3.31 |
| Pik3r6 | 3.31 |
| C1qa | 3.31 |
| Fgd1 | 3.30 |
| Gm17745 | 3.30 |
| Apol9b | 3.30 |
| Cmtm7 | 3.29 |
| Bicd1 | 3.29 |
| Rgs2 | 3.29 |
| Nos1ap | 3.29 |
| Bcl2a1d | 3.29 |
| Eif4e3 | 3.28 |
| Sgtb | 3.28 |
| Fut7 | 3.28 |
| Kif19a | 3.27 |
| Mtmr7 | 3.27 |
| Fam114a1 | 3.27 |
| Sdc4 | 3.27 |
| Farp1 | 3.26 |
| Fbxl21 | 3.25 |
| Ccrl2 | 3.25 |
| H1fx | 3.24 |
| Eif2c4 | 3.24 |
| Ube2l6 | 3.23 |
| Gpr68 | 3.23 |
| 4930544D05Rik | 3.23 |
| Hrh4 | 3.22 |
| Ryr1 | 3.22 |
| 9030418K01Rik | 3.22 |
| Acot11 | 3.22 |
| Pon3 | 3.22 |
| Serpine2 | 3.20 |
| Ly6a | 3.20 |
| Lrrn3 | 3.19 |
| B3galt5 | 3.19 |
| Ankrd29 | 3.19 |
| Ccl1 | 3.19 |
| Serpina3f | 3.19 |
| St14 | 3.15 |
| Dscam | 3.14 |
| Fam129a | 3.14 |
| Med12l | 3.14 |
| 1300014I06Rik | 3.13 |
| Rnf216 | 3.13 |
| St3gal5 | 3.13 |
| Slc35e4 | 3.12 |
| Rab3il1 | 3.12 |
| Tmem176a | 3.12 |
| Syngr3 | 3.12 |
| Il9r | 3.12 |
| Lrrk2 | 3.11 |
| Zfp532 | 3.11 |
| Ache | 3.10 |
| Wipf3 | 3.09 |
| Cdkn1a | 3.09 |
| Ccdc136 | 3.08 |
| Epn2 | 3.07 |
| Fam167a | 3.07 |
| Syp | 3.07 |
| Spry2 | 3.06 |
| Tiam1 | 3.06 |
| Gnaq | 3.05 |
| Armcx6 | 3.05 |
| Raph1 | 3.05 |
| F730043M19Rik | 3.05 |
| Lag3 | 3.05 |
| Wscd1 | 3.04 |
| Dkkl1 | 3.04 |
| Zfp839 | 3.04 |
| Armcx1 | 3.03 |
| Zkscan16 | 3.03 |
| 1700009P17Rik | 3.02 |
| Nkd1 | 3.01 |
| Cdkn2b | 3.01 |
| Igfbp6 | 3.01 |
| Dlg2 | 3.01 |
| Plscr1 | 3.00 |
| Cacna1i | 3.00 |
| Ckm | 3.00 |
| Kcnmb4 | 3.00 |
| Arhgap8 | 2.99 |
| Gspt2 | 2.99 |
| Foxd2 | 2.98 |
| Vat1l | 2.98 |
| Bfsp2 | 2.98 |
| Prrt2 | 2.98 |
| Wbscr17 | 2.98 |
| Car13 | 2.98 |
| Muc20 | 2.97 |
| Bzrap1 | 2.96 |
| Frem2 | 2.96 |
| Fcer2a | 2.96 |
| Chn2 | 2.95 |
| Blk | 2.95 |
| Kcnk5 | 2.95 |
| Mpzl1 | 2.95 |
| Aplp1 | 2.95 |
| Tlr4 | 2.95 |
| H2-DMb2 | 2.95 |
| Lyn | 2.94 |
| Meis2 | 2.94 |
| Camk1 | 2.93 |
| Pacsin3 | 2.93 |
| Tub | 2.93 |
| Cebpd | 2.93 |
| Gm5111 | 2.92 |
| Fasl | 2.92 |
| Lpcat2 | 2.91 |
| Mybpc2 | 2.90 |
| Sytl3 | 2.90 |
| H2-Eb2 | 2.90 |

TABLE 14-continued

Differentially expressed genes in CD8+NKG2D+ memory T cells vs. CD8$^+$NKG2D$^-$ memory T cells isolated from cutaneous lymph nodes obtained from alopecic mice. RNAseq was performed on cRNA made isolated from flow-sorted cells (BD influx) from total cutaneous lymph nodes from two alopecic mice.

| GeneSymbol | FC |
|---|---|
| Hdac11 | 2.89 |
| Slc43a3 | 2.89 |
| Klf12 | 2.89 |
| Blnk | 2.89 |
| Atp2b4 | 2.88 |
| Faim3 | 2.88 |
| C1qc | 2.88 |
| Epb4.1l3 | 2.87 |
| Ms4a1 | 2.87 |
| Prr5l | 2.86 |
| Fcrla | 2.86 |
| Ell3 | 2.86 |
| Prdx4 | 2.85 |
| Adcy9 | 2.85 |
| Pbx3 | 2.85 |
| Chmp4c | 2.84 |
| Osbpl1a | 2.84 |
| Apbb1 | 2.84 |
| Cd79a | 2.84 |
| Slc6a8 | 2.83 |
| Zcchc14 | 2.83 |
| 5730416F02Rik | 2.83 |
| Gm9199 | 2.82 |
| Ern1 | 2.82 |
| Lxn | 2.82 |
| Armc2 | 2.82 |
| Cr2 | 2.82 |
| Ptpn13 | 2.81 |
| Bcl11a | 2.81 |
| Scd1 | 2.81 |
| Chst3 | 2.80 |
| Gcnt2 | 2.80 |
| Lyl1 | 2.80 |
| Itga2 | 2.79 |
| Scn4a | 2.78 |
| Ccl5 | 2.78 |
| March1 | 2.76 |
| Siglecg | 2.76 |
| Islr | 2.76 |
| Spib | 2.76 |
| Ndrg1 | 2.75 |
| Tex15 | 2.75 |
| Rgs1 | 2.74 |
| 5031414D18Rik | 2.74 |
| Frmd4b | 2.74 |
| Ankrd6 | 2.74 |
| Bcar3 | 2.74 |
| Rhbdf1 | 2.72 |
| Slco4a1 | 2.72 |
| Capg | 2.71 |
| H2-DMb1 | 2.71 |
| Hhex | 2.71 |
| Postn | 2.71 |
| Myo1e | 2.71 |
| Il15 | 2.70 |
| Soat2 | 2.69 |
| Casp1 | 2.69 |
| Itga3 | 2.69 |
| Rtn1 | 2.68 |
| Sema6b | 2.68 |
| Ciita | 2.68 |
| Haao | 2.68 |
| Atf6 | 2.68 |
| Kcng1 | 2.67 |
| Ptk7 | 2.67 |
| Kdelc2 | 2.67 |
| Cd180 | 2.67 |
| Rhbdl3 | 2.66 |
| Cd86 | 2.66 |
| Naip5 | 2.66 |
| Slc15a3 | 2.65 |
| BC013712 | 2.65 |
| Cd74 | 2.64 |
| C77080 | 2.64 |
| Fam43a | 2.63 |
| S100a6 | 2.63 |
| Lmo2 | 2.63 |
| Col8a2 | 2.63 |
| Celf5 | 2.63 |
| Lhfp14 | 2.63 |
| Col1a1 | 2.62 |
| Ppap2c | 2.62 |
| Ccl3 | 2.62 |
| Rasgrp3 | 2.62 |
| Klhl30 | 2.62 |
| Clu | 2.62 |
| Cd19 | 2.61 |
| Syk | 2.61 |
| Cpne7 | 2.61 |
| Rasgef1b | 2.61 |
| Gm11435 | 2.60 |
| Vpreb3 | 2.60 |
| Lhx2 | 2.58 |
| Cybb | 2.58 |
| Mapk8ip1 | 2.58 |
| Hck | 2.57 |
| 1110046J04Rik | 2.57 |
| Fam59a | 2.57 |
| Stx11 | 2.56 |
| Btk | 2.56 |
| H1f0 | 2.56 |
| Vav3 | 2.56 |
| F2rl2 | 2.55 |
| Hspa2 | 2.55 |
| Slc29a4 | 2.55 |
| Tubb4a | 2.54 |
| Arsb | 2.54 |
| Trim7 | 2.54 |
| Mef2c | 2.54 |
| Asb14 | 2.54 |
| 2010001M09Rik | 2.54 |
| Ehd2 | 2.54 |
| Itpripl2 | 2.53 |
| Ifitm3 | 2.53 |
| Zfp941 | 2.53 |
| Pax5 | 2.53 |
| Cd24a | 2.52 |
| Arhgef40 | 2.51 |
| Rab30 | 2.51 |
| H2-Eb1 | 2.50 |
| Serpinb6a | 2.50 |
| Kynu | 2.50 |
| Klra7 | 2.48 |
| Maf | 2.48 |
| Fcgr2b | 2.48 |
| H2-Ea-ps | 2.47 |
| Crip3 | 2.47 |
| Abhd4 | 2.47 |
| Fcrl1 | 2.47 |
| Egln3 | 2.47 |
| Kif15 | 2.46 |
| H2-Ab1 | 2.46 |
| Jazf1 | 2.46 |
| Dennd5a | 2.46 |
| Hgfac | 2.45 |
| Rtp3 | 2.45 |
| 9130206I24Rik | 2.45 |
| Cited2 | 2.45 |
| Sult4a1 | 2.45 |
| Gls2 | 2.44 |
| Cd80 | 2.44 |
| Tmem176b | 2.44 |
| Vcam1 | 2.44 |
| Ptms | 2.43 |

TABLE 14-continued

Differentially expressed genes in CD8+NKG2D+ memory T cells vs. CD8+NKG2D− memory T cells isolated from cutaneous lymph nodes obtained from alopecic mice. RNAseq was performed on cRNA made isolated from flow-sorted cells (BD influx) from total cutaneous lymph nodes from two alopecic mice.

| GeneSymbol | FC |
| --- | --- |
| Tmem154 | 2.43 |
| Ccl4 | 2.43 |
| Rgs16 | 2.42 |
| Pawr | 2.42 |
| Wdfy4 | 2.42 |
| Olfm1 | 2.42 |
| H2-Aa | 2.42 |
| Stac2 | 2.41 |
| Il18 | 2.40 |
| Fam164a | 2.40 |
| Phlda3 | 2.39 |
| Ctnnal1 | 2.39 |
| Tnfsf10 | 2.39 |
| Cubn | 2.38 |
| Abi2 | 2.38 |
| 2410004P03Rik | 2.38 |
| Trim36 | 2.38 |
| Bmf | 2.37 |
| Adap1 | 2.36 |
| Rarg | 2.36 |
| Tmem151a | 2.36 |
| Ly6d | 2.36 |
| Irf5 | 2.35 |
| Bhlhe40 | 2.35 |
| Zfp608 | 2.34 |
| Fam184a | 2.33 |
| Matb | 2.33 |
| Coch | 2.32 |
| Gpr179 | 2.32 |
| Ffar1 | 2.32 |
| H2-Ob | 2.32 |
| Nav2 | 2.32 |
| Srpk3 | 2.31 |
| Cd209b | 2.31 |
| Arhgef12 | 2.31 |
| Arvcf | 2.31 |
| Serpina3g | 2.30 |
| Ppp1r3f | 2.30 |
| Cdc25c | 2.30 |
| Tmem159 | 2.30 |
| Atcay | 2.30 |
| Sept4 | 2.29 |
| Cacna1e | 2.29 |
| Plxna1 | 2.29 |
| Fzd6 | 2.29 |
| Zcchc24 | 2.29 |
| Ttbk1 | 2.28 |
| Cd40 | 2.28 |
| Atp6v0a1 | 2.28 |
| Gnao1 | 2.27 |
| Gsg2 | 2.27 |
| Dock5 | 2.26 |
| Tlr9 | 2.26 |
| Fbxo6 | 2.26 |
| 2410022L05Rik | 2.26 |
| Ltbp4 | 2.25 |
| Ncf2 | 2.25 |
| Cela1 | 2.25 |
| Ncr1 | 2.25 |
| Irf4 | 2.25 |
| Bank1 | 2.24 |
| Ell2 | 2.23 |
| 1190002F15Rik | 2.23 |
| Unc5b | 2.23 |
| Bspry | 2.23 |
| D17H6S56E-3 | 2.23 |
| Chst2 | 2.23 |
| Slc41a3 | 2.22 |
| Ctla2b | 2.22 |
| Gas2l3 | 2.22 |
| Casp4 | 2.22 |
| Dcxr | 2.21 |
| Ndrg4 | 2.21 |
| Muc1 | 2.21 |
| Lass6 | 2.21 |
| Pls3 | 2.21 |
| Dok3 | 2.20 |
| Carhsp1 | 2.20 |
| Ppfibp1 | 2.20 |
| Stxbp1 | 2.20 |
| Ctsh | 2.20 |
| Edaradd | 2.20 |
| Galnt10 | 2.20 |
| Prr5 | 2.19 |
| Rcbtb2 | 2.19 |
| Pik3c2b | 2.19 |
| Nqo2 | 2.19 |
| Fbxo30 | 2.18 |
| Mki67 | 2.17 |
| Prnp | 2.17 |
| Ahr | 2.16 |
| C030034L19Rik | 2.16 |
| Lgals1 | 2.16 |
| Gm11110 | 2.15 |
| Jup | 2.15 |
| Fam20a | 2.15 |
| Sfpi1 | 2.15 |
| Lrfn4 | 2.14 |
| Cdkn2c | 2.14 |
| Crybg3 | 2.14 |
| Trerf1 | 2.14 |
| Dok4 | 2.14 |
| Cdk6 | 2.13 |
| S1pr3 | 2.13 |
| Rxra | 2.13 |
| Cd163l1 | 2.13 |
| Pwwp2b | 2.12 |
| 1700017B05Rik | 2.12 |
| 2310010M20Rik | 2.12 |
| Nek2 | 2.12 |
| Lix1l | 2.12 |
| Ggta1 | 2.11 |
| Rorc | 2.11 |
| Fosb | 2.11 |
| Rimkla | 2.11 |
| Txlnb | 2.10 |
| Smox | 2.10 |
| Tcf4 | 2.10 |
| Fgd2 | 2.10 |
| Cd300lf | 2.10 |
| Map3k13 | 2.10 |
| Neil3 | 2.09 |
| Optn | 2.09 |
| A930038C07Rik | 2.09 |
| Klra5 | 2.08 |
| Cyp4f18 | 2.08 |
| Akap17b | 2.08 |
| 2700081O15Rik | 2.07 |
| Pcyox1l | 2.07 |
| Cd226 | 2.07 |
| Aurkb | 2.07 |
| St6galnac6 | 2.06 |
| Mfge8 | 2.06 |
| Slamf1 | 2.06 |
| Zdhhc2 | 2.06 |
| Bag2 | 2.05 |
| Gpr55 | 2.05 |
| Dip2a | 2.05 |
| BC064078 | 2.05 |
| S1pr5 | 2.05 |
| Mlkl | 2.04 |
| Arap3 | 2.04 |
| Ctla2a | 2.04 |
| Gypc | 2.04 |

TABLE 14-continued

Differentially expressed genes in CD8+NKG2D+ memory T cells vs. CD8+NKG2D− memory T cells isolated from cutaneous lymph nodes obtained from alopecic mice. RNAseq was performed on cRNA made isolated from flow-sorted cells (BD influx) from total cutaneous lymph nodes from two alopecic mice.

| GeneSymbol | FC |
|---|---|
| Ccdc88a | 2.04 |
| Serpinb1a | 2.03 |
| Fam19a3 | 2.03 |
| Cdk1 | 2.03 |
| Trib1 | 2.01 |
| Gadd45b | 2.01 |
| Pfn2 | 2.01 |
| Klrd1 | 2.01 |
| Trp53i11 | 2.01 |
| Cd22 | 2.00 |
| Mtss1 | 2.00 |
| Adam19 | 2.00 |
| Nusap1 | 2.00 |
| Hk3 | 0.50 |
| Pak1 | 0.50 |
| Irgc1 | 0.50 |
| Zfp296 | 0.50 |
| Il6st | 0.50 |
| Oas2 | 0.49 |
| Il6ra | 0.49 |
| Ctsf | 0.49 |
| Lef1 | 0.49 |
| Gm4951 | 0.49 |
| Gpr133 | 0.49 |
| Olfr1033 | 0.49 |
| Bambi-ps1 | 0.48 |
| Gtf2ird1 | 0.48 |
| Dtx1 | 0.48 |
| Maml3 | 0.47 |
| Plaur | 0.47 |
| Id3 | 0.47 |
| Tnfrsf25 | 0.47 |
| Susd4 | 0.47 |
| Wfikkn2 | 0.47 |
| 4921525O09Rik | 0.46 |
| Klra3 | 0.46 |
| 1110032F04Rik | 0.46 |
| Car12 | 0.46 |
| Pard6g | 0.46 |
| Slc7a4 | 0.46 |
| Lrp12 | 0.46 |
| Spats2l | 0.45 |
| Dleu7 | 0.45 |
| Cacna2d4 | 0.45 |
| Dst | 0.45 |
| Osbpl6 | 0.45 |
| Tmem108 | 0.44 |
| 4930417O13Rik | 0.44 |
| Angptl2 | 0.44 |
| Adam6b | 0.44 |
| Lrrc9 | 0.44 |
| 2310042E22Rik | 0.44 |
| Lars2 | 0.44 |
| Ankrd55 | 0.44 |
| Ly6k | 0.43 |
| Kazn | 0.43 |
| Dapl1 | 0.43 |
| Slc16a5 | 0.43 |
| Unc13a | 0.42 |
| Gpr113 | 0.42 |
| Siglech | 0.42 |
| Olig3 | 0.42 |
| Ksr2 | 0.42 |
| Card9 | 0.42 |
| Rasip1 | 0.42 |
| Dlc1 | 0.41 |
| Gm19705 | 0.41 |
| Syde2 | 0.41 |
| Actn1 | 0.41 |
| Epx | 0.41 |
| Mir5109 | 0.41 |
| Gpr83 | 0.40 |
| Neb | 0.40 |
| Sall2 | 0.40 |
| Fam5b | 0.40 |
| Prickle1 | 0.40 |
| Nme4 | 0.40 |
| Lif | 0.40 |
| Auts2 | 0.39 |
| Col6a4 | 0.39 |
| Ccdc164 | 0.39 |
| Apol11b | 0.39 |
| Plac8 | 0.39 |
| Kcnf1 | 0.38 |
| Gm15708 | 0.38 |
| Wnt5b | 0.38 |
| Plat | 0.38 |
| Nmnat2 | 0.38 |
| 4933440M02Rik | 0.38 |
| Dcaf12l1 | 0.38 |
| Nacc2 | 0.38 |
| She | 0.37 |
| Snord69 | 0.37 |
| Mical3 | 0.37 |
| Cox6a2 | 0.36 |
| Dmbt1 | 0.36 |
| Aldh1l1 | 0.36 |
| Scarna6 | 0.36 |
| Lrp3 | 0.35 |
| Car11 | 0.35 |
| Il1r2 | 0.35 |
| Atp6v1g3 | 0.35 |
| Clec9a | 0.34 |
| Slc6a9 | 0.34 |
| Tnni3 | 0.34 |
| Gpr125 | 0.34 |
| Ikzf2 | 0.34 |
| Slc7a10 | 0.33 |
| Lman1l | 0.33 |
| A430105I19Rik | 0.33 |
| Eng | 0.32 |
| Snora17 | 0.32 |
| Gria4 | 0.32 |
| Fgfr1 | 0.32 |
| BC048644 | 0.31 |
| D830046C22Rik | 0.31 |
| Hs6st2 | 0.31 |
| Hoxa5 | 0.31 |
| Alpl | 0.30 |
| Pgpep1l | 0.30 |
| Adam6a | 0.29 |
| Hoxa3 | 0.29 |
| Fam110b | 0.28 |
| Padi1 | 0.28 |
| Serpina9 | 0.28 |
| Igfbp4 | 0.28 |
| Pdzk1ip1 | 0.27 |
| Fzd1 | 0.27 |
| 4930546C10Rik | 0.27 |
| Foxp3 | 0.26 |
| Hoxa6 | 0.26 |
| Hoxa7 | 0.26 |
| Edn3 | 0.26 |
| Btc | 0.26 |
| Myl10 | 0.26 |
| Hoxa1 | 0.25 |
| Dnahc7a | 0.24 |
| Mira | 0.24 |
| Pcdhga10 | 0.24 |
| Lrrc3b | 0.23 |
| Slc4a4 | 0.23 |
| Rprl3 | 0.23 |
| Shc2 | 0.22 |
| Expi | 0.22 |

TABLE 14-continued

Differentially expressed genes in CD8+NKG2D+ memory T cells vs. CD8+NKG2D− memory T cells isolated from cutaneous lymph nodes obtained from alopecic mice. RNAseq was performed on cRNA made isolated from flow-sorted cells (BD influx) from total cutaneous lymph nodes from two alopecic mice.

| GeneSymbol | FC |
| --- | --- |
| Shisa2 | 0.22 |
| Gm12709 | 0.22 |
| Fbln2 | 0.21 |
| Sec1 | 0.21 |
| C85492 | 0.21 |
| Lamc3 | 0.21 |
| Dbx1 | 0.20 |
| Atp1b1 | 0.20 |
| Nek5 | 0.19 |
| Actg2 | 0.19 |
| Dntt | 0.17 |
| Nrg2 | 0.17 |
| Sostdc1 | 0.14 |
| Trnp1 | 0.14 |
| Lama1 | 0.14 |
| Rprl2 | 0.13 |
| 0610012H03Rik | 0.12 |
| Lrrc32 | 0.10 |

Figure 54H:
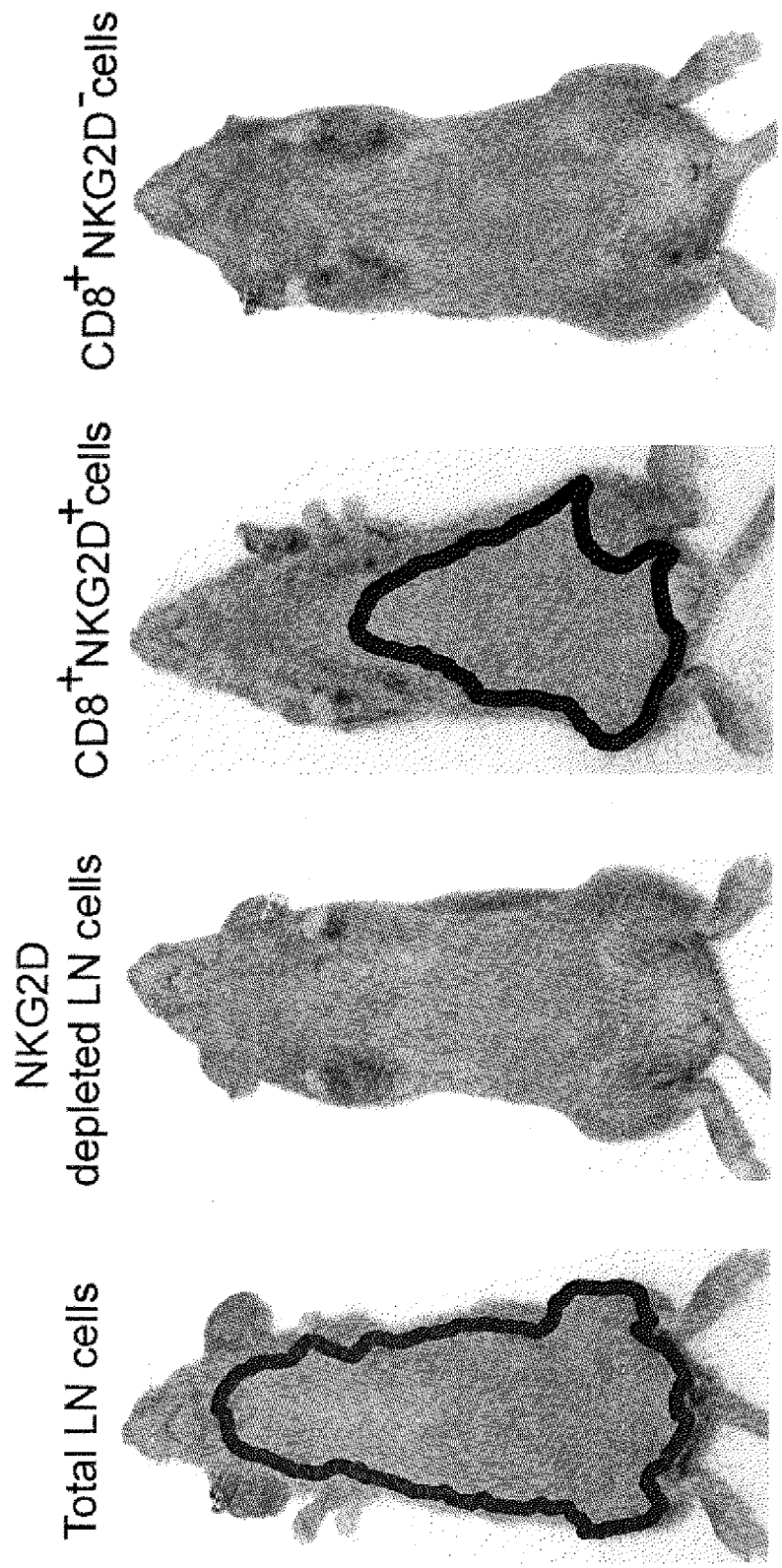
FIG. 54H shows the cellular phenotype and function of $CD8^+NKG2D^+$ cytotoxic T lymphocytes in AA mice. C3H/HeJ mice were injected subcutaneously with $2 \times 10^6$ cells from four different populations. Hair loss developed in recipients after either injection of total LN cells or $CD8^+NKG2D^+$ T cells alone (5 out of 5 mice per group), whereas mice receiving $CD8^+NKG2D^-$ T cells or LN cells depleted of NKG2D+ cells did not develop alopecia (0 out of 5 mice per group). ***p value=<0.001.
Figure 56A:
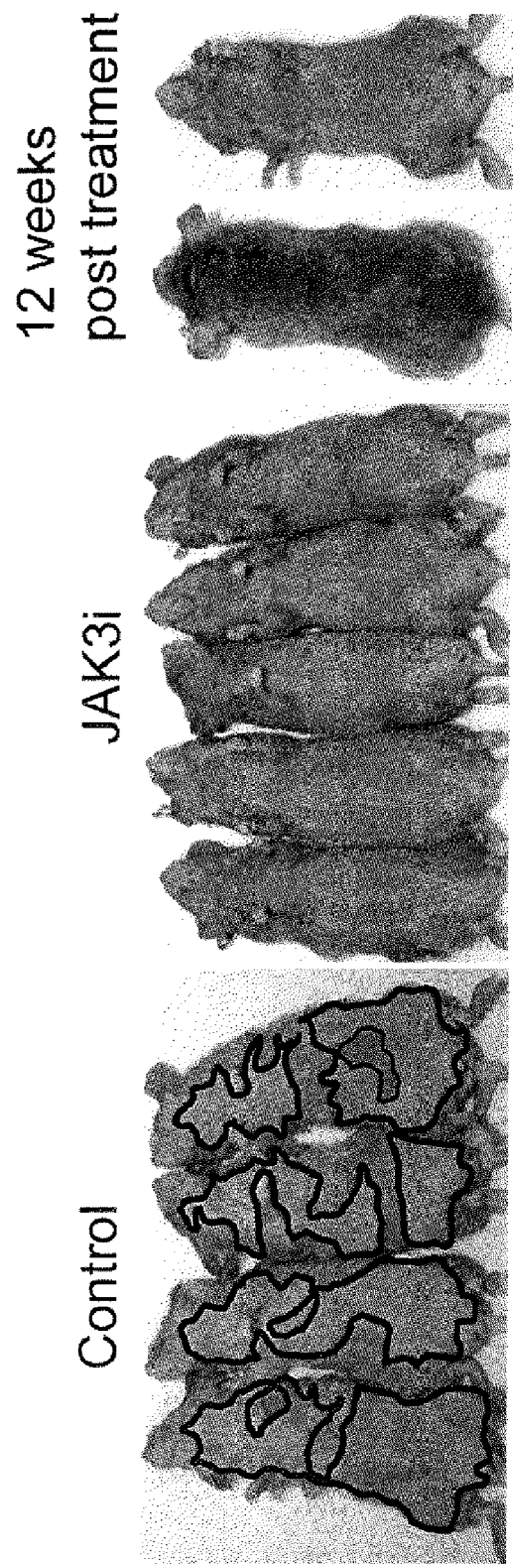
FIG. 56A shows targeting $CD8^+NKG2D^+$ cytotoxic T lymphocytes with JAK3i prevents the onset of alopecia in grafted C3H/HeJ mice. C3H/HeJ grafted mice were treated systemically from the time of grafting. The onset of alopecia is inhibited by JAK3i, tofacitinib treatment. The durability of disease prevention was demonstrated by treatment withdrawal for an additional 12 weeks after treatment withdrawal.
Figure 56B:
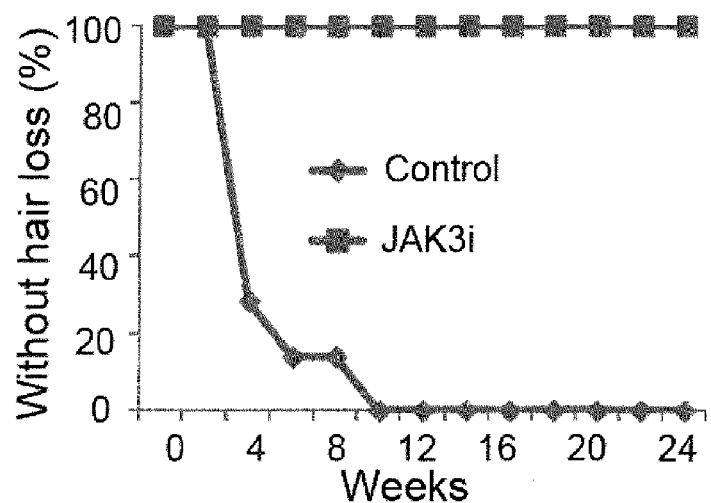
FIG. 56B shows targeting CD8+NKG2D+ cytotoxic T lymphocytes with JAK3i prevents the onset of alopecia in grafted C3H/HeJ mice. C3H/HeJ grafted mice were treated systemically from the time of grafting. The onset of alopecia is inhibited by JAK3i, tofacitinib treatment.
Figure 56C:
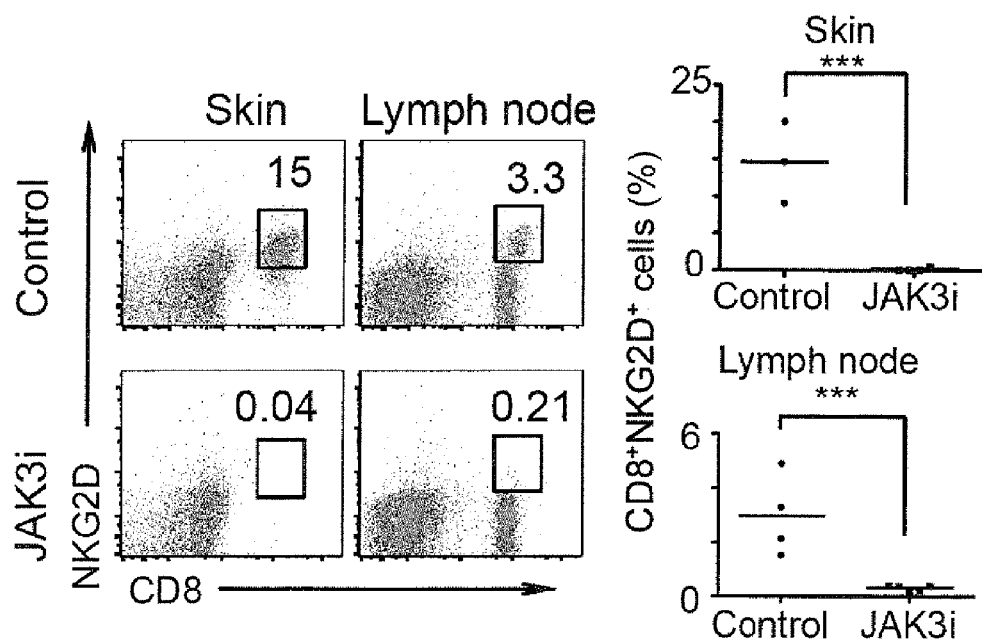
FIG. 56C shows targeting CD8+NKG2D+ cytotoxic T lymphocytes with JAK3 prevents the onset of alopecia in grafted C3H/HeJ mice. The frequency of CD8+NKG2D+ T cells in skin and cutaneous lymph nodes of JAK3i treated mice were significantly decreased compared to control mice. ***p value=<0.001.
Figure 56D:
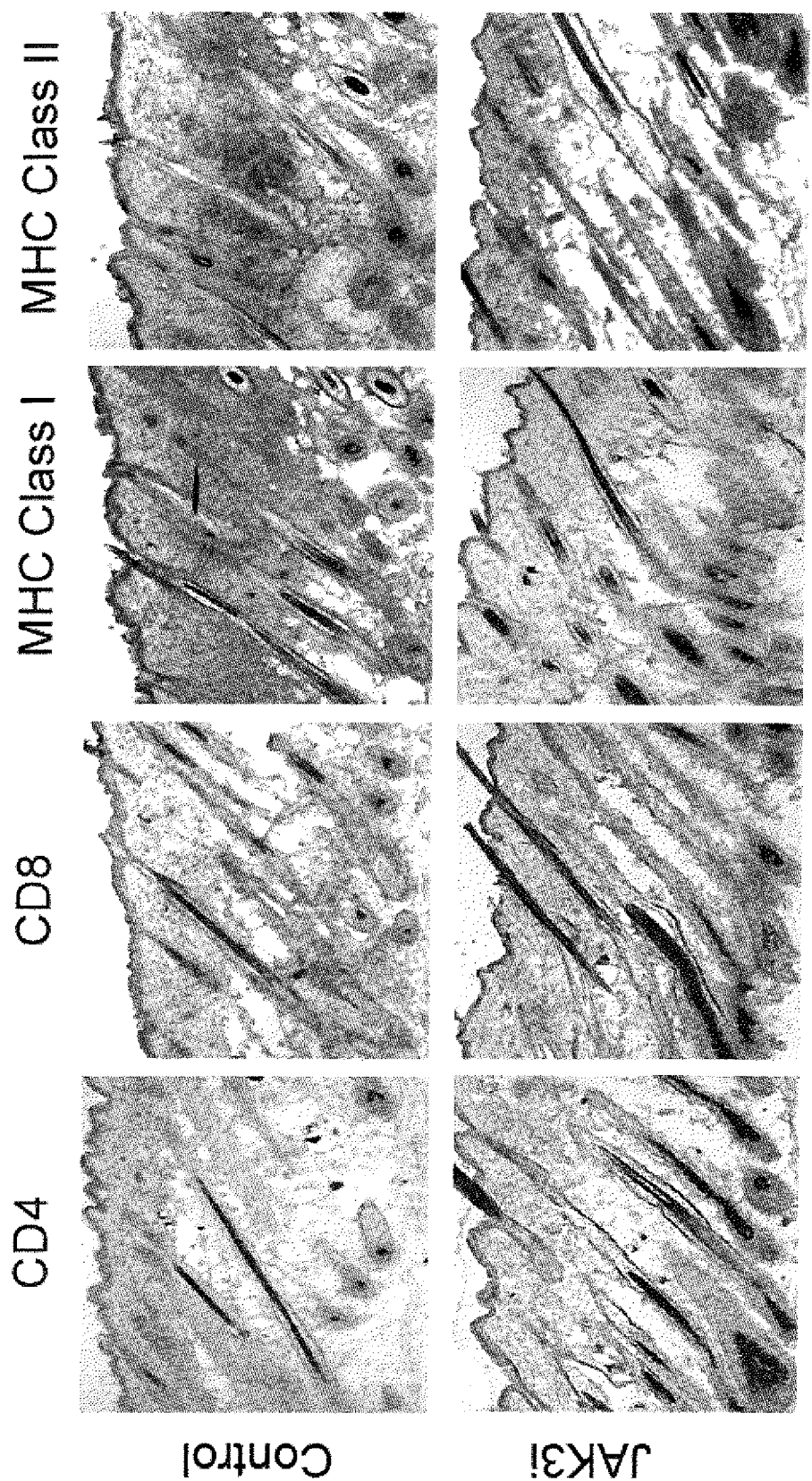
FIG. 56D shows targeting CD8+NKG2D+ cytotoxic T lymphocytes with JAK3i prevents the onset of alopecia in grafted C3H/HeJ mice. Immunohistochemical staining of skin biopsies showed that the expression of CD4, CD8, MHC class I and II in skin are significantly decreased in JAK3i treated mice compared to control mice.
Figure 56E:
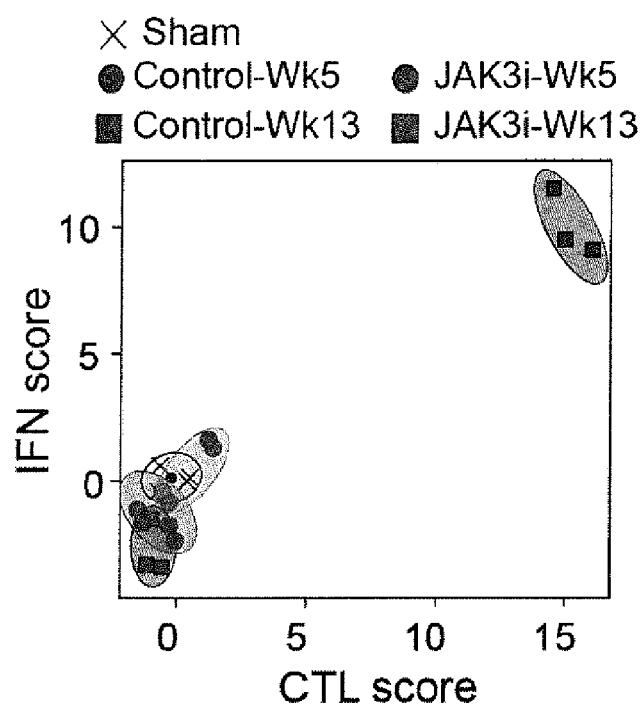
FIG. 56E shows targeting CD8+NKG2D+ cytotoxic T lymphocytes with JAK3i prevents the onset of alopecia in grafted C3H/HeJ mice. ALADIN score (a summary statistic of expression of IFN signature and CTL signature genes) from JAK3i treated mice showed normalization. For gene expression studies, mice grafted with autologous health skin were included as sham-operated controls.
Figure 56F:
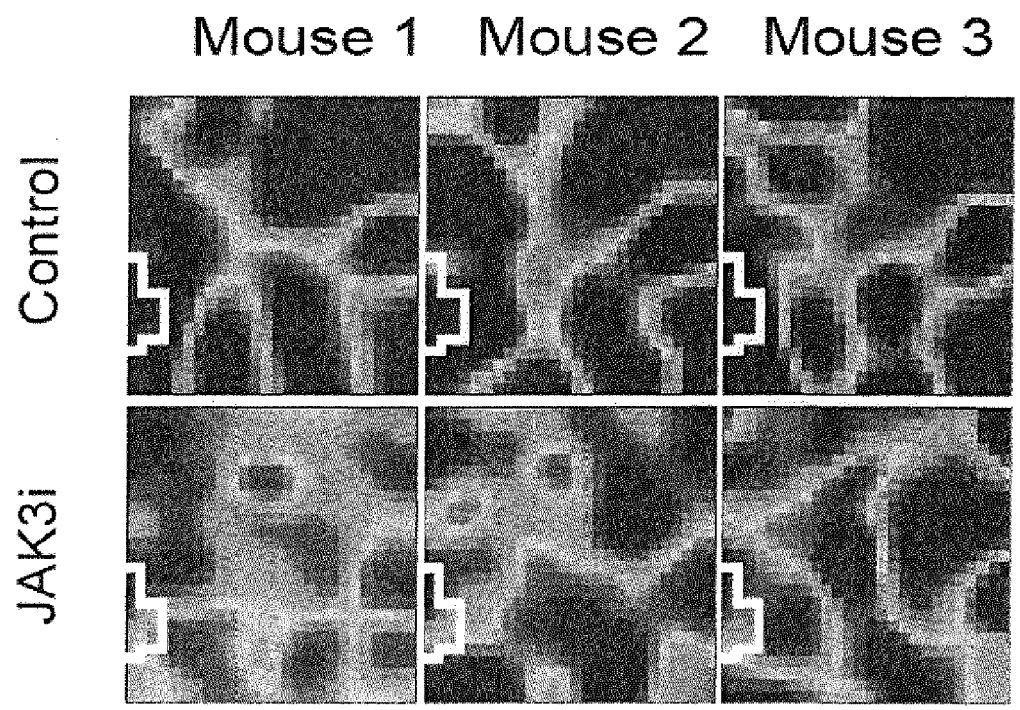
FIG. 56F shows targeting CD8+NKG2D+ cytotoxic T lymphocytes with JAK3i prevents the onset of alopecia in grafted C3H/HeJ mice. GEDI results of JAK3i treated mice showed reduction in CTL and IFN signatures.

To evaluate the requirement of these 'NK-type' CD8 T cells in disease pathogenesis, an adoptive transfer approach was used. Cytotoxic CD8+NKG2D+ cells transferred alone, as well as total lymph node cells, were both able to give rise to AA in five recipients, whereas lymph node populations depleted of NKG2D+ cells were unable to transfer disease (FIG. 54H). Not only are 'NK-type' CD8+NKG2D+ T cells the dominant cell type in the dermal infiltrate, but, moreover, they are both necessary and sufficient for T cell mediated transfer of alopecia areata.

Figure 60:
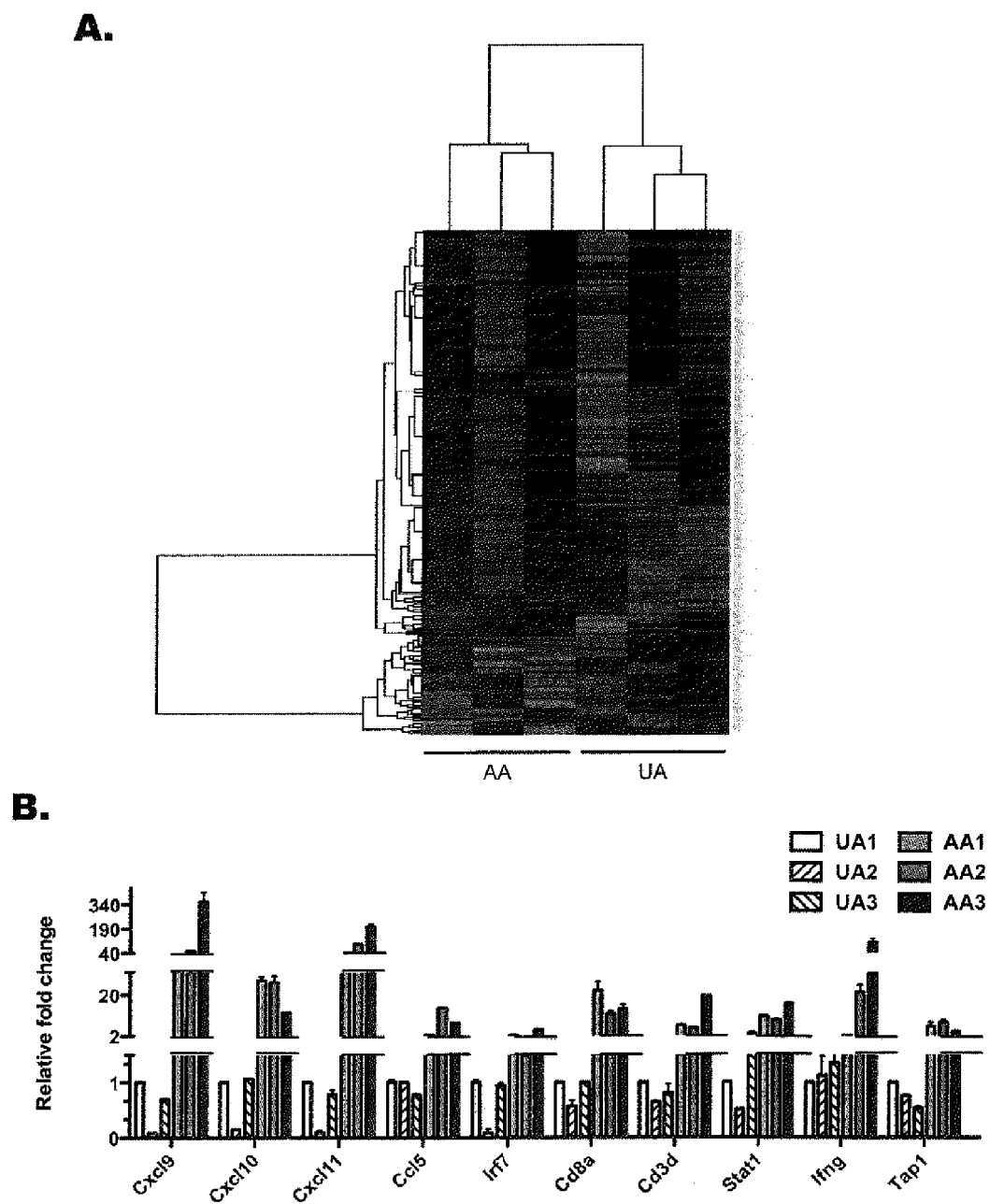
FIG. 60 shows validation of mouse RNA expression studies. To determine the expression signature of C3H/HeJ mouse skin affected with alopecia areata, lesional skin was isolated from three affected female mice and three unaffected aged-matched controls. Total and small RNAs were isolated from whole skin and biotin-labeled eRNA was generated through in vitro transcription, followed by hybridization to the Affymetrix Mouse 430 2.0 Genechip. Data analysis was done as outlined in the Methods.

Using comparative genomics in order to characterize the transcriptional landscape of AA lesional skin from C3H/HeJ mice as well as humans with AA, AFFYMETRIX™ profiling was first performed of whole skin from C3H/HeJ mice with spontaneous AA versus unaffected C3H/HeJ skin (FIG. 55A, top panel and FIG. 60). In parallel, human skin was similarly profiled from perilesional biopsies of active disease in five AA patients versus normal controls (Tables 15-17).

TABLE 15

Differentially expressed genes in the skin of alopecic female C3H/HeJ mice vs. skin obtained from age-matched female C3H/HeJ mice without alopecia (n = 3 per group).

| Affy_ID | GeneSymbol | FC |
| --- | --- | --- |
| 1419762_at | Ubd | 135.60 |
| 1418652_at | Cxcl9 | 74.98 |
| 1417898_a_at | Gzma | 56.37 |
| 1419697_at | Cxcl11 | 53.33 |
| 1418930_at | Cxcl10 | 37.58 |
| 1419042_at | Iigp1 | 34.65 |
| 1418776_at | Gbp8 | 33.06 |
| 1418126_at | Ccl5 | 27.95 |
| 1419043_a_at | Iigp1 | 25.36 |
| 1438676_at | Gbp6 | 25.11 |
| 1423467_at | Ms4a4b | 23.27 |
| 1453196_a_at | Oasl2 | 23.06 |
| 1419060_at | Gzmb | 21.74 |
| 1417141_at | Igtp | 21.08 |
| 1435639_at | 2610528A11Rik | 20.88 |
| 1423555_a_at | Ifi44 | 20.58 |
| 1417292_at | Ifi47 | 18.63 |
| 1425394_at | BC023105 | 18.43 |
| 1420549_at | Gbp1 | 17.81 |
| 1417793_at | Irgm2 | 17.25 |
| 1435906_x_at | Gbp2 | 15.15 |
| 1450033_a_at | Stat1 | 14.48 |
| 1418825_at | Irgm1 | 14.46 |
| 1444078_at | Cd8a | 14.23 |
| 1422812_at | Cxcr6 | 13.98 |
| 1427747_a_at | Lcn2 | 13.89 |
| 1420699_at | Clec7a | 13.82 |
| 1418240_at | Gbp2 | 13.32 |
| 1450783_at | Ifit1 | 13.13 |
| 1418392_a_at | Gbp3 | 12.61 |
| 1424305_at | Igj | 12.53 |
| 1434380_at | Gbp7 | 12.51 |
| 1424865_at | Pyy | 12.17 |
| 1422588_at | Krt6b | 12.07 |
| 1434046_at | AA467197 | 11.98 |
| 1418580_at | Rtp4 | 11.29 |
| 1419709_at | Stfa3 | 11.04 |
| 1425156_at | Gbp7 | 10.72 |
| 1449254_at | Spp1 | 10.61 |
| 1440481_at | Stat1 | 10.53 |
| 1449153_at | Mmp12 | 10.18 |
| 1424921_at | Bst2 | 9.80 |
| 1429947_a_at | Zbp1 | 9.65 |
| 1456907_at | Cxcl9 | 9.62 |
| 1421075_s_at | Cyp7b1 | 8.74 |
| 1451777_at | Ddx60 | 8.72 |
| 1421688_a_at | Ccl1 | 8.65 |
| 1421074_at | Cyp7b1 | 8.56 |
| 1419604_at | Zbp1 | 8.51 |
| 1419714_at | Cd274 | 8.41 |
| 1427102_at | Slfn4 | 8.40 |
| 1424761_at | Fam115c | 8.26 |
| 1419135_at | Ltb | 8.24 |
| 1450034_at | Stat1 | 7.98 |
| 1425832_a_at | Cxcr6 | 7.98 |
| 1420915_at | Stat1 | 7.67 |
| 1438037_at | Herc6 | 7.62 |
| 1448436_a_at | Irf1 | 7.61 |
| 1448932_at | Krt16 | 7.12 |
| 1435710_at | AI661384 | 7.10 |
| 1451564_at | Parp14 | 7.08 |
| 1452614_at | Bcl2l15 | 7.00 |
| 1417256_at | Mmp13 | 6.88 |
| 1447541_s_at | Itgae | 6.79 |
| 1432026_a_at | Herc6 | 6.70 |
| 1434372_at | AW112010 | 6.62 |
| 1459913_at | Tnfsf10 | 6.51 |
| 1451426_at | Dhx58 | 6.51 |
| 1452405_x_at | Trav9d-3 | 6.44 |
| 1429570_at | Mlkl | 6.41 |
| 1444064_at | Samhd1 | 6.28 |
| 1451860_a_at | Trim30a | 6.23 |
| 1453080_at | Apol7a | 6.22 |
| 1420380_at | Ccl2 | 6.12 |
| 1434438_at | Samhd1 | 6.11 |
| 1450696_at | Psmb9 | 6.06 |
| 1451537_at | Chi3l1 | 5.99 |
| 1450165_at | Slfn2 | 5.88 |
| 1424727_at | Ccr5 | 5.83 |
| 1421256_at | Gzmc | 5.80 |
| 1448162_at | Vcam1 | 5.80 |
| 1453913_a_at | Tap2 | 5.79 |
| 1418191_at | Usp18 | 5.73 |
| 1425005_at | Klrc1 | 5.65 |
| 1439680_at | Tnfsf10 | 5.64 |
| 1433935_at | AU020206 | 5.51 |
| 1426113_x_at | Trav9d-3 | 5.51 |
| 1422415_at | Ang2 | 5.44 |
| 1460245_at | Klrd1 | 5.41 |
| 1426971_at | Uba7 | 5.34 |
| 1443698_at | Xaf1 | 5.32 |
| 1418131_at | Samhd1 | 5.26 |
| 1419591_at | Gsdmc | 5.20 |
| 1416897_at | Parp9 | 5.11 |

TABLE 15-continued

Differentially expressed genes in the skin of alopecic female C3H/HeJ mice vs. skin obtained from age-matched female C3H/HeJ mice without alopecia (n = 3 per group).

| Affy_ID | GeneSymbol | FC |
|---|---|---|
| 1417244_a_at | Irf7 | 5.08 |
| 1449216_at | Itgae | 5.06 |
| 1448632_at | Psmb10 | 5.06 |
| 1439825_at | Dtx3l | 5.02 |
| 1416714_at | Irf8 | 5.00 |
| 1425917_at | H28 | 4.99 |
| 1447621_s_at | Tmem173 | 4.93 |
| 1425396_a_at | Lck | 4.88 |
| 1418536_at | H2-Q7 | 4.84 |
| 1449025_at | Ifit3 | 4.75 |
| 1436649_at | Ikzf3 | 4.75 |
| 1425947_at | Ifng | 4.71 |
| 1417172_at | Ube2l6 | 4.70 |
| 1438855_x_at | Tnfaip2 | 4.70 |
| 1422962_a_at | Psmb8 | 4.69 |
| 1421186_at | Ccr2 | 4.66 |
| 1418204_s_at | Aif1 | 4.61 |
| 1421911_at | Stat2 | 4.57 |
| 1450753_at | Nkg7 | 4.55 |
| 1450424_a_at | Il18bp | 4.53 |
| 1450403_at | Stat2 | 4.52 |
| 1452565_x_at | LOC641050 | 4.44 |
| 1441054_at | Apol8 | 4.43 |
| 1449328_at | Ly75 | 4.39 |
| 1422601_at | Serpinb9 | 4.39 |
| 1422177_at | Il13ra2 | 4.39 |
| 1426170_a_at | Cd8b1 | 4.38 |
| 1460603_at | Samd9l | 4.37 |
| 1448754_at | Rbp1 | 4.31 |
| 1417822_at | D17H6S56E-5 | 4.28 |
| 1435208_at | Dtx3l | 4.26 |
| 1418649_at | Egln3 | 4.26 |
| 1422160_at | H2-T24 | 4.23 |
| 1456064_at | AI504432 | 4.21 |
| 1449184_at | Pglyrp1 | 4.19 |
| 1438498_at | Zmynd15 | 4.19 |
| 1449195_s_at | Cxcl16 | 4.11 |
| 1439034_at | Spn | 4.10 |
| 1450678_at | Itgb2 | 4.10 |
| 1437176_at | Nlrc5 | 4.09 |
| 1458299_s_at | Nfkbie | 4.07 |
| 1421262_at | Lipg | 4.06 |
| 1426039_a_at | Alox12e | 4.05 |
| 1429184_at | Gvin1 | 4.05 |
| 1448380_at | Lgals3bp | 4.04 |
| 1436576_at | Fam26f | 4.01 |
| 1453939_x_at | Gm9706 | 3.99 |
| 1434457_at | Sp100 | 3.98 |
| 1425295_at | Ear11 | 3.97 |
| 1425065_at | Oas2 | 3.97 |
| 1449846_at | Ear2 | 3.97 |
| 1450582_at | H2-Q5 | 3.96 |
| 1440926_at | Flt1 | 3.94 |
| 1457140_s_at | Rassf10 | 3.91 |
| 1455500_at | Rnf213 | 3.90 |
| 1426970_a_at | Uba7 | 3.89 |
| 1448452_at | Irf8 | 3.88 |
| 1451673_at | Cd8a | 3.88 |
| 1437929_at | Dact2 | 3.86 |
| 1426774_at | Parp12 | 3.84 |
| 1418648_at | Egln3 | 3.82 |
| 1437811_x_at | Cotl1 | 3.78 |
| 1428420_a_at | 1200009I06Rik | 3.78 |
| 1417961_a_at | Trim30a | 3.77 |
| 1425225_at | Fcgr4 | 3.74 |
| 1421812_at | Tapbp | 3.74 |
| 1451905_a_at | Mx1 | 3.72 |
| 1441752_at | Art3 | 3.69 |
| 1448301_s_at | Serpinb1a | 3.69 |
| 1436172_at | Gm20559 | 3.68 |
| 1418133_at | Bcl3 | 3.67 |
| 1418655_at | B4galnt1 | 3.66 |
| 1417821_at | D17H6S56E-5 | 3.66 |
| 1417171_at | Itk | 3.63 |
| 1460227_at | Timp1 | 3.61 |
| 1455161_at | AI504432 | 3.61 |
| 1421228_at | Ccl7 | 3.60 |
| 1434905_at | Ndufa4l2 | 3.60 |
| 1460218_at | Cd52 | 3.60 |
| 1460437_at | Cyth4 | 3.54 |
| 1430005_a_at | Batf2 | 3.53 |
| 1450188_s_at | Lipg | 3.53 |
| 1419698_at | Cxcl11 | 3.52 |
| 1439790_at | Serpinb9 | 3.51 |
| 1419413_at | Ccl17 | 3.51 |
| 1421009_at | Rsad2 | 3.50 |
| 1436838_x_at | Cotl1 | 3.50 |
| 1455269_a_at | Caro1a | 3.50 |
| 1422828_at | Cd3d | 3.49 |
| 1440866_at | Eif2ak2 | 3.47 |
| 1420437_at | Ido1 | 3.45 |
| 1439814_at | Atp8b4 | 3.44 |
| 1441706_at | Dscaml1 | 3.44 |
| 1421322_a_at | Irf9 | 3.43 |
| 1427076_at | Mpeg1 | 3.43 |
| 1435454_a_at | BC006779 | 3.41 |
| 1444619_x_at | Psmb8 | 3.40 |
| 1444350_at | Slfn10-ps | 3.39 |
| 1425335_at | Cd8a | 3.38 |
| 1450484_a_at | Cmpk2 | 3.38 |
| 1435832_at | Lrrc4 | 3.38 |
| 1424067_at | Icam1 | 3.37 |
| 1416318_at | Serpinb1a | 3.37 |
| 1445897_s_at | Ifi35 | 3.35 |
| 1450291_s_at | Ms4a4c | 3.34 |
| 1416273_at | Tnfaip2 | 3.34 |
| 1453304_s_at | Ly6e | 3.33 |
| 1418770_at | Cd2 | 3.32 |
| 1434067_at | AI662270 | 3.32 |
| 1428735_at | Cd69 | 3.31 |
| 1424965_at | Lpxn | 3.31 |
| 1455393_at | Cp | 3.31 |
| 1429567_at | Rassf10 | 3.30 |
| 1436905_x_at | Laptm5 | 3.30 |
| 1428485_at | Car12 | 3.28 |
| 1456211_at | Nlrp10 | 3.28 |
| 1438531_at | A730054J21Rik | 3.26 |
| 1449175_at | Gpr65 | 3.25 |
| 1424923_at | Serpina3g | 3.24 |
| 1417995_at | Ptpn22 | 3.23 |
| 1440990_at | Kif26b | 3.20 |
| 1420338_at | Alox15 | 3.18 |
| 1419300_at | Flt1 | 3.17 |
| 1419128_at | Itgax | 3.16 |
| 1426872_at | Fcgbp | 3.15 |
| 1425336_x_at | H2-K1 | 3.15 |
| 1448759_at | Il2rb | 3.14 |
| 1419178_at | Cd3g | 3.11 |
| 1420412_at | Tnfsf10 | 3.11 |
| 1433465_a_at | AI467606 | 3.11 |
| 1418203_at | Pmaip1 | 3.11 |
| 1430208_at | Krt42 | 3.09 |
| 1421628_at | Il18r1 | 3.08 |
| 1417620_at | Rac2 | 3.08 |
| 1454850_at | Tbc1d10c | 3.07 |
| 1439221_s_at | Cd40 | 3.07 |
| 1438658_at | S1pr3 | 3.06 |
| 1426278_at | Ifi27l2a | 3.06 |
| 1429692_s_at | Gch1 | 3.04 |
| 1458148_at | Nlrc3 | 3.03 |
| 1440927_x_at | Apol11b | 3.03 |
| 1436236_x_at | Cotl1 | 3.03 |
| 1448940_at | Trim21 | 3.02 |
| 1421217_a_at | Lgals9 | 3.02 |
| 1451756_at | Flt1 | 3.01 |
| 1455048_at | Igsf3 | 3.01 |
| 1435560_at | Itgal | 3.01 |
| 1425719_a_at | Nmi | 2.99 |

TABLE 15-continued

Differentially expressed genes in the skin of alopecic female C3H/HeJ mice vs. skin obtained from age-matched female C3H/HeJ mice without alopecia (n = 3 per group).

| Affy_ID | GeneSymbol | FC |
|---|---|---|
| 1439956_at | Ms4a6b | 2.98 |
| 1436562_at | Ddx58 | 2.98 |
| 1422632_at | Ctsw | 2.98 |
| 1436472_at | Slfn9 | 2.98 |
| 1427013_at | Car9 | 2.98 |
| 1449361_at | Tbx21 | 2.98 |
| 1426025_s_at | Laptm5 | 2.97 |
| 1438052_at | A130071D04Rik | 2.97 |
| 1426276_at | Ifih1 | 2.97 |
| 1456890_at | Ddx58 | 2.96 |
| 1416295_a_at | Il2rg | 2.94 |
| 1434873_a_at | Acap1 | 2.93 |
| 1456103_at | Pml | 2.93 |
| 1418678_at | Has2 | 2.92 |
| 1420697_at | Slc15a3 | 2.91 |
| 1436058_at | Rsad2 | 2.90 |
| 1425294_at | Slamf8 | 2.90 |
| 1459151_x_at | Ifi35 | 2.90 |
| 1418991_at | Bak1 | 2.89 |
| 1439068_at | Erap1 | 2.89 |
| 1424617_at | Ifi35 | 2.89 |
| 1417189_at | Psme2 | 2.89 |
| 1451544_at | Tapbpl | 2.88 |
| 1419412_at | Xcl1 | 2.88 |
| 1419539_at | Irx4 | 2.88 |
| 1452592_at | Mgst2 | 2.87 |
| 1420774_a_at | 4930583H14Rik | 2.86 |
| 1440169_x_at | Ifnar2 | 2.86 |
| 1420499_at | Gch1 | 2.85 |
| 1416002_x_at | Cotl1 | 2.85 |
| 1423754_at | Ifitm3 | 2.84 |
| 1416942_at | Erap1 | 2.84 |
| 1449169_at | Has2 | 2.83 |
| 1419609_at | Ccr1 | 2.83 |
| 1449591_at | Casp4 | 2.81 |
| 1436598_at | Icos | 2.81 |
| 1427381_at | Irg1 | 2.81 |
| 1419879_s_at | Trim25 | 2.81 |
| 1449143_at | Rtp4 | 2.80 |
| 1449839_at | Casp3 | 2.78 |
| 1426599_a_at | Slc2a1 | 2.78 |
| 1452117_a_at | Fyb | 2.77 |
| 1434773_a_at | Slc2a1 | 2.77 |
| 1450378_at | Tapbp | 2.76 |
| 1419561_at | Ccl3 | 2.76 |
| 1427007_at | Sash3 | 2.76 |
| 1422706_at | Pmepa1 | 2.76 |
| 1427892_at | Myo1g | 2.75 |
| 1451335_at | Plac8 | 2.73 |
| 1425974_a_at | Trim25 | 2.72 |
| 1426600_at | Slc2a1 | 2.67 |
| 1418826_at | Ms4a6b | 2.67 |
| 1430244_at | 4921509J17Rik | 2.66 |
| 1457664_x_at | C2 | 2.65 |
| 1416564_at | Sox7 | 2.65 |
| 1433466_at | AI467606 | 2.65 |
| 1425801_x_at | Cotl1 | 2.64 |
| 1435945_a_at | Kcnn4 | 2.63 |
| 1434268_at | Adar | 2.63 |
| 1420353_at | Lta | 2.63 |
| 1418741_at | Itgb7 | 2.62 |
| 1416246_a_at | Coro1a | 2.62 |
| 1422280_at | Gzmk | 2.61 |
| 1421596_s_at | H28 | 2.60 |
| 1415834_at | Dusp6 | 2.60 |
| 1438364_x_at | Ang4 | 2.60 |
| 1439819_at | AU015263 | 2.60 |
| 1451755_a_at | Apobec1 | 2.59 |
| 1416296_at | Il2rg | 2.59 |
| 1439276_at | Adar | 2.59 |
| 1417495_x_at | Cp | 2.59 |
| 1453352_at | Atp10b | 2.58 |
| 1437478_s_at | Ethd2 | 2.58 |
| 1434366_x_at | C1qb | 2.58 |
| 1417185_at | Ly6a | 2.58 |
| 1443858_at | Trim12c | 2.58 |
| 1417494_a_at | Cp | 2.58 |
| 1427746_x_at | H2-K1 | 2.57 |
| 1421034_a_at | Il4ra | 2.56 |
| 1422005_at | Eif2ak2 | 2.56 |
| 1455000_at | Gpr68 | 2.56 |
| 1415803_at | Cx3cl1 | 2.55 |
| 1422782_s_at | Tlr3 | 2.55 |
| 1416097_at | Lrrc4 | 2.54 |
| 1460651_at | Lat | 2.53 |
| 1427325_s_at | Akna | 2.53 |
| 1425603_at | Tmem176a | 2.49 |
| 1439595_at | Tcra | 2.49 |
| 1424041_s_at | C1s | 2.49 |
| 1418718_at | Cxcl16 | 2.48 |
| 1456061_at | Gimap8 | 2.47 |
| 1417056_at | Psme1 | 2.46 |
| 1418981_at | Casp12 | 2.46 |
| 1421211_a_at | Ciita | 2.46 |
| 1449235_at | Fasl | 2.45 |
| 1449265_at | Casp1 | 2.44 |
| 1424383_at | Tmem51 | 2.44 |
| 1425405_a_at | Adar | 2.43 |
| 1425902_a_at | Nfkb2 | 2.42 |
| 1452817_at | Smyd3 | 2.42 |
| 1416871_at | Adam8 | 2.42 |
| 1457917_at | Lck | 2.42 |
| 1449127_at | Selplg | 2.42 |
| 1416514_a_at | Fscn1 | 2.42 |
| 1439773_at | Ly6e | 2.41 |
| 1436223_at | Itgb8 | 2.41 |
| 1454268_a_at | Cyba | 2.41 |
| 1451821_a_at | Sp100 | 2.41 |
| 1444242_at | Slco2a1 | 2.40 |
| 1415983_at | Lcp1 | 2.40 |
| 1418293_at | Ifit2 | 2.39 |
| 1420671_x_at | Ms4a4c | 2.39 |
| 1450534_x_at | H2-K1 | 2.39 |
| 1418077_at | Trim21 | 2.39 |
| 1417496_at | Cp | 2.38 |
| 1435415_x_at | Marcksl1 | 2.37 |
| 1451320_at | Arhgap8 | 2.37 |
| 1427041_at | BC013712 | 2.36 |
| 1422139_at | Plau | 2.36 |
| 1441768_at | 9430051O21Rik | 2.35 |
| 1449455_at | Hck | 2.35 |
| 1421358_at | H2-M3 | 2.34 |
| 1436312_at | Ikzf1 | 2.34 |
| 1444632_at | BC064078 | 2.33 |
| 1450791_at | Nppb | 2.33 |
| 1424927_at | Glipr1 | 2.33 |
| 1419764_at | Chi3l3 | 2.33 |
| 1426093_at | Trim34a | 2.33 |
| 1420515_a_at | Pglyrp2 | 2.33 |
| 1448061_at | Msr1 | 2.33 |
| 1418641_at | Lcp2 | 2.32 |
| 1418842_at | Hcls1 | 2.31 |
| 1434400_at | Tgif2 | 2.31 |
| 1439494_at | Slc5a9 | 2.30 |
| 1448757_at | Pml | 2.28 |
| 1431339_a_at | Efhd2 | 2.28 |
| 1455581_x_at | Gm20559 | 2.28 |
| 1437132_x_at | Nedd9 | 2.27 |
| 1456307_s_at | Adcy7 | 2.27 |
| 1422932_a_at | Vav1 | 2.27 |
| 1450446_a_at | Socs1 | 2.27 |
| 1434068_s_at | AI662270 | 2.26 |
| 1416069_at | Pfkp | 2.26 |
| 1421210_at | Ciita | 2.26 |
| 1437785_at | Adamts9 | 2.25 |
| 1436230_at | Gpr114 | 2.25 |
| 1425119_at | Oas1b | 2.25 |
| 1449310_at | Ptger2 | 2.25 |

TABLE 15-continued

Differentially expressed genes in the skin of alopecic female C3H/HeJ mice vs. skin obtained from age-matched female C3H/HeJ mice without alopecia (n = 3 per group).

| Affy_ID | GeneSymbol | FC |
|---|---|---|
| 1440721_at | 5930433N17Rik | 2.25 |
| 1430352_at | Adamts9 | 2.25 |
| 1456377_x_at | Limd2 | 2.25 |
| 1449991_at | Cd244 | 2.25 |
| 1416051_at | C2 | 2.25 |
| 1455132_at | Rasal3 | 2.24 |
| 1422124_a_at | Ptprc | 2.24 |
| 1448576_at | Il7r | 2.23 |
| 1421931_at | Icos | 2.22 |
| 1436199_at | Trim14 | 2.21 |
| 1446509_at | Smox | 2.20 |
| 1430148_at | Rab19 | 2.20 |
| 1450170_x_at | H2-D1 | 2.19 |
| 1439736_at | 5830453J16Rik | 2.19 |
| 1451567_a_at | Ifi203 | 2.19 |
| 1433920_at | Sema4c | 2.18 |
| 1420913_at | Slco2a1 | 2.18 |
| 1439148_a_at | Pfkl | 2.18 |
| 1452544_x_at | H2-D1 | 2.18 |
| 1441600_at | C920021A13 | 2.17 |
| 1422804_at | Serpinb6b | 2.16 |
| 1453228_at | Stx11 | 2.15 |
| 1427682_a_at | Egr2 | 2.15 |
| 1428378_at | Zc3hav1 | 2.15 |
| 1430165_at | Stk17b | 2.15 |
| 1451321_a_at | Rbm43 | 2.15 |
| 1457780_at | Stx11 | 2.15 |
| 1439764_s_at | Igf2bp2 | 2.14 |
| 1435913_at | B4galnt4 | 2.14 |
| 1449220_at | Gimap3 | 2.13 |
| 1456251_x_at | Tspo | 2.13 |
| 1422781_at | Tlr3 | 2.13 |
| 1423135_at | Thy1 | 2.13 |
| 1424375_s_at | Gimap4 | 2.12 |
| 1428660_s_at | Tor3a | 2.12 |
| 1439012_a_at | Dck | 2.12 |
| 1441912_x_at | C2 | 2.12 |
| 1424704_at | Runx2 | 2.11 |
| 1424953_at | BC021614 | 2.11 |
| 1431843_at | Nfkbie | 2.10 |
| 1417219_s_at | Tmsb10 | 2.10 |
| 1448160_at | Lcp1 | 2.10 |
| 1427352_at | Krt79 | 2.10 |
| 1419194_s_at | Gmfg | 2.09 |
| 1460675_at | Igsf8 | 2.09 |
| 1426568_at | Slc2a9 | 2.08 |
| 1424961_at | Tapbpl | 2.08 |
| 1418099_at | Tnfrsf1b | 2.08 |
| 1422527_at | H2-DMa | 2.08 |
| 1426554_a_at | Pgam1 | 2.08 |
| 1438941_x_at | Ampd2 | 2.08 |
| 1450648_s_at | H2-Ab1 | 2.07 |
| 1440165_at | Ptprc | 2.07 |
| 1437724_x_at | Pitpnm1 | 2.07 |
| 1434364_at | Map3k14 | 2.06 |
| 1419537_at | Tfec | 2.06 |
| 1425728_at | Gm12185 | 2.06 |
| 1455966_s_at | Nudt21 | 2.05 |
| 1419282_at | Ccl12 | 2.05 |
| 1420404_at | Cd86 | 2.05 |
| 1415765_at | Hnrnpul2 | 2.05 |
| 1422511_a_at | Ogfr | 2.05 |
| 1425548_a_at | Lst1 | 2.05 |
| 1427683_at | Egr2 | 2.05 |
| 1453757_at | Herc6 | 2.04 |
| 1435331_at | Pyhin1 | 2.04 |
| 1419119_at | Hcst | 2.03 |
| 1458229_at | Robo2 | 2.03 |
| 1422808_s_at | Dock2 | 2.03 |
| 1437213_at | Nudt21 | 2.02 |
| 1429831_at | Pik3ap1 | 2.01 |
| 1439808_at | Ipcef1 | 2.01 |
| 1428891_at | Parm1 | 2.01 |
| 1427765_a_at | Tcrb-J | 2.01 |
| 1426133_a_at | Mitd1 | 2.00 |
| 1425016_at | Ephb2 | 2.00 |
| 1422562_at | Rrad | 2.00 |
| 1418110_a_at | Inpp5d | 2.00 |
| 1420272_at | Samhd1 | 2.00 |
| 1417928_at | Pdlim4 | 2.00 |
| 1460220_a_at | Csf1 | 2.00 |
| 1451828_a_at | Acsl4 | 2.00 |
| 1435672_at | 3830612M24 | 1.99 |
| 1453181_x_at | Plscr1 | 1.99 |
| 1428767_at | Gsdmd | 1.99 |
| 1436861_at | Il7 | 1.99 |
| 1437270_a_at | Clcf1 | 1.99 |
| 1419202_at | Cst7 | 1.98 |
| 1435529_at | Gm14446 | 1.98 |
| 141980_x_at | Arhgap9 | 1.98 |
| 1429525_s_at | Myo1f | 1.98 |
| 1437308_s_at | F2r | 1.98 |
| 1419676_at | Mx2 | 1.98 |
| 1455019_x_at | Ckap4 | 1.98 |
| 1438948_x_at | Tspo | 1.97 |
| 1448618_at | Mvp | 1.97 |
| 1436365_at | Zbtb7c | 1.97 |
| 1418464_at | Matn4 | 1.97 |
| 1439093_at | Hspa4l | 1.97 |
| 1435193_at | A230050P20Rik | 1.97 |
| 1439065_x_at | Gm13152 | 1.97 |
| 1423306_at | 2010002N04Rik | 1.97 |
| 1430658_a_at | Gsdma2 | 1.97 |
| 1419469_at | Gnb4 | 1.96 |
| 1426725_s_at | Ets1 | 1.96 |
| 1417288_at | Plekha2 | 1.96 |
| 1456586_x_at | Mvp | 1.96 |
| 1426415_a_at | Trim25 | 1.95 |
| 1437249_at | Skap1 | 1.95 |
| 1433517_at | Myeov2 | 1.95 |
| 1425374_at | Oas3 | 1.95 |
| 1425681_a_at | Prnd | 1.95 |
| 1436659_at | Dclk1 | 1.94 |
| 1446326_at | Col1a2 | 1.94 |
| 1435596_at | Pion | 1.94 |
| 1416492_at | Ccne1 | 1.94 |
| 1422701_at | Zap70 | 1.93 |
| 1435517_x_at | Ralb | 1.93 |
| 1436902_x_at | Tmsb10 | 1.93 |
| 1425166_at | Rbl1 | 1.93 |
| 1421207_at | Lif | 1.93 |
| 1460134_at | 9330175E14Rik | 1.93 |
| 1420273_x_at | Samhd1 | 1.93 |
| 1443621_at | Xaf1 | 1.92 |
| 1425078_x_at | C130026I21Rik | 1.92 |
| 1427994_at | Cd300lf | 1.91 |
| 1456545_at | Il18rap | 1.91 |
| 1418346_at | Insl6 | 1.91 |
| 1428372_at | St5 | 1.91 |
| 1417045_at | Bid | 1.91 |
| 1433699_at | Tnfaip3 | 1.91 |
| 1440275_at | Runx3 | 1.91 |
| 1460253_at | Cmtm7 | 1.91 |
| 1421188_at | Ccr2 | 1.90 |
| 1427911_at | Tmem173 | 1.90 |
| 1420653_at | Tgfb1 | 1.90 |
| 1437643_at | Cenpj | 1.90 |
| 1443687_x_at | H2-DMb2 | 1.90 |
| 1440299_at | E330016A19Rik | 1.90 |
| 1425151_a_at | Noxo1 | 1.90 |
| 1441097_at | Vangl1 | 1.90 |
| 1449988_at | Gimap1 | 1.89 |
| 1427404_x_at | Gm5506 | 1.89 |
| 1425617_at | Dhx9 | 1.88 |
| 1426926_at | Plcg2 | 1.88 |
| 1424037_at | Itpka | 1.88 |
| 1449925_at | Cxcr3 | 1.88 |
| 1435394_s_at | Rhoc | 1.87 |

TABLE 15-continued

Differentially expressed genes in the skin of alopecic female C3H/HeJ mice vs. skin obtained from age-matched female C3H/HeJ mice without alopecia (n = 3 per group).

| Affy_ID | GeneSymbol | FC |
|---|---|---|
| 1453392_at | Ttc39b | 1.87 |
| 1449473_s_at | Cd40 | 1.87 |
| 1419186_a_at | St8sia4 | 1.86 |
| 1455898_x_at | Slc2a3 | 1.86 |
| 1430447_a_at | Lair1 | 1.86 |
| 1418353_at | Cd5 | 1.85 |
| 1449425_at | Wnt2 | 1.85 |
| 1439114_at | Ddx60 | 1.85 |
| 1425084_at | Gimap7 | 1.85 |
| 1425819_at | Zbtb7c | 1.85 |
| 1416001_a_at | Cotl1 | 1.84 |
| 1422704_at | Gyk | 1.84 |
| 1445452_at | Traf1 | 1.84 |
| 1438852_x_at | Mcm6 | 1.84 |
| 1436423_at | Themis | 1.84 |
| 1417599_at | Cd276 | 1.84 |
| 1421930_at | Icos | 1.84 |
| 1421814_at | Msn | 1.83 |
| 1419132_at | Tlr2 | 1.83 |
| 1448568_a_at | Slc20a1 | 1.83 |
| 1423602_at | Traf1 | 1.83 |
| 1451931_x_at | H2-1 | 1.82 |
| 1456836_at | Itk | 1.82 |
| 1453129_a_at | Rgs12 | 1.82 |
| 1426454_at | Arhgdib | 1.82 |
| 1451385_at | Fam162a | 1.82 |
| 1419470_at | Gnb4 | 1.82 |
| 1435697_a_at | Cytip | 1.82 |
| 1424214_at | Parm1 | 1.81 |
| 1458524_at | Fndc3a | 1.81 |
| 1455051_at | Rnf31 | 1.81 |
| 1452163_at | Ets1 | 1.81 |
| 1448328_at | Sh3bp2 | 1.80 |
| 1456700_x_at | Marcks | 1.80 |
| 1451784_x_at | H2-D1 | 1.80 |
| 1437606_at | Btbd19 | 1.80 |
| 1439476_at | Dsg2 | 1.80 |
| 1440878_at | Runx1 | 1.79 |
| 1453472_a_at | Slamf7 | 1.79 |
| 1434653_at | Ptk2b | 1.79 |
| 1436708_x_at | Mcm4 | 1.79 |
| 1454592_at | 9430012M22Rik | 1.79 |
| 1433954_at | 4632419I22Rik | 1.78 |
| 1426315_a_at | 6330416G13Rik | 1.78 |
| 1451289_at | Dclk1 | 1.78 |
| 1443686_at | H2-DMb2 | 1.78 |
| 1449903_at | Crtam | 1.78 |
| 1418090_at | Plvap | 1.78 |
| 1460250_at | Sostdc1 | 1.77 |
| 1435749_at | Gda | 1.77 |
| 1450269_a_at | Pfk1 | 1.77 |
| 1438910_a_at | Stom | 1.77 |
| 1437868_at | Fam46a | 1.77 |
| 1448449_at | Ripk3 | 1.77 |
| 1424496_at | 5133401N09Rik | 1.77 |
| 1438854_x_at | Pitpnm1 | 1.77 |
| 1424930_s_at | Fam83f | 1.77 |
| 1460378_a_at | Tes | 1.77 |
| 1448914_a_at | Csf1 | 1.76 |
| 1448659_at | Casp7 | 1.76 |
| 1427689_a_at | Tnip1 | 1.76 |
| 1428242_at | Hmha1 | 1.76 |
| 1455975_x_at | Rnf114 | 1.76 |
| 1453076_at | Batf3 | 1.76 |
| 1419125_at | Ptpn18 | 1.76 |
| 1424524_at | Dram1 | 1.76 |
| 1453202_at | E330016A19Rik | 1.76 |
| 1428346_at | Trafd1 | 1.76 |
| 1451987_at | Arrb2 | 1.76 |
| 1417790_at | Dok1 | 1.76 |
| 1418244_at | Naa20 | 1.75 |
| 1416226_at | Arpc1b | 1.75 |
| 1438634_x_at | Lasp1 | 1.75 |
| 1419209_at | Cxcl1 | 1.75 |
| 1451363_a_at | Dennd2d | 1.75 |
| 1430622_at | 4833423F13Rik | 1.74 |
| 1447788_s_at | Tspyl3 | 1.74 |
| 1456310_a_at | 2610002J02Rik | 1.74 |
| 1455251_at | Itga1 | 1.74 |
| 1416750_at | Sigmar1 | 1.74 |
| 1421830_at | Ak4 | 1.74 |
| 1417346_at | Pycard | 1.74 |
| 1436958_x_at | Tpm3 | 1.74 |
| 1434069_at | Prex1 | 1.74 |
| 1440249_at | Aknad1 | 1.74 |
| 1442849_at | Lrp1 | 1.74 |
| 1451174_at | Lrrc33 | 1.73 |
| 1451411_at | Gprc5b | 1.73 |
| 1460469_at | Tnfrsf9 | 1.73 |
| 1452661_at | Tfrc | 1.73 |
| 1430534_at | Rnase6 | 1.73 |
| 1456028_x_at | Marcks | 1.73 |
| 1448731_at | Il10ra | 1.73 |
| 1418257_at | Slc12a7 | 1.73 |
| 1420170_at | Myh9 | 1.72 |
| 1424032_at | Hvcn1 | 1.72 |
| 1435748_at | Gda | 1.72 |
| 1451285_at | Fus | 1.72 |
| 1454607_s_at | Psat1 | 1.72 |
| 1434089_at | Synpo | 1.71 |
| 1421525_a_at | Naip5 | 1.71 |
| 1458415_at | Clec2e | 1.71 |
| 1419721_at | Niacr1 | 1.71 |
| 1453328_at | 2700008G24Rik | 1.71 |
| 1435337_at | Tshz3 | 1.71 |
| 1456011_x_at | Acaa1a | 1.71 |
| 1423986_a_at | Shisa5 | 1.71 |
| 1427386_at | Arhgef16 | 1.70 |
| 1443123_at | Tanc2 | 1.70 |
| 1418674_at | Osmr | 1.70 |
| 1445588_at | Ankrd44 | 1.70 |
| 1424552_at | Casp8 | 1.70 |
| 1439261_x_at | Mitd1 | 1.70 |
| 1452428_a_at | B2m | 1.70 |
| 1418045_at | Inpp1 | 1.70 |
| 1441317_x_at | Jakmip1 | 1.70 |
| 1436589_x_at | Prkd2 | 1.70 |
| 1437503_a_at | Shisa5 | 1.70 |
| 1421578_at | Ccl4 | 1.70 |
| 1435227_at | Bcl11b | 1.70 |
| 1436177_at | Plekha2 | 1.70 |
| 1457644_s_at | Cxcl1 | 1.70 |
| 1429527_a_at | Plscr1 | 1.70 |
| 1433531_at | Acsl4 | 1.69 |
| 1420731_a_at | Csrp2 | 1.69 |
| 1438097_at | Rab20 | 1.69 |
| 1426239_s_at | Arrb2 | 1.69 |
| 1427182_s_at | D18Ertd653e | 1.69 |
| 1435338_at | Cdk6 | 1.69 |
| 1433885_at | Iqgap2 | 1.69 |
| 1450852_s_at | F2r | 1.69 |
| 1446507_at | Kif24 | 1.69 |
| 1450456_at | Il21r | 1.69 |
| 1418612_at | Slfn1 | 1.68 |
| 1438974_x_at | Pitpnm1 | 1.68 |
| 1439030_at | Gmppb | 1.68 |
| 1416619_at | 4632428N05Rik | 1.68 |
| 1441880_x_at | Tmem149 | 1.68 |
| 1448797_at | Elk3 | 1.68 |
| 1443794_x_at | Noc4l | 1.68 |
| 1452289_a_at | Rnf135 | 1.68 |
| 1450918_s_at | Src | 1.67 |
| 1420955_at | Vsnl1 | 1.67 |
| 1418751_at | Sit1 | 1.67 |
| 1447568_at | Gatc | 1.67 |
| 1460700_at | Stat3 | 1.67 |
| 1419911_at | Coro1c | 1.66 |
| 1452966_at | Bcl11b | 1.66 |

TABLE 15-continued

Differentially expressed genes in the skin of alopecic female C3H/HeJ mice vs. skin obtained from age-matched female C3H/HeJ mice without alopecia (n = 3 per group).

| Affy_ID | GeneSymbol | FC |
|---|---|---|
| 1421550_a_at | Trim34a | 1.66 |
| 1423686_a_at | Prr13 | 1.66 |
| 1455287_at | Cdk6 | 1.66 |
| 1439422_a_at | Fam132a | 1.66 |
| 1416935_at | Trpv2 | 1.66 |
| 1436183_at | Zc3hav1 | 1.66 |
| 1451314_a_at | Vcam1 | 1.66 |
| 1417300_at | Smpdl3b | 1.66 |
| 1419097_a_at | Stom | 1.66 |
| 1446939_at | Trim12a | 1.65 |
| 1423411_at | Rbm47 | 1.65 |
| 1450355_a_at | Capg | 1.65 |
| 1436220_at | Zfp287 | 1.65 |
| 1429742_at | Rcbtb2 | 1.65 |
| 1455221_at | Abcg1 | 1.65 |
| 1438934_x_at | Sema4a | 1.65 |
| 1452836_at | Lpin2 | 1.65 |
| 1427874_at | Rnf114 | 1.64 |
| 1452425_at | Tnfrsf14 | 1.64 |
| 1422303_a_at | Tnfrsf18 | 1.64 |
| 1418396_at | Gpsm3 | 1.64 |
| 1451462_a_at | Ifnar2 | 1.64 |
| 1447711_x_at | 4933412E12Rik | 1.64 |
| 1454757_s_at | Ifi27l1 | 1.64 |
| 1424246_a_at | Tes | 1.64 |
| 1459872_x_at | H2-DMa | 1.64 |
| 1424304_at | Tpcn2 | 1.64 |
| 1416695_at | Tspo | 1.64 |
| 1451475_at | Plxnd1 | 1.64 |
| 1428727_at | Cep192 | 1.64 |
| 1440779_s_at | Slc5a9 | 1.63 |
| 1433451_at | Cdk5r1 | 1.63 |
| 1450531_at | H2-B1 | 1.63 |
| 1458601_at | 8030447M02Rik | 1.63 |
| 1426739_at | Donson | 1.63 |
| 1423350_at | Socs5 | 1.63 |
| 1456467_s_at | Nlk | 1.63 |
| 1447803_x_at | Capg | 1.63 |
| 1453201_at | Rassf10 | 1.63 |
| 1438148_at | Cxcl3 | 1.63 |
| 1444197_at | Rinl | 1.63 |
| 1428859_at | Paox | 1.63 |
| 1455656_at | Btla | 1.63 |
| 1455080_at | Ppp1r16b | 1.63 |
| 1424857_a_at | Trim34a | 1.62 |
| 1450140_a_at | Cdkn2a | 1.62 |
| 1438095_x_at | Noc4l | 1.62 |
| 1460231_at | Irf5 | 1.62 |
| 1426318_at | Serpinb1b | 1.62 |
| 1427348_at | Zc3h12a | 1.62 |
| 1451862_a_at | Prf1 | 1.62 |
| 1442944_at | C76555 | 1.62 |
| 1420635_a_at | Tcirg1 | 1.62 |
| 1435143_at | Elk3 | 1.62 |
| 1449623_at | Txnrd3 | 1.61 |
| 1458345_s_at | Colec11 | 1.61 |
| 1423812_s_at | Vopp1 | 1.61 |
| 1417561_at | Apoc1 | 1.61 |
| 1455818_at | 4930427A07Rik | 1.60 |
| 1426757_at | Ampd2 | 1.60 |
| 1418265_s_at | Irf2 | 1.60 |
| 1434185_at | Acaca | 1.60 |
| 1437327_x_at | Enoph1 | 1.60 |
| 1456240_x_at | Cdca4 | 1.60 |
| 1443086_at | Alcam | 1.60 |
| 1442018_at | Btg1 | 1.60 |
| 1418686_at | Oas1c | 1.60 |
| 1441843_s_at | 5230400M03Rik | 1.60 |
| 1443882_at | Slc26a2 | 1.60 |
| 1420909_at | Vegfa | 1.60 |
| 1439587_at | Lemd3 | 1.60 |
| 1433169_at | 5830456J23Rik | 1.60 |
| 1437451_at | Ecscr | 1.59 |
| 1436074_at | Nfkbid | 1.59 |
| 1437789_at | Birc6 | 1.59 |
| 1450716_at | Adamts1 | 1.59 |
| 1438828_at | Rapgef6 | 1.59 |
| 1453064_at | Etaa1 | 1.59 |
| 1439047_s_at | Recql | 1.59 |
| 1435316_at | Psma6 | 1.59 |
| 1428484_at | Osbpl3 | 1.59 |
| 1417627_a_at | Limk1 | 1.59 |
| 1459884_at | Cox7c | 1.59 |
| 1455660_at | Csf2rb | 1.59 |
| 1448511_at | Ptprcap | 1.59 |
| 1440245_at | Ccdc88b | 1.59 |
| 1418587_at | Traf3 | 1.59 |
| 1424339_at | Oasl1 | 1.58 |
| 1416166_a_at | Prdx4 | 1.58 |
| 1427095_at | Cdcp1 | 1.58 |
| 1456288_at | Slfn5 | 1.58 |
| 1452239_at | Gt(ROSA)26Sor | 1.58 |
| 1449516_x_at | Rgs3 | 1.58 |
| 1424829_at | A830007P12Rik | 1.58 |
| 1454402_at | Zfp942 | 1.58 |
| 1434139_at | Parp11 | 1.58 |
| 1428583_at | Nufip2 | 1.58 |
| 1451097_at | Vasp | 1.58 |
| 1458595_at | Intu | 1.58 |
| 1457550_at | 9530059O14Rik | 1.58 |
| 1419530_at | Il12b | 1.58 |
| 1447762_x_at | Car12 | 1.58 |
| 1417588_at | Galnt3 | 1.58 |
| 1437052_s_at | Slc2a3 | 1.58 |
| 1435084_at | C730049O14Rik | 1.58 |
| 1419235_s_at | Helb | 1.57 |
| 1440147_at | Lgi2 | 1.57 |
| 1460347_at | Krt14 | 1.57 |
| 1452991_at | Chd2 | 1.57 |
| 1429758_at | 1700017B05Rik | 1.57 |
| 1449508_at | Il27ra | 1.57 |
| 1416087_at | Ap1s1 | 1.57 |
| 1438673_at | Slc4a7 | 1.57 |
| 1438750_at | Atrx | 1.57 |
| 1423869_s_at | Txnrd3 | 1.57 |
| 1420692_at | Il2ra | 1.57 |
| 1449227_at | Ch25h | 1.57 |
| 1425241_a_at | Wsb1 | 1.57 |
| 1450387_s_at | Ak4 | 1.56 |
| 1427164_at | Il13ra1 | 1.56 |
| 1455084_x_at | Shmt2 | 1.56 |
| 1452169_a_at | Dgkz | 1.56 |
| 1420505_a_at | Stxbp1 | 1.56 |
| 1455839_at | Uggt1 | 1.56 |
| 1428118_at | Lingo1 | 1.56 |
| 1427539_at | Zwint | 1.56 |
| 1418271_at | Bhlhe22 | 1.56 |
| 1447851_x_at | Atp10a | 1.56 |
| 1452837_at | Lpin2 | 1.56 |
| 1420171_s_at | Myh9 | 1.55 |
| 1439253_x_at | Prelid1 | 1.55 |
| 1452803_at | Glipr2 | 1.55 |
| 1456914_at | Slc16a4 | 1.55 |
| 1448202_x_at | Prelid1 | 1.55 |
| 1452391_at | Cxadr | 1.55 |
| 1435595_at | 1810011O10Rik | 1.55 |
| 1452903_at | 6230427J02Rik | 1.55 |
| 1451110_at | Egln1 | 1.55 |
| 1435564_at | Neurl1b | 1.55 |
| 1422489_at | Mogs | 1.55 |
| 1452337_at | 4930427A07Rik | 1.54 |
| 1459983_at | Impa2 | 1.54 |
| 1432997_at | 5830462P14Rik | 1.54 |
| 1457304_at | D13Ertd787e | 1.54 |
| 1417955_at | Ccdc71 | 1.54 |
| 1428034_a_at | Tnfrsf9 | 1.54 |
| 1439455_x_at | Capza1 | 1.54 |
| 1451608_a_at | Tspan33 | 1.54 |

TABLE 15-continued

Differentially expressed genes in the skin of alopecic female C3H/HeJ mice vs. skin obtained from age-matched female C3H/HeJ mice without alopecia (n = 3 per group).

| Affy_ID | GeneSymbol | FC |
|---|---|---|
| 1417878_at | E2f1 | 1.54 |
| 1448894_at | Akr1b8 | 1.54 |
| 1455067_at | Psd4 | 1.53 |
| 1457410_at | Arhgap5 | 1.53 |
| 1436848_x_at | Impa1 | 1.53 |
| 1436395_at | Card6 | 1.53 |
| 1436729_at | Afap1 | 1.53 |
| 1437185_s_at | Tmsb10 | 1.53 |
| 1428018_a_at | AF251705 | 1.53 |
| 1431528_at | 5830427D02Rik | 1.53 |
| 1425760_a_at | Pitpnm1 | 1.53 |
| 1418492_at | Grem2 | 1.53 |
| 1445201_at | Zfp53 | 1.53 |
| 1459894_at | Iqgap2 | 1.53 |
| 1438154_x_at | 2610002J02Rik | 1.53 |
| 1434573_at | Traf3ip3 | 1.53 |
| 1433739_at | Nol10 | 1.53 |
| 1434070_at | Jag1 | 1.52 |
| 1423826_at | Noc4l | 1.52 |
| 1416875_at | Parvg | 1.52 |
| 1447792_x_at | Gpr174 | 1.52 |
| 1417128_at | Plekho1 | 1.52 |
| 1427260_a_at | Tpm3 | 1.52 |
| 1416379_at | Panx1 | 1.52 |
| 1437239_x_at | Phc2 | 1.52 |
| 1451415_at | 1810011O10Rik | 1.52 |
| 1448713_at | Stat4 | 1.52 |
| 1421937_at | Dapp1 | 1.51 |
| 1433748_at | Zdhhc18 | 1.51 |
| 1454350_at | Intu | 1.51 |
| 1429128_x_at | Nfkb2 | 1.51 |
| 1418004_a_at | Tmem176b | 1.51 |
| 1423154_at | BC005537 | 1.51 |
| 1426677_at | Flna | 1.51 |
| 1448600_s_at | Vav3 | 1.51 |
| 1457539_at | D10Ertd709e | 1.51 |
| 1420914_at | Slco2a1 | 1.51 |
| 1429247_at | Anxa6 | 1.51 |
| 1452411_at | Lrrc1 | 1.51 |
| 1449619_s_at | Arhgap9 | 1.51 |
| 1420351_at | Tnfrsf4 | 1.51 |
| 1437242_at | Ttll2 | 1.51 |
| 1439444_x_at | Tmed10 | 1.50 |
| 1448933_at | Pcdhb17 | 1.50 |
| 1434219_at | Stim2 | 1.50 |
| 1455428_at | Fam53b | 1.50 |
| 1419226_at | Cd96 | 1.50 |
| 1435169_at | A930001N09Rik | 0.67 |
| 1451348_at | Deptor | 0.67 |
| 1425411_at | Arl4a | 0.67 |
| 1428864_at | Dusp8 | 0.67 |
| 1426522_at | Hadhb | 0.67 |
| 1417312_at | Dkk3 | 0.67 |
| 1418190_at | Pon1 | 0.67 |
| 1454078_a_at | Gal3st1 | 0.66 |
| 1425145_at | Il1rl1 | 0.66 |
| 1417421_at | S100a1 | 0.66 |
| 1460192_at | Osbpl1a | 0.66 |
| 1419963_at | Deptor | 0.66 |
| 1415743_at | Hdac5 | 0.66 |
| 1435559_at | Myo6 | 0.66 |
| 1450395_at | Slc22a5 | 0.66 |
| 1428469_a_at | Dzip1 | 0.66 |
| 1429884_at | Srgap2 | 0.66 |
| 1450971_at | Gadd45b | 0.66 |
| 1436344_at | C2cd2 | 0.66 |
| 1418921_at | Cadm3 | 0.65 |
| 1421471_at | Npy1r | 0.65 |
| 1453571_at | Deptor | 0.65 |
| 1452283_at | Rassf8 | 0.65 |
| 1416268_at | Ets2 | 0.65 |
| 1423364_a_at | Aktip | 0.65 |
| 1453069_at | Pik3cb | 0.65 |
| 1422838_at | Kcnu1 | 0.65 |
| 1433977_at | Hs3st3b1 | 0.65 |
| 1426010_a_at | Epb4.1l3 | 0.65 |
| 1455029_at | Kif21a | 0.65 |
| 1460406_at | Pls1 | 0.65 |
| 1434581_at | 2410066E13Rik | 0.65 |
| 1422740_at | Tnfrsf21 | 0.65 |
| 1435396_at | Stxbp6 | 0.65 |
| 1419688_at | Gpc6 | 0.65 |
| 1418658_at | Fam82b | 0.65 |
| 1419457_at | Rgnef | 0.65 |
| 1443904_at | Fads6 | 0.65 |
| 1425186_at | Lmbrd1 | 0.65 |
| 1450286_at | Npr3 | 0.65 |
| 1425037_at | Fgd4 | 0.64 |
| 1437871_at | Pgm5 | 0.64 |
| 1416774_at | Wee1 | 0.64 |
| 1458129_at | Rora | 0.64 |
| 1433460_at | Ttc7b | 0.64 |
| 1451200_at | Kif1b | 0.64 |
| 1448320_at | Stim1 | 0.64 |
| 1452309_at | Cgnl1 | 0.64 |
| 1454824_s_at | Mtus1 | 0.64 |
| 1415981_at | Herpud2 | 0.64 |
| 1419505_a_at | Ggps1 | 0.64 |
| 1457686_at | Akap17b | 0.63 |
| 1437149_at | Slc6a6 | 0.63 |
| 1437661_at | AU021092 | 0.63 |
| 1443906_at | Cd55 | 0.63 |
| 1451714_a_at | Map2k3 | 0.63 |
| 1435693_at | Mall | 0.63 |
| 1451563_at | Emr4 | 0.63 |
| 1452333_at | Smarca2 | 0.63 |
| 1428835_at | Myh14 | 0.63 |
| 1433711_s_at | Sesn1 | 0.63 |
| 1448669_at | Dkk3 | 0.63 |
| 1416778_at | Sdpr | 0.63 |
| 1449082_at | Mfap5 | 0.63 |
| 142589_a_at | Grtp1 | 0.63 |
| 1418250_at | Arl4d | 0.63 |
| 1458882_at | Serpinb8 | 0.62 |
| 1418714_at | Dusp8 | 0.62 |
| 1431216_s_at | Dnajc6 | 0.62 |
| 1426208_x_at | Plagl1 | 0.62 |
| 1425138_at | Guca1b | 0.62 |
| 1425318_a_at | Tmem116 | 0.62 |
| 1423176_at | Tob1 | 0.62 |
| 1425515_at | Pik3r1 | 0.62 |
| 1455665_at | Lonrf1 | 0.62 |
| 1426576_at | Sgms1 | 0.62 |
| 1440559_at | Hmga2-ps1 | 0.62 |
| 1417545_at | Trpv4 | 0.62 |
| 1418954_at | Camkk1 | 0.62 |
| 1424701_at | Pcdh20 | 0.62 |
| 1454881_s_at | Upk3b | 0.62 |
| 1419378_a_at | Fxyd2 | 0.62 |
| 1448926_at | Hoxa5 | 0.62 |
| 1437731_at | C2cd2 | 0.62 |
| 1436501_at | Mtus1 | 0.61 |
| 1450110_at | Adh7 | 0.61 |
| 1417013_at | Hspb8 | 0.61 |
| 1443969_at | Irs2 | 0.61 |
| 1450206_at | Dlc1 | 0.61 |
| 1428774_at | Gpc6 | 0.61 |
| 1422904_at | Fmo2 | 0.61 |
| 1425321_a_at | Clmn | 0.61 |
| 1426743_at | Appl2 | 0.61 |
| 1427945_at | Dpyd | 0.61 |
| 1428321_at | Eml1 | 0.60 |
| 1431226_a_at | Fndc4 | 0.60 |
| 1421848_at | Slc22a5 | 0.60 |
| 1428731_at | Usp54 | 0.60 |
| 1456939_at | Fam154b | 0.60 |
| 1424408_at | Lims2 | 0.60 |
| 1426139_a_at | Ccrl1 | 0.60 |

TABLE 15-continued

Differentially expressed genes in the skin of alopecic female C3H/HeJ mice vs. skin obtained from age-matched female C3H/HeJ mice without alopecia (n = 3 per group).

| Affy_ID | GeneSymbol | FC |
|---|---|---|
| 1426332_a_at | Cldn3 | 0.60 |
| 1416823_a_at | Osbpl1a | 0.60 |
| 1423994_at | Kif1b | 0.60 |
| 1415904_at | Lpl | 0.60 |
| 1429656_at | Rhobtb1 | 0.60 |
| 1421158_at | Cghl1 | 0.60 |
| 1456150_at | Jhdm1d | 0.60 |
| 1454604_s_at | Tspan12 | 0.59 |
| 1434307_at | Tmem64 | 0.59 |
| 1431188_a_at | Tom1 | 0.59 |
| 1416926_at | Trp53inp1 | 0.59 |
| 1423447_at | Clpx | 0.59 |
| 1451782_a_at | Slc29a1 | 0.59 |
| 1423174_a_at | Pard6b | 0.59 |
| 1436293_x_at | Ildr2 | 0.59 |
| 1444073_at | Maf | 0.59 |
| 1447462_at | D7Wsu130e | 0.59 |
| 1424280_at | Mospd1 | 0.59 |
| 1451270_at | Dusp18 | 0.59 |
| 1451207_at | Micu1 | 0.59 |
| 1455056_at | Lmo7 | 0.59 |
| 1437409_s_at | Gpr126 | 0.59 |
| 1436988_at | Ism1 | 0.58 |
| 1420718_at | Odz2 | 0.58 |
| 1425456_a_at | Map2k3 | 0.58 |
| 1450318_a_at | P2ry2 | 0.58 |
| 1436853_a_at | Snca | 0.58 |
| 1424437_s_at | Abcg4 | 0.58 |
| 1426285_at | Lama2 | 0.58 |
| 1417962_s_at | Ghr | 0.58 |
| 1455340_at | Dennd5b | 0.58 |
| 1415874_at | Spry1 | 0.58 |
| 1435105_at | Rnf208 | 0.58 |
| 1428240_at | Nrxn1 | 0.58 |
| 1425906_a_at | Sema3e | 0.58 |
| 1454926_at | Sphkap | 0.58 |
| 1416316_at | Slc27a2 | 0.58 |
| 1434917_at | Cobl | 0.57 |
| 1429778_at | Optn | 0.57 |
| 1436350_at | Fam171b | 0.57 |
| 1452207_at | Cited2 | 0.57 |
| 1428547_at | Nt5e | 0.57 |
| 1426263_at | Cadm4 | 0.57 |
| 1429036_at | Otop3 | 0.57 |
| 1435763_at | Tbc1d16 | 0.57 |
| 1420942_s_at | Rgs5 | 0.57 |
| 1450974_at | Timp4 | 0.57 |
| 1434639_at | Klhl29 | 0.56 |
| 1421346_a_at | Slc6a6 | 0.56 |
| 1433742_at | Kank1 | 0.56 |
| 1435207_at | Dixdc1 | 0.56 |
| 1450838_x_at | Rpl37 | 0.56 |
| 1457671_at | Homer2 | 0.56 |
| 1422008_a_at | Aqp3 | 0.56 |
| 1415864_at | Bpgm | 0.56 |
| 1437181_at | Peli2 | 0.56 |
| 1416072_at | Cd34 | 0.56 |
| 1460514_s_at | Ascl2 | 0.56 |
| 1420941_at | Rgs5 | 0.56 |
| 1423966_at | Cd99l2 | 0.55 |
| 1435435_at | Cttnbp2 | 0.55 |
| 1428336_at | Agpat4 | 0.55 |
| 1419458_at | Rgnef | 0.55 |
| 1424567_at | Tspan2 | 0.55 |
| 1419491_at | Defb1 | 0.55 |
| 1415865_s_at | Bpgm | 0.55 |
| 1422667_at | Krt15 | 0.55 |
| 1417355_at | Peg3 | 0.55 |
| 1439478_at | Acot2 | 0.55 |
| 1450460_at | Aqp3 | 0.55 |
| 1426510_at | Seepdh | 0.55 |
| 422996_at | Acot2 | 0.55 |
| 1433454_at | Abtb2 | 0.55 |
| 1436640_x_at | Agpat4 | 0.55 |
| 1453008_at | Trnp1 | 0.55 |
| 1424392_at | Adhfe1 | 0.54 |
| 1417332_at | Rfx2 | 0.54 |
| 1419197_x_at | Hamp | 0.54 |
| 1429001_at | Pir | 0.54 |
| 1438496_a_at | Ddx26b | 0.54 |
| 1454699_at | Sesn1 | 0.54 |
| 1437217_at | Ankrd6 | 0.54 |
| 1418412_at | Tpd52l1 | 0.54 |
| 1424747_at | Kif1c | 0.54 |
| 1454646_at | Tcp11l2 | 0.54 |
| 1421040_a_at | Gsta2 | 0.53 |
| 1434326_x_at | Coro2b | 0.53 |
| 1417027_at | Trim2 | 0.53 |
| 1460242_at | Cd55 | 0.53 |
| 1453119_at | Otud1 | 0.53 |
| 1420688_a_at | Sgce | 0.53 |
| 1450119_at | Dst | 0.53 |
| 1448119_at | Bpgm | 0.53 |
| 1456481_at | Esyt3 | 0.53 |
| 1422168_a_at | Bdnf | 0.53 |
| 1434542_at | Gpt2 | 0.52 |
| 1422905_s_at | Fmo2 | 0.52 |
| 1425809_at | Fabp4 | 0.52 |
| 1439549_at | Prrg3 | 0.52 |
| 1448416_at | Mgp | 0.52 |
| 1437197_at | Sorbs2 | 0.52 |
| 1422619_at | Ppap2a | 0.52 |
| 1436737_a_at | Sorbs1 | 0.52 |
| 1422620_s_at | Ppap2a | 0.52 |
| 1427378_at | Krt75 | 0.52 |
| 1416779_at | Sdpr | 0.51 |
| 1451501_a_at | Ghr | 0.51 |
| 1423506_a_at | Nnat | 0.51 |
| 1422974_at | Nt5e | 0.51 |
| 1425761_a_at | Nfatc1 | 0.51 |
| 1458268_s_at | Igfbp3 | 0.51 |
| 1460241_a_at | St3gal5 | 0.50 |
| 1417028_a_at | Trim2 | 0.50 |
| 1456397_at | Cdh4 | 0.50 |
| 1434156_at | Rab11fip4 | 0.50 |
| 1429024_at | Rbm20 | 0.50 |
| 1441254_at | Pard3b | 0.50 |
| 1419289_a_at | Syngr1 | 0.50 |
| 1422112_at | Ccbp2 | 0.50 |
| 1444559_at | Phtf2 | 0.50 |
| 1451410_a_at | Crip3 | 0.50 |
| 1420017_at | Tspan8 | 0.50 |
| 1416194_at | Cyp4b1 | 0.50 |
| 1434013_at | Ablim3 | 0.49 |
| 1419706_a_at | Akap12 | 0.49 |
| 1451762_a_at | Kif1b | 0.49 |
| 1427371_at | Abca8a | 0.49 |
| 1424007_at | Gdf10 | 0.49 |
| 1424155_at | Fabp4 | 0.48 |
| 1428357_at | 2610019F03Rik | 0.48 |
| 1454654_at | Dirc2 | 0.48 |
| 1456796_at | Snai3 | 0.48 |
| 1417702_a_at | Hnmt | 0.48 |
| 1450738_at | Kif21a | 0.48 |
| 1422007_at | Aqp3 | 0.48 |
| 1417014_at | Hspb8 | 0.47 |
| 1438422_at | Lrrc20 | 0.47 |
| 1417029_a_at | Trim2 | 0.47 |
| 1417673_at | Grb14 | 0.47 |
| 1428471_at | Sorbs1 | 0.47 |
| 1439117_at | Clmn | 0.47 |
| 1427946_s_at | Dpyd | 0.46 |
| 1418317_at | Lhx2 | 0.46 |
| 1424367_a_at | Homer2 | 0.46 |
| 1454691_at | Nrxn1 | 0.46 |
| 1419082_at | Serpinb2 | 0.46 |
| 1434651_a_at | Cldn3 | 0.46 |
| 1460569_x_at | Cldn3 | 0.45 |

TABLE 15-continued

Differentially expressed genes in the skin of alopecic female C3H/HeJ mice vs. skin obtained from age-matched female C3H/HeJ mice without alopecia (n = 3 per group).

| Affy_ID | GeneSymbol | FC |
|---|---|---|
| 1431056_a_at | Lp1 | 0.45 |
| 1443832_s_at | Sdpr | 0.45 |
| 1451701_x_at | Cldn3 | 0.45 |
| 1419490_at | Fam19a5 | 0.45 |
| 1428792_at | Bcas1 | 0.45 |
| 1419492_s_at | Defb1 | 0.45 |
| 1424393_s_at | Adhfe1 | 0.44 |
| 1448978_at | Ngef | 0.44 |
| 1429344_at | 9.13E+15 | 0.44 |
| 1437637_at | Phtf2 | 0.44 |
| 1425826_a_at | Sorbs1 | 0.44 |
| 1451620_at | C1ql3 | 0.44 |
| 1450759_at | Bmp6 | 0.43 |
| 1433638_s_at | Hoxd8 | 0.43 |
| 1415996_at | Txnip | 0.43 |
| 1448551_a_at | Trim2 | 0.43 |
| 1426981_at | Pcsk6 | 0.43 |
| 1427673_a_at | Sema3e | 0.43 |
| 1451527_at | Pcolce2 | 0.43 |
| 1434877_at | Nptx1 | 0.42 |
| 1453435_a_at | Fmo2 | 0.42 |
| 1449621_s_at | Thsd1 | 0.42 |
| 1431805_a_at | Rhpn2 | 0.42 |
| 1449824_at | Prg4 | 0.41 |
| 1416129_at | Errfi1 | 0.41 |
| 1434628_a_at | Rhpn2 | 0.41 |
| 1455214_at | Mitf | 0.41 |
| 1427345_a_at | Sult1a1 | 0.41 |
| 1418205_at | Thsd1 | 0.40 |
| 1419414_at | Gng13 | 0.40 |
| 1437840_s_at | D2hgdh | 0.40 |
| 1423635_at | Bmp2 | 0.40 |
| 1423679_at | 2810432L12Rik | 0.39 |
| 1418063_at | Kera | 0.39 |
| 1434667_at | Col8a2 | 0.39 |
| 1424649_a_at | Tspan8 | 0.39 |
| 1446498_at | Il20ra | 0.39 |
| 1441918_x_at | Serpinb6e | 0.39 |
| 1415997_at | Txnip | 0.39 |
| 1431833_a_at | Hmgcs2 | 0.38 |
| 1418589_a_at | Mlf1 | 0.38 |
| 1419717_at | Sema3e | 0.38 |
| 1429166_s_at | Clmn | 0.38 |
| 1435459_at | Fmo2 | 0.38 |
| 1434669_at | Ralgps1 | 0.38 |
| 1431099_at | Hoxd8 | 0.38 |
| 1434657_at | Gls | 0.37 |
| 1418595_at | Plin4 | 0.36 |
| 1434474_at | Abca5 | 0.36 |
| 1417168_a_at | Usp2 | 0.36 |
| 1427029_at | Htra3 | 0.35 |
| 1456895_at | Cd209b | 0.34 |
| 1416225_at | Adh1 | 0.34 |
| 1454969_at | Lypd6 | 0.34 |
| 1456741_s_at | Gpm6a | 0.34 |
| 1442226_at | Sema3e | 0.33 |
| 1451478_at | Angptl7 | 0.33 |
| 1418706_at | Slc38a3 | 0.32 |
| 1436279_at | Slc26a7 | 0.32 |
| 1460244_at | Upb1 | 0.32 |
| 1459737_5_at | Ttr | 0.31 |
| 1419816_s_at | Errfi1 | 0.31 |
| 1417765_a_at | Amy1 | 0.30 |
| 1446681_at | BB086117 | 0.30 |
| 1433837_at | 8430408G22Rik | 0.30 |
| 1454965_at | Fam171b | 0.29 |
| 1433596_at | Dnajc6 | 0.29 |
| 1425357_a_at | Grem1 | 0.29 |
| 1455913_x_at | Ttr | 0.29 |
| 1433836_a_at | 8430408G22Rik | 0.28 |
| 1451382_at | Chac1 | 0.28 |
| 1454608_x_at | Ttr | 0.26 |
| 1433877_at | Fam46b | 0.26 |
| 1425281_a_at | Tsc22d3 | 0.25 |
| 1451535_at | Il31ra | 0.24 |
| 1423405_at | Timp4 | 0.23 |
| 1435184_at | Npr3 | 0.23 |
| 1437665_at | Il22ra2 | 0.22 |
| 1456512_at | Pdzrn4 | 0.22 |
| 1417788_at | Sncg | 0.21 |
| 1460012_at | Wfdc3 | 0.20 |
| 1452543_a_at | Scgb1a1 | 0.19 |
| 1419332_at | Egfl6 | 0.19 |
| 1436643_x_at | Hamp2 | 0.18 |
| 1453327_at | Krt24 | 0.17 |
| 1456487_at | Adcy1 | 0.14 |
| I449545_at | Fgfl8 | 0.12 |

By comparing the corresponding lists of genes identified as differentially expressed to each other (FIG. 55A, bottom panel), three striking gene expression signatures were uncovered in this analysis. First, many of the upregulated genes in alopecic skin of both species were IFN-response genes, including the IFN-inducible chemokines CXCL 9,10 and 11[11] (FIG. 55A, FIG. 60). Secondly, several key CTL-specific transcripts were identified, including CD8A and granzymes A and B (FIG. 55A).

In turn, using CTL effectors, the small molecule JAK3 inhibitor, tofacitinib (JAK3>JAK1>>JAK2 selectivity)[18], was shown to block IL-15 triggered pSTAT3 activation (FIG. 55B), and inhibit CTL effector functions, including dermal sheath cell cytotoxicity (FIG. 55C), and granzyme B/IFNγ production (FIG. 55D). Thus, hair follicle production of IL-15 provides a cytokine axis that can be interrupted pharmacologically by inhibiting its signaling in immune effectors.

Next, it was determined whether the effects of IL-15 blockade could be recapitulated by intervening downstream using small molecule inhibitors of JAK3. Using tofacitinib, systemic administration of JAK3i (FIG. 56) treatment prevented the development of AA and the expansion of CD8+NKG2D+ T cells in all grafted recipients. Skin of mice treated with the protein tyrosine kinase inhibitor (PTKi) showed no histological signs of inflammation and prevented the emergence of the skin ALADIN (Alopecia Areata Disease Activity Index) transcriptional signature and Gene Expression Dynamic Index (GEDI) analysis in all mice (FIG. 56).

Figure 61A:
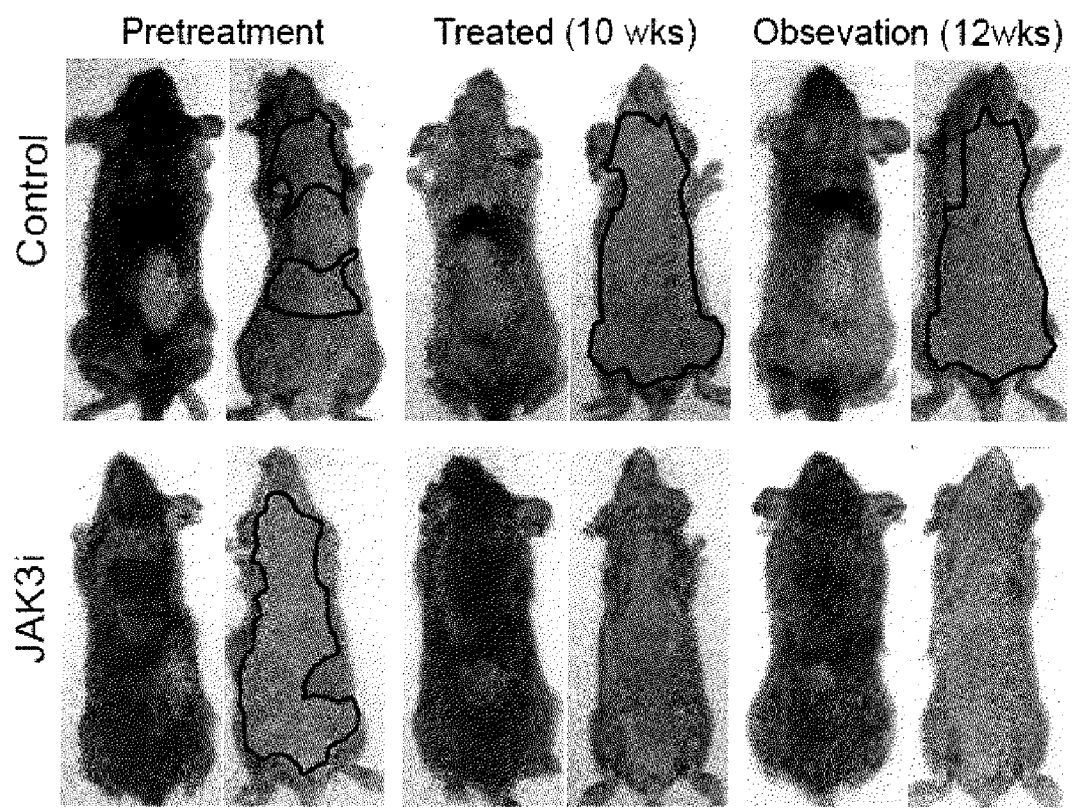
FIG. 61A shows systemic treatment of AA mice with JAK3 inhibitor. C3H/HeJ mice with long-standing alopecia areata were treated with tofacitinib with Alzet osmotic mini-pumps (pumps, model 2004, Durect Corporation) implanted subcutaneously on the back of each mouse to deliver vehicle (poly (ethylene glycol) (PEG)300) or vehicle containing JAK3i tofacitinib (Abmole) at 15 mg/kg/day for 12 wks. Alopecia areata reversal was complete on both the back and belly.
Figure 61B:
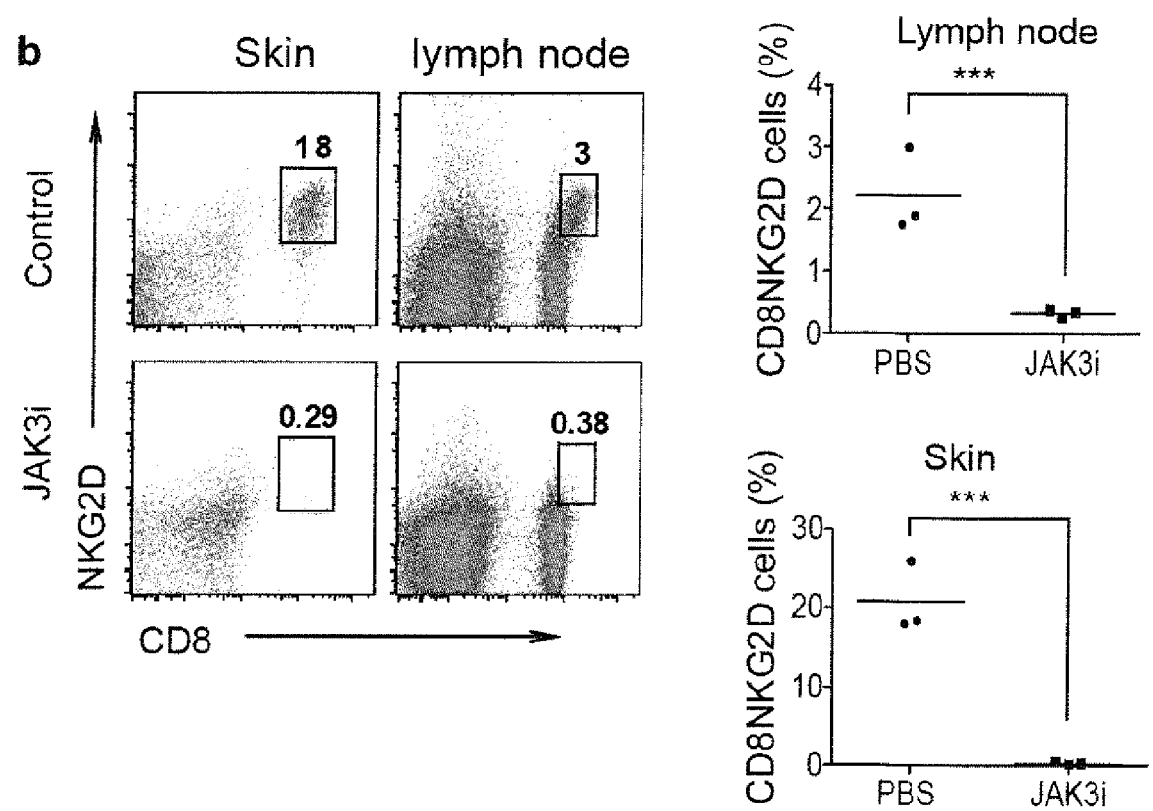
FIG. 61B shows systemic treatment of AA mice with JAK3 inhibitor. Flow cytometric analysis of skin and cutaneous lymph node populations shows elimination of the CD8+ NKG2D+ T cell population in treated mice (n=3 per group).
Figure 61C:
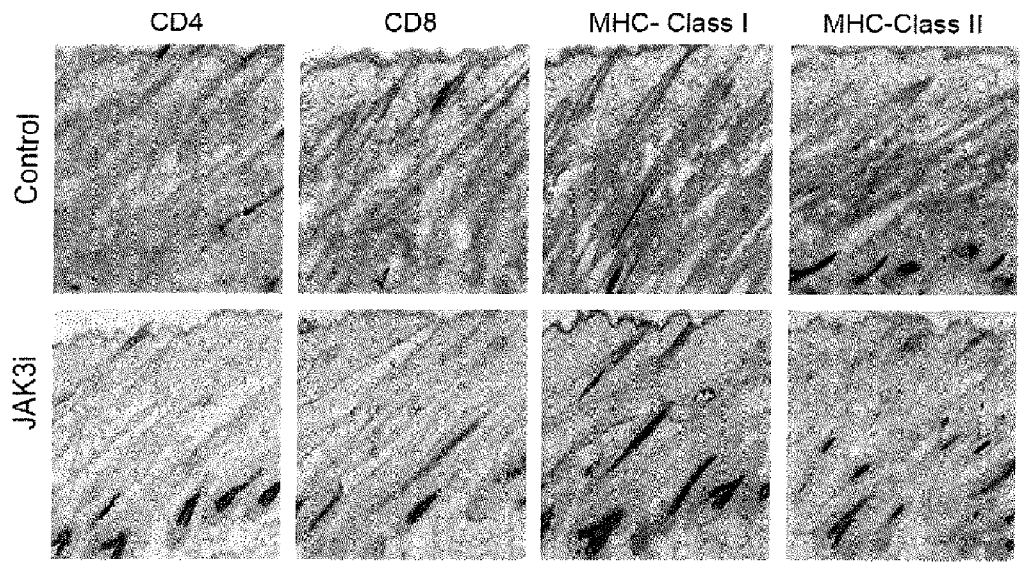
FIG. 61C shows systemic treatment of AA mice with JAK3 inhibitor. Immunostaining of skin from mice treated with tofactinib or placebo demonstrates elimination of CD8 infiltration and MHC I and II upregulation in tofacitinib treated mice.
Figure 62:
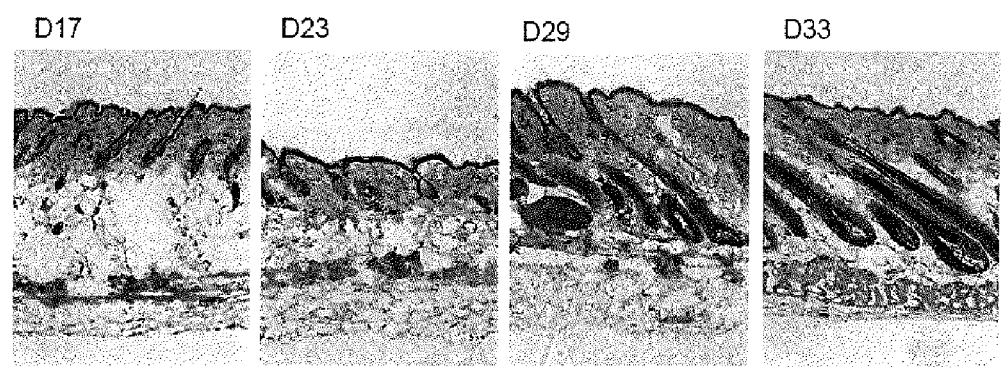
FIG. 62 depicts JAK-STAT signaling in normal hair follicle development. To analyze the status of the JAK-STAT signaling pathway during a normal hair cycle, mRNA was collected from skin of three mice at postnatal days 17, 23, 29, 33. Samples represent the telogen to anagen transition as evident in the photomicrographs of H&E stains from these time points. Day 17=early telogen; day 23=late telogen; day 29=early anagen; day 33=full anagen. cDNA was made and probed on JAK-STAT qPCR arrays. JAK-STAT signaling is up in telogen and down in anagen (see FIG. 63).

To evaluate the efficacy of JAK3i in the clinical context of AA, it was determined whether systemic JAK3i treatment could reverse established disease by initiating therapy 7 weeks after grafting, a time point at which all mice had developed extensive AA. Importantly, systemic therapy induced hair regrowth all over the body, and likewise eliminated the expansion of CD8+NKG2D+ T cells and reversed histological markers of disease (FIG. 61), an effect that persisted 2-3 months after the cessation of treatment.

Figure 57A:
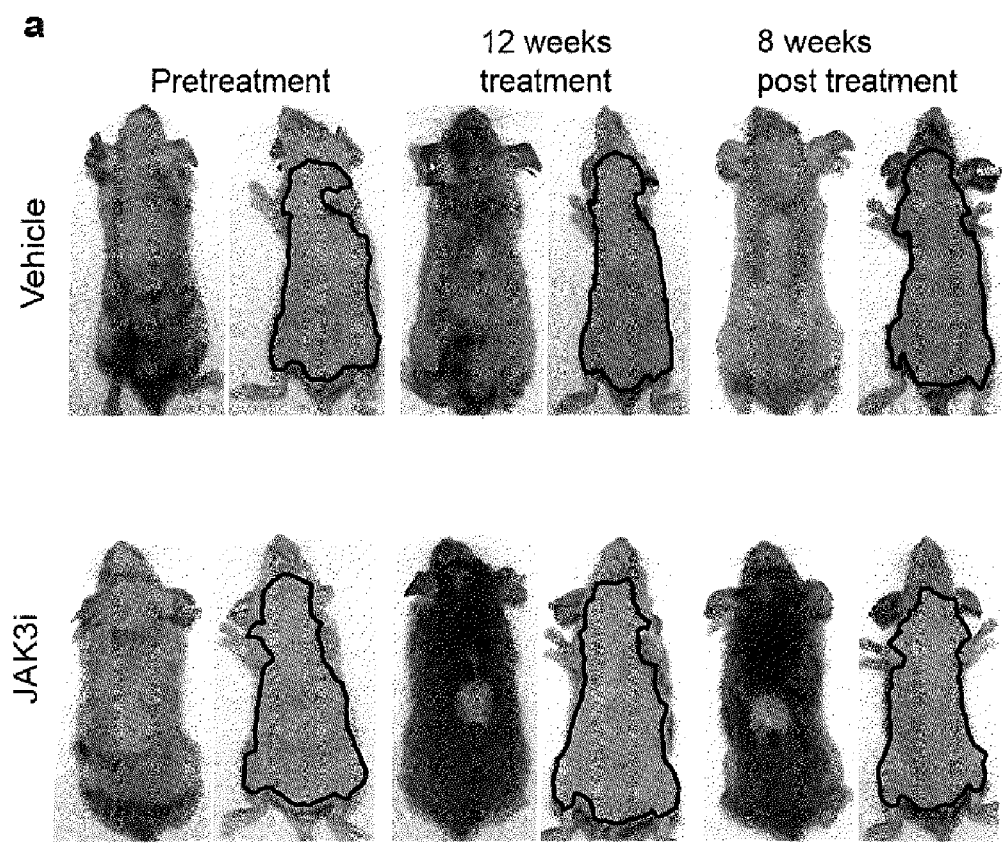
FIG. 57A shows reversal of established AA with topical small molecule inhibitor of the downstream effector kinase JAK3. Three-to-five per group of mice with long-standing AA (at least 12 weeks after grafting) were treated topically on the dorsal back with 0.5% JAK3i, tofacitinib or (top panels) vehicle alone (AQUAPHOR™) by daily application for 12 weeks. A full coat of hair emerged in the JAK3i treated mice by 7 weeks of treatment and further developed by 12 weeks. The durability of hair regrowth was measured for an additional 8 weeks after treatment withdrawal with no evidence of disease recurrence.
Figure 57B:
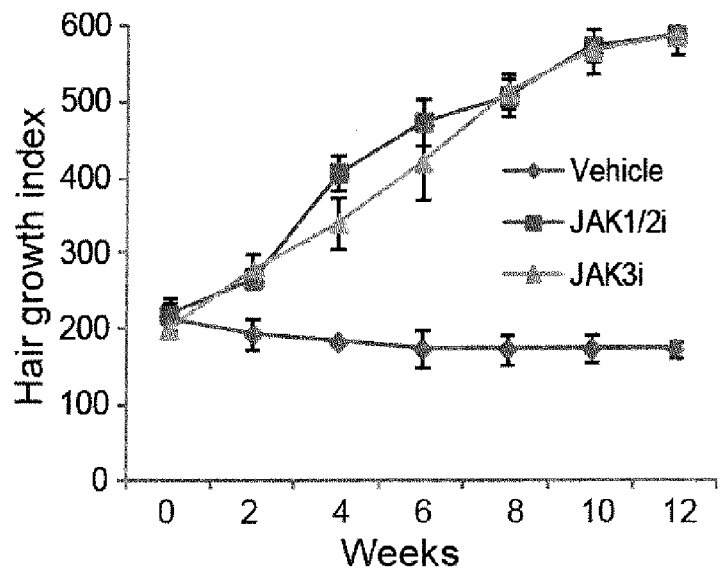
FIG. 57B shows reversal of established AA with topical small molecule inhibitor of the downstream effector kinase JAK3. The graph depicts a time course of hair regrowth index shown as weeks after treatment.
Figure 57C:
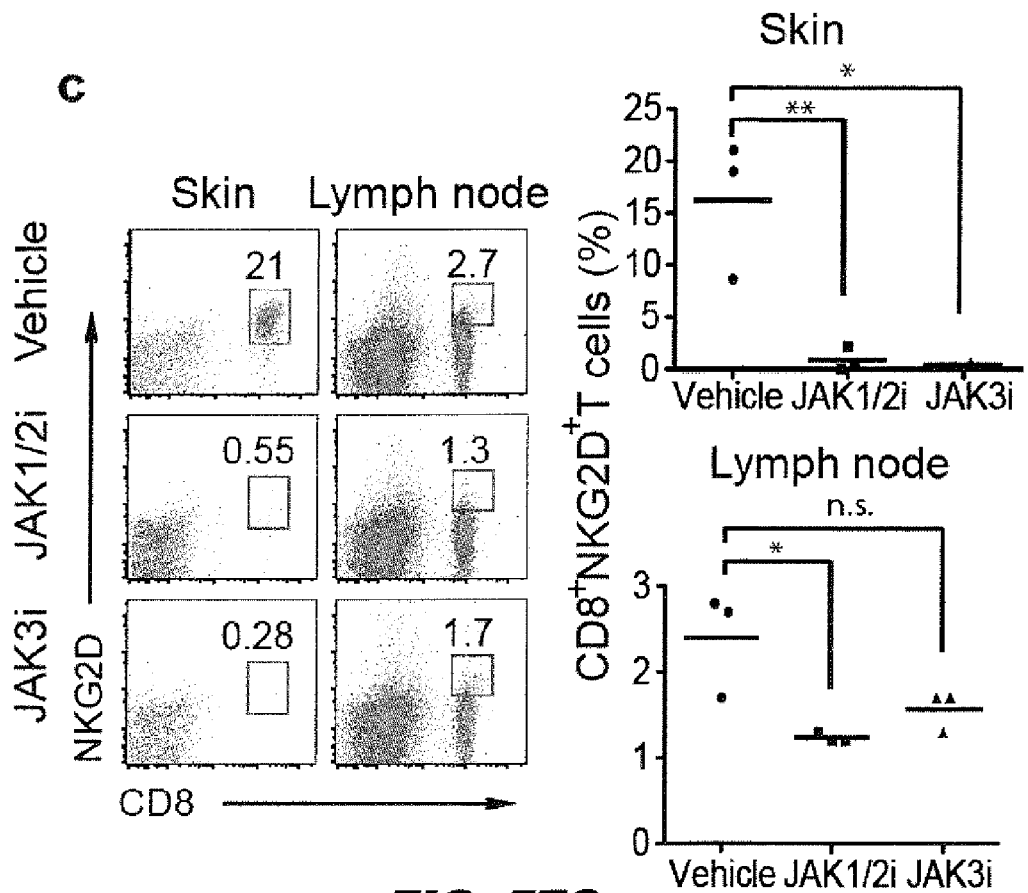
FIG. 57C shows reversal of established AA with topical small molecule inhibitor of the downstream effector kinase, JAK3. The plots depict the frequency of CD8+NKG2D+ T cells in the skin of JAK3i-treated mice was significantly decreased compared to control mice. *p value=<0.05, **p value=<0.01, n.s.=not significant.
Figure 57D:
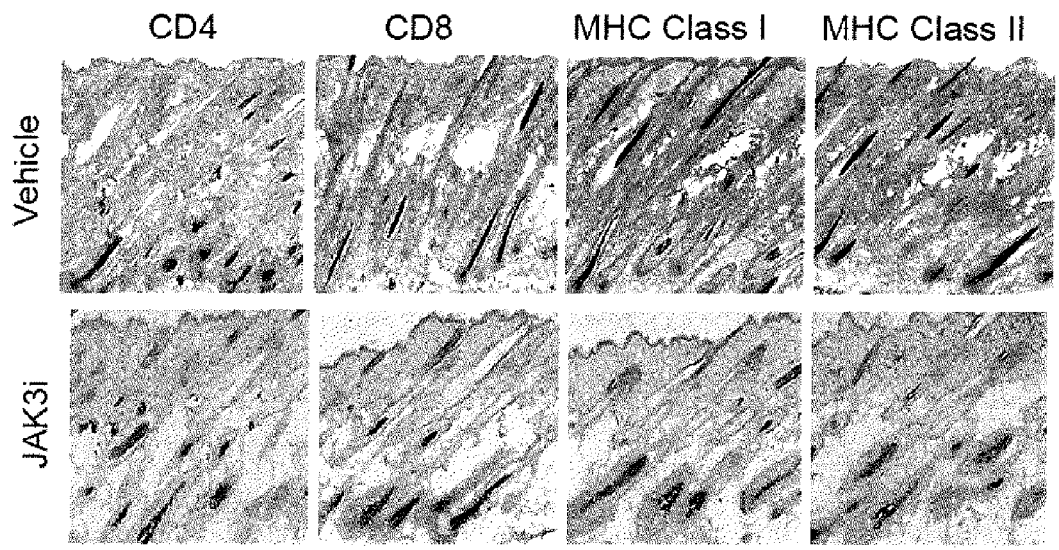
FIG. 57D shows reversal of established AA with topical small molecule inhibitor of the downstream effector kinase, JAK3. Immunohistochemical staining of skin biopsies shows treatment-related loss of expression of CD4, CD8, MHC class I and II markers.
Figure 57E:
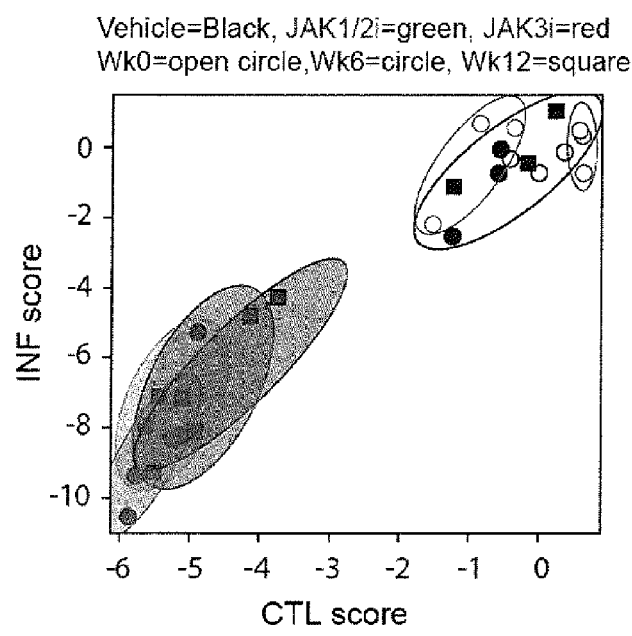
FIG. 57E shows reversal of established AA with topical small molecule inhibitor of the downstream effector kinase, JAK3. The ALADIN score shows treatment-related loss of CTL and IFN signatures.
Figure 57F:
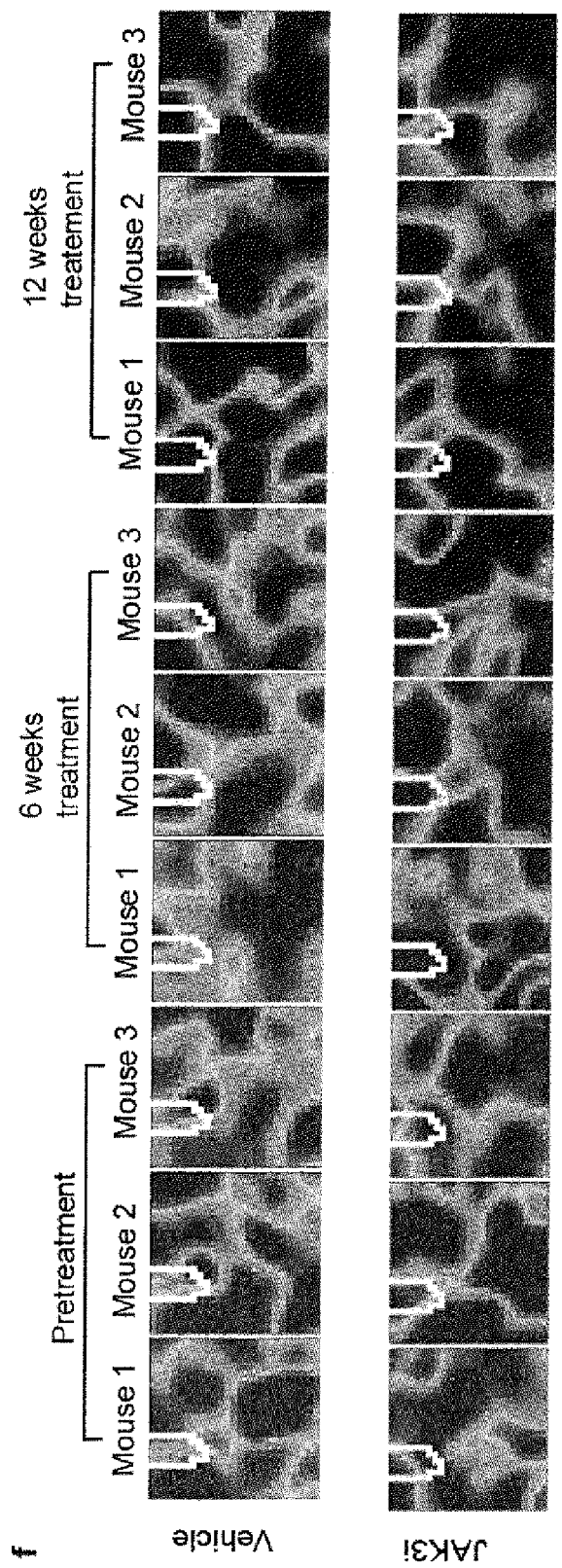
FIG. 57F shows reversal of established AA with topical small molecule inhibitor of the downstream effector kinase, JAK3. GEDI analysis shows territories of gene expression with treatment-related reversal of pathogenic signatures.

Finally, to test a more clinically convenient route of delivery, it was determined whether topical administration of PTKis could reverse long-standing alopecia areata with similar kinetics as systemic delivery. In established disease, topical tofacitinib, was highly effective in reversing disease in treated lesions (applied to back skin), and complete hair regrowth was observed within 12 weeks following topical therapy (FIG. 57A-B). Topical therapy was associated with the disappearance of CD8+NKG2D+ T cells in the treated skin (FIG. 57C) and the reversal of histological markers of disease (FIG. 57D), as well as the normalization of the ALA- DIN transcriptional signature (FIG. 57E), and the GEDI index in all treated mice (FIG. 57F). Notably, untreated areas on the abdomen remained alopecic (FIG. 57A, middle panels), demonstrating that topical therapy was locally effective and therapeutic effects were not the result of systemic absorption. Further, these effects were durable 2-3 months after the cessation of treatment (FIG. 57A, right panels).

Taken together, the data identify CD8+NKG2D+ T cells as the immune cellular effectors responsible for autoimmune attack of the hair follicle and provide support for a model of AA pathogenesis.

Importantly, these common mechanistic underpinnings were first revealed by in the GWAS study, which placed AA squarely among this group of allied autoimmune diseases involving NKG2DL mediated recruitment of CD8 T cell effectors, including type I diabetes[23,24], celiac disease[16,25] and rheumatoid arthritis[26]. These pathways can be interrupted by small molecule inhibitors of the IL-15 downstream effector JAK kinases, the latter being particularly appealing as a topical therapeutic approach in this cutaneous disease. FDA-approved JAK inhibitors were used to show the therapeutic effect, arguing for clinical evaluation in AA with these compounds or other JAK PTKis in clinical development[28].

In a very short time since the GWAS findings, not only have the specific subset of cytotoxic T cells that give rise to AA been identified, but they have successfully targeted them for elimination using clinically relevant, rational therapies selected on the basis of our mechanistic studies. The findings illustrate the power of GWAS studies in uncovering new disease pathways, and, coupled with translational approaches[29], have rapidly opened a new and unexpected avenue for intervention in AA.

Methods

Mice.

7-10 week old female C57Bl.6 and C3H/HeJ mice (Jackson Laboratories, Bar Harbor, Me.) were used and maintained under specific pathogen-free conditions.

Transfer of Alopecia Areata Using Grafted C3H/HeJ Skin.

Normal-haired C3H/HeJ mice were grafted at 8 weeks of age (during the second telogen) with skin from a C3H/HeJ mouse that developed AA spontaneously, as described previously[7]. In brief, mice spontaneously affected with AA were euthanized, full thickness skin grafts of approximately 2 □cm in diameter were removed and grafted to normal-haired C3H/HeJ mice. Hair loss typically began at around 4-6 weeks after grafting.

Flow Cytometric Analysis of Skin and Cutaneous Lymph Nodes.

To make a single cell suspension of mouse skin, fat was removed from the overlying skin in cold PBS and then incubated in collagenase type I (2 mg/ml in PBS) at 32° C. for 75 minutes. After digestion the skin was minced in RPMI/10% fetal bovine serum, filtered through a 70 mM cell strainer, and centrifuged at 1100 g for 5 minutes. The pellet was resuspended in RPMI/10% fetal bovine serum, filtered through a 40 mM cell strainer and spun at 400 g for 5 mins. The pellet was resuspended in FACs buffer (PBS/5% BSA), DAPI to gate on live cells and staining antibodies (listed in Supplemental Data). Cutaneous lymph nodes were pooled minced in RPMI, filtered through a 40 mM cell strainer, centrifuged at 400 g for 5 minutes stained and analysed on a BD LSR II flow cytometer.

Transfer of T Cell Populations into Recipient C3H/HeJ Mice.

For positive selection of T cell populations, lymph node cells were obtained from 5 C3H/HeJ alopecic mice, stained with anti-CD4, anti-CD8, and anti-NKG2D antibodies, then sorted (BD Influx) to obtain two fractions: CD8+NKG2D+ T cells, and CD8+NKG2D− T cells. Three to five 7-week-old C3H/HeJ mice per group were injected subcutaneously with two million sorted cells of each population. For negatively selected populations, NKG2D+ cells were depleted by incubating total lymph node cells from 3 alopecic C3H/HeJ mice with biotinylated anti-NKG2D (CX5) and then with streptavidin-conjugated beads (Miltenyi) prior to removal on a Miltenyi magnetic column. Five million cells (either CD8/NKG2D-depleted or total lymph node cells) were suspended in 100 ul PBS and transferred into each of 5 mice by subcutaneous injection.

Prevention and Treatment Studies.

For prevention studies, mice were treatment beginning the day of grafting (n=5-10 mice per group). For JAK3i experiments: mice were implanted subcutaneously with ALZET™ osmotic mini-pumps (pumps, model 2004, Durect Corporation) on the back of each mouse to deliver vehicle (poly (ethylene glycol) (PEG)300) or vehicle containing the JAK3i tofacitinib (Abmole) at 15 mg/kg/day for 12 weeks.

For topical treatment studies, grafted mice with long-standing AA (more than 8 weeks) were treated once daily for 12 weeks to affected skin on the dorsal back with vehicle (AQUAPHOR™) or vehicle containing the JAK3 inhibitor (0.5% ointment). Full-thickness skin biopsies were excised from the dorsal surface of each mouse at interim time points, and skin samples were either snap frozen in liquid nitrogen for RNA extraction or snap frozen in OCT for immunostaining. Hair status was examined twice weekly and hair growth index calculated as described[30].

Immunohistochemistry and Immunofluorescence.

8 mM acetone-fixed frozen mouse skin sections were air-dried and stained overnight with anti-mouse Abs (see below) at 4° C. in a moist chamber. Human hair follicles were microdissected and embedded in OCT compound prior to sectioning and staining (see below).

Primary Dermal Sheath and Lymphokine-Activated Killer (LAK) Cell Culture.

Dermal sheath (DS) cells were isolated from microdissected mouse vibrissa follicles and cultured in 20% FBS DMEM with 5 ng/ml murine FGF (Pepro Tech). LAK cells were generated from splenocytes plated at $4 \times 10^6$ in 6-well plates with 50 nM JAK3i (tofacitinib) or 50 ng/ml murine IL-15 plus 50 nM JAK3i, and incubated at 37° C. in a 5% $CO_2$ incubator for 96 hours.

In Vitro Cytotoxicity Assays.

Determination of specific killing of target cells was performed using CFSE-labeled DS cells at targets mixed with different ratios of effector cells incubated for 5 hours at 37° C. 5% CO2 with or without neutralizing rat anti-mouse NKG2D antibody (20 ug/ml) (Biolegend, CX5). Specific lysis of DS cells was determined flow cytometrically by measuring cell death of CFSE+ DS cells using Annexin V/7-AAD.

Gene Expression Analysis in Human and Mouse Skin and T Cells.

Total RNA was isolated using the MIRNEASY™ Mini Kit (Qiagen Inc., Valencia, Calif., USA) with on-column DNA digestion using the RNase-free DNase set (Qiagen, Inc.). For RNAseq analysis CD3+CD8+CD44+NKG2D+ and CD3+CD8+CD44+NKG2D− cells were flow-sorted from lymph nodes of alopecic C3H/HeJ mice. RNA was extracted as above and prepared for RNA-seq using the TRUSEQ™ RNA Sample Prep Kit v2. Samples were sequenced on the HISEQ™ 2000 sequencer (Illumina, San Diego, Calif.) for 50 cycles. RNA-Seq files were demultiplexed by the Rockefeller University Genomics Core Facility.

For global transcriptional profiling in mouse skin, total extracted RNA was processed using the 3' IVT EXPRESS KIT™ from AFFYMETRIX™. Resulting biotinylated cDNA samples were hybridized to the Mouse Genome 430 2.0 gene chips and subsequently washed, stained with streptavidin-phycoerythrin, and scanned on an HP GENEARRAY™ Scanner (Hewlett-Packard Company, Palo Alto, Calif.).

For human AA samples, perilesional punch biopsies from 5 patients with patchy alopecia areata who were not undergoing local or systemic treatments were collected and compared to scalp biopsies from 5 unrelated unaffected individuals.

Extracted total RNA were reverse transcribed and amplified using the OVATION™ RNA Amplification V2 kit (NuGEN Technologies, Inc., San Carlos, Calif.). Amplified cDNA was biotinylated with the ENCORE™ Biotin Module (NuGEN Technologies) and then hybridized to the U133A Plus 2.0 gene chips.

Antibodies used for flow cytometry and immunostaining.

Flow cytometric analysis used the following anti-mouse antibodies: CD3 (17A2, Ebioscience), CD4 (GK1.5, BD), CD8a (53-6.7, BD), CD8a (YTS156.7.7, Biolegend), NKG2D (CX5, Ebioscience), NKG2A/C/E (clone 20d5, Ebioscience), CD44 (IM7, BD), CD45 (30-F11, BD), CD49b (Dx5, BD), CD62L (MEL-14, BD), CD69 (H1.2F3, BD), CD103 (2E7, eBioscience), IFNγ (XMG1.2, Ebioscience), Granzyme B (NGZB, eBioscience), Rae-1 (186107, R&D).

For immunohistochemical studies of mouse skin, 8 μM methanol-fixed frozen skin sections were stained with primary rat antibodies (Biolegend) including: anti-CD4 (clone RM4-5), anti-CD8 (clone 53-6.7), Biotin anti-MHC class I (clone 36-7.5), anti-MHC class II (clone M5/114.15.2). Biotinylated goat anti-rat IgG (Life Technologies) was used as secondary antibody. For immunofluorescence studies anti-H60 (R&D, clone 205326), anti-Pan Rae-1(R&D, clone 186107), anti-NKG2D (R&D clone 191004), anti-K71 (Abcam) primary antibody were used in immunofluorescence. ALEXA FLUOR™ Fluor 488 or ALEXA FLUOR™ Fluor 594-conjugated goat anti-Rat, donkey anti-Rabbit or donkey anti-Goat antibody was used as secondary antibody (Life Technologies).

Human hair follicles were microdissected and embedded in OCT compound prior to sectioning and staining. 8 μM methanol-fixed frozen sections were stained with CD8 (SCBT, C8/144B) followed by staining with Alexa Fluor 488 or Alexa Fluor 594-conjugated secondary antibody (Life Technologies). All images were captured with an SDRC Zeiss Exciter Confocal Microscope.

Statistical Analysis and Quality Control of Gene Expression Signatures

RNA-Seq Analysis.

Samples were sequenced on the HiSeq 2000 sequencer (Illumina, San Diego, Calif.) for 50 cycles. RNA-Seq files were demultiplexed by the Rockefeller University Genomics Core Facility. Quality control of the sample fastq files was performed using fastqc[S1]. TopHat[S2] was used to map transcripts to the UCSC mm9 reference genome from iGenome. The RefSeq gene annotation packaged with this iGenome version of the UCSC mm9 were used. The htseq-count utility from the HTSeq package was used to convert TopHat bam files to counts that could be used as input for downstream analysis of differential expression with edgeR[S2]. Absent genes were removed and a pseudocount of 1 was added in order to avoid division by zero in downstream analysis. EdgeR was used to identify differentially expressed genes using a matched pairs design with three biological replicates.

Microarray Analysis.

Quality Control, Preprocessing.

For the mouse cDNA samples were hybridized to the Mouse Genome 430 2.0 gene chips and subsequently washed, stained with streptavidin-phycoerythrin, and scanned on an HP GeneArray Scanner (Hewlett-Packard Company, Palo Alto, Calif.). For the human, amplified cDNA was hybridized to the U133A 2.0 gene chips.

Quality control was performed using the affyanalysisQC package from arrayanalysis.org/. AffyanalysisQC uses R/BioConductor packages: affy, affycomp, affypdnn, affyPLM, affyQCReport, ArrayTools, bioDistm biomaRt, simpleaffy, yaqcaffy to perform QC within a single script. RMA normalization[S4] was performed on each experimental group separately. Batch effect correction using ComBat was required for the prevention experiments.

Microarray preprocessing was performed using BioConductor in R. Preprocessing of the three experiments, 1) spontaneous AA mice vs. normal mice, 2) prevention mice with three treatments vs placebo and sham-operated mice, and 3) treatment mice for two treatments vs. placebo were performed separately using the same pipeline. In addition to the preprocessing that was done for the mouse skin samples, Harshlight was used to correct for image defects for the human skin samples.

Identification of Gene Signatures.

Unsupervised Analysis.

Hierarchical clustering was performed using Cluster[S5] on the 363 genes from the human 5×5 and 583 genes from the spontaneous mouse 3×3 in order that met the threshold abs (log FC)>1, unadjusted p-value <=0.05. Genes were first selected that met the threshold log FC >1, and unadjusted p-value <=0.05. Genes were median centered and normalized. Spearman rank correlation was used as the similarity measure and average linkage was used to perform row (genes) and column (sample) clustering. Visualization of the hierarchical clusters was performed with java TreeView[S6]. Gene Expression Dynamic Index (GEDI) analysis was used to visualize how "metagenes" identified with a self organizing map algorithm vary across samples[S7]. Metagenes are clusters of genes that show similar expression patterns across samples and that are assigned to a single pixel in a two dimensional grid. Neighboring pixels demonstrate similar expression patterns to one another.

Supervised Analysis.

Initial analysis of differential gene expression was performed on the spontaneous mouse 3×3 and the human 5×5 data sets using limma[S8]. A threshold of 1.5 fold change and unadjusted p-value of 0.05.

RT-PGR Validation.

Predicted differentially expressed genes in human and mouse were confirmed using RT-PCR. First-strand cDNA was synthesized using a ratio of 2:1 random primers: Oligo (dT) primer and SUPERSCRIPT™ III RT (Invitrogen) according to the manufacturer's instructions. qRT-PCR was performed on an ABI 7300™ machine and analyzed with ABI Relative Quantification Study™ software (Applied Biosystems, Foster City, Calif., USA). Primers were designed according to ABI guidelines and all reactions were performed using Power SYBR™ Green PCR Master Mix (Applied Biosystems), 250 nM primers (Invitrogen) and 20 ng cDNA in a 20 μL reaction volume. Primer sequences are provided in Table 16.

TABLE 16

RT-PCR Primers for mouse mRNA validation studies.
Mouse RT-PCR

| Gene | Forward Primer | SEQ ID NO: | Reverse Primer | SEQ ID NO: |
|---|---|---|---|---|
| Cd8a | GAGACCAGAAGATTGTCGGC | 12 | GCCTGGGACATTTGCAAACA | 13 |
| Cd3d | ACTGTGTGGAGCTAGACTCG | 14 | CTGTACTGGGTATCTTCACG | 15 |
| Stat1 | CGCAACTACAAAGTCATGGC | 16 | ATCCAGTTCGCTTAGGGTCG | 17 |
| Ifng | ACGGCACAGTCATTGAAAGC | 18 | GCTGATGGCCTGATTGTCTT | 19 |
| Tap1 | CCTGCTTATCTTGGATGATGC | 20 | GGTAGCACCCTCCTCTCTT | 21 |
| Cxcl9 | ACGGAGATCAAACCTGCCTA | 22 | TTCCCCCTCTTTTGCTTTTT | 23 |
| Cxcl10 | ATCCACCGCTGAGAGACATC | 24 | CCTTGAGTCCCACTCAGACC | 25 |
| Cxcl11 | TAGCCCTGGCTGCAATATCT | 26 | ACTTTGTCGCAGCCGTTACT | 27 |
| Irf7 | GCACCCTCCTTTTCACTGAG | 28 | GCCAAGGTGGCTGTAGATGT | 29 |
| Ccl5 | CCCTCACCATCATCCTCACT | 30 | GAGCACTTGCTGCTGGTGTA | 31 |
| H60a | TGCCTGATTCTGAGCCTTTTCA | 32 | ATTCACTGAGCACTGTCCATGTAGAT | 33 |
| H60b | AGGCCTTTTGGTCCTGCTGAAT | 34 | ATGTTTTTATCACCAAAATCAAGGAGT | 35 |
| H60c | AGATTTCAGTTGCTGCCTCA | 36 | ACATGTGCAGCAGTGGTTG | 37 |

Commercial Solaris real-time PCR system primers and probe sets AX-047904-01, AAX-047854-01, AX-047833-01, AX-049954-01, AX-042357-01 and AX-040917-00 (Thermo Scientific) were used for PCR of Rae-1a, Rae-1b, Rae-1c, Rae-1d, Rae-1e and GAPDH. Results are expressed as 'fold increase' in mRNA expression.

TABLE 17

RT-PCR Primers for human mRNA validation studies.
Human RT-PCR

| Gene | SEQ ID NO. | Forward Primer | SEQ ID NO. | Reverse Primer |
|---|---|---|---|---|
| GZMA | 38 | AGATTTCTGGCATCCTCTC | 39 | GACCATGTAGGGTCTTGA |
| IL15 | 40 | TTTCAGTGCAGGGCTTCCT | 41 | GGGTGAACATCACTTTCCC |
| STAT1 | 42 | GCAGGTTCACCAGCTTTAT | 43 | TGAAGATTACGCTTGCTTT |
| CXCL9 | 44 | GTAGTGAGAAAGGGTCGC | 45 | AGGGCTTGGGGCAAATTG |
| IFNG | 46 | TCGGTAACTGACTTGAATGTCCA | 47 | TCGCTTCCCTGTTTTAGCTGC |

The following PCR protocol was used: step 1: 50° C. for 2 min; step 2: 95° C. for 10 min; step 3: 95° C. for 15 s; step 4: 60° C. for 1 min; repeat steps 3 and 4 for 40 cycles. All samples were run in quadruplicate for three independent runs and normalized against an endogenous internal control as indicated.

ALADIN Scores.

The IFN and CTL signatures were used to develop a bivariate score statistic. Individual signature IFN and CTL scores were determined following procedures used in human SLE[S9, S10]. The sets of genes selected to comprise our IFN and CTL signatures were CD8A, GZMB, and ICOS for the CTL signature, and CXCL9, CXCL10, CXCL11, STAT1, and MX1 for the IFN signature. The scores for the prevention mice were calculated in relation to the sham mice; whereas, the scores for the topical treatment experiments were calculated relative to all the samples at week zero.

References

1 McDonagh, A. J. & Messenger, A. G. The pathogenesis of alopecia areata. *Dermatol Clin* 14, 661-670 (1996).
2 McElwee, K. J., Tobin, D. J., Bystryn, J. C., King, L. E., Jr. & Sundberg, J. P. Alopecia areata: an autoimmune disease? *Exp Dermatol* 8, 371-379 (1999).
3 Petukhova, L. et al. Genome-wide association study in alopecia areata implicates both innate and adaptive immunity. *Nature* 466, 113-117 (2010).
4 Gilhar, A., Ullmann, Y., Berkutzki, T., Assy, B. & Kalish, R. S. Autoimmune hair loss (alopecia areata) transferred by T lymphocytes to human scalp explants on SCID mice. *J Clin Invest* 101, 62-67 (1998).
5 McElwee, K. J. et al. Transfer of CD8(+) cells induces localized hair loss whereas CD4(+)/CD25(−) cells promote systemic alopecia areata and CD4(+)/CD25(+) cells blockade disease onset in the C3H/HeJ mouse model. *J Invest Dermatol* 124, 947-957 (2005).
6 Sundberg, J. P., Cordy, W. R. & King, L. E., Jr. Alopecia areata in aging C3H/HeJ mice. *J Invest Dermatol* 102, 847-856 (1994).
7 McElwee, K. J., Boggess, D., King, L. E., Jr. & Sundberg, J. P. Experimental induction of alopecia areata-like hair loss in C3H/HeJ mice using full-thickness skin grafts. *J Invest Dermatol* 111, 797-803 (1998).
8 Best, J. A. et al. Transcriptional insights into the CD8(+) T cell response to infection and memory T cell formation. *Nat Immunol*, 4, 404-12 (2013).
9 Bezman, N. A. et al. Molecular definition of the identity and activation of natural killer cells. *Nat Immunol* 13, 1000-1009 (2012).
10 Heng, T. S. & Painter, M. W. The Immunological Genome Project: networks of gene expression in immune cells. *Nat Immunol* 9, 1091-1094 (2008).
11 Kota, R. S. et al. Regulation of gene expression in RAW 264.7 macrophage cell line by interferon-gamma. *Biochem Biophys Res Commun* 342, 1137-1146 (2006).
12 Fehniger, T. A. & Caligiuri, M. A. Interleukin 15: biology and relevance to human disease. *Blood* 97, 14-32 (2001).
13 Ye, W., Young, J. D. & Liu, C. C. Interleukin-15 induces the expression of mRNAs of cytolytic mediators and augments cytotoxic activities in primary murine lymphocytes. *Cell Immunol* 174, 54-62 (1996).
14 Meresse, B. et al. Reprogramming of CTLs into natural killer-like cells in celiac disease. *J Exp Med* 203, 1343-1355 (2006).
15 Saikali, P., Antel, J. P., Pittet, C. L., Newcombe, J. & Arbour, N. Contribution of astrocyte-derived IL-15 to CD8 T cell effector functions in multiple sclerosis. *J Immunol* 185, 5693-5703 (2010).
16 Meresse, B. et al. Coordinated induction by IL15 of a TCR-independent NKG2D signaling pathway converts CTL into lymphokine-activated killer cells in celiac disease. *Immunity* 21, 357-366 (2004).
17 Quintas-Cardama, A. et al. Preclinical characterization of the selective JAK1/2 inhibitor INCB018424: therapeutic implications for the treatment of myeloproliferative neoplasms. *Blood* 115, 3109-3117 (2010).
18 Ghoreschi, K. et al. Modulation of innate and adaptive immune responses by tofacitinib (CP-690,550). *Journal of Immunology* 186, 4234-4243 (2011).
19 Eichler, G. S., Huang, S. & Ingber, D. E. Gene Expression Dynamics Inspector (GEDI): for integrative analysis of expression profiles. *Bioinformatics* 19, 2321-2322 (2003).
20 Paus, R., Nickoloff, B. J. & Ito, T. A 'hairy' privilege. *Trends Immunol* 26, 32-40 (2005).
21 Freyschmidt-Paul, P. et al. Interferon-gamma-deficient mice are resistant to the development of alopecia areata. *The British journal of dermatology* 155, 515-521 (2006).
22 Waldmann, T. A. The biology of interleukin-2 and interleukin-15: implications for cancer therapy and vaccine design. *Nature reviews. Immunology* 6, 595-601 (2006).
23 Ogasawara, K. et al. NKG2D blockade prevents autoimmune diabetes in NOD mice. *Immunity* 20, 757-767 (2004).
24 Markiewicz, M. A. et al. RAE lepsilon ligand expressed on pancreatic islets recruits NKG2D receptor-expressing cytotoxic T cells independent of T cell receptor recognition. *Immunity* 36, 132-141 (2012).
25 Hue, S. et al. A direct role for NKG2D/MICA interaction in villous atrophy during celiac disease. *Immunity* 21, 367-377 (2004).
26 Andersson, A. K., Feldmann, M. & Brennan, F. M. Neutralizing IL-21 and IL-15 inhibits pro-inflammatory cytokine production in rheumatoid arthritis. *Scand J Immunol* 68, 103-111 (2008).
27 Baslund, B. et al. Targeting interleukin-15 in patients with rheumatoid arthritis: a proof-of-concept study. *Arthritis and rheumatism* 52, 2686-2692 (2005).
28 Dolgin, E. Companies hope for kinase inhibitor JAKpot. *Nature reviews. Drug discovery* 10, 717-718 (2011).
29 Fugger, L., McVean, G. & Bell, J. I. Genomewide association studies and common disease—realizing clinical utility. *The New England Journal of Medicine* 367, 2370-2371 (2012).
30 Tang, L. et al. Topical mechlorethamine restores autoimmune-arrested follicular activity in mice with an alopecia areata-like disease by targeting infiltrated lymphocytes. *J Invest Dermatol* 120, 400-406 (2003).
S1 Andrews, S. bioinformatics.babraham.ac.uk/projects/fastqc/
S2 Trapnell, C., Pachter, L. & Salzberg, S. L. TopHat: discovering splice junctions with RNA-Seq. Bioinformatics 25, 1105-1111, doi:10.1093/bioinformatics/btp120 (2009).
S3 Robinson, M. D., McCarthy, D. J. & Smyth, G. K. edgeR: a Bioconductor package for differential expression analysis of digital gene expression data. Bioinformatics 26, 139-140, doi:10.1093/bioinformatics/btp616 (2010).
S4 Irizarry, R. A. et al. Summaries of Affymetrix GeneChip probe level data. Nucleic acids research 31, e15 (2003).
S5 Eisen, M. B., Spellman, P. T., Brown, P. O. & Botstein, D. Cluster analysis and display of genome-wide expression patterns. Proceedings of the National Academy of Sciences of the United States of America 95, 14863-14868 (1998).
S6 Saldanha, A. J. Java Treeview—extensible visualization of microarray data. Bioinformatics 20, 3246-3248, doi: 10.1093/bioinformatics/bth349 (2004).

S7 Eichler, G. S., Huang, S. & Ingber, D. E. Gene Expression Dynamics Inspector (GEDI): for integrative analysis of expression profiles. Bioinformatics 19, 2321-2322 (2003).

S8 Smyth, G. K. Limma: linear models for microarray data. In: "Bioinformatics and Computational biology Solutions using R and Bioconductor". 397-420 (Springer, New York, 2005).

S9 Kirou, K. A. et al. Coordinate overexpression of interferon-alpha-induced genes in systemic lupus erythematosus. Arthritis and rheumatism 50, 3958-3967, doi:10.1002/art.20798 (2004).

S10 Feng, X. et al. Association of increased interferon-inducible gene expression with disease activity and lupus nephritis in patients with systemic lupus erythematosus. Arthritis and rheumatism 54, 2951-2962, doi:10.1002/art.22044 (2006).

Example 11

Effect of JAK3 Inhibitor on the Induction of Hair Growth

The JAK-STAT signaling pathway has been implicated in several developmental processes, and most recently in stem cell maintenance, activation and differentiation. In the course of the inventor's topical treatment studies using JAK3 in the C3H/HeJ AA mouse model, it was noticed that the hairs that regrew did so with two striking features that were different from systemic administration: 1) hair regrowth was very rapid; and 2) the hair coat was darkly pigmented. Without being bound by theory, in addition to the JAK3 inhibitor eliminating pathogenic T cells from the skin, the JAK3 inhibitor also has a direct effect on the hair follicle itself, for example, via an anagen-promoting effect.

Figure 63:
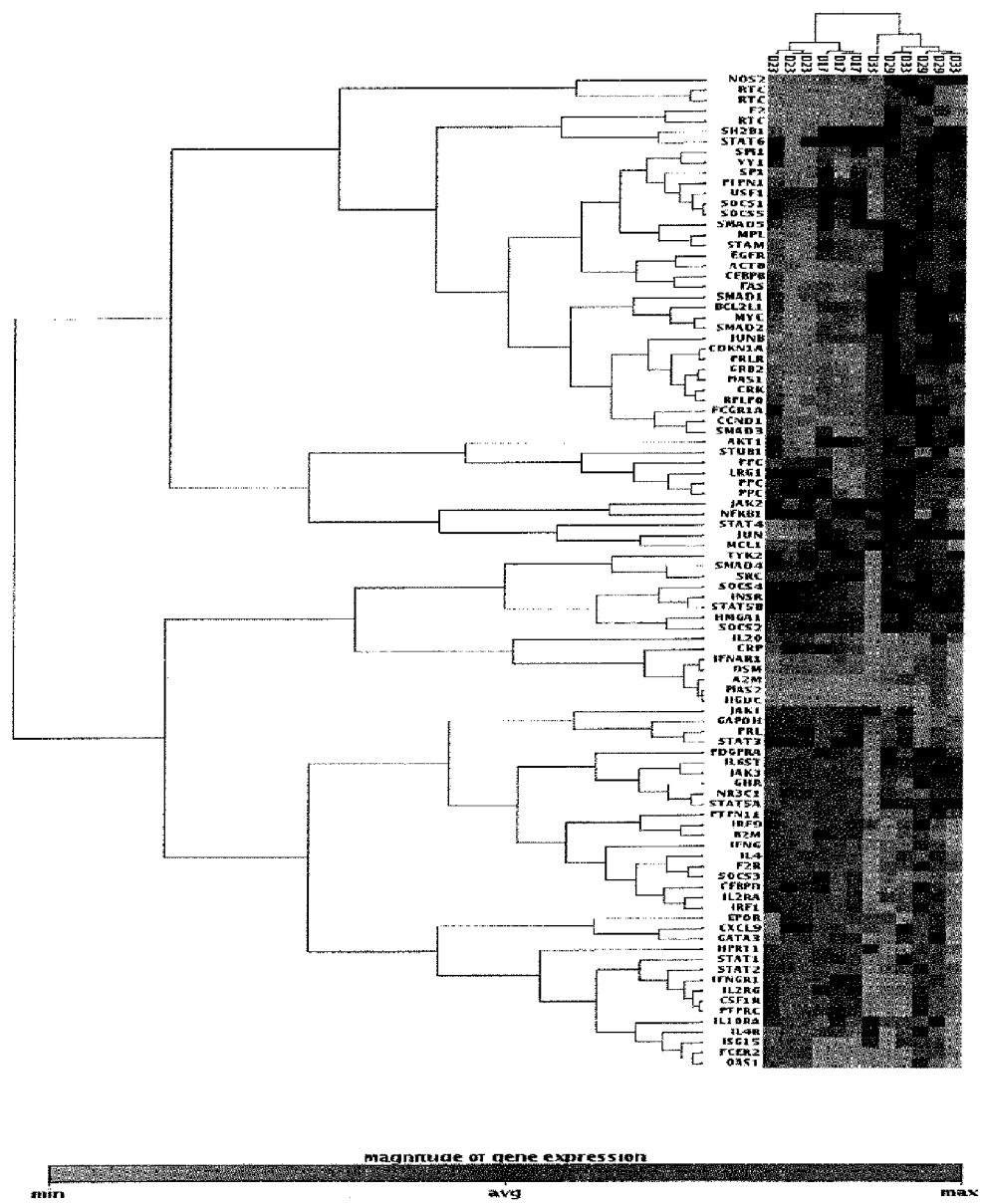
FIG. 63 is a heat map showing a hierarchical cluster analysis. mRNA isolated from mouse skin at each time point (D17, 23, 29, 33) were probed on JAK-STAT qPCR array. Red=induced, Green=repressed. Shown are all genes of the array. Several clusters of genes are evident that are upregulated in both telogen time points (d17 and d23), or upregulated in both anagen time points (d29 and d33).
Figure 64A:
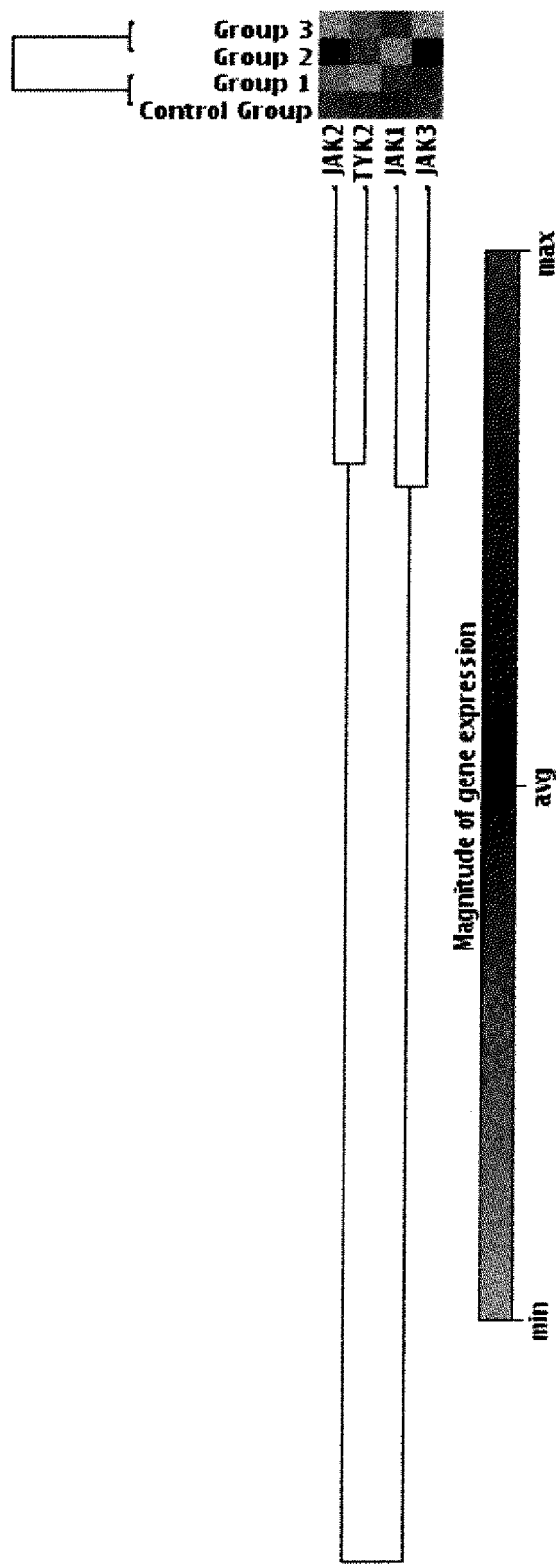
FIG. 64A is a heat map showing a hierarchical cluster analysis. The figure shows averages of 3 biological replicates/time point. The Control group: D17 (Telogen); Group 1: D23 (telogen); Group 2: D29 (anagen); and Group 3: D33 (anagen). JAK1 and 3 are upregulated in telogen group (red in control group and Group 1). Expression of JAK-STAT signaling pathway components is up in telogen and down in anagen.
Figure 64B:
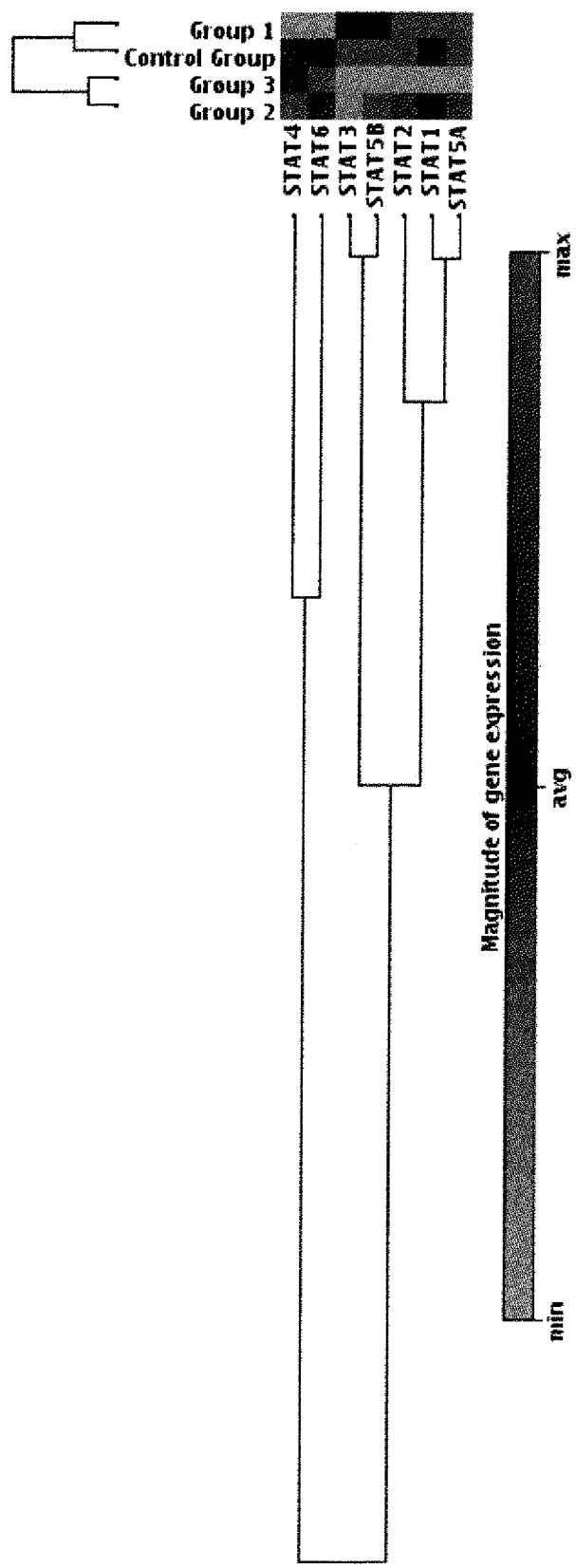
FIG. 64B is a heat map showing a hierarchical cluster analysis. The figure shows averages of 3 biological replicates/time point. The Control group: D17 (Telogen); Group 1: D23 (telogen); Group 2: D29 (anagen); and Group 3: D33 (anagen). Stat 1/2/3/5 are upregulated in telogen (red in control group and group 1). Expression of JAK-STAT signaling pathway components is up in telogen and down in anagen.
Figure 65:
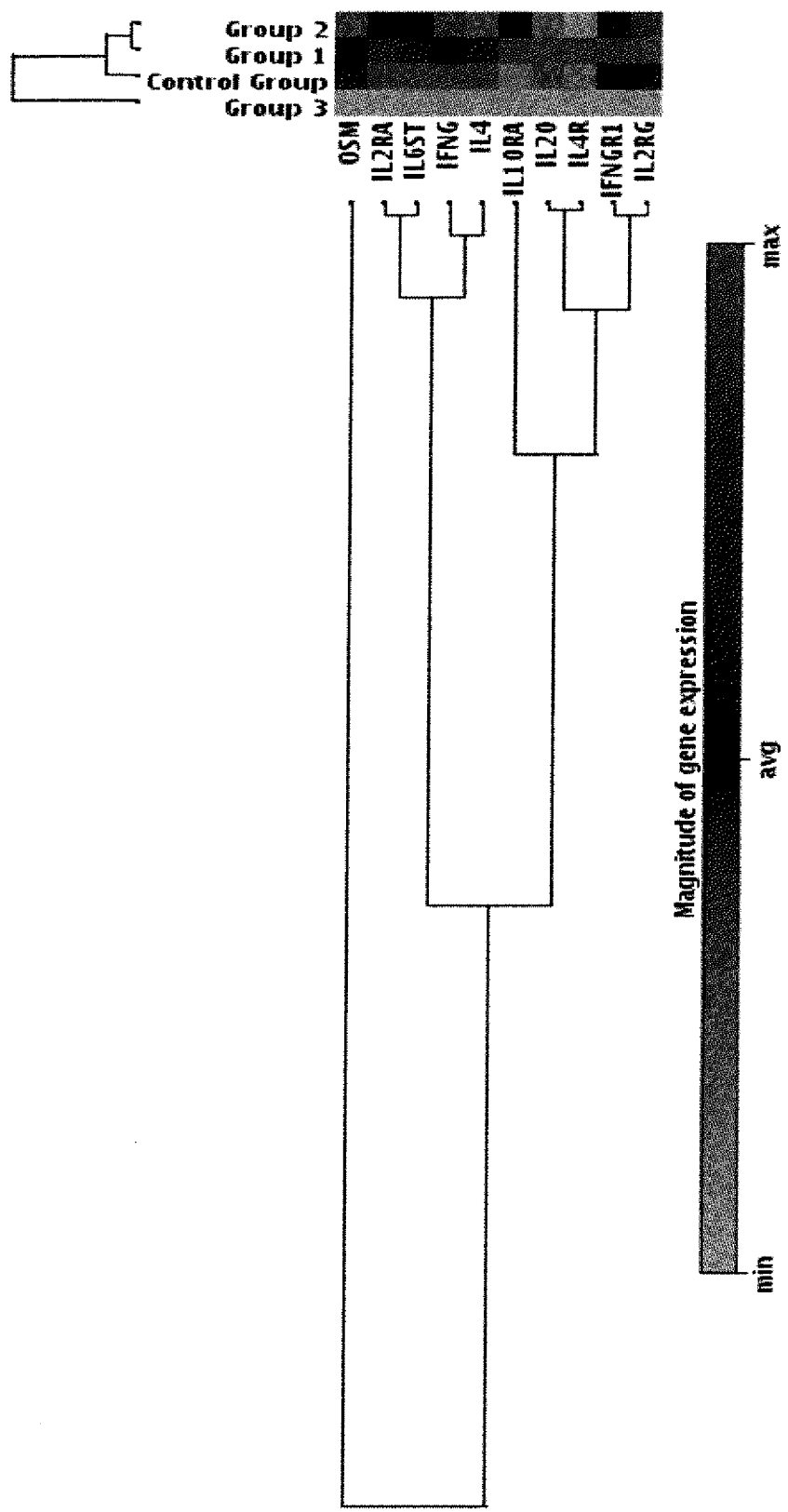
FIG. 65 is a heat map (top) showing a cluster analysis. The Control group: D17 (Telogen); Group 1: D23 (telogen); Group 2: D29 (anagen); and Group 3: D33 (anagen). Potential ligands for JAK STAT or targets for JAK3i: OSM, IL6st (GP130), IL-4, IL-2Rg, CSF1R, and others upregulated in telogen samples.
Figures 2, 66:
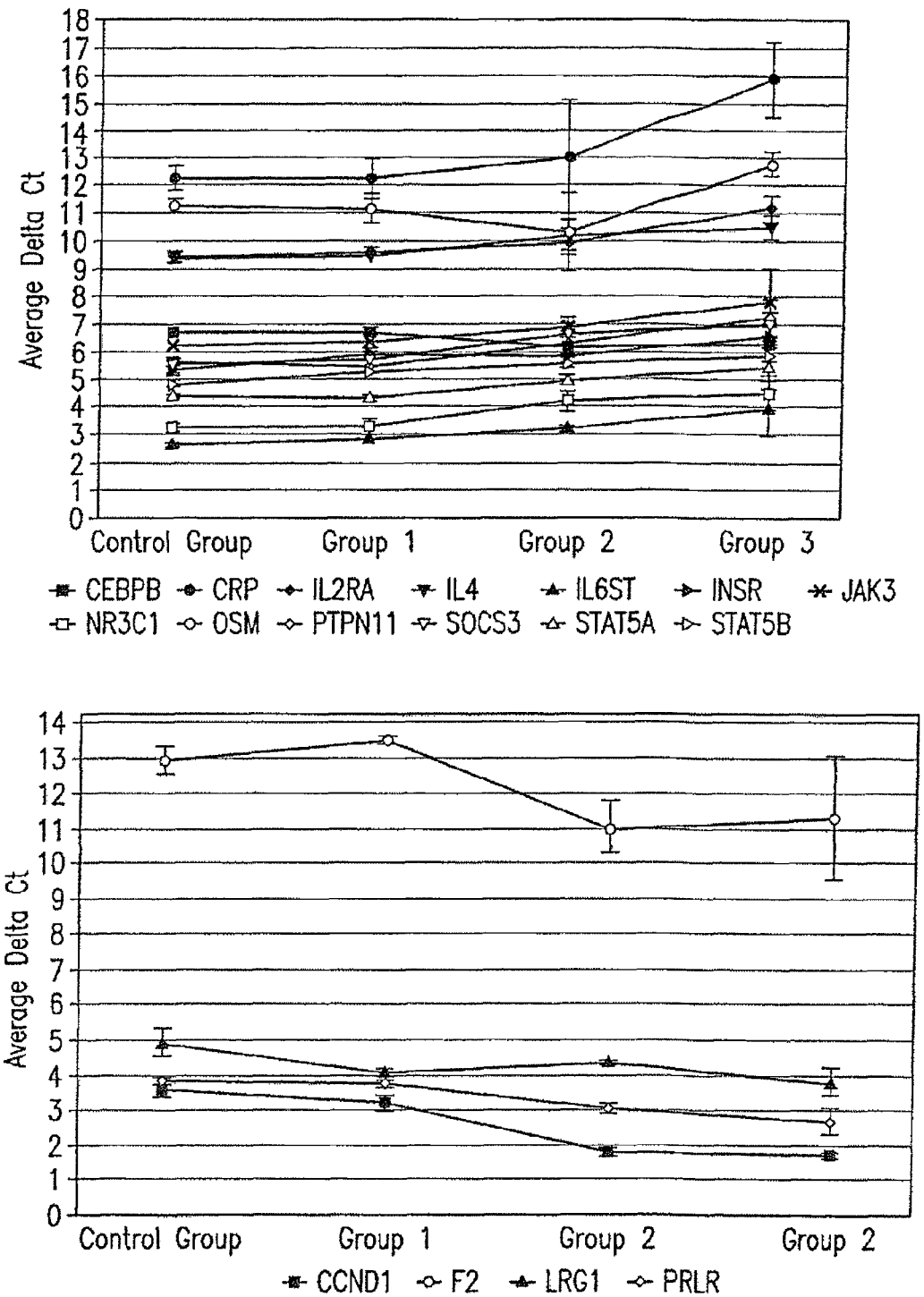
FIG. 66 shows summaries of genes upregulated in telogen as well as down-regulated in telogen. The Control group: D17 (Telogen); Group 1: D23 (telogen); Group 2: D29 (anagen); and Group 3: D33 (anagen). CRP, a well-defined gene upregulated by JAK/STAT signaling, is strikingly increased in telogen.
Figure 67:
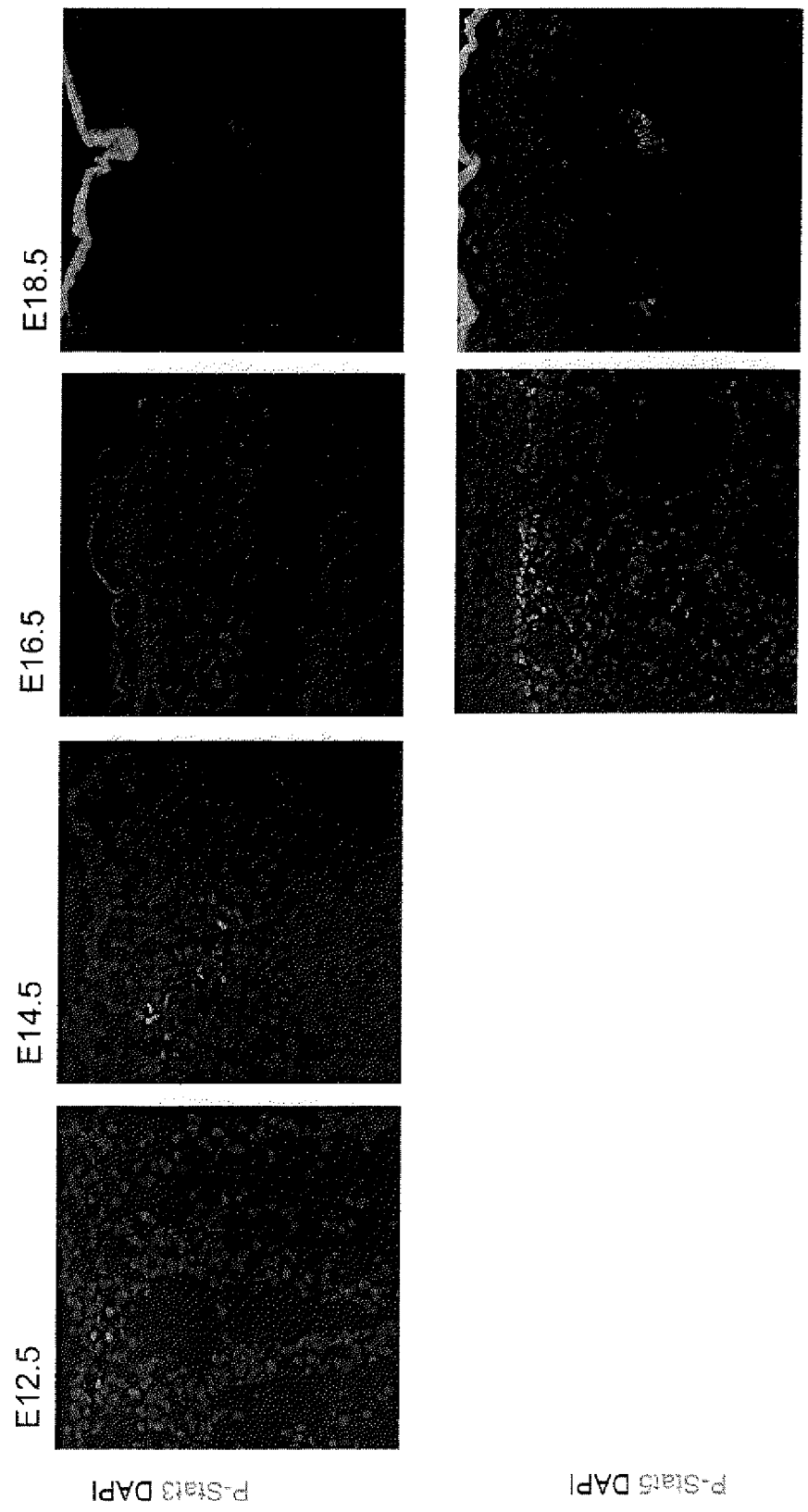
FIG. 67 are photomicrographs showing JAK-STAT in hair follicle development: Embryonic development. Stat 3 and Stat 5 were identified to be differentially expressed between telogen and anagen. To examine the pattern of expression in embryonic development, the activated (phosphorylated) forms of these proteins were stained. As shown, P-Stat 3 is expressed in epithelial layers during early stages of development and then can be faintly seen in the dermal papilla. P-Stat5 expression appears later, at E16.5, in scattered dermal cells and becomes pronounced in the dermal condensate by E18.5.
Figure 68:
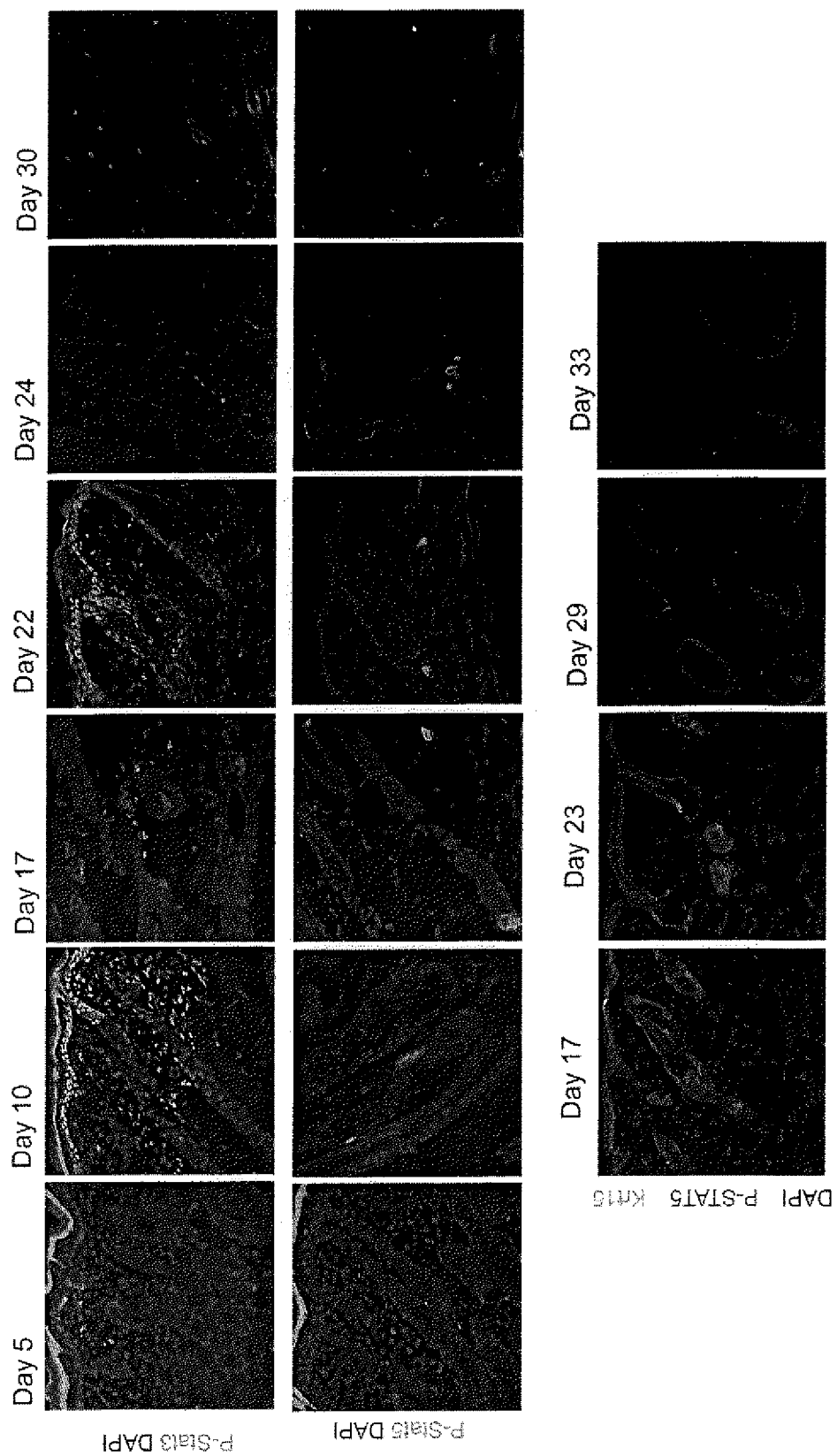
FIG. 68 are photomicrographs showing JAK-STAT in hair follicle development: post-natal development. P-Stat3 is expressed in the basal layers of the epidermis and upper epithelial layers of the follicle during neonatal skin development. Expression can also be detected in the dermal papilla, most obviously during telogen (D17). P-Stat5 is highly expressed in the dermal papilla in all stage of the hair cycle. In telogen, expression of P-Stat5 maybe limited to a subset of DP cells, closest to the K15+ bulge (D17, bottom).

The dynamics of the JAK-STAT signaling pathway were first interrogated using a targeted RT-PCR array containing readouts of JAK-STAT signaling (FIG. 63), and compared gene expression between the telogen vs. anagen stages of the normal hair cycle (FIGS. 64-66).

This data revealed that many components of JAK-STAT signaling were upregulated in telogen and downregulated in anagen phase of the normal hair cycle, indicating that in the context of the hair cycle, JAK-STAT signaling can be associated with maintaining stem cell quiescence in telogen (FIG. 66).

To test whether inhibition of JAK-STAT signaling could therefore trigger the telogen-to-anagen transition, a topical JAK3 inhibitor was applied to test whether anagen could be induced in normal mouse skin in telogen.

Indeed, topical administration of a JAK3 inhibitor resulted in a striking anagen induction in mouse skin in telogen, compared to vehicle alone. This was associated with marked proliferation of keratinocyte matrix cells, and the induction and growth of robust pigmented anagen hairs after 1-2 weeks (see FIGS. 69-74).

Figure 69:
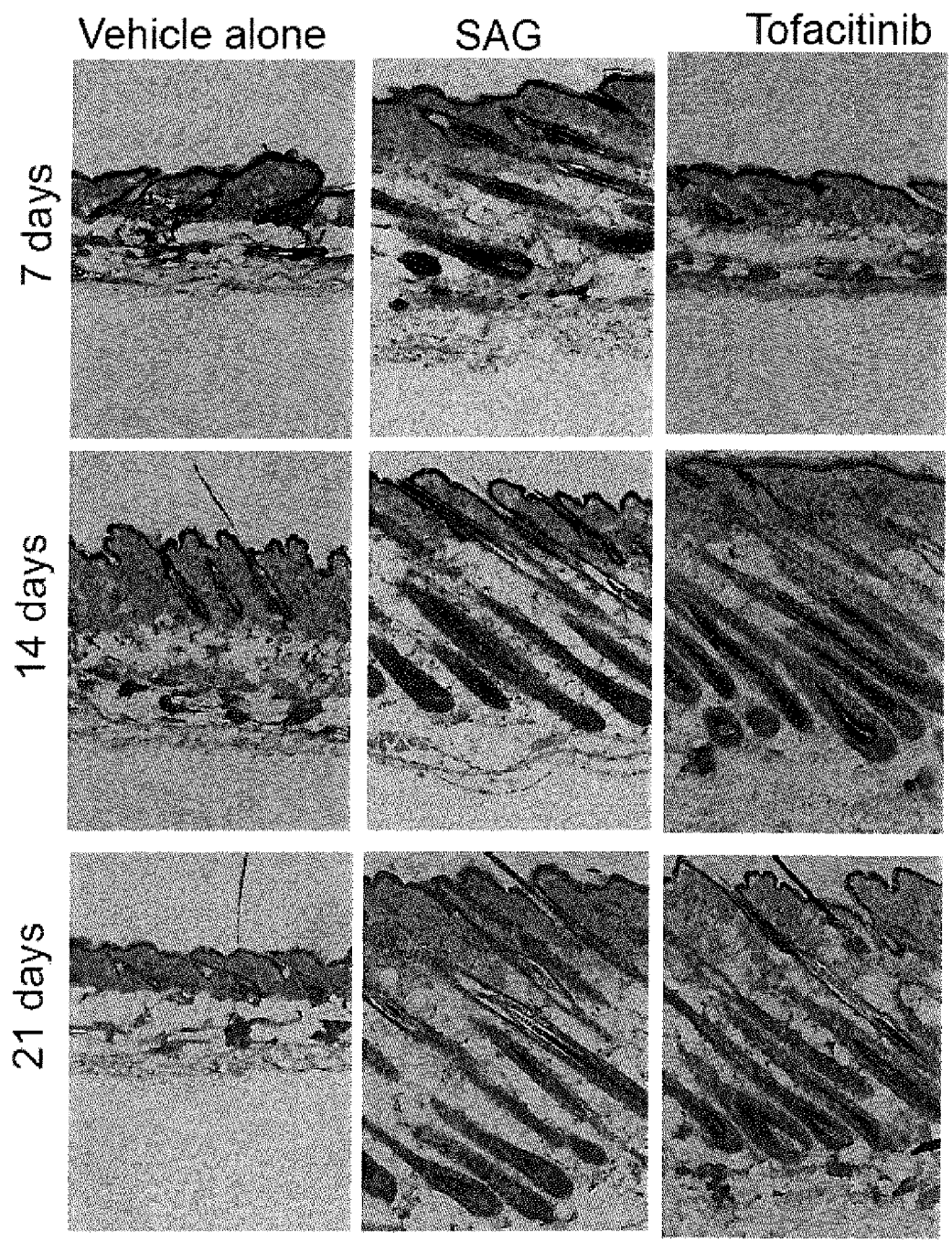
FIG. 69 are photomicrographs showing the effect of a JAK-STAT inhibitor on the hair cycle of normal mice: Induction of anagen. Inhibition of the JAK-STAT pathway during telogen (by application of a JAK inhibitor) results in early onset of anagen. 7-8 weeks old animals in telogen were treated with controls or JAK STAT inhibitors. Negative (vehicle alone; Left Panel) and positive (SAG=sonic hedgehog agonist; Middle panel) controls show that DMSO treatment alone does not induce anagen, while treatment with sonic hedgehog agonist results in early (4-7 days post treatment) induction of anagen, as expected. Right: Treatment with the Jak 3 inhibitor Tofacitinib (10 mg/mL) results in marked induction of anagen after 2 weeks or 3 weeks of treatment compared to vehicle treated mice which remain in telogen.
Figure 70:
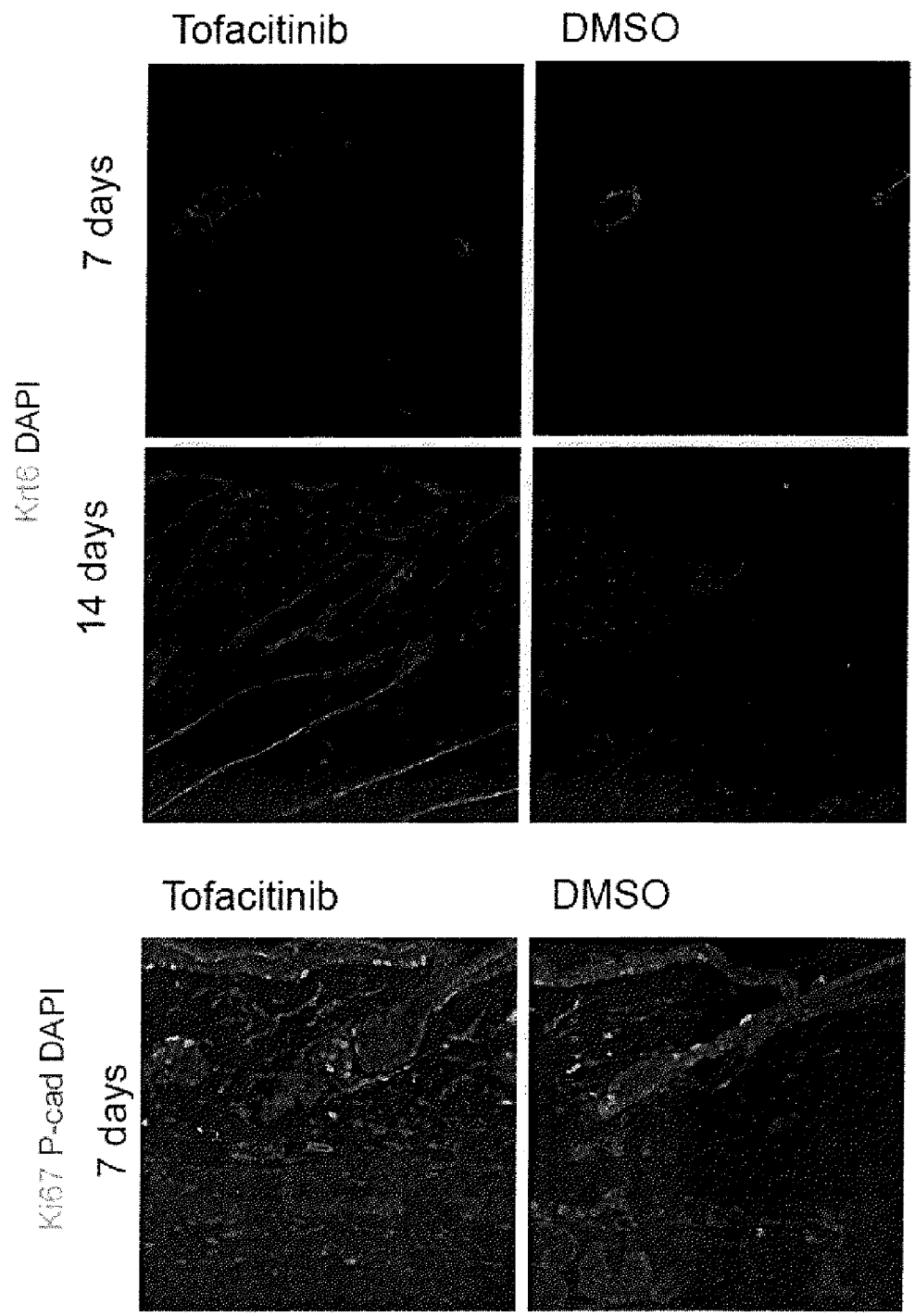
FIG. 70 are photomicrographs showing effects of drug treatment on keratinocyte proliferation in vivo. Tofacitinib does not appear to cause hyperpoliferation of the epidermis. Top: Krt6, a marker of keratinocyte proliferation typically expressed in the inner root sheath of the follicle. Bottom: the effects of drug treatment on proliferation of the follicle. In tofacitinib treatead skin, proliferation in the secondary germ occurs later, indicating that Tofacitinib can induce anagen.
Figure 72:
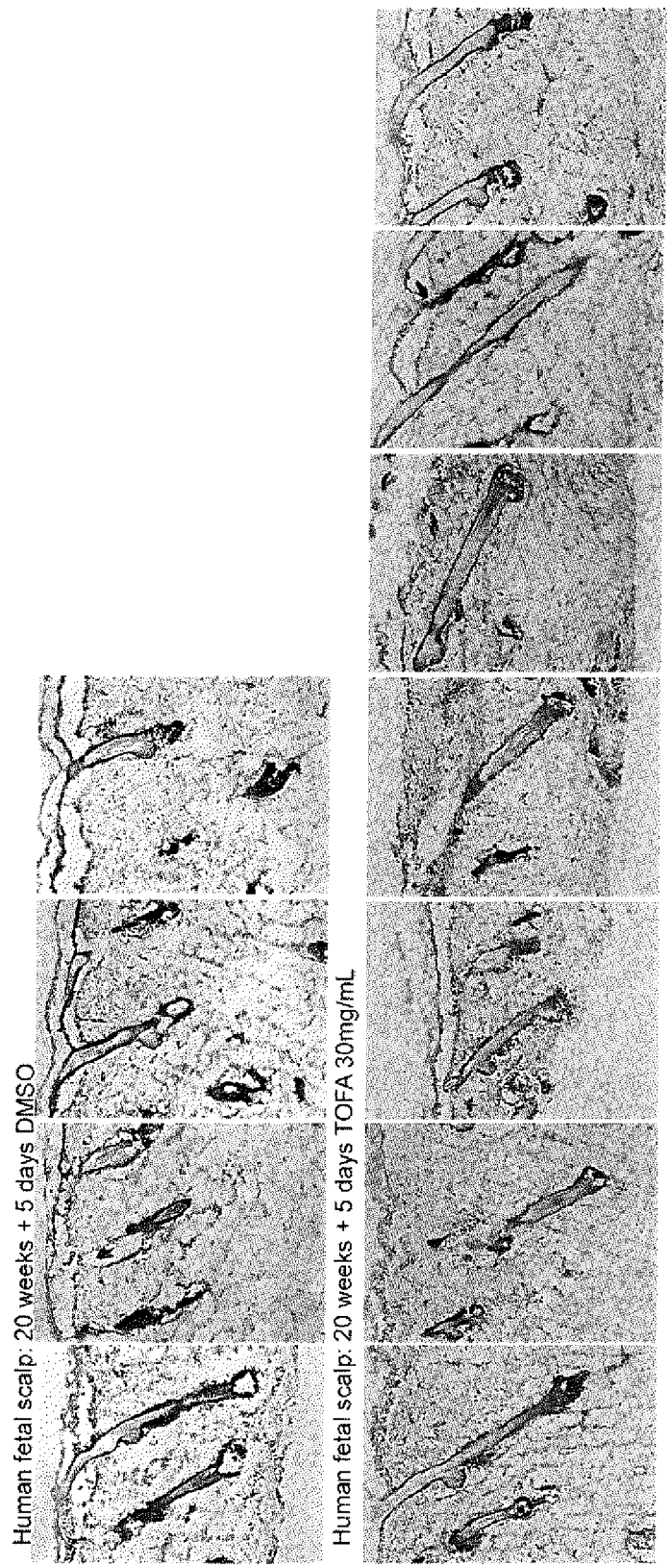
FIG. 72 are photomicrographs showing the effect of Jak inhibitors on human hair follicle morphogenesis: drug treatments of human fetal scalp. Human embryonic scalp at 20 weeks was obtained and treated in vitro with 30 mg/mL of the Jak3 inhibitor, Tofacitinib, or vehicle alone. Skin was harvested and sectioned and assessed for hair follicle morphology. Hairs in treated skin appear more advanced in the first anagen of morphogenesis compared to DMSO treated scalp.
Figure 73:
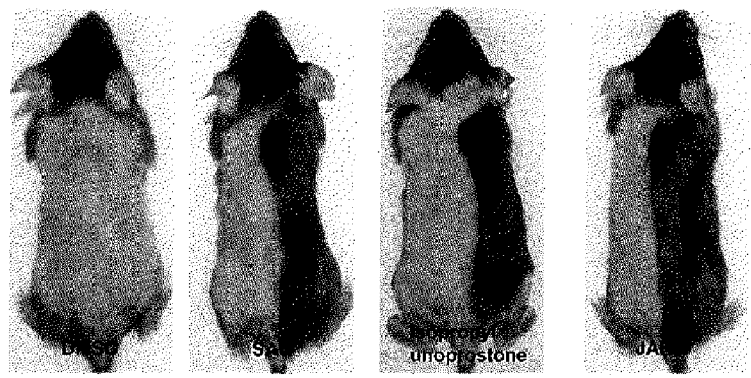
FIG. 73 shows topical treatment with a JAK inhibitor. Seven-week-old normal C57BL/6 mice were shaved in telogen and treated with 1% Jak3 inhibitor (Tofacitinib; Right panel), 1.5 mg/ml Isopropyl unoprostone (LATISSE™; Middle Right panel), 100 uM SAG (shh agonist; Middle Left panel), or DMSO as vehicle (Left Panel) by daily application for 3 weeks. Effect is durable out to a little more than 1 month at the time the image was taken. Right half of each mouse was administered topical drug, left half of each mouse was treated with DMSO alone.
Figure 74:
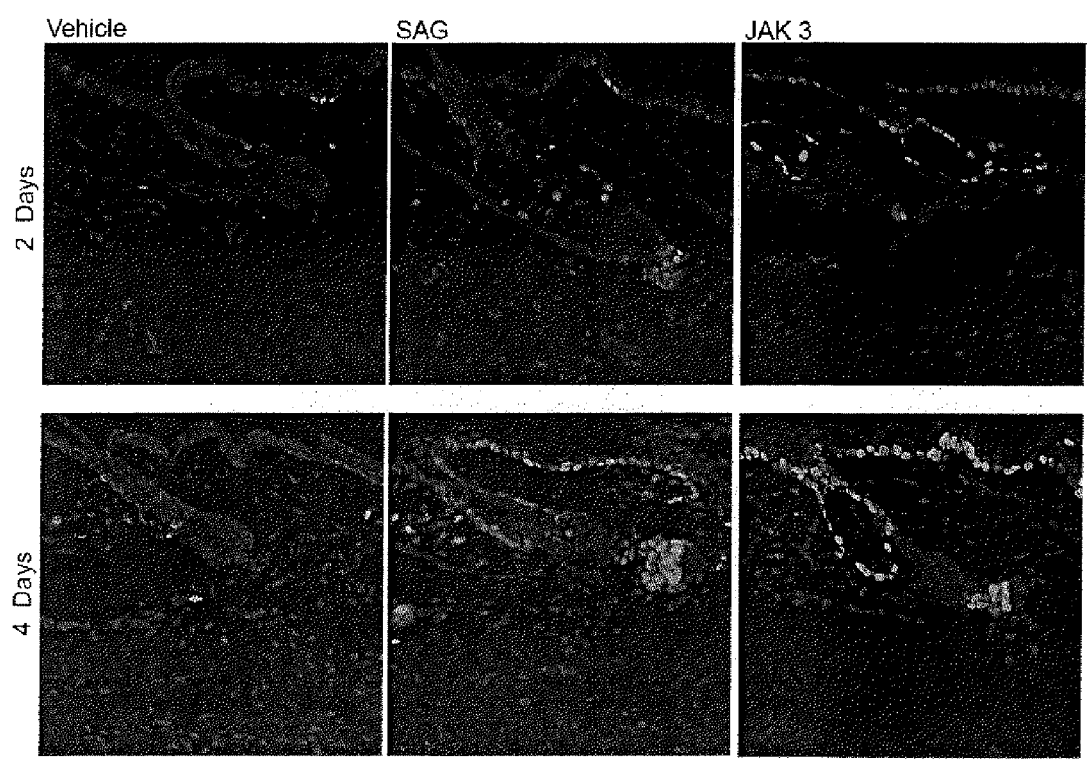
FIG. 74 are photomicrographs of Ki67 staining (green) showing marked proliferation in the telogen hair follicle in Tofacitinib and SAG treated skin, compared to vehicle, indicative of the start of Anagen.

This observation was compared to a positive control SAG (sonic hedgehog agonist) which is known to have the same effect, and the JAK3 inhibitor was comparable in its effect on anagen induction (FIGS. 69, 73, 74).

Without being bound by theory, these findings indicate that blockade of JAK-STAT signaling in telogen mimics in part the molecular events of anagen initiation, and can be a useful therapeutic agent for hair growth, using topical JAK inhibitors to induce telogen hairs to re-enter anagen.

What is claimed:

1. A method of treating a hair-loss disorder in a mammalian subject in need thereof, the method comprising administering to the subject INCB 018424.

2. The method of claim 1, wherein the hair-loss disorder is selected from androgenetic alopecia, telogen effluvium, alopecia areata, tinea capitis, hypotrichosis, and hereditary hypotrichosis simplex.

3. The method of claim 2, wherein the alopecia areata is alopecia totalis or alopecia universalis.

4. The method of claim 1 wherein the hair loss-disorder is androgenetic alopecia.

5. The method of claim 1 wherein the hair loss-disorder is alopecia areata.

6. A method for inducing hair growth in a subject, the method comprising:

(a) administering to the subject an effective amount of INCB 018424,
    thereby inducing hair growth in the subject.

7. The method of claim 6, wherein the subject suffers from a hair-loss disorder, wherein the hair-loss disorder is selected from androgenetic alopecia, telogen effluvium, alopecia areata, tinea capitis, hypotrichosis, and hereditary hypotrichosis simplex.

8. The method of claim 7, wherein the alopecia areata is alopecia totalis or alopecia universalis.

9. The method of claim 7 wherein the hair loss-disorder is androgenetic alopecia.

10. The method of claim 7 wherein the hair loss-disorder is alopecia areata.

* * * * *

UNITED STATES PATENT AND TRADEMARK OFFICE
CERTIFICATE OF CORRECTION

| | | |
|---|---|---|
| PATENT NO. | : 9,198,911 B2 | |
| APPLICATION NO. | : 13/886252 | |
| DATED | : December 1, 2015 | |
| INVENTOR(S) | : Angela M. Christiano and Raphael Clynes | |

It is certified that error appears in the above-identified patent and that said Letters Patent is hereby corrected as shown below:

In the Specification,

Column 1, line 20, STATEMENT REGARDING FEDERALLY SPONSORED RESEARCH OR DEVELOPMENT:

Government Interests "This invention was made with government support under Grants Nos. RO1AR56016 and R21AR061881 awarded by the National Institutes Of Health/National Institute Of Arthritis and Musculoskeletal and Skin Diseases. The Government has certain rights in the invention." should read -- This invention was made with government support under AR056016 and AR061881 awarded by the National Institutes of Health. The government has certain rights in the invention. --

Signed and Sealed this
Ninth Day of August, 2016

Michelle K. Lee
*Director of the United States Patent and Trademark Office*